(12) United States Patent
Rackelmann et al.

(10) Patent No.: US 8,822,449 B2
(45) Date of Patent: Sep. 2, 2014

(54) SUBSTITUTED AMINOINDANES AND ANALOGS THEREOF, AND THE PHARMACEUTICAL USE THEREOF

(75) Inventors: Nils Rackelmann, Frankfurt am Main (DE); Laurent Bialy, Frankfurt am Main (DE); Heinrich Englert, Frankfurt am Main (DE); Klaus Wirth, Paris (FR); Petra Arndt, Frankfurt am Main (DE); John Weston, Frankfurt am Main (DE); Uwe Heinelt, Frankfurt am Main (DE); Markus Follmann, Wülfrath (DE)

(73) Assignee: Sanofi, Paris (FR)

( * ) Notice: Subject to any disclaimer, the term of this patent is extended or adjusted under 35 U.S.C. 154(b) by 217 days.

(21) Appl. No.: 13/061,805

(22) PCT Filed: Aug. 25, 2009

(86) PCT No.: PCT/EP2009/006135
§ 371 (c)(1),
(2), (4) Date: Apr. 29, 2011

(87) PCT Pub. No.: WO2010/025856
PCT Pub. Date: Mar. 11, 2010

(65) Prior Publication Data
US 2011/0201590 A1 Aug. 18, 2011

(30) Foreign Application Priority Data
Sep. 2, 2008 (EP) .................................. 08290826

(51) Int. Cl.
| | | |
|---|---|---|
| A61K 31/454 | (2006.01) | |
| A61K 31/4025 | (2006.01) | |
| A61K 31/5377 | (2006.01) | |
| A61K 31/4995 | (2006.01) | |
| A61K 31/496 | (2006.01) | |
| A61K 31/4439 | (2006.01) | |
| A61K 31/4178 | (2006.01) | |
| A61K 31/407 | (2006.01) | |
| C07D 243/08 | (2006.01) | |
| C07D 413/12 | (2006.01) | |
| C07D 403/12 | (2006.01) | |
| C07D 401/12 | (2006.01) | |
| C07D 487/04 | (2006.01) | |
| A61P 25/00 | (2006.01) | |
| A61P 11/00 | (2006.01) | |
| A61P 13/12 | (2006.01) | |
| A61P 1/00 | (2006.01) | |
| A61P 9/12 | (2006.01) | |
| A61P 9/00 | (2006.01) | |
| A61P 3/06 | (2006.01) | |
| A61P 3/10 | (2006.01) | |
| A61P 3/00 | (2006.01) | |

(52) U.S. Cl.
USPC ................... 514/210.2; 514/235.5; 514/249; 514/254.08; 514/322; 514/326; 514/338; 514/397; 514/412; 540/575; 544/129; 544/349; 544/373; 546/199; 546/210; 546/276.7; 548/311.7; 548/453

(58) Field of Classification Search
USPC ........................................................ 548/262.2
See application file for complete search history.

(56) References Cited

U.S. PATENT DOCUMENTS

| | | | | |
|---|---|---|---|---|
| 5,149,714 | A * | 9/1992 | Freedman | 514/655 |
| 5,744,641 | A * | 4/1998 | Gericke et al. | 564/228 |
| 5,773,463 | A * | 6/1998 | Harling et al. | 514/473 |
| 6,703,405 | B2 * | 3/2004 | Hofmeister et al. | 514/307 |

FOREIGN PATENT DOCUMENTS

| | | |
|---|---|---|
| DE | 19945302 A1 | 3/2001 |
| EP | 0303961 A2 | 2/1989 |
| EP | 0371508 A1 | 6/1990 |
| WO | WO95/04028 A1 | 2/1995 |
| WO | WO 9504028 A1 * | 2/1995 |
| WO | WO96/02494 A1 | 2/1996 |
| WO | WO01/44164 A1 | 6/2001 |
| WO | WO01/72742 A1 | 10/2001 |
| WO | WO2006/074813 A1 | 7/2006 |
| WO | WO 2007007069 A1 * | 1/2007 |
| WO | WO01/79186 A1 | 4/2012 |

OTHER PUBLICATIONS

Campbell, C. A. et al. Characterization of SB-221420-A—a neuronal Ca2+ and Na2+ channel antagonist in experimental models of stroke. Eur. J. Pharm. 2000, 401, 419-428.*

(Continued)

Primary Examiner — Samantha Shterengarts
Assistant Examiner — Amanda L Aguirre
(74) Attorney, Agent, or Firm — Scully, Scott, Murphy & Presser, P.C.

(57) ABSTRACT

The invention relates to substituted aminoindanes and analogs thereof of formula (I) and the pharmaceutical use thereof. Medicaments which comprise compounds of this type are suitable for the prevention or treatment of diverse disorders such as, for example, of respiratory disorders, cystic fibrosis disorders, acute or chronic renal disorders or bowel disorders.

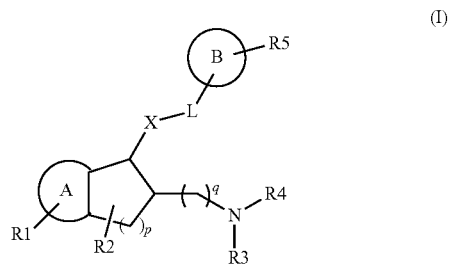

15 Claims, No Drawings

(56) References Cited

OTHER PUBLICATIONS

Ettmayer, P. et al. Lessons Learned from Marketed and Investigational Prodrugs. J. Med. Chem. 2004, 47, 2394-2404.*
Testa, B. Prodrug Research: Futile or Fertile? Biochem. Pharmacol. 2004, 68, 2097-2106.*
Stella, V. J. Prodrugs as Therapeutics. Expert Opin. Ther. Patents 2004, 14, 277-280.*
Wolff, M. E. Burger's Medicinal Chemistry and Drug Discovery, 1994, John Wiley & Sons, 5th Ed., vol. 1, pp. 975-977.*
Vippagunta, S. R. et al., Crystalline Solids. Adv. Drug Deliver. Rev. 2001, 48, 3-26.*
Morissette, S. L. et al. High-Throughput Crystallization: Polymorphs, Salts, Co-Crystals and Solvates of Pharmaceutical Solids. Adv. Drug Deliver. Rev. 2004, 56, 275-300.*
Tanigawa, T. Obstructive Sleep Apea: Its prevention and Screening May Contribute to the Prevention of Hypertension, Diabetes and Cardiovascular Diseases. EPMA Journal 2011, 2, 83-89.*
Freedman, Jules et al., "The Mitsunobu Reaction of Some Indan Amino Alcohols," Journal of Organic Chemistry (1991), vol. 56, pp. 670-672.
Campbell, Colin A. et al., "Characterisation of SB-221420-A—a neuronal Ca2+ and Na+ channel antagonist in experimental models of stroke," European Journal of Pharmacology (2000), vol. 401, pp. 419-428.
International Preliminary Report on Patentability dated Sep. 7, 2010 issued in PCT/EP2009/006135.

* cited by examiner

SUBSTITUTED AMINOINDANES AND ANALOGS THEREOF, AND THE PHARMACEUTICAL USE THEREOF

The invention relates to substituted aminoindanes and analogs thereof, and to the pharmaceutical use thereof. Medicaments comprising compounds of this type are suitable for the prevention or treatment of diverse disorders.

Previously disclosed NHE3 inhibitors are derived for example from compounds of the acylguanidine type (EP 0 825 178), norbornylamine type (WO 01/44164), 2-guanidino-quinazoline type (WO 01/79186, WO 03/051866), benzamidine type (WO 01/21582, WO 01/72742), 4-phenyltetrahydroisoquinoline type (WO 06/074813) or benzimidazole type (WO 03/101984). Squalamine, which is likewise described as NHE3 inhibitor (M. Donowitz et al. Am. J. Physiol. 276 (Cell Physiol. 45): C136-C144), appears to act not directly but by an indirect mechanism and thus reaches its maximum strength of effect only after one hour.

Starting from this, it has surprisingly been found that compounds of the formula I represent excellent inhibitors of the sodium-hydrogen exchanger (NHE), especially of the sodium-hydrogen exchanger of subtype 3 (NHE3). The invention consequently relates to compounds of the formula I

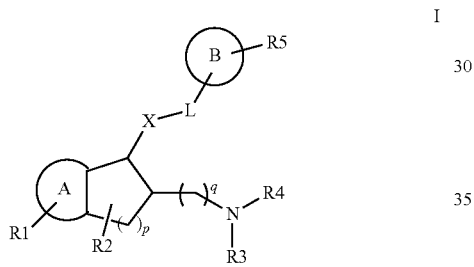

in which

A is a 6 to 10 membered aryl radical or a 5 to 10 membered heteroaryl radical, where the aryl and heteroaryl radical may be mono- or bicyclic, and the heteroaryl radical may comprise one or more heteroatoms selected from the group of nitrogen, oxygen and sulfur;
  where one or more hydrogen atoms in said mono- or bicyclic aryl or heteroaryl radicals may be replaced by substituents R1 which are selected independently of one another from the group of F, Cl, Br, I, $(C_1-C_{10})$-alkyl-, $(C_2-C_{10})$-alkenyl-, $(C_2-C_{10})$-alkynyl-, $(C_3-C_{14})$-cycloalkyl-, $(C_4-C_{20})$-cycloalkylalkyl-, $(C_4-C_{20})$-cycloalkylalkyloxy-, $(C_1-C_{10})$-alkoxy-, $(C_1-C_{10})$-alkylthio-, $(C_6-C_{14})$-aryl-, $(C_2-C_{13})$-heteroaryl, —CN, —NR13R14, —C(O)R12, —SF$_5$, —S(O)$_n$R12, —C(O)OR12, —C(O)NR13R14, —S(O)$_n$NR13R14;
    where two adjacent radicals R1 may also form a saturated or partly unsaturated $(C_5-C_{10})$-cycloalkyl radical or a saturated or partly unsaturated $(C_2-C_9)$-cycloheteroalkyl radicals, where the cycloheteroalkyl radical may comprise 1, 2 or 3 nitrogen, 1 or 2 oxygen, 1 or 2 sulfur, 1 or 2 nitrogen and 1 oxygen or 1 sulfur atom;
      where said alkyl, alkenyl, alkynyl, cycloalkyl, cycloalkylalkyl, cycloalkylalkyloxy, cycloheteroalkyl, alkoxy, and alkylthio radicals may be substituted independently of one another one or more times by F, OH or $(C_1-C_{10})$-alkoxy;

B is a mono- or fused bicyclic radical selected from the group of
  6 to 10 membered aryl radicals,
  of 5 to 10 membered heteroaryl radicals,
  of 3 to 10 membered cycloalkyl radicals,
  of 9 to 14 membered cycloalkylaryl radicals,
  of 8 to 14 membered cycloalkylheteroaryl radicals,
  of 3 to 10 membered cycloheteroalkyl radicals,
  of 9 to 14 membered cycloheteroalkylaryl radicals and
  of 8 to 14 membered cycloheteroalkylheteroaryl radicals,
    where the cycloalkyl or cycloheteroalkyl units may be saturated or partly unsaturated, and where the heterocyclic groups may comprise one or more heteroatoms selected from the group of nitrogen, oxygen and sulfur;
    where one or more hydrogen atoms in the radicals B may be replaced by substituents R5 which are selected independently of one another from the group of $(C_1-C_{10})$-alkyl radicals, of $(C_2-C_{10})$-alkenyl radicals, of $(C_2-C_{10})$-alkynyl radicals, of $(C_1-C_{10})$-alkoxy radicals, of $(C_1-C_{10})$-alkylthio radicals, of $(C_3-C_{14})$-cycloalkyl radicals, of $(C_4-C_{20})$-cycloalkylalkyl radicals, of $(C_4-C_{20})$-cycloalkylalkyloxy, of $(C_2-C_{19})$-cycloheteroalkyl radicals, of $(C_3-C_{19})$-cycloheteroalkylalkyl radicals, of $(C_3-C_{11})$-cycloalkyloxy radicals, of $(C_2-C_{11})$-cycloheteroalkyloxy radicals, of $(C_6-C_{10})$-aryl radicals, of $(C_1-C_9)$-heteroaryl radicals, of $(C_9-C_{14})$-cycloalkylaryl radicals, of $(C_5-C_{13})$-cycloalkylheteroaryl radicals, $(C_7-C_{13})$-cycloheteroalkylaryl radicals, $(C_4-C_{12})$-cycloheteroalkylheteroaryl radicals, where
      the cycloalkyl and cycloheteroalkyl units may be saturated or partly unsaturated,
      and where one or more hydrogen atoms in said radicals R5 may be replaced by further radicals which are selected independently of one another from the group of R11 radicals,
    it is further possible for R5 to be one or more radicals which are selected independently of one another from the group of OH, (=O), NH$_2$, F, Cl, Br, I, CN, NO$_2$, —NR17R18, —NR16COR17, —NR16COOR17, —NR16CONR17R18, —NR16-S(O)$_2$—R17, —NR16-S(O)$_2$—NR17R18, —COOR16, —COR16; —CO(NR17R18), S(O)$_n$R16, —S(O)$_2$NR17R18,
      where R16, R17 and R18 independently of one another for a radical selected from the group of H, $(C_2-C_{19})$-cycloheteroalkyl, $(C_3-C_{14})$-cycloalkyl, $(C_6-C_{10})$-aryl, $(C_1-C_{10})$-alkyl radicals,
      all of which may be substituted independently of one another by OH, (=O), F, Cl, Br, I, CN, NO$_2$, —NR13R14, —NR13COR12, —NR13COOR12, —NR12CONR13R14, —NR13-S(O)$_2$—R12, —NR12-S(O)$_2$—R13R14, —COOR12, —COR12; —CO(NR13R14), —S(O)$_n$R12, —S(O)$_2$NR13R14, $(C_3-C_{14})$-cycloalkyl, $(C_4-C_{20})$-cycloalkylalkyl, $(C_2-C_{19})$-cycloheteroalkyl, $(C_3-C_{19})$-cycloheteroalkylalkyl, $(C_6-C_{10})$-aryl and $(C_1-C_9)$-heteroaryl,
      and where R17 and R18 can form together with the nitrogen to which they are bonded a 4-7 membered, saturated, unsaturated or partly unsaturated heterocycle having 1 to 13 carbon atoms which may additionally comprise one or more heteroatoms from the list —O—, —S(O)$_n$—, =N— and —NR15-, where the heterocycle formed may be substituted independently of one another one or more times by F, OH, (=O), $NH_2$, $NH(C_1-C_4)$alkyl, $N((C_1-C_4)$alkyl$)_2$, CN or $(C_1-C_{10})$-alkoxy, $(C_1-C_{10})$-alkyl, $(C_2-C_{10})$-alkenyl, $(C_2-C_{10})$-alkynyl, $(C_3-C_{14})$-cycloalkyl, $(C_4-C_{20})$-cycloalkylalkyl, $(C_2-C_{20})$-cycloheteroalkyl, $(C_3-C_{19})$-cycloheteroalkylalkyl, each of which may in turn carry independently of one another one or more radicals F, OH, (=O), $NH_2$, $NH(C_1-C_4)$alkyl, $N((C_1-C_4)$alkyl$)_2$, CN or $(C_1-C_{10})$-alkoxy;

L is a covalent bond or an alkylene bridge having 1 to 10 carbon atoms,
which may carry independently of one another one or more substituents from the group of radicals $(C_1-C_{10})$-alkyl, $(C_3-C_{14})$-cycloalkyl, $(C_4-C_{20})$-cycloalkylalkyl radical, —COR12, —CO(NR13R14), $S(O)_nR12$, —$S(O)_2NR13R14$, (=O) and F; where the alkyl, cycloalkyl and cycloalkyl radicals may be substituted one or more times by F;

X is a group —N(R6)-, —O—, —$S(O)_n$—, or alkylene having 1 to 5 carbon atoms, where
R6 may be hydrogen or may be $(C_1-C_{10})$-alkyl, $(C_3-C_{14})$-cycloalkyl, $(C_4-C_{20})$-cycloalkylalkyl radical, all of which may be substituted independently of one another one or more times by F, or R6 may be —COR12; —CO(NR13R14), $S(O)_nR12$, —$S(O)_2NR13R14$;

R2 is absent or is one or more substituents which may be selected independently of one another from the group of F, $(C_1-C_{10})$-alkyl and $(C_1-C_{10})$-alkoxy radical, where the alkyl and alkoxy radicals may be substituted independently of one another one or more times by F;

R3 and R4 are independently of one another a hydrogen radical or a radical which is selected from the group of $(C_1-C_{10})$-alkyl radicals, of $(C_2-C_{10})$-alkenyl radicals, of $(C_2-C_{10})$-alkynyl radicals, of $(C_3-C_{14})$-cycloalkyl radicals, of $(C_4-C_{20})$-cycloalkylalkyl radicals, of $(C_2-C_{19})$-cycloheteroalkyl radicals, of $(C_3-C_{19})$-cycloheteroalkylalkyl radicals, of $(C_6-C_{10})$-aryl radicals, of $(C_7-C_{20})$-arylalkyl radicals, of $(C_1-C_9)$-heteroaryl radicals, of $(C_2-C_{19})$-heteroarylalkyl radicals, where
the radicals R3 and R4 may be substituted independently of one another one or more times by a radical from the group of OH, $NH_2$, (=O), F, Cl, Br, I, CN, $NO_2$, —NR13R14, —NR13COR12, —NR13COOR12, —NR12CONR13R14, —NR13-$S(O)_2$—R12, —NR13-$S(O)_2$—NR13R14, —COOR12, —COR12; —CO(NR13R14), $S(O)_nR12$, —$S(O)_2R13R14$, or R3 and R4 form together with the nitrogen to which they are bonded a 4-10 membered, saturated, unsaturated or partly unsaturated heterocycle which may additionally comprise one or more heteroatoms from the list —O—, —$S(O)_n$—, =N— and —NR8-, where
the heterocyclic radicals may be substituted independently of one another one or more times by radicals selected from the group of R7 and R9, and where
the heterocyclic radicals may be bridged by a bond, by a saturated or unsaturated $(C_1-C_{10})$-alkyl or $(C_1-C_9)$-heteroalkyl chain or by —NR15-, —O—, —S—, and where
the alkyl and heteroalkyl chains may also form a spirocyclic ring system with the ring system formed by R3 and R4, where the alkyl and heteroalkyl bridges may be substituted independently of one another one or more times by radicals selected from the group of R7 and R9, and where
R8 in the group NR8 may form with the ring which R3 and R4 may form a further saturated, unsaturated or partly unsaturated heterocycle which may be substituted independently of one another one or more times by radicals selected from the group of R7 and R9, and may additionally comprise one or more heteroatoms from the list —O—, —$S(O)_n$—, —N= and —NR19-;

R7 are a $(C_1-C_{10})$-alkyl radical or $(C_1-C_{14})$-cycloalkyl radical, where the alkyl radical may be substituted independently of one another one or more times by R9;

R8 is an H, a $(C_1-C_{10})$-alkyl radical or $(C_1-C_{14})$-cycloalkyl radical, COR12, —CO(NR13R14), $S(O)_nR12$, —$S(O)_2NR13R14$, where the alkyl radical may be substituted independently of one another one or more times by R10;

R9 is a radical selected from the group of OH, (=O), F, Cl, Br, I, CN, $NO_2$, —NR13R14, —NR13COR12, —NR13COOR12, —NR12CONR13R14, —NR13-$S(O)_2$—R12, —NR13-$S(O)_2$—NR13R14, —COOR12, —COR12, —CO(NR13R14), $S(O)_nR12$, —$S(O)_2NR13R14$, $(C_3-C_{14})$-cycloalkyl, $(C_4-C_{20})$-cycloalkylalkyl, $(C_1-C_{10})$-alkoxy, $(C_2-C_{19})$-cycloheteroalkyl, $(C_3-C_{19})$-cycloheteroalkylalkyl, $(C_6-C_{10})$-aryl radicals, of $(C_1-C_9)$-heteroaryl radicals;

R10 is a radical selected from the group of F, OH, CN, $(C_1-C_{10})$-alkoxy, $(C_1-C_{10})$-alkylthio, $NO_2$, —NR13R14, —NR13COR12, —NR13COOR12, —NR13CONR13R14, —NR13-$S(O)_2$—R12, —NR12-$S(O)_2$—NR13R14, —COOR12, —COR12, —CO(NR13R14), $S(O)_nR12$, —$S(O)_2NR13R14$;

R11 is a radical selected from the group of $(C_1-C_{10})$-alkyl, $(C_2-C_{10})$-alkenyl, $(C_2-C_{10})$-alkynyl, $(C_1-C_{10})$-alkoxy, $(C_1-C_{20})$-alkylthio, $(C_3-C_{14})$-cycloalkyl, $(C_4-C_{10})$—cycloalkylalkyl, $(C_2-C_{13})$-cycloheteroalkyl, $(C_4-C_{19})$-cycloheteroalkylalkyl, $(C_3-C_{14})$-cycloalkyloxy, $(C_2-C_{13})$-cycloheteroalkyloxy,
all of which may be substituted independently of one another one or more times by R10;
(=O), Cl, Br, I and R10;

R12, R13 and R14 may independently of one another be H, $(C_1-C_{10})$-alkyl, $(C_2-C_{10})$-alkenyl, $(C_2-C_{10})$-alkynyl, $(C_3-C_{14})$-cycloalkyl, $(C_4-C_{10})$-cycloalkylalkyl, $(C_2-C_{13})$-cycloheteroalkyl, $(C_3-C_{19})$-cycloheteroalkylalkyl, $(C_6-C_{10})$-aryl, each of which may be substituted independently of one another one or more times by F, OH, (=O), $NH_2$, $NH(C_1-C_4)$alkyl, $N((C_1-C_4)$alkyl$)_2$, CN or $(C_1-C_{10})$-alkoxy; or where R13 and R14 may form together with the nitrogen to which they are bonded a 4-7 membered, saturated, unsaturated or partly unsaturated heterocycle having 1 to 13 carbon atoms, which may additionally comprise one or more heteroatoms from the list —O—, —$S(O)_n$—, =N— and —NR15-, where
the formed heterocycle may be substituted independently of one another one or more times by F, OH, (=O), $NH_2$, $NH(C_1-C_4)$alkyl, $N((C_1-C_4)$alkyl$)_2$, CN or $(C_1-C_{10})$-alkoxy, $(C_1-C_{10})$-alkyl, $(C_2-C_{10})$-alkenyl, $(C_2-C_{10})$-alkynyl, $(C_3-C_{14})$-cycloalkyl, $(C_4-C_{20})$-cycloalkylalkyl, $(C_2-C_{20})$-cycloheteroalkyl, $(C_3-C_{19})$-cycloheteroalkylalkyl, each of which may in turn carry independently of one another one or more radicals F, OH, (=O), $NH_2$, $NH(C_1-C_4)$alkyl, $N((C_1-C_4)$alkyl$)_2$, CN or $(C_1-C_{10})$-alkoxy;

R15 is a radical selected from the group of H, $(C_1-C_{10})$-alkyl, $(C_2-C_{10})$-alkenyl, $(C_2-C_{10})$-alkynyl, $(C_3-C_{14})$-cycloalkyl, $(C_4-C_{20})$-cycloalkylalkyl, $(C_2-C_{13})$-cycloheteroalkyl, $(C_3-C_{19})$-cycloheteroalkylalkyl, each of which may be substituted independently of one another one or more times by F, OH, CN or $(C_1-C_{10})$-alkoxy;

R19 is an H, a $(C_1-C_{10})$-alkyl radical or $(C_1-C_{14})$-cycloalkyl radical, COR12, —CO(NR13R14), $S(O)_nR12$, —S(O)$_2$NR13R14, where the alkyl radical may be substituted independently of one another one or more times by R10;

and in which n is 0, 1 or 2;

p is 1 or 2 and q is 0 or 1, and the pharmaceutically acceptable salts thereof, and in which i) in the case where A is phenyl, B is phenyl or benzodioxolanyl, X is —O— or —S—, L is a bond and R3 and R4 are H, $(C_1-C_{10})$-alkyl, $(C_3-C_{14})$-cycloalkyl, $(C_7-C_{20})$-aralkyl or R3 and R4 together are an unsubstituted pyrrolidinyl, morpholinyl, piperidinyl or piperazinyl radical or 4-methylpiperazinyl radical, at least one R5 radical which is not a $(C_1-C_{10})$-alkyl, $(C_1-C_{10})$-alkoxy, OH, $CF_3$, F, Cl, Br or I radical must be present, ii) in the case where A is phenyl, X is —O—, —S— or —NH— and R3 and R4 are a $(C_1-C_{10})$-alkyl, $(C_3-C_{14})$-cycloalkyl or a $(C_4-C_{20})$-cycloalkylalkyl radical, at least one R5 radical which is not an F, Cl, Br, I, $(C_1-C_4)$-alkyl, $(C_1-C_4)$-alkoxy, $CF_3$, $OCF_3$, CN, $NO_2$, $NH_2$, —NH(($C_1$-$C_{10}$)-alkyl), —N(($C_1$-$C_{10}$-alkyl)$_2$, unsubstituted or substituted benzoyl or an unsubstituted or substituted phenyl-$(CH_2)_r$—Y—$(CH_2)_s$— radical, with Y being a bond or an oxygen and r and s being 0 to 4, where r+s is not greater than 4, must be present.

In one embodiment compounds of the formula I and the pharmaceutically acceptable salts thereof are preferred wherein L is a covalent bond;

X is a group —O—; and q is 0.

Preferred substances of the invention are compounds having the formula Ia and the pharmaceutically acceptable salts thereof

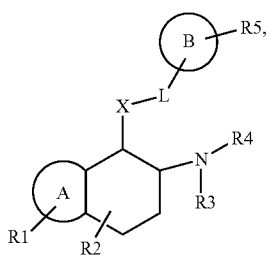

Ia where

A is a phenyl or 5 to 6 membered heteroaryl radical, where the heteroaryl radical may comprise as heteroatoms 1, 2 or 3 nitrogen atoms, 1 oxygen atom, 1 sulfur atom, 1 or 2 nitrogen and 1 oxygen or 1 sulfur atom, where one or more hydrogen atoms in said phenyl or heteroaryl radical may be replaced independently of one another by a radical R1, and/or B is a 6 to 10 membered monocyclic or fused bicyclic aryl group, a 5 to 10 membered monocyclic or fused bicyclic heteroaryl group, a 9 to 14 membered fused bicyclic cycloalkylaryl group, an 8 to 14 membered fused bicyclic cycloalkylheteroaryl group, a 9 to 14 membered fused bicyclic cycloheteroalkylaryl group or an 8 to 14 membered fused bicyclic cylcoheteroalkylheteroaryl group, each of which may be substituted independently of one another one or more times by R5 where the cycloalkyl and cycloheteroalkyl units may be saturated or partly unsaturated, and where the cycloheteroalkylaryl groups may comprise as heteroatoms 1 or 2 nitrogen atoms, 1 or 2 oxygen atoms, 1 or 2 sulfur atoms, 1 nitrogen atom and 1 oxygen or 1 sulfur atom or 1 oxygen and 1 sulfur atom, and the heteroaryl and cycloalkylheteroaryl groups may comprise 1, 2, 3 or 4 nitrogen atoms, 1 oxygen atom, 1 sulfur atom, 1 or 2 nitrogen atoms and 1 oxygen or sulfur atom or 1 oxygen and 1 sulfur atom, and the cycloheteroalkylheteroaryl group may comprise as heteroatoms 1, 2, 3 or 4 nitrogen atoms, 1 or 2 oxygen atoms, 1 or 2 sulfur atoms, 1, 2 or 3 nitrogen atom and 1 oxygen or 1 sulfur atom or 1 oxygen and 1 sulfur atom, and/or X is a group —N(R6)-, —O— or —S(O)$_n$—, where R6 is H or $(C_1-C_5)$-alkyl and n is 1 or 2, and/or R2 is absent or is one or more substituents which may be selected independently of one another from the group of F and of $(C_1-C_6)$-alkyl radicals, where the alkyl radicals may be substituted independently of one another one or more times by F, and/or L is a covalent bond, a —C(O)— bridge or a methylene bridge in which one or two hydrogen atoms may be replaced by F;

where the radicals R1, R3, R4 and R5 have the abovementioned meaning.

In one embodiment compounds of the formula Ia and the pharmaceutically acceptable salts thereof are preferred wherein L is a covalent bond; and X is a group —O—.

Particularly preferred compounds of the invention are tetrahydronaphthalenes of the formula Ib and the pharmaceutically acceptable salts thereof where

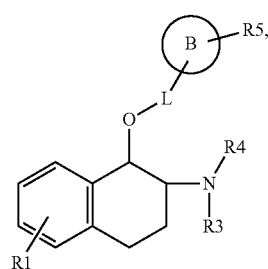

Ib

B may be a phenyl group, a naphthyl group, a pyridinyl group, a quinolinyl group, an isoquinolinyl group, an indolyl group, a benzothiophenyl group, a benzodihydrothiophenyl group, a benzofuranyl group, a benzodihydrofuranyl group, an isobenzodihydrofuranyl group, a benzopyrrolidinyl group, a benzoimidazolyl group, a benzopyrazolyl group, a benzotriazolyl group, a benzothiazolyl group, a benzoxathiolyl group, an indolinyl group, benzodioxolyl group, a tetrahydroisoquinolinyl group, a tetrahydroquinolinyl group, where one, two, three or four hydrogen atoms in group B may be replaced by radicals from the group of R5, where each R5 radical is selected independently of one another from the group of
- $(C_1-C_4)$-alkyl which may be wholly or partly fluorinated, or a hydrogen may be replaced by a CN, $NH_2$, OH, $NH(C_1-C_4)$alkyl, $N((C_1-C_4)$-alkyl$)_2$, $(C_1-C_4)$-alkoxy,
- $(C_1-C_4)$-alkoxy which may be wholly or partly fluorinated,
- $(C_1-C_4)$-alkylthio which may be wholly or partly fluorinated,
- $(C_2-C_5)$-cycloheteroalkyl and $(C_2-C_5)$-cycloheteroalkyl-$(C_1-C_4)$-alkyl,
  where the cycloheteroalkyl ring may be monocyclic, bicyclic, saturated or partly unsaturated, and may comprise 1 or 2 nitrogen atoms, 1 oxygen atoms, 1 nitrogen and 1 sulfur atom or 1 nitrogen and 1 oxygen atom, and
  where the cycloheteroalkyl ring may carry further substituents from the group of —F, —Cl, —Br, =O, —$NH_2$, $NH(C_1-C_4)$alkyl, $N((C_1-C_4)$alkyl$)_2$, $(C_1-C_4)$-alkoxy, —CN, $(C_1-C_4)$-alkyl, $(C_3-C_{10})$—cycloalkyl,
- phenyl, naphthyl,
- $(C_1-C_6)$-heteroaryl, where the heteroaryl ring may be a monocyclic or fused bicyclic ring which may comprise 1, 2, 3 or 4 nitrogen atoms, 1 oxygen atom, 1 sulfur atom, 1 or 2 nitrogen atoms and 1 oxygen or sulfur atom, and
  where the heteroaryl ring may carry further substituents from the group of —F, —Cl, —Br, =O, —OH, —$NH_2$, $NH(C_1-C_4)$alkyl, $N((C_1-C_4)$alkyl$)_2$, $(C_1-C_4)$-alkoxy, —CN, $(C_1-C_4)$-alkyl, $(C_3-C_{10})$-cycloalkyl, —C(O)O—$(C_1-C_4)$-alkyl,
- H, OH, (=O), F, Cl, Br, CN, $NO_2$, —NR17R18, —NR16COR17, —NR16COOR17, —NR16CONR17R18, —NR16-$S(O)_2$—R17, —NR16-$S(O)_2$—NR17R18, —COOR16, —COR16; —CO(NR17R18), —$S(O)_n$R16, with n=1 or 2, —$S(O)_2$NR17R18, where
  R16, R17 and R18 may independently of one another be a hydrogen radical or a radical selected from the group of unsubstituted or substituted $(C_1-C_4)$-alkyl radicals,
    where the substituents of the alkyl radicals are selected from F, OH, (=O), $NH_2$, $NH(C_1-C_4)$alkyl, $N((C_1-C_4)$alkyl$)_2$, —CN or $(C_1-C_{10})$-alkoxy,
  R17 and R18 may form together with the nitrogen to which they are bonded a 5-6 membered, saturated, unsaturated or partly unsaturated heterocycle having 1 to 5 carbon atoms, which may additionally comprise one or more heteroatoms from the list —O—, —$S(O)_n$— with n=0, 1 or 2, =N—, —NH— and —N$((C_1-C_4)$alkyl), where the formed heterocycle independently of one another may be substituted one or more times by $(C_1-C_{10})$-alkyl, $(C_3-C_{14})$-cycloalkyl, $(C_4-C_{20})$-cycloalkylalkyl, $(C_2-C_{20})$-cycloheteroalkyl, $(C_3-C_{19})$-cycloheteroalkylalkyl, each of which may in turn carry independently of one another one or more radicals F, OH, (=O) or $(C_1-C_{10})$-alkoxy,
R1 is absent or is one, two or three radicals which are selected independently of one another from the group of F, Cl, Br, I, $(C_1-C_6)$-alkyl, $(C_1-C_6)$-alkoxy, where the alkyl and alkoxy radical may be substituted one or more times by F, and/or
L is a bond or —$CH_2$—, and/or R3 and R4 are independently of one another a radical selected from the group of H, $(C_1-C_4)$-alkyl-, $(C_3-C_7)$-cycloalkyl-, $(C_3-C_6)$-cycloheteroalkyl, phenyl, phenyl-$(C_1-C_4)$-alkyl, $(C_1-C_6)$-heteroaryl, where
  the radicals R3 and R4 may be substituted independently of one another one, two or three times by a radical from the group of OH, (=O), F, Cl, Br, CN, $NO_2$, —NR13R14, —NR13COR12, —NR13COOR12, —NR12CONR13R14, —NR13-$S(O)_2$—R12, —NR13-$S(O)_2$—NR13R14, —COOR12, —COR12; —CO(NR13R14), $S(O)_n$R12, —$S(O)_2$NR13R14,
  where R12, R13 and R14 are H or $(C_1-C_4)$-alkyl, or
R3 and R4 form together with the nitrogen to which they are bonded a 4-8 membered, saturated, unsaturated or partly unsaturated heterocycle which may additionally comprise one or more heteroatoms from the list —O—, —$S(O)_n$— with n=0, 1 or 2, =N— and —NR8-, where
  the heterocyclic radicals may be substituted independently of one another one or more times by radicals selected from the group of R7 and R9,
  where the heterocyclic radicals may be bridged by a bond, $(C_1-C_7)$-alkyl, saturated or unsaturated $(C_1-C_6)$-heteroalkyl chains or by —NH—, —$N(C_1-C_4)$-alkyl)-, and where
  the alkyl and heteroalkyl chains may also form a spirocyclic ring system with the ring system formed by R3 and R4,
and where R8 may form with the ring which the radicals R3 and R4 may form a further saturated, unsaturated or partly unsaturated heterocycle which may additionally comprise one or two heteroatoms from the list —O—, —$S(O)_n$—, with n=0, 1 or 2, =N—, —NH— and —$N((C_1-C_4)$-alkyl);
where R7, R8 and R9 have the meaning indicated above.

In one embodiment compounds of the formula Ib and the pharmaceutically acceptable salts thereof are preferred wherein
L is a covalent bond.

A further group of preferred compounds has a structure according to formula Ic and the pharmaceutically acceptable salts thereof

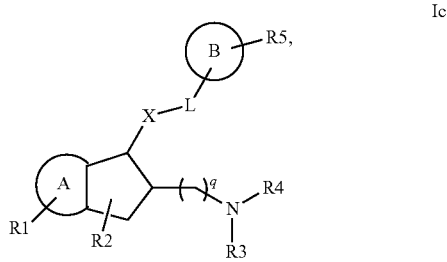

where
B is a 6 to 10 membered monocyclic or fused bicyclic aryl group, a 5 to 10 membered monocyclic or fused bicyclic heteroaryl group, a 9 to 14 membered fused bicyclic cycloalkylaryl group, an 8 to 14 membered fused bicyclic cycloalkylheteroaryl group, a fused 9 to 14 membered bicyclic cycloheteroalkylaryl group or an 8 to 14 membered fused bicyclic cycloheteroalkylheteroaryl group, each of which may be substituted independently of one another one or more times by R5 where the cycloalkyl and cycloheteroalkyl units may be saturated or partly unsaturated, and
where the cycloheteroalkylaryl groups may comprise as heteroatoms 1 or 2 nitrogen atoms, 1 or 2 oxygen atoms, 1 or 2 sulfur atoms, 1 nitrogen atom and 1 oxygen or 1 sulfur atom or 1 oxygen and 1 sulfur atom,
and the heteroaryl and cycloalkylheteroaryl groups may comprise 1, 2, 3 or 4 nitrogen atoms, 1 oxygen atom, 1 sulfur atom, 1 or 2 nitrogen atoms and 1 oxygen or 1 sulfur atom or 1 oxygen and 1 sulfur atom,
and the cycloheteroalkylheteroaryl group may comprise as heteroatoms 1, 2, 3 or 4 nitrogen atoms, 1 or 2 oxygen atoms, 1 or 2 sulfur atoms, 1, 2 or 3 nitrogen atom and 1 oxygen or 1 sulfur atom or 1 oxygen and 1 sulfur atom, and/or
X is a group —N(R6)-, —O— or —S(O)$_n$—,
where R6 is H or ($C_1$-$C_5$)-alkyl and n is 1 or 2, and/or
R2 is absent or is one or more substituents which may be selected independently of one another from the group of F and of ($C_1$-$C_6$)-alkyl radicals, where the alkyl radicals may be substituted independently of one another one or more times by F, and/or
L is a covalent bond, a —C(O)-bridge or a methylene bridge which may be substituted independently of one another one or more times by F;
q is 0 or 1;
where the radicals A, R1, R3, R4 and R5 have the abovementioned meaning.

Particularly preferred compounds have a structure according to formula Ic and the pharmaceutically acceptable salts thereof, where
A is a phenyl or a 5 to 6 membered heteroaryl radical, where the heteroaryl radical may comprise as heteroatoms 1, 2 or 3 nitrogen atoms, 1 oxygen atom, 1 sulfur atom, 1 or 2 nitrogen and 1 oxygen or 1 sulfur atom, where one or more hydrogen atoms in the phenyl or heteroaryl radical may be replaced independently of one another by a radical R1, and/or
B is a 6 to 10 membered monocyclic or fused bicyclic aryl group, a 5 to 10 membered monocyclic or fused bicyclic heteroaryl group, a 9 to 14 membered fused bicyclic cycloalkylaryl group, an 8 to 14 membered fused bicyclic cycloalkylheteroaryl group, a fused 9 to 14 membered bicyclic cycloheteroalkylaryl group or an 8 to 14 membered fused bicyclic cycloheteroalkylheteroaryl group, each of which may be substituted independently of one another one or more times by R5,
where the cycloalkyl and cycloheteroalkyl units may be saturated or partly unsaturated, and
where the cycloheteroalkylaryl groups may comprise as heteroatoms 1 nitrogen atom, 1 or 2 oxygen atoms, 1 or 2 sulfur atoms, 1 nitrogen atom and 1 oxygen or 1 sulfur atom or 1 oxygen and 1 sulfur atom,
and the heteroaryl and cycloalkylheteroaryl groups may comprise 1, 2 or 3 nitrogen atoms, 1 oxygen atom, 1 sulfur atom, 1 nitrogen and 1 oxygen or sulfur atom or 1 oxygen and one sulfur atom,
and the cycloheteroalkylheteroaryl group may comprise as heteroatoms 1, 2, 3 or 4 nitrogen atoms, 1 or 2 oxygen atoms, 1 or 2 sulfur atoms, 1 or 2 nitrogen atoms and 1 oxygen or 1 sulfur atom or 1 oxygen and 1 sulfur atom, and/or
X is a group —N(R6)-, —O— or —S(O)$_n$—,
where R6 is H or ($C_1$-$C_5$)-alkyl and n is 1 or 2, and/or
R2 is absent or is one or more substituents which may be selected independently of one another from the group of F and of ($C_1$-$C_6$)-alkyl radicals, where the alkyl radicals may be substituted independently of one another one or more times by F, and/or
L is a covalent bond, a —C(O)— bridge or a methylene bridge which may be substituted once or twice by F;
q is 0 or 1;
where said R1, R3, R4 and R5 radical has the abovementioned meaning.

In one embodiment compounds of the formula Ic and the pharmaceutically acceptable salts thereof are preferred wherein
L is a covalent bond;
X is a group —O—;
and
q is 0.

Aminoindanes of the formula Id and the pharmaceutically acceptable salts thereof are particularly preferred

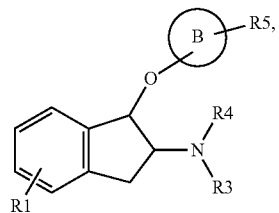

where
B may be a phenyl group, a naphthyl group, a pyridinyl group, a quinolinyl group, an isoquinolinyl group, an indolyl group, a benzothiophenyl group, a benzodihydrothiophenyl group, a benzofuranyl group, a benzodihydrofuranyl group, an isobenzodihydrofuranyl group, a benzopyrrolidinyl group, a benzoimidazolyl group, a benzopyrazolyl group, a benzotriazolyl group, a benzothiazolyl group, a benzoxathiolyl group, an indolinyl group, benzodioxolyl group, a tetrahydroisoquinolinyl group, a tetrahydroquinolinyl group, where one, two, three or four hydrogen atoms in the group B may be replaced by radicals from the group R5, where
each R5 radical is selected independently of one another from the group of
($C_1$-$C_4$)-alkyl which may be wholly or partly fluorinated, or one hydrogen may be replaced by a CN, $NH_2$, OH, NH($C_1$-$C_4$)alkyl, N(($C_1$-$C_4$)alkyl)$_2$, ($C_1$-$C_4$)alkoxy,
($C_1$-$C_4$)-alkoxy which may be wholly or partly fluorinated,
($C_1$-$C_4$)-alkylthio which may be wholly or partly fluorinated,
($C_2$-$C_5$)-cycloheteroalkyl and ($C_2$-$C_5$)-cycloheteroalkyl-($C_1$-$C_4$)-alkyl,
where the cycloheteroalkyl ring may be saturated or partly unsaturated and may comprise 1 or 2 nitrogen atoms, 1 oxygen atoms, 1 nitrogen and 1 sulfur atom or 1 nitrogen and 1 oxygen atom, and
where the cycloheteroalkyl ring may carry further substituents from the group of —F, —Cl, —Br, =O, —$NH_2$, —CN, ($C_1$-$C_4$)-alkyl, ($C_3$-$C_{10}$)-cycloalkyl, OH, NH($C_1$-$C_4$)-alkyl, N(($C_1$-$C_4$)-alkyl)$_2$, ($C_1$-$C_{10}$)-alkoxy,
phenyl, naphthyl,
($C_1$-$C_6$)-heteroaryl, where the heteroaryl ring may be a monocyclic or fused bicyclic ring which may comprise 1, 2, 3 or 4 nitrogen atoms, 1 oxygen atom, 1 sulfur atom, 1 or 2 nitrogen atoms and 1 oxygen or sulfur atom, and
where the heteroaryl ring may carry further substituents from the group of —F, —Cl, —Br, =O, —NH$_2$, —CN, ($C_1$-$C_4$)-alkyl, ($C_3$-$C_{10}$-cycloalkyl, OH, NH($C_1$-$C_4$)-alkyl, N(($C_1$-$C_4$)-alkyl)$_2$, ($C_1$-$C_{10}$-alkoxy, —C(O)O—($C_1$-$C_4$)-alkyl,
H, OH, (=O), F, Cl, Br, CN, NO$_2$, —NR17R18, —NR16COR17, —NR16COOR17, —NR16CONR17R18, —NR16-S(O)$_2$—R17, —NR16-S(O)$_2$—NR17R18, —COOR16, —COR16; —CO(NR17R18), S(O)$_n$R16, with n=1 or 2, —S(O)$_2$NR17R18, where
R16, R17 and R18 may be independently of one another a hydrogen radical or a radical selected from the group of unsubstituted or substituted ($C_1$-$C_4$)-alkyl radicals,
where the substituents of the alkyl radicals are selected from F, OH, (=O), NH$_2$, NH($C_1$-$C_4$) alkyl, N(($C_1$-$C_4$)alkyl)$_2$, CN or ($C_1$-$C_{10}$)-alkoxy,
R17 and R18 may form together with the nitrogen to which they are bonded a 5-6 membered, saturated, unsaturated or partly unsaturated heterocycle having 1 to 5 carbon atoms, which may additionally comprise one or more heteroatoms from the list —O—, —S(O)$_n$— with n=0, 1 or 2, =N—, —NH— and N(($C_1$-$C_4$)alkyl)-, where the formed heterocycle independently of one another one or more times by ($C_1$-$C_{10}$)-alkyl, ($C_3$-$C_{14}$)-cycloalkyl, ($C_4$-$C_{20}$)-cycloalkylalkyl, ($C_2$-$C_{20}$)-cycloheteroalkyl, ($C_3$-$C_{19}$)-cycloheteroalkylalkyl, each of which may in turn carry independently of one another one or more radicals F, OH, (=O), NH$_2$, NH($C_1$-$C_4$)alkyl, N(($C_1$-$C_4$)alkyl)$_2$, CN or ($C_1$-$C_{10}$)-alkoxy,
R1 is absent or is one, two or three radicals which are selected independently of one another from the group of F, Cl, Br, I, ($C_1$-$C_6$)-alkyl, ($C_1$-$C_6$)-alkoxy, where the alkyl and alkoxy radical may be substituted one or more times by F, and/or
R3 and R4 are independently of one another a radical selected from the group of H, ($C_1$-$C_4$)-alkyl, ($C_3$-$C_7$)-cycloalkyl-, ($C_3$-$C_7$)-cycloalkyl-($C_1$-$C_4$)-alkyl-, ($C_3$-$C_6$)-cycloheteroalkyl-, phenyl-, phenyl-($C_1$-$C_4$)-alkyl-, ($C_1$-$C_5$)-heteroaryl, where
the radicals R3 and R4 may be substituted independently of one another one, two or three times by a radical from the group of OH, (=O), F, Cl, Br, CN, NO$_2$, —NR13R14, —NR13COR12, —NR13COOR12, —NR12CONR13R14, —NR13-S(O)$_2$—R12, —NR13-S(O)$_2$—NR13R14, —COOR12, —COR12; —CO(NR13R14), —S(O)$_n$R12, —S(O)$_2$NR13R14,
where R12, R13 and R14 are H or ($C_1$-$C_4$)-alkyl, or
R3 and R4 form together with the nitrogen to which they are bonded a 4-8 membered, saturated, unsaturated or partly unsaturated heterocycle which may additionally comprise one or more heteroatoms from the list —O—, —S(O)$_n$—, with n=0, 1 or 2, =N— and —NR8-, where the heterocyclic radicals may be substituted independently of one another one or more times by a radical selected from the group of radicals R7 and R9,
where the heterocyclic radicals may be bridged by a bond, ($C_1$-$C_7$)-alkyl, ($C_1$-$C_6$)-saturated or unsaturated heteroalkyl chains or by —NH—, —N($C_1$-$C_4$)-alkyl-, and where the alkyl and heteroalkyl chains may also form a spirocyclic ring system with the ring system formed by R3 and R4,
and where R8 in the group NR8 may form with the ring which the radicals R3 and R4 may form a further saturated, unsaturated or partly unsaturated heterocycle which may additionally comprise one or two heteroatoms from the list —O—, —S(O)$_n$—, with n=0, 1 or 2, =N— and —NR19-, with R19 equal to H or ($C_1$-$C_4$)-alkyl,
where the radicals R7, R8 and R9 have the abovementioned meaning.

Preferred aminoindanes have a structure according to the formula Id and the pharmaceutically acceptable salts thereof, where
B is a phenyl group, a naphthyl group, a pyridinyl group, a quinolinyl group, an isoquinolinyl group, an indolyl group, a benzothiophenyl group, a benzodihydrothiophenyl group, a benzofuranyl group, a benzodihydrofuranyl group, an isobenzodihydrofuranyl group, a benzopyrrolidinyl group, a benzoimidazolyl group, a benzopyrazolyl group, a benzotriazolyl group, a benzothiazolyl group, a benzoxathiolyl group, an indolinyl group, benzodioxolyl group, a tetrahydroisoquinolinyl group, a tetrahydroquinolinyl group, where one, two, three or four hydrogen atoms in group B may be replaced by radicals from the group R5, where
one of the R5 radicals is selected from the group of
($C_2$-$C_5$)-cycloheteroalkyl,
where the cycloheteroalkyl ring may be saturated or partly unsaturated and may comprise 1 or 2 nitrogen atoms, 1 oxygen atoms, 1 nitrogen and 1 sulfur atom or 1 nitrogen and 1 oxygen atom, and
where the cycloheteroalkyl ring may carry further substituents from the group of —F, —Cl, —Br, =O, —NH$_2$—, —CN, ($C_1$-$C_4$)-alkyl, ($C_3$-$C_{10}$)-cycloalkyl,
($C_1$-$C_6$)-heteroaryl, where the heteroaryl ring may be a monocyclic or fused bicyclic ring which may comprise 1, 2, 3 or 4 nitrogen atoms, 1 oxygen atom, 1 sulfur atom, 1 or 2 nitrogen atoms and 1 oxygen or sulfur atom, and
where the heteroaryl ring may carry further substituents from the group of —F, —Cl, —Br, =O, —NH$_2$, —CN, ($C_1$-$C_4$)-alkyl, ($C_3$-$C_{10}$)—cycloalkyl, —C(O)O—($C_1$-$C_4$)-alkyl,
OH, (=O), NH$_2$, NO$_2$, —NR17R18, —NR16COR17, —NR16COOR17, —NR16CONR17R18, —NR16-S(O)$_2$—R17, —NR16-S(O)$_2$—NR17R18, —COOR16, —COR16; —CO(NR17R18), S(O)$_2$R16, —S(O)$_2$NR17R18, where
R16, R17 and R18 may be independently of one another a hydrogen radical or a radical selected from the group of unsubstituted or substituted ($C_1$-$C_4$)-alkyl radicals,
where the substituents of the alkyl radicals are selected from F, OH, (=O), NH$_2$, NH($C_1$-$C_4$) alkyl, N(($C_1$-$C_4$)alkyl)$_2$, CN or ($C_1$-$C_{10}$)-alkoxy
R17 and R18 may form together with the nitrogen to which they are bonded a 5-6 membered, saturated, unsaturated or partly unsaturated heterocycle having 1 to 5 carbon atoms which may additionally comprise one or more heteroatoms from the list —O—, —S(O)$_n$—, with n=0, 1 or 2, =N—, —NH— and —N(($C_1$-$C_4$)-alkyl)-, where the formed heterocycle independently of one another may be substituted one or more times by ($C_1$-$C_{10}$)-alkyl, ($C_3$-$C_{14}$)-cycloalkyl, ($C_4$-$C_{20}$)-cycloalkylalkyl, $(C_2-C_{20})$-cycloheteroalkyl, $(C_3-C_{19})$-cycloheteroalkylalkyl, each of which in turn may carry independently of one another one or more radicals F, OH, (=O), $NH_2$, $NH(C_1-C_4)$alkyl, $N((C_1-C_4)$alkyl$)_2$, CN or $(C_1-C_{10})$-alkoxy, and further radicals R5 is selected independently of one another from the group of
- $(C_1-C_4)$-alkyl which may be wholly or partly fluorinated, or a hydrogen may be replaced by a CN, $NH_2$, OH, $NH(C_1-C_4)$alkyl, $N((C_1-C_4)$alkyl$)_2$, $(C_1-C_4)$-alkoxy,
- $(C_1-C_4)$-alkoxy which may be wholly or partly fluorinated,
- $(C_1-C_4)$-alkylthio which may be wholly or partly fluorinated,
- phenyl,
- OH, (=O), F, Cl, Br, CN, —NR17R18, NR16COR17, —COOR16, —COR16; —CO(NR17R18), where
  - R16, R17 and R18 may be independently of one another a hydrogen radical or a radical selected from the group of unsubstituted or substituted $(C_1-C_4)$-alkyl radicals,
    where the substituents of the alkyl radicals are selected from F, OH, (=O), $NH_2$, $NH(C_1-C_4)$alkyl, $N((C_1-C_4)$alkyl$)_2$, CN or $(C_1-C_{10})$-alkoxy-F,
  - R17 and R18 may form together with the nitrogen to which they are bonded a 4-7 membered, saturated, unsaturated or partly unsaturated heterocycle having 1 to 5 carbon atoms, which may additionally comprise one or more heteroatoms from the list —O—, —S(O)$_n$—, with n=0, 1 or 2, =N—, —NH— and N($(C_1-C_4)$alkyl)-, where the formed heterocycle independently of one another may be substituted one or more times by $(C_1-C_{10})$-alkyl, $(C_3-C_{14})$-cycloalkyl, $(C_4-C_{20})$-cycloalkylalkyl, $(C_2-C_{20})$-cycloheteroalkyl, $(C_3-C_{19})$-cycloheteroalkylalkyl, each of which in turn may carry independently of one another one or more radicals F, OH, (=O), $NH_2$, $NH(C_1-C_4)$alkyl, $N((C_1-C_4)$alkyl$)_2$, CN or $(C_1-C_{10})$-alkoxy, and/or R1 is absent or is one, two or three radicals which are selected independently of one another from the group of F, Cl, Br, I, $(C_1-C_6)$-alkyl, $(C_1-C_6)$-alkoxy, where the alkyl and alkoxy radical may be substituted one or more times by F, and/or R3 and R4 is independently of one another a radical selected from the group of H, $(C_1-C_5)$-alkyl-, phenyl-$(C_1-C_4)$-alkyl-, $NH_2$—$(C_1-C_4)$-alkyl-, $N((C_1-C_4)$-alkyl$)_2$-$(C_1-C_4)$-alkyl-, $(C_1-C_4)$-alkoxy-$(C_1-C_4)$-alkyl-, $(C_3-C_7)$-cycloalkyl-$(C_1-C_4)$-alkyl- and $(C_4-C_5)$-cycloheteroalkyl- that comprises an —NH—, —O— or —S— group, or R3 and R4 form together with the nitrogen to which they are bonded a 4-8 membered, saturated, unsaturated or partly unsaturated heterocycle which may additionally comprise one or more heteroatoms from the list —O—, —S(O)$_n$—, with n=0, 1 or 2, =N— and —NR8-, where
the heterocyclic radicals may be substituted independently of one another one or more times by radicals selected from the group of radicals R7 and R9,
where the heterocyclic radicals may be bridged by a bond, $(C_1-C_7)$-alkyl, $(C_1-C_6)$-saturated or unsaturated heteroalkyl chains or by —NH—, N($(C_1-C_4)$alkyl)-, and where the alkyl and heteroalkyl chains may also form a spirocyclic ring system with the ring system formed by R3 and R4,
and where R8 may form with the ring which the radicals R3 and R4 form a further saturated, unsaturated or partly unsaturated heterocycle which may additionally comprise one or two heteroatoms from the list —O—, —S(O)$_n$—, with n=0, 1 or 2, —NH— and —N($(C_1-C_4)$alkyl)-, and/or R7 are H, a $(C_1-C_5)$-alkyl radical or $(C_3-C_6)$-cycloalkyl radical, where the alkyl radical may be substituted independently of one another one or more times by R9, and/or R8 is an H, a $(C_1-C_5)$-alkyl radical or $(C_1-C_6)$-cycloalkyl radical, where the alkyl radical may be substituted independently of one another one or more times by F, OH, $NH_2$, CN, $NO_2$, $(C_1-C_{10})$-alkoxy, $(C_1-C_{10})$-alkylthio, —NR13R14, —NR13COR12, —NR13COOR12, —NR13CONR13R14, —NR13-S(O)$_2$—R12, —NR12-S(O)$_2$—NR13R14, —COOR12, —COR12; —CO(NR13R14), S(O)$_n$R12, —S(O)$_2$NR13R14, COR12, —CO(NR13R14), S(O)$_n$R12, —S(O)$_2$NR13R14 and/or R9 is a radical selected from the group of OH, $NH_2$, (=O), F, Cl, Br, I, CN, —NR13R14, —NR13COR12, —NR13COOR12, —NR12CONR13R14, —NR13-S(O)$_2$—R12, —NR13-S(O)$_2$—NR13R14, —COOR12, —COR12; —CO(NR13R14), S(O)$_n$R12, —S(O)$_2$NR13R14, $(C_3-C_6)$-cycloalkyl, $(C_4-C_7)$-cycloalkylalkyl, $(C_1-C_5)$-alkoxy, $(C_2-C_6)$-cycloheteroalkyl, $(C_3-C_{10})$— cycloheteroalkylalkyl, phenyl, of the $(C_1-C_5)$-heteroaryl radicals,
where R12, R13 and R14 are independently of one another a hydrogen radical or a radical selected from the group of unsubstituted or substituted $(C_1-C_4)$-alkyl radicals, where the substituents of the alkyl radicals are selected from F, OH, (=O), $NH_2$, $NH(C_1-C_4)$alkyl, $N((C_1-C_4)$alkyl$)_2$, CN or $(C_1-C_{10})$-alkoxy, In one embodiment compounds of the formulae I, Ia, Ib, Ic and Id are preferred, where R3 and R4 form together with the nitrogen to which they are bonded a 4-10 membered, saturated, unsaturated or partly unsaturated heterocycle which may additionally comprise one or more heteroatoms from the list —O—, —S(O)$_n$—, =N— and —NR8-, where
the heterocyclic radicals may be substituted independently of one another one or more times by radicals selected from the group of R7 and R9, and where
the heterocyclic radicals formed by R3 and R4 may be bridged by a bond, by a saturated or unsaturated $(C_1-C_{10})$-alkyl or $(C_1-C_9)$-heteroalkyl chain or by —NR15-, —O— or —S—, and where
the alkyl and heteroalkyl chains may also form a spirocyclic ring system with the ring system formed by R3 and R4, where the alkyl and heteroalkyl bridges may be substituted independently of one another one or more times by radicals selected from the group of R7 and R9,
and where
R8 in the group —NR8- may form with the ring which R3 and R4 may form a further saturated, unsaturated or partly unsaturated heterocycle which may be substituted independently of one another one or more times by radicals selected from the group of R7 and R9, and may additionally comprise one or more heteroatoms from the list —O—, —S(O)$_n$—, —N= and —NR19-;

and where n, R7, R8, R9 and R19 have the meaning indicated above.

In one embodiment compounds of the formulae I, Ia, Ib, Ic and Id are more preferred, where R3 and R4 form together with the nitrogen to which they are bonded a 4-8 membered, saturated, unsaturated or partly unsaturated heterocycle which may additionally comprise one or more heteroatoms from the list —O—, —S(O)$_n$—, with n=0, 1 or 2, =N— and —NR8-, where the heterocyclic radicals may be substituted independently of one another one or more times by radicals selected from the group of radicals R7 and R9, where the heterocyclic radicals may be bridged by a bond, ($C_1$-$C_7$)-alkyl, ($C_1$-$C_6$)-saturated or unsaturated heteroalkyl chains or by —NH—, N(($C_1$-$C_4$)alkyl)-, and where the alkyl and heteroalkyl chains may also form a spirocyclic ring system with the ring system formed by R3 and R4, and where R8 may form with the ring which the radicals R3 and R4 form a further saturated, unsaturated or partly unsaturated heterocycle which may additionally comprise one or two heteroatoms from the list —O—, —S(O)$_n$—, with n=0, 1 or 2, —NH— and —N(($C_1$-$C_4$)alkyl)-;

and where R7, R8 and R9 have the meaning indicated above.

In another embodiment compounds of the formulae I, Ia, Ib, Ic and Id are particularly preferred, where R3 and R4 form together with the nitrogen to which they are bonded a 4-8 membered, saturated, unsaturated or partly unsaturated heterocycle which may additionally comprise one or more heteroatoms from the list —O—, —S(O)$_n$—, with n=0, 1 or 2, =N— and —NR8-, where the heterocyclic radicals may be substituted independently of one another one or more times by radicals selected from the group of radicals R7 and R9, and where R8 may form with the ring which the radicals R3 and R4 form may form together with an adjacent C atom a fused triazole or pyrrolidine ring;

and where R7, R8 and R9 have the meaning indicated above.

In another embodiment compounds of the formulae I, Ia, Ib, Ic and Id are preferred, where R3 and R4 are independently of one another a hydrogen radical or a radical which is selected from the group of ($C_1$-$C_{10}$)-alkyl radicals, of ($C_2$-$C_{10}$)-alkenyl radicals, of ($C_2$-$C_{10}$)-alkynyl radicals, of ($C_3$-$C_{14}$)-cycloalkyl radicals, of ($C_4$-$C_{20}$)-cycloalkylalkyl radicals, of ($C_2$-$C_{19}$)-cycloheteroalkyl radicals, of ($C_3$-$C_{19}$)-cycloheteroalkylalkyl radicals, of ($C_6$-$C_{10}$)-aryl radicals, of ($C_7$-$C_{20}$)-arylalkyl radicals, of ($C_1$-$C_9$)-heteroaryl radicals, of ($C_2$-$C_{19}$)-heteroarylalkyl radicals, where the radicals R3 and R4 may be substituted independently of one another one or more times by a radical from the group of OH, NH$_2$, (=O), F, Cl, Br, I, CN, NO$_2$, —NR13R14, —NR13COR12, —NR13COOR12, —NR12CONR13R14, —NR13-S(O)$_2$—R12, —NR13-S(O)$_2$—NR13R14, —COOR12, —COR12; —CO(NR13R14), S(O)$_n$R12, —S(O)$_2$R13R14;

and where R12, R13 and R14 have the meaning indicated above.

In another embodiment compounds of the formulae I, Ia, Ib, Ic and Id are particularly preferred, where R3 and R4 are independently of one another a radical selected from the group of H, ($C_1$-$C_5$)-alkyl-, phenyl-($C_1$-$C_4$)-alkyl-, NH$_2$—($C_1$-$C_4$)-alkyl-, N(($C_1$-$C_4$)-alkyl)$_2$-($C_1$-$C_4$)-alkyl-, ($C_1$-$C_4$)-alkoxy-($C_1$-$C_4$)-alkyl-, ($C_3$-$C_7$)-cycloalkyl-($C_1$-$C_4$)-alkyl- and ($C_4$-$C_6$)-cycloheteroalkyl- that comprises an —NH—, —O— or —S— group.

The membership of rings means in the context of the present invention the number of ring atoms which form the respective ring system or fused ring system.

6 to 10 membered aryl radicals which may stand for the cyclic radicals A and B mean in particular phenyl and naphthyl.

Preferred 5 to 10 membered heteroaryl radical which may stand for a cyclic radical A are selected from the group of furanyl, thiophenyl, pyrrolyl, imidazolyl, pyrazolyl, triazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl. A particularly preferred heteroaryl radical A is thiophenyl.

In one embodiment of the invention, A is phenyl or a 5- or 6-membered heteroaryl radical, in another embodiment A is phenyl or thiophenyl, in another embodiment A is phenyl, in another embodiment A is thiophenyl, all of which may be substituted as indicated.

Preferred 5 to 10 membered heteroaryl radical which may stand for a cyclic radical B are selected from the group of furanyl, thiophenyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, isoindolyl, quinolyl, isoquinolyl, phthalazinyl, quinoxalinyl, quinazolinyl, cinnolinyl, benzothiophenyl, isobenzothiophenyl, benzofuranyl, isobenzofuranyl, benzoimidazolyl, benzopyrazolyl, benzotriazolyl, benzoxazolyl, isobenzoxazolyl, benzothiazolyl, isobenzothiazolyl.

Preferred 3 to 10 membered cycloalkyl radicals which may stand for a cyclic radical B are selected from the group of cyclopropanyl, cyclobutanyl, cylopentanyl, cyclohexanyl, cycloheptanyl, cyclooctanyl, cyclopropenyl, cyclobutenyl, cyclopentenyl, cyclohexenyl, cycloheptenyl, cyclooctenyl and norbornene.

Preferred 9 to 14 membered cycloalkylaryl radicals which may stand for a cyclic radical B are selected from the group of fused ring systems having a cycloalkyl ring and an aryl ring. Particularly preferred cycloalkylaryl radicals are indenyl, dihydronaphthyl, tetrahydronaphthyl and indanyl.

Preferred 8 to 14 membered cycloalkylheteroaryl radicals which may stand for a cyclic radical B are selected from the group of fused ring systems having a cycloalkyl ring and a heteroaryl ring.

Preferred 3 to 10 membered cycloheteroalkyl radicals which may stand for a cyclic radical B are selected from the group of oxiranyl, thiiranyl, aziridinyl, oxetanyl, thietanyl, azetidinyl, pyrrolidinyl, dihydropyrrolyl, dihydroimidazolyl, dihydropyrazolyl, tetrahydropyrazolyl, oxolanyl, dihydrofuranyl, dioxolanyl, thiolanyl, dihydrothiophenyl, oxazolanyl, dihydrooxazolyl, isooxazolanyl, dihydroisooxazolyl, thiazolidinyl, dihydrothiazolyl, isothiazolidinyl, dihydroisothiazolyl, oxathiolanyl, 2H-pyranyl, 4H-pyranyl, tetrahydropyranyl, 2H-thiapyranyl, 4H-thiapyranyl, di-, tetrahydrothiapyranyl, piperidinyl, di-, tetrahydropyridyl, piperazinyl, tetrahydropyrazinyl, di-, tetra-, hexahydropyridazinyl, di-, tetra-, hexahydropyrimidinyl, morpholinyl, thiomorpholinyl, dioxanyl, dithianyl, azepanyl, thiepanyl and oxepinyl, where two of these heterocyclic rings may also form a saturated or partly unsaturated fused bicyclic ring system.

Examples of such bicyclic ring systems are octahydropyrrolo[1,2-a]pyrazinyl, octahydropyrrolo[3,4-b]pyrrolyl, hexahydropyrrolo[3,4-c]pyrrolyl and octahydropyrrolo[3,4-c]pyrrolyl.

Preferred 9 to 14 membered cycloheteroalkylaryl radicals which may stand for a cyclic radical B are selected from the group of fused ring systems having a cycloheteroalkyl ring and an aryl ring. Particularly preferred cycloheteroalkylaryl radicals are benzodihydrothiophenyl, benzodihydrofuranyl, benzodioxolanyl, benzodihydroimidazolyl, benzodihydroyrazolyl, benzodihydrotriazolyl, benzopiperazinyl, benzodihydrothiazolyl, benzomorpholinyl, benzodihydropyrrolyl, benzodihydrooxazolyl, dihydroquinolinyl, dihydroisoquinolinyl, tetrahydroisoquinolinyl, tetrahydroquinolinyl, benzoxathiolyl, isobenzoxathiolyl and benzodioxolyl Preferred 8 to 14 membered cycloheteroalkylheteroaryl radicals which may stand for a cyclic radical B are selected from the group of fused ring systems having a cycloheteroalkyl ring and a heteroaryl ring.

Particularly preferred mono- or bicyclic radicals which may stand for the group B are selected from the group of phenyl, naphthyl, pyridyl, quinolinyl, isoquinolinyl, indolyl, benzodihydropyrrolyl, benzdihydroisopyrrolyl, benzothiophenyl, benzodihydrothiophenyl, benzofuranyl, benzoisofuranyl, benzodihydrofuranyl, benzoimidazolyl, benzopyrazolyl, benzotriazolyl, thiazolyl, benzothiazolyl, benzoxathiolanyl, benzodioxolanyl, tetrahydroisoquinolinyl or tetrahydroquinolinyl. In this connection, the radicals B can be bonded to the group -LX— as pyrid-2, 3 or 4-yl, quinol-1, 2, 3, 4, 5, 6, 7 or 8-yl, isoquinol-1, 2, 3, 4, 5, 6, 7 or 8-yl, indol-1, 2, 3, 4, 5, 6 or 7-yl, isoindol-1, 2, 3, 4, 5, 6, or 7-yl, benzo[b]thiophen-2, 3, 4, 5, 6 or 7-yl, benzo[c]thiophen-1, 3, 4, 5, 6 or 7-yl, benzo[b]dihydrothiophen-2, 3, 4, 5, 6 or 7-yl, benzo[c]dihydrothiophen-1, 3, 4, 5, 6 or 7-yl, benzo[b]furan-2, 3, 4, 5, 6, or 7-yl, benzo[c]furan-1, 3, 4, 5, 6, or 7-yl, benzo[b]dihydrofuran-2, 3, 4, 5, 6, or 7-yl, benzo[c]dihydrofuran-1, 3, 4, 5, 6, or 7-yl, benzo[b]pyrrolidin-1, 2, 3, 4, 5, 6 or 7-yl, benzo[c]pyrrolidin-1, 2, 3, 4, 5, 6 or 7-yl, benzoimidazol-1, 2, 3, 4, 5, 6 or 7-yl, benzopyrazol-1, 2, 3, 4, 5, 6 or 7-yl, benzotriazol-1, 2, 4, 5, 6 or 7-yl, thiazo-2, 4 or 5-yl, benzothiazol-2, 3, 4, 5, 6 or 7-yl, benzoxathiolan-2, 4, 5, 6 or 7-yl, benzodioxolan-2, 4, 5, 6 or 7-yl, tetrahydroisoquinol-1, 2, 3, 4, 5, 6, 7 or 8-yl or tetrahydroquinol-1, 2, 3, 4, 5, 6, 7 or 8-yl.

One, two, three or four hydrogen atoms in group B can preferably be replaced by radicals which are selected independently of one another from the group of R5. In one embodiment of the invention, one, two or three hydrogen atoms, and in another embodiment one or two hydrogen atoms, can be replaced by radicals which are selected independently of one another from the group R5.

Particularly preferred for B are the following groups:

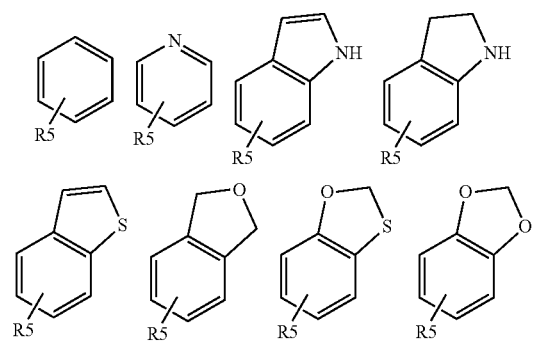

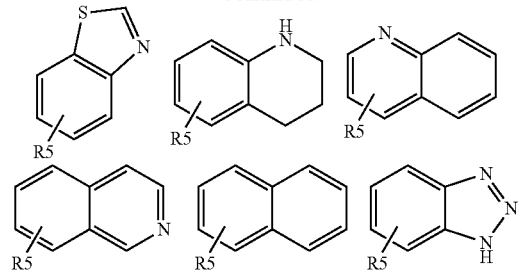

where the substituents R5 in the bicyclic ring systems B may be located on both rings.

In one embodiment of the invention, B is selected from the group of phenyl, naphthyl, pyridyl, quinolinyl or isoquinolinyl, in another embodiment from the group of phenyl and pyridyl, and in another embodiment B is phenyl, in another embodiment pyridyl, all of which may be substituted as indicated.

L is preferably a covalent single bond, a —C(O)— bridge or a methylene bridge.

In one embodiment of the invention, L is a covalent single bond, in another embodiment is a —C(O)— bridge, in another embodiment is a methylene bridge.

X is preferably a group —N(R6)-, —O— or —S(O)$_n$—.

In one embodiment of the invention, X is a group —N(R6)-, in another embodiment is —O—, in another embodiment is —S(O)n-.

In one embodiment of the invention, one, two or three H atoms, in another embodiment one or two H atoms, in the aryl or heteroaryl radicals standing for A may be replaced by substituents R1.

Preferred R1 radicals are selected from the group of F, Cl, Br, I, $(C_1-C_6)$-alkyl, $(C_1-C_6)$-alkoxy, where the alkyl and alkoxy radicals may be substituted one or more times by F. Particularly preferred R1 radicals are selected from the group of F, Cl, methyl, ethyl, propyl, butyl, methoxy, ethoxy, trifluoromethyl, pentafluoroethyl, trifluoroethyl, especially —CH$_2$—CF$_3$, difluoroethyl, especially —CH$_2$—CHF$_2$, monofluoroethyl, especially —CH$_2$—CH$_2$F, methoxy, ethoxy, trifluoromethoxy, pentafluoroethoxy, trifluoroethoxy, especially —O—CF$_2$—CF$_3$, difluoroethoxy, especially —O—CH$_2$—CHF$_2$, monofluoroethoxy, especially —O—CH$_2$—CH$_2$F.

Preferred R2 radicals are selected from the group of F, $(C_1-C_6)$-alkyl, where the alkyl radicals may be substituted independently of one another one or more times by F, and particularly preferred radicals are F, methyl, ethyl, propyl, butyl, trifluoromethyl, trifluoroethyl, e.g. —CF$_2$—CF$_3$, —CH$_2$—CHF$_2$, —CH$_2$—CH$_2$F.

Preferred R3 and R4 radicals are selected independently of one another from the group of
hydrogen, $(C_1-C_4)$-alkyl, such as, for example, methyl, ethyl, n-propyl, isopropyl, n-butyl, tertiary butyl,
  where the alkyl radical may be substituted by one or two radicals from the group of —N$(C_1-C_4$-alkyl)$_2$ and —O—$(C_1-C_4$-alkyl), especially by —N(CH$_3$)$_2$, —N(C$_2$CH$_5$)$_2$, resulting for example in —CH$_2$—N(CH$_3$)$_2$, —CH$_2$—CH$_2$—N(CH$_3$)$_2$, —CH$_2$—CH$_2$—CH$_2$—N(CH$_3$)$_2$, —CH$_2$—OCH$_3$, or —CH$_2$—CH$_2$—OCH$_3$ radicals,
$(C_3-C_7)$-cycloalkyl, such as, for example, cyclopropanyl, cyclobutanyl, cyclopentanyl, cyclohexanyl or cycloheptanyl, (C₃-C₇)-cycloalkyl-(C₁-C₄)-alkyl, such as, for example, cyclopropanylmethyl, cyclopropanylethyl, cyclobutanylmethyl, cyclobutanylethyl, cyclopentanylmethyl, cyclopentanylethyl, cyclohexanylmethyl or cylohexanylethyl, (C₃-C₆)-cycloheteroalkyl, such as, for example, piperidinyl, piperazinyl, hexahydropyrimidinyl, hexahydropyridazolyl, morpholinyl, thiomorpholinyl, pyrrolidinyl, tetrahydrofuranyl or tetrahydrothiophenyl, phenyl, phenyl-(C₁-C₄)-alkyl, such as, for example, phenylmethyl, phenylethyl, phenylpropyl or phenylbutyl, (C₁-C₅)-heteroaryl, such as, for example, furanyl, thiophenyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl or pyridazinyl.

The R3 and R4 radicals preferably form together with the nitrogen atom to which they are bonded the following groups:

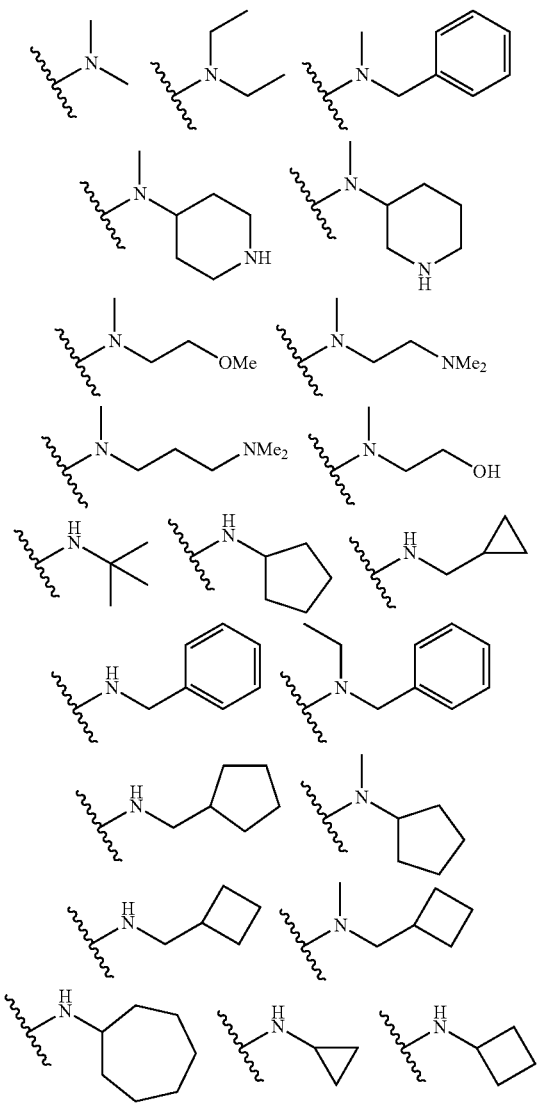

The R3 and R4 radicals particularly preferably form a 4-8 membered, saturated, unsaturated or partly unsaturated heterocycle. The 4-8 membered, saturated, unsaturated or partly unsaturated heterocycle may additionally comprise one or more heteroatomic groups selected from the list —O—, —S(O)ₙ—, with n=0, 1 or 2, =N— and —NR8-. —NR8- may form together with an adjacent C atom a fused triazole or pyrrolidine ring, e.g. octahydropyrrolo[1,2-a]pyrazinyl and tetrahydro-[1,2,4]triazolo[4,3-a]pyrazinyl.

Preferred heterocycles formed by R3 and R4 are selected from the group of azetidinyl, pyrrolidinyl, piperidinyl, piperazinyl, morpholinyl, thiomorpholinyl, oxothiomorpholinyl, dioxothiomorpholinyl, azepanyl, 1,4-diazepanyl, pyrrolyl, pyrazolyl and imidazolyl. The heterocyclic rings may be bridged by a covalent bond, a (C₁-C₇)-alkylene bridge or a (C₁-C₆)-heteroalkylene bridge or an —NH— bridge or an —N(C₁-C₄)-alkylene bridge, thus forming a fused or bridged bicyclic ring system. The (C₁-C₇)-alkylene bridge or the (C₁-C₆)-heteroalkylene bridge may also form a spirocyclic ring system with the ring system formed by R3 and R4. Examples of such fused, bridged or spirocyclic ring systems formed by R3 and R4 are diazabicyclo[3.2.1]octanyl, especially a 3,8-diazabicyclo[3.2.1]octanyl, a diazabicyclo[2.2.1]heptanyl, especially a 2,5-diazabicyclo[2.2.1]heptanyl, octahydropyrrolo[3,4-b]pyrrolyl, hexahydropyrrolo[3,4-c]pyrrolyl, octahydropyrrolo[3,4-c]pyrrolyl and diazaspirononanyl, especially 2,7-diazaspiro[4.4]nonanyl.

In one embodiment of the invention, R3 and R4 form together with the nitrogen atom to which they are bonded a heterocyclic radical selected from the group of azetidinyl, pyrrolidinyl, piperidinyl, piperazinyl, morpholinyl, thiomorpholinyl, azepanyl and 1,4-diazepanyl, in another embodiment a heterocyclic radical selected from the group of azetidinyl, pyrrolidinyl, piperidinyl and morpholinyl, in another embodiment a heterocyclic radical selected from the group of azetidinyl, pyrrolidinyl, piperidinyl, in another embodiment an azetidinyl radical, in another embodiment a pyrrolidinyl radical, in another embodiment a piperidinyl radical, in another embodiment a morpholinyl radical, all of which may be substituted as indicated.

The heterocyclic groups formed by R3 and R4 may carry further substituents independently of one another selected from the group of R7 and R9. Preferred substituents of this group are F, Cl, Br, I, (C₁-C₄)-alkyl, where the alkyl radicals may be substituted one or more times by F, such as, for example, methyl, ethyl, n-propyl, isopropyl, n-butyl, tert-butyl, —CF₃, —CH₂—CF₃, —CH₂—CH₂—CF₃, —CH₂—CH₂—CH₂—CF₃, —CH₂F, —CH₂—CH₂F, —CH₂—CH₂—CH₂—CH₂F, (C₃-C₇)-cycloalkyl, such as, for example, cyclopropyl, cyclopentyl, —OH, hydroxy-(C₁-C₄)-alkyl, such as, for example, —CH₂—OH, —CH₂—CH₂—OH, —CH₂—CH₂—CH₂—OH, (C₁-C₄)-alkyl-O—, such as, for example, —OCH₃, (C₁-C₄)-alkoxy-(C₁-C₄)-alkyl, such as, for example, —CH₂—OCH₃, —CH₂—CH₂—OCH₃, —CH₂—CH₂—CH₂—OCH₃, —SO₂—(C₁-C₄)-alkyl, such as, for example, —SO₂—CH₃, —NH₂, N((C₁-C₄)-alkyl)₂-, such as, for example: —N(CH₃)₂, —N(C₂H₅)₂, NH₂(C₁-C₄)-alkyl-, N((C₁-C₄)-alkyl)₂-(C₁-C₄)-alkyl, such as, for example, —CH₂—NH₂, —CH₂—CH₂—NH₂, —CH₂—CH₂—CH₂—NH₂, —CN, NC—(C₁-C₄)-alkyl-, such as, for example, —CH₂—CN, —CH₂—CH₂—CN, —CH₂—CH₂—CH₂—CN —NH—(C₁-C₄)-alkyl, where the alkyl group may be substituted one or more times by F, such as, for example, —NH—CH₂—F, —NH—CH₂—CH₂—F, —NH—CH₂—CF₃, —NH—CH₂—CH₂—CF₃, —NH—(C₁-C₄)-alkyl-OH, —NH—(C₁-C₄)-alkyl-O—(C₁-C₄)-alkyl, such as, for example, —NH—CH₂—OH, —NH—CH₂—CH₂—OH, —NH—(C₁-C₄)-alkyl-CN, such as, for example, —NH—CH₂—CN, —NH—CH₂—CH₂—CN, —NH—(C₁-C₄)-alkyl-O—(C₁-C₄)-alkyl-OH, such as, for example, —NH—CH₂—CH₂—O—CH₂—CH₂—OH, —NH—C(O)—(C$_1$-C$_4$)-alkyl, where the alkyl group may be substituted one or more times by F, such as, for example, —NH—C(O)—CH$_3$, —NH—C(O)—CF$_3$, pyrrolidinyl, pyrrolidinyl-(C$_1$-C$_4$)-alkyl, such as, for example, N-pyrrolidinyl-CH$_2$—, pyrimidinyl, such as, for example, pyrimidin-2-yl.

In one embodiment of the invention, the heterocyclic groups formed by R3 and R4 together with the nitrogen atom to which they are bonded may carry substituents R7 and R9 which are selected independently of one another from the group of methyl, ethyl, CF$_3$, F, Cl, CN, NH$_2$, N(CH$_3$)$_2$, OH, OCH$_3$, SO$_2$CH$_3$, in another embodiment substituents R9 which are selected independently of one another from the group of F, Cl, CN, NH$_2$, N(CH$_3$)$_2$, OH, OCH$_3$, SO$_2$CH$_3$. In one embodiment of the invention, the heterocyclic groups formed by R3 and R4 together with the nitrogen atom to which they are bonded may carry one, two or three substituents R7 and R9, in another embodiment one or two substituents, in another embodiment one substituent.

The R3 and R4 radicals particularly preferably form together with the nitrogen to which they are bonded one of the following heterocyclic ring systems:

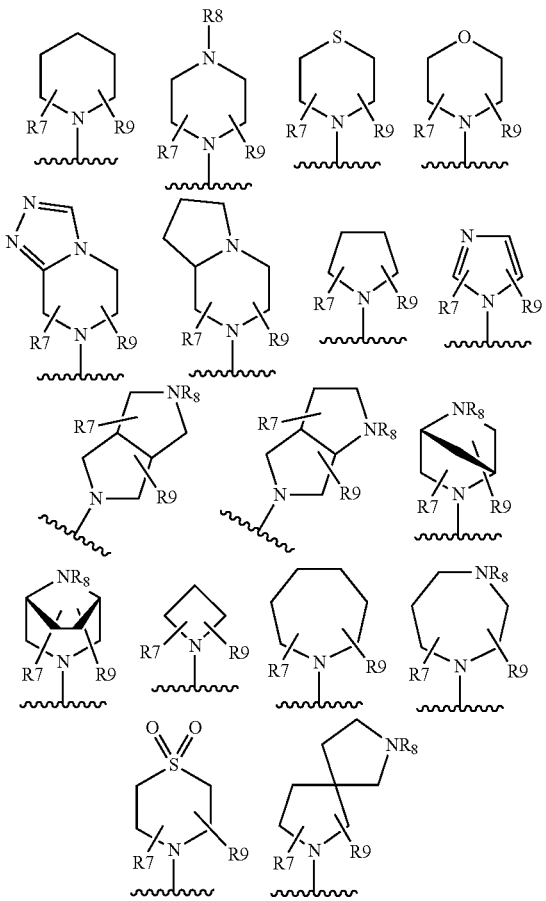

Preferred R5 radicals are selected independently of one another from the group of F, Cl, Br, I, =O, —CN, —OH, —NH$_2$, —NO$_2$, (C$_1$-C$_4$)-alkyl, such as, for example, methyl, ethyl, n-propyl, isopropyl, n-butyl, tert-butyl, where the alkyl radical may be substituted one or more times by F, such as, for example, in —CF$_3$, —CF$_2$H;

(C$_1$-C$_4$)-alkoxy, such as, for example, —OCH$_3$, —OC$_2$H$_5$, where the alkyl radical may be substituted one or more times by F, such as, for example, in —OCF$_3$, —OCHF$_2$, —OCH$_2$F, —S—(C$_1$-C$_4$)-alkyl, such as, for example, —SCH$_3$, where the alkyl radical may be substituted one or more times by F, such as, for example, in —SCF$_3$, (C$_1$-C$_4$)-alkoxy-(C$_1$-C$_4$)-alkyl, such as, for example, in —CH$_2$—OCH$_3$, —CH$_2$—CH$_2$—OCH$_3$ —NC—(C$_1$-C$_4$)-alkyl-, such as, for example, in —CH$_2$—CN, NH$_2$—(C$_1$-C$_4$)-alkyl-, such as, for example, in —CH$_2$—NH$_2$, N((C$_1$-C$_4$)-alkyl)$_2$-(C$_1$-C$_4$)-alkyl-, such as, for example, in —CH$_2$—N(CH$_3$)$_2$, (C$_1$-C$_4$)-alkyl-C(O)—NH—(C$_1$-C$_4$)-alkyl-, such as, for example, —CH$_2$—NH—C(O)CH$_3$, N((C$_1$-C$_4$)-alkyl)$_2$-C(O)—(C$_1$-C$_4$)-alkyl-, such as, for example, —CH$_2$—C(O)—N(CH$_3$)$_2$, —SO$_2$—(C$_1$-C$_4$)-alkyl, such as, for example, —SO$_2$CH$_3$, where the alkyl group may be substituted one or more times by F, such as, for example, in —SO$_2$CF$_3$, —SO$_2$NH$_2$, —SO$_2$N((C$_1$-C$_4$)-alkyl)$_2$, such as, for example, —SO$_2$N(CH$_3$)$_2$, —SO$_2$N(C$_2$H$_5$)$_2$, —SO$_2$—NH—(C$_1$-C$_4$)-alkyl, such as, for example, —SO$_2$—NH—CH$_3$, —SO$_2$—NH—CH$_2$—CH$_3$, —SO$_2$—NH—CH$_2$—CH$_2$—CH$_3$, where the alkyl radical may be substituted one or more times by F, such as, for example, in —SO$_2$—NH—CH$_2$—CF$_3$, —SO$_2$—NH—CH$_2$—CH$_2$—CF$_3$, —NH—C(O)—(C$_1$-C$_4$)-alkyl, such as, for example, —NH—C(O)—CH$_3$, —NH—C(O)—NH$_2$, —NH—C(O)—N((C$_1$-C$_4$)-alkyl)$_2$, such as, for example, —NH—C(O)—N(CH$_3$)$_2$, —NH—C(O)—O—(C$_1$-C$_4$)-alkylphenyl, such as, for example, —NH—C(O)—O—CH$_2$—C$_6$H$_6$, —NH—C(O)—O—(C$_1$-C$_4$)-alkyl-COOH, such as, for example, —NH—C(O)—O—CH$_2$—COOH, —NH—C(O)—O—(C$_1$-C$_4$)-alkyl-COO(C$_1$-C$_4$)-alkyl, such as, for example, —NH—C(O)—O—CH$_2$—COOCH$_3$, —NH—SO$_2$—(C$_1$-C$_4$)-alkyl, such as, for example, —NH—SO$_2$CH$_3$, —N((C$_1$-C$_4$)-alkyl)-SO$_2$—(C$_1$-C$_4$)-alkyl, such as, for example, —N(CH$_3$)—SO$_2$CH$_3$, —C(O)—(C$_1$-C$_4$)-alkyl), such as, for example, —C(O)—CH$_3$, —C(O)—CH$_2$—CH$_3$, —C(O)—NH$_2$, —C(O)—N((C$_1$-C$_4$)-alkyl)$_2$, such as, for example, —C(O)—N(CH$_3$)$_2$, —C(O)—N(C$_2$H$_5$)$_2$, —C(O)—O(C$_1$-C$_4$)-alkyl, such as, for example, —C(O)—OCH$_3$, —C(O)phenyl, —O-phenyl, —COOH, —COO(C$_1$-C$_4$)-alkyl, such as, for example, —COOCH$_3$, —COOC$_2$H$_5$, (C$_1$-C$_4$)-alkyl-(C$_3$-C$_7$)-cycloheteroalkyl-C(O)—, such as, for example, (C$_1$-C$_4$)-alkyl-piperazinyl- or -pyrimdinyl- or -piperidinyl- or -tetrahydropyridazinyl-C(O)—, in particular 4-methylpiperazin-1-yl-C(O)—, (C$_3$-C$_7$)-cycloheteroalkyl-(C$_1$-C$_4$)-alkyl-, such as, for example, piperidinyl- or piperazinyl- or pyrimidinyl- or tetrahydropyridazinyl-(C$_1$-C$_4$)-alkyl-, in particular piperidin-1-yl-methyl-.

The preferred aryl radical R5 is phenyl.

Further preferred R5 radicals are heteroaryl radicals, especially those selected from the group of pyrrol-1, 2, or 3-yl, pyrazol-1, 3, 4 or 5-yl, imidazol-1, 2, 4 or 5-yl, 1,2,3-triazol-1, 2, 4 or 5-yl, 1,2,4-triazol-1, 3 or 4-yl, tetrazol-1, 2 or 5-yl, 1,3,4-oxadiazol-3 or 4-yl, 1,2-isoxazoly-2, 3, 4 or 5-yl, oxazol-2, 3, 4 or 5-yl, thiazol-2, 3, 4 or 5-yl, isothiazol-2, 3, 4 or 5-yl, thiadiazol-2, 3, 4 or 5-yl pyrid-2, 3 or 4-yl, benzo[b]furan-2, 3, 4, 5, 6 or 7-yl, benzo[b]thiophen-2, 3, 4, 5, 6 or 7-yl, indol-1, 2, 3, 4, 5, 6 or 7-yl, isoindol-1, 2, 3, 4, 5, 6 or 7-yl, benzothiazol-2, 4, 5, 6 or 7-yl, benzoisothiazol-3, 4, 5, 6 or 7-yl, benzoxazol-2, 4, 5, 6 or 7-yl, benzoisoxazol-3, 4, 5, 6 or 7-yl, benzodiazol-1, 2, 4, 5, 6 or 7-yl and benzoisodiazol-1, 2, 3, 4, 5, 6 or 7-yl.

Preferred cycloheteroalkyl radicals R5 are selected from the group of piperidin-1, 2, 3 or 4-yl, piperazin-1, 2 or 3-yl, pyrimidin-1, 2, 4 or 5-yl, tetrahydropyridazin-1, 3 or 4-yl, 2H-pyridin-1, 2, 3, 4, 5 or 6-yl, 4H-pyridin-1, 2, 3 or 4-yl, morpholin-2, 3 or 4-yl, thiomorpholin-2, 3 or 4-yl, pyrrolidin-1, 2 or 3-yl, dihydropyrrolidin-1, 2 or 3-yl, imidazolidin-1, 2 or 4-yl, dihydroimidazol-1, 2 or 4-yl, thiazolidin-2, 3, 4 or 5-yl, isothiazolidin-2, 3, 4 or 5-yl and oxazolan-2, 3, 4 or 5-yl.

Preferred cycloheteroalkylaryl radicals R5 are selected from the group of benzo[b]dihydrofuran-2, 3, 4, 5, 6 or 7-yl, benzo[c]dihydrofuran-1, 3, 4, 5, 6 or 7-yl, benzo[b]dihydrofuran-2, 3, 4, 5, 6 or 7-yl, benzo[c]dihydrothiophen-1, 3, 4, 5, 6 or 7-yl, benzo[b]dihydrothiophen-1, 2, 3, 4, 5, 6 or 7-yl, benzo[c]dihydropyrrol-1, 2, 3, 4, 5, 6 or 7-yl, benzodioxolan-2, 4, 5, 6 or 7-yl and benzoxathiolan-2, 4, 5, 6 or 7-yl, tetrahydroquinol-2, 3, 4, 5, 6, 7 or 8-yl and isoquinol-1, 3, 4, 5, 6, 7 or 8-yl.

The preferred aryl, heteroaryl, cycloheteroalkyl, cycloheteroalkylaryl and cycloheteroalkylheteroaryl radicals may carry one or more, preferably one, two, three or four, further substituents which are selected independently of one another from the group of R11 radicals. Particularly preferred R11 radicals are selected from the group of F, Cl, Br, I, —CN, NH$_2$, OH, =O, (C$_1$-C$_4$)-alkyl-, such as, for example, methyl, ethyl, n-propyl, isopropyl, n-butyl, tert-butyl and (C$_1$-C$_4$)-alkyloxy-, such as, for example, —OCH$_3$, —OC$_2$H$_5$, where the alkyl and alkoxy radicals may be substituted one or more times by F, —SO$_2$CH$_3$, —SO$_2$NH$_2$, —NH—C(O)—CH$_3$, —C(O)—NH$_2$ and —NH—C(O)—NH$_2$, —COOCH$_3$, —COOC$_2$H$_5$.

Particularly preferred aryl, heteroaryl, cycloheteroalkyl, cycloheteroalkylaryl and cycloheteroalkylheteroaryl radicals R5 are:

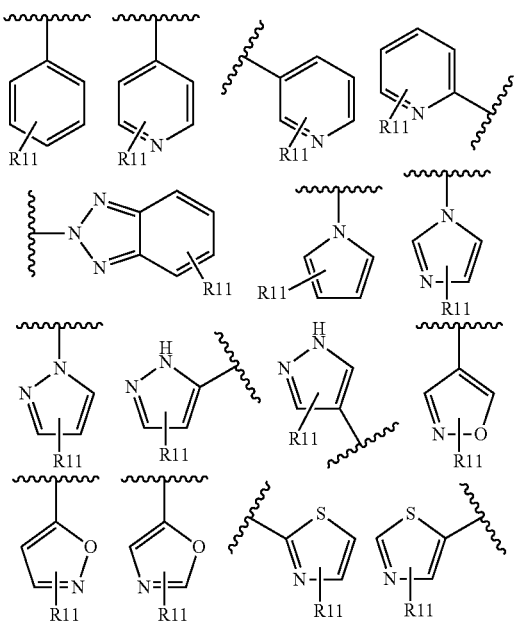

-continued

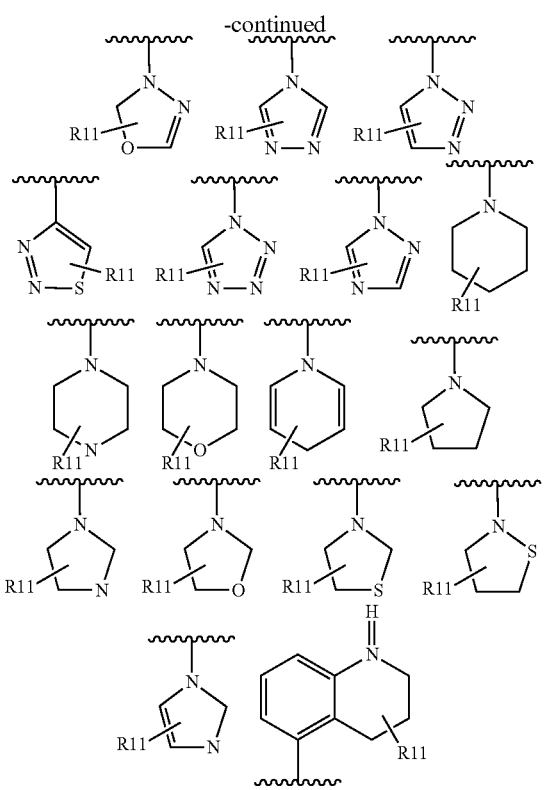

In one embodiment of the invention, the R5 radicals can be selected independently of one another from the group of F, Cl, Br, CN, methyl, ethyl, propyl, tertiary butyl, NH$_2$, OCH$_3$, SO$_2$CH$_3$, SO$_2$NH$_2$, C(O)NH$_2$, —NH—C(O)—CH$_3$, pyrazol-1, 2 or 3-yl, imidazol-1, 2 or 3-yl, 1,2,3-triazol-1 or 2-yl, 1,2,4-triazol-1, 3 or 4-yl, tetrazol-1, 2 or 5-yl, thiazol-2, 3 or 4-yl, 1,3,4-oxadiazol-3 or 4-yl, oxazol-2 or 3-yl, isooxazol-2, or 3-yl, triazol-1 or 2-yl, piperidin-1-yl, piperazin-1-yl, pyrrolidin-1-yl, oxazolidin-3-yl, isoxazolidin-2-yl, tetrahydroimidazol-1-yl, dihydroimidazol-1-yl, isothiazol-1-yl and morpholin-4-yl, where the cyclic radicals R5 may carry further substituents R11. In another embodiment, one of the R5 radicals is selected from the group of F, Cl, CN, methyl, ethyl, tertiary butyl, OCH$_3$, SO$_2$CH$_3$, SO$_2$NH$_2$, C(O)NH$_2$ and —NH—C(O)—CH$_3$. In another embodiment, one of the R5 radicals is selected from pyrazol-1, 2 or 3-yl, imidazol-1-yl, 1,2,3-triazol-1 or 2-yl, 1,2,4-triazol-1, 3 or 4-yl, thiazol-2 or 4-yl, oxazol-2 or 3-yl, isooxazol-2, or 3-yl, triazol-1 or 2-yl, tetrazol-1-yl, all of which may carry further substituents from the group of methyl, ethyl, cyclopropyl, methoxy, CN, OH, NH$_2$, N(CH$_3$)$_2$, or selected from the group of piperidin-1-yl, piperazin-1-yl, pyrrolidin-1-yl, oxazolidin-3-yl, isoxazolidin-2-yl, tetrahydroimidazol-1-yl, all of which may carry further substituents R11 selected from the group of methyl, ethyl, cyclopropyl, methoxy, CN, (=O), OH, NH$_2$ and N(CH$_3$)$_2$.

In one embodiment of the invention, one of the R5 radicals is selected from the group of F, Cl, Br, CN, methyl, ethyl, propyl, tertiary butyl, NH$_2$, OCH$_3$, SO$_2$CH$_3$, SO$_2$NH$_2$, C(O)NH$_2$, —NH—C(O)—CH$_3$ and one of the R5 radicals is selected from the group of pyrazol-1, 2 or 3-yl, imidazol-1, 2 or 3-yl, 1,2,3-triazol-1 or 2-yl, 1,2,4-triazol-1, 3 or 4-yl, thiazol-2, 3 or 4-yl, 1,3,4-oxadiazol-3 or 4-yl, oxazol-2 or 3-yl, isooxazol-2, or 3-yl, triazol-1 or 2-yl, tetrazol-1-yl, all of which may carry substituents R11 selected from the group of methyl, ethyl, cyclopropyl, methoxy, CN, OH, NH$_2$, N(CH$_3$)$_2$, or selected from the group of piperidin-1-yl, piperazin-1-yl, pyrrolidin-1-yl, oxazolidin-3-yl, isoxazolidin-2-yl, tetrahydroimidazol-1-yl, dihydroimidazol-1-yl, isothiazol-1-yl and morpholin-4-yl, all of which may carry substituents R11 selected from the group of methyl, ethyl, cyclopropyl, methoxy, CN, (=O), OH, NH$_2$ and N(CH$_3$)$_2$.

In one embodiment of the invention, the substituents R11 are selected from the group of methyl, ethyl, cyclopropyl, methoxy, CN, (=O), OH, $NH_2$, $N(CH_3)_2$, $SO_2Me$ and $CO_2Me$.

($C_1$-$C_{10}$)-Alkyl radicals may in the context of the present invention be straight-chain or branched. This also applies when they carry substituents or occur as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl and hexyl. Preferred alkyl radicals are methyl, ethyl, n-propyl, isopropyl, n-butyl and tert-butyl.

($C_2$-$C_{10}$)-Alkenyl radicals in the context of the present invention may likewise be straight-chain or branched. This also applies when they carry substituents or occur as substituents of other radicals. Examples of alkenyl radicals are ethenyl, propenyl and butenyl.

($C_2$-$C_{10}$)-Alkynyl radicals in the context of the present invention may likewise be straight-chain or branched. This also applies when they carry substituents or occur as substituents of other radicals. Examples of alkynyl radicals are ethynyl, propynyl and butynyl.

($C_3$-$C_{14}$)-Cycloalkyl radicals in the context of the present invention may be saturated or partly unsaturated. This also applies when they carry substituents or occur as substituents of other radicals. Cycloalkyl radicals having 3, 4, 5, 6, 7 or 8 carbon atoms are preferred. Examples of cycloalkyl radicals are cyclopropyl, cyclobutyl, cyclopentyl, cyclohexyl, cycloheptyl and cyclooctyl.

($C_2$-$C_{19}$)-Cycloheteroalkyl radicals in the context of the present invention may be saturated or partly unsaturated. This also applies when they carry substituents or occur as substituents of other radicals. The cycloheteroalkyl radicals preferably have heteroatoms selected from the group of nitrogen, oxygen and sulfur. Cycloheteroalkyl radicals having 2, 3, 4, 5, 6, 7, 8 or 9 carbon atoms are preferred, it being possible for 1 or 2 nitrogen atoms, 1 or 2 oxygen atoms, 1 or 2 sulfur atoms, 1 nitrogen and 1 oxygen atom or 1 sulfur atom or 1 oxygen and 1 sulfur atom to be present as heteroatoms. The cycloheteroalkyl radicals can be attached by any position. Examples of such heterocycles are selected from the group of oxiranyl, thiiranyl, aziridinyl, oxetanyl, thietanyl, azetidinyl, diazetidinyl, pyrrolidinyl, dihydropyrrolyl, dihydroimidazolyl, dihydropyrazolyl, tetrahydropyrazolyl, oxolanyl, dihydrofuranyl, dioxolanyl, thiolanyl, dihydrothiophenyl, oxazolanyl, dihydrooxazolyl, isooxazolanyl, dihydroisooxazolyl, thiazolidinyl, dihydrothiazolyl, isothiazolidinyl, dihydroisothiazolyl, oxathiolidinyl, 2H-pyranyl, 4H-pyranyl, tetrahydropyranyl, 2H-thiopyranyl, 4H-thiopyranyl, tetrahydrothiopyranyl, piperidinyl, di-, tetrahydropyridyl, piperazinyl, di-, tetrahydropyrazinyl, di-, tetra-, hexahydropyridazinyl, di-, tetra-, hexahydropyrimidinyl, morpholinyl, thiomorpholinyl, azepanyl, thiepanyl and oxepinyl, it also being possible for two of these heterocyclic rings to form a saturated or partly unsaturated fused bicyclic ring system. Examples of such bicyclic ring systems are octahydropyrrolo[1,2a]pyrazinyl, octahydropyrrolo[3,4b]pyrrolyl, hexahydropyrrolo[3,4-c]pyrrolyl- and octahydropyrrolo[3,4-c]pyrrolyl.

Examples of preferred ($C_6$-$C_{10}$)-aryl radicals are phenyl and naphthyl. This also applies when they carry substituents or occur as substituents of other radicals.

($C_1$-$C_9$)-Heteroaryl radicals are aromatic ring compounds in which one or more ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms. This also applies when they carry substituents or occur as substituents of other radicals. The heteroaryl radicals may be attached by all positions. Heteroaryl means for example furanyl, thiophenyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl.

Particularly preferred heteroaryl radicals are 2- or 3-thiophenyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or -5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl.

($C_9$-$C_{14}$)-Cycloalkylaryl radicals are preferably selected from the group of fused ring systems having a cycloalkyl ring and an aryl ring, in particular a phenyl ring. Particularly preferred cycloalkylaryl radicals are indenyl, dihydronaphthyl, tetrahydronaphthyl and indanyl.

($C_5$-$C_{13}$)-Cycloalkylheteroaryl radicals are preferably selected from the group of fused ring systems having a cycloalkyl ring and a heteroaryl ring.

($C_7$-$C_{13}$)-Cycloheteroalkylaryl radicals are preferably fused ring systems having a cycloheteroalkyl ring and an aryl ring, in particular a phenyl ring. Particularly preferred cycloheteroalkylaryl radicals are benzodihydrothiophenyl, benzothiolanyl, benzodihydrofuranyl, benzooxolanyl, benzodioxolanyl, benzodihydropyrrolyl, benzodihydroimidazolyl, benzodihydropyrazolyl, benzodihydrotriazolyl, benzopiperazinyl, benzodihydrothiazolyl, benzomorpholinyl benzodihydrooxazolyl, dihydroquinolinyl, dihydroisoquinolinyl, tetrahydroisoquinolinyl and tetrahydroquinolinyl.

($C_4$-$C_{12}$)-Cycloheteroalkylheteroaryl radicals are preferably selected from the group of fused ring systems having a cycloheteroalkyl ring and a heteroaryl ring.

In one embodiment of the invention, p is 1, and in another embodiment, p is 2. In one embodiment of the invention, q is 0, and in another embodiment, q is 1.

If the compounds of the formula I comprise one or more centers of asymmetry, these may have independently of one another either the S or the R configuration. The compounds may be in the form of optical isomers, diastereomers, racemates or mixtures in all ratios thereof. The compounds of the formula I may furthermore be in the form of rotational isomers.

Particular preference is given to stereoisomers of the formula I in which the radical XLBR5 bonded at position 1 is directed downwards and the radical —$(CH_2)_q$NR3R4 bonded at position 2 is directed upwards, the direction being defined starting from a plane which is spanned by the three carbon atoms in positions 1, 2 and 3, and the molecule assuming the following orientation (formula Ie):

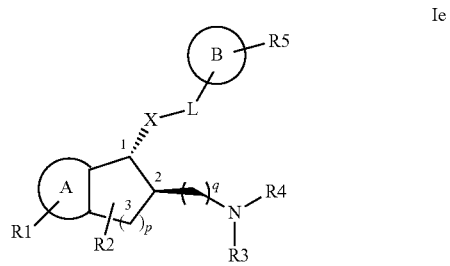

Ie

Compounds of formula I with trans-1S,2S configuration at position 1 and 2 are preferred.

The present invention includes all possible tautomeric forms of the compounds of the formulae I.

Particularly preferred compounds of formula I are selected from the group of

| Example | Configuration | Name |
|---|---|---|
| 1 | trans-1S,2S-3'R- | ((R)-1-{trans-(1S,2S)-1-[4-(3,5-dimethyl-[1,2,4]triazol-4-yl)phenoxy]indan-2-yl}piperidin-3-yl)-(3,3,3-trifluoropropyl)amine |
| 2 | trans-1S,2S | 3-[trans-(1S,2S)-4,6-dichloro-1-(4-[1,2,4]triazol-1-ylphenoxy)indan-2-yl]-3,8-diazabicyclo[3.2.1]octane |
| 3 | trans-1S,2S- | 2-[trans-(1S,2S)-4,6-dichloro-1-(4-methanesulfonylphenoxy)indan-2-yl]octahydropyrrolo[3,4-c]pyrrole |
| 4 | rac-trans-1,2- | 2-[rac-trans-(1,2)-1-(2,4-dichloro-3-methylphenoxy)indan-2-yl]octahydropyrrolo[3,4-c]pyrrole |
| 5 | rac-trans-1,2- | 2-[rac-trans-(1,2)-1-(2-fluoro-6-methoxyphenoxy)indan-2-yl]octahydropyrrolo[3,4-c]pyrrole |
| 6 | rac-trans-1,2- | 2-[rac-trans-(1,2)-1-(3-chloro-2-methylphenoxy)indan-2-yl]octahydropyrrolo[3,4-c]pyrrole |
| 7 | rac-trans-1,2- | 2-[rac-trans-(1,2)-1-(4-imidazol-1-ylphenoxy)indan-2-yl]octahydropyrrolo[3,4-c]pyrrole |
| 8 | trans-1S,2S | 2-[trans-(1S,2S)-4,6-dichloro-1-(4-methanesulfonylphenoxy)indan-2-yl]-5-methyloctahydropyrrolo[3,4-c]pyrrole |
| 9 | rac-trans-1,2- | 2-[rac-trans-(1,2)-1-(2,4-difluorophenoxy)indan-2-yl]octahydropyrrolo[3,4-c]pyrrole |
| 10 | rac-trans-1,2- | 2-[rac-trans-(1,2)-1-(2-bromo-4-methylphenoxy)indan-2-yl]octahydropyrrolo[3,4-c]pyrrole |
| 11 | rac-trans-1,2- | 2-[rac-trans-(1,2)-1-(2-bromophenoxy)indan-2-yl]octahydropyrrolo[3,4-c]pyrrole |
| 12 | rac-trans-1,2- | 2-[rac-trans-(1,2)-1-(2-tert-butyl-4-ethylphenoxy)indan-2-yl]octahydropyrrolo[3,4-c]pyrrole |
| 13 | rac-trans-1,2- | 2-[rac-trans-(1,2)-1-(3-piperazin-1-ylphenoxy)indan-2-yl]octahydropyrrolo[3,4-c]pyrrole |
| 14 | rac-trans-1,2- | 2-[rac-trans-(1,2)-1-(3-piperidin-1-ylmethylphenoxy)indan-2-yl]octahydropyrrolo[3,4-c]pyrrole |
| 15 | rac-trans-1,2- | 2-[rac-trans-(1,2)-1-(3-piperidin-1-ylphenoxy)indan-2-yl]octahydropyrrolo[3,4-c]pyrrole |
| 16 | rac-trans-1,2- | 2-[rac-trans-(1,2)-1-(4-fluoro-2-methylphenoxy)indan-2-yl]octahydropyrrolo[3,4-c]pyrrole |
| 17 | rac-trans-1,2- | 2-[rac-trans-(1,2)-1-(4-piperazin-1-ylphenoxy)indan-2-yl]octahydropyrrolo[3,4-c]pyrrole |
| 18 | rac-trans-1,2- | 2-[rac-trans-(1,2)-1-(6-chloropyridin-3-yloxy)indan-2-yl]octahydropyrrolo[3,4-c]pyrrole |
| 19 | rac-trans-1,2- | 2-{rac-trans-(1,2)-1-[4-(2-methoxyethyl)phenoxy]indan-2-yl}octahydropyrrolo[3,4-c]pyrrole |
| 20 | rac-trans-1,2- | 2-{rac-trans-(1,2)-1-[4-bromo-2-(1H-pyrazol-3-yl)phenoxy]indan-2-yl}octahydropyrrolo[3,4-c]pyrrole |
| 21 | trans-1S,2S-cis-3'-5'- | (3R,5S)-1-[trans-(1S,2S)-4,6-dichloro-1-(4-methanesulfonylphenoxy)indan-2-yl]-3,5-dimethylpiperazine |
| 22 | rac-trans-1,2- | (4-methylpiperazin-1-yl)-[4-(rac-trans-(1,2)-2-pyrrolidin-1-ylindan-1-yloxy)phenyl]methanone |
| 23 | trans-1S,2S-3'R- | (R)-1-(trans-(1R,2R)-4,6-dichloro-1-phenoxyindan-2-yl)piperidin-3-ylamine |
| 24 | trans-1S,2S-3'R- | (R)-1-[(1S,2S)-4,6-dichloro-1-(2-chloro-4-methanesulfonylbenzyloxy)indan-2-yl]pyrrolidin-3-ol |
| 25 | trans-1S,2S-3'R | (R)-1-[(1S,2S)-4,6-dichloro-1-(2-methanesulfonylphenoxy)indan-2-yl]piperidin-3-ylamine |
| 26 | trans-1S,2S-3'R- | (R)-1-[(1S,2S)-4,6-dichloro-1-(4-methanesulfonylphenylamino)indan-2-yl]pyrrolidin-3-ol |
| 27 | trans-1S,2S-3'R | (R)-1-[(1S,2S)-4,6-dichloro-1-(5-fluoroquinolin-8-yloxy)indan-2-yl]piperidin-3-ylamine |
| 28 | trans-1S,2S-3'R- | (R)-1-[(1S,2S)-4,6-difluoro-1-(4-methanesulfonylphenoxy)indan-2-yl]pyrrolidin-3-ol |
| 29 | rac-trans-1,2-3'R- | (R)-1-[rac-trans-(1,2)-1-(1H-benzotriazol-4-yloxy)-1,2,3,4-tetrahydronaphthalen-2-yl]piperidin-3-ylamine |
| 30 | rac-trans-1,2-3'R- | (R)-1-[rac-trans-(1,2)-1-(1H-indol-4-yloxy)indan-2-yl]piperidin-3-ylamine |
| 31 | rac-trans-1,2-3'R- | (R)-1-[rac-trans-(1,2)-1-(2,3-dichloro-4-methanesulfonylphenoxy)indan-2-yl]piperidin-3-ylamine |
| 32 | rac-trans-1,2-3'R- | (R)-1-[rac-trans-(1,2)-1-(2,4-difluorophenoxy)-1,2,3,4-tetrahydronaphthalen-2-yl]piperidin-3-ylamine |
| 33 | rac-trans-1,2-3'R- | (R)-1-[rac-trans-(1,2)-1-(2,4-difluorophenoxy)indan-2-yl]piperidin-3-ylamine |
| 34 | rac-trans-1,2-3'R- | (R)-1-[rac-trans-(1,2)-1-(2,6-dimethoxyphenoxy)-1,2,3,4-tetrahydronaphthalen-2-yl]piperidin-3-ylamine |
| 35 | rac-trans-1,2-3'R- | (R)-1-[rac-trans-(1,2)-1-(2-bromo-4-methylphenoxy)-1,2,3,4-tetrahydronaphthalen-2-yl]piperidin-3-ylamine |

-continued

| Example | Configuration | Name |
|---|---|---|
| 36 | rac-trans-1,2-3'R- | (R)-1-[rac-trans-(1,2)-1-(2-bromophenoxy)-1,2,3,4-tetrahydronaphthalen-2-yl]piperidin-3-ylamine |
| 37 | rac-trans-1,2-3'R | (R)-1-[rac-trans-(1,2)-1-(2-chloro-4-methanesulfonylphenoxy)indan-2-yl]piperidin-3-ylamine |
| 38 | rac-trans-1,2-3'R- | (R)-1-[rac-trans-(1,2)-1-(2-chloro-4-methylphenoxy)-1,2,3,4-tetrahydronaphthalen-2-yl]piperidin-3-ylamine |
| 39 | rac-trans-1,2-3'R- | (R)-1-[rac-trans-(1,2)-1-(2-chloro-6-methylphenoxy)-1,2,3,4-tetrahydronaphthalen-2-yl]piperidin-3-ylamine |
| 40 | rac-trans-1,2-3'R- | (R)-1-[rac-trans-(1,2)-1-(2-chloropyridin-4-yloxy)-1,2,3,4-tetrahydronaphthalen-2-yl]piperidin-3-ylamine |
| 41 | rac-trans-1,2-3'R- | (R)-1-[rac-trans-(1,2)-1-(2-chloroquinolin-8-yloxy)-1,2,3,4-tetrahydronaphthalen-2-yl]piperidin-3-ylamine |
| 42 | rac-trans-1,2-3'R- | (R)-1-[rac-trans-(1,2)-1-(2-fluoro-4-methoxyphenoxy)-1,2,3,4-tetrahydronaphthalen-2-yl]piperidin-3-ylamine |
| 43 | rac-trans-1,2-3'R- | (R)-1-[rac-trans-(1,2)-1-(2-fluoro-5-methylphenoxy)-1,2,3,4-tetrahydronaphthalen-2-yl]piperidin-3-ylamine |
| 44 | rac-trans-1,2-3'R- | (R)-1-[rac-trans-(1,2)-1-(2-fluoro-6-methoxyphenoxy)-1,2,3,4-tetrahydronaphthalen-2-yl]piperidin-3-ylamine |
| 45 | rac-trans-1,2-3'R- | (R)-1-[rac-trans-(1,2)-1-(2-methanesulfonylphenoxy)-1,2,3,4-tetrahydronaphthalen-2-yl]piperidin-3-ylamine |
| 46 | rac-trans-1,2-3'R- | (R)-1-[rac-trans-(1,2)-1-(2-methoxy-5-methylphenoxy)-1,2,3,4-tetrahydronaphthalen-2-yl]piperidin-3-ylamine |
| 47 | rac-trans-1,2-3'R- | (R)-1-[rac-trans-(1,2)-1-(2-methylbenzothiazol-5-yloxy)indan-2-yl]piperidin-3-ylamine |
| 48 | rac-trans-1,2-3'R- | (R)-1-[rac-trans-(1,2)-1-(2-morpholin-4-ylphenoxy)-1,2,3,4-tetrahydronaphthalen-2-yl]piperidin-3-ylamine |
| 49 | rac-trans-1,2-3'R- | (R)-1-[rac-trans-(1,2)-1-(2-tert-butyl-4-ethylphenoxy)indan-2-yl]piperidin-3-ylamine |
| 50 | rac-trans-1,2-3'R- | (R)-1-[rac-trans-(1,2)-1-(2-trifluoromethoxyphenoxy)-1,2,3,4-tetrahydronaphthalen-2-yl]piperidin-3-ylamine |
| 51 | rac-trans-1,2-3'R- | (R)-1-[rac-trans-(1,2)-1-(3,4-difluorophenoxy)-1,2,3,4-tetrahydronaphthalen-2-yl]piperidin-3-ylamine |
| 52 | rac-trans-1,2-3'R- | (R)-1-[rac-trans-(1,2)-1-(3-chloro-4-fluorophenoxy)-1,2,3,4-tetrahydronaphthalen-2-yl]piperidin-3-ylamine |
| 53 | rac-trans-1,2-3'R- | (R)-1-[rac-trans-(1,2)-1-(3-chloro-4-methylphenoxy)-1,2,3,4-tetrahydronaphthalen-2-yl]piperidin-3-ylamine |
| 54 | rac-trans-1,2-3'R- | (R)-1-[rac-trans-(1,2)-1-(3-chloro-5-methoxyphenoxy)-1,2,3,4-tetrahydronaphthalen-2-yl]piperidin-3-ylamine |
| 55 | rac-trans-1,2-3'R- | (R)-1-[rac-trans-(1,2)-1-(3-chlorophenoxy)-1,2,3,4-tetrahydronaphthalen-2-yl]piperidin-3-ylamine |
| 56 | rac-trans-1,2-3'R- | (R)-1-[rac-trans-(1,2)-1-(3-difluoromethoxyphenoxy)-1,2,3,4-tetrahydronaphthalen-2-yl]piperidin-3-ylamine |
| 57 | rac-trans-1,2-3'R- | (R)-1-[rac-trans-(1,2)-1-(3-fluorophenoxy)-1,2,3,4-tetrahydronaphthalen-2-yl]piperidin-3-ylamine |
| 58 | rac-trans-1,2-3'R- | (R)-1-[rac-trans-(1,2)-1-(3-piperidin-1-ylmethylphenoxy)indan-2-yl]piperidin-3-ylamine |
| 59 | rac-trans-1,2-3'R- | (R)-1-[rac-trans-(1,2)-1-(3-piperidin-1-ylphenoxy)indan-2-yl]piperidin-3-ylamine |
| 60 | rac-trans-1,2-3'R- | (R)-1-[rac-trans-(1,2)-1-(3-tetrazol-1-ylphenoxy)-1,2,3,4-tetrahydronaphthalen-2-yl]piperidin-3-ylamine |
| 61 | rac-trans-1,2-3'R- | (R)-1-[rac-trans-(1,2)-1-(4-[1,2,4]triazol-1-ylphenoxy)-1,2,3,4-tetrahydronaphthalen-2-yl]piperidin-3-ylamine |
| 62 | rac-trans-1,2-3'R- | (R)-1-[rac-trans-(1,2)-1-(4-[1,2,4]triazol-1-ylphenoxy)indan-2-yl]piperidin-3-ylamine |
| 63 | rac-trans-1,2-3'R- | (R)-1-[rac-trans-(1,2)-1-(4-bromo-3-methoxyphenoxy)-1,2,3,4-tetrahydronaphthalen-2-yl]piperidin-3-ylamine |
| 64 | rac-trans-1,2-3'R- | (R)-1-[rac-trans-(1,2)-1-(4-chloro-2-methoxyphenoxy)-1,2,3,4-tetrahydronaphthalen-2-yl]piperidin-3-ylamine |
| 65 | rac-trans-1,2-3'R- | (R)-1-[rac-trans-(1,2)-1-(4-chloro-3-methylphenoxy)-1,2,3,4-tetrahydronaphthalen-2-yl]piperidin-3-ylamine |
| 66 | rac-trans-1,2-3'R- | (R)-1-[rac-trans-(1,2)-1-(4-chlorophenoxy)-1,2,3,4-tetrahydronaphthalen-2-yl]piperidin-3-ylamine |
| 67 | rac-trans-1,2-3'R- | (R)-1-[rac-trans-(1,2)-1-(4-dimethylaminomethylphenoxy)-1,2,3,4-tetrahydronaphthalen-2-yl]piperidin-3-ylamine |
| 68 | rac-trans-1,2-3'R- | (R)-1-[rac-trans-(1,2)-1-(4-fluoro-2-isoxazol-5-ylphenoxy)-1,2,3,4-tetrahydronaphthalen-2-yl]piperidin-3-ylamine |
| 69 | rac-trans-1,2-3'R- | (R)-1-[rac-trans-(1,2)-1-(4-fluoro-3-trifluoromethylphenoxy)-1,2,3,4-tetrahydronaphthalen-2-yl]piperidin-3-ylamine |
| 70 | rac-trans-1,2-3'R- | (R)-1-[rac-trans-(1,2)-1-(4-fluorophenoxy)-1,2,3,4-tetrahydronaphthalen-2-yl]piperidin-3-ylamine |
| 71 | rac-trans-1,2-3'R- | (R)-1-[rac-trans-(1,2)-1-(4-imidazol-1-ylphenoxy)-1,2,3,4-tetrahydronaphthalen-2-yl]piperidin-3-ylamine |
| 72 | rac-trans-1,2-3'R- | (R)-1-[rac-trans-(1,2)-1-(4-imidazol-1-ylphenoxy)indan-2-yl]piperidin-3-ylamine |

-continued

| Example | Configuration | Name |
|---------|---------------|------|
| 73 | rac-trans-1,2-3'R- | (R)-1-[rac-trans-(1,2)-1-(4-methanesulfonylphenoxy)-1,2,3,4-tetrahydronaphthalen-2-yl]piperidin-3-ylamine |
| 74 | rac-trans-1,2-3'R- | (R)-1-[rac-trans-(1,2)-1-(4-methylsulfanylphenoxy)-1,2,3,4-tetrahydronaphthalen-2-yl]piperidin-3-ylamine |
| 75 | rac-trans-1,2-3'R- | (R)-1-[rac-trans-(1,2)-1-(4-piperazin-1-ylphenoxy)-1,2,3,4-tetrahydronaphthalen-2-yl]piperidin-3-ylamine |
| 76 | rac-trans-1,2-3'R- | (R)-1-[rac-trans-(1,2)-1-(4-piperazin-1-ylphenoxy)indan-2-yl]piperidin-3-ylamine |
| 77 | rac-trans-1,2-3'R- | (R)-1-[rac-trans-(1,2)-1-(4-trifluoromethylphenoxy)-1,2,3,4-tetrahydronaphthalen-2-yl]piperidin-3-ylamine |
| 78 | rac-trans-1,2-3'R- | (R)-1-[rac-trans-(1,2)-1-(5,7-dimethylquinolin-8-yloxy)-1,2,3,4-tetrahydronaphthalen-2-yl]piperidin-3-ylamine |
| 79 | rac-trans-1,2-3'R- | (R)-1-[rac-trans-(1,2)-1-(5-fluoroquinolin-8-yloxy)-1,2,3,4-tetrahydronaphthalen-2-yl]piperidin-3-ylamine |
| 80 | rac-trans-1,2-3'R- | (R)-1-[rac-trans-(1,2)-1-(6-aminonaphthalen-1-yloxy)-1,2,3,4-tetrahydronaphthalen-2-yl]piperidin-3-ylamine |
| 81 | rac-trans-1,2-3'R- | (R)-1-[rac-trans-(1,2)-1-(6-chloropyridin-3-yloxy)-1,2,3,4-tetrahydronaphthalen-2-yl]piperidin-3-ylamine |
| 82 | rac-trans-1,2-3'R- | (R)-1-[rac-trans-(1,2)-1-(6-chloropyridin-3-yloxy)indan-2-yl]piperidin-3-ylamine |
| 83 | rac-trans-1,2-3'R- | (R)-1-[rac-trans-(1,2)-1-(benzo[1,3]dioxol-5-yloxy)indan-2-yl]piperidin-3-ylamine |
| 84 | rac-trans-1,2-3'R- | (R)-1-[rac-trans-(1,2)-1-(isoquinolin-7-yloxy)-1,2,3,4-tetrahydronaphthalen-2-yl]piperidin-3-ylamine |
| 85 | rac-trans-1,2-3'R- | (R)-1-[rac-trans-(1,2)-1-(isoquinolin-7-yloxy)indan-2-yl]piperidin-3-ylamine |
| 86 | rac-trans-1,2-3'R- | (R)-1-[rac-trans-(1,2)-1-(pyridin-4-yloxy)indan-2-yl]piperidin-3-ylamine |
| 87 | rac-trans-1,2-3'R- | (R)-1-[rac-trans-(1,2)-1-(quinolin-3-yloxy)-1,2,3,4-tetrahydronaphthalen-2-yl]piperidin-3-ylamine |
| 88 | rac-trans-1,2-3'R- | (R)-1-[rac-trans-(1,2)-1-(quinolin-4-yloxy)indan-2-yl]piperidin-3-ylamine |
| 89 | rac-trans-1,2-3'R- | (R)-1-[rac-trans-(1,2)-1-(quinolin-5-yloxy)-1,2,3,4-tetrahydronaphthalen-2-yl]piperidin-3-ylamine |
| 90 | rac-trans-1,2-3'R- | (R)-1-[rac-trans-(1,2)-4-chloro-6-fluoro-1-(3-methyl-4-trifluoromethanesulfonylphenoxy)indan-2-yl]piperidin-3-ylamine |
| 91 | rac-trans-1,2-3'R- | (R)-1-[rac-trans-(1,2)-4-chloro-6-fluoro-1-(4-methanesulfonylphenoxy)indan-2-yl]piperidin-3-ylamine |
| 92 | rac-trans-1,2-3'R- | (R)-1-[rac-trans-(1,2)-6-chloro-4-fluoro-1-(3-methyl-4-trifluoromethanesulfonylphenoxy)indan-2-yl]piperidin-3-ylamine |
| 93 | rac-trans-1,2-3'R- | (R)-1-[rac-trans-(1,2)-6-chloro-4-fluoro-1-(4-methanesulfonylphenoxy)indan-2-yl]piperidin-3-ylamine |
| 94 | trans-1S,2S-3'R- | (R)-1-[trans-(1R,2R)-4,6-dichloro-1-(2-fluoro-6-methoxyphenoxy)indan-2-yl]piperidin-3-ylamine |
| 95 | trans-1S,2S-3'R- | (R)-1-[trans-(1S,2S)-1-(4-methanesulfonylphenoxy)indan-2-yl]piperidin-3-ylamine |
| 96 | trans-1S,2S-3'R- | (R)-1-[trans-(1S,2S)-4,6-dichloro-1-(2-methylbenzothiazol-5-yloxy)indan-2-yl]pyrrolidin-3-ol |
| 97 | trans-1S,2S-3'R- | (R)-1-[trans-(1S,2S)-4,6-dichloro-1-(4-[1,2,4]triazol-1-ylphenoxy)indan-2-yl]piperidin-3-ylamine |
| 98 | trans-1S,2S-3'R- | (R)-1-[trans-(1S,2S)-4,6-dichloro-1-(4-imidazol-1-ylphenoxy)indan-2-yl]piperidin-3-ylamine |
| 99 | trans-1S,2S-3'R- | (R)-1'-[trans-(1S,2S)-4,6-dichloro-1-(4-methanesulfonylphenoxy)indan-2-yl]-[1,3']bipyrrolidinyl |
| 100 | trans-1S,2S-3'R- | (R)-1-[trans-(1S,2S)-4,6-dichloro-1-(4-methanesulfonylphenoxy)indan-2-yl]-3-fluoropyrrolidine |
| 101 | trans-1S,2S-3'R- | (R)-1-[trans-(1S,2S)-4,6-dichloro-1-(4-methanesulfonylphenoxy)indan-2-yl]-3-methylpiperazine |
| 102 | trans-1S,2S-3'R- | (R)-1-[trans-(1S,2S)-4,6-dichloro-1-(4-methanesulfonylphenoxy)indan-2-yl]piperidin-3-ylamine |
| 103 | trans-1S,2S-3'R- | (R)-1-[trans-(1S,2S)-4,6-dichloro-1-(4-methanesulfonylphenoxy)indan-2-yl]pyrrolidin-3-ol |
| 104 | trans-1S,2S-3'R- | (R)-1-[trans-(1S,2S)-4,6-dichloro-1-(4-methanesulfonylphenoxy)indan-2-yl]pyrrolidin-3-ylamine |
| 105 | trans-1S,2S-3'R- | (R)-1-[trans-(1S,2S)-4,6-dichloro-1-(4-methanesulfonylphenoxy)indan-2-yl]pyrrolidine-3-carbonitrile |
| 106 | trans-1S,2S-3'R- | (R)-1-[trans-(1S,2S)-6-chloro-1-(2-chloro-4-methanesulfonylphenoxy)-4-fluoroindan-2-yl]pyrrolidin-3-ol |
| 107 | trans-1S,2S-3'R- | (R)-1-[trans-(1S,2S)-6-chloro-1-(2-chloro-4-methanesulfonylphenoxy)indan-2-yl]pyrrolidin-3-ol |
| 108 | trans-1S,2S-3'R- | (R)-1-[trans-(1S,2S)-6-chloro-4-fluoro-1-(4-methanesulfonylphenoxy)indan-2-yl]pyrrolidin-3-ol |

-continued

| Example | Configuration | Name |
|---|---|---|
| 109 | trans-1S,2S-3'R- | (R)-1-{(1S,2S)-1-[2-chloro-4-(3,5-dimethyl-[1,2,4]triazol-4-yl)phenoxy]-4,6-difluoroindan-2-yl}pyrrolidin-3-ol |
| 110 | trans-1S,2S-3'R- | (R)-1-{(1S,2S)-1-[4-(3,5-dimethyl-[1,2,4]triazol-4-yl)phenoxy]-2-fluorophenoxy]-4,6-difluoroindan-2-yl}pyrrolidin-3-ol |
| 111 | trans-1S,2S-rac-3'- | (R)-1-{(1S,2S)-4,6-dichloro-1-[4-(3,5-dimethyl-[1,2,4]triazol-4-yl)phenoxy]indan-2-yl}-3-methylpyrrolidin-3-ol |
| 112 | trans-1S,2S-3'R- | (R)-1-{(1S,2S)-4,6-dichloro-1-[4-(5-methyltetrazol-1-yl)phenoxy]indan-2-yl}pyrrolidin-3-ol |
| 113 | trans-1S,2S-3'R | (R)-1-{(1S,2S)-4,6-dichloro-1-[4-fluoro-2-(1H-pyrazol-3-yl)phenoxy]indan-2-yl}piperidin-3-ylamine |
| 114 | trans-1S,2S-3'R- | (R)-1-{(1S,2S)-4,6-dichloro-1-[5-(3,5-dimethyl-[1,2,4]triazol-4-yl)-2-fluorophenoxy]indan-2-yl}pyrrolidin-3-ol |
| 115 | rac-trans-1,2-3'R- | (R)-1-{rac-trans-(1,2)-1-[4-(2-methoxyethyl)phenoxy]-1,2,3,4-tetrahydronaphthalen-2-yl}piperidin-3-ylamine |
| 116 | rac-trans-1,2-3'R- | (R)-1-{rac-trans-(1,2)-1-[4-(2-methoxyethyl)phenoxy]indan-2-yl}piperidin-3-ylamine |
| 117 | rac-trans-1,2-3'R- | (R)-1-{rac-trans-(1,2)-1-[4-bromo-2-(1H-pyrazol-3-yl)phenoxy]-1,2,3,4-tetrahydronaphthalen-2-yl}piperidin-3-ylamine |
| 118 | rac-trans-1,2-3'R- | (R)-1-{rac-trans-(1,2)-1-[4-bromo-2-(1H-pyrazol-3-yl)phenoxy]indan-2-yl}piperidin-3-ylamine |
| 119 | rac-trans-1,2-3'R- | (R)-1-{rac-trans-(1,2)-1-[4-chloro-2-(1H-pyrazol-3-yl)phenoxy]-1,2,3,4-tetrahydronaphthalen-2-yl}piperidin-3-ylamine |
| 120 | rac-trans-1,2-3'R- | (R)-1-{rac-trans-(1,2)-1-[4-fluoro-2-(1H-pyrazol-3-yl)phenoxy]-1,2,3,4-tetrahydronaphthalen-2-yl}piperidin-3-ylamine |
| 121 | trans-1S,2S-3'R- | (R)-1-{trans-(1S,2S)-1-[4-(3,5-dimethyl-[1,2,4]triazol-4-yl)phenoxy]indan-2-yl}piperidin-3-ylamine |
| 122 | trans-1S,2S-3'R- | (R)-1-{trans-(1S,2S)-4,6-dichloro-1-[2-chloro-4-(3,5-dimethyl-[1,2,4]triazol-4-yl)phenoxy]indan-2-yl}pyrrolidin-3-ol |
| 123 | trans-1S,2S-3'R- | (R)-1-{trans-(1S,2S)-4,6-dichloro-1-[3-(1,1-dioxo-1lambda6-isothiazolidin-2-yl)phenoxy]indan-2-yl}pyrrolidin-3-ol |
| 124 | trans-1S,2S-3'R- | (R)-1-{trans-(1S,2S)-4,6-dichloro-1-[4-(1,3,5-trimethyl-1H-pyrazol-4-yl)phenoxy]indan-2-yl}pyrrolidin-3-ol |
| 125 | trans-1S,2S-3'R- | (R)-1-{trans-(1S,2S)-4,6-dichloro-1-[4-(2,4-dimethyl-thiazol-5-yl)phenoxy]indan-2-yl}pyrrolidin-3-ol |
| 126 | trans-1S,2S-3'R- | (R)-1-{trans-(1S,2S)-4,6-dichloro-1-[4-(3,5-dimethyl-[1,2,4]triazol-4-yl)-2,3-difluorophenoxy]indan-2-yl}pyrrolidin-3-ol |
| 127 | trans-1S,2S-3'R- | (R)-1-{trans-(1S,2S)-4,6-dichloro-1-[4-(3,5-dimethyl-[1,2,4]triazol-4-yl)-2,3-dimethylphenoxy]indan-2-yl}pyrrolidin-3-ol |
| 128 | trans-1S,2S-3'R- | (R)-1-{trans-(1S,2S)-4,6-dichloro-1-[4-(3,5-dimethyl-[1,2,4]triazol-4-yl)-2,3-dimethylphenoxy]indan-2-yl}pyrrolidin-3-ol |
| 130 | trans-1S,2S-3'R- | (R)-1-{trans-(1S,2S)-4,6-dichloro-1-[4-(3,5-dimethyl-[1,2,4]triazol-4-yl)-2-fluorophenoxy]indan-2-yl}pyrrolidin-3-ol |
| 131 | trans-1S,2S-3'R- | (R)-1-{trans-(1S,2S)-4,6-dichloro-1-[4-(3,5-dimethyl-[1,2,4]triazol-4-yl)-2-methylphenoxy]indan-2-yl}pyrrolidin-3-ol |
| 132 | trans-1S,2S-3'R- | (R)-1-{trans-(1S,2S)-4,6-dichloro-1-[4-(3,5-dimethyl-[1,2,4]triazol-4-yl)phenoxy]indan-2-yl}piperidin-3-ol |
| 133 | trans-1S,2S-3'R- | (R)-1-{trans-(1S,2S)-4,6-dichloro-1-[4-(3,5-dimethyl-[1,2,4]triazol-4-yl)phenoxy]indan-2-yl}pyrrolidin-3-ol |
| 134 | trans-1S,2S-3'R- | (R)-1-{trans-(1S,2S)-4,6-dichloro-1-[4-(3,5-dimethyl-[1,2,4]triazol-4-yl)phenoxy]indan-2-yl}pyrrolidine-3-carbonitrile |
| 135 | trans-1S,2S-3'R- | (R)-1-{trans-(1S,2S)-4,6-dichloro-1-[4-(3,5-dimethylisoxazol-4-yl)phenoxy]indan-2-yl}pyrrolidin-3-ol |
| 136 | trans-1S,2S-3'R- | (R)-1-{trans-(1S,2S)-4,6-dichloro-1-[4-(3,5-dimethylpyrazol-1-yl)-2-fluorophenoxy]indan-2-yl}pyrrolidin-3-ol |
| 137 | trans-1S,2S-3'R- | (R)-1-{trans-(1S,2S)-4,6-dichloro-1-[4-fluoro-2-(2H-pyrazol-3-yl)phenoxy]indan-2-yl}pyrrolidin-3-ol |
| 138 | trans-1S,2S-3'R- | (R)-1-{trans-(1S,2S)-6-chloro-1-[2-chloro-4-(3,5-dimethyl-[1,2,4]triazol-4-yl)phenoxy]-4-fluoroindan-2-yl}pyrrolidin-3-ol |
| 139 | trans-1S,2S-3'R- | (R)-1-{trans-(1S,2S)-6-chloro-1-[2-chloro-4-(3,5-dimethyl-[1,2,4]triazol-4-yl)phenoxy]indan-2-yl}pyrrolidin-3-ol |

-continued

| Example | Configuration | Name |
|---|---|---|
| 140 | trans-1S,2S-3'R- | (R)-1-{trans-(1S,2S)-6-chloro-1-[4-(1,3,5-trimethyl-1H-pyrazol-4-yl)phenoxy]indan-2-yl}pyrrolidin-3-ol |
| 141 | trans-1S,2S-3'R- | (R)-1-{trans-(1S,2S)-6-chloro-1-[4-(3,5-dimethyl-[1,2,4]triazol-4-yl)-2,3-dimethylphenoxy]-4-fluoroindan-2-yl}pyrrolidin-3-ol |
| 142 | trans-1S,2S-3'R- | (R)-1-{trans-(1S,2S)-6-chloro-1-[4-(3,5-dimethyl-[1,2,4]triazol-4-yl)-2-fluorophenoxy]-4-fluoroindan-2-yl}pyrrolidin-3-ol |
| 143 | trans-1S,2S-3'R- | (R)-1-{trans-(1S,2S)-6-chloro-1-[4-(3,5-dimethyl-[1,2,4]triazol-4-yl)-2-fluorophenoxy]indan-2-yl}pyrrolidin-3-ol |
| 144 | trans-1S,2S-3'R- | (R)-1-{trans-(1S,2S)-6-chloro-1-[4-(3,5-dimethyl-[1,2,4]triazol-4-yl)phenoxy]-4-fluoroindan-2-yl}pyrrolidin-3-ol |
| 145 | trans-1S,2S-3'R- | (R)-1-{trans-(1S,2S)-6-chloro-1-[4-(3,5-dimethyl-[1,2,4]triazol-4-yl)phenoxy]indan-2-yl}pyrrolidin-3-ol |
| 146 | trans-1S,2S-rac-3'- | (S)-1-[(1S,2S)-4,6-dichloro-1-(4-methanesulfonylphenoxy)indan-2-yl]-3-methylpyrrolidin-3-ol |
| 147 | rac-trans-1,2-3'S- | (S)-1-[rac-trans-(1,2)-1-(1H-benzotriazol-4-yloxy)-1,2,3,4-tetrahydronaphthalen-2-yl]piperidin-3-ylamine |
| 148 | rac-trans-1,2-3'S- | (S)-1-[rac-trans-(1,2)-1-(1H-indol-6-yloxy)-1,2,3,4-tetrahydronaphthalen-2-yl]piperidin-3-ylamine |
| 149 | rac-trans-1,2-3'S- | (S)-1-[rac-trans-(1,2)-1-(2,4-difluorophenoxy)-1,2,3,4-tetrahydronaphthalen-2-yl]piperidin-3-ylamine |
| 150 | rac-trans-1,2-3'S- | (S)-1-[rac-trans-(1,2)-1-(2-bromo-4-methylphenoxy)-1,2,3,4-tetrahydronaphthalen-2-yl]piperidin-3-ylamine |
| 151 | rac-trans-1,2-3'S- | (S)-1-[rac-trans-(1,2)-1-(2-bromophenoxy)-1,2,3,4-tetrahydronaphthalen-2-yl]piperidin-3-ylamine |
| 152 | rac-trans-1,2-3'S- | (S)-1-[rac-trans-(1,2)-1-(2-chloro-4-methylphenoxy)-1,2,3,4-tetrahydronaphthalen-2-yl]piperidin-3-ylamine |
| 153 | rac-trans-1,2-3'S- | (S)-1-[rac-trans-(1,2)-1-(2-chloropyridin-4-yloxy)-1,2,3,4-tetrahydronaphthalen-2-yl]piperidin-3-ylamine |
| 154 | rac-trans-1,2-3'S- | (S)-1-[rac-trans-(1,2)-1-(2-chloroquinolin-8-yloxy)-1,2,3,4-tetrahydronaphthalen-2-yl]piperidin-3-ylamine |
| 155 | rac-trans-1,2-3'S- | (S)-1-[rac-trans-(1,2)-1-(2-fluoro-5-methylphenoxy)-1,2,3,4-tetrahydronaphthalen-2-yl]piperidin-3-ylamine |
| 156 | rac-trans-1,2-3'S- | (S)-1-[rac-trans-(1,2)-1-(2-methanesulfonylphenoxy)-1,2,3,4-tetrahydronaphthalen-2-yl]piperidin-3-ylamine |
| 157 | rac-trans-1,2-3'S- | (S)-1-[rac-trans-(1,2)-1-(2-methoxy-5-methylphenoxy)-1,2,3,4-tetrahydronaphthalen-2-yl]piperidin-3-ylamine |
| 158 | rac-trans-1,2-3'S- | (S)-1-[rac-trans-(1,2)-1-(2-morpholin-4-ylphenoxy)-1,2,3,4-tetrahydronaphthalen-2-yl]piperidin-3-ylamine |
| 159 | rac-trans-1,2-3'S- | (S)-1-[rac-trans-(1,2)-1-(2-trifluoromethoxyphenoxy)-1,2,3,4-tetrahydronaphthalen-2-yl]piperidin-3-ylamine |
| 160 | rac-trans-1,2-3'S- | (S)-1-[rac-trans-(1,2)-1-(3-chloro-2-methylphenoxy)-1,2,3,4-tetrahydronaphthalen-2-yl]piperidin-3-ylamine |
| 161 | rac-trans-1,2-3'S- | (S)-1-[rac-trans-(1,2)-1-(3-chloro-4-methylphenoxy)-1,2,3,4-tetrahydronaphthalen-2-yl]piperidin-3-ylamine |
| 162 | rac-trans-1,2-3'S- | (S)-1-[rac-trans-(1,2)-1-(3-chloro-5-fluorophenoxy)-1,2,3,4-tetrahydronaphthalen-2-yl]piperidin-3-ylamine |
| 163 | rac-trans-1,2-3'S- | (S)-1-[rac-trans-(1,2)-1-(3-chloro-5-methoxyphenoxy)-1,2,3,4-tetrahydronaphthalen-2-yl]piperidin-3-ylamine |
| 164 | rac-trans-1,2-3'S- | (S)-1-[rac-trans-(1,2)-1-(3-chloro-5-methoxyphenoxy)indan-2-yl]piperidin-3-ylamine |
| 165 | rac-trans-1,2-3'S- | (S)-1-[rac-trans-(1,2)-1-(3-chlorophenoxy)-1,2,3,4-tetrahydronaphthalen-2-yl]piperidin-3-ylamine |
| 166 | rac-trans-1,2-3'S- | (S)-1-[rac-trans-(1,2)-1-(3-difluoromethoxyphenoxy)-1,2,3,4-tetrahydronaphthalen-2-yl]piperidin-3-ylamine |
| 167 | rac-trans-1,2-3'S- | (S)-1-[rac-trans-(1,2)-1-(3-dimethylaminomethylphenoxy)indan-2-yl]piperidin-3-ylamine |
| 168 | rac-trans-1,2-3'S- | (S)-1-[rac-trans-(1,2)-1-(3-fluorophenoxy)-1,2,3,4-tetrahydronaphthalen-2-yl]piperidin-3-ylamine |
| 169 | rac-trans-1,2-3'S- | (S)-1-[rac-trans-(1,2)-1-(3-piperazin-1-ylphenoxy)indan-2-yl]piperidin-3-ylamine |
| 170 | rac-trans-1,2-3'S- | (S)-1-[rac-trans-(1,2)-1-(3-piperidin-1-ylmethylphenoxy)indan-2-yl]piperidin-3-ylamine |
| 171 | rac-trans-1,2-3'S- | (S)-1-[rac-trans-(1,2)-1-(4-[1,2,4]triazol-1-ylphenoxy)-1,2,3,4-tetrahydronaphthalen-2-yl]piperidin-3-ylamine |
| 172 | rac-trans-1,2-3'S- | (S)-1-[rac-trans-(1,2)-1-(4-[1,2,4]triazol-1-ylphenoxy)indan-2-yl]piperidin-3-ylamine |
| 173 | rac-trans-1,2-3'S- | (S)-1-[rac-trans-(1,2)-1-(4-bromo-3-methoxyphenoxy)-1,2,3,4-tetrahydronaphthalen-2-yl]piperidin-3-ylamine |
| 174 | rac-trans-1,2-3'S- | (S)-1-[rac-trans-(1,2)-1-(4-chloro-2-methoxyphenoxy)-1,2,3,4-tetrahydronaphthalen-2-yl]piperidin-3-ylamine |

-continued

| Example | Configuration | Name |
|---|---|---|
| 175 | rac-trans-1,2-3'S- | (S)-1-[rac-trans-(1,2)-1-(4-chlorophenoxy)-1,2,3,4-tetrahydronaphthalen-2-yl]piperidin-3-ylamine |
| 176 | rac-trans-1,2-3'S- | (S)-1-[rac-trans-(1,2)-1-(4-difluoromethoxyphenoxy)-1,2,3,4-tetrahydronaphthalen-2-yl]piperidin-3-ylamine |
| 177 | rac-trans-1,2-3'S- | (S)-1-[rac-trans-(1,2)-1-(4-dimethylaminomethylphenoxy)-1,2,3,4-tetrahydronaphthalen-2-yl]piperidin-3-ylamine |
| 178 | rac-trans-1,2-3'S- | (S)-1-[rac-trans-(1,2)-1-(4-fluoro-2-isoxazol-5-yl)phenoxy)-1,2,3,4-tetrahydronaphthalen-2-yl]piperidin-3-ylamine |
| 179 | rac-trans-1,2-3'S- | (S)-1-[rac-trans-(1,2)-1-(4-fluorophenoxy)-1,2,3,4-tetrahydronaphthalen-2-yl]piperidin-3-ylamine |
| 180 | rac-trans-1,2-3'S- | (S)-1-[rac-trans-(1,2)-1-(4-imidazol-1-ylphenoxy)-1,2,3,4-tetrahydronaphthalen-2-yl]piperidin-3-ylamine |
| 181 | rac-trans-1,2-3'S- | (S)-1-[rac-trans-(1,2)-1-(4-imidazol-1-ylphenoxy)indan-2-yl]piperidin-3-ylamine |
| 182 | rac-trans-1,2-3'S- | (S)-1-[rac-trans-(1,2)-1-(4-methanesulfonylphenoxy)-1,2,3,4-tetrahydronaphthalen-2-yl]piperidin-3-ylamine |
| 183 | rac-trans-1,2-3'S- | (S)-1-[rac-trans-(1,2)-1-(4-methylsulfanylphenoxy)-1,2,3,4-tetrahydronaphthalen-2-yl]piperidin-3-ylamine |
| 184 | rac-trans-1,2-3'S- | (S)-1-[rac-trans-(1,2)-1-(4-piperazin-1-ylphenoxy)-1,2,3,4-tetrahydronaphthalen-2-yl]piperidin-3-ylamine |
| 185 | rac-trans-1,2-3'S- | (S)-1-[rac-trans-(1,2)-1-(4-piperazin-1-ylphenoxy)indan-2-yl]piperidin-3-ylamine |
| 186 | rac-trans-1,2-3'S- | (S)-1-[rac-trans-(1,2)-1-(4-trifluoromethylphenoxy)-1,2,3,4-tetrahydronaphthalen-2-yl]piperidin-3-ylamine |
| 187 | rac-trans-1,2-3'S- | (S)-1-[rac-trans-(1,2)-1-(5,7-dimethylquinolin-8-yloxy)-1,2,3,4-tetrahydronaphthalen-2-yl]piperidin-3-ylamine |
| 188 | rac-trans-1,2-3'S- | (S)-1-[rac-trans-(1,2)-1-(5-fluoroquinolin-8-yloxy)-1,2,3,4-tetrahydronaphthalen-2-yl]piperidin-3-ylamine |
| 189 | rac-trans-1,2-3'S- | (S)-1-[rac-trans-(1,2)-1-(6-aminonaphthalen-1-yloxy)-1,2,3,4-tetrahydronaphthalen-2-yl]piperidin-3-ylamine |
| 190 | rac-trans-1,2-3'S- | (S)-1-[rac-trans-(1,2)-1-(6-chloropyridin-3-yloxy)-1,2,3,4-tetrahydronaphthalen-2-yl]piperidin-3-ylamine |
| 191 | rac-trans-1,2-3'S- | (S)-1-[rac-trans-(1,2)-1-(pyridin-4-yloxy)-1,2,3,4-tetrahydronaphthalen-2-yl]piperidin-3-ylamine |
| 192 | rac-trans-1,2-3'S- | (S)-1-[rac-trans-(1,2)-1-(quinolin-3-yloxy)-1,2,3,4-tetrahydronaphthalen-2-yl]piperidin-3-ylamine |
| 193 | rac-trans-1,2-3'S- | (S)-1-[rac-trans-(1,2)-1-(quinolin-5-yloxy)-1,2,3,4-tetrahydronaphthalen-2-yl]piperidin-3-ylamine |
| 194 | rac-trans-1,2-3'S- | (S)-1-[rac-trans-(1,2)-1-(quinolin-5-yloxy)indan-2-yl]piperidin-3-ylamine |
| 195 | trans-1S,2S-2'S- | (S)-1-[trans-(1S,2S)-4,6-dichloro-1-(4-methanesulfonylphenoxy)indan-2-yl]-2-pyrrolidin-1-ylmethylpyrrolidine |
| 196 | trans-1S,2S-3'S- | (S)-1-[trans-(1S,2S)-4,6-dichloro-1-(4-methanesulfonylphenoxy)indan-2-yl]-3-fluoropyrrolidine |
| 197 | trans-1S,2S-3'S- | (S)-1-[trans-(1S,2S)-4,6-dichloro-1-(4-methanesulfonylphenoxy)indan-2-yl]-3-methylpiperazine |
| 198 | trans-1S,2S-3'S- | (S)-1-[trans-(1S,2S)-4,6-dichloro-1-(4-methanesulfonylphenoxy)indan-2-yl]pyrrolidin-3-ol |
| 199 | trans-1S,2S-3'S- | (S)-1-[trans-(1S,2S)-4,6-dichloro-1-(4-methanesulfonylphenoxy)indan-2-yl]pyrrolidin-3-ylamine |
| 200 | trans-1S,2S-3'S- | (S)-1-{(1S,2S)-4,6-dichloro-1-[4-(3,5-dimethyl-[1,2,4]triazol-4-yl)-2-fluorophenoxy]indan-2-yl}pyrrolidin-3-ol |
| 201 | rac-trans-1,2-3'S- | (S)-1-{rac-trans-(1,2)-1-[3-(2-aminoethyl)-1H-indol-5-yloxy]-1,2,3,4-tetrahydronaphthalen-2-yl}piperidin-3-ylamine |
| 202 | rac-trans-1,2-3'S- | (S)-1-{rac-trans-(1,2)-1-[4-(2-methoxyethyl)phenoxy]-1,2,3,4-tetrahydronaphthalen-2-yl}piperidin-3-ylamine |
| 203 | rac-trans-1,2-3'S- | (S)-1-{rac-trans-(1,2)-1-[4-bromo-2-(1H-pyrazol-3-yl)phenoxy]-1,2,3,4-tetrahydronaphthalen-2-yl}piperidin-3-ylamine |
| 204 | rac-trans-1,2-3'S- | (S)-1-{rac-trans-(1,2)-1-[4-bromo-2-(1H-pyrazol-3-yl)phenoxy]indan-2-yl}piperidin-3-ylamine |
| 205 | rac-trans-1,2-3'S- | (S)-1-{rac-trans-(1,2)-1-[4-fluoro-2-(1H-pyrazol-3-yl)phenoxy]-1,2,3,4-tetrahydronaphthalen-2-yl}piperidin-3-ylamine |
| 206 | trans-1S,2S-3'S- | (S)-1-{trans-(1S,2S)-4,6-dichloro-1-[4-(3,5-dimethyl-[1,2,4]triazol-4-yl)phenoxy]indan-2-yl}pyrrolidin-3-ol |
| 207 | trans-1S,2S-3'S- | (S)-1-{trans-(1S,2S)-4,6-dichloro-1-[4-(3,5-dimethyl-[1,2,4]triazol-4-yl)phenoxy]indan-2-yl}pyrrolidin-3-ylamine |
| 208 | trans-1S,2S-3'S- | (S)-2-[(S)-4-(S)-chloro-6-chloro-1-(4-methanesulfonylphenoxy)indan-2-yl]octahydropyrrolo[1,2-a]pyrazine |

-continued

| Example | Configuration | Name |
|---|---|---|
| 209 | trans-1S,2S-2'R-5'S | (S)-2-[trans-(1S,2S)-4,6-dichloro-1-(4-methanesulfonylphenoxy)indan-2-yl]-2,5-diazabicyclo[2.2.1]heptane |
| 210 | trans-1S,2S-3'R- | (S)-3-{3-[(1S,2S)-6-chloro-4-fluoro-2-((R)-3-hydroxypyrrolidin-1-yl)indan-1-yloxy]-4-fluorophenyl}-4-isopropyloxazolidin-2-one |
| 211 | trans-1S,2S-3'R- | (S)-3-{4-chloro-3-[(1S,2S)-6-chloro-4-fluoro-2-((R)-3-hydroxypyrrolidin-1-yl)indan-1-yloxy]phenyl}-4-isopropyloxazolidin-2-one |
| 212 | rac-trans-1,2- | [3-(rac-trans-(1,2)-2-diethylaminoindan-1-yloxy)phenyl]-urea |
| 213 | rac-trans-1,2- | [3-methoxy-2-(rac-trans-(1,2)-2-morpholin-4-yl-1,2,3,4-tetrahydronaphthalen-1-yloxy)phenyl]acetonitrile |
| 214 | rac-trans-1,2-rac-3'- | [rac-trans-(1,2)-1-(1H-indol-4-yloxy)indan-2-yl]methylpiperidin-3-ylamine |
| 215 | rac-trans-1,2- | [rac-trans-(1,2)-1-(2-fluoro-6-methoxyphenoxy)indan-2-yl]methylpiperidin-4-ylamine |
| 216 | rac-trans-1,2- | [rac-trans-(1,2)-4,6-dichloro-1-(4-imidazol-1-ylphenoxy)indan-2-yl]dimethylamine |
| 217 | rac-trans-1,2 | [rac-trans-(1,2)-4,6-dichloro-1-(4-methanesulfonylphenoxy)indan-2-ylmethyl]dimethylamine |
| 218 | trans-1S,2S | [trans-(1S,2S)-4,6-dichloro-1-(4-methanesulfonylphenoxy)indan-2-yl]-(2-methoxyethyl)-methylamine |
| 219 | trans-1S,2S-3'R- | {(R)-1-[trans-(1S,2S)-1-(4-methanesulfonylphenoxy)indan-2-yl]piperidin-3-yl}-(2,2,2-trifluoroethyl)amine |
| 220 | trans-1S,2S-3'R- | {(R)-1-[trans-(1S,2S)-1-(4-methanesulfonylphenoxy)indan-2-yl]piperidin-3-yl}-(3,3,3-trifluoropropyl)amine |
| 221 | trans-1S,2S-3'R- | {(R)-1-[trans-(1S,2S)-4,6-dichloro-1-(4-[1,2,4]triazol-1-ylphenoxy)indan-2-yl]piperidin-3-yl}-(3,3,3-trifluoropropyl)amine |
| 222 | trans-1S,2S-3'R- | {(R)-1-[trans-(1S,2S)-4,6-dichloro-1-(4-methanesulfonylphenoxy)indan-2-yl]piperidin-3-yl}-(2-fluoroethyl)amine |
| 223 | trans-1S,2S-3'R- | {(R)-1-[trans-(1S,2S)-4,6-dichloro-1-(4-methanesulfonylphenoxy)indan-2-yl]piperidin-3-yl}-(3,3,3-trifluoropropyl)amine |
| 224 | trans-1S,2S-3'R- | {(R)-1-[trans-(1S,2S)-4,6-dichloro-1-(4-methanesulfonylphenoxy)indan-2-yl]piperidin-3-yl}-dimethylamine |
| 225 | trans-1S,2S-3'R- | {(R)-1-[trans-(1S,2S)-4,6-dichloro-1-(4-methanesulfonylphenoxy)indan-2-yl]piperidin-3-ylamino}acetonitrile |
| 226 | trans-1S,2S-3'R- | {(R)-1-[trans-(1S,2S)-4,6-dichloro-1-(4-methanesulfonylphenoxy)indan-2-yl]pyrrolidin-3-yl}-(2-fluoroethyl)amine |
| 227 | trans-1S,2S-3'R- | {(R)-1-[trans-(1S,2S)-4,6-dichloro-1-(4-methanesulfonylphenoxy)indan-2-yl]pyrrolidin-3-yl}methanol |
| 228 | trans-1S,2S-2'S | {(S)-1-[trans-(1S,2S)-4,6-dichloro-1-(4-methanesulfonylphenoxy)indan-2-yl]pyrrolidin-2-yl}methanol |
| 229 | rac-trans-1,2-3'R- | {2-[rac-trans-(1,2)-2-((R)-3-aminopiperidin-1-yl)-1,2,3,4-tetrahydronaphthalen-1-yloxy]-3-methoxyphenyl}acetonitrile |
| 230 | rac-trans-1,2-3'R- | {3-[rac-trans-(1,2)-2-((R)-3-aminopiperidin-1-yl)-1,2,3,4-tetrahydronaphthalen-1-yloxy]phenyl}acetonitrile |
| 231 | rac-trans-1,2-3'R- | {3-[rac-trans-(1,2)-2-((R)-3-aminopiperidin-1-yl)indan-1-yloxy]phenyl}urea |
| 232 | rac-trans-1,2-3'S- | {3-[rac-trans-(1,2)-2-((S)-3-aminopiperidin-1-yl)indan-1-yloxy]phenyl}urea |
| 233 | rac-trans-1,2-rac-3'- | {3-[rac-trans-(1,2)-2-(3-aminomethylpyrrolidin-1-yl)indan-1-yloxy]phenyl}urea |
| 234 | rac-trans-1,2-rac-3'- | {3-[rac-trans-(1,2)-2-(3-aminopyrrolidin-1-yl)indan-1-yloxy]phenyl}urea |
| 235 | rac-trans-1,2- | {3-[rac-trans-(1,2)-2-(4-aminomethylpiperidin-1-yl)indan-1-yloxy]phenyl}urea |
| 236 | trans-1S,2S-3'R- | {3-chloro-4-[(1S,2S)-4,6-dichloro-2-((R)-3-hydroxypyrrolidin-1-yl)indan-1-yloxy]phenylcarbamoyloxy}acetic acid |
| 237 | rac-trans-1,2-3'R- | {4-[rac-trans-(1,2)-2-((R)-3-aminopiperidin-1-yl)-1,2,3,4-tetrahydronaphthalen-1-yloxy]phenyl}carbamic acid benzyl ester |

-continued

| Example | Configuration | Name |
|---|---|---|
| 238 | rac-trans-1,2-3'R- | {4-[rac-trans-(1,2)-2-((R)-3-aminopiperidin-1-yl)indan-1-yloxy]phenyl}carbamic acid benzyl ester |
| 239 | rac-trans-1,2-3'S- | {4-[rac-trans-(1,2)-2-((S)-3-aminopiperidin-1-yl)-1,2,3,4-tetrahydronaphthalen-1-yloxy]phenyl}carbamic acid benzyl ester |
| 240 | rac-trans-1,2-rac-3'- | {4-[rac-trans-(1,2)-2-(3-aminomethylpyrrolidin-1-yl)indan-1-yloxy]phenyl}carbamic acid benzyl ester |
| 241 | rac-trans-1,2-rac-3'- | {4-[rac-trans-(1,2)-2-(3-aminopyrrolidin-1-yl)indan-1-yloxy]phenyl}carbamic acid benzyl ester |
| 242 | rac-trans-1,2- | {4-[rac-trans-(1,2)-6-fluoro-1-(4-methanesulfonylphenoxy)indan-2-yl]piperazin-1-yl}acetonitrile |
| 243 | trans-1S,2S | {trans-(1S,2S)-4,6-dichloro-1-[4-(3,5-dimethyl-[1,2,4]triazol-4-yl)phenoxy]indan-2-yl}-(2-methoxyethyl)-methylamine |
| 244 | rac-trans-1,2- | 1-(4-methanesulfonylphenoxy)indan-2-ylmethyl]-dimethylamine |
| 245 | trans-1S,2S- | 1-[(1S,2S)-4,6-dichloro-1-(2-methanesulfonylphenoxy)indan-2-yl]azetidine |
| 246 | trans-1S,2S- | 1-[(1S,2S)-4,6-dichloro-1-(2-methanesulfonylphenoxy)indan-2-yl]piperazine |
| 247 | trans-1S,2S- | 1-[(1S,2S)-4,6-dichloro-1-(2-methanesulfonylphenoxy)indan-2-yl]pyrrolidine |
| 248 | trans-1S,2S- | 1-[(1S,2S)-4,6-dichloro-1-(3-tetrazol-1-ylphenoxy)indan-2-yl]piperazine |
| 249 | trans-1S,2S-rac-3'- | 1-[(1S,2S)-4,6-dichloro-1-(4-methanesulfonylphenoxy)indan-2-yl]-3-methanesulfonylpyrrolidine |
| 250 | trans-1S,2S- | 1-[(1S,2S)-4,6-dichloro-1-(4-methanesulfonylphenoxy)indan-2-yl]-4,4-difluoropiperidine |
| 251 | rac-trans-1,2- | 1-[1-(2-chloro-4-nitrophenoxy)indan-2-yl]pyrrolidine |
| 252 | rac-trans-1,2- | 1-[1-(4-methanesulfonylphenoxy)-2-methylindan-2-yl]pyrrolidine |
| 253 | rac-trans-4,5- | 1-[1,3-dichloro-4-(4-methanesulfonylphenoxy)-4,5,6,7-tetrahydrobenzo[c]thiophen-5-yl]pyrrolidine |
| 254 | rac-trans-1,2- | 1-[3-(rac-trans-(1,2)-2-pyrrolidin-1-ylindan-1-yloxy)phenyl]-1,3-dihydroimidazol-2-one |
| 255 | rac-trans-1,2- | 1-[3-(rac-trans-(1,2)-2-pyrrolidin-1-ylindan-1-yloxy)phenyl]pyrrolidin-2-one |
| 256 | rac-trans-1,2- | 1-[3-(rac-trans-(1,2)-2-pyrrolidin-1-ylindan-1-yloxy)phenyl]pyrrolidine-2,5-dione |
| 257 | rac-trans-1,2- | 1-[3-(rac-trans-(1,2)-4,6-dichloro-2-piperazin-1-ylindan-1-yloxy)phenyl]-3-methyl-1,3-dihydroimidazol-2-one |
| 258 | rac-trans-1,2- | 1-[3-(rac-trans-(1,2)-4,6-dichloro-2-piperazin-1-ylindan-1-yloxy)phenyl]-3-methylimidazolidin-2-one |
| 259 | trans-1S,2S- | 1-[4-((1S,2S)-2-azetidin-1-yl-4,6-dichloroindan-1-yloxy)phenyl]pyrrolidin-2-one |
| 260 | trans-1S,2S- | 1-[4-((1S,2S)-4,6-dichloro-2-pyrrolidin-1-ylindan-1-yloxy)phenyl]pyrrolidin-2-one |
| 261 | rac-cis-1,2 | 1-[rac-cis-(1,2)-1-(4-methanesulfonylphenoxy)indan-2-yl]-1H-imidazole |
| 262 | rac-trans-1,2-rac-3'- | 1-[rac-trans-(1,2)-1-(1H-indol-6-yloxy)indan-2-yl]pyrrolidin-3-ylamine |
| 263 | rac-trans-1,2 | 1-[rac-trans-(1,2)-1-(2,3-dichloro-4-methanesulfonylphenoxy)indan-2-yl]pyrrolidine |
| 264 | rac-trans-1,2- | 1-[rac-trans-(1,2)-1-(2,6-dichloro-4-methanesulfonylphenoxy)indan-2-yl]pyrrolidine |
| 265 | rac-trans-1,2 | 1-[rac-trans-(1,2)-1-(2-chloro-4-methanesulfonylphenoxy)indan-2-yl]pyrrolidine |
| 266 | rac-trans-1,2-rac-3'- | 1-[rac-trans-(1,2)-1-(2-fluoro-6-methoxyphenoxy)indan-2-yl]pyrrolidin-3-ylamine |
| 267 | rac-trans-1,2-rac-3'- | 1-[rac-trans-(1,2)-1-(2-tert-butyl-4-ethylphenoxy)indan-2-yl]pyrrolidin-3-ylamine |
| 268 | rac-trans-1,2 | 1-[rac-trans-(1,2)-1-(3-chloro-4-methanesulfonylphenoxy)indan-2-yl]pyrrolidine |
| 269 | rac-trans-1,2- | 1-[rac-trans-(1,2)-1-(3-methanesulfonylphenoxy)indan-2-yl]pyrrolidine |
| 270 | rac-trans-1,2-rac-3'- | 1-[rac-trans-(1,2)-1-(3-piperazin-1-ylphenoxy)indan-2-yl]pyrrolidin-3-ylamine |
| 271 | rac-trans-1,2- | 1-[rac-trans-(1,2)-1-(4-methanesulfonyl-3-methylphenoxy)indan-2-yl]pyrrolidine |
| 272 | rac-trans-1,2- | 1-[rac-trans-(1,2)-1-(4-methanesulfonylphenoxy)indan-2-yl]piperazine |
| 273 | rac-trans-1,2- | 1-[rac-trans-(1,2)-1-(4-methanesulfonylphenoxy)indan-2-yl]pyrrolidine |

-continued

| Example | Configuration | Name |
|---|---|---|
| 274 | rac-trans-1,2 | 1-[rac-trans-(1,2)-1-(4-methanesulfonylphenoxy)indan-2-ylmethyl]pyrrolidine |
| 275 | rac-trans-1,2-rac-3'- | 1-[rac-trans-(1,2)-1-(quinolin-4-yloxy)indan-2-yl]pyrrolidin-3-ylamine |
| 276 | rac-trans-1,2- | 1-[rac-trans-(1,2)-4,6-dichloro-1-(4-[1,2,4]triazol-1-ylphenoxy)indan-2-yl]piperazine |
| 277 | rac-trans-1,2- | 1-[rac-trans-(1,2)-4,6-dichloro-1-(4-methanesulfonylphenoxy)indan-2-yl]-[1,4]diazepane |
| 278 | rac-trans-1,2 | 1-[rac-trans-(1,2)-4,6-dichloro-1-(4-methanesulfonylphenoxy)indan-2-yl]-1H-imidazole |
| 279 | rac-trans-1,2- | 1-[rac-trans-(1,2)-4,6-dichloro-1-(4-methanesulfonylphenoxy)indan-2-yl]-4-methyl-[1,4]diazepane |
| 280 | rac-trans-1,2 | 1-[rac-trans-(1,2)-4,6-dichloro-1-(4-methanesulfonylphenoxy)indan-2-ylmethyl]pyrrolidine |
| 281 | rac-trans-1,2- | 1-[rac-trans-(1,2)-4-chloro-6-fluoro-1-(4-methanesulfonyl-3-methylphenoxy)indan-2-yl]piperazine |
| 282 | rac-trans-1,2- | 1-[rac-trans-(1,2)-4-chloro-6-fluoro-1-(4-methanesulfonyl-3-methylphenoxy)indan-2-yl]pyrrolidine |
| 283 | rac-trans-1,2- | 1-[rac-trans-(1,2)-4-chloro-6-fluoro-1-(4-methanesulfonylphenoxy)indan-2-yl]piperazine |
| 284 | rac-trans-1,2- | 1-[rac-trans-(1,2)-4-chloro-6-fluoro-1-(4-methanesulfonylphenoxy)indan-2-yl]pyrrolidine |
| 285 | rac-trans-1,2- | 1-[rac-trans-(1,2)-4-fluoro-1-(4-methanesulfonylphenoxy)indan-2-yl]pyrrolidine |
| 286 | rac-trans-1,2- | 1-[rac-trans-(1,2)-5,6-dichloro-1-(4-methanesulfonylphenoxy)indan-2-yl]-[1,4]diazepane |
| 287 | rac-trans-1,2- | 1-[rac-trans-(1,2)-5,7-dichloro-1-(4-methanesulfonylphenoxy)indan-2-yl]piperazine |
| 288 | rac-trans-1,2- | 1-[rac-trans-(1,2)-6,7-dichloro-1-(4-methanesulfonylphenoxy)indan-2-yl]-[1,4]diazepane |
| 289 | rac-trans-1,2- | 1-[rac-trans-(1,2)-6-chloro-1-(4-methanesulfonylphenoxy)indan-2-yl]piperazine |
| 290 | rac-trans-1,2- | 1-[rac-trans-(1,2)-6-chloro-4-fluoro-1-(3-methyl-4-trifluoromethanesulfonylphenoxy)indan-2-yl]piperazine |
| 291 | rac-trans-1,2- | 1-[rac-trans-(1,2)-6-chloro-4-fluoro-1-(4-methanesulfonyl-3-methylphenoxy)indan-2-yl]pyrrolidine |
| 292 | rac-trans-1,2- | 1-[rac-trans-(1,2)-6-chloro-4-fluoro-1-(4-methanesulfonylphenoxy)indan-2-yl]piperazine |
| 293 | rac-trans-1,2- | 1-[rac-trans-(1,2)-6-chloro-4-fluoro-1-(4-methanesulfonylphenoxy)indan-2-yl]pyrrolidine |
| 294 | rac-trans-1,2- | 1-[rac-trans-(1,2)-6-fluoro-1-(4-methanesulfonylphenoxy)indan-2-yl]piperazine |
| 295 | trans-1S,2S | 1-[trans-(1S,2S)-4,6-dichloro-1-(2-chloro-4-methanesulfonylphenoxy)indan-2-yl]-[1,4]diazepane |
| 296 | trans-1S,2S | 1-[trans-(1S,2S)-4,6-dichloro-1-(4-[1,2,4]triazol-1-ylphenoxy)indan-2-yl]-4-methylpiperazine |
| 297 | trans-1S,2S | 1-[trans-(1S,2S)-4,6-dichloro-1-(4-imidazol-1-ylphenoxy)indan-2-yl]-4-methylpiperazine |
| 298 | trans-1S,2S- | 1-[trans-(1S,2S)-4,6-dichloro-1-(4-methanesulfonylphenoxy)indan-2-yl]-[1,4]diazepane |
| 299 | trans-1S,2S-3'epimer1- | 1-[trans-(1S,2S)-4,6-dichloro-1-(4-methanesulfonylphenoxy)indan-2-yl]-3-propylpiperidin-3-ylamine |
| 300 | trans-1S,2S-3'epimer2- | 1-[trans-(1S,2S)-4,6-dichloro-1-(4-methanesulfonylphenoxy)indan-2-yl]-3-propylpiperidin-3-ylamine |
| 301 | trans-1S,2S-rac-3'- | 1-[trans-(1S,2S)-4,6-dichloro-1-(4-methanesulfonylphenoxy)indan-2-yl]-3-trifluoromethylpiperazine |
| 302 | trans-1S,2S-rac-3'- | 1-[trans-(1S,2S)-4,6-dichloro-1-(4-methanesulfonylphenoxy)indan-2-yl]-3-trifluoromethylpyrrolidin-3-ylamine |
| 303 | trans-1S,2S | 1-[trans-(1S,2S)-4,6-dichloro-1-(4-methanesulfonylphenoxy)indan-2-yl]-4-(2-fluoroethyl)-[1,4]diazepane |
| 304 | trans-1S,2S | 1-[trans-(1S,2S)-4,6-dichloro-1-(4-methanesulfonylphenoxy)indan-2-yl]-4-(2-methoxyethyl)-[1,4]diazepane |
| 305 | trans-1S,2S | 1-[trans-(1S,2S)-4,6-dichloro-1-(4-methanesulfonylphenoxy)indan-2-yl]-4-methyl-[1,4]diazepane |
| 306 | trans-1S,2S | 1-[trans-(1S,2S)-4,6-dichloro-1-(4-methanesulfonylphenoxy)indan-2-yl]-4-methylpiperazine |
| 307 | trans-1S,2S | 1-[trans-(1S,2S)-4,6-dichloro-1-(4-methanesulfonylphenoxy)indan-2-yl]azetidin-3-ol |

-continued

| Example | Configuration | Name |
|---|---|---|
| 308 | trans-1S,2S | 1-[trans-(1S,2S)-4,6-dichloro-1-(4-methanesulfonylphenoxy)indan-2-yl]piperazine |
| 309 | trans-1S,2S | 1-{(1S,2S)-4,6-dichloro-1-[4-fluoro-2-(1H-pyrazol-3-yl)phenoxy]indan-2-yl}piperazine |
| 310 | trans-1S,2S-3'R- | 1-{2-chloro-5-[(1S,2S)-4,6-dichloro-2-((R)-3-hydroxypyrrolidin-1-yl)indan-1-yloxy]phenyl}-3-methyl-1,3-dihydroimidazol-2-one |
| 311 | trans-1S,2S-3'R- | 1-{2-chloro-5-[(1S,2S)-4,6-dichloro-2-((R)-3-hydroxypyrrolidin-1-yl)indan-1-yloxy]phenyl}-3-methylimidazolidin-2-one |
| 312 | trans-1S,2S-3'R- | 1-{3-[(1S,2S)-4,6-dichloro-2-((R)-3-hydroxypyrrolidin-1-yl)indan-1-yloxy]-2-methylphenyl}-3-methyl-1,3-dihydroimidazol-2-one |
| 313 | trans-1S,2S-3'R- | 1-{3-[(1S,2S)-4,6-dichloro-2-((R)-3-hydroxypyrrolidin-1-yl)indan-1-yloxy]-4-fluorophenyl}-3-methyl-1,3-dihydroimidazol-2-one |
| 314 | trans-1S,2S-3'R- | 1-{3-[(1S,2S)-4,6-dichloro-2-((R)-3-hydroxypyrrolidin-1-yl)indan-1-yloxy]-4-fluorophenyl}-3-methylimidazolidin-2-one |
| 315 | trans-1S,2S-3'R- | 1-{3-[(1S,2S)-4,6-dichloro-2-((R)-3-hydroxypyrrolidin-1-yl)indan-1-yloxy]phenyl}pyrrolidin-2-one |
| 316 | trans-1S,2S-3'R- | 1-{3-[(1S,2S)-4,6-dichloro-2-((R)-3-hydroxypyrrolidin-1-yl)indan-1-yloxy]phenyl}pyrrolidine-2,5-dione |
| 317 | trans-1S,2S-3'R- | 1-{3-[(1S,2S)-4,6-difluoro-2-((R)-3-hydroxypyrrolidin-1-yl)indan-1-yloxy]-4-fluorophenyl}-3-methyl-1,3-dihydroimidazol-2-one |
| 318 | trans-1S,2S-3'R- | 1-{3-[(1S,2S)-6-chloro-4-fluoro-2-((R)-3-hydroxypyrrolidin-1-yl)indan-1-yloxy]-4-fluorophenyl}-3-methyl-1,3-dihydroimidazol-2-one |
| 319 | trans-1S,2S-3'R- | 1-{3-[trans-(1S,2S)-4,6-dichloro-2-((R)-3-hydroxypyrrolidin-1-yl)indan-1-yloxy]phenyl}-3-methylimidazolidin-2-one |
| 320 | trans-1S,2S-3'R- | 1-{3-[trans-(1S,2S)-6-chloro-4-fluoro-2-((R)-3-hydroxypyrrolidin-1-yl)indan-1-yloxy]phenyl}-3-methylimidazolidin-2-one |
| 321 | trans-1S,2S-3'R- | 1-{3-chloro-4-[(1S,2S)-4,6-dichloro-2-((R)-3-hydroxypyrrolidin-1-yl)indan-1-yloxy]phenyl}pyrrolidin-2-one |
| 322 | trans-1S,2S-3'R- | 1-{3-chloro-4-[(1S,2S)-4,6-dichloro-2-((R)-3-hydroxypyrrolidin-1-yl)indan-1-yloxy]phenyl}pyrrolidine-2,5-dione |
| 323 | trans-1S,2S-3'R- | 1-{4-[(1S,2S)-4,6-dichloro-2-((R)-3-hydroxypyrrolidin-1-yl)indan-1-yloxy]-3-fluorophenyl}-1,3-dihydroimidazol-2-one |
| 324 | trans-1S,2S-3'R- | 1-{4-[(1S,2S)-4,6-dichloro-2-((R)-3-hydroxypyrrolidin-1-yl)indan-1-yloxy]-3-fluorophenyl}-2,6-dimethyl-1H-pyridin-4-one |
| 325 | trans-1S,2S-3'R- | 1-{4-[(1S,2S)-4,6-dichloro-2-((R)-3-hydroxypyrrolidin-1-yl)indan-1-yloxy]phenyl}-1,3-dihydroimidazol-2-one |
| 326 | rac-trans-1,2-3'R- | 1-{4-[rac-trans-(1,2)-2-((R)-3-aminopiperidin-1-yl)-1,2,3,4-tetrahydronaphthalen-1-yloxy]phenyl}pyrrolidine-2,5-dione |
| 327 | rac-trans-1,2-3'S- | 1-{4-[rac-trans-(1,2)-2-((S)-3-aminopiperidin-1-yl)-1,2,3,4-tetrahydronaphthalen-1-yloxy]-3,5-difluorophenyl}propan-1-one |
| 328 | rac-trans-1,2-3'S- | 1-{4-[rac-trans-(1,2)-2-((S)-3-aminopiperidin-1-yl)-1,2,3,4-tetrahydronaphthalen-1-yloxy]phenyl}pyrrolidine-2,5-dione |
| 329 | trans-1S,2S-3'R- | 1-{4-[trans-(1S,2S)-4,6-dichloro-2-((R)-3-hydroxypyrrolidin-1-yl)indan-1-yloxy]-3-fluorophenyl}-3-methyl-1,3-dihydroimidazol-2-one |
| 330 | trans-1S,2S-3'R- | 1-{4-[trans-(1S,2S)-4,6-dichloro-2-((R)-3-hydroxypyrrolidin-1-yl)indan-1-yloxy]-3-fluorophenyl}-3-methylimidazolidin-2-one |
| 331 | trans-1S,2S-3'R- | 1-{4-[trans-(1S,2S)-4,6-dichloro-2-((R)-3-hydroxypyrrolidin-1-yl)indan-1-yloxy]phenyl}-3-methyl-1,3-dihydroimidazol-2-one |
| 332 | trans-1S,2S-3'R- | 1-{4-[trans-(1S,2S)-4,6-dichloro-2-((R)-3-hydroxypyrrolidin-1-yl)indan-1-yloxy]phenyl}-3-methylimidazolidin-2-one |
| 333 | trans-1S,2S-3'R- | 1-{4-[trans-(1S,2S)-4,6-dichloro-2-((R)-3-hydroxypyrrolidin-1-yl)indan-1-yloxy]phenyl}pyrrolidin-2-one |
| 334 | trans-1S,2S-3'R- | 1-{4-[trans-(1S,2S)-4,6-dichloro-2-((R)-3-hydroxypyrrolidin-1-yl)indan-1-yloxy]phenyl}pyrrolidine-2,5-dione |

-continued

| Example | Configuration | Name |
|---|---|---|
| 335 | trans-1S,2S-3'R- | 1-{4-chloro-3-[(1S,2S)-4,6-dichloro-2-((R)-3-hydroxypyrrolidin-1-yl)indan-1-yloxy]phenyl}-3-methyl-1,3-dihydroimidazol-2-one |
| 336 | trans-1S,2S-3'R- | 1-{4-chloro-3-[(1S,2S)-4,6-dichloro-2-((R)-3-hydroxypyrrolidin-1-yl)indan-1-yloxy]phenyl}pyrrolidin-2-one |
| 337 | trans-1S,2S-3'R- | 1-{4-chloro-3-[(1S,2S)-4,6-dichloro-2-((R)-3-hydroxypyrrolidin-1-yl)indan-1-yloxy]phenyl}pyrrolidine-2,5-dione |
| 338 | trans-1S,2S-3'R- | 1-{4-chloro-3-[(1S,2S)-4,6-difluoro-2-((R)-3-hydroxypyrrolidin-1-yl)indan-1-yloxy]phenyl}-3-methyl-1,3-dihydroimidazol-2-one |
| 339 | trans-1S,2S-3'R- | 1-{4-chloro-3-[(1S,2S)-6-chloro-4-fluoro-2-((R)-3-hydroxypyrrolidin-1-yl)indan-1-yloxy]phenyl}-3-methyl-1,3-dihydroimidazol-2-one |
| 340 | trans-1S,2S-3'R- | 1-{4-chloro-3-[(1S,2S)-6-chloro-4-fluoro-2-((R)-3-hydroxypyrrolidin-1-yl)indan-1-yloxy]phenyl}-3-methylimidazolidin-2-one |
| 341 | trans-1S,2S-3'R- | 1-{4-chloro-3-[(1S,2S)-6-chloro-4-fluoro-2-((R)-3-hydroxypyrrolidin-1-yl)indan-1-yloxy]phenyl}pyrrolidin-2-one |
| 342 | rac-trans-1,2-rac-3'- | 1-{rac-trans-(1,2)-1-[4-(2-methoxyethyl)phenoxy]indan-2-yl}pyrrolidin-3-ylamine |
| 343 | rac-trans-1,2- | 1-{rac-trans-(1,2)-1-[4-bromo-2-(1H-pyrazol-3-yl)phenoxy]indan-2-yl}piperidin-4-ylamine |
| 344 | trans-1S,2S- | 1-{trans-(1S,2S)-4,6-dichloro-1-[2-chloro-4-(3,5-dimethyl-[1,2,4]triazol-4-yl)phenoxy]indan-2-yl}-[1,4]diazepane |
| 345 | trans-1S,2S | 1-{trans-(1S,2S)-4,6-dichloro-1-[2-chloro-4-(3,5-dimethyl-[1,2,4]triazol-4-yl)phenoxy]indan-2-yl}-4-methyl-[1,4]diazepane |
| 346 | trans-1S,2S | 1-{trans-(1S,2S)-4,6-dichloro-1-[4-(3,5-dimethyl-[1,2,4]triazol-4-yl)-2-fluorophenoxy]indan-2-yl}-4-methyl-[1,4]diazepane |
| 347 | trans-1S,2S | 1-{trans-(1S,2S)-4,6-dichloro-1-[4-(3,5-dimethyl-[1,2,4]triazol-4-yl)phenoxy]indan-2-yl}-[1,4]diazepane |
| 348 | trans-1S,2S- | 1-{trans-(1S,2S)-4,6-dichloro-1-[4-(3,5-dimethyl-[1,2,4]triazol-4-yl)phenoxy]indan-2-yl}-4-(2-methoxyethyl)-[1,4]diazepane |
| 349 | trans-1S,2S- | 1-{trans-(1S,2S)-4,6-dichloro-1-[4-(3,5-dimethyl-[1,2,4]triazol-4-yl)phenoxy]indan-2-yl}-4-methyl-[1,4]diazepane |
| 350 | trans-1S,2S- | 1-{trans-(1S,2S)-4,6-dichloro-1-[4-(3,5-dimethylisoxazol-4-yl)phenoxy]indan-2-yl}-4-(2-methoxyethyl)-[1,4]diazepane |
| 351 | trans-1S,2S- | 1-Cyclopropyl-4-[trans-(1S,2S)-4,6-dichloro-1-(4-methanesulfonylphenoxy)indan-2-yl]piperazine |
| 352 | rac-trans-1,2- | 1-methyl-3-[3-(rac-trans-(1,2)-2-pyrrolidin-1-ylindan-1-yloxy)phenyl]-1,3-dihydroimidazol-2-one |
| 353 | trans-1S,2S- | 2-((1S,2S)-2-azetidin-1-yl-4,6-dichloroindan-1-yloxy)-5-chlorobenzamide |
| 354 | trans-1S,2S-3'R- | 2,2,2-trifluoro-N-{(R)-1-[trans-(1S,2S)-1-(4-methanesulfonylphenoxy)indan-2-yl]piperidin-3-yl}acetamide |
| 355 | rac-trans-1,2- | 2,3-dichloro-4-(rac-trans-(1,2)-2-diethylaminoindan-1-yloxy)benzenesulfonamide |
| 356 | rac-trans-1,2- | 2,3-dichloro-4-(rac-trans-(1,2)-2-dimethylaminoindan-1-yloxy)benzenesulfonamide |
| 357 | rac-trans-1,2- | 2,3-dichloro-4-(rac-trans-(1,2)-2-pyrrolidin-1-ylindan-1-yloxy)benzenesulfonamide |
| 358 | rac-trans-1,2- | 2,3-dichloro-4-(rac-trans-(1,2)-4,6-dichloro-2-morpholin-4-ylindan-1-yloxy)benzenesulfonamide |
| 359 | rac-trans-1,2-3'R- | 2,3-dichloro-4-[rac-trans-(1,2)-2-((R)-3-methoxypyrrolidin-1-yl)indan-1-yloxy]benzenesulfonamide |
| 360 | rac-trans-1,2-rac-3'- | 2,3-dichloro-4-[rac-trans-(1,2)-2-(methylpiperidin-3-ylamino)indan-1-yloxy]benzenesulfonamide |
| 361 | trans-1S,2S-rac-3'- | 2,3-dichloro-4-[trans-(1S,2S)-2-(3-hydroxy-piperidin-1-yl)indan-1-yloxy]benzenesulfonamide |
| 362 | rac-trans-1,2- | 2,3-dichloro-N,N-dimethyl-4-(rac-trans-(1,2)-2-pyrrolidin-1-ylindan-1-yloxy)benzenesulfonamide |
| 363 | rac-trans-1,2- | 2-[3-(rac-trans-(1,2)-2-pyrrolidin-1-ylindan-1-yloxy)phenyl]isothiazolidine 1,1-dioxide |
| 364 | rac-trans-1,2- | 2-[4-(rac-trans-(1,2)-2-pyrrolidin-1-ylindan-1-yloxy)phenyl]thiazole |
| 365 | rac-trans-1,2-3'R- | 2-[rac-trans-(1,2)-2-((R)-3-aminopiperidin-1-yl)-1,2,3,4-tetrahydronaphthalen-1-yloxy]-5-chlorobenzamide |

-continued

| Example | Configuration | Name |
|---|---|---|
| 366 | rac-trans-1,2-3'R- | 2-[rac-trans-(1,2)-2-((R)-3-aminopiperidin-1-yl)-1,2,3,4-tetrahydronaphthalen-1-yloxy]-5-chlorobenzonitrile |
| 367 | rac-trans-1,2-3'R- | 2-[rac-trans-(1,2)-2-((R)-3-aminopiperidin-1-yl)-1,2,3,4-tetrahydronaphthalen-1-yloxy]-6-fluorobenzonitrile |
| 368 | rac-trans-1,2-3'R- | 2-[rac-trans-(1,2)-2-((R)-3-aminopiperidin-1-yl)-1,2,3,4-tetrahydronaphthalen-1-yloxy]benzamide |
| 369 | rac-trans-1,2-3'S- | 2-[rac-trans-(1,2)-2-((S)-3-aminopiperidin-1-yl)-1,2,3,4-tetrahydronaphthalen-1-yloxy]-5-bromobenzonitrile |
| 370 | rac-trans-1,2-3'S- | 2-[rac-trans-(1,2)-2-((S)-3-aminopiperidin-1-yl)-1,2,3,4-tetrahydronaphthalen-1-yloxy]-5-chlorobenzamide |
| 371 | rac-trans-1,2-3'S- | 2-[rac-trans-(1,2)-2-((S)-3-aminopiperidin-1-yl)-1,2,3,4-tetrahydronaphthalen-1-yloxy]-5-chlorobenzonitrile |
| 372 | rac-trans-1,2-3'S- | 2-[rac-trans-(1,2)-2-((S)-3-aminopiperidin-1-yl)-1,2,3,4-tetrahydronaphthalen-1-yloxy]-6-fluorobenzonitrile |
| 373 | rac-trans-1,2-3'S- | 2-[rac-trans-(1,2)-2-((S)-3-aminopiperidin-1-yl)-1,2,3,4-tetrahydronaphthalen-1-yloxy]benzamide |
| 374 | rac-trans-1,2-rac-3'- | 2-[rac-trans-(1,2)-2-(3-aminomethylpyrrolidin-1-yl)indan-1-yloxy]-6-fluorobenzonitrile |
| 375 | rac-trans-1,2-rac-3'- | 2-[rac-trans-(1,2)-2-(3-aminopyrrolidin-1-yl)indan-1-yloxy]-5-chlorobenzonitrile |
| 376 | rac-trans-1,2- | 2-[rac-trans-(1,2)-2-(4-aminomethylpiperidin-1-yl)indan-1-yloxy]-5-chlorobenzonitrile |
| 377 | rac-trans-1,2- | 2-[rac-trans-(1,2)-4,6-dichloro-1-(4-[1,2,4]triazol-1-ylphenoxy)indan-2-yl]octahydropyrrolo[3,4-c]pyrrole |
| 378 | trans-1S,2S-rac-3'- | 2-[trans-(1S,2S)-4,6-dichloro-1-(4-methanesulfonylphenoxy)indan-2-yl]-2,7-diaza-spiro[4.4]nonane |
| 379 | trans-1S,2S-3'R- | 2-{(R)-1-[trans-(1S,2S)-4,6-dichloro-1-(4-methanesulfonylphenoxy)indan-2-yl]piperidin-3-ylamino}-ethanol |
| 380 | rac-trans-1,2-3'R- | 2-{4-[rac-trans-(1,2)-2-((R)-3-aminopiperidin-1-yl)-1,2,3,4-tetrahydronaphthalen-1-yloxy]phenyl}-N,N-dimethylacetamide |
| 381 | rac-trans-1,2-3'R- | 2-{4-[rac-trans-(1,2)-2-((R)-3-aminopiperidin-1-yl)indan-1-yloxy]phenyl}thiazole-4-carbonitrile |
| 382 | rac-trans-1,2-3'S- | 2-{4-[rac-trans-(1,2)-2-((S)-3-aminopiperidin-1-yl)-1,2,3,4-tetrahydronaphthalen-1-yloxy]phenyl}-N,N-dimethylacetamide |
| 383 | rac-trans-1,2- | 2-{4-[rac-trans-(1,2)-4,6-dichloro-1-(4-methanesulfonylphenoxy)indan-2-yl]-[1,4]diazepan-1-yl}-ethanol |
| 384 | rac-trans-1,2- | 2-{4-[rac-trans-(1,2)-6-chloro-1-(4-methanesulfonylphenoxy)indan-2-yl]piperazin-1-yl}-ethanol |
| 385 | trans-1S,2S | 2-{4-[trans-(1S,2S)-4,6-dichloro-1-(4-methanesulfonylphenoxy)indan-2-yl]-[1,4]diazepan-1-yl}-ethanol |
| 386 | rac-trans-1,2-rac-3'- | 2-{5-[rac-trans-(1,2)-2-(3-aminomethylpyrrolidin-1-yl)indan-1-yloxy]-1H-indol-3-yl}acetamide |
| 387 | rac-trans-1,2-rac-3'- | 2-{5-[rac-trans-(1,2)-2-(3-aminopyrrolidin-1-yl)indan-1-yloxy]-1H-indol-3-yl}acetamide |
| 388 | rac-trans-1,2- | 2-{5-[rac-trans-(1,2)-2-(4-aminomethylpiperidin-1-yl)indan-1-yloxy]-1H-indol-3-yl}acetamide |
| 389 | rac-trans-1,2- | 2-chloro-4-(2-pyrrolidin-1-ylmethylindan-1-yloxy)benzenesulfonamide |
| 390 | rac-trans-1,2- | 2-chloro-4-(2-pyrrolidin-1-ylmethylindan-1-yloxy)benzoic acid |
| 391 | rac-trans-1,2- | 2-chloro-4-(2-pyrrolidin-1-ylmethylindan-1-yloxy)benzonitrile |
| 392 | rac-trans-1,2 | 2-chloro-4-(rac-trans-(1,2)-2-pyrrolidin-1-ylindan-1-yloxy)benzonitrile |
| 393 | rac-trans-1,2- | 2-chloro-4-[rac-trans-(1,2)-2-(hexahydropyrrolo[3,4-c]pyrrol-2-yl)indan-1-yloxy]benzonitrile |
| 394 | trans-1S,2S- | 2-chloro-4-methanesulfonylaminobenzoic acid (1S,2S)-2-pyrrolidin-1-ylindan-1-yl ester |
| 395 | rac-trans-1,2- | 2-chloro-8-(rac-trans-(1,2)-2-morpholin-4-yl-1,2,3,4-tetrahydronaphthalen-1-yloxy)quinoline |
| 396 | rac-trans-1,2- | 2-fluoro-4-(rac-trans-(1,2)-2-morpholin-4-yl-1,2,3,4-tetrahydronaphthalen-1-yloxy)benzonitrile |
| 397 | rac-trans-1,2- | 2-fluoro-4-[rac-trans-(1,2)-2-(hexahydropyrrolo[3,4-c]pyrrol-2-yl)indan-1-yloxy]benzonitrile |
| 398 | rac-trans-1,2- | 2-fluoro-6-[rac-trans-(1,2)-2-(hexahydropyrrolo[3,4-c]pyrrol-2-yl)indan-1-yloxy]benzonitrile |
| 399 | rac-trans-1,2- | 2-methyl-4-(rac-trans-(1,2)-2-morpholin-4-yl-1,2,3,4-tetrahydronaphthalen-1-yloxy)-1H-indole |
| 400 | rac-trans-1,2- | 3-(rac-trans-(1,2)-2-morpholin-4-yl-1,2,3,4-tetrahydronaphthalen-1-yloxy)quinoline |

-continued

| Example | Configuration | Name |
|---|---|---|
| 401 | rac-trans-1,2- | 3-(rac-trans-(1,2)-2-pyrrolidin-1-ylindan-1-yloxy)phenylamine |
| 402 | rac-trans-1,2 | 3,5-dichloro-4-(rac-trans-(1,2)-2-pyrrolidin-1-ylindan-1-yloxy)benzenesulfonamide |
| 403 | rac-trans-1,2 | 3,5-dichloro-N,N-dimethyl-4-(rac-trans-(1,2)-2-pyrrolidin-1-ylindan-1-yloxy)benzenesulfonamide |
| 404 | rac-trans-1,2- | 3,5-dimethyl-4-[3-(rac-trans-(1,2)-2-pyrrolidin-1-ylindan-1-yloxy)phenyl]-4H-[1,2,4]triazole |
| 405 | rac-trans-1,2- | 3,5-dimethyl-4-[4-(rac-trans-(1,2)-2-pyrrolidin-1-ylindan-1-yloxy)phenyl]-4H-[1,2,4]triazole |
| 406 | trans-1S,2S- | 3,5-dimethyl-4-[4-(trans-(1S,2S)-2-pyrrolidin-1-ylindan-1-yloxy)-3-trifluoromethylphenyl]-4H-[1,2,4]triazole |
| 407 | trans-1S,2S | 3,5-dimethyl-4-[4-(trans-(1S,2S)-2-pyrrolidin-1-ylindan-1-yloxy)phenyl]-isoxazole |
| 408 | trans-1S,2S- | 3,5-dimethyl-4-[5-methyl-2-(trans-(1S,2S)-2-pyrrolidin-1-ylindan-1-yloxy)phenyl]isoxazole |
| 409 | rac-trans-1,2- | 3-[3-(rac-trans-(1,2)-2-pyrrolidin-1-ylindan-1-yloxy)phenyl]oxazolidin-2-one |
| 410 | rac-trans-1,2- | 3-[rac-trans-(1,2)-2-(hexahydropyrrolo[3,4-c]pyrrol-2-yl)indan-1-yloxy]benzamide |
| 411 | rac-trans-1,2-3'R- | 3-[rac-trans-(1,2)-2-((R)-3-aminopiperidin-1-yl)indan-1-yloxy]benzamide |
| 412 | rac-trans-1,2-3'S- | 3-[rac-trans-(1,2)-2-((S)-3-aminopiperidin-1-yl)-1,2,3,4-tetrahydronaphthalen-1-yloxy]benzamide |
| 413 | rac-trans-1,2-3'S- | 3-[rac-trans-(1,2)-2-((S)-3-aminopiperidin-1-yl)indan-1-yloxy]benzamide |
| 414 | rac-trans-1,2-rac-3'- | 3-[rac-trans-(1,2)-2-(3-aminomethylpyrrolidin-1-yl)indan-1-yloxy]benzamide |
| 415 | rac-trans-1,2-rac-3'- | 3-[rac-trans-(1,2)-2-(3-aminopyrrolidin-1-yl)indan-1-yloxy]benzamide |
| 416 | trans-1S,2S-3'R- | 3-{3-[(1S,2S)-4,6-dichloro-2-((R)-3-hydroxypyrrolidin-1-yl)indan-1-yloxy]-4-fluorophenyl}-5,5-dimethylimidazolidine-2,4-dione |
| 417 | trans-1S,2S-3'R- | 3-{3-[(1S,2S)-4,6-dichloro-2-((R)-3-hydroxypyrrolidin-1-yl)indan-1-yloxy]-4-fluorophenyl}imidazolidine-2,4-dione |
| 418 | trans-1S,2S-3'R- | 3-{3-[(1S,2S)-4,6-dichloro-2-((R)-3-hydroxypyrrolidin-1-yl)indan-1-yloxy]-4-fluorophenyl}oxazolidine-2,4-dione |
| 419 | trans-1S,2S-3'R- | 3-{3-[(1S,2S)-4,6-dichloro-2-((R)-3-hydroxypyrrolidin-1-yl)indan-1-yloxy]phenyl}oxazolidin-2-one |
| 420 | trans-1S,2S-3'R- | 3-{3-[(1S,2S)-6-chloro-4-fluoro-2-((R)-3-hydroxypyrrolidin-1-yl)indan-1-yloxy]-4-fluorophenyl}-5,5-dimethylimidazolidine-2,4-dione |
| 421 | trans-1S,2S-3'R- | 3-{3-[(1S,2S)-6-chloro-4-fluoro-2-((R)-3-hydroxypyrrolidin-1-yl)indan-1-yloxy]-4-fluorophenyl}imidazolidine-2,4-dione |
| 422 | trans-1S,2S-3'R- | 3-{3-chloro-4-[(1S,2S)-4,6-dichloro-2-((R)-3-hydroxypyrrolidin-1-yl)indan-1-yloxy]phenyl}-1-methylimidazolidine-2,4-dione |
| 423 | trans-1S,2S-3'R- | 3-{3-chloro-4-[(1S,2S)-4,6-dichloro-2-((R)-3-hydroxypyrrolidin-1-yl)indan-1-yloxy]phenyl}-5,5-dimethylimidazolidine-2,4-dione |
| 424 | trans-1S,2S-3'R- | 3-{3-chloro-4-[(1S,2S)-4,6-dichloro-2-((R)-3-hydroxypyrrolidin-1-yl)indan-1-yloxy]phenyl}oxazolidine-2,4-dione |
| 425 | trans-1S,2S-3'R- | 3-{4-[(1S,2S)-4,6-dichloro-2-((R)-3-hydroxypyrrolidin-1-yl)indan-1-yloxy]phenyl}-5,5-dimethylimidazolidine-2,4-dione |
| 426 | trans-1S,2S-3'R- | 3-{4-[(1S,2S)-4,6-dichloro-2-((R)-3-hydroxypyrrolidin-1-yl)indan-1-yloxy]phenyl}imidazolidine-2,4-dione |
| 427 | trans-1S,2S-3'R- | 3-{4-[(1S,2S)-4,6-dichloro-2-((R)-3-hydroxypyrrolidin-1-yl)indan-1-yloxy]phenyl}oxazolidine-2,4-dione |
| 428 | trans-1S,2S-3'R- | 3-{4-[(1S,2S)-4,6-dichloro-2-((R)-3-hydroxypyrrolidin-1-yl)indan-1-yloxy]phenyl}thiazolidine-2,4-dione |
| 429 | trans-1S,2S-3'R- | 3-{4-[trans-(1S,2S)-4,6-dichloro-2-((R)-3-hydroxypyrrolidin-1-yl)indan-1-yloxy]phenyl}oxazolidin-2-one |
| 430 | trans-1S,2S-3'R- | 3-{4-chloro-3-[(1S,2S)-4,6-dichloro-2-((R)-3-hydroxypyrrolidin-1-yl)indan-1-yloxy]phenyl}-1-methylimidazolidine-2,4-dione |
| 431 | trans-1S,2S-3'R- | 3-{4-chloro-3-[(1S,2S)-4,6-dichloro-2-((R)-3-hydroxypyrrolidin-1-yl)indan-1-yloxy]phenyl}-5,5-dimethylimidazolidine-2,4-dione |
| 432 | trans-1S,2S-3'R- | 3-{4-chloro-3-[(1S,2S)-4,6-dichloro-2-((R)-3-hydroxypyrrolidin-1-yl)indan-1-yloxy]phenyl}-5,5-dimethyloxazolidine-2,4-dione |

-continued

| Example | Configuration | Name |
|---|---|---|
| 433 | trans-1S,2S-3'R- | 3-{4-chloro-3-[(1S,2S)-4,6-dichloro-2-((R)-3-hydroxypyrrolidin-1-yl)indan-1-yloxy]phenyl}imidazolidine-2,4-dione |
| 434 | trans-1S,2S-3'R- | 3-{4-chloro-3-[(1S,2S)-4,6-dichloro-2-((R)-3-hydroxypyrrolidin-1-yl)indan-1-yloxy]phenyl}oxazolidin-2-one |
| 435 | trans-1S,2S-3'R- | 3-{4-chloro-3-[(1S,2S)-6-chloro-4-fluoro-2-((R)-3-hydroxypyrrolidin-1-yl)indan-1-yloxy]phenyl}-1-methylimidazolidine-2,4-dione |
| 436 | trans-1S,2S-3'R- | 3-{4-chloro-3-[(1S,2S)-6-chloro-4-fluoro-2-((R)-3-hydroxypyrrolidin-1-yl)indan-1-yloxy]phenyl}-5,5-dimethylimidazolidine-2,4-dione |
| 437 | trans-1S,2S-3'R- | 3-{4-chloro-3-[(1S,2S)-6-chloro-4-fluoro-2-((R)-3-hydroxypyrrolidin-1-yl)indan-1-yloxy]phenyl}-5,5-dimethyloxazolidine-2,4-dione |
| 438 | trans-1S,2S-3'R- | 3-{4-chloro-3-[(1S,2S)-6-chloro-4-fluoro-2-((R)-3-hydroxypyrrolidin-1-yl)indan-1-yloxy]phenyl}imidazolidine-2,4-dione |
| 439 | trans-1S,2S-3'R- | 3-{4-chloro-3-[(1S,2S)-6-chloro-4-fluoro-2-((R)-3-hydroxypyrrolidin-1-yl)indan-1-yloxy]phenyl}oxazolidin-2-one |
| 440 | rac-trans-1,2- | 3-chloro-4-(2-piperidin-1-ylmethylindan-1-yloxy)benzenesulfonamide |
| 441 | rac-trans-1,2- | 3-chloro-4-(2-pyrrolidin-1-ylindan-1-yloxy)pyridine |
| 442 | rac-trans-1,2- | 3-chloro-4-(2-pyrrolidin-1-ylmethylindan-1-yloxy)benzenesulfonamide |
| 443 | rac-trans-1,2- | 3-chloro-4-(2-pyrrolidin-1-ylmethylindan-1-yloxy)pyridine |
| 444 | rac-trans-1,2 | 3-chloro-4-(rac-trans-(1,2)-2-pyrrolidin-1-ylindan-1-yloxy)benzenesulfonamide |
| 445 | rac-trans-1,2- | 3-chloro-4-[rac-trans-(1,2)-2-(hexahydropyrrolo[3,4-c]pyrrol-2-yl)indan-1-yloxy]benzonitrile |
| 446 | trans-1S,2S-3'R- | 3-chloro-4-[trans-(1S,2S)-6-chloro-2-((R)-3-hydroxypyrrolidin-1-yl)indan-1-yloxy]benzoic acid methyl ester |
| 447 | rac-trans-1,2 | 3-chloro-N,N-dimethyl-4-(rac-trans-(1,2)-2-pyrrolidin-1-ylindan-1-yloxy)benzenesulfonamide |
| 448 | rac-trans-1,2- | 3-Cyclopropyl-5-methyl-4-[4-(rac-trans-(1,2)-2-pyrrolidin-1-ylindan-1-yloxy)phenyl]-4H-[1,2,4]triazole |
| 449 | rac-trans-1,2- | 3-fluoro-4-(2-morpholin-4-ylmethylindan-1-yloxy)benzenesulfonamide |
| 450 | rac-trans-1,2- | 3-fluoro-4-(2-piperidin-1-ylmethylindan-1-yloxy)benzenesulfonamide |
| 451 | rac-trans-1,2- | 3-fluoro-4-(2-pyrrolidin-1-ylindan-1-yloxy)benzenesulfonamide |
| 452 | rac-trans-1,2- | 3-fluoro-4-(2-pyrrolidin-1-ylmethylindan-1-yloxy)benzenesulfonamide |
| 453 | rac-trans-1,2- | 3-methyl-4-[4-(rac-trans-(1,2)-2-pyrrolidin-1-ylindan-1-yloxy)phenyl]-4H-[1,2,4]triazole |
| 454 | trans-1S,2S- | 4-((1S,2S)-2-azetidin-1-yl-4,6-dichloroindan-1-yloxy)-3-fluorobenzonitrile |
| 455 | trans-1S,2S- | 4-((1S,2S)-2-pyrrolidin-1-ylindan-1-ylsulfanyl)benzonitrile |
| 456 | trans-1S,2S- | 4-((1S,2S)-4,6-dichloro-2-piperazin-1-ylindan-1-yloxy)-3-fluorobenzonitrile |
| 457 | trans-1S,2S- | 4-((1S,2S)-4,6-dichloro-2-pyrrolidin-1-ylindan-1-yloxy)benzenesulfonamide |
| 458 | trans-1S,2S- | 4-(2,5-dioxopyrrolidin-1-yl)benzoic acid (1S,2S)-2-pyrrolidin-1-ylindan-1-yl ester |
| 459 | rac-trans-1,2- | 4-(2-benzylaminoindan-1-yloxy)-3-fluorobenzenesulfonamide |
| 460 | rac-trans-1,2- | 4-(2-cyclopentylaminoindan-1-yloxy)-3-fluorobenzenesulfonamide |
| 461 | trans-1S,2S- | 4-(2-Oxopyrrolidin-1-yl)benzoic acid (1S,2S)-2-pyrrolidin-1-ylindan-1-yl ester |
| 462 | rac-trans-1,2- | 4-(2-pyrrolidin-1-ylmethylindan-1-yloxy)-3-trifluoromethylpyridine |
| 463 | rac-trans-1,2-3'R- | 4-(rac-trans-(1,2)-(R)-2-[1,3']Bipyrrolidinyl-1'-ylindan-1-yloxy)benzenesulfonamide |
| 464 | rac-trans-1,2- | 4-(rac-trans-(1,2)-2-azepan-1-ylindan-1-yloxy)benzenesulfonamide |
| 465 | rac-trans-1,2- | 4-(rac-trans-(1,2)-2-piperidin-1-ylindan-1-yloxy)benzenesulfonamide |
| 466 | rac-trans-1,2- | 4-(rac-trans-(1,2)-2-pyrrolidin-1-ylindan-1-yloxy)benzenesulfonamide |
| 467 | rac-trans-1,2- | 4-(rac-trans-(1,2)-2-pyrrolidin-1-ylindan-1-yloxy)benzoic acid methyl ester |
| 468 | rac-trans-1,2 | 4-(rac-trans-(1,2)-2-pyrrolidin-1-ylindan-1-yloxy)benzonitrile |

-continued

| Example | Configuration | Name |
|---|---|---|
| 469 | rac-trans-1,2- | 4-(rac-trans-(1,2)-2-pyrrolidin-1-ylindan-1-yloxy)-N-(2,2,2-trifluoroethyl)benzenesulfonamide |
| 470 | rac-trans-1,2- | 4-(rac-trans-(1,2)-2-pyrrolidin-1-ylindan-1-yloxy)-N-(3,3,3-trifluoropropyl)benzenesulfonamide |
| 471 | rac-trans-1,2- | 4-(rac-trans-(1,2)-4-chloro-2-pyrrolidin-1-ylindan-1-yloxy)benzenesulfonamide |
| 472 | rac-trans-1,2- | 4-(rac-trans-(1,2)-4-methyl-2-pyrrolidin-1-ylindan-1-yloxy)benzenesulfonamide |
| 473 | rac-trans-1,2- | 4-(rac-trans-(1,2)-6-chloro-2-pyrrolidin-1-ylindan-1-yloxy)benzenesulfonamide |
| 474 | rac-trans-1,2- | 4-(rac-trans-(1,2)-6-fluoro-2-pyrrolidin-1-ylindan-1-yloxy)benzenesulfonamide |
| 475 | rac-trans-1,2- | 4-(rac-trans-(1,2)-6-methyl-2-pyrrolidin-1-ylindan-1-yloxy)benzenesulfonamide |
| 476 | rac-trans-1,2- | 4-(rac-trans-(1,2)-7-chloro-2-pyrrolidin-1-ylindan-1-yloxy)benzenesulfonamide |
| 477 | trans-1S,2S- | 4-(trans-(1S,2S)-4,6-dichloro-2-piperazin-1-ylindan-1-yloxy)-3-fluorobenzonitrile |
| 478 | rac-cis-1,2- | 4-[(1R,2S)-1-(2-chloro-4-nitrophenoxy)indan-2-yl]morpholine |
| 479 | trans-1S,2S-3'R | 4-[(1S,2S)-2-((R)-3-aminopiperidin-1-yl)-4,6-dichloroindan-1-yloxy]-3-fluorobenzonitrile |
| 480 | trans-1S,2S-3'R | 4-[(1S,2S)-2-((R)-3-aminopiperidin-1-yl)-4,6-dichloroindan-1-yloxy]benzenesulfonamide |
| 481 | trans-1S,2S-3'R- | 4-[(1S,2S)-4,6-dichloro-2-((R)-3-hydroxypyrrolidin-1-yl)indan-1-ylamino]-N,N-dimethylbenzenesulfonamide |
| 482 | trans-1S,2S-3'R- | 4-[(1S,2S)-4,6-dichloro-2-((R)-3-hydroxypyrrolidin-1-yl)indan-1-yloxymethyl]-3-fluorobenzonitrile |
| 483 | trans-1S,2S- | 4-[(1S,2S)-4,6-dichloro-2-(1,1-dioxo-1lambda6-thiomorpholin-4-yl)indan-1-yloxy]benzenesulfonamide |
| 484 | trans-1S,2S- | 4-[(1S,2S)-4,6-dichloro-2-(4,4-difluoropiperidin-1-yl)indan-1-yloxy]benzenesulfonamide |
| 485 | trans-1S,2S- | 4-[(1S,2S)-4,6-dichloro-2-(4-methylpiperazin-1-yl)indan-1-yloxy]-3-fluorobenzonitrile |
| 486 | rac-trans-1,2- | 4-[1-(3-chloropyridin-4-yloxy)indan-2-ylmethyl]morpholine |
| 487 | rac-trans-1,2- | 4-[1-(4-methanesulfonylphenoxy)indan-2-ylmethyl]morpholine |
| 488 | rac-trans-1,2- | 4-[2,3-dimethyl-4-(rac-trans-(1,2)-2-pyrrolidin-1-ylindan-1-yloxy)phenyl]-3,5-dimethyl-4H-[1,2,4]triazole |
| 489 | trans-1S,2S- | 4-[2-fluoro-5-(trans-(1S,2S)-2-pyrrolidin-1-ylindan-1-yloxy)phenyl]-3,5-dimethylisoxazole |
| 490 | rac-trans-1,2- | 4-[3-chloro-4-(rac-trans-(1,2)-2-pyrrolidin-1-ylindan-1-yloxy)phenyl]-3,5-dimethyl-4H-[1,2,4]triazole |
| 491 | trans-1S,2S- | 4-[3-chloro-4-(trans-(1S,2S)-2-pyrrolidin-1-ylindan-1-yloxy)phenyl]-3,5-dimethyl-4H-[1,2,4]triazole |
| 492 | trans-1S,2S- | 4-[3-chloro-4-(trans-(1S,2S)-6-chloro-2-pyrrolidin-1-ylindan-1-yloxy)phenyl]-3,5-dimethyl-4H-[1,2,4]triazole |
| 493 | trans-1S,2S | 4-[3-chloro-4-(trans-(1S,2S)-6-chloro-2-pyrrolidin-1-ylindan-1-yloxy)phenyl]-3,5-dimethyl-4H-[1,2,4]triazole |
| 494 | rac-trans-1,2- | 4-[3-fluoro-4-(-2-methyl-2-pyrrolidin-1-ylindan-1-yloxy)phenyl]-3,5-dimethyl-4H-[1,2,4]triazole |
| 495 | rac-trans-1,2- | 4-[4-((4S,5S)-1,3-dichloro-5-pyrrolidin-1-yl-4,5,6,7-tetrahydrobenzo[c]thiophen-4-yloxy)-3-fluorophenyl]-3,5-dimethyl-4H-[1,2,4]triazole |
| 496 | rac-trans-4,5- | 4-[4-(1,3-dichloro-5-pyrrolidin-1-yl-4,5,6,7-tetrahydrobenzo[c]thiophen-4-yloxy)phenyl]-3,5-dimethyl-4H-[1,2,4]triazole |
| 497 | rac-trans-1,2- | 4-[4-(rac-trans-(1,2)-3,3-dimethyl-2-pyrrolidin-1-ylindan-1-yloxy)phenyl]-3,5-dimethyl-4H-[1,2,4]triazole |
| 498 | rac-trans-1,2- | 4-[4-(rac-trans-(1,2)-5,6-dichloro-2-pyrrolidin-1-ylindan-1-yloxy)phenyl]-3,5-dimethyl-4H-[1,2,4]triazole |
| 499 | trans-1S,2S | 4-[4-(trans-(1S,2S)-4,6-dichloro-2-pyrrolidin-1-ylindan-1-yloxy)-3-fluorophenyl]-3,5-dimethyl-4H-[1,2,4]triazole |
| 500 | trans-1S,2S | 4-[4-(trans-(1S,2S)-4,6-dichloro-2-pyrrolidin-1-ylindan-1-yloxy)phenyl]-3,5-dimethyl-4H-[1,2,4]triazole |
| 501 | trans-1S,2S | 4-[4-(trans-(1S,2S)-6-chloro-2-pyrrolidin-1-ylindan-1-yloxy)-3-fluorophenyl]-3,5-dimethyl-4H-[1,2,4]triazole |
| 502 | trans-1S,2S | 4-[4-(trans-(1S,2S)-6-chloro-2-pyrrolidin-1-ylindan-1-yloxy)phenyl]-3,5-dimethyl-4H-[1,2,4]triazole |
| 503 | trans-1S,2S- | 4-[5-fluoro-2-(trans-(1S,2S)-2-pyrrolidin-1-ylindan-1-yloxy)phenyl]-3,5-dimethylisoxazole |
| 504 | rac-trans-1,2- | 4-[rac-trans-(1,2)-2-(Hexahydropyrrolo[3,4-c]pyrrol-2-yl)indan-1-yloxy]-1H-indole |
| 505 | rac-trans-1,2- | 4-[rac-trans-(1,2)-2-(Hexahydropyrrolo[3,4-c]pyrrol-2-yl)indan-1-yloxy]-2,6-dimethylbenzonitrile |

| Example | Configuration | Name |
|---|---|---|
| 506 | rac-trans-1,2- | 4-[rac-trans-(1,2)-1-(2-methanesulfonylphenoxy)-1,2,3,4-tetrahydronaphthalen-2-yl]morpholine |
| 507 | rac-trans-1,2- | 4-[rac-trans-(1,2)-1-(4-fluoro-2-isoxazol-5-ylphenoxy)-1,2,3,4-tetrahydronaphthalen-2-yl]morpholine |
| 508 | rac-trans-1,2- | 4-[rac-trans-(1,2)-1-(4-methanesulfonylphenoxy)-1,2,3,4-tetrahydronaphthalen-2-yl]morpholine |
| 509 | rac-trans-1,2-3'R- | 4-[rac-trans-(1,2)-2-((R)-3-aminopiperidin-1-yl)-1,2,3,4-tetrahydronaphthalen-1-yloxy]-2,3-difluorobenzonitrile |
| 510 | rac-trans-1,2-3'R- | 4-[rac-trans-(1,2)-2-((R)-3-aminopiperidin-1-yl)-1,2,3,4-tetrahydronaphthalen-1-yloxy]-2-fluorobenzonitrile |
| 511 | rac-trans-1,2-3'R- | 4-[rac-trans-(1,2)-2-((R)-3-aminopiperidin-1-yl)-1,2,3,4-tetrahydronaphthalen-1-yloxy]-3,5-dimethylbenzonitrile |
| 512 | rac-trans-1,2-3'R- | 4-[rac-trans-(1,2)-2-((R)-3-aminopiperidin-1-yl)-1,2,3,4-tetrahydronaphthalen-1-yloxy]-3-chloro-5-methoxy-benzonitrile |
| 513 | rac-trans-1,2-3'R- | 4-[rac-trans-(1,2)-2-((R)-3-aminopiperidin-1-yl)-1,2,3,4-tetrahydronaphthalen-1-yloxy]-3-chlorobenzoic acid methyl ester |
| 514 | rac-trans-1,2-3'R- | 4-[rac-trans-(1,2)-2-((R)-3-aminopiperidin-1-yl)-1,2,3,4-tetrahydronaphthalen-1-yloxy]-3-chlorobenzonitrile |
| 515 | rac-trans-1,2-3'R- | 4-[rac-trans-(1,2)-2-((R)-3-aminopiperidin-1-yl)-1,2,3,4-tetrahydronaphthalen-1-yloxy]-3-fluorobenzonitrile |
| 516 | rac-trans-1,2-3'R- | 4-[rac-trans-(1,2)-2-((R)-3-aminopiperidin-1-yl)-1,2,3,4-tetrahydronaphthalen-1-yloxy]benzonitrile |
| 517 | rac-trans-1,2-3'R- | 4'-[rac-trans-(1,2)-2-((R)-3-aminopiperidin-1-yl)-1,2,3,4-tetrahydronaphthalen-1-yloxy]-biphenyl-4-carbonitrile |
| 518 | rac-trans-1,2-3'R- | 4-[rac-trans-(1,2)-2-((R)-3-aminopiperidin-1-yl)indan-1-yloxy]-2,3-dichlorobenzenesulfonamide |
| 519 | rac-trans-1,2-3'R- | 4-[rac-trans-(1,2)-2-((R)-3-aminopiperidin-1-yl)indan-1-yloxy]-2,3-dichlorobenzenesulfonamide |
| 520 | rac-trans-1,2-3'R | 4-[rac-trans-(1,2)-2-((R)-3-aminopiperidin-1-yl)indan-1-yloxy]-2,3-dichloro-N,N-dimethylbenzenesulfonamide |
| 521 | rac-trans-1,2-3'R- | 4-[rac-trans-(1,2)-2-((R)-3-aminopiperidin-1-yl)indan-1-yloxy]-2-chlorobenzonitrile |
| 522 | rac-trans-1,2-3'R- | 4-[rac-trans-(1,2)-2-((R)-3-aminopiperidin-1-yl)indan-1-yloxy]-2-fluorobenzonitrile |
| 523 | rac-trans-1,2-3'R- | 4-[rac-trans-(1,2)-2-((R)-3-aminopiperidin-1-yl)indan-1-yloxy]-3-chlorobenzonitrile |
| 524 | rac-trans-1,2-3'R- | 4-[rac-trans-(1,2)-2-((R)-3-aminopiperidin-1-yl)indan-1-yloxy]benzamide |
| 525 | rac-trans-1,2-3'R- | 4-[rac-trans-(1,2)-2-((R)-3-aminopiperidin-1-yl)indan-1-yloxy]benzamide |
| 526 | rac-trans-1,2-3'R- | 4-[rac-trans-(1,2)-2-((R)-3-Hydroxymethylpyrrolidin-1-yl)indan-1-yloxy]benzenesulfonamide |
| 527 | rac-trans-1,2-3'R- | 4-[rac-trans-(1,2)-2-((R)-3-Hydroxypyrrolidin-1-yl)indan-1-yloxy]benzenesulfonamide |
| 528 | rac-trans-1,2-3'S- | 4-[rac-trans-(1,2)-2-((S)-3-aminopiperidin-1-yl)-1,2,3,4-tetrahydronaphthalen-1-yloxy]-2,3-difluorobenzonitrile |
| 529 | rac-trans-1,2-3'S- | 4-[rac-trans-(1,2)-2-((S)-3-aminopiperidin-1-yl)-1,2,3,4-tetrahydronaphthalen-1-yloxy]-2-chlorobenzonitrile |
| 530 | rac-trans-1,2-3'S- | 4-[rac-trans-(1,2)-2-((S)-3-aminopiperidin-1-yl)-1,2,3,4-tetrahydronaphthalen-1-yloxy]-2-fluorobenzonitrile |
| 531 | rac-trans-1,2-3'S- | 4-[rac-trans-(1,2)-2-((S)-3-aminopiperidin-1-yl)-1,2,3,4-tetrahydronaphthalen-1-yloxy]-3-chlorobenzoic acid methyl ester |
| 532 | rac-trans-1,2-3'S- | 4-[rac-trans-(1,2)-2-((S)-3-aminopiperidin-1-yl)-1,2,3,4-tetrahydronaphthalen-1-yloxy]-3-chlorobenzonitrile |
| 533 | rac-trans-1,2-3'S- | 4-[rac-trans-(1,2)-2-((S)-3-aminopiperidin-1-yl)-1,2,3,4-tetrahydronaphthalen-1-yloxy]-3-fluorobenzonitrile |
| 534 | rac-trans-1,2-3'S- | 4-[rac-trans-(1,2)-2-((S)-3-aminopiperidin-1-yl)-1,2,3,4-tetrahydronaphthalen-1-yloxy]-3-nitrobenzonitrile |
| 535 | rac-trans-1,2-3'S- | 4-[rac-trans-(1,2)-2-((S)-3-aminopiperidin-1-yl)-1,2,3,4-tetrahydronaphthalen-1-yloxy]benzonitrile |
| 536 | rac-trans-1,2-3'S- | 4-[rac-trans-(1,2)-2-((S)-3-aminopiperidin-1-yl)indan-1-yloxy]-2,3-dichlorobenzenesulfonamide |
| 537 | rac-trans-1,2-3'S- | 4-[rac-trans-(1,2)-2-((S)-3-aminopiperidin-1-yl)indan-1-yloxy]benzamide |
| 538 | rac-trans-1,2-rac-3'- | 4-[rac-trans-(1,2)-2-(3-aminomethylpyrrolidin-1-yl)indan-1-yloxy]-2,3-dichlorobenzenesulfonamide |
| 539 | rac-trans-1,2-rac-3'- | 4-[rac-trans-(1,2)-2-(3-aminomethylpyrrolidin-1-yl)indan-1-yloxy]-2,6-dimethylbenzonitrile |
| 540 | rac-trans-1,2-rac-3'- | 4-[rac-trans-(1,2)-2-(3-aminomethylpyrrolidin-1-yl)indan-1-yloxy]-2-chlorobenzonitrile |
| 541 | rac-trans-1,2-rac-3'- | 4-[rac-trans-(1,2)-2-(3-aminomethylpyrrolidin-1-yl)indan-1-yloxy]-3-chlorobenzonitrile |
| 542 | rac-trans-1,2-rac-3'- | 4-[rac-trans-(1,2)-2-(3-aminopyrrolidin-1-yl)indan-1-yloxy]-2,3-dichlorobenzenesulfonamide |

-continued

| Example | Configuration | Name |
|---|---|---|
| 543 | rac-trans-1,2-rac-3'- | 4-[rac-trans-(1,2)-2-(3-aminopyrrolidin-1-yl)indan-1-yloxy]-3-chlorobenzonitrile |
| 544 | rac-trans-1,2-rac-3'- | 4-[rac-trans-(1,2)-2-(3-aminopyrrolidin-1-yl)indan-1-yloxy]benzamide |
| 545 | rac-trans-1,2- | 4-[rac-trans-(1,2)-2-(4-aminomethylpiperidin-1-yl)indan-1-yloxy]-2,3-dichlorobenzenesulfonamide |
| 546 | rac-trans-1,2- | 4-[rac-trans-(1,2)-2-(4-aminomethylpiperidin-1-yl)indan-1-yloxy]-2-chlorobenzonitrile |
| 547 | rac-trans-1,2- | 4-[rac-trans-(1,2)-2-(4-aminomethylpiperidin-1-yl)indan-1-yloxy]-3-chlorobenzonitrile |
| 548 | rac-trans-1,2- | 4-[rac-trans-(1,2)-2-(4-aminomethylpiperidin-1-yl)indan-1-yloxy]benzamide |
| 549 | rac-trans-1,2- | 4-[rac-trans-(1,2)-4,6-dichloro-1-(4-[1,2,4]triazol-1-ylphenoxy)indan-2-yl]morpholine |
| 550 | trans-1S,2S-3'R- | 4-[trans-(1S,2S)-2-((R)-3-aminopiperidin-1-yl)-4,6-dichloroindan-1-yloxy]-2,3-dichlorobenzenesulfonamide |
| 551 | trans-1S,2S-3'R- | 4-[trans-(1S,2S)-2-((R)-3-aminopiperidin-1-yl)-4,6-dichloroindan-1-yloxy]-3-fluorobenzonitrile |
| 552 | trans-1S,2S-3'R- | 4-[trans-(1S,2S)-2-((R)-3-aminopiperidin-1-yl)indan-1-yloxy]benzenesulfonamide |
| 553 | trans-1S,2S-3'R- | 4-[trans-(1S,2S)-4,6-dichloro-2-((R)-3-hydroxypyrrolidin-1-yl)indan-1-yloxy]-3-fluorobenzoic acid methyl ester |
| 554 | trans-1S,2S-3'R- | 4-[trans-(1S,2S)-4,6-dichloro-2-((R)-3-hydroxypyrrolidin-1-yl)indan-1-yloxy]-3-fluorobenzonitrile |
| 555 | trans-1S,2S-3'S- | 4-[trans-(1S,2S)-4,6-dichloro-2-((S)-3-hydroxypyrrolidin-1-yl)indan-1-yloxy]-3-fluorobenzonitrile |
| 556 | trans-1S,2S | 4-[trans-(1S,2S)-4,6-dichloro-2-(4-methyl-[1,4]diazepan-1-yl)indan-1-yloxy]-3-fluorobenzonitrile |
| 557 | trans-1S,2S-3'R- | 4-[trans-(1S,2S)-6-chloro-4-fluoro-2-((R)-3-hydroxypyrrolidin-1-yl)indan-1-yloxy]-3-fluorobenzonitrile |
| 558 | trans-1S,2S-3'R- | 4-{3-chloro-4-[trans-(1S,2S)-6-chloro-2-((R)-3-fluoropyrrolidin-1-yl)indan-1-yloxy]phenyl}-3,5-dimethyl-4H-[1,2,4]triazole |
| 559 | trans-1S,2S-3'S- | 4-{3-chloro-4-[trans-(1S,2S)-6-chloro-2-((S)-3-fluoropyrrolidin-1-yl)indan-1-yloxy]phenyl}-3,5-dimethyl-4H-[1,2,4]triazole |
| 560 | trans-1S,2S-3'R- | 4-{4-[(1S,2S)-4,6-dichloro-2-((R)-3-hydroxypyrrolidin-1-yl)indan-1-yloxy]-3-fluorophenyl}morpholine-3,5-dione |
| 561 | trans-1S,2S-3'R- | 4-{4-[trans-(1S,2S)-4,6-dichloro-2-((R)-3-fluoropyrrolidin-1-yl)indan-1-yloxy]phenyl}-3,5-dimethyl-4H-[1,2,4]triazole |
| 562 | trans-1S,2S-2'S- | 4-{4-[trans-(1S,2S)-4,6-dichloro-2-((S)-2-methoxymethylpyrrolidin-1-yl)indan-1-yloxy]phenyl}-3,5-dimethyl-4H-[1,2,4]triazole |
| 563 | trans-1S,2S-3'R- | 4-{4-[trans-(1S,2S)-6-chloro-2-((R)-3-fluoropyrrolidin-1-yl)indan-1-yloxy]-3-fluorophenyl}-3,5-dimethyl-4H-[1,2,4]triazole |
| 564 | trans-1S,2S | 4-{trans-(1S,2S)-4,6-dichloro-1-[4-(3,5-dimethyl-[1,2,4]triazol-4-yl)-2-fluorophenoxy]indan-2-yl}morpholine |
| 565 | trans-1S,2S | 4-{trans-(1S,2S)-4,6-dichloro-1-[4-(3,5-dimethyl-[1,2,4]triazol-4-yl)-2-fluorophenoxy]indan-2-yl}thiomorpholine 1,1-dioxide |
| 566 | trans-1S,2S- | 4-{trans-(1S,2S)-6-chloro-1-[2-chloro-4-(3,5-dimethyl-[1,2,4]triazol-4-yl)phenoxy]indan-2-yl}morpholine |
| 567 | trans-1S,2S- | 4-{trans-(1S,2S)-6-chloro-1-[2-chloro-4-(3,5-dimethyl-[1,2,4]triazol-4-yl)phenoxy]indan-2-yl}thiomorpholine 1,1-dioxide |
| 568 | rac-trans-1,2- | 5-(rac-trans-(1,2)-2-diethylaminoindan-1-yloxy)-1,3-dimethyl-1,3-dihydroindol-2-one |
| 569 | rac-trans-1,2- | 5-(rac-trans-(1,2)-2-morpholin-4-yl-1,2,3,4-tetrahydronaphthalen-1-yloxy)naphthalen-2-ylamine |
| 570 | rac-trans-1,2- | 5-(rac-trans-(1,2)-2-morpholin-4-yl-1,2,3,4-tetrahydronaphthalen-1-yloxy)quinoline |
| 571 | rac-trans-1,2- | 5-(rac-trans-(1,2)-2-pyrrolidin-1-ylindan-1-yloxy)-3H-isobenzofuran-1-one |
| 572 | rac-trans-1,2- | 5-(rac-trans-(1,2)-4,6-dichloro-2-piperazin-1-ylindan-1-yloxy)-2-methylbenzothiazole |
| 573 | rac-trans-1,2- | 5,7-dimethyl-8-(rac-trans-(1,2)-2-morpholin-4-yl-1,2,3,4-tetrahydronaphthalen-1-yloxy)quinoline |
| 574 | trans-1S,2S-3'R- | 5-[(1S,2S)-4,6-dichloro-2-((R)-3-hydroxypyrrolidin-1-yl)indan-1-yloxy]-3,4-dihydro-1H-quinolin-2-one |
| 575 | trans-1S,2S- | 5-[5-fluoro-2-(trans-(1S,2S)-2-pyrrolidin-1-ylindan-1-yloxy)phenyl]-1H-pyrazole |
| 576 | rac-trans-1,2- | 5-[rac-trans-(1,2)-2-(hexahydropyrrolo[3,4-c]pyrrol-2-yl)indan-1-yloxy]-2-methylbenzothiazole |
| 577 | rac-trans-1,2- | 5-[rac-trans-(1,2)-2-(hexahydropyrrolo[3,4-c]pyrrol-2-yl)indan-1-yloxy]benzo[1,3]oxathiol-2-one |

-continued

| Example | Configuration | Name |
|---|---|---|
| 578 | rac-trans-1,2-3'R- | 5-[rac-trans-(1,2)-2-((R)-3-aminopiperidin-1-yl)-1,2,3,4-tetrahydronaphthalen-1-yloxy]benzo[1,3]oxathiol-2-one |
| 579 | rac-trans-1,2-3'R- | 5-[rac-trans-(1,2)-2-((R)-3-aminopiperidin-1-yl)indan-1-yloxy]benzo[1,3]oxathiol-2-one |
| 580 | rac-trans-1,2-3'S- | 5-[rac-trans-(1,2)-2-((S)-3-aminopiperidin-1-yl)-1,2,3,4-tetrahydronaphthalen-1-yloxy]benzo[1,3]oxathiol-2-one |
| 581 | trans-1S,2S-diastereomer1 | 5-[trans-(1S,2S)-4,6-dichloro-1-(4-methanesulfonylphenoxy)indan-2-yl]-1-methyloctahydropyrrolo[3,4-b]pyrrole |
| 582 | trans-1S,2S-diastereomer2 | 5-[trans-(1S,2S)-4,6-dichloro-1-(4-methanesulfonylphenoxy)indan-2-yl]-1-methyloctahydropyrrolo[3,4-b]pyrrole |
| 583 | rac-trans-1,2-3'R- | 5-{4-[rac-trans-(1,2)-2-((R)-3-aminopiperidin-1-yl)-1,2,3,4-tetrahydronaphthalen-1-yloxy]phenyl}oxazole-4-carboxylic acid ethyl ester |
| 584 | rac-trans-1,2-3'S- | 5-{4-[rac-trans-(1,2)-2-((S)-3-aminopiperidin-1-yl)-1,2,3,4-tetrahydronaphthalen-1-yloxy]phenyl}oxazole-4-carboxylic acid ethyl ester |
| 585 | rac-trans-1,2- | 5-chloro-2-(rac-trans-(1,2)-2-morpholin-4-yl-1,2,3,4-tetrahydronaphthalen-1-yloxy)benzonitrile |
| 586 | rac-trans-1,2- | 5-fluoro-8-(rac-trans-(1,2)-2-morpholin-4-yl-1,2,3,4-tetrahydronaphthalen-1-yloxy)quinoline |
| 587 | rac-trans-1,2- | 6-[rac-trans-(1,2)-2-(Hexahydropyrrolo[3,4-c]pyrrol-2-yl)indan-1-yloxy]-1H-indole |
| 588 | rac-trans-1,2- | 7-(rac-trans-(1,2)-2-morpholin-4-yl-1,2,3,4-tetrahydronaphthalen-1-yloxy)isoquinoline |
| 589 | rac-trans-1,2- | 7-[rac-trans-(1,2)-2-(Hexahydropyrrolo[3,4-c]pyrrol-2-yl)indan-1-yloxy]isoquinoline |
| 590 | rac-trans-1,2- | 7-[rac-trans-(1,2)-1-(4-methanesulfonylphenoxy)indan-2-yl]-5,6,7,8-tetrahydro-[1,2,4]triazolo[4,3-a]pyrazine |
| 591 | trans-1S,2S- | 8-((1S,2S)-2-azetidin-1-yl-4,6-dichloroindan-1-yloxy)-5-fluoroquinoline |
| 592 | trans-1S,2S- | 8-((1S,2S)-4,6-dichloro-2-piperazin-1-ylindan-1-yloxy)-5-fluoroquinoline |
| 593 | trans-1S,2S- | 8-((1S,2S)-4,6-dichloro-2-pyrrolidin-1-ylindan-1-yloxy)-5-fluoroquinoline |
| 594 | rac-trans-1,2- | 8-(rac-trans-(1,2)-2-morpholin-4-yl-1,2,3,4-tetrahydronaphthalen-1-yloxy)quinoline-2-carbonitrile |
| 595 | rac-trans-1,2- | 8-(rac-trans-(1,2)-2-pyrrolidin-1-ylindan-1-yloxy)quinoline |
| 596 | rac-trans-1,2-3'S- | 8-[rac-trans-(1,2)-2-((S)-3-aminopiperidin-1-yl)-1,2,3,4-tetrahydronaphthalen-1-yloxy]quinoline-2-carbonitrile |
| 597 | rac-trans-1,2- | benzyl[1-(4-methanesulfonylphenoxy)indan-2-yl]amine |
| 598 | rac-trans-1,2-rac-3'- | C-(1-{rac-trans-(1,2)-1-[4-(2-methoxyethyl)phenoxy]indan-2-yl}pyrrolidin-3-yl)methylamine |
| 599 | rac-trans-1,2- | C-(1-{rac-trans-(1,2)-1-[4-bromo-2-(1H-pyrazol-3-yl)phenoxy]indan-2-yl}piperidin-4-yl)methylamine |
| 600 | rac-trans-1,2-rac-3'- | C-(1-{rac-trans-(1,2)-1-[4-bromo-2-(1H-pyrazol-3-yl)phenoxy]indan-2-yl}pyrrolidin-3-yl)methylamine |
| 601 | rac-trans-1,2-rac-3'- | C-{1-[rac-trans-(1,2)-1-(1H-indol-4-yloxy)indan-2-yl]pyrrolidin-3-yl}methylamine |
| 602 | rac-trans-1,2-rac-3'- | C-{1-[rac-trans-(1,2)-1-(2,4-difluorophenoxy)indan-2-yl]pyrrolidin-3-yl}methylamine |
| 603 | rac-trans-1,2- | C-{1-[rac-trans-(1,2)-1-(2-bromo-4-methylphenoxy)indan-2-yl]piperidin-4-yl}methylamine |
| 604 | rac-trans-1,2- | C-{1-[rac-trans-(1,2)-1-(2-fluoro-6-methoxyphenoxy)indan-2-yl]piperidin-4-yl}methylamine |
| 605 | rac-trans-1,2-rac-3'- | C-{1-[rac-trans-(1,2)-1-(2-fluoro-6-methoxyphenoxy)indan-2-yl]pyrrolidin-3-yl}methylamine |
| 606 | rac-trans-1,2- | C-{1-[rac-trans-(1,2)-1-(2-methoxy-5-methylphenoxy)indan-2-yl]piperidin-4-yl}methylamine |
| 607 | rac-trans-1,2-rac-3'- | C-{1-[rac-trans-(1,2)-1-(2-methoxy-5-methylphenoxy)indan-2-yl]pyrrolidin-3-yl}methylamine |
| 608 | rac-trans-1,2-rac-3'- | C-{1-[rac-trans-(1,2)-1-(2-methylbenzothiazol-5-yloxy)indan-2-yl]pyrrolidin-3-yl}methylamine |
| 609 | rac-trans-1,2- | C-{1-[rac-trans-(1,2)-1-(2-tert-butyl-4-ethylphenoxy)indan-2-yl]piperidin-4-yl}methylamine |
| 610 | rac-trans-1,2-rac-3'- | C-{1-[rac-trans-(1,2)-1-(2-tert-butyl-4-ethylphenoxy)indan-2-yl]pyrrolidin-3-yl}methylamine |
| 611 | rac-trans-1,2-rac-3'- | C-{1-[rac-trans-(1,2)-1-(3-chloro-2-methylphenoxy)indan-2-yl]pyrrolidin-3-yl}methylamine |
| 612 | rac-trans-1,2- | C-{1-[rac-trans-(1,2)-1-(3-chloro-5-methoxyphenoxy)indan-2-yl]piperidin-4-yl}methylamine |
| 613 | rac-trans-1,2-rac-3'- | C-{1-[rac-trans-(1,2)-1-(3-chloro-5-methoxyphenoxy)indan-2-yl]pyrrolidin-3-yl}methylamine |
| 614 | rac-trans-1,2- | C-{1-[rac-trans-(1,2)-1-(3-ethoxyphenoxy)indan-2-yl]piperidin-4-yl}methylamine |

-continued

| Example | Configuration | Name |
|---|---|---|
| 615 | rac-trans-1,2-rac-3'- | C-{1-[rac-trans-(1,2)-1-(3-ethoxyphenoxy)indan-2-yl]pyrrolidin-3-yl}methylamine |
| 616 | rac-trans-1,2- | C-{1-[rac-trans-(1,2)-1-(3-piperazin-1-ylphenoxy)indan-2-yl]piperidin-4-yl}methylamine |
| 617 | rac-trans-1,2-rac-3'- | C-{1-[rac-trans-(1,2)-1-(3-piperazin-1-ylphenoxy)indan-2-yl]pyrrolidin-3-yl}methylamine |
| 618 | rac-trans-1,2-rac-3'- | C-{1-[rac-trans-(1,2)-1-(4-[1,2,4]triazol-1-ylphenoxy)indan-2-yl]pyrrolidin-3-yl}methylamine |
| 619 | rac-trans-1,2- | C-{1-[rac-trans-(1,2)-1-(4-piperazin-1-ylphenoxy)indan-2-yl]piperidin-4-yl}methylamine |
| 620 | rac-trans-1,2- | C-{1-[rac-trans-(1,2)-1-(benzo[1,3]dioxol-5-yloxy)indan-2-yl]piperidin-4-yl}methylamine |
| 621 | rac-trans-1,2-rac-3'- | C-{1-[rac-trans-(1,2)-1-(benzo[1,3]dioxol-5-yloxy)indan-2-yl]pyrrolidin-3-yl}methylamine |
| 622 | rac-trans-1,2- | C-{1-[rac-trans-(1,2)-1-(quinolin-4-yloxy)indan-2-yl]piperidin-4-yl}methylamine |
| 623 | rac-trans-1,2- | Cyclopentyl-[1-(4-methanesulfonylphenoxy)indan-2-yl]amine |
| 624 | rac-trans-1,2- | Cyclopropylmethyl-[1-(4-methanesulfonylphenoxy)indan-2-yl]amine |
| 625 | rac-trans-1,2- | Diethyl-[rac-trans-(1,2)-1-(2-methylbenzothiazol-5-yloxy)indan-2-yl]amine |
| 626 | rac-trans-1,2- | Diethyl-[rac-trans-(1,2)-1-(3-piperazin-1-ylphenoxy)indan-2-yl]amine |
| 627 | rac-trans-1,2- | Diethyl-[rac-trans-(1,2)-1-(4-piperazin-1-ylphenoxy)indan-2-yl]amine |
| 628 | rac-trans-1,2- | Diethyl-{rac-trans-(1,2)-1-[4-(2-methoxyethyl)phenoxy]indan-2-yl}amine |
| 629 | rac-trans-1,2- | methyl-[rac-trans-(1,2)-1-(3-piperazin-1-ylphenoxy)indan-2-yl]piperidin-4-ylamine |
| 630 | rac-trans-1,2- | methyl-[rac-trans-(1,2)-1-(4-piperazin-1-ylphenoxy)indan-2-yl]piperidin-4-ylamine |
| 631 | trans-1S,2S-3'R- | N-(3-{trans-(1S,2S)-2-[(R)-3-(2-fluoroethylamino)piperidin-1-yl]indan-1-yloxy}phenyl)-acetamide |
| 632 | trans-1S,2S-3'R- | N-(3-{trans-(1S,2S)-2-[(R)-3-(3,3,3-trifluoropropylamino)piperidin-1-yl]indan-1-yloxy}-phenyl)acetamide |
| 633 | rac-trans-1,2- | N,N-diethyl-4-(rac-trans-(1,2)-2-pyrrolidin-1-ylindan-1-yloxy)benzamide |
| 634 | rac-trans-1,2- | N,N-dimethyl-2-[4-(rac-trans-(1,2)-2-pyrrolidin-1-ylindan-1-yloxy)phenyl]acetamide |
| 635 | rac-trans-1,2- | N-[2-(rac-trans-(1,2)-2-pyrrolidin-1-ylindan-1-yloxy)phenyl]acetamide |
| 636 | rac-trans-1,2- | N-[3-(rac-trans-(1,2)-2-azepan-1-ylindan-1-yloxy)phenyl]acetamide |
| 637 | rac-trans-1,2- | N-[3-(rac-trans-(1,2)-2-diethylaminoindan-1-yloxy)phenyl]acetamide |
| 638 | rac-trans-1,2- | N-[3-(rac-trans-(1,2)-2-dimethylaminoindan-1-yloxy)phenyl]acetamide |
| 639 | rac-trans-1,2- | N-[3-(rac-trans-(1,2)-2-piperazin-1-ylindan-1-yloxy)phenyl]acetamide |
| 640 | rac-trans-1,2- | N-[3-(rac-trans-(1,2)-2-pyrrolidin-1-ylindan-1-yloxy)benzyl]acetamide |
| 641 | rac-trans-1,2- | N-[3-(rac-trans-(1,2)-2-pyrrolidin-1-ylindan-1-yloxy)phenyl]acetamide |
| 642 | rac-trans-1,2- | N-[3-(rac-trans-(1,2)-2-thiomorpholin-4-ylindan-1-yloxy)phenyl]acetamide |
| 643 | rac-trans-1,2- | N-[3-(rac-trans-(1,2)-2-thiomorpholin-4-ylindan-1-yloxy)phenyl]acetamide |
| 644 | rac-trans-1,2- | N-[3-(rac-trans-(1,2)-4,6-dichloro-2-[1,4]diazepan-1-ylindan-1-yloxy)phenyl]acetamide |
| 645 | rac-trans-1,2- | N-[3-(rac-trans-(1,2)-4,6-dichloro-2-dimethylaminoindan-1-yloxy)phenyl]acetamide |
| 646 | rac-trans-1,2- | N-[3-(rac-trans-(1,2)-4,6-dichloro-2-morpholin-4-ylindan-1-yloxy)phenyl]acetamide |
| 647 | rac-trans-1,2- | N-[3-(rac-trans-(1,2)-4,6-dichloro-2-piperazin-1-ylindan-1-yloxy)phenyl]acetamide |
| 648 | rac-trans-1,2- | N-[3-(rac-trans-(1,2)-4,6-dichloro-2-pyrrolidin-1-ylindan-1-yloxy)phenyl]acetamide |
| 649 | rac-trans-1,2- | N-[3-(rac-trans-(1,2)-4-chloro-2-pyrrolidin-1-ylindan-1-yloxy)phenyl]acetamide |
| 650 | rac-trans-1,2- | N-[3-(rac-trans-(1,2)-4-chloro-6-fluoro-2-piperazin-1-ylindan-1-yloxy)phenyl]acetamide |
| 651 | rac-trans-1,2- | N-[3-(rac-trans-(1,2)-4-chloro-6-fluoro-2-pyrrolidin-1-ylindan-1-yloxy)phenyl]acetamide |

-continued

| Example | Configuration | Name |
|---|---|---|
| 652 | rac-trans-1,2- | N-[3-(rac-trans-(1,2)-4-fluoro-2-pyrrolidin-1-ylindan-1-yloxy)phenyl]acetamide |
| 653 | rac-trans-1,2- | N-[3-(rac-trans-(1,2)-4-methyl-2-pyrrolidin-1-ylindan-1-yloxy)phenyl]acetamide |
| 654 | rac-trans-1,2- | N-[3-(rac-trans-(1,2)-5,7-dichloro-2-dimethylaminoindan-1-yloxy)phenyl]acetamide |
| 655 | rac-trans-1,2- | N-[3-(rac-trans-(1,2)-5-chloro-2-pyrrolidin-1-ylindan-1-yloxy)phenyl]acetamide |
| 656 | rac-trans-1,2- | N-[3-(rac-trans-(1,2)-5-fluoro-2-pyrrolidin-1-ylindan-1-yloxy)phenyl]acetamide |
| 657 | rac-trans-1,2- | N-[3-(rac-trans-(1,2)-6-chloro-2-piperazin-1-ylindan-1-yloxy)phenyl]acetamide |
| 658 | rac-trans-1,2- | N-[3-(rac-trans-(1,2)-6-chloro-2-pyrrolidin-1-ylindan-1-yloxy)phenyl]acetamide |
| 659 | rac-trans-1,2- | N-[3-(rac-trans-(1,2)-6-chloro-4-fluoro-2-piperazin-1-ylindan-1-yloxy)phenyl]acetamide |
| 660 | rac-trans-1,2- | N-[3-(rac-trans-(1,2)-6-chloro-4-fluoro-2-pyrrolidin-1-ylindan-1-yloxy)phenyl]acetamide |
| 661 | rac-trans-1,2- | N-[3-(rac-trans-(1,2)-6-fluoro-2-pyrrolidin-1-ylindan-1-yloxy)phenyl]acetamide |
| 662 | rac-trans-1,2- | N-[3-(rac-trans-(1,2)-7-chloro-2-pyrrolidin-1-ylindan-1-yloxy)phenyl]acetamide |
| 663 | trans-1S,2S | N-[3-(trans-(1S,2S)-2-piperidin-1-ylindan-1-yloxy)phenyl]acetamide |
| 664 | trans-1S,2S | N-[3-(trans-(1S,2S)-4,6-dichloro-2-3,8-diazabicyclo[3.2.1]oct-3-ylindan-1-yloxy)phenyl]acetamide |
| 665 | trans-1S,2S | N-[3-(trans-(1S,2S)-4,6-dichloro-2-piperazin-1-ylindan-1-yloxy)phenyl]acetamide |
| 666 | rac-trans-1,2- | N-[4-(rac-trans-(1,2)-2-pyrrolidin-1-ylindan-1-yloxy)phenyl]acetamide |
| 667 | rac-trans-1,2- | N-[4-(rac-trans-(1,2)-2-pyrrolidin-1-ylindan-1-yloxy)-pyridin-2-yl]acetamide |
| 668 | rac-trans-1,2- | N-[6-(rac-trans-(1,2)-2-pyrrolidin-1-ylindan-1-yloxy)-pyridin-2-yl]acetamide |
| 669 | rac-trans-1,2- | N-[rac-trans-(1,2)-1-(4-methanesulfonylphenoxy)indan-2-yl]-N,N',N'-trimethylpropane-1,3-diamine |
| 670 | rac-trans-1,2-3'R- | N-[rac-trans-(1,2)-3-((R)-2-[1,3']bipyrrolidinyl-1'-ylindan-1-yloxy)phenyl]acetamide |
| 671 | trans-1S,2S- | N-[trans-(1S,2S)-4,6-dichloro-1-(4-methanesulfonylphenoxy)indan-2-yl]-N,N',N'-trimethyl-ethane-1,2-diamine |
| 672 | trans-1S,2S- | N-[trans-(1S,2S)-4,6-dichloro-1-(4-methanesulfonylphenoxy)indan-2-yl]-N,N',N'-trimethylpropane-1,3-diamine |
| 673 | trans-1S,2S-3'R- | N-{3-[(1S,2S)-6-chloro-4-fluoro-2-((R)-3-hydroxypyrrolidin-1-yl)indan-1-yloxy]-4-fluorophenyl}-N-methyl-methanesulfonamide |
| 674 | rac-trans-1,2- | N-{3-[rac-trans-(1,2)-2-(hexahydropyrrolo[3,4-c]pyrrol-2-yl)indan-1-yloxy]phenyl}acetamide |
| 675 | rac-trans-1,2-3'R- | N-{3-[rac-trans-(1,2)-2-((R)-3-aminopiperidin-1-yl)-1,2,3,4-tetrahydronaphthalen-1-yloxy]-4-propylphenyl}acetamide |
| 676 | rac-trans-1,2-3'R- | N-{3-[rac-trans-(1,2)-2-((R)-3-aminopiperidin-1-yl)-1,2,3,4-tetrahydronaphthalen-1-yloxy]phenyl}acetamide |
| 677 | rac-trans-1,2-3'R- | N-{3-[rac-trans-(1,2)-2-((R)-3-aminopiperidin-1-yl)-4-chloro-6-fluoroindan-1-yloxy]phenyl}acetamide |
| 678 | rac-trans-1,2-3'R- | N-{3-[rac-trans-(1,2)-2-((R)-3-aminopiperidin-1-yl)-6-chloro-4-fluoroindan-1-yloxy]phenyl}acetamide |
| 679 | rac-trans-1,2-3'R- | N-{3-[rac-trans-(1,2)-2-((R)-3-aminopiperidin-1-yl)indan-1-yloxy]phenyl}acetamide |
| 680 | rac-trans-1,2-3'R- | N-{3-[rac-trans-(1,2)-2-((R)-3-hydroxymethylpyrrolidin-1-yl)indan-1-yloxy]phenyl}acetamide |
| 681 | rac-trans-1,2-3'R- | N-{3-[rac-trans-(1,2)-2-((R)-3-hydroxypyrrolidin-1-yl)indan-1-yloxy]phenyl}acetamide |
| 682 | rac-trans-1,2-3'R- | N-{3-[rac-trans-(1,2)-2-((R)-3-methoxypyrrolidin-1-yl)indan-1-yloxy]phenyl}acetamide |
| 683 | rac-trans-1,2-3'S- | N-{3-[rac-trans-(1,2)-2-((S)-3-aminopiperidin-1-yl)-1,2,3,4-tetrahydronaphthalen-1-yloxy]-4-propylphenyl}acetamide |
| 684 | rac-trans-1,2-3'S- | N-{3-[rac-trans-(1,2)-2-((S)-3-aminopiperidin-1-yl)-1,2,3,4-tetrahydronaphthalen-1-yloxy]phenyl}acetamide |
| 685 | rac-trans-1,2-3'S- | N-{3-[rac-trans-(1,2)-2-((S)-3-aminopiperidin-1-yl)indan-1-yloxy]phenyl}acetamide |
| 686 | rac-trans-1,2-rac-3'- | N-{3-[rac-trans-(1,2)-2-(3-aminomethylpyrrolidin-1-yl)indan-1-yloxy]phenyl}acetamide |

| Example | Configuration | Name |
|---|---|---|
| 687 | rac-trans-1,2-rac-3'- | N-{3-[rac-trans-(1,2)-2-(3-aminopyrrolidin-1-yl)indan-1-yloxy]phenyl}acetamide |
| 688 | rac-trans-1,2- | N-{3-[rac-trans-(1,2)-2-(4-aminomethylpiperidin-1-yl)indan-1-yloxy]phenyl}acetamide |
| 689 | rac-trans-1,2- | N-{3-[rac-trans-(1,2)-4,6-dichloro-2-(hexahydropyrrolo[3,4-c]pyrrol-2-yl)indan-1-yloxy]phenyl}acetamide |
| 690 | trans-1S,2S-3'R- | N-{3-[trans-(1S,2S)-2-((R)-3-aminopiperidin-1-yl)-4,6-dichloroindan-1-yloxy]phenyl}acetamide |
| 691 | trans-1S,2S-3'R- | N-{3-[trans-(1S,2S)-2-((R)-3-aminopiperidin-1-yl)indan-1-yloxy]phenyl}acetamide |
| 692 | trans-1S,2S-3'R- | N-{3-[trans-(1S,2S)-2-((R)-3-dimethylaminopiperidin-1-yl)indan-1-yloxy]phenyl}acetamide |
| 693 | trans-1S,2S-rac 3'- | N-{3-[trans-(1S,2S)-2-(3-amino-3-propylpiperidin-1-yl)-4,6-dichloroindan-1-yloxy]phenyl}acetamide |
| 694 | trans-1S,2S-3'R- | N-{3-[trans-(1S,2S)-4,6-dichloro-2-((R)-3-dimethylaminopiperidin-1-yl)indan-1-yloxy]phenyl}acetamide |
| 695 | trans-1S,2S-3'R- | N-{3-[trans-(1S,2S)-4,6-dichloro-2-((R)-3-hydroxymethylpyrrolidin-1-yl)indan-1-yloxy]phenyl}acetamide |
| 696 | trans-1S,2S-3'R- | N-{3-[trans-(1S,2S)-4,6-dichloro-2-((R)-3-hydroxypyrrolidin-1-yl)indan-1-yloxy]phenyl}acetamide |
| 697 | trans-1S,2S | N-{3-[trans-(1S,2S)-4,6-dichloro-2-(4-methylpiperazin-1-yl)indan-1-yloxy]phenyl}acetamide |
| 698 | trans-1S,2S-3'R- | N-{4-[(1S,2S)-4,6-dichloro-2-((R)-3-hydroxypyrrolidin-1-yl)indan-1-yloxy]phenyl}-N-methylmethanesulfonamide |
| 699 | trans-1S,2S-3'R- | N-{4-[(1S,2S)-4,6-dichloro-2-((R)-3-hydroxypyrrolidin-1-yl)indan-1-ylsulfanyl]phenyl}acetamide |
| 700 | rac-trans-1,2- | N-ethyl-4-(rac-trans-(1,2)-2-pyrrolidin-1-ylindan-1-yloxy)benzenesulfonamide |
| 701 | rac-trans-1,2- | tert-butyl-[1-(4-methanesulfonylphenoxy)indan-2-yl]amine |
| 702 | trans-1S,2S- | 2-{[trans-(1S,2S)-4,6-Dichloro-1-(4-methanesulfonyl-phenoxy)-indan-2-yl]-methyl-amino}-ethanol |
| 703 | rac-trans-1,2- | 4-(rac-trans-(1,2)-2-Cyclopropylamino-indan-1-yloxy)-3-fluoro-benzenesulfonamide |
| 704 | trans-1S,2S- | 2-({trans-(1S,2S)-4,6-Dichloro-1-[4-(3,5-dimethyl-[1,2,4]triazol-4-yl)-2-fluoro-phenoxy]-indan-2-yl}-methyl-amino)-ethanol |
| 705 | rac-trans-1,2- | Cyclopentylmethyl-[rac-trans-(1,2)-1-(4-methanesulfonyl-phenoxy)-indan-2-yl]-amine |
| 706 | rac-cis-1,2- | Cyclobutyl-[rac-cis-(1,2)-1-(4-methanesulfonyl-phenoxy)-indan-2-yl]-amine |
| 707 | trans-1S,2S- | (4-Methanesulfonyl-phenyl)-((1S,2S)-2-pyrrolidin-1-yl-indan-1-yl)-amine |
| 708 | rac-trans-1,2- | Cyclobutyl-[rac-trans-(1,2)-1-(4-methanesulfonyl-phenoxy)-indan-2-yl]-amine |
| 709 | rac-trans-1,2- | 4-(rac-trans-(1,2)-2-Cyclobutylamino-indan-1-yloxy)-3-fluoro-benzenesulfonamide |
| 710 | trans-1S,2S-3'R- | 2-Chloro-4-(3,5-dimethyl-[1,2,4]triazol-4-yl)-benzoic acid trans-(1S,2S)-4,6-dichloro-2-((R)-3-hydroxy-pyrrolidin-1-yl)-indan-1-yl ester |
| 711 | rac-trans-1,2- | Cycloheptyl-[rac-trans-(1,2)-1-(4-methanesulfonyl-phenoxy)-indan-2-yl]-amine |
| 712 | trans-1S,2S-3'R- | (R)-1-{trans-(1S,2S)-4,6-Dichloro-1-[4-(2-ethyl-4-methyl-imidazol-1-yl)-phenoxy]-indan-2-yl}-pyrrolidin-3-ol |
| 713 | rac-trans-1,2- | 4-(rac-trans-(1,2)-2-Cycloheptylamino-indan-1-yloxy)-3-fluoro-benzenesulfonamide |
| 714 | trans-1S,2S-3'R- | (R)-1-{trans-(1S,2S)-4,6-Dichloro-1-[4-(2-isopropyl-4-methyl-imidazol-1-yl)-phenoxy]-indan-2-yl}-pyrrolidin-3-ol |
| 715 | trans-1S,2S-3'R- | (R)-1-{trans-(1S,2S)-4,6-Dichloro-1-[4-(3-isopropyl-5-methyl-[1,2,4]triazol-4-yl)-phenoxy]-indan-2-yl}-pyrrolidin-3-ol |
| 716 | trans-1S,2S-3'R- | (R)-1-{trans-(1S,2S)-4,6-Dichloro-1-[4-(3-ethyl-5-isopropyl-[1,2,4]triazol-4-yl)-phenoxy]-indan-2-yl}-pyrrolidin-3-ol |
| 717 | rac-trans-1,2- | Cyclobutylmethyl-[rac-trans-(1,2)-1-(4-methanesulfonyl-phenoxy)-indan-2-yl]-amine |
| 718 | rac-trans-1,2- | 4-[rac-trans-(1,2)-2-(Cyclobutylmethyl-amino)-indan-1-yloxy]-3-fluoro-benzenesulfonamide |
| 719 | trans-1S,2S-3'R- | (R)-1-{trans-(1S,2S)-6-Chloro-1-[4-(2-ethyl-4-methyl-imidazol-1-yl)-phenoxy]-4-fluoro-indan-2-yl}-pyrrolidin-3-ol |
| 720 | trans-1S,2S-3'R- | (R)-1-{trans-(1S,2S)-6-Chloro-4-fluoro-1-[4-(2-isopropyl-4-methyl-imidazol-1-yl)-phenoxy]-indan-2-yl}-pyrrolidin-3-ol |

-continued

| Example | Configuration | Name |
|---|---|---|
| 721 | trans-1S,2S-3'R- | (R)-1-{trans-(1S,2S)-6-Chloro-4-fluoro-1-[4-(3-isopropyl-5-methyl-[1,2,4]triazol-4-yl)-phenoxy]-indan-2-yl}-pyrrolidin-3-ol |
| 722 | trans-1S,2S-3'R- | (R)-1-{trans-(1S,2S)-6-Chloro-1-[4-(3-ethyl-5-isopropyl-[1,2,4]triazol-4-yl)-phenoxy]-4-fluoro-indan-2-yl}-pyrrolidin-3-ol |
| 723 | rac-trans-1,2- | (1-Ethyl-propyl)-[rac-trans-(1,2)-1-(4-methanesulfonyl-phenoxy)-indan-2-yl]-amine |
| 724 | trans-1S,2S-3'R- | (R)-1-{trans-(1S,2S)-1-[4-(4-tert-Butyl-2-isopropyl-imidazol-1-yl)-phenoxy]-6-chloro-4-fluoro-indan-2-yl}-pyrrolidin-3-ol |
| 725 | trans-1S,2S-3'R- | (R)-1-{trans-(1S,2S)-4,6-Dichloro-1-[5-(2-ethyl-4-methyl-imidazol-1-yl)-2-fluoro-phenoxy]-indan-2-yl}-pyrrolidin-3-ol |
| 726 | trans-1S,2S- | N-{trans-(1S,2S)-4,6-Dichloro-1-[4-(3,5-dimethyl-[1,2,4]triazol-4-yl)-2-fluoro-phenoxy]-indan-2-yl}-N,N',N'-trimethyl-ethane-1,2-diamine |
| 727 | trans-1S,2S-3'R- | (R)-1-{trans-(1S,2S)-4,6-Dichloro-1-[4-(2,4-dimethyl-imidazol-1-yl)-2-fluoro-phenoxy]-indan-2-yl}-pyrrolidin-3-ol |
| 728 | trans-1S,2S-3'R- | (R)-1-[trans-(1S,2S)-4,6-Dichloro-1-(4-imidazol-1-yl-phenoxy)-indan-2-yl]-pyrrolidin-3-ol |
| 729 | trans-1S,2S-3'R- | (R)-1-{trans-(1S,2S)-1-[4-(4-tert-Butyl-2-methyl-imidazol-1-yl)-2-fluoro-phenoxy]-4,6-dichloro-indan-2-yl}-pyrrolidin-3-ol |
| 730 | rac-trans-1,2- | Cyclopentyl-[rac-trans-(1,2)-1-(4-methanesulfonyl-phenoxy)-indan-2-yl]-methyl-amine |
| 731 | trans-1S,2S-3'R- | (R)-1-{trans-(1S,2S)-4,6-Dichloro-1-[4-(2-methanesulfonyl-imidazol-1-yl)-phenoxy]-indan-2-yl}-pyrrolidin-3-ol |
| 732 | trans-1S,2S-3'R- | (R)-1-{trans-(1S,2S)-4,6-Dichloro-1-[4-(2-isopropyl-imidazol-1-yl)-phenoxy]-indan-2-yl}-pyrrolidin-3-ol |
| 733 | trans-1S,2S-3'R- | 3-{4-[trans-(1S,2S)-4,6-Dichloro-2-((R)-3-hydroxy-pyrrolidin-1-yl)-indan-1-yloxy]-phenyl}-5-methyl-3H-[1,3,4]oxadiazol-2-one |
| 734 | rac-trans-1,2- | Cyclobutyl-[rac-trans-(1,2)-1-(4-methanesulfonyl-phenoxy)-indan-2-yl]-methyl-amine |
| 735 | trans-1S,2S-3'R- | 3-{4-[trans-(1S,2S)-4,6-Dichloro-2-((R)-3-hydroxy-pyrrolidin-1-yl)-indan-1-yloxy]-phenyl}-3H-[1,3,4]oxadiazol-2-one |
| 736 | trans-1S,2S-3'R- | 2-{4-[trans-(1S,2S)-4,6-Dichloro-2-((R)-3-hydroxy-pyrrolidin-1-yl)-indan-1-yloxy]-phenyl}-4-ethyl-2,4-dihydro-[1,2,4]triazol-3-one |
| 737 | trans-1S,2S-3'R- | 2-{4-[trans-(1S,2S)-4,6-Dichloro-2-((R)-3-hydroxy-pyrrolidin-1-yl)-indan-1-yloxy]-phenyl}-4-ethyl-5-methyl-2,4-dihydro-[1,2,4]triazol-3-one |
| 738 | trans-1S,2S-3'R- | (R)-1-{trans-(1S,2S)-6-Chloro-1-[4-(2,4-dimethyl-imidazol-1-yl)-2-fluoro-phenoxy]-4-fluoro-indan-2-yl}-pyrrolidin-3-ol |
| 739 | trans-1S,2S-3'R- | (R)-1-{trans-(1S,2S)-4,6-Dichloro-1-[2-fluoro-4-(2-methanesulfonyl-imidazol-1-yl)-phenoxy]-indan-2-yl}-pyrrolidin-3-ol |
| 740 | trans-1S,2S-3'R- | 1-{4-[trans-(1S,2S)-4,6-Dichloro-2-((R)-3-hydroxy-pyrrolidin-1-yl)-indan-1-yloxy]-3-fluoro-phenyl}-1H-imidazole-2-carboxylic acid methyl ester |
| 741 | trans-1S,2S-3'R- | 4-[trans-(1S,2S)-4,6-Dichloro-2-((R)-3-hydroxy-pyrrolidin-1-yl)-indan-1-yloxy]-3-fluoro-benzenesulfonamide |
| 742 | trans-1S,2S-3'R- | (R)-1-{trans-(1S,2S)-4,6-Dichloro-1-[4-(4-methyl-piperazine-1-sulfonyl)-phenoxy]-indan-2-yl}-pyrrolidin-3-ol |
| 743 | trans-1S,2S-3'R- | 4-[trans-(1S,2S)-4,6-Dichloro-2-((R)-3-hydroxy-pyrrolidin-1-yl)-indan-1-yloxy]-benzenesulfonamide |
| 744 | trans-1S,2S-3'R- | (R)-1-{trans-(1S,2S)-4,6-Dichloro-1-[4-(morpholine-4-sulfonyl)-phenoxy]-indan-2-yl}-pyrrolidin-3-ol |
| 745 | trans-1S,2S-3'R- | 1-{5-[trans-(1S,2S)-4,6-Dichloro-2-((R)-3-hydroxy-pyrrolidin-1-yl)-indan-1-yloxy]-2-fluoro-phenyl}-3-methyl-1,3-dihydro-imidazol-2-one |
| 746 | trans-1S,2S- | Cyclopentyl-{trans-(1S,2S)-4,6-dichloro-1-[4-(3,5-dimethyl-[1,2,4]triazol-4-yl)-2-fluoro-phenoxy]-indan-2-yl}-amine |
| 747 | trans-1S,2S- | Cyclopentyl-[trans-(1S,2S)-4,6-dichloro-1-(4-methanesulfonyl-phenoxy)-indan-2-yl]-amine |
| 748 | trans-1S,2S- | 4-(trans-(1S,2S)-4,6-Dichloro-2-cyclopentylamino-indan-1-yloxy)-3-fluoro-benzenesulfonamide |
| 749 | trans-1S,2S- | {trans-(1S,2S)-6-Chloro-1-[4-(3,5-dimethyl-[1,2,4]triazol-4-yl)-2-fluoro-phenoxy]-4-fluoro-indan-2-yl}-cyclopentyl-amine |

-continued

| Example | Configuration | Name |
| --- | --- | --- |
| 750 | trans-1S,2S- | 4-(trans-(1S,2S)-6-Chloro-2-cyclopentylamino-4-fluoro-indan-1-yloxy)-3-fluoro-benzenesulfonamide |
| 751 | trans-1S,2S- | [trans-(1S,2S)-6-Chloro-4-fluoro-1-(4-methanesulfonyl-phenoxy)-indan-2-yl]-cyclopentyl-amine |
| 752 | trans-1S,2S- | 1-[4-(trans-(1S,2S)-6-Chloro-2-cyclopentylamino-4-fluoro-indan-1-yloxy)-3-fluoro-phenyl]-pyrrolidine-2,5-dione |
| 753 | trans-1S,2S- | 3-[4-(trans-(1S,2S)-6-Chloro-2-cyclopentylamino-4-fluoro-indan-1-yloxy)-3-fluoro-phenyl]-imidazolidine-2,4-dione |
| 754 | trans-1S,2S- | {trans-(1S,2S)-6-Chloro-4-fluoro-1-[2-fluoro-4-(2-methanesulfonyl-imidazol-1-yl)-phenoxy]-indan-2-yl}-cyclopentyl-amine |
| 755 | trans-1S,2S- | 1-[4-(trans-(1S,2S)-6-Chloro-2-cyclopentylamino-4-fluoro-indan-1-yloxy)-3-fluoro-phenyl]-3-methyl-1,3-dihydro-imidazol-2-one |
| 756 | trans-1S,2S- | 1-[3-(trans-(1S,2S)-6-Chloro-2-cyclopentylamino-4-fluoro-indan-1-yloxy)-4-fluoro-phenyl]-3-methyl-1,3-dihydro-imidazol-2-one | and the pharmaceutically acceptable salts thereof.

Because of their NHE-inhibitory properties, the compounds of the formula I are suitable for the prevention and treatment of diseases which are caused by activation of or by an activated NHE, and of diseases which are caused secondarily by the NHE-related damage. The compounds of the formula I can also be employed for the treatment and prevention of diseases where NHE is only partially inhibited, for example by use of a lower dosage. Where mention is made hereinafter of compounds of the formula I or of compounds of the invention, the pharmaceutically acceptable salts thereof are always included even if this is not explicitly mentioned.

Accordingly, the present invention further relates to the use of the compounds of the formula I for the prevention and treatment of acute or chronic diseases in veterinary and human medicine.

As a consequence of their pharmacological effects, the compounds of the formula I are particularly suitable for leading to an improvement in respiratory drive. They can therefore be used for the treatment of impaired respiratory conditions like those which may occur for example in the following clinical conditions and diseases: impaired central respiratory drive (e.g. central sleep apneas, sudden infant death, postoperative hypoxia), muscle-related respiratory impairments, respiratory impairments following long-term ventilation, respiratory impairments associated with adaptation to high altitude, obstructive and mixed form of sleep apneas, sleep-related respiratory impairments, sleep hypoventilation syndrome, upper airway resistance syndrome, acute and chronic pulmonary diseases with hypoxia and hypercapnia.

In addition, the compounds increase the tone of the muscles of the upper airways, so that snoring is suppressed. Said compounds are therefore used in particular for the prevention and treatment of sleep apneas, of the upper airway resistance syndrome, of muscle-related respiratory impairments and for the prevention and treatment of snoring.

Combination of an NHE inhibitor of the formula I with a carbonic anhydrase inhibitor (e.g. acetazolamide) is in this connection also advantageous, the latter bringing about a metabolic acidosis and thus itself increasing respiratory activity, so that an enhanced effect and reduced use of active ingredient can be achieved.

The compounds of the invention preserve, as a result of their NHE3-inhibitory effect, the cellular energy reserves which are rapidly exhausted during toxic and pathogenic events and thus lead to cell damage or cell death. In this connection, the energy-costly ATP-consuming sodium absorption in the proximal tubule temporarily ceases under the influence of NHE3 inhibitors, and the cell is thus able to survive an acute pathogenic, ischemic or toxic situation. The compounds are therefore suitable for example as pharmaceuticals for the treatment of ischemic situations, especially ischemic noxae, for example of acute renal failure.

The compounds are further suitable also for the treatment of chronic renal disorders and types of nephritis which lead, as a consequence of increased protein excretion, to chronic renal failure. Accordingly, the compounds of the formula I are suitable for the manufacture of a medicament for the treatment of late damage from diabetes, of diabetic nephropathy and of chronic renal disorders, in particular of all renal inflammations (nephritides) which are associated with an increased protein/albumin excretion.

It has emerged that the compounds of the invention have an inhibiting and delaying effect on glucose absorption and thereby are able to reduce the blood glucose and have a beneficial influence on further metabolic parameters such as triglycerides. Because of these effects, the compounds of the invention can advantageously be used for the prevention and therapy of the metabolic syndrome, diabetes mellitus and hyperlipidemias.

It has emerged that the compounds of the invention have a mild laxative effect and accordingly can also be used advantageously as laxatives or if there is a risk of constipation and for the prophylaxis and treatment of constipation.

The compounds of the invention can further be used advantageously for the prevention and therapy of acute and chronic disorders of the intestinal tract which are induced for example by ischemic states in the intestinal region and/or by subsequent reperfusion or by inflammatory states and events. Such complications may arise for example through deficient intestinal peristalsis as are frequently to be observed for example following surgical interventions, associated with constipation or greatly reduced intestinal activity.

It is possible with the compounds of the invention to prevent the formation of gallstones.

In general, the NHE inhibitors described herein can beneficially be combined with other compounds which likewise regulate the intracellular pH, those suitable being inhibitors of the enzyme group of carbonic anhydratases, inhibitors of systems which transport bicarbonate ions, such as the sodium-bicarbonate cotransporter (NBC) or the sodium-dependent chloride-bicarbonate exchanger (NCBE), and with other NHE inhibitors having an inhibitory effect on other NHE subtypes, as combination partners, because they may enhance or modulate the pharmacologically relevant pH-regulating effects of the NHE inhibitors described herein.

Since sodium ion/proton exchange is significantly elevated in essential hypertensives, the compounds of the formula I are suitable for the prevention and treatment of high blood pressure and of cardiovascular disorders. They can be used in this connection alone or with a suitable combination partner for the treatment of high blood pressure and for the treatment of cardiovascular disorders. Thus, for example, one or more diuretics having a thiazide-like action, loop diuretics, aldosterone and pseudoaldosterone antagonists such as hydrochlorothiazide, indapamide, polythiazide, furosemide, piretanide, torasemide, bumetanide, amiloride, triamterene, spironolactone or eplerone, can be combined with compounds of the formula I. The NHE inhibitors of the present invention can moreover be used in combination with calcium antagonists such as verapamil, diltiazem, amlodipine or nifedipine, and with ACE inhibitors such as, for example, ramipril, enalapril, lisinopril, fosinopril or captopril. Further beneficial combination partners are also β blockers such as metoprolol, albuterol etc., antagonists of the angiotensin receptor and its receptor subtypes such as losartan, irbesartan, valsartan, omapatrilat, gemopatrilat, endothelin antagonists, renin inhibitors, adenosine receptor agonists, inhibitors and activators of potassium channels such as glibenclamide, glimepiride, diazoxide, cromokalim, minoxidil and derivatives thereof, activators of the mitochondrial ATP-sensitive potassium channel (mitoK(ATP) channel), inhibitors of further potassium channels such as of Kv1.5 etc.

NHE inhibitors are additionally suitable for the treatment of non-insulin-dependent diabetes (NIDDM), in which case for example insulin resistance is restrained. It may in this connection be beneficial, for enhancing the antidiabetic efficacy and quality of the effect of the compounds of the invention, to combine them with a biguanide such as metformin, with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizer or with meglitinide.

Said compounds are therefore advantageously used alone or in combination with other pharmaceuticals or active ingredients for the manufacture of a medicament for the treatment or prophylaxis of impairments of respiratory drive, of respiratory disorders, sleep-related respiratory disorders, sleep apneas, of snoring, of acute and chronic renal disorders, of acute renal failure and of chronic renal failure, of impairments of bowel function, of high blood pressure, of essential hypertension.

The compounds of the invention are further suited for treating cystic fibrosis (mucoviscidosis). Lack of the CFTR protein in cystic fibrosis has been shown to activate the NHE3 leading to an excessive absorption of salt and water in the intestine (gut, gall system, pancreas), seminal fluid, the upper airway and the lung. This leads to a drying of the feces (obstipation), of the intestinal secretions and of the lung fluid with the consequence of a viscoelastic mucus in the lung that gives rise to frequent airway infections and finally to a deterioration of lung function which is an important cause for mortality. Moreover, an excessive activation of the NHE3 leads to a more acidic environment in the gut impairing digestion (maldigestion) and a more acidic pH of the lung fluid favouring bacterial infections (particularly *Pseudomonas aeruginosa* infections). Compounds can be administered systemically (per os, i.m., i.v., s.c.) or given as an inhalation for a treatment of the airway and lung symptoms.

Compounds have a potential in acute and chronic airway diseases and infections as mucolytics by inhibiting salt and water absorption in the upper airway and in the lungs leading to a liquidification of the mucus. This effect is of therapeutic utility in acute and chronic viral, bacterial and fungal infections of the upper airways and the lungs and in chronic inflammatory lung diseases such as asthma and COPD.

The invention further relates to the use of the compounds of the formula I and the pharmaceutically acceptable salts thereof for the use as medicaments and to a medicament comprising compounds of the formula I or pharmaceutically acceptable salts thereof.

The invention further relates to the use of these compounds or the pharmaceutically acceptable salts for the treatment or prophylaxis of disorders by complete or partial inhibition of the $Na^+/H^+$ exchange by NHE3.

Therefore, a further aspect of the invention is the use of a compound of the formula I and/or its pharmaceutically acceptable salts as claimed in one or more of claims 1 to 15 alone or in combination with other pharmaceuticals or active ingredients for the manufacture of a medicament for the treatment or prophylaxis of impairments of respiratory drive, of respiratory disorders, of sleep-related respiratory disorders, sleep apneas, of snoring, of cystic fibrosis, upper and lower airway diseases that are associated with viscous mucus, of acute and chronic renal disorders, of acute renal failure and of chronic renal failure, of impairments of bowel function, of constipation, of high blood pressure, of essential hypertension, of cardiovascular disorders, of central nervous system disorders, of disorders resulting from CNS overexcitability, epilepsy and centrally induced spasms or of anxiety states, depressions and psychoses, of ischemic states of the peripheral or central nervous system or of stroke, degenerative CNS disorders, reduced memory capacity, dementia and Alzheimer's disease, and of acute and chronic damage and disorders of peripheral organs or limbs caused by ischemic or reperfusion events, of atherosclerosis, of impairments of lipid metabolism, of hyperlipidemias, of thromboses, of diabetes mellitus, of impairments of biliary function, of infestation by ectoparasites, of disorders resulting from endothelial dysfunction, of protozoal diseases, of malaria, of states of shock or of diabetes and late damage from diabetes or of diseases in which cell proliferation represents a primary or secondary cause, for the preservation and storage of transplants for surgical procedures, for use in surgical operations and organ transplantations and for maintaining health and prolonging life.

The invention also relates to medicines for human, veterinary or phytoprotective use comprising an effective amount of a compound of the formula I and/or of a pharmaceutically acceptable salt thereof, as well as medicines for human, veterinary or phytoprotective use comprising an effective amount of a compound of the formula I and/or of a pharmaceutically acceptable salt thereof alone or in combination with one or more other pharmacological active ingredients or pharmaceuticals.

Pharmaceuticals which comprise a compound of the formula I or the pharmaceutically acceptable salts thereof can be administered for example orally, parenterally, intramuscularly, intravenously, rectally, nasally, pharyngeally, by inhalation, subcutaneously or by a suitable transcutaneous dosage form, the preferred administration depending on the respective manifestation of the disorder. The compounds of the formula I can moreover be used alone or together with pharmaceutical excipients, specifically both in veterinary and in human medicine and in crop protection. The pharmaceuticals comprise active ingredients of the formula I and/or pharmaceutically acceptable salts thereof generally in an amount of from 0.01 mg to 1 g per dose unit.

The skilled worker is familiar on the basis of his expert knowledge with the excipients suitable for the desired pharmaceutical formulation. Besides solvents, gel formers, suppository bases, tablet excipients and other active ingredient carriers it is possible to use for example antioxidants, dispersants, emulsifiers, antifoams, masking flavors, preservatives, solubilizers or colorants.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry and as wet granules. Examples of suitable oily carriers or solvents are vegetable or animal oils, such as sunflower oil or fish liver oil.

For subcutaneous, percutaneous or intravenous administration, the active compounds used are converted, if desired with the substances usual for this purpose, such as solubilizers, emulsifiers or further excipients, into solution, suspension or emulsion. Examples of suitable solubilizers are: water, physiological saline or alcohols, e.g. ethanol, propanol, glycerol, as well as sugar solutions such as glucose or mannitol solutions, or also a mixture of the various solvents mentioned.

Suitable as pharmaceutical formulation for administration in the form of aerosols or sprays are for example solutions, suspensions or emulsions of the active ingredient of the formula I in a pharmaceutically acceptable solvent such as, in particular, ethanol or water, or a mixture of such solvents. The formulation may, if required, also comprise other pharmaceutical excipients such as surfactants, emulsifiers and stabilizers, and a propellant gas. Such a preparation normally comprises the active ingredient in a concentration of about 0.1 to 10, in particular of about 0.3 to 3% by weight.

The dosage of the active ingredient of the formula I to be administered and the frequency of administration depend on the potency and duration of action of the compounds used; additionally also on the nature and severity of the disease to be treated and on the gender, age, weight and individual response of the mammal to be treated.

On average, the daily dose of a compound of the formula I for a patient weighing about 75 kg is at least 0.001 mg/kg, preferably 0.1 mg/kg, to a maximum of 30 mg/kg, preferably 1 mg/kg, of body weight. In acute situations, for example immediately after suffering apneic states at high altitude, higher doses may also be necessary. Up to 300 mg/kg per day may be necessary in particular on i.v. administration, for example for an infarct patient in intensive care. The daily dose can be divided into one or more, for example up to 4, single doses.

If the compounds of the formula I comprise one or more acidic or basic groups or one or more basic heterocycles, the corresponding physiologically or toxicologically acceptable salts are also included in the invention, especially the pharmaceutically acceptable salts. The compounds of the formula I may thus be deprotonated on an acidic group and be used for example as alkali metal salts, preferably sodium or potassium salts, or as ammonium salts, for example as salts with ammonia or organic amines or amino acids. Compounds of the formula I comprising at least one basic group can also be prepared in the form of their physiologically tolerated acid addition salts, e.g. with the following acids: from inorganic acids such as hydrochloric acid, sulfuric acid or phosphoric acid or from organic acids such as acetic acid, citric acid, tartaric acid, lactic acid, malonic acid, methanesulfonic acid, fumaric acid. Suitable acid addition salts in this connection are salts of all pharmacologically acceptable acids, for example halides, in particular hydrochlorides, lactates, sulfates, citrates, tartrates, acetates, phosphates, methylsulfonates, p-toluenesulfonates, adipates, fumarates, gluconates, glutamates, glycerolphosphates, maleates and pamoates (this group also corresponds to the physiologically acceptable anions); but also trifluoroacetates.

The present invention further comprises derivatives of the compounds of the formula I, for example solvates, such as hydrates and alcohol adducts, esters, prodrugs and other physiologically acceptable derivatives of the compounds of the formula I, and active metabolites of the compounds of the formula I. The invention likewise comprises all crystal modifications of the compounds of the formula I.

Processes for Preparing Compounds of the Formula I:

General processes suitable for preparing compounds of the general formula I are described below. The compounds of the formula I can in this connection be prepared by different chemical processes. The groups and radicals A, B, L, X, R1, R2, R3, R4 and R5 and index p mentioned in the following methods have the abovementioned meaning unless they are explicitly defined otherwise.

Abbreviations:
HPLC high performance liquid chromatography
LC liquid chromatography
Rt retention time
THF tetrahydrofuran
TFA trifluoroacetic acid
FA formic acid
DMSO dimethyl sulfoxide
abs. absolute
DMF dimethylformamide
AcN acetonitrile
rt room temperature
min. minutes
h hour(s)
CI chemical ionization
ES=ESI electrospray ionization
dba dibenzylideneacetone Method A:

For example as shown in scheme A that starting from epoxides of the formula II which initially, after epoxide ring opening with an amine of the formula HNR3R4, afford a corresponding 1-amino 2-ol intermediate of the formula III, which is subsequently subjected to a Mitsunobu reaction with an aryl or heteroaryl compounds B—OH which may be substituted one or more times by R5. Phenols are preferably employed in this reaction. It is also possible alternatively to employ aryl or heteroaryl thiols B—SH or aryl- or heteroarylcarboxylic acids B—$CO_2H$ which may be substituted one or more times by R5 in order to obtain the corresponding —S— or —$CO_2H$— bridged derivatives. Mitsunobu reactions are, as is known, carried out in the presence of a phosphine, e.g. such as triphenylphosphine and of azodicarboxylic esters such as, for example, diisopropyl azodicarboxylate in inert solvents such as acetonitrile, $CH_2Cl_2$ or tetrahydrofuran. In the case of 1-amino 2-ols of the formula III, this entails migration of the amine residue NR3R4 into position 2 of the basic structure (J. Org. Chem. 1991, 56, 670-672).

Scheme A: Synthesis of compounds of the formula I via Mitsunobu inversion

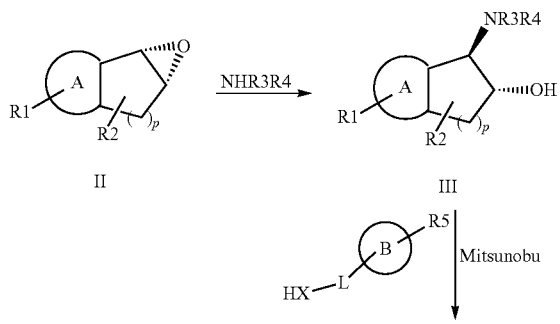

acetic acid, to obtain the compounds of the formula I. After deprotection, these functional groups can be further modified where appropriate, for example by alkylation with an alkylating agent or by acylation and subsequent reduction in order to obtain further compounds I.

The starting materials employed in scheme A, such as the epoxides of the formula II, the amine NHR3R4, and the hydroxyaryls or hydroxyheteroaryls or the thiol derivatives thereof are either commercially available, known from the literature or can be synthesized easily in analogy to compounds known from the literature. A few suitable synthetic schemes for such starting materials are reproduced by way of example in the experimental section.

Method B:

A further method for preparing compounds of the formula I is depicted in scheme B.

Scheme B: Synthesis of the compounds I by nucleophilic aromatic substitution

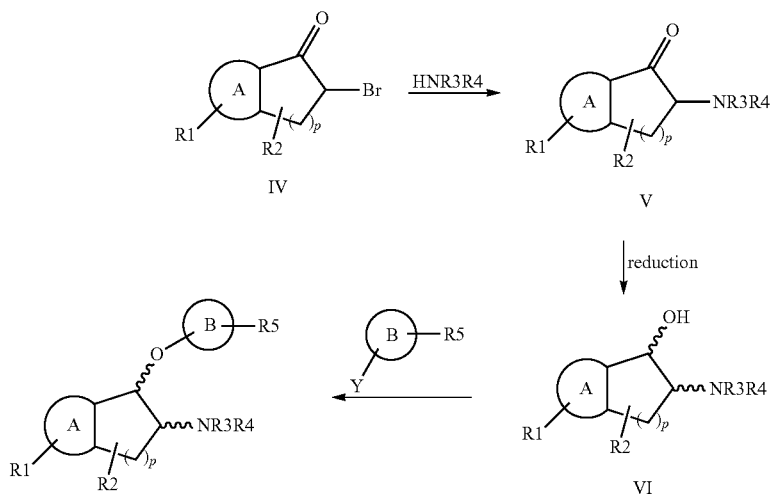

-continued

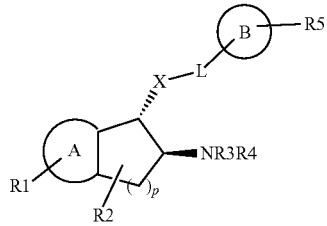

in which L is a covalent bond or —C(=O)— and X is O, or L is a covalent bond and X is S.

It is possible in this way to prepare a large number of compounds I, preferably those in which the two substituents are in a trans configuration relative to one another. If one of the radicals R3 and R4 of the amine substituent is to be replaced by a further functional group such as, for example, a hydroxy group or an amino group, care must be taken where appropriate to protect such groups during the Mitsunobu reaction. This can take place for example by trialkyl or triarylsilyl groups in the case of OH groups or by the BOC protective groups in the case of amino groups. After the Mitsunobu reaction, the protective group is then removed again, for example by treatment with hydrochloric acid or trifluoro- In this process, 2-bromo 1-one compounds of the formula IV are reacted with amines of the formula R3-NH—R4 to give the corresponding amino ketones V. The keto group is then reduced to the 1-hydroxy group, resulting in the intermediates of the formula VI. It is possible in this connection for products VI with both the cis and the trans configuration with regard to centers 1 and 2 to be produced. The resulting intermediates of the formula VI are then arylated by nucleophilic aromatic substitution on aryl or heteroaryl compounds B—Y, where B may be substituted one or more times by R5, using a strong base such as, for example, sodium hydride or powdered NaOH in an inert solvent such as DMSO. Y is in this connection a suitable leaving group such as, for example, fluorine, chlorine or trifluoromesyloxy. If the radicals R3 and R4 are substituted for example by amino or hydroxy groups, these should be protected where appropriate by base-stable protective groups such as, for instance, alkyl- or aryl-substituted silyl groups.

It is also possible with this process to have recourse to a large extent to known or commercially available bromo ketones IV or can easily be obtained for example by bromination under standard conditions from the appropriate ketones.

Method C:

A further process relates to those compounds of the formula I in which the amine group NR3R4 is linked via a carbon-containing bridge to position 2, that is q is 1 in general formula I.

Scheme C: Synthesis of compounds of the formula I via Mannich-like products

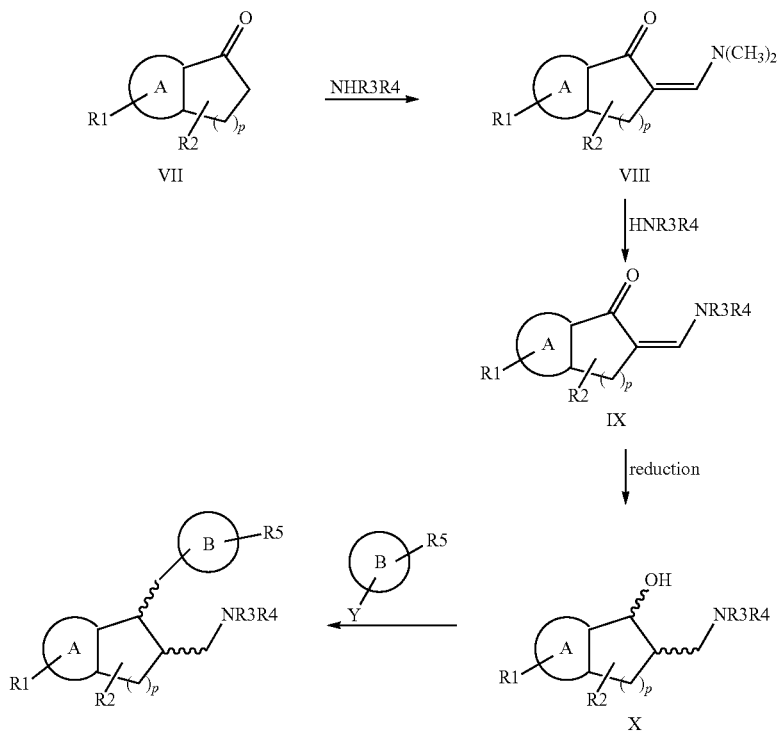

In this case, ketones of the formula VII are reacted with formamide acetals, preferably N,N-dimethylformamide dimethyl acetal, in order to obtain the corresponding dimethylaminomethylene compounds of the formula VIII. The dimethylamino group can be replaced in the next stage by other amino groups to give aminomethylene compounds of the formula IX. This can take place for example by heating compounds of the formula VIII in DMF in the presence of excess amine HNR3R4. Subsequent reduction, for example by sodium borohydride in methanol, ordinarily affords mixtures of stereoisomeric amine alcohols of the formula X which can, where appropriate after separation into the individual components, be arylated in analogy to the illustration in scheme B to give the compounds I of the invention.

Method D:

A further process for preparing compounds of the formula I is represented in scheme D. 1-Amino-2-indanol III and analogs thereof are reacted in an inert solvent such as, for example, THF in the presence of a suitable azide source such as, for example, diphenylphosphoryl azide (DPPA) under Mitsunobu conditions. In this case too, the amine residue migrates from position 1 to position 2 as described in scheme A. There is preferential formation of 1-azido-2-indanamines with the transconfiguration, which are reacted in situ after addition of suitable reducing agents such as, for example, LiAlH$_4$ directly to give diamines of the general formula XI with the trans configuration. In order obtain compounds of the formula I, compounds of the formula XI are arylated with palladium catalysis for example under Buchwald conditions known from the literature (J. Am. Chem. Soc. 1997, 8451-8458).

Scheme D: Synthesis of compounds I via Mitsunobu inversion and subsequent arylation

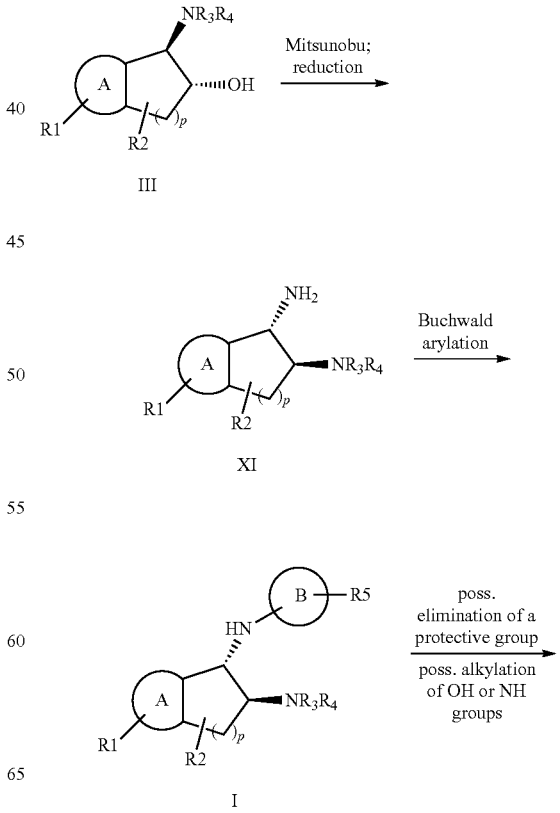

-continued

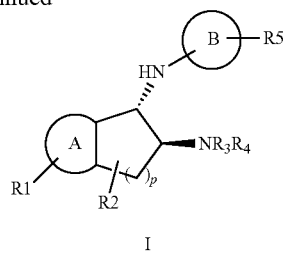

I

Method E:

A further process for preparing compounds of the formula I is depicted in scheme E. Benzoic esters I which are synthesized as in scheme A are hydrolyzed in a known manner to give compounds of the general formula VI. This takes place for example in solvents such as acetone/water mixtures and using suitable bases such as sodium hydroxide. Compounds of the formula VI are then reacted with suitable alkylating agents such as, for example, benzyl bromides in solvents such as, for example, THF in the presence of suitable bases such as sodium hydride. The compound I obtained in this way is available where appropriate for further manipulations.

Scheme E: Synthesis of the compounds I via alkylation

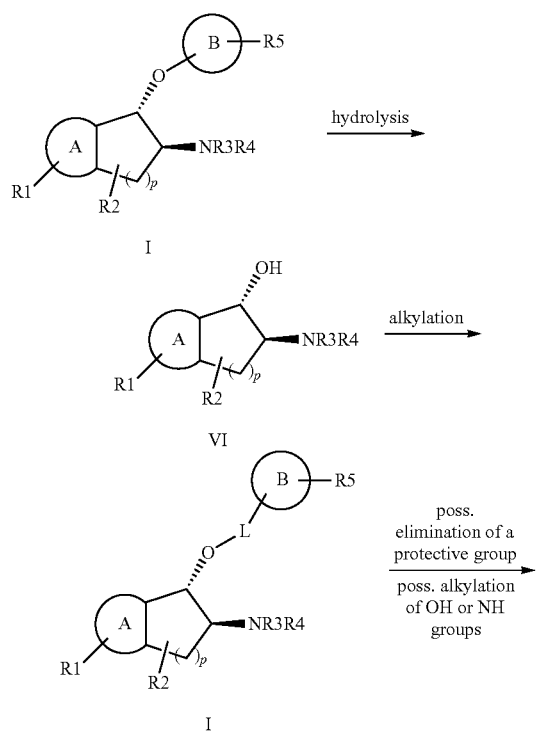

-continued

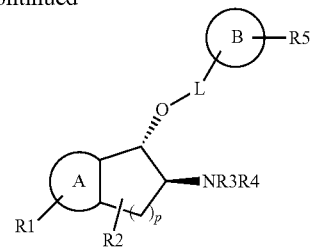

I in which L is an alkylene bridge.

If the compounds I contain further functional groups such as, for example, alcohols or amines, these can be reacted further in a known manner as in scheme F. Suitable examples are acylations, alkylations or acylation/reduction sequences. The procedure is described in the experimental section by means of exemplary embodiments.

Scheme F: Optional further reactions of compounds I

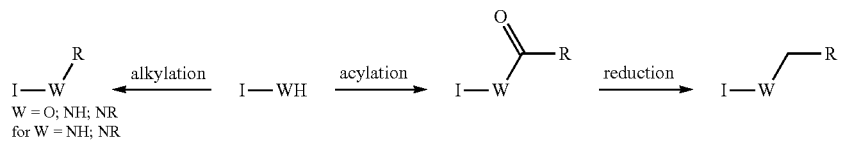

Method G:

A further process relates to those compounds of the formula I in which one or two substituents R3 or R4 at the amine group NR3R4 equals hydrogen, that is R3=H or R3=R4=H in general formula I.

Scheme G: Synthesis of compounds of the formula I via Pd catalyzed deprotection of allyl amines

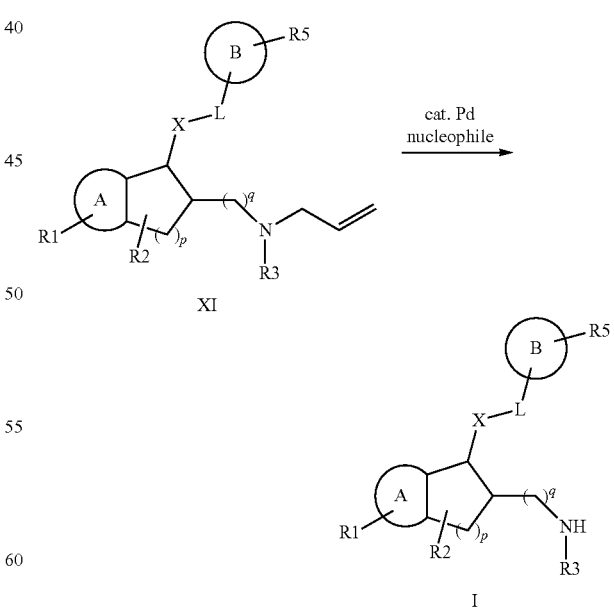

In this process allyl amines XI, which for example can be synthesized following method A, are deprotected using nucleophiles, e.g. such as thiosalicylic acid or dimethylbarbituric acid, in inert solvents such as $CH_2Cl_2$ or THF. The reaction is catalyzed by Pd. Suitable Pd sources are for example Pd(PPh$_3$)$_4$ or Pd(dba)$_2$ in the presence of stabilizing ligands such as bis(diphenylphosphino)butane. In case of bisallyl amines (R3=R4=allyl) both allyl groups can be cleaved using at least 2 equivalents of a suitable nucleophile and prolonged reaction times. Compounds of the general formula I, which are synthesized following method G, are available for further manipulations e.g. acylation or alkylation.

EXEMPLARY EMBODIMENTS

Reference in the following procedures to equivalents refers to the indication of the amount of substance unless explicitly mentioned otherwise.

The following LC methods were used to analyze the exemplary embodiments.

| Method | Conditions |
|---|---|
| LC method 1: | YMC Jsphere H80, 33 * 2, 4μ, H2O + 0.05% TFA:AcN + 0.05% TFA 2:98 (1 min) to 95:5 (5.0 min) to 95:5 (6.25 min); 1.0 ml/min, rt |
| LC method 2: | YMC Jsphere H80, 33 * 2, 4μ, H2O + 0.05% TFA:AcN + 0.05% TFA 95:5 (0 min) to 95:5 (0.5 min) to 5:95 (3.5 min) to 5:95 (4 min); 1.3 ml/min, rt |
| LC method 3: | YMC Jsphere H80, 33 * 2, 4μ, H2O + 0.1% FA:AcN + 0.08% FA 95:5 (0 min) to 5:95 (2.5 min) to 5:95 (3 min); 1.3 ml/min, rt |
| LC method 4: | YMC Jsphere H80, 33 * 2, 4μ, H2O + 0.05% TFA:AcN + 0.05% TFA 95:5 (0 min) to 5:95 (2.5 min) to 5:95 (3 min); 1.3 ml/min, rt |
| LC method 5: | YMC Jsphere H80, 33 * 2, 4μ, H2O + 0.05% FA:AcN + 0.05% FA 95:5 (0 min) to 5:95 (2.5 min); 1.0 ml/min, rt |
| LC method 6: | YMC Jsphere H80, 33 * 2, 4μ, H2O + 0.05% TFA:AcN + 0.05% TFA 5:95 (0 min) to 95:5 (3.4 min) to 95:5 (4.4 min); 1.0 ml/min, rt |
| LC method 7: | YMC Jsphere H80, 33 * 2, 4μ, H2O + 0.05% TFA:AcN + 0.05% TFA 95:5 (0 min) to 5:95 (2.5 min); 1.3 ml/min, rt |
| LC method 8: | Waters XBridge C18 4.6 * 50 mm; 2.5μ, H2O + 0.1% FA:AcN + 0.08% FA 97:3 (0 min) to 40:60 (3.5 min) to 2:98 (4 min) to 2:98 (5 min) to 97:3 (5.2 min) to 97:3 (6.5 min); 1.3 ml/min, rt |
| LC method 9: | WatersXBridge C18, 4, 6 * 50, 2, 5μ, H2O + 0.05% TFA:AcN + 0.05% TFA 95:5 (0 min) to 95:5 (0.3 min) to 5:95 (3.5 min) to 5:95 (4 min); 1.7 ml/min, 40° C. |
| LC method 10: | YMC Jsphere H80, 33 * 2, 4μ, H2O + 0.05% TFA:AcN + 0.05% TFA 95:5 (0 min) to 5:95 (2.5 min) to 95:5; 1.3 ml/min, rt |
| LC method 11: | YMC Jsphere H80, 33 * 2, 4μ, H2O + 0.05% TFA:AcN + 0.05% TFA 95:5 (0 min) to 5:95 (2.5 min) to 95:5 (3.2 min); 1.3 ml/min, rt |
| LC method 12: | YMC Jsphere H80, 33 * 2, 4μ, H2O + 0.05% TFA:AcN + 0.05% TFA 95:5 (0 min) to 5:95 (3.7 min); 1.0 ml/min, rt |
| LC method 13: | YMC Jsphere H80, 33 * 2, 4μ, H2O + 0.1% FA:AcN + 0.08% FA 95:5 (0 min) to 5:95 (2.5 min); 1.3 ml/min, rt |
| LC method 14: | YMC Jsphere H80, 33 * 2, 4μ, H2O + 0.05% TFA:AcN + 0.05% TFA 95:5 (0 min) to 95:5 (0.5 min) to 5:95 (3.5 min) to 5:95 (4 min); 1.3 ml/min, rt |
| LC method 15: | WatersXBridge C18, 4, 6 * 50, 2, 5μ, H2O + 0.05% TFA:AcN + 0.05% TFA 95:5 (0 min) to 95:5 (0.2 min) to 5:95 (2.4 min) to 5:95 (3.2 min), to 95:5 (3.3 min) to 95:5 (4.0 min); 1.7 ml/min, 40° C. |
| LC method 16: | WatersXBridge C18, 4, 6 * 50, 2, 5μ, H2O + 0.05% TFA:AcN + 0.05% TFA 95:5 (0 min) to 5:95 (3.3 min) to 5:95 (3.85 min) to 95:5 (4 min); 1.7 ml/min, 40° C. |
| LC method 17: | YMC Jsphere H80 33 * 2, 4μ, H2O + 0.05% TFA:AcN + 0.05% TFA 98:2 (1 min) to 5:95 (5.0 min) to 5:95 (6.25 min); 1.0 ml/min, rt |
| LC method 18: | YMC Jsphere H80, 33 * 2, 4μ, H2O + 0.05% TFA:AcN + 0.05% TFA 5:95 (0 min) to 95:5 (2.5 min) to 95:5 (3 min); 1.3 ml/min, rt |
| LC method 19: | WatersXBridge C18, 4, 6 * 50, 2, 5μ, H2O + 0.05% TFA:AcN + 0.05% TFA 95:5 (0 min) to 95:5 (0.2 min) to 5:95 (2.4 min) to 5:95 (3.2 min), to 95:5 (3.3 min), to 95:5 (3.8 min), to 95:5 (4.0 min) 1.7 ml/min, 40° C. |
| LC method 20: | Merck Chromolith FastGrad. RP-18e, 50 × 2 mm, 0.05% TFA:AcN + 0.05% TFA 98:2 (0.2 min) to 2:98 (2.4 min) to 2:98 (3.2 min) to 98:2 (3.3 min) to 98:2 (4 min); 2.0 ml/min, 50° C. |
| LC method 21: | Merck Chromolith FastGrad. RP-18e, 50 × 2 mm, 0.05% TFA:AcN + 0.05% TFA 98:2 (0.2 min) to 2:98 (2.4 min) to 2:98 (3.2 min) to 98:2 (3.3 min) to 98:2 (4 min); 2.4 ml/min, 50° C. |
| LC method 22: | Waters UPLC BEH C18XBridge C18 2.1 * 50 mm; 1.7u, H2O + 0.1% FA:AcN + 0.08% FA 95:5 (0 min) to to 5:95 (1.1 min) to 5:95 (1.7 min) to 95:5 (1.8 min) to 95:5 (2 min); 0.9 ml/min, 55° C. |
| LC method 23: | Waters XBridge C18 4.6 * 50 mm; 2, 5u, H2O + 0.1% FA:AcN + 0.1% FA 97:3 (0 min) to 40:60 (3.5 min) to 2:98 (4 min) to 2:98 (5 min) to 97:3 (5.2 min) to 97:3 (6.5 min); 1.3 ml/min, 45° C. |
| LC method 24: | WatersXBridge C18, 4, 6 * 50, 2, 5μ, H2O + 0.05% TFA:AcN + 0.05% TFA 95:5 (0 min) to 95:5 (0.2 min) to 5:95 (2.4 min) to 5:95 (3.5 min), to 95:5 (3.6 min) to t 95:5 (4.5 min); 1.7 ml/min, 50° C. |
| LC method 25: | YMC-Pack Jsphere H80 33 * 2.1, 4u, H2O + 0.05% TFA:CH3OH + 0.05% TFA 98:2 (1 min) to 5:95 (5.0 min) to 5:95 (6.25 min); 1 ml/min, rt |

Scheme 1: General synthesis scheme for indane oxides

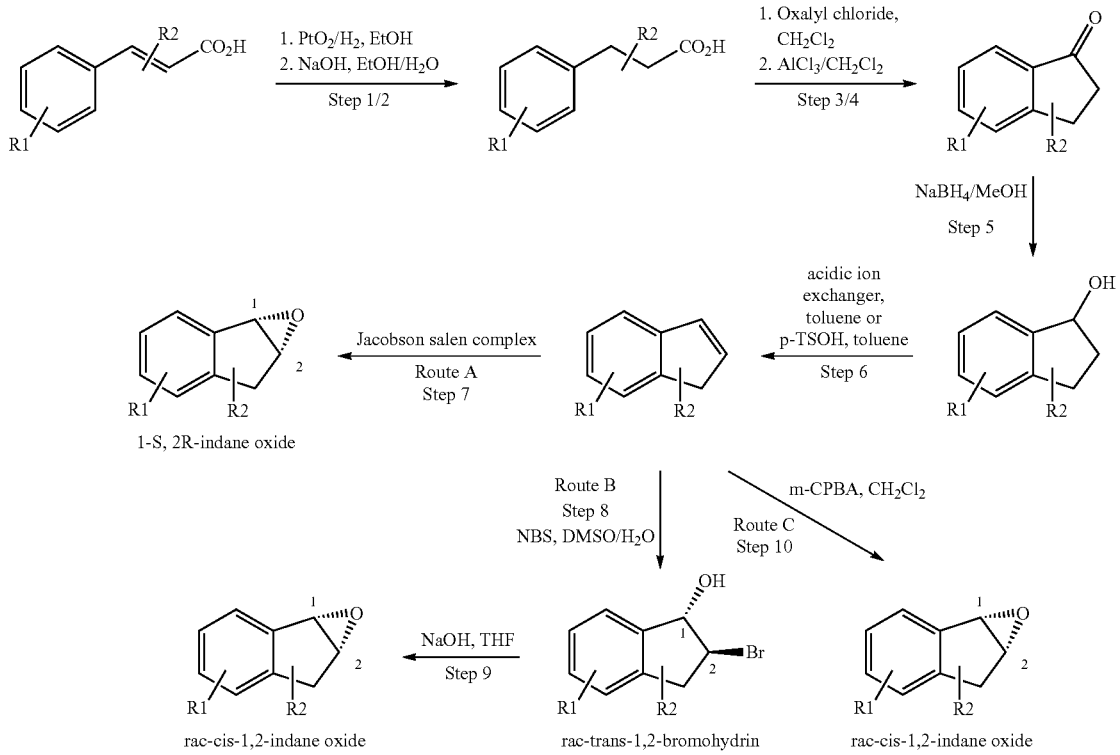

General Synthetic Methods:

Step 1/2: Cinnamic acid (1 equivalent) and PtO$_2$ (2.2 mol %) were suspended in ethanol (EtOH) (8 ml/mmol of cinnamic acid) and vigorously stirred under an H$_2$ atmosphere (1 bar) until the reaction mixture no longer absorbs H$_2$. The suspension was filtered and the residue was washed with EtOH. The solvent of the filtrate was removed in vacuo, and the resulting crude mixture of propionic acid and propionic ester was employed without further purification in the next reaction.

The mixture from reaction step 1 was dissolved in EtOH (2 ml/mmol of intermediate from step 1), and an aqueous NaOH solution (2.5 equivalents based on the intermediate from step 1) was added. The solution was stirred for 16 h, and the volume of the mixture was reduced by applying a vacuum. The resulting solution was diluted with water and acidified with aqueous 2 N HCl. The suspension was filtered and the residue was washed with water. The desired propionic acids resulted as solid.

Step 3/4: Oxalyl chloride (3.40 equivalents) was cautiously added to a solution of the propionic acid (1 equivalent) in CH$_2$Cl$_2$ (1.4 ml/mmol of propionic acid) and DMF (0.01 ml/mmol of propionic acid) so that the solution foams. The resulting clear solution was stirred for a further 6 h and then volatile constituents were removed in vacuo. The appropriate acid chloride was employed without further workup in the next reaction step.

A solution of the acid chloride in CH$_2$Cl$_2$ (1.2 ml/mmol of propionic acid from step 3) was added dropwise to a solution of AlCl$_3$ (1.30 equivalents) in CH$_2$Cl$_2$ (0.75 ml/mmol AlCl$_3$) at 0° C. After the addition was complete, the ice bath was removed and heated under reflux for a further 3 h. The mixture was poured into ice-water, and the aqueous phase was extracted with CH$_2$Cl$_2$. The combined organic phases were dried with Na$_2$SO$_4$ and filtered, and the solvent was removed in vacuo. The crude products were purified by column chromatography. If the ring closure did not take place regioselectively, the regioisomers were separated by column chromatography.

Step 5: NaBH$_4$ (1 mmol/mmol of indanone) was cautiously added in portions to a solution of the indanone (1 equivalent) in EtOH (4 ml/mmol of indanones) at 10° C. After addition was complete, the solution was stirred at room temperature (rt) for 3-16 h and then the volume of the reaction solution was reduced in vacuo. The suspension was added to ice-water, and the aqueous phase was extracted with ethyl acetate. The combined organic phases were dried with Na$_2$SO$_4$ and filtered, and the solvent was removed in vacuo. The crude products were purified by column chromatography.

Step 6: DOWEX® (MARATHON® MSC (H) ion-exchange resin; 0.02 g/mmol of indanol) was added to a solution of the indanol (1 equivalent) in toluene (3 ml/mmol of indanol) and the suspension was heated to reflux with a water trap for 1 h. The cooled suspension was filtered, the residue was washed with toluene, and the solvent of the combined organic phases was removed in vacuo. The crude product was purified by column chromatography.

Alternatively, in step 6 a solution of the indanol (1 equivalent) and p-toluenesulfonic acid monohydrate (0.1 equivalent) in toluene (4 ml/mmol of indanol) was heated under reflux with a water trap for 1-2 h. The solution was cooled to room temperature (rt) and washed with saturated aqueous NaHCO$_3$ solution. The organic phase was dried with Na$_2$SO$_4$ and filtered, and the solvent was removed in vacuo. The crude products were purified by column chromatography.

Step 7: 4-(3-Phenylpropyl)pyridine N-oxide (0.04 equivalents) was added to a solution of the indene (1 equivalent) in $CH_2Cl_2$ (1.2 ml/mmol of indene) and (S,S)-(+)-N,N'-bis(3,5-di-tert-butylsalicylidene)-1,2-cyclohexanediaminomanganese(III) chloride (0.01 equivalent). The reaction solution was stirred for 10 min and cooled to −2° C. Half-saturated aqueous $K_2CO_3$ solution (0.5 ml/mmol of indene) was added and, while stirring this suspension vigorously, aqueous NaOCl solution (1.25 ml/mmol of indene; 13% free chlorine) was slowly added dropwise. Immediately thereafter the pH was adjusted to pH 11-12 with 0.1 M phosphate buffer (pH=7.5). The 2 phase system was stirred vigorously for 4 h, during which the temperature slowly rose to 5° C. The phases were separated and the aqueous phase was extracted with $CH_2Cl_2$. The combined organic phases were washed with saturated aqueous $Na_2S_2O_3$ solution and water, dried with $Na_2SO_4$ and filtered, and the solvent was removed in vacuo. The crude products were purified by column chromatography. The resulting product was additionally recrystallized from heptane.

Step 8: NBS (2 equivalents) was added in small portions to a solution of the indene (1 equivalent) in DMSO (1 ml/mmol of indene) and water (0.025 ml/mmol of indene) at 25° C. in such a way that the temperature did not rise above 35° C. The solution was stirred at room temperature (rt) for 2 h and poured onto ice. The aqueous phase was extracted with ethyl acetate, and the combined organic phases were washed with brine and then dried with $Na_2SO_4$ and filtered, and the solvent was removed in vacuo. The crude products were purified by column chromatography.

Step 9: Powdered NaOH (6.6 equivalents) was added to a solution of the bromohydrin (1 equivalent) in THF (7 ml/mmol of bromohydrin). The suspension was stirred at room temperature (rt) until the precursor was completely reacted, and the reaction was monitored by thin-layer chromatography (TLC). The suspension was filtered and the residue was washed with ethyl acetate. The combined organic phases were dried with $Na_2SO_4$ and again filtered, and the solvent was removed in vacuo. The crude products were purified by column chromatography.

Step 10: mCPBA (1.1 equivalents) was added in small portions to a solution of the indene (1 equivalent) in $CH_2Cl_2$ (2.5 ml/mmol of indene). The suspension was vigorously stirred for 2 days and then filtered. The residue was washed with $CH_2Cl_2$, and the combined organic phases were washed successively with saturated aqueous $Na_2SO_3$ solution and saturated aqueous $NaHCO_3$ solution, dried with $Na_2SO_4$ and filtered, and the solvent was removed in vacuo. The crude products were purified by column chromatography.

Scheme 2: Synthesis of indane oxide analogs

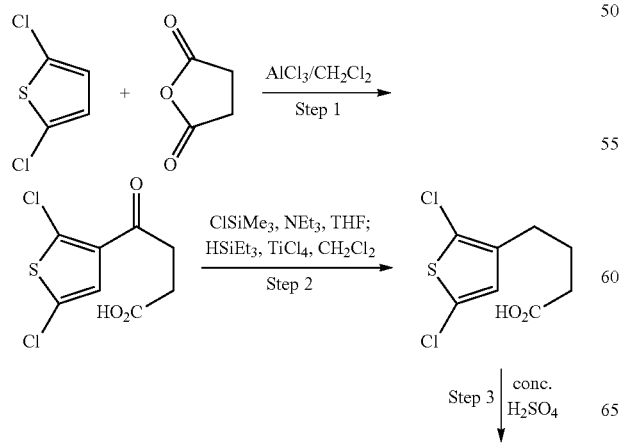

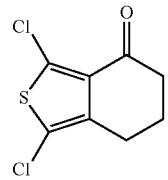

General Synthetic Methods:

Step 1: A solution of 2,5-dichlorothiophene (1.0 equivalents) in $CH_2Cl_2$ (0.75 ml/mmol of thiophene) was slowly added dropwise to a suspension of $AlCl_3$ (1.25 equivalents) and succinic anhydride (1.0 equivalents) in $CH_2Cl_2$ (1.00 ml/mmol $AlCl_3$) at 0° C. After the addition was complete, the ice bath was removed and stirred at room temperature (rt) for a further 4 h. The mixture was poured into ice-water, and the aqueous phase was extracted with $CH_2Cl_2$. The combined organic phases were extracted with 2N aqueous NaOH solution, and the combined aqueous phases were then acidified with conc. HCl. The acidic aqueous solution was extracted with $CH_2Cl_2$, and the combined organic phases were dried with $Na_2SO_4$ and filtered, and the solvent was removed in vacuo. The resulting crude product was purified by column chromatography.

Step 2: A solution of the precursor (1.0 equivalents) and $N(C_2H_5)_3$ (1.10 equivalents) in THF (0.80 ml/mmol of precursor) was slowly added dropwise to a solution of ClSi$(CH_3)_3$ (1.10 equivalents) in THF (1.70 ml/mmol ClSi$(CH_3)_3$) at 0° C. After the addition was complete, stirring was continued at 0° C. for 15 min and the resulting suspension was filtered. The solvent of the filtrate was removed in vacuo, and the residue was dissolved in $CH_2Cl_2$ (2.00 ml/mmol of precursor). HSi$(C_2H_5)_3$ (3.0 equivalents) and $TiCl_4$ (3.0 equivalents, 1M in $CH_2Cl_2$) was added to the solution at room temperature (rt). The solution was stirred at room temperature (rt) for 20 h and then poured into ice-water. The aqueous phase was extracted with $CH_2Cl_2$. The combined organic phases were extracted with aqueous saturated $NaHCO_3$ solution, and the combined aqueous phases were then cautiously acidified with conc. HCl. The acidic aqueous solution was extracted with ethyl acetate, and the combined organic phases were dried with $Na_2SO_4$ and filtered, and the solvent was removed in vacuo. The crude product was purified by column chromatography.

Step 3: The carboxylic acid (1.00 equivalents) was dissolved at 0° C. in conc. $H_2SO_4$ (6.30 ml/mmol of carboxylic acid) and then stirred at room temperature (rt) for 4 h. The solution was poured into ice-water, and the aqueous phase was extracted with ethyl acetate. The combined organic phases were dried with $Na_2SO_4$ and filtered, and the solvent was removed in vacuo. The crude product was purified by column chromatography.

The further reactions to give the epoxide took place in analogy to scheme 1/route B.

Scheme 3: Synthesis of tetrahydronaphthalene oxides (route D)

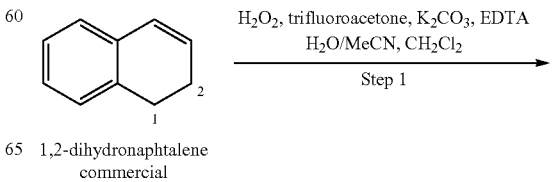

1,2-dihydronaphtalene commercial

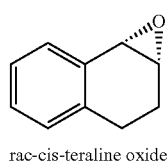

rac-cis-teraline oxide

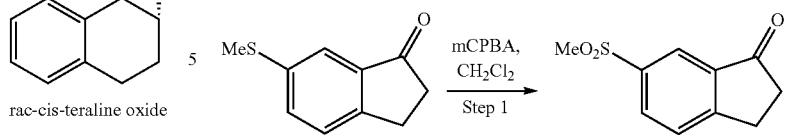

Scheme 4: Synthesis of indane oxide intermediates:

General Synthetic Methods:

Step 1: At 0° C., 1,2-dihydronaphthalene (1.00 equivalents) and 1,1,1-trifluoroacetone (0.15 equivalents) were added to 1.5 M aqueous potassium carbonate solution ($4\times10^{-4}$ M in EDTA, 1.55 ml/mmol of 1,2-dihydronaphthalene) and acetonitrile (1.55 ml/mmol of 1,2-dihydronaphthalene) and stirred for 5 min. This was followed by cautious addition of 30% strength hydrogen peroxide (4.00 equivalents). The reaction mixture was stirred at 0° C. for 4.5 h (reaction monitored by TLC) and then ethyl acetate was added. After separation of the phases, the aqueous phase was extracted twice with ethyl acetate, the combined organic phases were washed with saturated aqueous NaCl solution, dried with MgSO$_4$ and filtered, and the solvent was removed in vacuo. The crude product was purified by column chromatography.

General Synthetic Methods:

Step 1: mCPBA (meta-chloroperbenzoic acid, 2.2 equivalents) was added in small portions to a solution of the indanone (1 equivalent) in CH$_2$Cl$_2$ (4.0 ml/mmol of indanone) at room temperature (rt). The suspension was vigorously stirred overnight and then, at 0° C., an aqueous Na$_2$S$_2$O$_5$ solution was added. The two-phase mixture was stirred for 10 min and filtered, the phases were separated, and the aqueous phase was extracted with CH$_2$Cl$_2$. The combined organic phases were washed with saturated aqueous saturated NaHCO$_3$ solution, dried with Na$_2$SO$_4$ and filtered, and the solvent was removed in vacuo. The crude product was purified by column chromatography.

The following indane oxides and analogs were synthesized by the methods described:

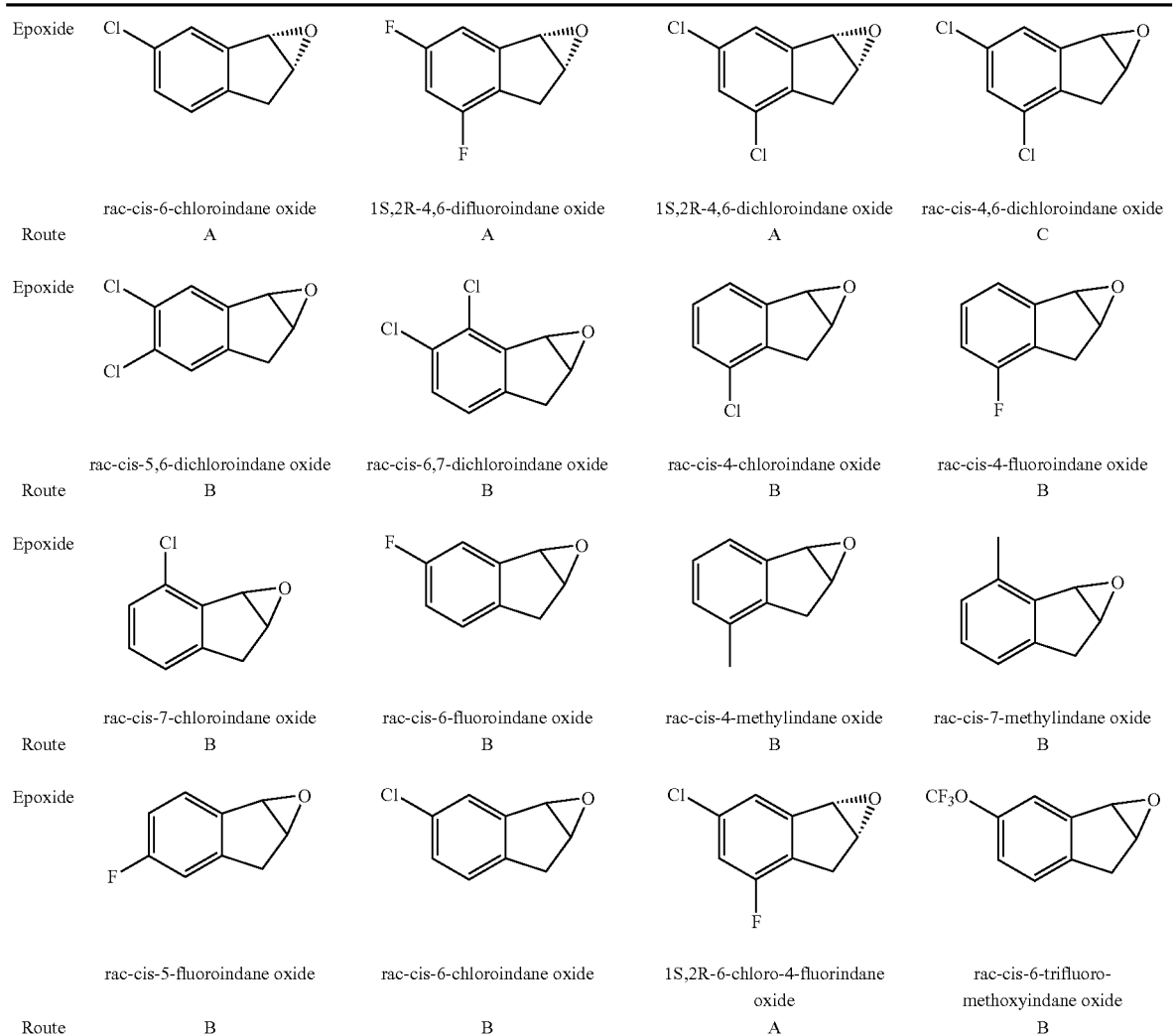

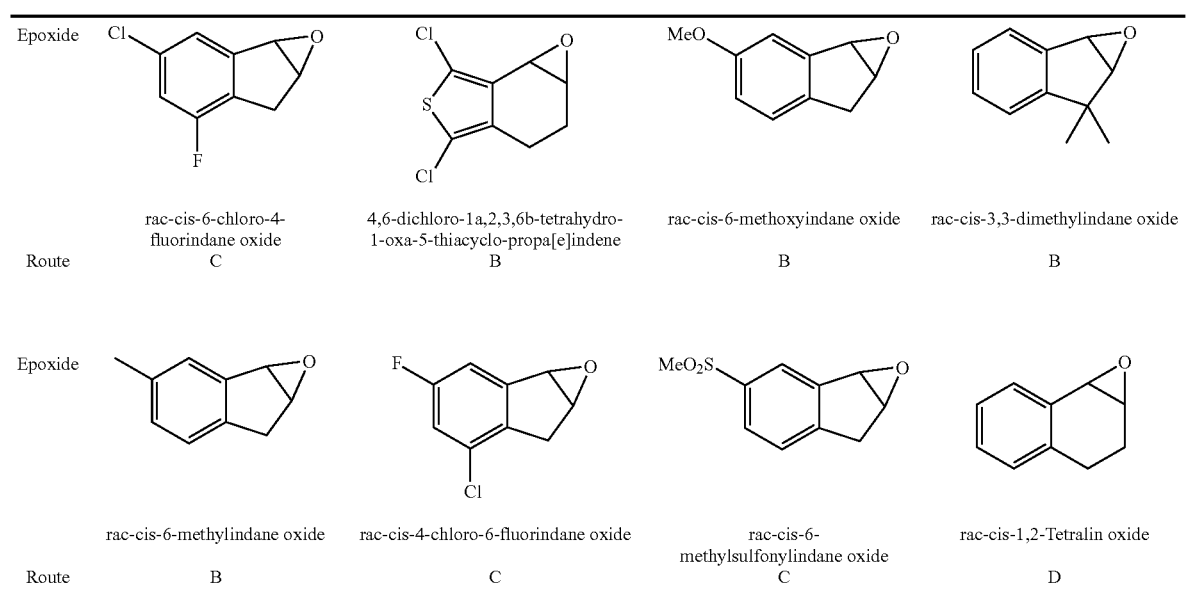

| Epoxide | | | | |
|---|---|---|---|---|
| | rac-cis-6-chloro-4-fluorindane oxide | 4,6-dichloro-1a,2,3,6b-tetrahydro-1-oxa-5-thiacyclo-propa[e]indene | rac-cis-6-methoxyindane oxide | rac-cis-3,3-dimethylindane oxide |
| Route | C | B | B | B |

| Epoxide | | | | |
|---|---|---|---|---|
| | rac-cis-6-methylindane oxide | rac-cis-4-chloro-6-fluorindane oxide | rac-cis-6-methylsulfonylindane oxide | rac-cis-1,2-Tetralin oxide |
| Route | B | C | C | D |

General Synthesis of Phenols:

Scheme 5: Deprotection of phenol ethers

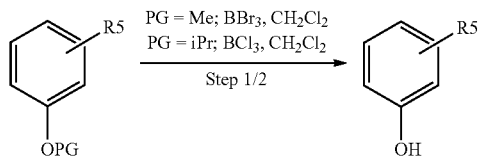

General Synthetic Methods:

Step 1/2: At −10° C., BBr$_3$ (1M solution in CH$_2$Cl$_2$; 2.5 equivalents) was added dropwise to a solution of the methyl ether (1 equivalent) in CH$_2$Cl$_2$ (7 ml/mmol ether) and the cooling bath was removed. The suspension was stirred for a total of 4 h, checking the progress of the reaction by TLC monitoring and, after the reaction was complete, the suspension was added to ice-water. The resulting aqueous suspension was neutralized with NaHCO$_3$ and extracted with ethyl acetate. The combined organic phases were dried with Na$_2$SO$_4$ and filtered, and the solvent was removed in vacuo. The crude products were purified by column chromatography.

At −78° C., BCl$_3$ (1M solution in hexane; 2.0 equivalents) was added dropwise to a solution of the isopropyl ether (1 equivalent) in CH$_2$Cl$_2$ (6 ml/mmol ether) and the cooling bath was removed. The suspension was stirred for a total of 3 h (TLC monitoring) and added to ice-water. The resulting aqueous suspension was neutralized with NaHCO$_3$ and extracted with ethyl acetate. The combined organic phases were dried with Na$_2$SO$_4$ and filtered, and the solvent was removed in vacuo. The crude products were purified by column chromatography.

Scheme 6: Synthesis of heterocyclic phenols

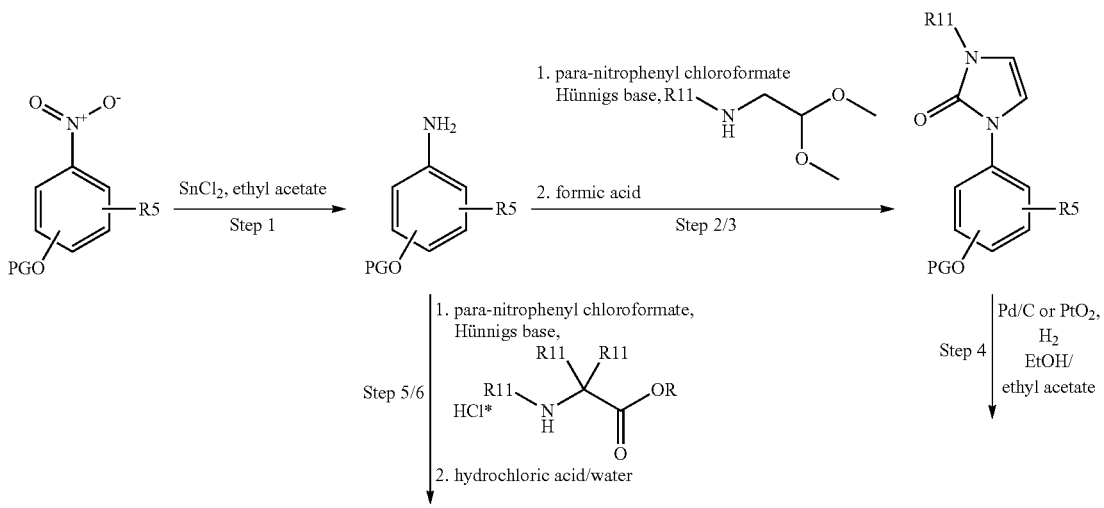

-continued

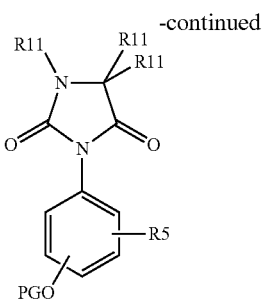

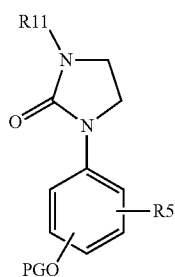

General Synthetic Methods:

Step 1: $SnCl_2 \cdot 2H_2O$ (5 equivalents) was added in small portions to a solution of the nitrophenol (1 equivalent) in ethyl acetate (6 ml/mmol of precursor). The suspension was heated under reflux for 1-6 h (TLC monitoring). The reaction was stopped with water and basified with aqueous 2 N NaOH solution. The resulting suspension was filtered and the filtrate was extracted with ethyl acetate. The combined organic phases were dried with $Na_2SO_4$ and filtered, and the solvent was removed in vacuo. The crude products were purified by column chromatography.

Step 2/3: At 0° C., a solution of the appropriate aniline (1.0 equivalents) and Hünig's base (1.1 equivalents) in $CH_2Cl_2$ (1.3 ml/mmol of aniline) was added dropwise to a solution of 4-nitrophenyl chloroformate (1.5 equivalents) in $CH_2Cl_2$ (0.4 ml/mmol of formate) so that the temperature did not rise above 5° C. The solution was stirred at room temperature (rt) for a further 2 h and then cooled to 0° C. The appropriate amino acetal (2.3 equivalents) was added, and the suspension was stirred at room temperature (rt) for a further 4 h. The reaction was diluted with $CH_2Cl_2$ and washed successively with water, aqueous 2 N NaOH solution and aqueous saturated $NH_4Cl$ solution. The combined organic phases were dried with $Na_2SO_4$ and filtered, and the solvent was removed in vacuo. The crude product was employed without further purification in the next reaction step.

The crude product from the preceding step (1 equivalent) was dissolved at 0° C. in formic acid (1.5 ml/mmol of precursor) and stirred at room temperature (rt) for 2-16 h (with TLC monitoring). The volume of the reaction solution was reduced by a factor of 2 in vacuo, and the resulting solution was diluted with water. The aqueous phase was extracted with ethyl acetate, and the combined organic phases were cautiously washed with saturated aqueous $NaHCO_3$ solution. The combined organic phases were dried with $Na_2SO_4$ and filtered, and the solvent was removed in vacuo. The crude products were purified by column chromatography.

Step 4: $PtO_2$ (5 mol %) was added to a solution of the precursor (1 equivalent) in an EtOH/ethyl acetate mixture (1:1 5 ml/mmol of precursor). The suspension was vigorously stirred under an $H_2$ atmosphere (1.5 bar) for 5 h (TLC monitoring). The suspension was filtered and the residue was washed with EtOH. The solvent of the organic phases was removed in vacuo, and the resulting crude product was employed in the next reaction step.

Step 5/6: At 0° C., a solution of the appropriate aniline (1.0 equivalents) and Hünig's base (3.5 equivalents) in $CH_2Cl_2$ (1.3 ml/mmol of aniline) was added dropwise to a solution of 4-nitrophenyl chloroformate (1.5 equivalents) in $CH_2Cl_2$ (0.4 ml/mmol of formate) so that the temperature did not rise above 5° C. The solution was stirred at room temperature (rt) for a further 2 h and then cooled to 0° C. The appropriate ammonium salt of the amino acid (1.6 equivalents) was added and the suspension was stirred at room temperature (rt) for a further 16 h. The reaction mixture was diluted with $CH_2Cl_2$ and washed successively with water, aqueous 2N NaOH solution and aqueous saturated $NH_4Cl$ solution. The combined organic phases were dried with $Na_2SO_4$ and filtered, and the solvent was removed in vacuo. The crude product was employed without further purification in the next reaction step.

The crude product from the preceding step (1 equivalent) was suspended at 0° C. in 10% strength aqueous HCl (3.0 ml/mmol of precursor) and heated under reflux for 2-16 h (TLC monitoring). The pH of the solution was adjusted to pH 8 with aqueous 2 N NaOH solution and extracted with ethyl acetate. The combined organic phases were dried with $Na_2SO_4$ and filtered, and the solvent was removed in vacuo. The crude products were purified by column chromatography. The phenol ethers obtained in this way were cleaved as described in scheme 5.

The following phenols were synthesized by the method described:

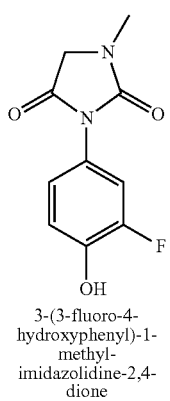
3-(3-fluoro-4-hydroxyphenyl)-1-methyl-imidazolidine-2,4-dione

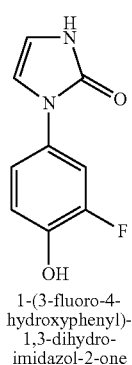
1-(3-fluoro-4-hydroxyphenyl)-1,3-dihydro-imidazol-2-one

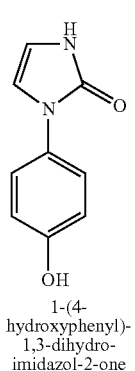
1-(4-hydroxyphenyl)-1,3-dihydro-imidazol-2-one

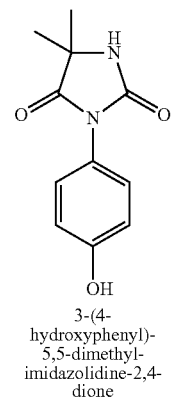
3-(4-hydroxyphenyl)-5,5-dimethyl-imidazolidine-2,4-dione

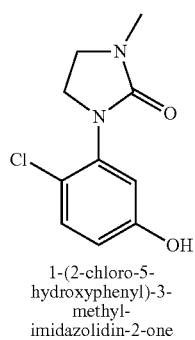

1-(2-chloro-5-hydroxyphenyl)-3-methyl-imidazolidin-2-one

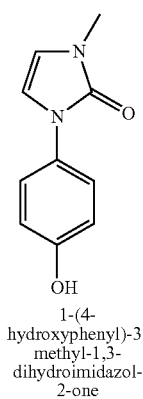

1-(4-hydroxyphenyl)-3-methyl-1,3-dihydroimidazol-2-one

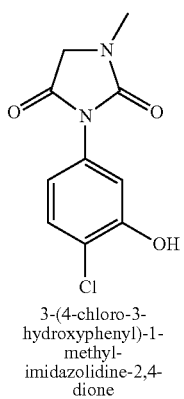

3-(4-chloro-3-hydroxyphenyl)-1-methyl-imidazolidine-2,4-dione

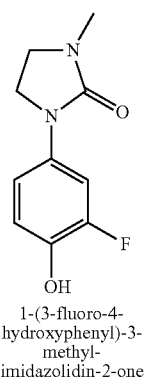

1-(3-fluoro-4-hydroxyphenyl)-3-methyl-imidazolidin-2-one

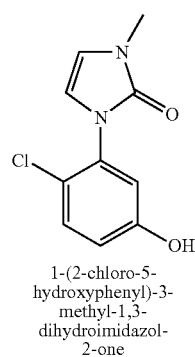

1-(2-chloro-5-hydroxyphenyl)-3-methyl-1,3-dihydroimidazol-2-one

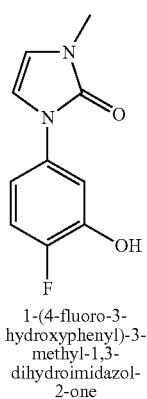

1-(4-fluoro-3-hydroxyphenyl)-3-methyl-1,3-dihydroimidazol-2-one

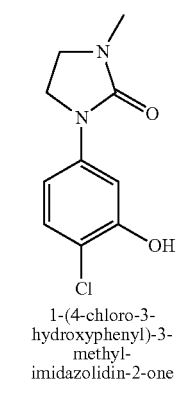

1-(4-chloro-3-hydroxyphenyl)-3-methyl-imidazolidin-2-one

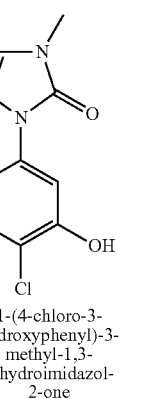

1-(4-chloro-3-hydroxyphenyl)-3-methyl-1,3-dihydroimidazol-2-one

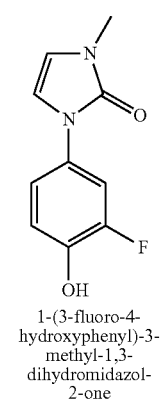

1-(3-fluoro-4-hydroxyphenyl)-3-methyl-1,3-dihydromidazol-2-one

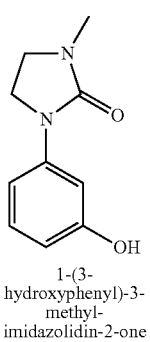

1-(3-hydroxyphenyl)-3-methyl-imidazolidin-2-one

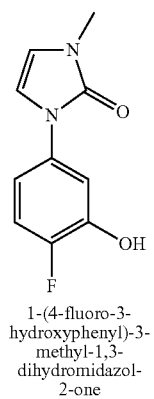

1-(4-fluoro-3-hydroxyphenyl)-3-methyl-1,3-dihydromidazol-2-one

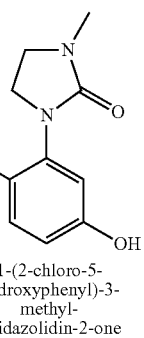

1-(2-chloro-5-hydroxyphenyl)-3-methyl-imidazolidin-2-one

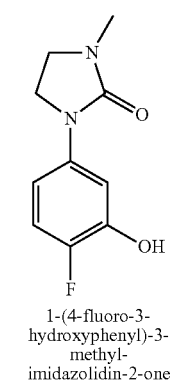

1-(4-fluoro-3-hydroxyphenyl)-3-methyl-imidazolidin-2-one

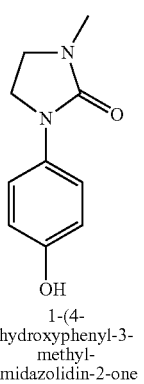

1-(4-hydroxyphenyl-3-methyl-imidazolidin-2-one

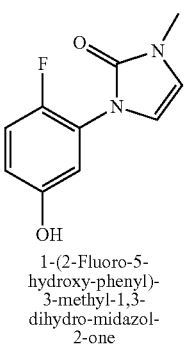

1-(2-Fluoro-5-hydroxy-phenyl)-3-methyl-1,3-dihydro-midazol-2-one

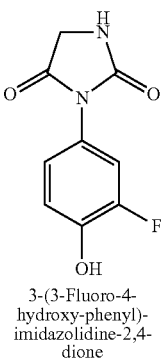

3-(3-Fluoro-4-hydroxy-phenyl)-imidazolidine-2,4-dione

Scheme 7: Synthesis of heterocyclic phenols

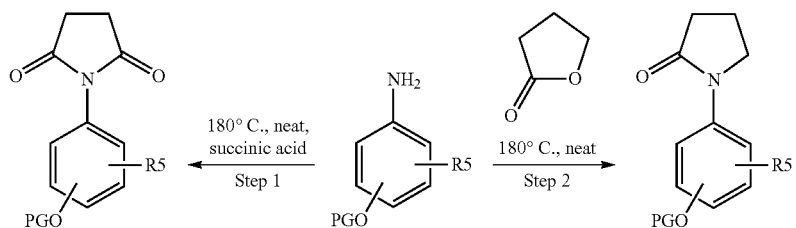

General Synthetic Method:

Step 1: A thoroughly blended mixture of the appropriate aniline (1 equivalent) and succinic acid (1 equivalent) was stirred at 180° C. for 2 h, during which a melt formed. The melt was cooled to room temperature (rt) (solidification of the melt) and dissolved in EtOH. The resulting solution was mixed with activated carbon and filtered, and the solvent was removed in vacuo. The residue was dissolved in ethyl acetate and washed with saturated aqueous $NaHCO_3$. The organic phase was dried with $Na_2SO_4$ and again filtered, and the solvent was removed in vacuo. The crude products were purified by column chromatography.

Step 2: A thoroughly blended mixture of the appropriate aniline (1 equivalent) and gamma-butyrolactone (1 equivalent) was stirred at 180° C. for 2 h, during which a melt formed. The melt was cooled to room temperature (rt) (solidification of the melt) and dissolved in EtOH. The resulting solution was mixed with activated carbon and filtered, and the solvent was removed in vacuo. The crude product was purified by column chromatography.

The phenol ethers obtained in this way were cleaved as described in scheme 5.

The following phenols were synthesized by the method described:

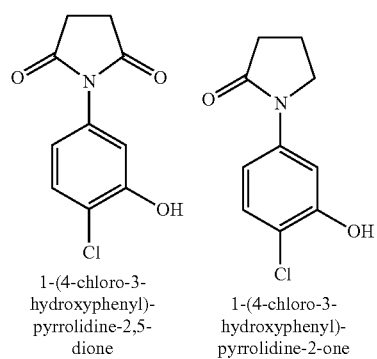

1-(4-hydroxyphenyl)-pyrrolidine-2,5-dione 1-(3-chloro-4-hydroxyphenyl)-pyrrolidine-2,5-dione

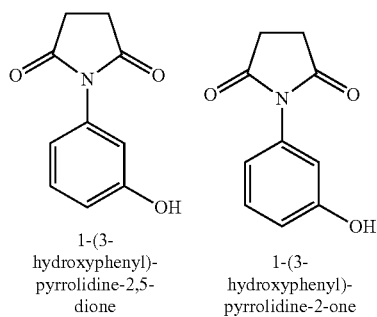

1-(4-hydroxyphenyl)-pyrrolidine-2-one 1-(3-chloro-4-hydroxyphenyl)-pyrrolidine-2-one -continued

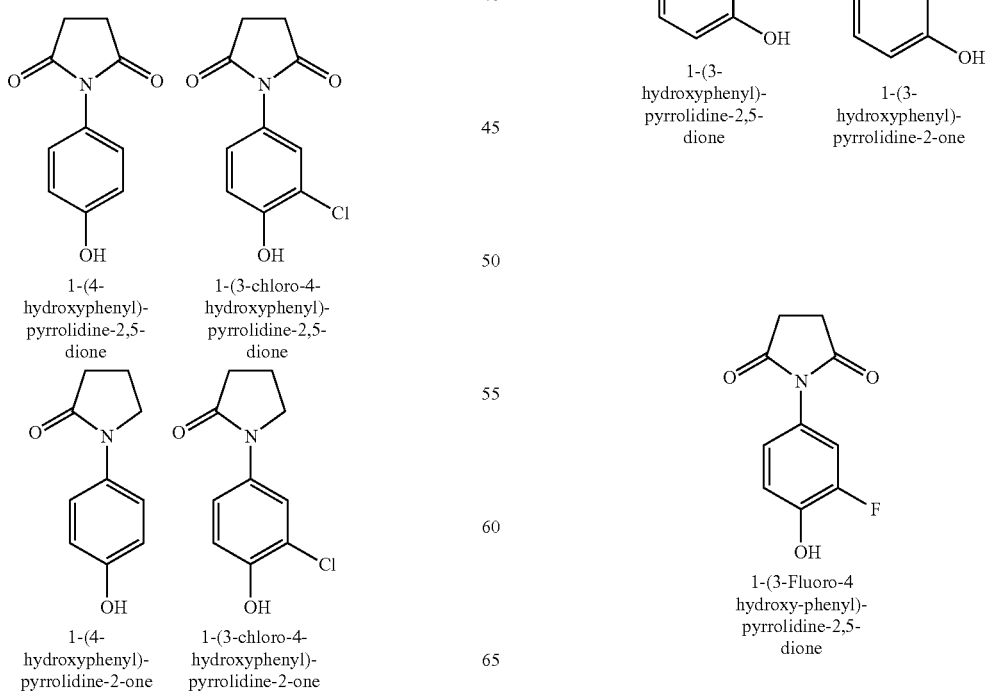

1-(4-chloro-3-hydroxyphenyl)-pyrrolidine-2,5-dione 1-(4-chloro-3-hydroxyphenyl)-pyrrolidine-2-one 1-(3-hydroxyphenyl)-pyrrolidine-2,5-dione 1-(3-hydroxyphenyl)-pyrrolidine-2-one

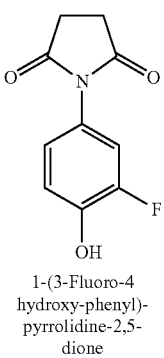

1-(3-Fluoro-4 hydroxy-phenyl)-pyrrolidine-2,5-dione

Scheme 8: Synthesis of heterocyclic phenols

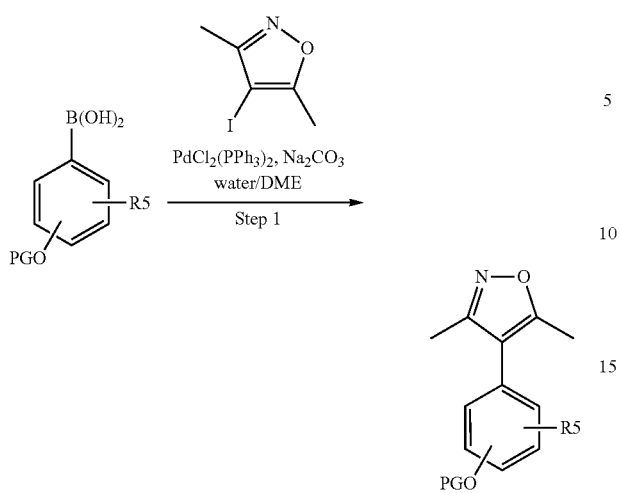

General Synthetic Method:

Step 1: Boronic acid (1 equivalent), aryl iodide (1 equivalent) and Na$_2$CO$_3$ (3.0 equivalents) were suspended in a water/DME mixture ((1:1; 3 ml/mmol of boronic acid). PdCl$_2$(PPh$_3$)$_2$ (2 mol %) was added and the suspension was stirred at 80° C. for 20 h (TLC monitoring). The suspension was subsequently diluted with ethyl acetate and water, the phases were separated, and the aqueous phase was extracted with ethyl acetate. The combined organic phases were dried with Na$_2$SO$_4$ and filtered, and the solvent was removed in vacuo. The crude products were purified by column chromatography.

The phenol ethers obtained in this way were cleaved as described in scheme 5.

The following phenols were synthesized by the method described:

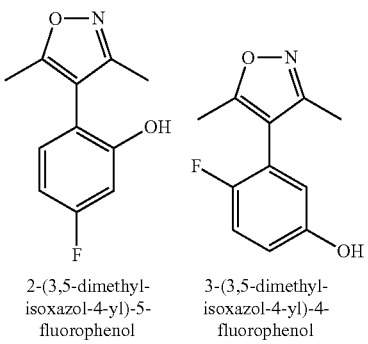

2-(3,5-dimethyl-isoxazol-4-yl)-5-fluorophenol 3-(3,5-dimethyl-isoxazol-4-yl)-4-fluorophenol Scheme 9: Synthesis of heterocyclic phenols

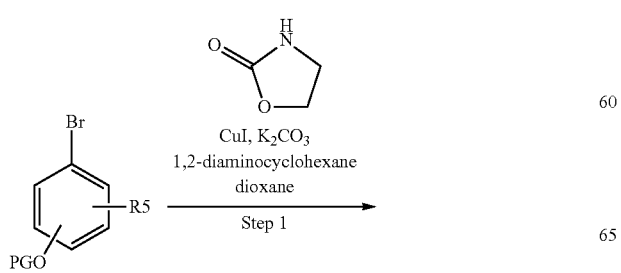

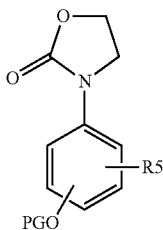

General Synthetic Method:

Step 1: Aryl bromide (1 equivalent), oxazolidone (1 equivalent), K$_2$CO$_3$ (2.0 equivalents), trans-diaminocyclohexane (10 mol %) and CuI (5 mol %) were suspended in dioxane (0.5 ml/mmol of aryl bromide). The suspension was heated under reflux for 16 h (TLC monitoring) and diluted with ethyl acetate and filtered through a little Celite. The organic phase was dried with Na$_2$SO$_4$ and filtered, and the solvent was removed in vacuo. The crude products were purified by column chromatography.

The phenol ethers obtained in this way were cleaved as described in scheme 5.

The following phenols were synthesized by the method described:

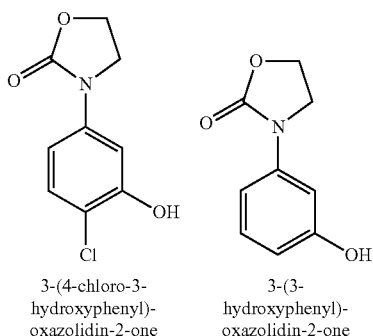

3-(4-chloro-3-hydroxyphenyl)-oxazolidin-2-one 3-(3-hydroxyphenyl)-oxazolidin-2-one

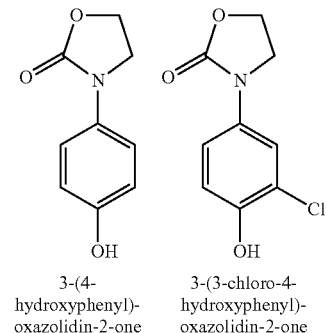

3-(4-hydroxyphenyl)-oxazolidin-2-one 3-(3-chloro-4-hydroxyphenyl)-oxazolidin-2-one

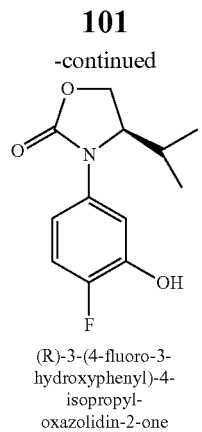

(R)-3-(4-fluoro-3-hydroxyphenyl)-4-isopropyl-oxazolidin-2-one

Scheme 10: Synthesis of heterocyclic phenols

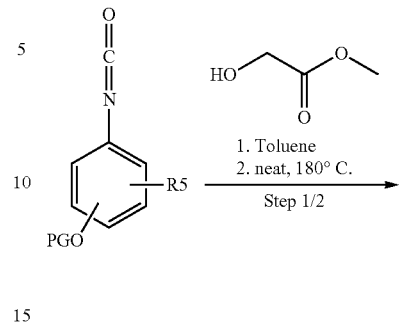

Scheme 11: Synthesis of heterocyclic phenols

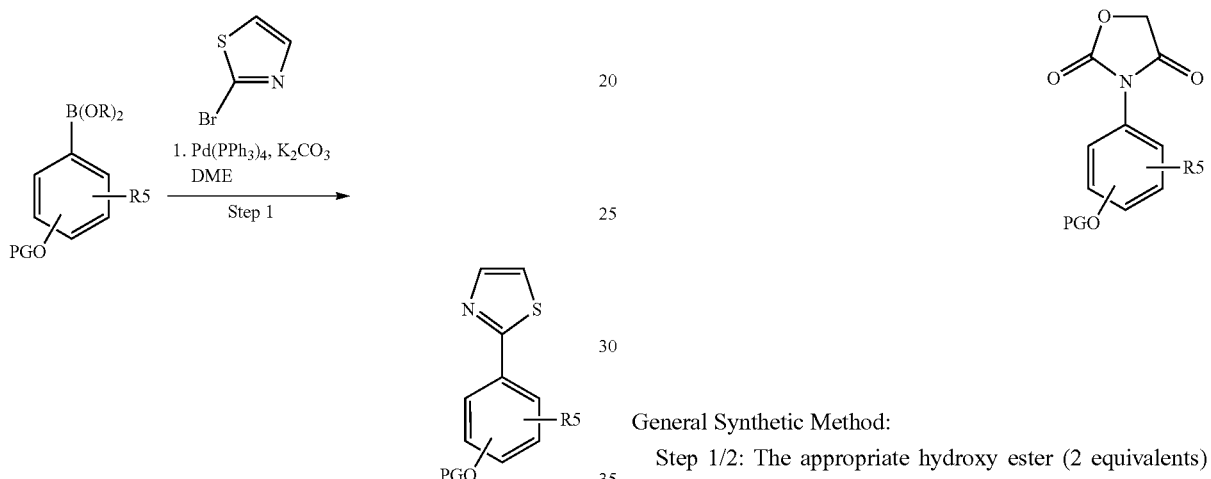

General Synthetic Method:

Step 1: Aryl bromide (1 equivalent), boronic acid (1 equivalent), $K_2CO_3$ (2.0 equivalents) and $Pd(PPh_3)_4$ (10 mol %) were suspended in DME (1.0 ml/mmol of aryl bromide). The suspension was heated to reflux for 48 h, and the reaction was monitored by TLC. The reaction mixture was diluted with ethyl acetate and water, the phases were separated, and the aqueous phase was extracted with ethyl acetate. The combined organic phases were dried with $Na_2SO_4$ and filtered, and the solvent was removed in vacuo. The crude products were purified by column chromatography.

The phenol ethers obtained in this way were cleaved as described in scheme 5.

The following phenol was synthesized by the method described:

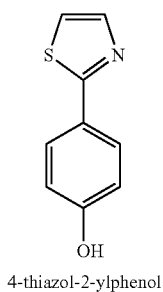

4-thiazol-2-ylphenol

General Synthetic Method:

Step 1/2: The appropriate hydroxy ester (2 equivalents) was added to a solution of the isocyanate (1 equivalent) in toluene (1.0 ml/mmol of isocyanate). The solution was heated at 110° C. in a closed vessel for 4 h, and the reaction was monitored by TLC. The solvent was removed in vacuo, and the crude products were purified by column chromatography. The product from the preceding reaction was heated without solvent at 180° C. for 4 h. After the reaction solution had cooled to room temperature (rt), the crude product was purified by column chromatography.

The phenol ethers obtained in this way were cleaved as described in scheme 5.

The following phenols were synthesized by the method described:

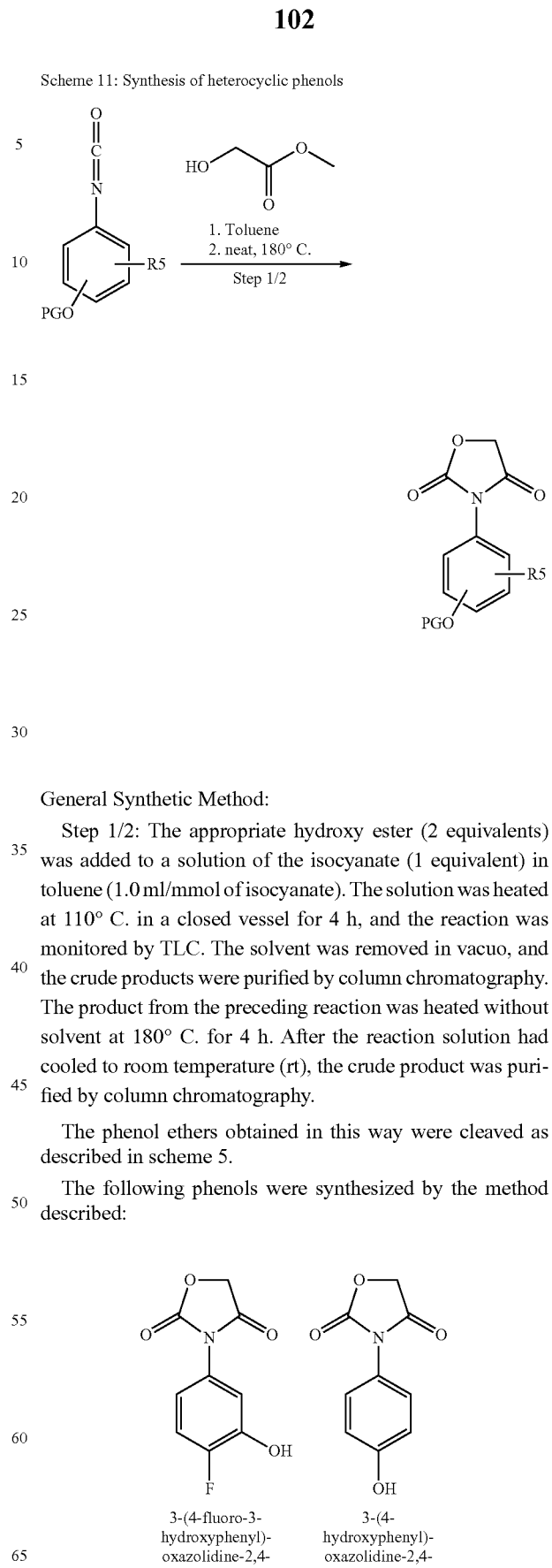

3-(4-fluoro-3-hydroxyphenyl)-oxazolidine-2,4-dione 3-(4-hydroxyphenyl)-oxazolidine-2,4-dione The following phenols were synthesized by the method described:

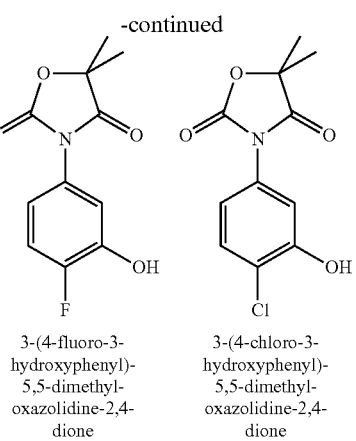

3-(4-fluoro-3-hydroxyphenyl)-5,5-dimethyl-oxazolidine-2,4-dione 3-(4-chloro-3-hydroxyphenyl)-5,5-dimethyl-oxazolidine-2,4-dione

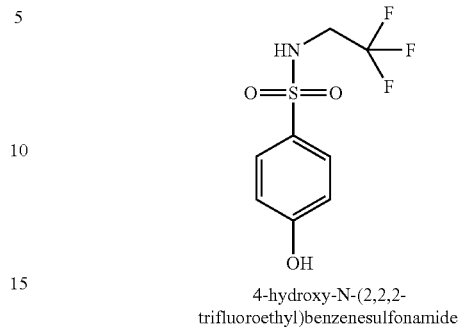

4-hydroxy-N-(2,2,2-trifluoroethyl)benzenesulfonamide 3-(3-chloro-4-hydroxyphenyl)-oxazolidine-2,4-dione 4-hydroxy-N-(3,3,3-trifluoropropyl)benzenesulfonamide N-ethyl-4-hydroxy-benzenesulfonamide Scheme 12: Conversion to sulfonamides

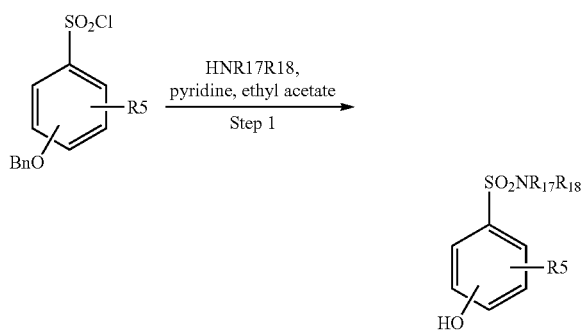

General Synthetic Method:

Step 1: At 0° C., the appropriate ammonium hydrochloride (3 equivalents) was added to a solution of the sulfonyl chloride (1 equivalent) in ethyl acetate (2 ml/mmol) and pyridine (6 equivalents). The suspension was stirred at room temperature (rt) for 16 h and the reaction was monitored by TLC. The reaction mixture was diluted with ethyl acetate and water, the phases were separated, and the aqueous phase was extracted with ethyl acetate. The combined organic phases were washed with saturated aqueous NH$_4$Cl solution, dried with Na$_2$SO$_4$ and filtered, and the solvent was removed in vacuo. The crude products were purified by column chromatography.

Scheme 13: Oxidation of phenyl sulfides

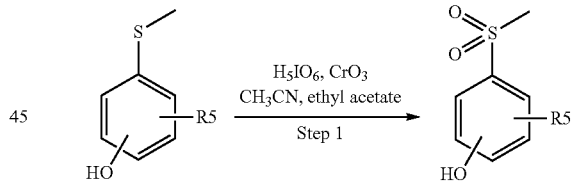

General Synthetic Method:

Step 1: A suspension of periodic acid (2.1 equivalents) in CH$_3$CN (3 ml/mmol of periodic acid) was stirred at room temperature (rt) until a clear solution had formed (about 50 min). Chromium trioxide (10 mol % relative to the sulfide) was added and stirred for a further 10 min. This orange-colored solution was slowly added at −35° C. to a solution of the appropriate sulfide (1 equivalent) in ethyl acetate (10 ml/mmol of sulfide). The temperature did not rise above −35° C. during this. The suspension which formed was stirred at this temperature for a further 60 min and stopped with 5 ml of saturated aqueous Na$_2$SO$_3$ solution. The suspension was filtered and the residue was washed with ethyl acetate. The filtrate was washed with saturated aqueous Na$_2$SO$_3$ solution, dried with Na$_2$SO$_4$ and filtered, and the solvent was removed in vacuo. The crude product was purified by column chromatography.

The following phenol was synthesized by the method described:

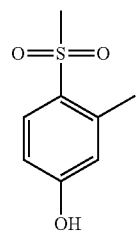

4-methanesulfonyl-3-methylphenol

Scheme 14: Synthesis of heterocyclic phenols

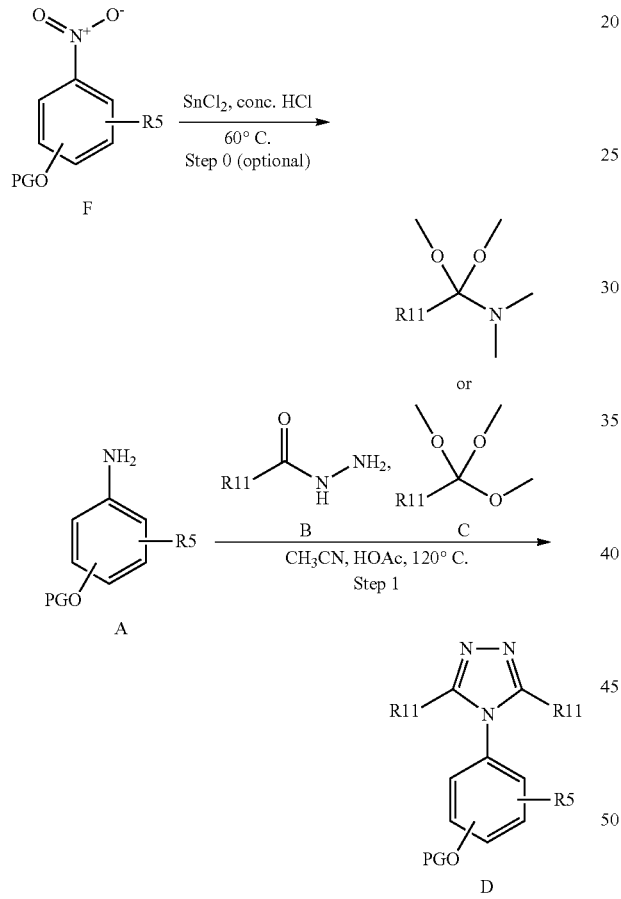

General Synthetic Method:

Step 0 (optional): 4.5 equivalents of SnCl2 are added to a solution of the aniline F (1 equivalent) in concentrated aqueous hydrochloric acid (0.36 ml/mmol of precursor) and the solution is heated to 60° C. After stirring overnight, the mixture was poured onto ice, adjusted to pH>10 with 10 M KOH and extracted 4 times with dichloromethane, and the collected organic phases were washed with saturated NaCl solution and dried over $Na_2SO_4$. The solvent was removed in vacuo.

Step 1: 1.1 equivalents of the dimethylamide dimethyl acetal or ortho ester C were added to a solution of the hydrazide B (1.1 equivalents) in acetonitrile (6 ml/mmol of precursor), and the solution was stirred at 50° C. for 30 min.

After addition of a solution of the aniline (A) in acetonitrile (3 ml/mmol of precursor) and acetic acid (9 ml/mmol of precursor), the mixture was heated in an open flask at 120° C. for 16 h. The solvent was removed in vacuo. The crude products were purified by column chromatography, using a dichloromethane/methanol gradient for elution.

The phenol ethers obtained in this way were cleaved as described in scheme 5.

The following phenols were synthesized by the method described:

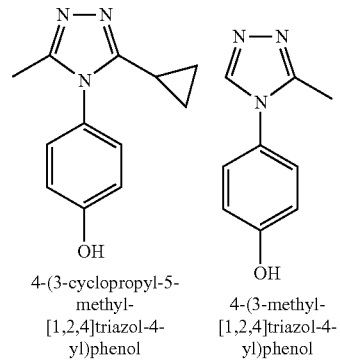

4-(3-cyclopropyl-5-methyl-[1,2,4]triazol-4-yl)phenol 4-(3-methyl-[1,2,4]triazol-4-yl)phenol

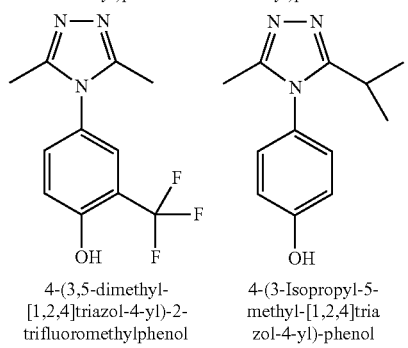

4-(3,5-dimethyl-[1,2,4]triazol-4-yl)-2-trifluoromethylphenol 4-(3-Isopropyl-5-methyl-[1,2,4]triazol-4-yl)-phenol

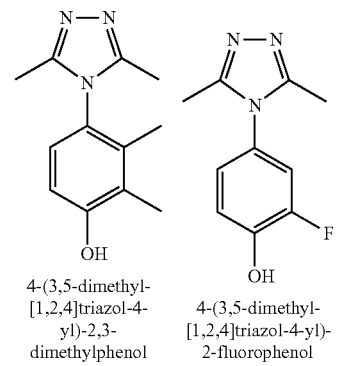

4-(3,5-dimethyl-[1,2,4]triazol-4-yl)-2,3-dimethylphenol 4-(3,5-dimethyl-[1,2,4]triazol-4-yl)-2-fluorophenol

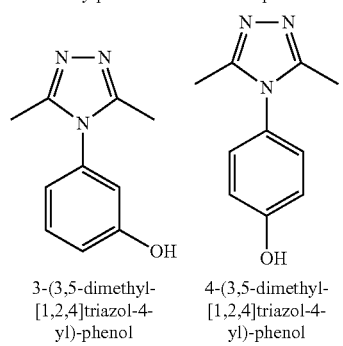

3-(3,5-dimethyl-[1,2,4]triazol-4-yl)-phenol 4-(3,5-dimethyl-[1,2,4]triazol-4-yl)-phenol

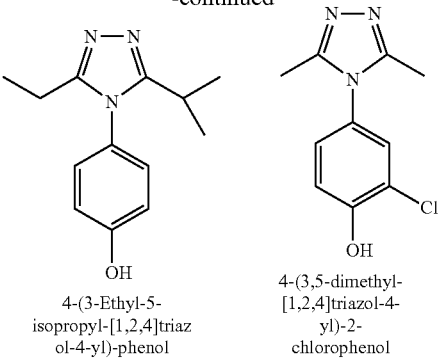

4-(3-Ethyl-5-isopropyl-[1,2,4]triazol-4-yl)-phenol 4-(3,5-dimethyl-[1,2,4]triazol-4-yl)-2-chlorophenol The following phenols were synthesized by the method described:

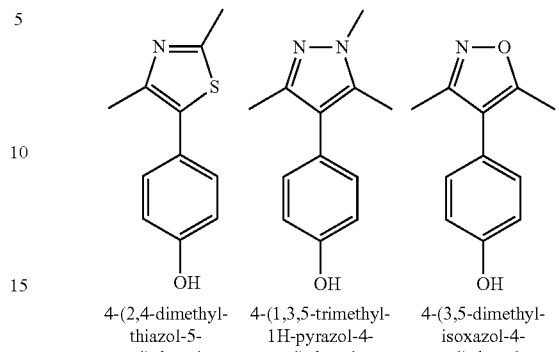

4-(2,4-dimethyl-thiazol-5-yl)phenol 4-(1,3,5-trimethyl-1H-pyrazol-4-yl)phenol 4-(3,5-dimethyl-isoxazol-4-yl)phenol Scheme 15: Synthesis of heterocyclic phenols

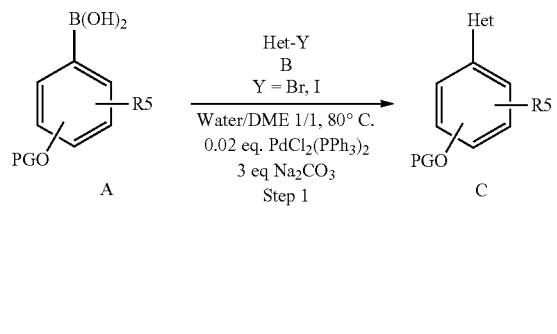

Scheme 16: Synthesis of heterocyclic phenols

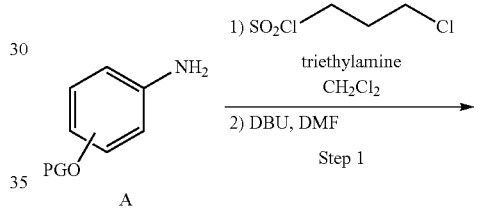

General Synthetic Method:

Step 1: Argon was passed through a mixture of the boric acid A (1 equivalent), the heteroaryl iodide/bromide B (1 equivalent) in water/DME 1/1 (3 ml/mmol of precursor) for 15 min. After addition of palladium dichlorobistriphenylphosphine (0.02 equivalents) and $Na_2CO_3$ (3.0 equivalents), the mixture was heated at 80° C. under argon (20 h). After the reaction was complete (LC-MS monitoring), the mixture was mixed with ethyl acetate and with saturated aqueous $NaHCO_3$ solution and extracted twice with ethyl acetate. The collected organic phases were washed with saturated NaCl solution and dried over $Na_2SO_4$. The solvent was removed in vacuo. The crude products were purified by column chromatography, using a heptane/ethyl acetate gradient for elution.

Variant A: After stirring for 1 hour, the resulting mixture was extracted three times with dichloromethane, and the collected organic phases were washed with saturated NaCl solution and dried over $Na_2SO_4$. The solvent was removed in vacuo.

Variant B: After stirring for 1 hour, the resulting mixture was neutralized with NaOH, and the product was either filtered off with suction or extracted 3 times with dichloromethane, and the collected organic phases were washed with saturated NaCl solution and dried over $Na_2SO_4$. The solvent was removed in vacuo.

The phenol ethers obtained in this way were cleaved as described in scheme 5.

General Synthetic Method:

Step 1: Triethylamine (2 equivalents) and, dropwise, 3-chloropropanesulfonyl chloride (1.3 equivalents) are successively added to a solution of the aniline A (1 equivalent) in dichloromethane (1.5 ml/mmol of precursor), and the mixture is stirred at room temperature for 16 h. After addition of dichloromethane (1 ml/mmol of precursor), the mixture is washed successively with aqueous 1 N HCl and sat. $NaHCO_3$ solution. The solvent was removed in vacuo. The product was dissolved in DMF (1.3 ml/mmol of precursor), and 1,8-diazabicyclo[5.4.0]undec-7-ene (DBU) (1.1 equivalents) was added. After stirring at 25° C. for 3 h and after addition of ethyl acetate/heptane 2/1, the organic phase was washed twice with 0.1 N HCl, and the organic phase was washed with saturated NaCl solution and dried over $Na_2SO_4$. The solvent was removed in vacuo.

The phenol ethers obtained in this way were cleaved as described in scheme 5.

The following phenols were synthesized by the method described:

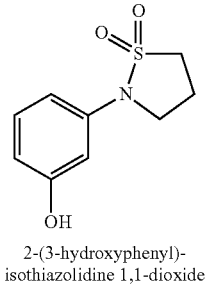 [SMILES: O=S1(=O)CCCN1c1cccc(O)c1]

2-(3-hydroxyphenyl)-
isothiazolidine 1,1-dioxide

Scheme 17: Conversion to sulfonamides

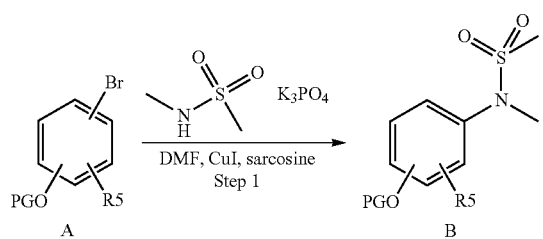

General Synthetic Method:

Step 1: A mixture of the bromide A (1 equivalent), N-methylmethanesulfonamide (1.2 equivalents), copper(I) iodide (0.2 equivalents), sarcosine (0.2 equivalents), K3PO4 (2.5 equivalents) in DMF (6 ml/mmol of precursor) was stirred at 150° C. for 24 h. The solvent was removed in vacuo. After addition of dichloromethane, the organic phase was washed with saturated NaHCO₃ solution and dried over Na₂SO₄. The solvent was removed in vacuo. The crude product was purified by flash chromatography on silica gel, using a dichloromethane/methanol gradient for elution.

The phenol ethers obtained in this way were cleaved as described in scheme 5.

The following phenol was synthesized by the method described:

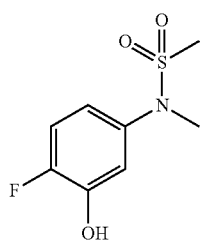

N-(4-fluoro-3-hydroxyphenyl)-
N-methylmethanesulfonamide

Scheme 18: Synthesis of heterocyclic phenols

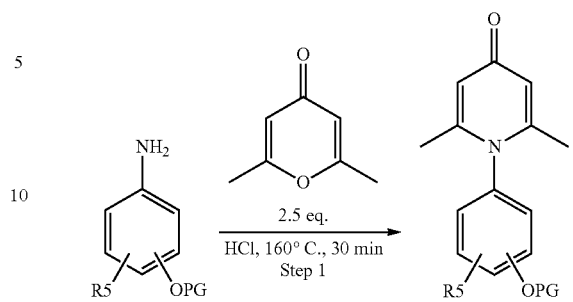

General Synthetic Method:

Step 1: A mixture of the amine (1 equivalent), 2,6-dimethyl-gamma-pyrone (2.5 equivalents) in 2 N aqueous HCl was heated at 160° C. in a microwave for 30 minutes. After addition of dichloromethane, the organic phase was washed with saturated NaHCO₃ solution and dried over Na₂SO₄. The solvent was removed in vacuo. The crude product was purified by flash chromatography on silica gel, using a dichloromethane/methanol gradient for elution.

The phenol ethers obtained in this way were cleaved as described in scheme 5.

The following phenol was synthesized by the method described:

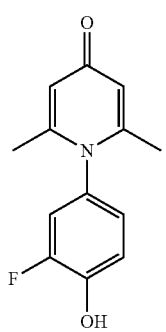

1-(3-fluoro-4-hydroxyphenyl)-
2,6-dimethyl-1H-pyridin-4-one

Scheme 19: Synthesis of heterocyclic phenols

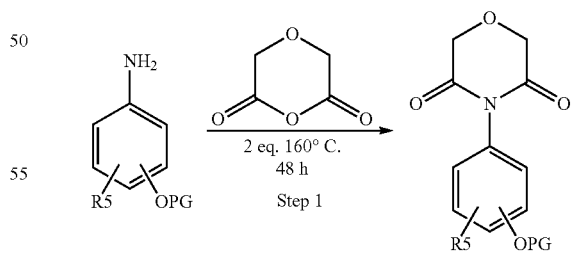

General Synthetic Method:

Step 1: A mixture of the amine (1 equivalent) and diglycol anhydride (2 equivalents) was heated at 160° C. for 48 h. After addition of dichloromethane, the organic phase was washed with saturated NaCl solution and dried over Na₂SO₄, and the solvent was removed in vacuo. The crude product was purified by flash chromatography on silica gel using a dichloromethane/methanol gradient for elution.

The phenol ethers obtained in this way were cleaved as described in scheme 5.

The following phenol was synthesized by the method described:

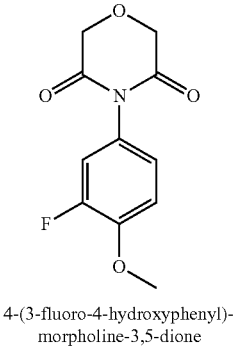 [SMILES: COc1ccc(N2C(=O)COCC2=O)cc1F]

4-(3-fluoro-4-hydroxyphenyl)-morpholine-3,5-dione

Scheme 20: Protection of secondary alcohols with ᵗBDPSiCl in the presence of secondary amines

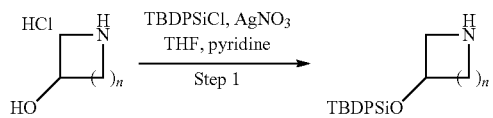

General Synthetic Method:

AgNO₃ (2.1 equivalents) was added to a suspension of the appropriate amino alcohol hydrochloride (1 equivalent) and tert-butyldiphenylsilyl chloride (1.2 equivalents) in a solution mixture of THF and pyridine (4:3; 1 ml/mmol of amino alcohol), a slight increase in temperature occurring. The suspension was stirred at room temperature (rt) for 16 h and filtered, and the residue was washed with ethyl acetate. The filtrate was diluted with ethyl acetate and washed with saturated aqueous NaHCO₃ solution. The organic phase was dried with Na₂SO₄ and filtered, and the solvent was removed in vacuo. The crude products were purified by column chromatography.

The following silyl ethers were synthesized by the method described:

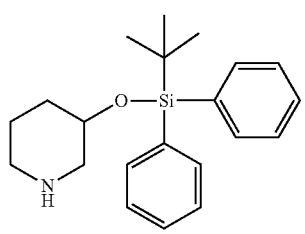
3-(tert-butyldiphenyl-silanyloxy)-piperidine

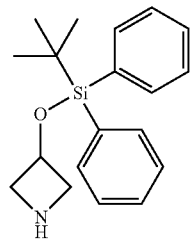
3-(tert-butyldiphenylsilanyloxy)-azetidine

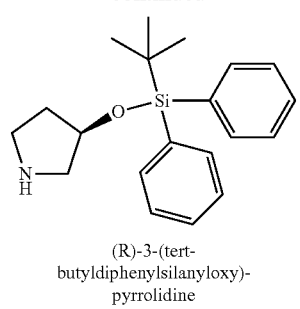

(R)-3-(tert-butyldiphenylsilanyloxy)-pyrrolidine

Scheme 21: Synthesis of heterocyclic phenols using CuCl

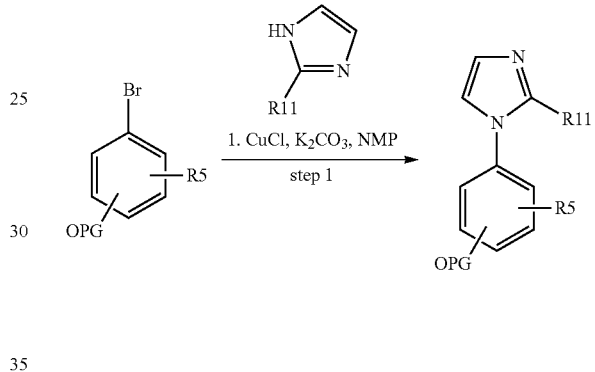

General Synthetic Method:

Step 1: A suspension of the bromide (1 equivalent), the imidazole (1.25 equivalents), CuCl (0.06 equivalents) and K₂CO₃ (1 equivalent) in NMP (2 ml/mmol bromide) was heated at 210° C. for 10 h. The mixture was cooled to it and diluted with water. The aqueous layer was extracted with ethyl acetate and the combined organic layers washed with saturated NaCl solution, dried over Na₂SO₄, and the solvent was removed in vacuo. The crude product was purified by flash chromatography on silica gel using an ethyl acetate/MeOH gradient for elution.

The phenol ethers obtained in this way were cleaved as described in scheme 5.

The following phenols were synthesized by the method described:

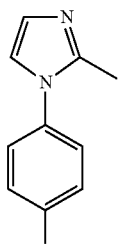
4-(2-Methyl-imidazol-1-yl)-phenol

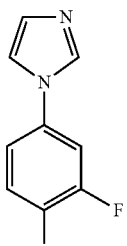
2-Fluoro-4-imidazol-1-yl-phenol

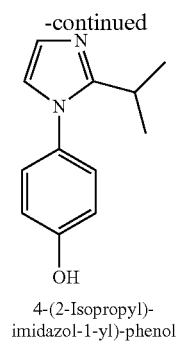

4-(2-Isopropyl)-
imidazol-1-yl)-phenol

Scheme 22: Synthesis of heterocyclic phenols via amidines

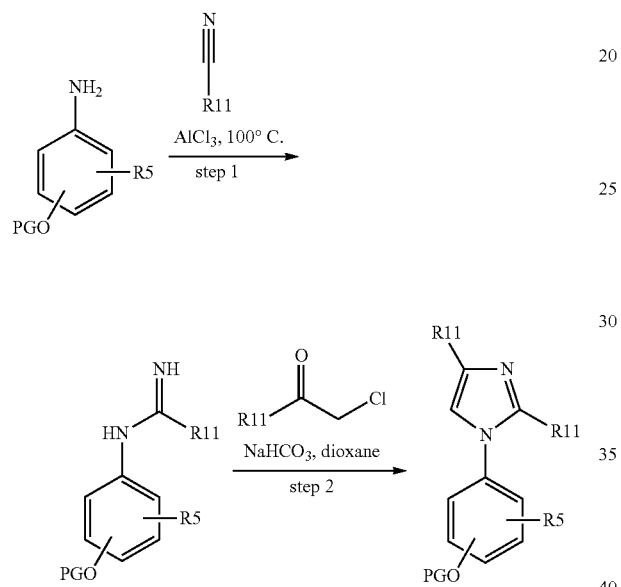

General Synthetic Method:

Step 1: To a suspension of the aniline (1 equivalent) in the corresponding nitrile (1 equivalent) at 0° C. AlCl$_3$ (1 equivalent) was added in small portions. The mixture was heated to 100° C. for 1 h while a solution was formed. The reaction mixture was cooled to 0° C. and carefully quenched with water. The aqueous suspension was adjusted to pH 10 with aqueous 2N NaOH. The aqueous layer was extracted with ethyl acetate, the combined organic layers washed with saturated NaCl solution, dried over Na$_2$SO$_4$, and the solvent was removed in vacuo. The crude product was purified by flash chromatography on silica gel using ethyl acetate/heptane/MeOH/NH$_3$ for elution.

Step 2: To a suspension of the amidine (1 equivalent) and NaHCO$_3$ (3 equivalents) in dioxane (2 ml/mmol amidine) the α-chloro-ketone (1.1 equivalent) was added and heated to 100° C. for 1 h. The mixture was cooled to rt, diluted with water and the aqueous layer extracted with ethyl acetate. The combined organic layers were washed with saturated NaCl solution, dried over Na$_2$SO$_4$, and the solvent was removed in vacuo. The crude product was purified by flash chromatography on silica gel using ethyl acetate/MeOH for elution.

The phenol ethers obtained in this way were cleaved as described in scheme 5.

The following phenols were synthesized by the method described:

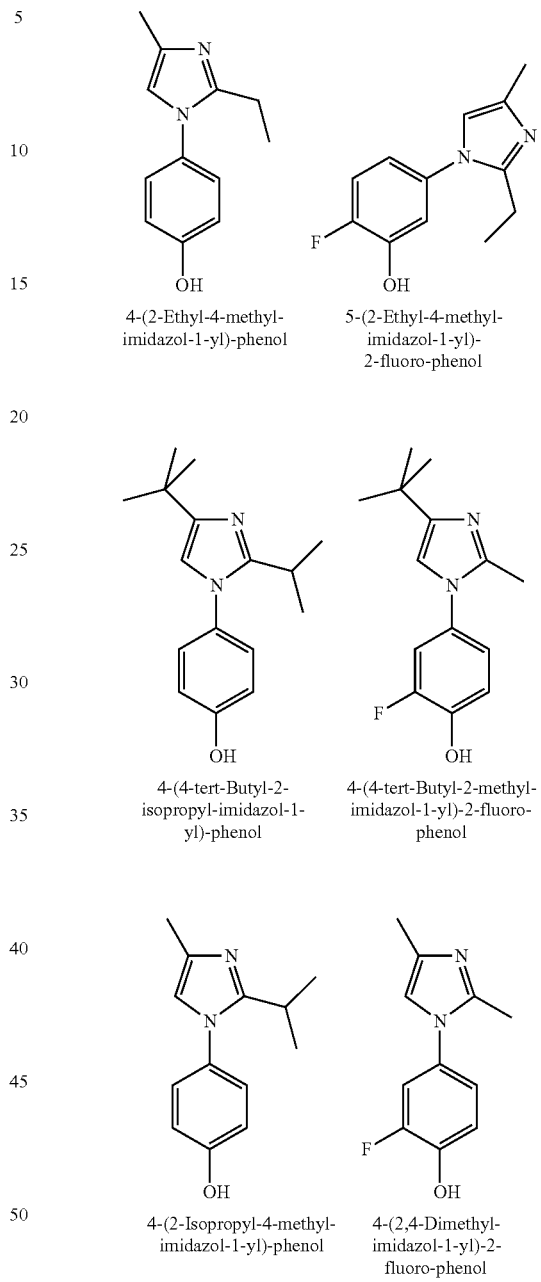

4-(2-Ethyl-4-methyl-imidazol-1-yl)-phenol 5-(2-Ethyl-4-methyl-imidazol-1-yl)-2-fluoro-phenol 4-(4-tert-Butyl-2-isopropyl-imidazol-1-yl)-phenol 4-(4-tert-Butyl-2-methyl-imidazol-1-yl)-2-fluoro-phenol 4-(2-Isopropyl-4-methyl-imidazol-1-yl)-phenol 4-(2,4-Dimethyl-imidazol-1-yl)-2-fluoro-phenol Scheme 23: Synthesis of heterocyclic phenols via sulfides

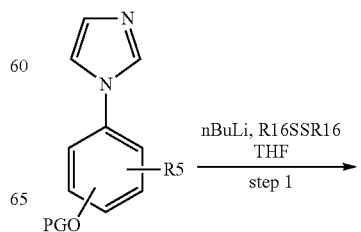

-continued

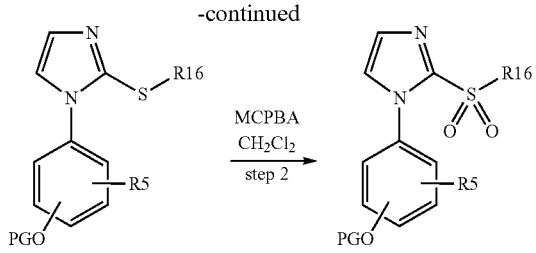

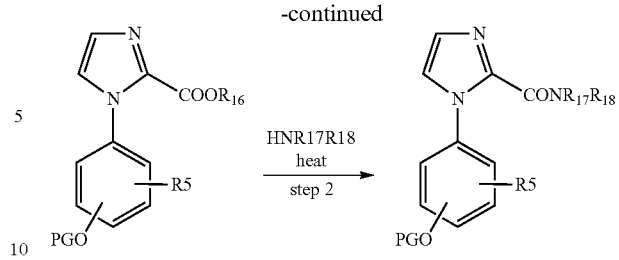

General Synthetic Method:

Step 1: To a solution of the imidazol (1 equivalent) in THF (5 ml/mmol imidazol) at −78° C. nBuLi (1.1 equivalent, 1M in hexanes) was added dropwise. The solution was allowed to reach −30° C. over a period of 30 min. The solution was cooled to −50° C. and the dialkyldisulfide (1.1 equivalent) was added. The cooling bath was removed and stirring was continued for 90 min while the suspension reached rt. Water was added and the aqueous layer was extracted with ethyl acetate, the combined organic layers washed with saturated NaCl solution, dried over $Na_2SO_4$ and the solvent was removed in vacuo. The crude product was purified by flash chromatography on silica gel using a ethyl acetate/heptane gradient for elution.

Step 2: To a solution of the alkyl sulfide (1 equivalent) at 0° C. in $CH_2Cl_2$ (12 ml/mmol sulphide) the peroxybenzoic acid (3 equivalents) was added in small portions. The turbid solution was vigorously stirred for 14 h. The solution was diluted with $CH_2Cl_2$ and washed three times with aqueous $Na_2CO_3$ solution. The organic layer was dried over $Na_2SO_4$ and the solvent was removed in vacuo. The crude product was purified by flash chromatography on silica gel using a ethyl acetate/MeOH gradient for elution.

The phenol ethers obtained in this way were cleaved as described in scheme 5.

The following phenols were synthesized by the method described:

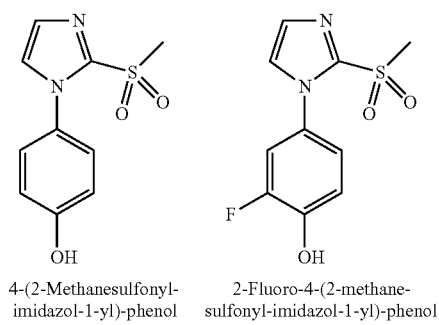 [SMILES: CS(=O)(=O)c1nccn1-c1ccc(O)cc1 ; CS(=O)(=O)c1nccn1-c1ccc(O)c(F)c1]

4-(2-Methanesulfonyl-imidazol-1-yl)-phenol

2-Fluoro-4-(2-methane-sulfonyl-imidazol-1-yl)-phenol

Scheme 24: Synthesis of heterocyclic phenols via carboxylic esters

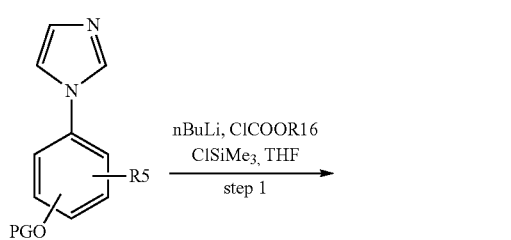

General Synthetic Method:

Step 1: To a solution of the imidazol (1 equivalent) in THF (5 ml/mmol imidazol) at −78° C. nBuLi was added dropwise. Within 30 min the solution was allowed to reach −30° C. The solution was cooled to −78° C. and trimethylchlorosilane (1.1 equivalents) was added dropwise. The ice bath was removed and within 60 min the solution reached rt. Again the solution was cooled back to −78° C., the chloroformiate (1.1 equivalents) was added and the ice bath removed. After 2 h the reaction mixture was poured into water and extracted with ethyl acetate, washed with saturated NaCl solution, dried over $Na_2SO_4$ and the solvent was removed in vacuo. The crude product was purified by flash chromatography on silica gel using an ethyl acetate/MeOH gradient for elution.

Step 2: The carboxylic ester (1 equivalent) was dissolved in a 2 M MeOH solution of the corresponding amine (10 equivalents) and stirred for 12 h at 60° C. The solvent was removed and the crude product purified by flash chromatography on silica gel using an ethyl acetate/methanol gradient for elution.

The phenol ethers obtained in this way were cleaved as described in scheme 5.

The following phenols were synthesized by the method described:

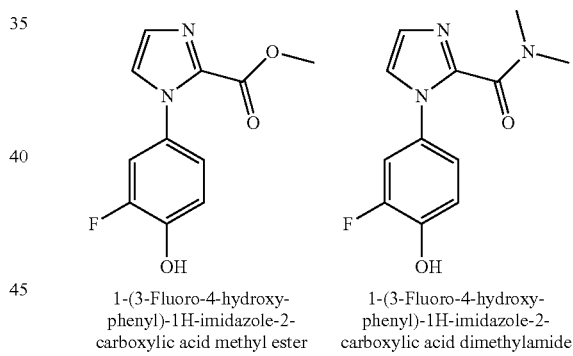

1-(3-Fluoro-4-hydroxy-phenyl)-1H-imidazole-2-carboxylic acid methyl ester 1-(3-Fluoro-4-hydroxy-phenyl)-1H-imidazole-2-carboxylic acid dimethylamide Scheme 25: Synthesis of heterocyclic phenols using sulfonyl chlorides

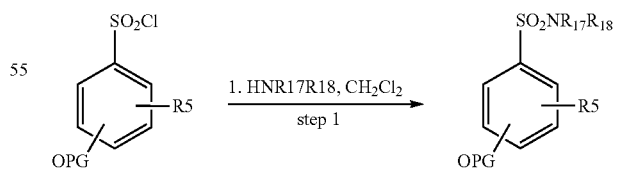

General Synthetic Method:

Step 1: To a solution of the sulfonyl chloride (1 equivalent) in $CH_2Cl_2$ (2 ml/mmol sulfonyl chloride) at 0° C. the amine (4 equivalents) was added dropwise. The suspension was stirred at it for 3 h. Water was added and the aqueous layer was extracted with $CH_2Cl_2$. The combined organic layers were washed with saturated NaCl solution, dried over $Na_2SO_4$ and the solvent was removed in vacuo. The crude product was purified by flash chromatography on silica gel using an ethyl acetate/methanol gradient for elution.

The phenol ethers obtained in this way were cleaved as described in scheme 5.

The following phenols were synthesized by the method described:

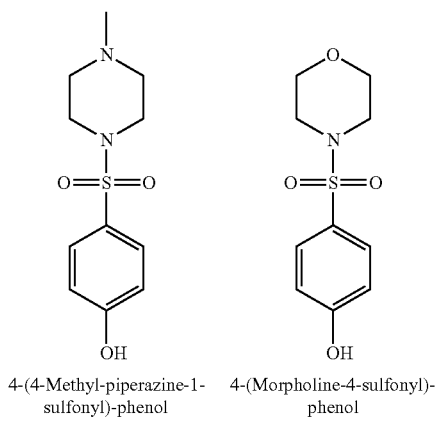 [SMILES: CN1CCN(S(=O)(=O)c2ccc(O)cc2)CC1 ; O=S(=O)(c1ccc(O)cc1)N1CCOCC1]

4-(4-Methyl-piperazine-1-sulfonyl)-phenol 4-(Morpholine-4-sulfonyl)-phenol

Scheme 26: Synthesis of heterocyclic phenols via acyl hydrazines

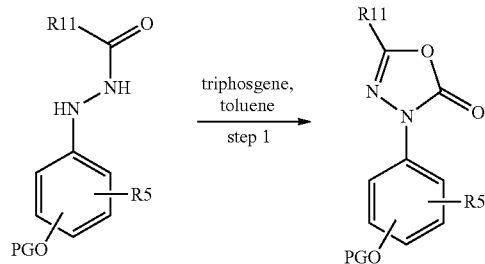

General Synthetic Method:

Step 1: To a solution of the acyl hydrazine (1 equivalent) in toluene (3 ml/mmol acyl hydrazine) at 0° C. triphosgene (0.33 equivalents) was added in portions. The suspension was heated to reflux for 2 h while a solution was formed. The solution was cooled to rt and the solvent removed in vacuo. The crude product was purified by flash chromatography on silica gel using an ethyl acetate/heptane gradient for elution.

The phenol ethers obtained in this way were cleaved as described in scheme 5.

The following phenols were synthesized by the method described:

Scheme 27: Synthesis of heterocyclic phenols via diacyl hydrazines

General Synthetic Method:

Step 1: To a solution of the acyl hydrazine (1 equivalent) in $CH_2Cl_2$ (1.5 ml/mmol acyl hydrazine) at it the isocyanate (12 equivalents) was added. The solution was heated to 55° C. in a sealed vial. The solution was cooled to it and the solvent was removed in vacuo. The crude product was purified by flash chromatography on silica gel using ethyl acetate/heptane/MeOH for elution.

Step 2: NaOH (1.25 equivalents) was dissolved in MeOH (3 ml/mmol NaOH) and the diacyl hydrazine (1 equivalent) was added. The solution was stirred at it for 16 h. The mixture was diluted with water and extracted with ethyl acetate. The combined organic layers were washed with saturated NaCl solution, dried over $Na_2SO_4$ and the solvent was removed in vacuo. The crude product was purified by flash chromatography on silica gel using an ethyl acetate/MeOH gradient for elution.

The phenol ethers obtained in this way were cleaved as described in scheme 5.

The following phenols were synthesized by the method described:

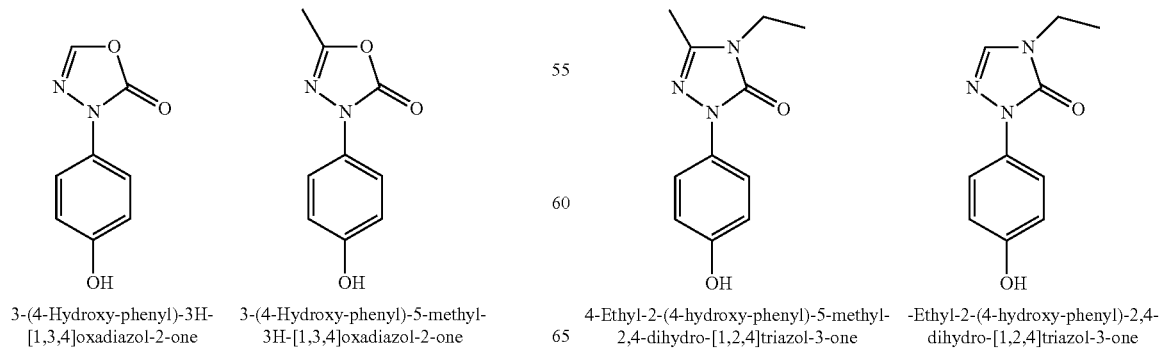

3-(4-Hydroxy-phenyl)-3H-[1,3,4]oxadiazol-2-one 3-(4-Hydroxy-phenyl)-5-methyl-3H-[1,3,4]oxadiazol-2-one 4-Ethyl-2-(4-hydroxy-phenyl)-5-methyl-2,4-dihydro-[1,2,4]triazol-3-one -Ethyl-2-(4-hydroxy-phenyl)-2,4-dihydro-[1,2,4]triazol-3-one Specific synthetic methods corresponding to: Scheme A/method A: Synthesis of compounds I via Mitsunobu inversion

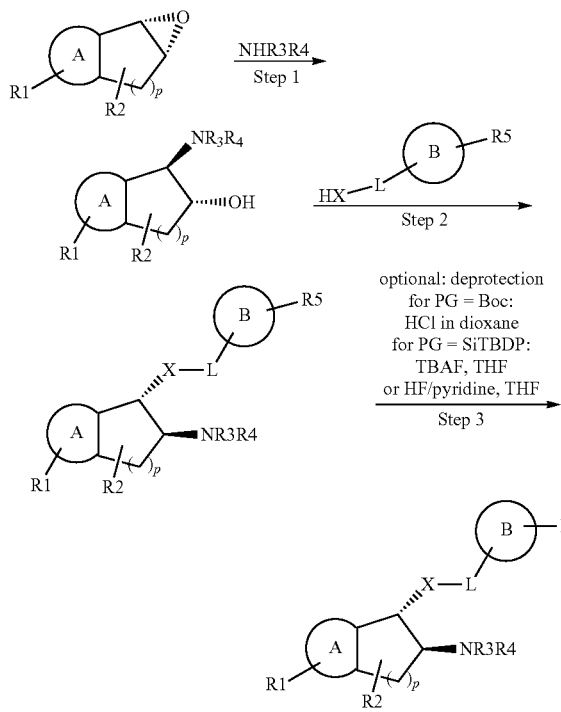

Synthetic Method:

Step 1: A solution of the epoxide (1 equivalent) and the appropriate secondary amine (1.05 equivalents) in acetonitrile (1 ml/mmol of epoxide) was heated at 80° C. for 1-6 h, monitoring by TLC. The solvent was removed in vacuo and the crude products were purified by column chromatography.

Step 2: A 1M solution of DIAD (diisopropylazodicarboxylate, 1.15 equivalents) in THF was added dropwise to a solution/suspension of the amino alcohol (1 equivalent), PPh3 (1.15 equivalents) and the appropriate phenol (1.15 equivalents) in THF (3 ml/mmol of amino alcohol). The solution was stirred at room temperature (rt) for 1-16 h, monitoring the reaction by TLC, and the solvent was removed in vacuo. The crude products were purified by column chromatography.

Step 3 (optional): tert-butyldiphenylsilyl ethers were cleaved either with TBAF (tetra-n-butylammonium fluoride) or HF/pyridine complex. N-Boc protective groups were removed with 4N HCl solution in dioxane or with TFA/CH$_2$Cl$_2$ 1/1.

Specific synthetic methods corresponding to: Scheme B/method B: Synthesis of compounds I via nucleophilic aromatic substitution (1)

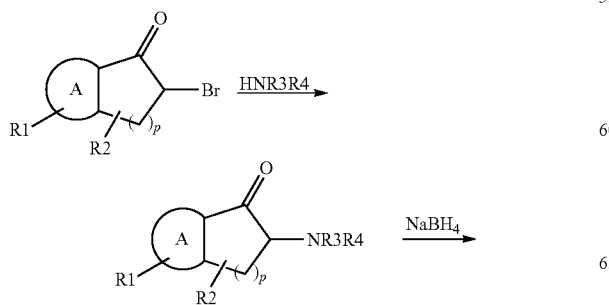

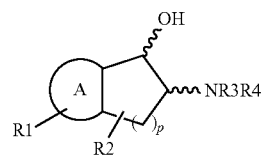

Synthetic Method:

1 equivalent of the 2-bromo-1-indanone are dissolved in dimethylformamide and, preferably at ice-bath temperature, the amine R—NH—R is added as quickly as possible, either in pure form as free base or as DMF solution. After relatively short reaction times (30 seconds to 1 hour), the reaction is stopped by adding sufficient dilute hydrochloric acid for the reaction mixture to have a pH of 1-5. The suspensions are extracted several times with acetic acid ethyl acetate, and 2-10 equivalents of sodium borohydride are added in portions to the remaining aqueous solution, which now contain the intermediate ketone. Stirring at room temperature for several hours is followed by concentration, and the reaction mixture is taken up with water and made weakly alkaline with concentrated sodium bicarbonate solution. The product is obtained by extraction with acetic acid ethyl acetate, initially as mixture of cis/trans isomers which is subjected in most cases to chromatography, it being possible in some cases for the isomers also to be separated in this way. However, cis/trans mixtures are in many cases employed for the following arylation and only then is a separation of the isomers undertaken.

The following 1-indanols were synthesized by the method described:

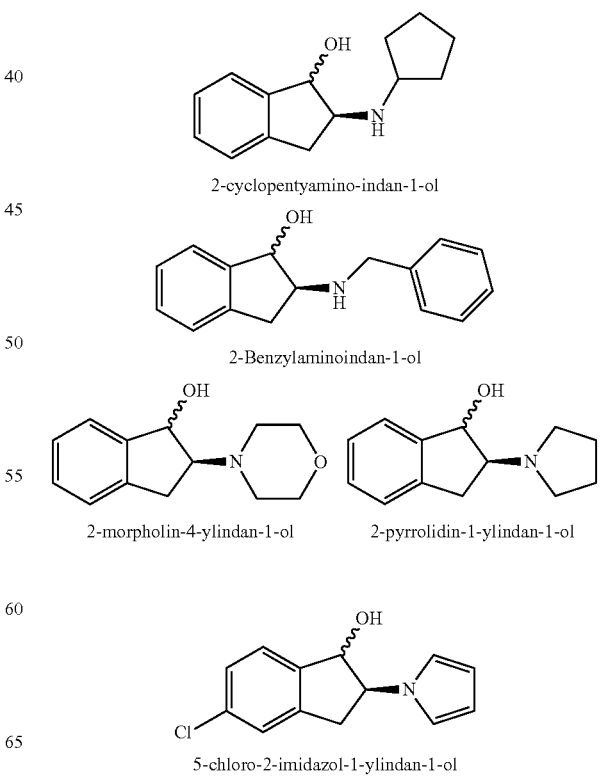

-continued

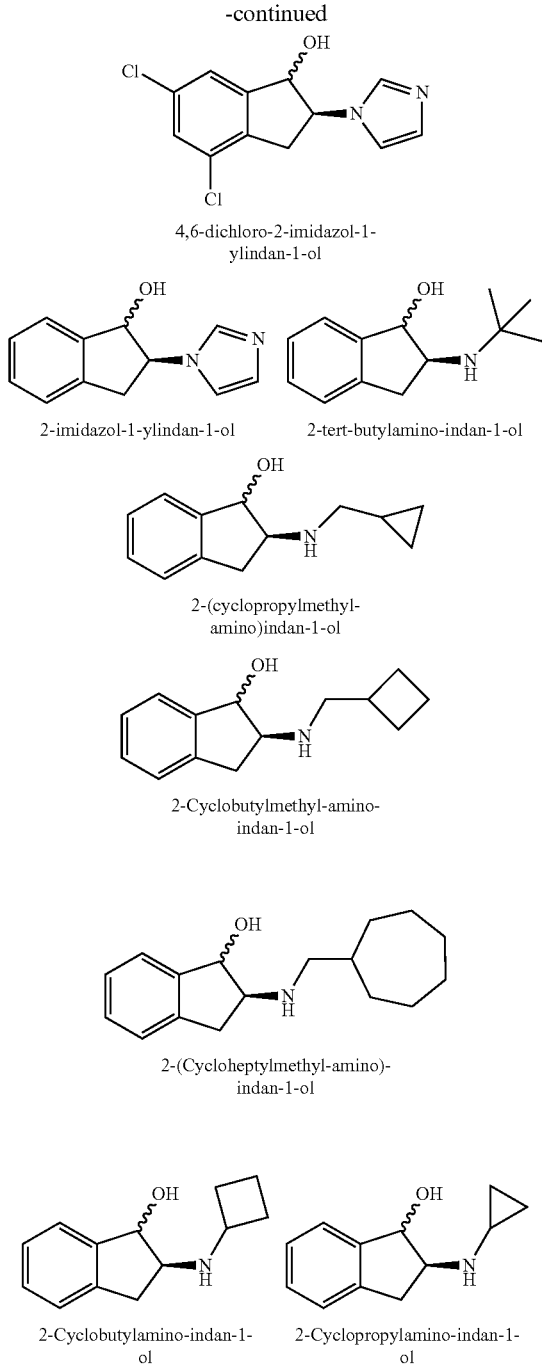

Specific synthetic methods corresponding to: Scheme B/method B: Synthesis of compounds I via nucleophilic aromatic substitution (2)

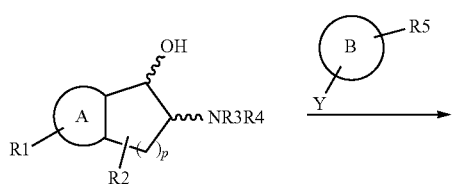

-continued

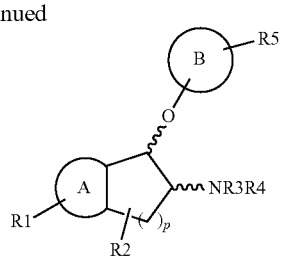

Synthetic Method:

1 equivalent of an indanol of the general formula VI or X (either as pure stereoisomer or as mixture of cis/trans isomers) are dissolved in 5-10 times the amount of absolute dimethyl sulfoxide, and 1.2 to 2 equivalents of a suitable aryl halide, preferably an aryl fluoride or aryl chloride, are added. 1.2 to 5 equivalents of freshly powdered sodium hydroxide are added to the solution while stirring at room temperature, and the mixture is stirred at room temperature for about 1 h or else at 60-80° C., for several hours, depending on the nature of the aryl halide. For workup, the mixture is diluted with water, the resulting suspension is extracted several times with acetic acid ethyl acetate, and the combined extracts are washed with water, dried with MgSO4 and concentrated in a rotary evaporator and then subjected to chromatography on silica gel.

Specific synthetic methods corresponding to: Scheme C/method C: Synthesis of Mannich-like products (1)

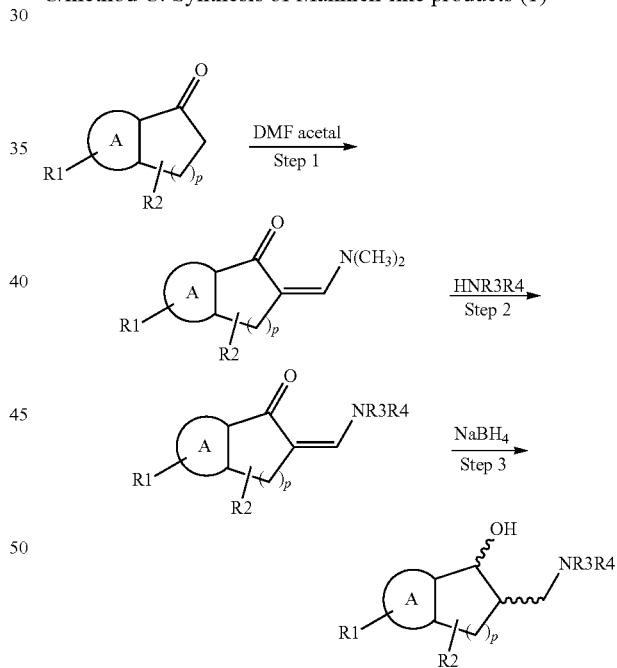

Synthetic Method:

Step 1: 1 equivalent of an indan-2-one are dissolved in an inert solvent such as tetrahydrofuran, dimethylformamide or acetonitrile, and 2-3 equivalents of dimethylformamide dimethyl acetal are added, and the mixture is boiled under reflux for several hours or, in the case of DMF, stirred at 80 to maximum of 120° C. with stirring for about 3-5 hours. An alternative possibility is also to dispense entirely with solvent, and in this case the precursor is dissolved in a sufficient amount of dimethylformamide dimethyl acetal and then stirred at 120° C. until conversion is complete. After cooling, the crystallized product can usually be directly filtered off with suction and further purified by chromatography or recrystallization.

Step 2: 1 equivalent of the 2-dimethylaminomethylene-1-indanone obtained in this way is dissolved in dimethylformamide, and at least 2 equivalents of the sec. amine NHR3R4 are added, either as free base or as hydrochloride. The mixture is stirred at temperatures of from 60° to 120° for several hours. After cooling, the solution is diluted with water and the product is isolated either by filtration with suction or by extraction with ethyl acetate.

Step 3: 1 equivalent of the 2-aminomethylene-1-indanone obtained in this way are dissolved in methanol and 10-20 equivalents, divided into 10-20 portions, are added in an interval of 15-30 minutes while stirring at room temperature. After the precursor has virtually completely disappeared, the solvent is removed in vacuo, and the residue is taken up with water. The crude product is obtained by extraction with acetic acid ethyl acetate, initially as mixture of cis/trans isomers, which is in most cases subjected to chromatography, it being possible in some cases also for the isomers to be separated in this way. However, in many cases, cis/trans mixtures are employed for the following arylation, and only then is a separation of the isomers undertaken.

The following 2-aminomethyl-1-indanols were synthesized by the method described:

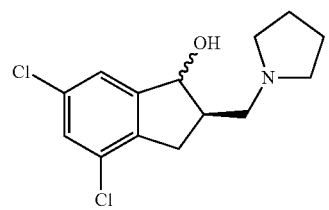

4,6-dichloro-2-pyrrolidin-1-ylmethylindan-1-ol

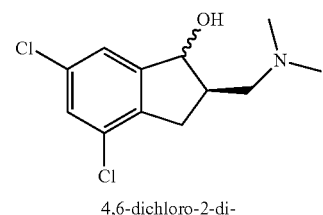

4,6-dichloro-2-dimethylaminomethylindan-1-ol

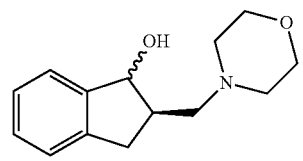

2-morpholin-4-yl-methylindan-1-ol

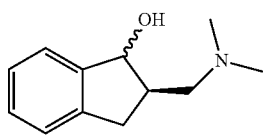

2-dimethylamino-methylindan-1-ol

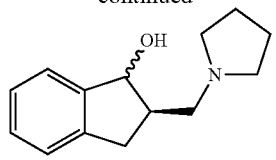

2-pyrrolidin-1-ylmethylindan-1-ol

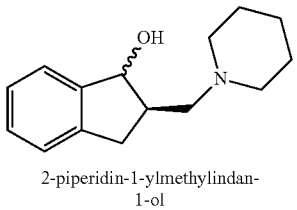

2-piperidin-1-ylmethylindan-1-ol

Specific synthetic methods corresponding to: Scheme C/method C: Synthesis of Mannich-like products (2)

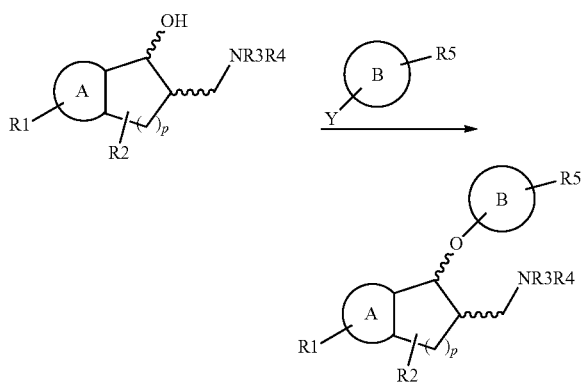

Synthetic Method:

1 equivalent of an indanol of the general formula VI or X (either as pure stereoisomer or as mixture of cis/trans isomers) are dissolved in 5-10 times the amount of absolute dimethyl sulfoxide, and 1.2 to 2 equivalents of a suitable aryl halide, preferably an aryl fluoride or aryl chloride, are added. 1.2 to 5 equivalents of freshly powdered sodium hydroxide are added to the solution while stirring at room temperature, and the mixture is stirred at room temperature for about 1 h or else at 60-80° C., for several hours, depending on the nature of the aryl halide. For workup, the mixture is diluted with water, the resulting suspension is extracted several times with acetic acid ethyl acetate, and the combined extracts are washed with water, dried with MgSO4 and concentrated in a rotary evaporator and then subjected to chromatography on silica gel.

Specific synthetic methods corresponding to: Scheme D/method D: Synthesis of diamines with the trans configuration and subsequent Buchwald arylation

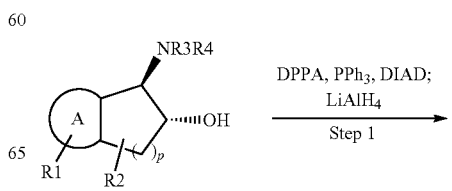

-continued

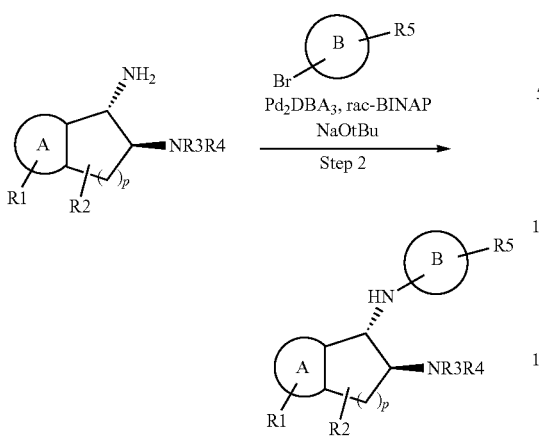

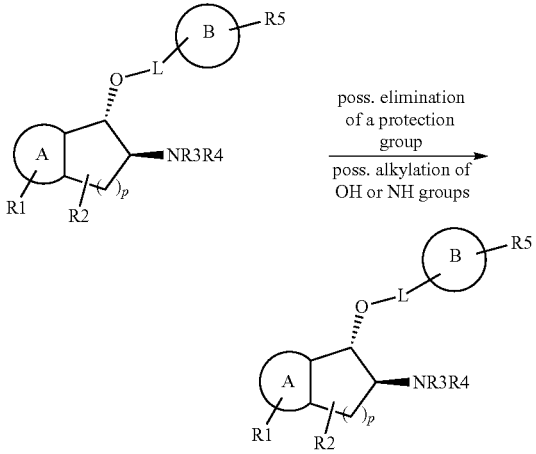

Synthetic Method:

Step 1: A 1M solution of DIAD (1.10 eq.) in THF was added dropwise to a solution of the amino alcohol (1 eq.), PPh$_3$ (1.10 eq.) and DPPA (1.10 eq.) in THF (7 ml/mmol of amino alcohol) at 0° C. The solution/suspension was stirred at 0° C. for 60 min (LC/MS monitoring) and cooled to −10° C. At this temperature, LiAlH$_4$ (2.00 eq. based on amino alcohol employed) was cautiously added in one portion, and the mixture was stirred while cooling in ice for a further 60 min. The suspension was poured onto ice-water and the aqueous phase was extracted with ethyl acetate. The combined organic phases were dried with Na$_2$SO$_4$ and filtered, and the solvent was removed in vacuo. The crude products were purified by column chromatography.

Step 2: The aryl bromide (0.95 eq.) was added to a solution of the diamine (1. eq.), Pd$_2$(dba)$_3$ (0.04 eq.), rac-BINAP (0.08 eq.), NaO$^t$Bu (1.40 eq.) in toluene (12 ml/mmol of diamine), and the mixture was heated at 70° C. for 10-18 h (TLC monitoring). The reaction was diluted with ethyl acetate and washed with water. The aqueous phase was extracted with ethyl acetate, and the combined organic phases were dried with Na$_2$SO$_4$ and filtered, and the solvent was removed in vacuo. The crude product was purified by column chromatography.

Specific synthetic methods corresponding to: Scheme E/method E: Synthesis of compounds I via alkylation

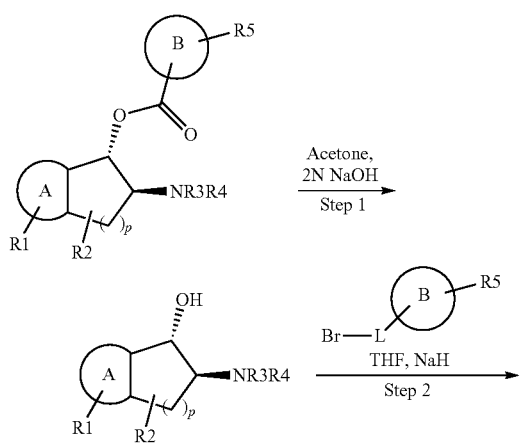

Synthetic Method:

Step 1: A 2N aqueous NaOH solution (1.10 eq.) was added at rt to a solution of the benzoic ester (1 eq.) in acetone (20 ml/mmol of benzoic ester), and the mixture was stirred at it for several hours until the precursor was completely reacted (TLC monitoring). The solvent was removed in vacuo, and the residue was mixed with water. The aqueous phase was extracted with ethyl acetate, and the combined organic phases were dried with Na$_2$SO$_4$ and filtered, and the solvent was removed in vacuo. The crude products were purified by column chromatography.

Step 2: NaH (1.30 eq. 80% in mineral oil) was added to a solution of the amino alcohol (1 eq.) in THF (7 ml/mmol of the amino alcohol) at 0° C., the ice bath was removed, and the mixture was allowed to warm to rt over the course of one hour. The alkylating reagent (1.10 eq.) was added, and the reaction was stirred at it until the reaction showed no further conversion (TLC monitoring). The mixture was poured onto saturated aqueous NaHCO$_3$ solution, and the aqueous phase was extracted with ethyl acetate. The combined organic phases were dried with Na$_2$SO$_4$ and filtered, and the solvent was removed in vacuo. The crude products were purified by column chromatography.

Specific synthetic methods corresponding to: Scheme F: Optional further reactions of compounds I

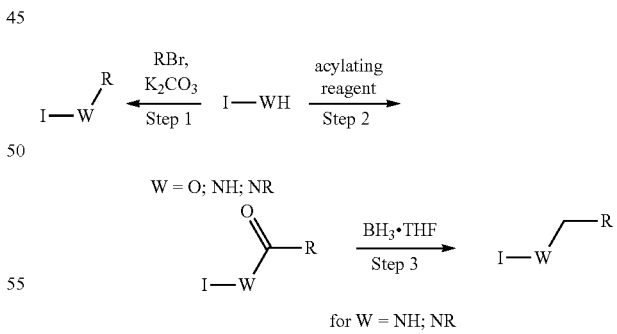

Synthetic Method:

Step 1: A mixture of I—WH (1 eq.), of the bromide RBr (1.6-6 eq.) and K2CO3 (1-2 eq.) were stirred in acetonitrile (5 ml/mmol) at 80° C. (16-48 h). Addition of dichloromethane and saturated NaHCO$_3$ solution was followed by extraction 3 times with dichloromethane. The collected organic phases were washed with sat. NaCl solution and dried (Na$_2$SO$_4$). The solvent was removed in vacuo, and the crude products were purified by column chromatography.

Step 2: (R=CF3) A solution of I—WH (1 eq.) and ethyl trifluoroacetate (1.3 eq.) was stirred in methanol overnight. The solvent was removed in vacuo. Addition of dichloromethane and saturated NaHCO$_3$ solution was followed by extraction 3 times with dichloromethane. The collected organic phases were washed with sat. NaCl solution and dried (Na$_2$SO$_4$). The solvent was removed in vacuo, and the crude products were purified by column chromatography.

Or:

(R=CH$_3$) A solution of the amine A (1 eq.) was stirred in acetic anhydride/pyridine 1/2 (9 ml/mmol of precursor). The solvent was removed in vacuo. The crude products were purified by column chromatography.

Step 3: A 1M solution of borane-THF complex in THF (2-9 eq.) was added dropwise to a solution of the amide (1 eq.) in THF (5 ml/mmol of precursor) at 0° C. After heating under reflux, concentrated hydrochloric acid was cautiously added to the mixture at 0° C., and the mixture was basified with NaOH and extracted 3 times with dichloromethane. The collected organic phases were washed with sat. NaCl solution and dried (Na$_2$SO$_4$). The solvent was removed in vacuo, and the crude products were purified by column chromatography.

Specific synthetic methods corresponding to: scheme G/method G: Synthesis of compounds of the formula I via Pd catalyzed deprotection of allyl amines

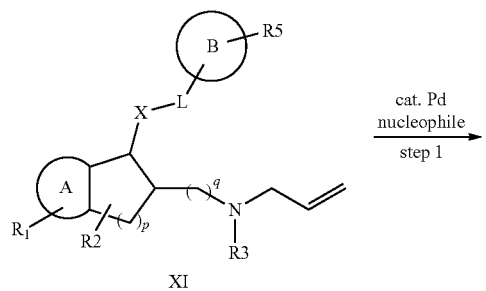

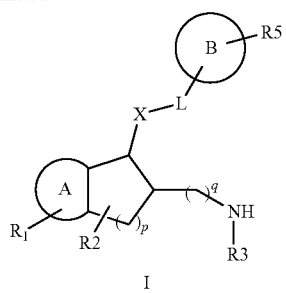

Synthetic Method:

Step 1: To a suspension of 1,3-dimethyl barbituric acid (2-6 equivalents) and Pd(PPh$_3$)$_4$ (0.05-0.10 equivalents) in CH$_2$Cl$_2$ (1.0 ml/mmol barbituric acid) under an argon atmosphere a solution of the allyl amine (1 equivalent) in CH$_2$Cl$_2$ (2.0 ml/mmol allyl amine) was added at room temperature. The solution was heated to reflux until the educt was completely converted (TLC control). The reaction mixture was cooled to room temperature and diluted with ethyl acetate. The organic layer was washed with saturated aqueous Na$_2$CO$_3$ solution, dried over Na$_2$SO$_4$ and the solvent removed in vacuo. The crude product was purified by flash chromatography on silica gel.

Synthesis of a Specific Example (Example 226) by Method A:

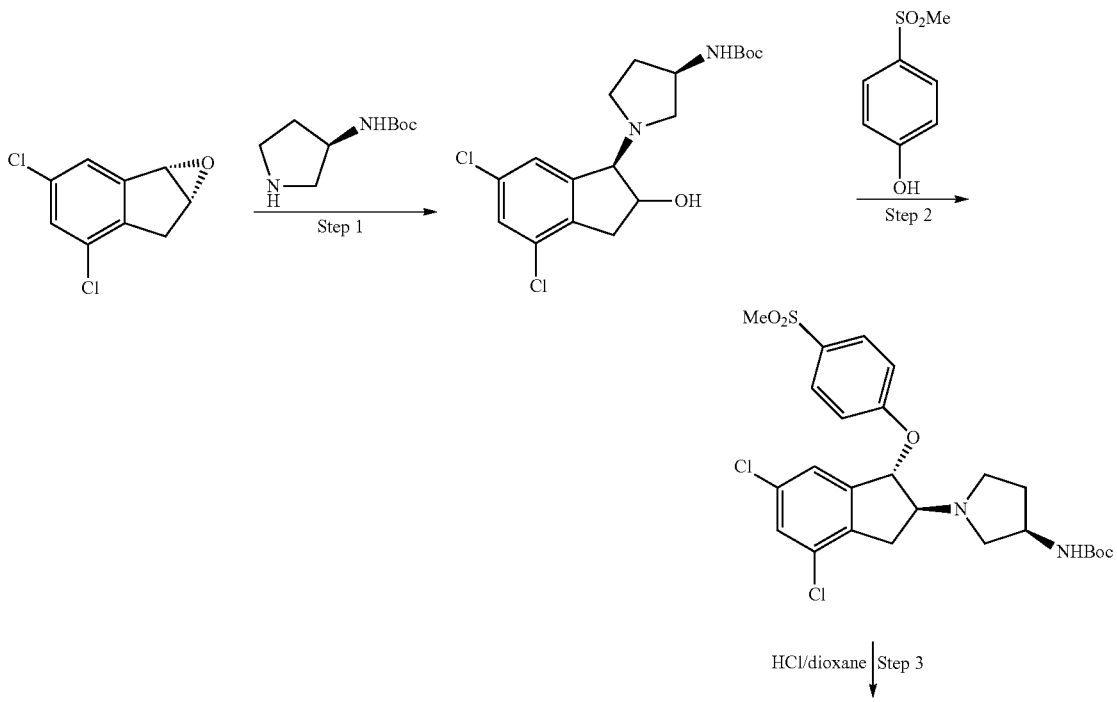

-continued

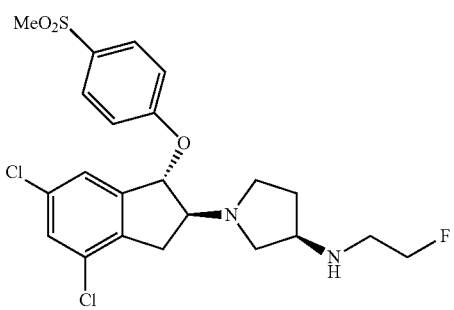

Example 226

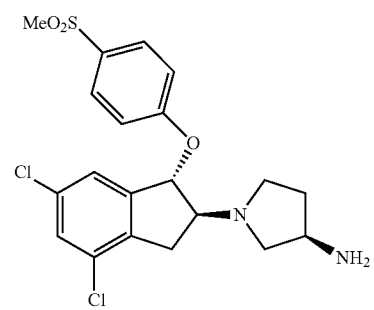

Step 4

Step 1: A suspension of the 4,6-dichloro epoxide (500 mg, 1 equivalent) and the appropriate secondary amine (486 mg, 1.05 equivalents) in acetonitrile (2.5 ml) was heated at 80° C. for 6 h. The solvent was removed in vacuo, and the crude products were purified by column chromatography ($CH_2Cl_2$/MeOH). 875 mg of a colorless foam were obtained.

Step 2: A 1M solution of DIAD (1.87 ml, 1.15 equivalents) in THF was added dropwise to a suspension of the amino alcohol (630 mg, 1 equivalent), $PPh_3$ (490 mg, 1.15 equivalents) and 4-methylsulfonylphenol (310 mg, 1.15 equivalents) in THF (3 ml). The solution was stirred at room temperature (rt) for 5 h, and the solvent was removed in vacuo. The crude products were purified by column chromatography (ethyl acetate/heptane/methanol). The product was obtained as a colorless foam which still contained traces of $OPPh_3$ (930 mg).

Step 3 (optional): A 4 M HCl solution in dioxane (5 ml) was added to a solution of the Boc-protected precursor (930 mg) in dioxane (5 ml) at 0° C., and the mixture was stirred at rt for 3.5 h. The resulting suspension was diluted with diethyl ether, filtered and washed with diethyl ether. The white solid was suspended in saturated aqueous $NaHCO_3$ solution, and the aqueous phase was extracted with ethyl acetate. The combined organic phases were dried with $Na_2SO_4$ and filtered, and the solvent was removed in vacuo. The desired product was obtained as a pale yellow solid (600 mg).

Step 4 (optional): 1-Bromo-2-fluoroethane (164 mg, 3 equivalents) was added to a suspension of the deprotected 3-aminopyrrolidine (190 mg, 1 equivalent) and $K_2CO_3$ (60 mg, 1 equivalent) in acetonitrile (4 ml) at rt, and the mixture was heated under reflux for 6 h. The solvent was removed in vacuo, the residue was suspended in water, and the aqueous phase was extracted with ethyl acetate. The combined organic phases were dried with $Na_2SO_4$ and filtered, and the solvent was removed in vacuo. The crude product was purified by column chromatography ($CH_2Cl_2$/MeOH). The desired product was obtained as a pale yellow oil (120 mg).

The following examples were synthesized in analogy to Example 226:

| Example | Structure | Synthetic method | LC method | Rt time [min] | MS [M + H+] ES+ |
|---|---|---|---|---|---|
| 1 | 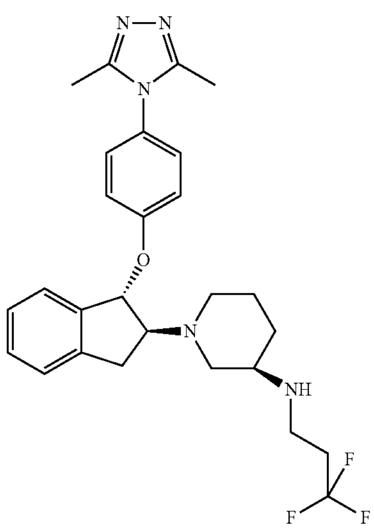 [SMILES: Cc1nnc(C)n1-c1ccc(O[C@H]2c3ccccc3C[C@@H]2N2CCC[C@@H](NCCC(F)(F)F)C2)cc1] | A | 14 | 1.56 | 500.30 |

-continued

| Example | Structure | Synthetic method | LC method | Rt time [min] | MS [M + H+] ES+ |
|---|---|---|---|---|---|
| 2 | 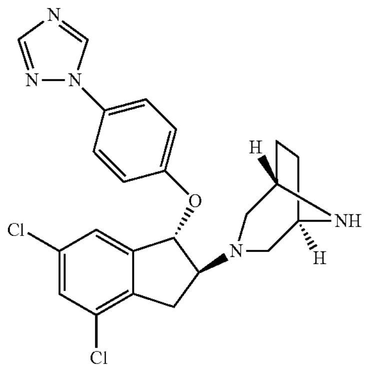 [SMILES: Clc1cc(Cl)c2c(c1)[C@H](Oc1ccc(-n3cncn3)cc1)[C@@H](N1C[C@H]3CC[C@@H](C1)N3)C2] | A | 1 | 2.90 | 456.15 |
| 3 | 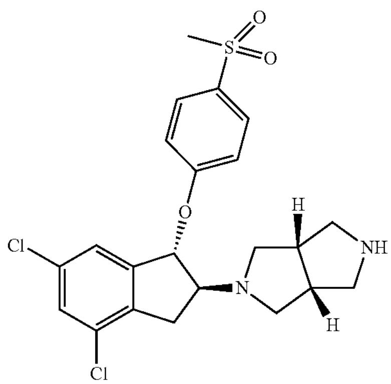 [SMILES: CS(=O)(=O)c1ccc(O[C@H]2c3cc(Cl)cc(Cl)c3C[C@@H]2N2C[C@H]3CNC[C@H]3C2)cc1] | A | 4 | 1.20 | 467.13 |
| 4 | 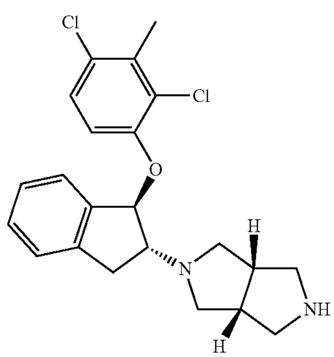 [SMILES: Cc1c(Cl)ccc(O[C@@H]2c3ccccc3C[C@H]2N2C[C@H]3CNC[C@H]3C2)c1Cl] | A | 12 | 1.48 | 403.20 |
| 5 | 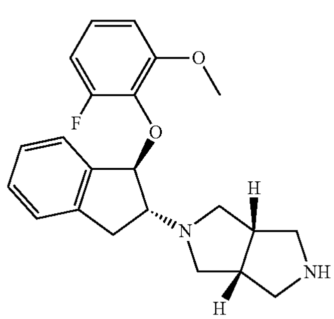 [SMILES: COc1cccc(F)c1O[C@@H]1c2ccccc2C[C@H]1N1C[C@H]2CNC[C@H]2C1] | A | 12 | 1.16 | 369.24 |

-continued

| Example | Structure | Synthetic method | LC method | Rt time [min] | MS [M + H+] ES+ |
|---|---|---|---|---|---|
| 6 | 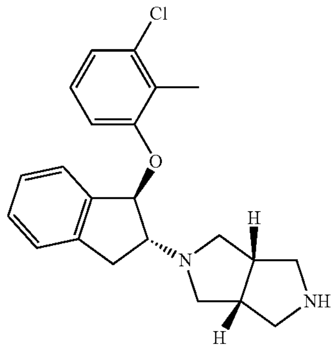 [SMILES: Cc1c(Cl)cccc1O[C@@H]1c2ccccc2C[C@H]1N1C[C@H]2CNC[C@H]2C1] | A | 12 | 1.40 | 369.23 |
| 7 | 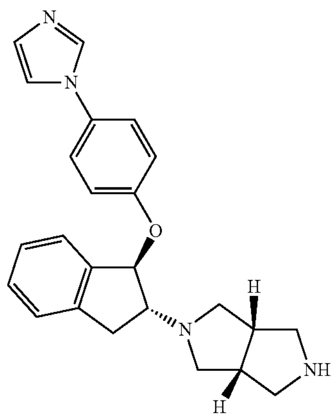 [SMILES: c1ccc2c(c1)C[C@@H](N1C[C@H]3CNC[C@H]3C1)[C@@H]2Oc1ccc(-n2ccnc2)cc1] | A | 12 | 0.83 | 387.27 |
| 8 | 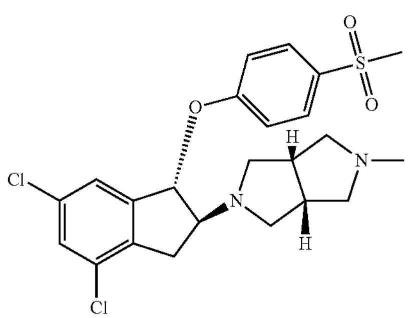 [SMILES: CN1C[C@@H]2CN([C@H]3Cc4c(Cl)cc(Cl)cc4[C@@H]3Oc3ccc(S(C)(=O)=O)cc3)C[C@@H]2C1] | A | 14 | 1.81 | 481.13 |
| 9 | 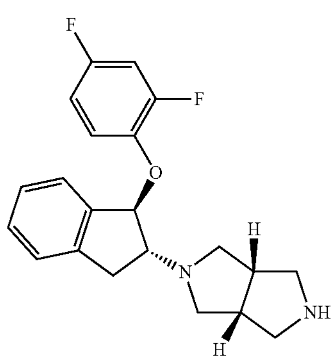 [SMILES: Fc1ccc(O[C@@H]2c3ccccc3C[C@H]2N2C[C@H]3CNC[C@H]3C2)c(F)c1] | A | 12 | 1.22 | 357.23 |

-continued

| Example | Structure | Synthetic method | LC method | Rt time [min] | MS [M + H+] ES+ |
|---|---|---|---|---|---|
| 10 | 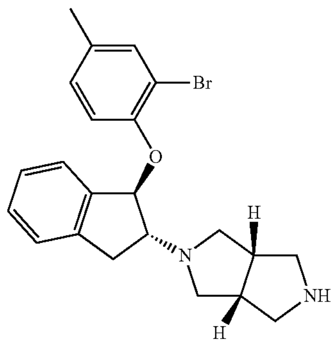 [SMILES: Cc1ccc(O[C@@H]2c3ccccc3C[C@H]2N2C[C@H]3CNC[C@H]3C2)c(Br)c1] | A | 12 | 1.38 | 413.18 |
| 11 | 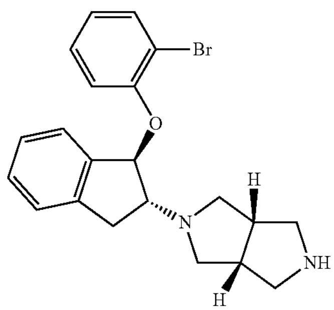 [SMILES: Brc1ccccc1O[C@@H]1c2ccccc2C[C@H]1N1C[C@H]2CNC[C@H]2C1] | A | 12 | 1.23 | 399.16 |
| 12 | 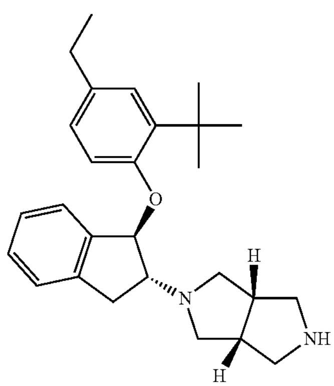 [SMILES: CCc1ccc(O[C@@H]2c3ccccc3C[C@H]2N2C[C@H]3CNC[C@H]3C2)c(C(C)(C)C)c1] | A | 12 | 1.25 | 405.23 |
| 13 | 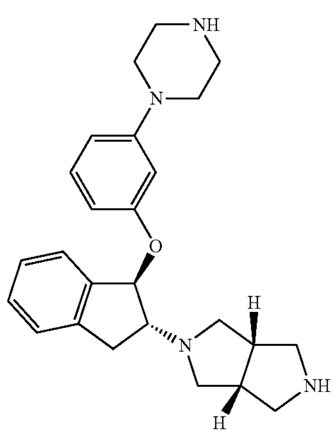 [SMILES: c1cc(O[C@@H]2c3ccccc3C[C@H]2N2C[C@H]3CNC[C@H]3C2)cc(N2CCNCC2)c1] | A | 12 | 0.87 | 405.32 |

| Example | Structure | Synthetic method | LC method | Rt time [min] | MS [M + H+] ES+ |
|---------|-----------|------------------|-----------|---------------|-----------------|
| 14 | 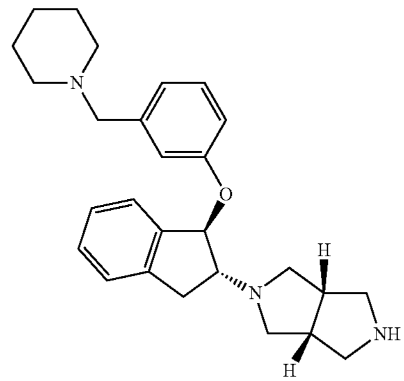 [SMILES: c1cc(CN2CCCCC2)cc(O[C@@H]2c3ccccc3C[C@H]2N2C[C@H]3CNC[C@H]3C2)c1] | A | 12 | 0.92 | 418.34 |
| 15 | 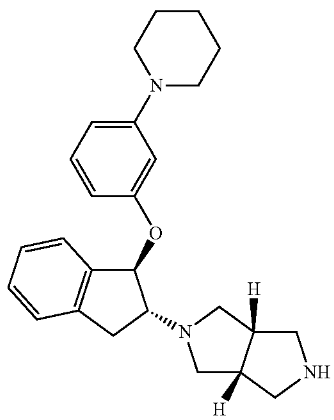 [SMILES: c1cc(O[C@@H]2c3ccccc3C[C@H]2N2C[C@H]3CNC[C@H]3C2)cc(N2CCCCC2)c1] | A | 12 | 1.28 | 404.32 |
| 16 | 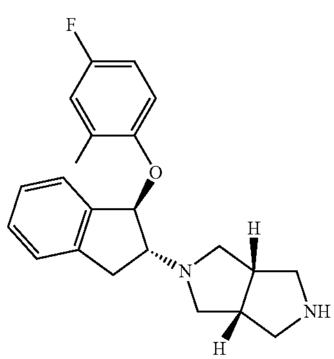 [SMILES: Cc1cc(F)ccc1O[C@@H]1c2ccccc2C[C@H]1N1C[C@H]2CNC[C@H]2C1] | A | 12 | 1.32 | 353.25 |
| 17 | 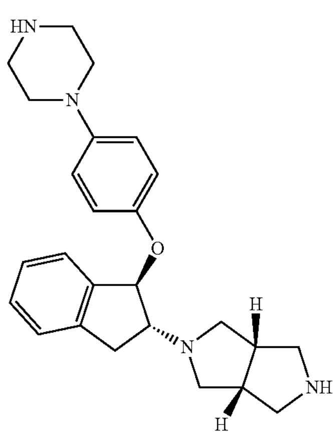 [SMILES: c1ccc2c(c1)C[C@@H](N1C[C@H]3CNC[C@H]3C1)[C@@H]2Oc1ccc(N2CCNCC2)cc1] | A | 12 | 0.83 | 405.33 |

-continued

| Example | Structure | Synthetic method | LC method | Rt time [min] | MS [M + H+] ES+ |
|---|---|---|---|---|---|
| 18 | 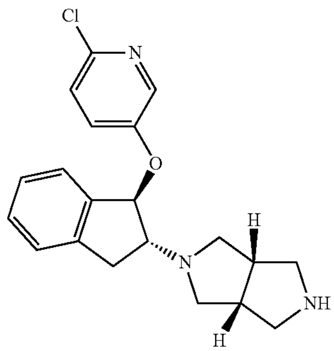 [SMILES: Clc1ccc(O[C@@H]2c3ccccc3C[C@H]2N2C[C@H]3CNC[C@H]3C2)cn1] | A | 12 | 1.08 | 356.20 |
| 19 | 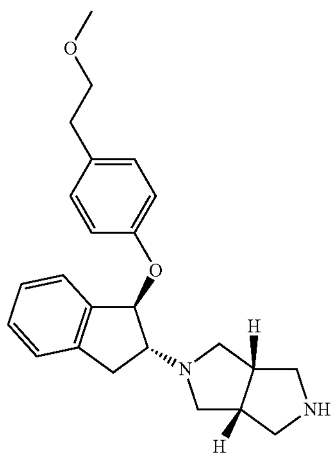 [SMILES: COCCc1ccc(O[C@@H]2c3ccccc3C[C@H]2N2C[C@H]3CNC[C@H]3C2)cc1] | A | 12 | 1.20 | 379.29 |
| 20 | 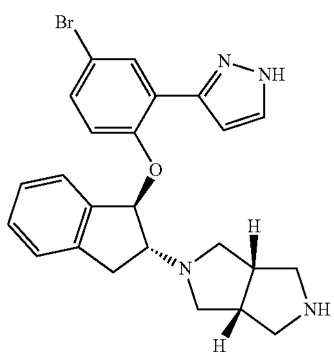 [SMILES: Brc1ccc(O[C@@H]2c3ccccc3C[C@H]2N2C[C@H]3CNC[C@H]3C2)c(-c2cc[nH]n2)c1] | A | 12 | 1.33 | 465.19 |
| 21 | 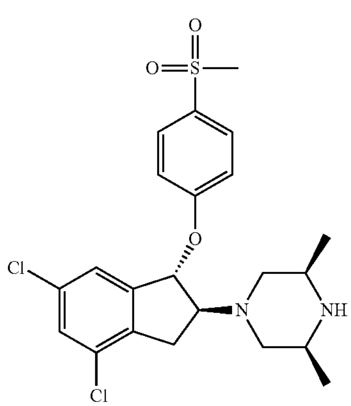 [SMILES: C[C@@H]1CN([C@H]2Cc3c(Cl)cc(Cl)cc3[C@@H]2Oc2ccc(S(C)(=O)=O)cc2)C[C@H](C)N1] | A | 14 | 2.06 | 469.12 |

-continued

| Example | Structure | Synthetic method | LC method | Rt time [min] | MS [M + H+] ES+ |
|---|---|---|---|---|---|
| 22 | 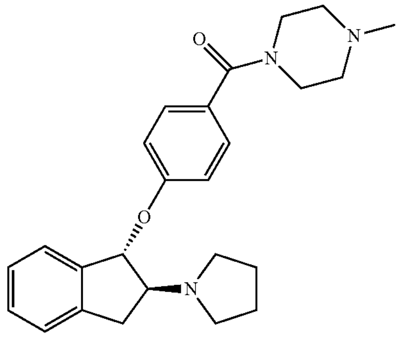 [SMILES: CN1CCN(C(=O)c2ccc(O[C@H]3c4ccccc4C[C@@H]3N3CCCC3)cc2)CC1] | A | 14 | 1.36 | 406.27 |
| 23 | 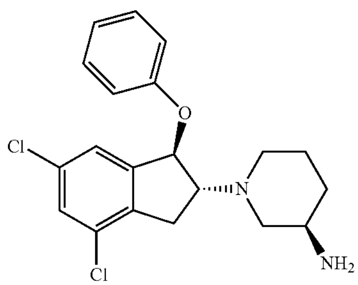 [SMILES: N[C@@H]1CCCN([C@@H]2Cc3c(Cl)cc(Cl)cc3[C@H]2Oc2ccccc2)C1] | A | 4 | 1.27 | 377.21 |
| 25 | 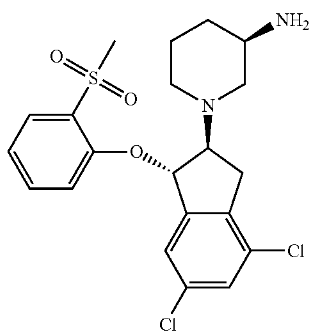 [SMILES: CS(=O)(=O)c1ccccc1O[C@H]1c2cc(Cl)cc(Cl)c2C[C@@H]1N1CCC[C@@H](N)C1] | A | 1 | 2.50 | 455.13 |
| 27 | 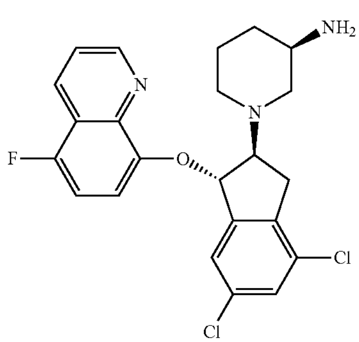 [SMILES: N[C@@H]1CCCN([C@H]2Cc3c(Cl)cc(Cl)cc3[C@@H]2Oc2ccc(F)c3cccnc23)C1] | A | 1 | 2.54 | 446.15 |

-continued

| Example | Structure | Synthetic method | LC method | Rt time [min] | MS [M + H+] ES+ |
|---|---|---|---|---|---|
| 28 | 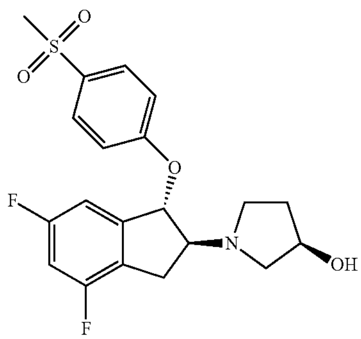 [SMILES: CS(=O)(=O)c1ccc(O[C@H]2c3cc(F)cc(F)c3C[C@@H]2N2CC[C@@H](O)C2)cc1] | A | 9 | 2.36 | 410.10 |
| 29 | 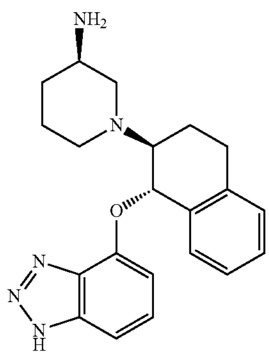 [SMILES: N[C@@H]1CCCN([C@H]2CCc3ccccc3[C@@H]2Oc2cccc3[nH]nnc23)C1] | A | 1 | 2.67 | 364.19 |
| 30 | 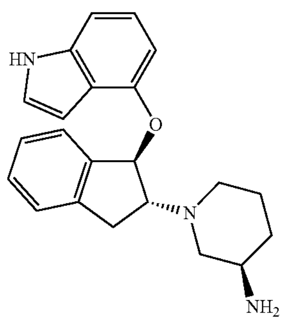 [SMILES: N[C@@H]1CCCN([C@@H]2Cc3ccccc3[C@H]2Oc2cccc3[nH]ccc23)C1] | A | 12 | 1.12 | 695.42 2M + H |
| 31 | 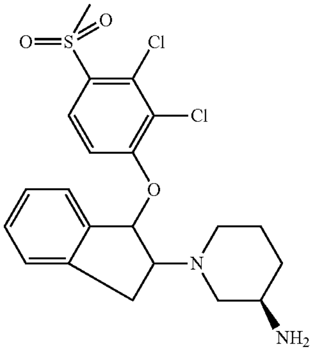 [SMILES: CS(=O)(=O)c1ccc(OC2c3ccccc3CC2N2CCC[C@@H](N)C2)c(Cl)c1Cl] | A | 6 | 1.20 | 455.14 |

-continued

| Example | Structure | Synthetic method | LC method | Rt time [min] | MS [M + H+] ES+ |
|---|---|---|---|---|---|
| 32 | 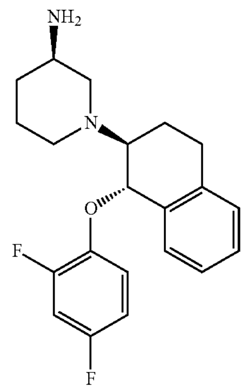 [SMILES: N[C@@H]1CCCN([C@H]2CCc3ccccc3[C@@H]2Oc2ccc(F)cc2F)C1] | A | 1 | 2.43 | 359.14 |
| 33 | 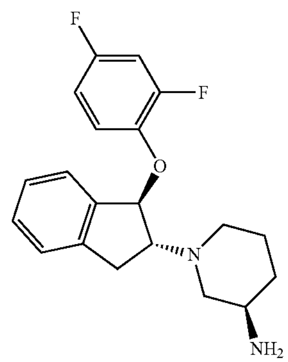 [SMILES: N[C@@H]1CCCN([C@@H]2Cc3ccccc3[C@H]2Oc2ccc(F)cc2F)C1] | A | 12 | 1.16 | 345.15 |
| 34 | 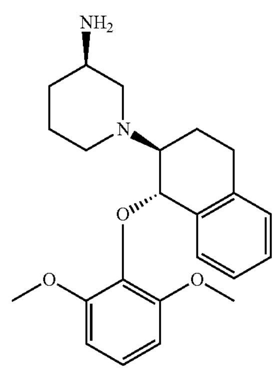 [SMILES: COc1cccc(OC)c1O[C@H]1c2ccccc2CC[C@@H]1N1CCC[C@@H](N)C1] | A | 1 | 2.27 | 383.19 |
| 35 | 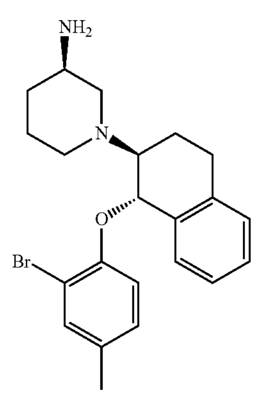 [SMILES: Cc1ccc(O[C@H]2c3ccccc3CC[C@@H]2N2CCC[C@@H](N)C2)c(Br)c1] | A | 1 | 2.60 | 415.09 |

-continued

| Example | Structure | Synthetic method | LC method | Rt time [min] | MS [M + H+] ES+ |
|---|---|---|---|---|---|
| 36 | 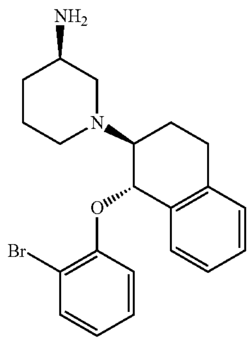 [SMILES: N[C@@H]1CCCN([C@H]2CCc3ccccc3[C@@H]2Oc2ccccc2Br)C1] | A | 9 | 2.41 | 401.09 |
| 37 | 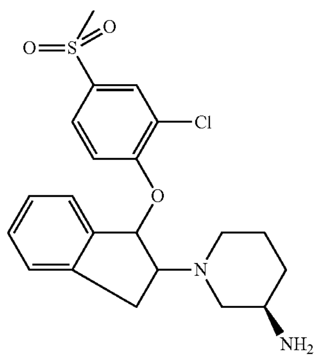 [SMILES: CS(=O)(=O)c1ccc(OC2c3ccccc3CC2N2CCC[C@@H](N)C2)c(Cl)c1] | A | 6 | 1.10 | 421.18 |
| 38 | 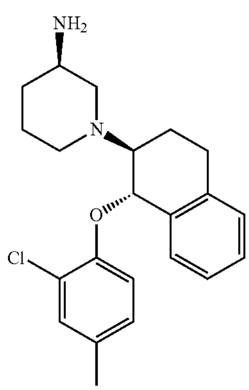 [SMILES: Cc1ccc(O[C@H]2c3ccccc3CC[C@@H]2N2CCC[C@@H](N)C2)c(Cl)c1] | A | 1 | 2.57 | 371.14 |
| 39 | 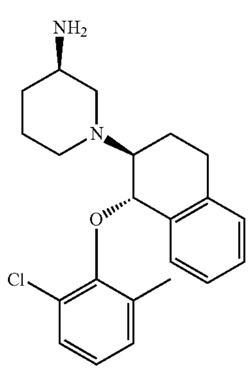 [SMILES: Cc1cccc(Cl)c1O[C@H]1c2ccccc2CC[C@@H]1N1CCC[C@@H](N)C1] | A | 1 | 2.32 | 371.16 |

-continued

| Example | Structure | Synthetic method | LC method | Rt time [min] | MS [M + H+] ES+ |
|---|---|---|---|---|---|
| 40 | 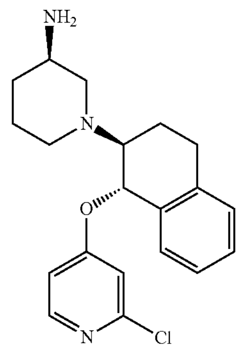 [SMILES: N[C@@H]1CCCN([C@H]2CCc3ccccc3[C@@H]2Oc2ccnc(Cl)c2)C1] | A | 1 | 2.30 | 358.14 |
| 41 | 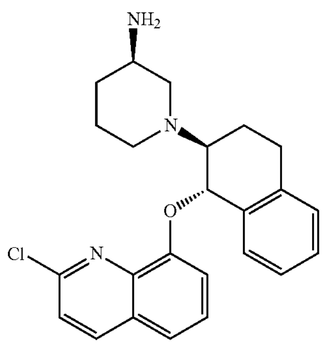 [SMILES: N[C@@H]1CCCN([C@H]2CCc3ccccc3[C@@H]2Oc2cccc3ccc(Cl)nc23)C1] | A | 1 | 2.45 | 408.14 |
| 42 | 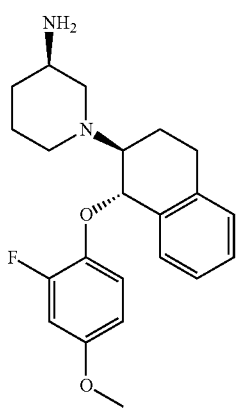 [SMILES: COc1ccc(O[C@H]2c3ccccc3CC[C@@H]2N2CCC[C@@H](N)C2)c(F)c1] | A | 1 | 2.40 | 371.16 |
| 43 | 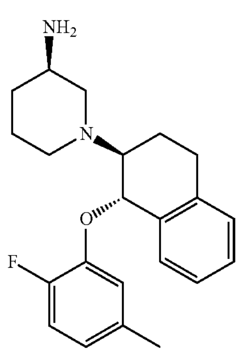 [SMILES: Cc1ccc(F)c(O[C@H]2c3ccccc3CC[C@@H]2N2CCC[C@@H](N)C2)c1] | A | 1 | 2.47 | 355.18 |

-continued

| Example | Structure | Synthetic method | LC method | Rt time [min] | MS [M + H+] ES+ |
|---|---|---|---|---|---|
| 44 | 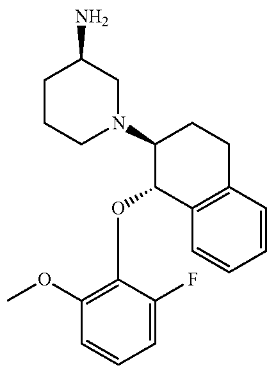 [SMILES: COc1cccc(F)c1O[C@H]1c2ccccc2CC[C@@H]1N1CCC[C@@H](N)C1] | A | 1 | 2.37 | 371.16 |
| 45 | 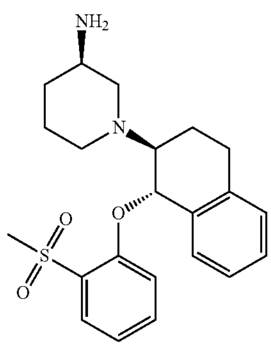 [SMILES: CS(=O)(=O)c1ccccc1O[C@H]1c2ccccc2CC[C@@H]1N1CCC[C@@H](N)C1] | A | 1 | 2.22 | 401.1 |
| 46 | 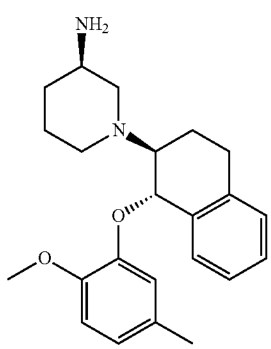 [SMILES: COc1ccc(C)cc1O[C@H]1c2ccccc2CC[C@@H]1N1CCC[C@@H](N)C1] | A | 1 | 2.65 | 367.2 |
| 47 | 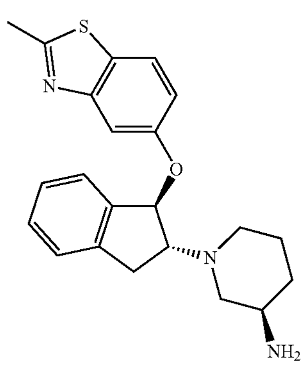 [SMILES: Cc1nc2cc(O[C@@H]3c4ccccc4C[C@H]3N3CCC[C@@H](N)C3)ccc2s1] | A | 12 | 1.16 | 380.18 |

-continued

| Example | Structure | Synthetic method | LC method | Rt time [min] | MS [M + H+] ES+ |
|---------|-----------|------------------|-----------|---------------|-----------------|
| 48 | 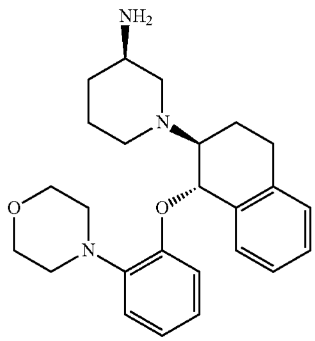 [SMILES: N[C@@H]1CCCN([C@H]2CCc3ccccc3[C@@H]2Oc2ccccc2N2CCOCC2)C1] | A | 9 | 2.23 | 408.25 |
| 49 | 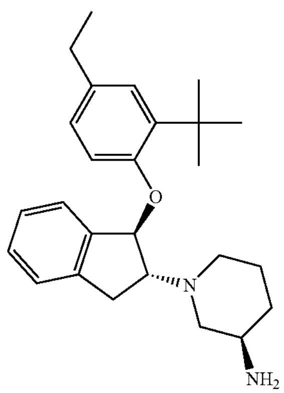 [SMILES: CCc1ccc(O[C@@H]2c3ccccc3C[C@H]2N2CCC[C@@H](N)C2)c(C(C)(C)C)c1] | A | 12 | 1.18 | 393.17 |
| 50 | 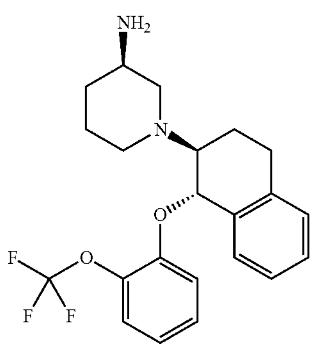 [SMILES: N[C@@H]1CCCN([C@H]2CCc3ccccc3[C@@H]2Oc2ccccc2OC(F)(F)F)C1] | A | 1 | 2.64 | 407.13 |
| 51 | 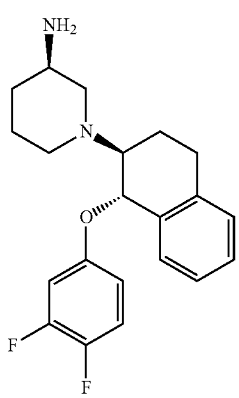 [SMILES: N[C@@H]1CCCN([C@H]2CCc3ccccc3[C@@H]2Oc2ccc(F)c(F)c2)C1] | A | 1 | 2.45 | 359.15 |

-continued

| Example | Structure | Synthetic method | LC method | Rt time [min] | MS [M + H+] ES+ |
|---|---|---|---|---|---|
| 52 | 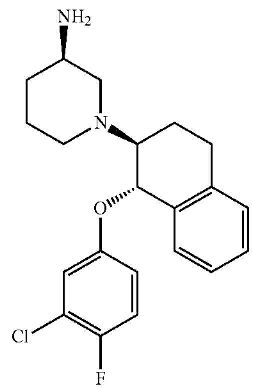 [SMILES: N[C@@H]1CCCN([C@H]2CCc3ccccc3[C@@H]2Oc2ccc(F)c(Cl)c2)C1] | A | 1 | 2.52 | 375.1 |
| 53 | 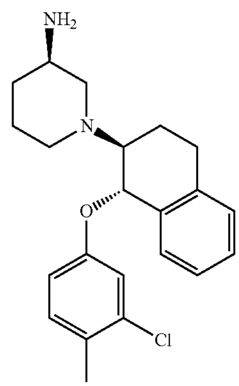 [SMILES: Cc1ccc(O[C@H]2c3ccccc3CC[C@@H]2N2CCC[C@@H](N)C2)cc1Cl] | A | 1 | 2.60 | 371.14 |
| 54 | 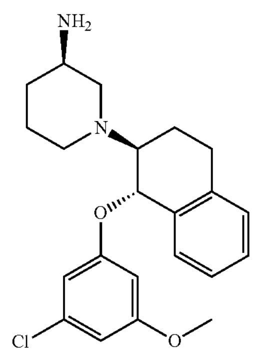 [SMILES: COc1cc(Cl)cc(O[C@H]2c3ccccc3CC[C@@H]2N2CCC[C@@H](N)C2)c1] | A | 1 | 2.40 | 387.15 |
| 55 | 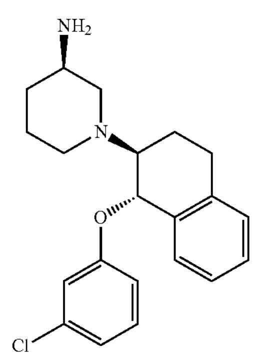 [SMILES: N[C@@H]1CCCN([C@H]2CCc3ccccc3[C@@H]2Oc2cccc(Cl)c2)C1] | A | 1 | 1.92 | 357.17 |

-continued

| Example | Structure | Synthetic method | LC method | Rt time [min] | MS [M + H+] ES+ |
|---|---|---|---|---|---|
| 56 | 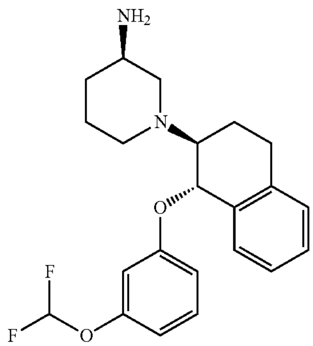 [SMILES: N[C@@H]1CCCN([C@H]2CCc3ccccc3[C@@H]2Oc2cccc(OC(F)F)c2)C1] | A | 1 | 2.50 | 389.1 |
| 57 | 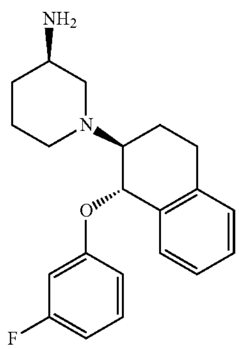 [SMILES: N[C@@H]1CCCN([C@H]2CCc3ccccc3[C@@H]2Oc2cccc(F)c2)C1] | A | 1 | 2.40 | 341.15 |
| 58 | 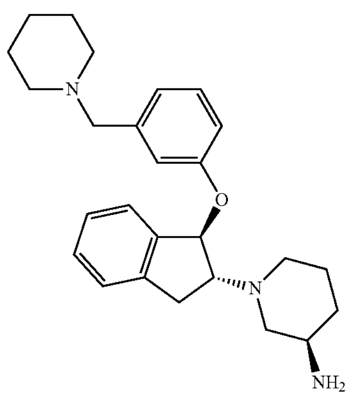 [SMILES: N[C@@H]1CCCN([C@@H]2Cc3ccccc3[C@H]2Oc2cccc(CN3CCCCC3)c2)C1] | A | 12 | 0.88 | 406.27 |
| 59 | 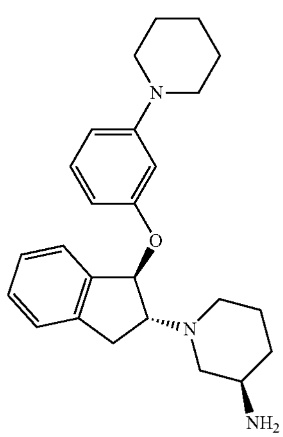 [SMILES: N[C@@H]1CCCN([C@@H]2Cc3ccccc3[C@H]2Oc2cccc(N3CCCCC3)c2)C1] | A | 12 | 1.38 | 392.30 |

| Example | Structure | Synthetic method | LC method | Rt time [min] | MS [M + H+] ES+ |
|---|---|---|---|---|---|
| 60 | 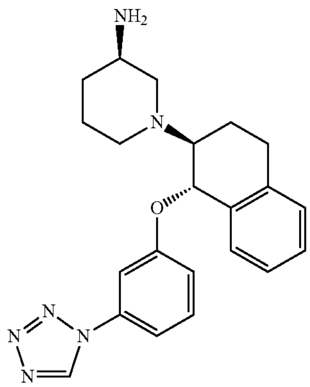 [SMILES: N[C@@H]1CCCN([C@H]2CCc3ccccc3[C@@H]2Oc2cccc(-n3cnnn3)c2)C1] | A | 1 | 2.29 | 391.17 |
| 61 | 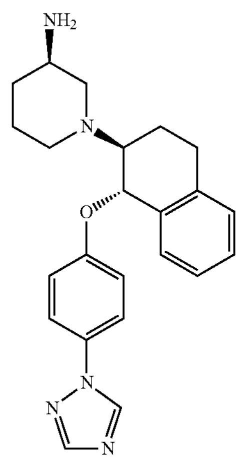 [SMILES: N[C@@H]1CCCN([C@H]2CCc3ccccc3[C@@H]2Oc2ccc(-n3cncn3)cc2)C1] | A | 1 | 2.20 | 390.17 |
| 62 | 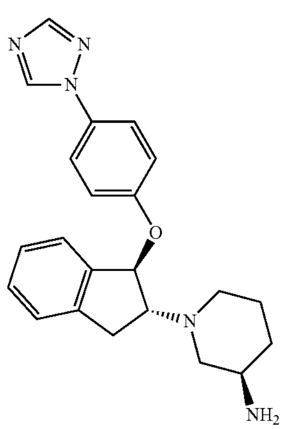 [SMILES: N[C@@H]1CCCN([C@@H]2Cc3ccccc3[C@H]2Oc2ccc(-n3cncn3)cc2)C1] | A | 12 | 1.00 | 376.20 |

-continued

| Example | Structure | Synthetic method | LC method | Rt time [min] | MS [M + H+] ES+ |
|---|---|---|---|---|---|
| 63 | 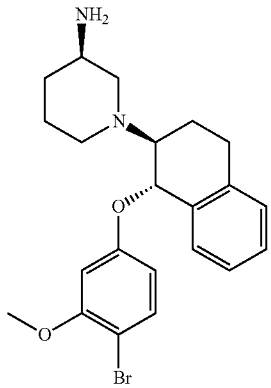 [SMILES: COc1cc(O[C@H]2c3ccccc3CC[C@@H]2N2CCC[C@@H](N)C2)ccc1Br] | A | 1 | 2.55 | 431.09 |
| 64 | 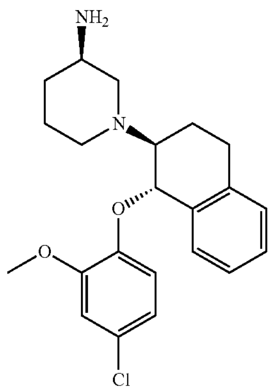 [SMILES: COc1cc(Cl)ccc1O[C@H]1c2ccccc2CC[C@@H]1N1CCC[C@@H](N)C1] | A | 1 | 2.54 | 387.13 |
| 65 | 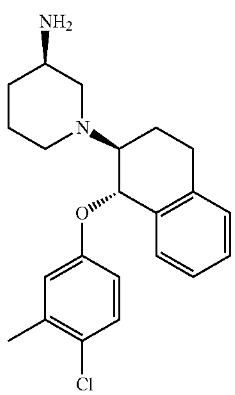 [SMILES: Cc1cc(O[C@H]2c3ccccc3CC[C@@H]2N2CCC[C@@H](N)C2)ccc1Cl] | A | 1 | 2.64 | 371.15 |
| 66 | 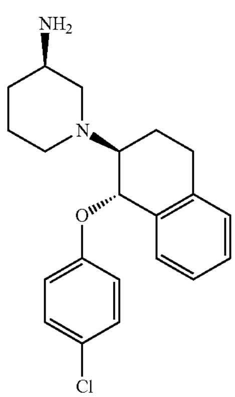 [SMILES: N[C@@H]1CCCN([C@H]2CCc3ccccc3[C@@H]2Oc2ccc(Cl)cc2)C1] | A | 1 | 2.48 | 357.13 |

-continued

| Example | Structure | Synthetic method | LC method | Rt time [min] | MS [M + H+] ES+ |
|---|---|---|---|---|---|
| 67 | 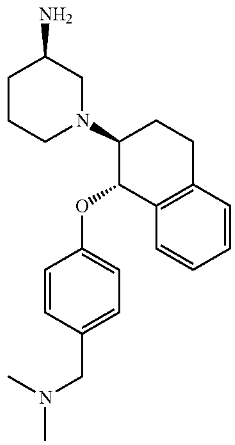 [SMILES: CN(C)Cc1ccc(O[C@H]2c3ccccc3CC[C@@H]2N2CCC[C@@H](N)C2)cc1] | A | 1 | 2.05 | 380.25 |
| 68 | 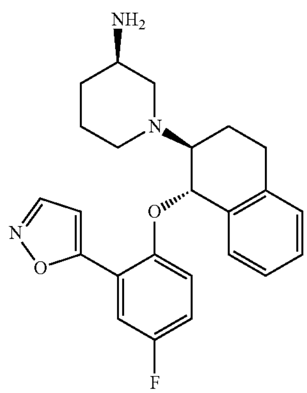 [SMILES: N[C@@H]1CCCN([C@H]2CCc3ccccc3[C@@H]2Oc2ccc(F)cc2-c2ccno2)C1] | A | 1 | 2.57 | 408.13 |
| 69 | 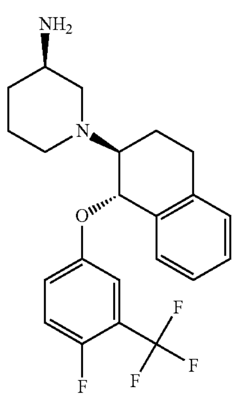 [SMILES: N[C@@H]1CCCN([C@H]2CCc3ccccc3[C@@H]2Oc2ccc(F)c(C(F)(F)F)c2)C1] | A | 1 | 2.64 | 409.11 |

-continued

| Example | Structure | Synthetic method | LC method | Rt time [min] | MS [M + H+] ES+ |
|---|---|---|---|---|---|
| 70 | 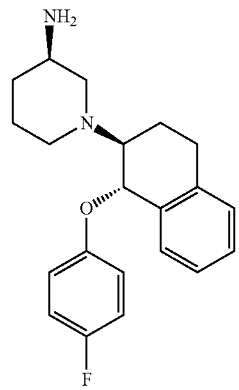 [SMILES: N[C@@H]1CCCN([C@H]2CCc3ccccc3[C@@H]2Oc2ccc(F)cc2)C1] | A | 1 | 2.37 | 341.12 |
| 71 | 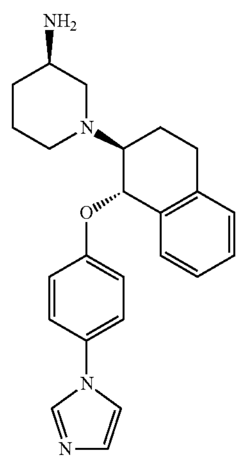 [SMILES: N[C@@H]1CCCN([C@H]2CCc3ccccc3[C@@H]2Oc2ccc(-n3ccnc3)cc2)C1] | A | 9 | 1.88 | 389.22 |
| 72 | 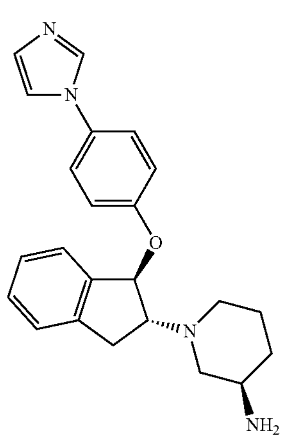 [SMILES: N[C@@H]1CCCN([C@@H]2Cc3ccccc3[C@H]2Oc2ccc(-n3ccnc3)cc2)C1] | A | 12 | 0.82 | 375.21 |

| Example | Structure | Synthetic method | LC method | Rt time [min] | MS [M + H+] ES+ |
|---------|-----------|------------------|-----------|---------------|-----------------|
| 73 | 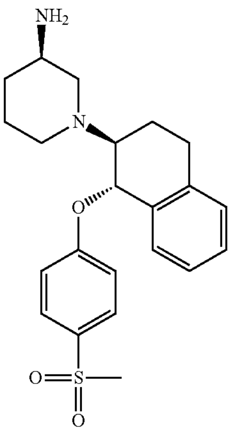 [SMILES: CS(=O)(=O)c1ccc(O[C@H]2c3ccccc3CC[C@@H]2N2CCC[C@@H](N)C2)cc1] | A | 1 | 2.22 | 401.13 |
| 74 | 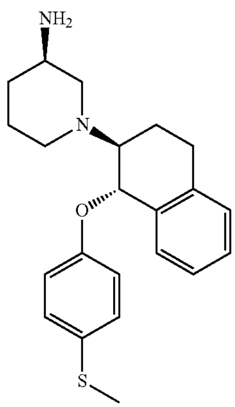 [SMILES: CSc1ccc(O[C@H]2c3ccccc3CC[C@@H]2N2CCC[C@@H](N)C2)cc1] | A | 1 | 2.47 | 369.15 |
| 75 | 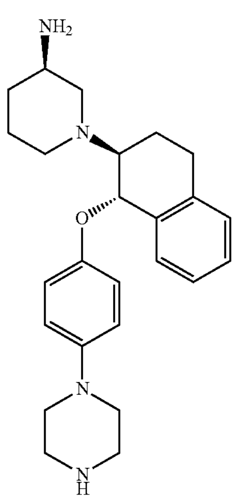 [SMILES: N[C@@H]1CCCN([C@H]2CCc3ccccc3[C@@H]2Oc2ccc(N3CCNCC3)cc2)C1] | A | 1 | 1.97 | 407.25 |

-continued

| Example | Structure | Synthetic method | LC method | Rt time [min] | MS [M + H+] ES+ |
|---|---|---|---|---|---|
| 76 | 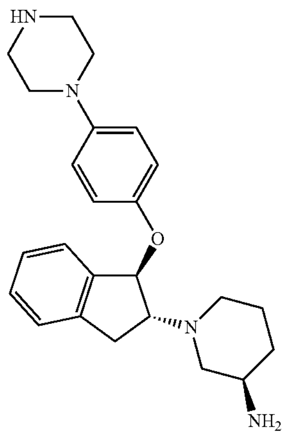 [SMILES: N[C@@H]1CCCN([C@@H]2Cc3ccccc3[C@H]2Oc2ccc(N3CCNCC3)cc2)C1] | A | 12 | 0.80 | 393.27 |
| 77 | 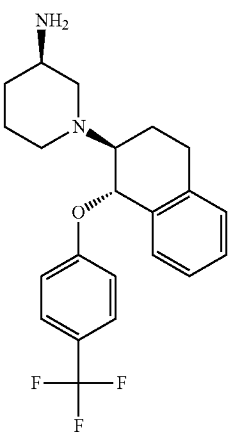 [SMILES: N[C@@H]1CCCN([C@H]2CCc3ccccc3[C@@H]2Oc2ccc(C(F)(F)F)cc2)C1] | A | 9 | 2.52 | 391.14 |
| 78 | 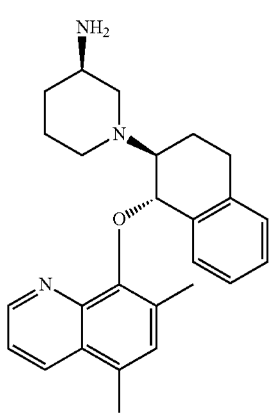 [SMILES: Cc1cc(C)c2cccnc2c1O[C@H]1c2ccccc2CC[C@@H]1N1CCC[C@@H](N)C1] | A | 1 | 2.47 | 402.17 |

| Example | Structure | Synthetic method | LC method | Rt time [min] | MS [M + H+] ES+ |
|---|---|---|---|---|---|
| 79 | 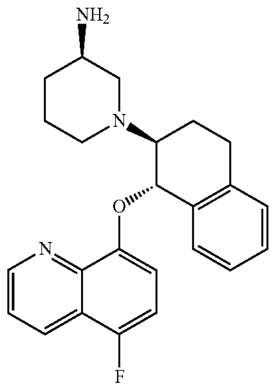 [SMILES: N[C@@H]1CCCN([C@H]2CCc3ccccc3[C@@H]2Oc2ccc(F)c3cccnc23)C1] | A | 1 | 2.40 | 392.14 |
| 80 | 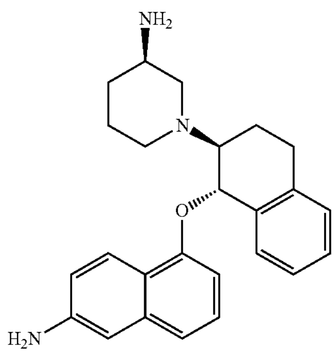 [SMILES: Nc1ccc2c(O[C@H]3c4ccccc4CC[C@@H]3N3CCC[C@@H](N)C3)cccc2c1] | A | 1 | 2.34 | 388.21 |
| 81 | 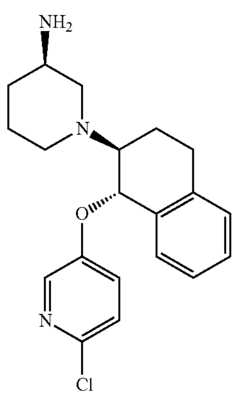 [SMILES: N[C@@H]1CCCN([C@H]2CCc3ccccc3[C@@H]2Oc2ccc(Cl)nc2)C1] | A | 1 | 2.57 | 358.14 |
| 82 | 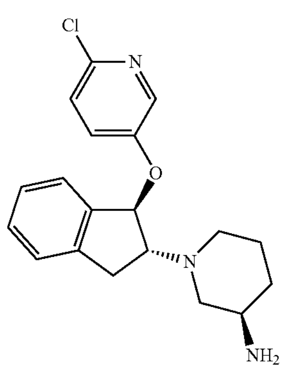 [SMILES: N[C@@H]1CCCN([C@@H]2Cc3ccccc3[C@H]2Oc2ccc(Cl)nc2)C1] | A | 12 | 1.05 | 344.16 |

-continued

| Example | Structure | Synthetic method | LC method | Rt time [min] | MS [M + H+] ES+ |
|---|---|---|---|---|---|
| 83 | 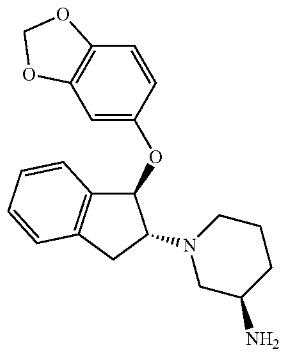 [SMILES: N[C@@H]1CCCN([C@@H]2Cc3ccccc3[C@H]2Oc2ccc3c(c2)OCO3)C1] | A | 12 | 1.08 | 353.20 |
| 84 | 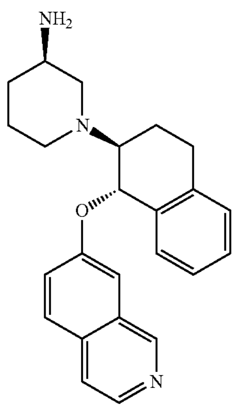 [SMILES: N[C@@H]1CCCN([C@H]2CCc3ccccc3[C@@H]2Oc2ccc3ccncc3c2)C1] | A | 1 | 2.02 | 374.18 |
| 85 | 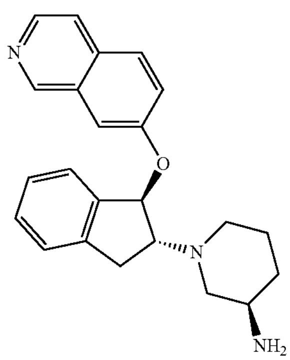 [SMILES: N[C@@H]1CCCN([C@@H]2Cc3ccccc3[C@H]2Oc2ccc3ccncc3c2)C1] | A | 12 | 0.85 | 360.23 |
| 86 | 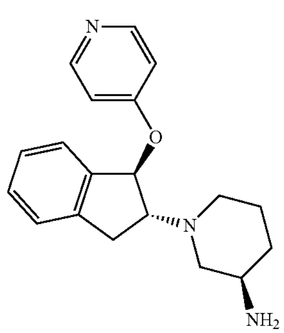 [SMILES: N[C@@H]1CCCN([C@@H]2Cc3ccccc3[C@H]2Oc2ccncc2)C1] | A | 12 | 0.66 | 619.42 2M + H |

-continued

| Example | Structure | Synthetic method | LC method | Rt time [min] | MS [M + H+] ES+ |
|---|---|---|---|---|---|
| 87 | 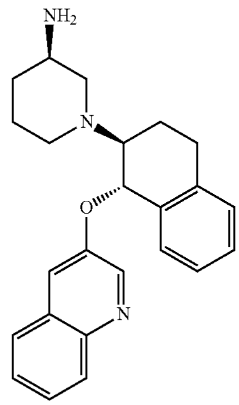 [SMILES: N[C@@H]1CCCN([C@H]2CCc3ccccc3[C@@H]2Oc2cnc3ccccc3c2)C1] | A | 9 | 2.16 | 374.21 |
| 88 | 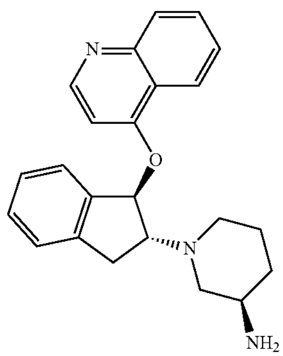 [SMILES: N[C@@H]1CCCN([C@@H]2Cc3ccccc3[C@H]2Oc2ccnc3ccccc23)C1] | A | 12 | 1.00 | 360.23 |
| 89 | 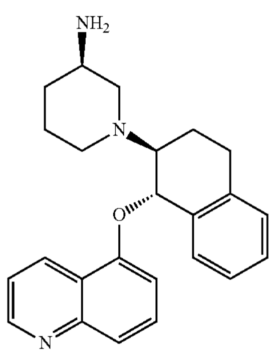 [SMILES: N[C@@H]1CCCN([C@H]2CCc3ccccc3[C@@H]2Oc2cccc3ncccc23)C1] | A | 9 | 1.93 | 374.22 |
| 90 | 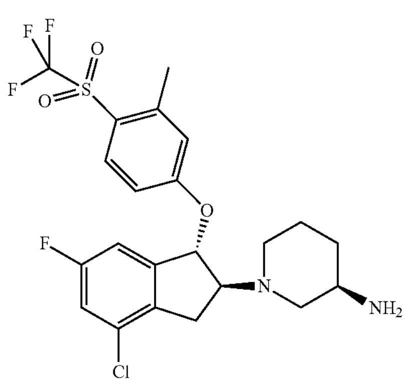 [SMILES: Cc1cc(O[C@H]2c3cc(F)cc(Cl)c3C[C@@H]2N2CCC[C@@H](N)C2)ccc1S(=O)(=O)C(F)(F)F] | A | 1 | 2.99 | 507.1 |

-continued

| Example | Structure | Synthetic method | LC method | Rt time [min] | MS [M + H+] ES+ |
|---|---|---|---|---|---|
| 91 | 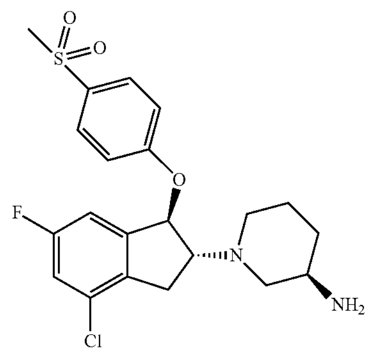 [SMILES: CS(=O)(=O)c1ccc(O[C@@H]2c3cc(F)cc(Cl)c3C[C@H]2N2CCC[C@@H](N)C2)cc1] | A | 14 | 1.76 | 439.1 |
| 92 | 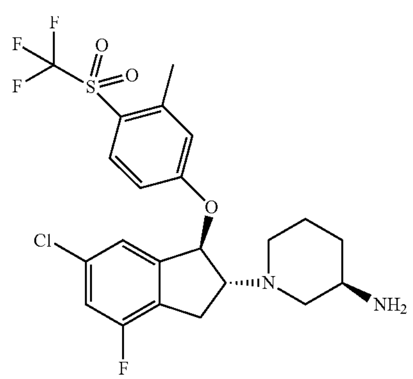 [SMILES: Cc1cc(O[C@@H]2c3cc(Cl)cc(F)c3C[C@H]2N2CCC[C@@H](N)C2)ccc1S(=O)(=O)C(F)(F)F] | A | 14 | 2.19 | 507.07 |
| 93 | 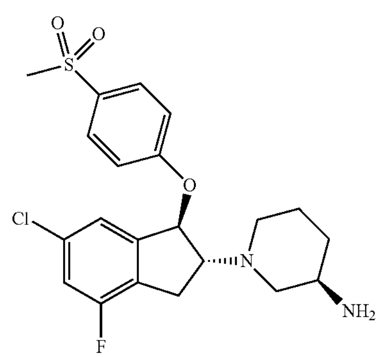 [SMILES: CS(=O)(=O)c1ccc(O[C@@H]2c3cc(Cl)cc(F)c3C[C@H]2N2CCC[C@@H](N)C2)cc1] | A | 1 | 2.45 | 439.14 |
| 94 | 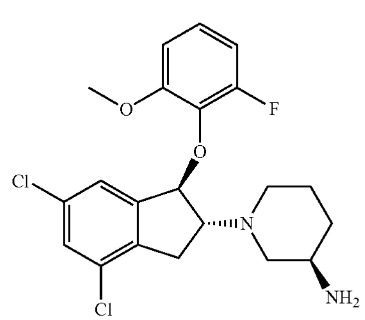 [SMILES: COc1cccc(F)c1O[C@@H]1c2cc(Cl)cc(Cl)c2C[C@H]1N1CCC[C@@H](N)C1] | A | 4 | 1.27 | 425.19 |

-continued

| Example | Structure | Synthetic method | LC method | Rt time [min] | MS [M + H+] ES+ |
|---|---|---|---|---|---|
| 95 | 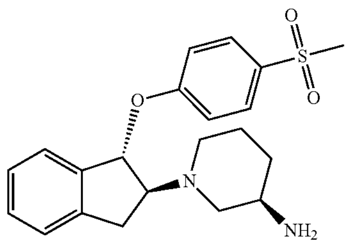 [SMILES: CS(=O)(=O)c1ccc(O[C@H]2c3ccccc3C[C@@H]2N2CCC[C@@H](N)C2)cc1] | A | 4 | 0.95 | 387.2 |
| 96 | 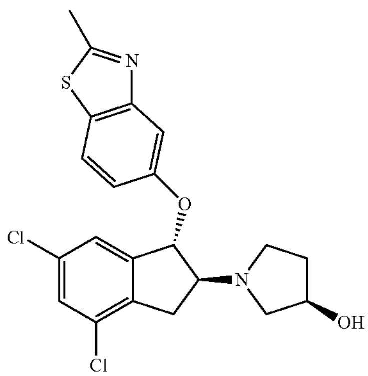 [SMILES: Cc1nc2cc(O[C@H]3c4cc(Cl)cc(Cl)c4C[C@@H]3N3CC[C@@H](O)C3)ccc2s1] | A | 1 | 2.84 | 434.99 |
| 97 | 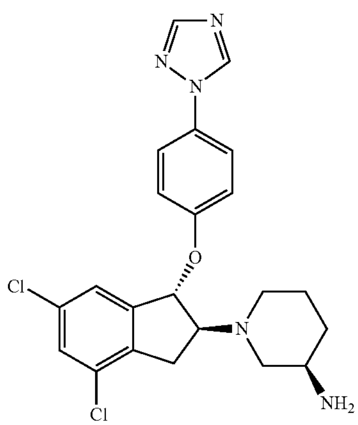 [SMILES: N[C@@H]1CCCN([C@H]2Cc3c(Cl)cc(Cl)cc3[C@@H]2Oc2ccc(-n3cncn3)cc2)C1] | A | 4 | 1.20 | 444.16 |
| 98 | 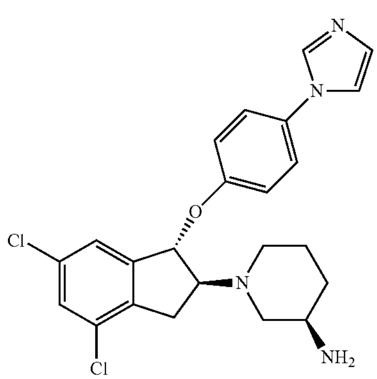 [SMILES: N[C@@H]1CCCN([C@H]2Cc3c(Cl)cc(Cl)cc3[C@@H]2Oc2ccc(-n3ccnc3)cc2)C1] | A | 4 | 1.04 | 443.17 |

-continued

| Example | Structure | Synthetic method | LC method | Rt time [min] | MS [M + H+] ES+ |
|---|---|---|---|---|---|
| 99 | 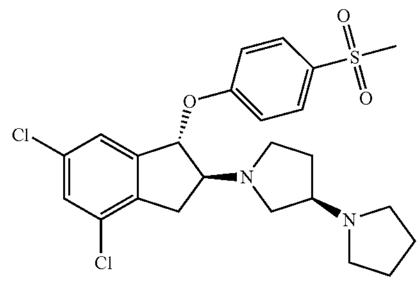 [SMILES: CS(=O)(=O)c1ccc(O[C@H]2c3cc(Cl)cc(Cl)c3C[C@@H]2N2CC[C@@H](N3CCCC3)C2)cc1] | A | 14 | 1.93 | 495.14 |
| 100 | 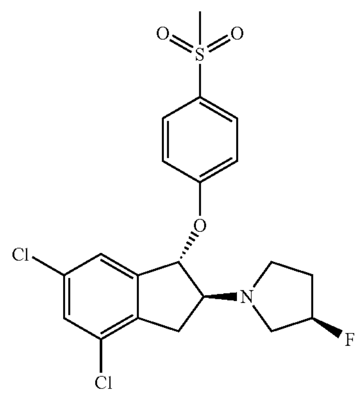 | A | 1 | 2.74 | 485.15 M + H + CH3CN |
| 101 | 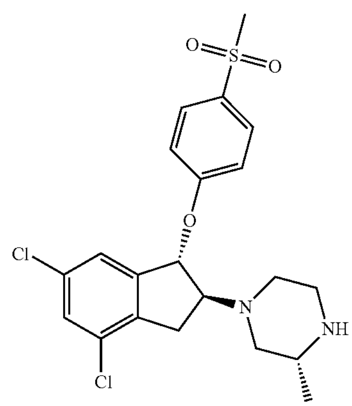 [SMILES: C[C@@H]1CN([C@H]2Cc3c(Cl)cc(Cl)cc3[C@@H]2Oc2ccc(S(C)(=O)=O)cc2)CCN1] | A | 9 | 2.70 | 455.06 |
| 102 | 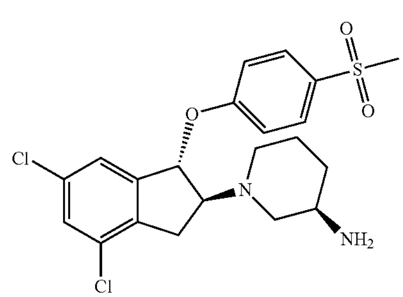 [SMILES: CS(=O)(=O)c1ccc(O[C@H]2c3cc(Cl)cc(Cl)c3C[C@@H]2N2CCC[C@@H](N)C2)cc1] | A | 4 | 1.22 | 455.09 |

-continued

| Example | Structure | Synthetic method | LC method | Rt time [min] | MS [M + H+] ES+ |
|---|---|---|---|---|---|
| 103 | 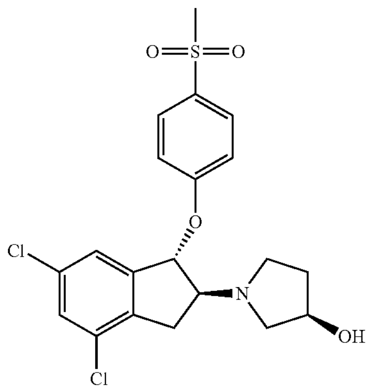 [SMILES: CS(=O)(=O)c1ccc(O[C@H]2c3cc(Cl)cc(Cl)c3C[C@@H]2N2CC[C@@H](O)C2)cc1] | A | 4 | 1.24 | 442.21 |
| 104 | 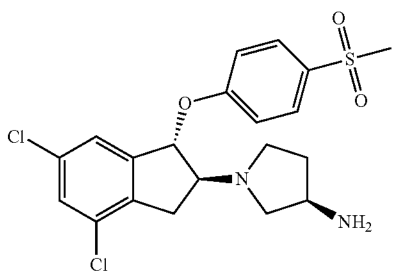 [SMILES: CS(=O)(=O)c1ccc(O[C@H]2c3cc(Cl)cc(Cl)c3C[C@@H]2N2CC[C@@H](N)C2)cc1] | A | 14 | 1.78 | 441.21 |
| 105 | 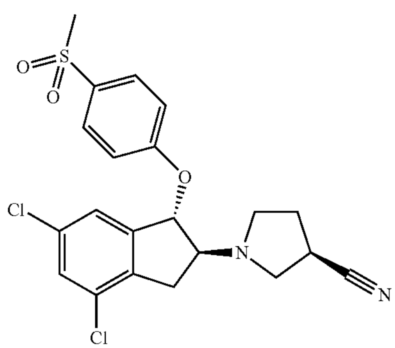 | A | 1 | 2.89 | 492.14 M + H + CH3CN |
| 106 | 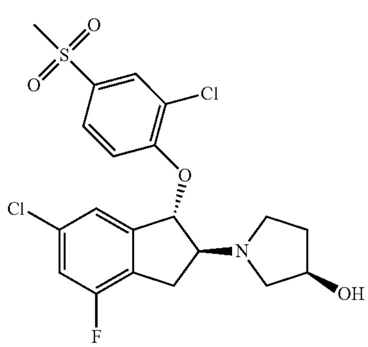 [SMILES: CS(=O)(=O)c1ccc(O[C@H]2c3cc(Cl)cc(F)c3C[C@@H]2N2CC[C@@H](O)C2)c(Cl)c1] | A | 9 | 2.62 | 459.98 |

-continued

| Example | Structure | Synthetic method | LC method | Rt time [min] | MS [M + H+] ES+ |
|---|---|---|---|---|---|
| 107 | 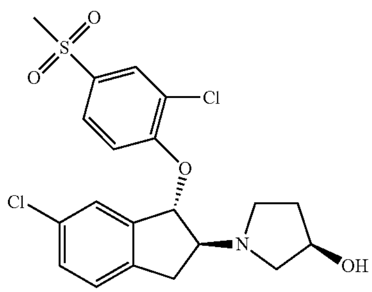 [SMILES: CS(=O)(=O)c1ccc(O[C@H]2c3cc(Cl)ccc3C[C@@H]2N2CC[C@@H](O)C2)c(Cl)c1] | A | 9 | 2.49 | 442.14 |
| 108 | 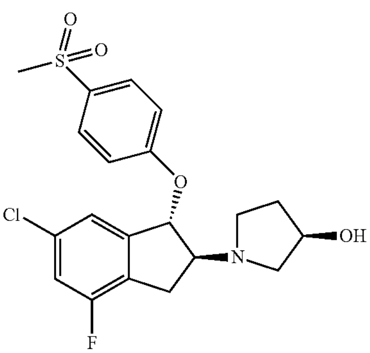 [SMILES: CS(=O)(=O)c1ccc(O[C@H]2c3cc(Cl)cc(F)c3C[C@@H]2N2CC[C@@H](O)C2)cc1] | A | 1 | 2.54 | 426.05 |
| 109 | 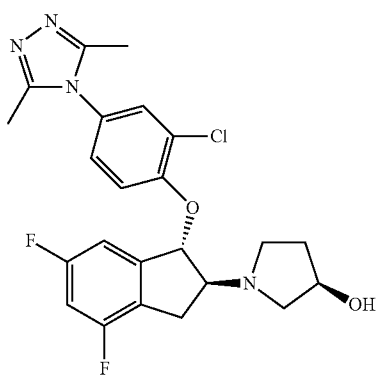 | A | 9 | 2.20 | 461.13 |
| 110 | 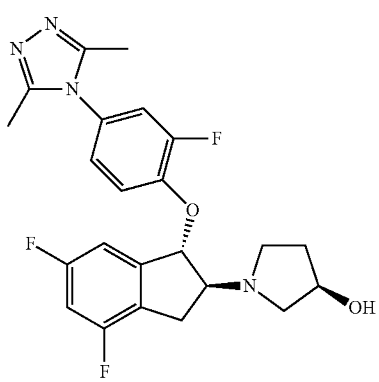 [SMILES: Cc1nnc(C)n1-c1ccc(O[C@H]2c3cc(F)cc(F)c3C[C@@H]2N2CC[C@@H](O)C2)c(F)c1] | A | 9 | 2.16 | 445.17 |

-continued

| Example | Structure | Synthetic method | LC method | Rt time [min] | MS [M + H+] ES+ |
|---|---|---|---|---|---|
| 111 | 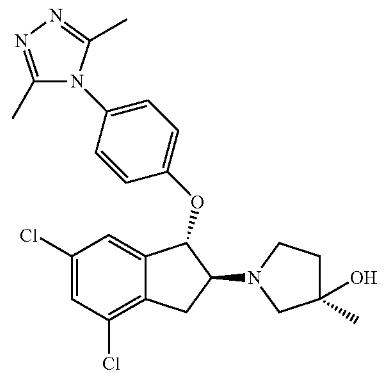 | A | 9 | 2.40 | 473.13 |
| 112 | 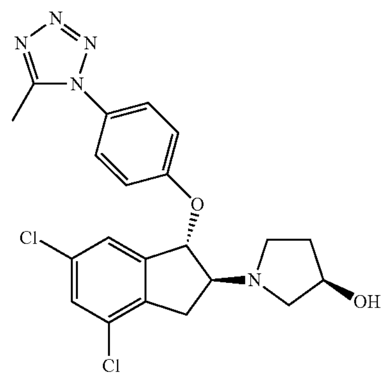 [SMILES: Cc1nnnn1-c1ccc(O[C@H]2c3cc(Cl)cc(Cl)c3C[C@@H]2N2CC[C@@H](O)C2)cc1] | A | 9 | 2.68 | 446.16 |
| 113 | 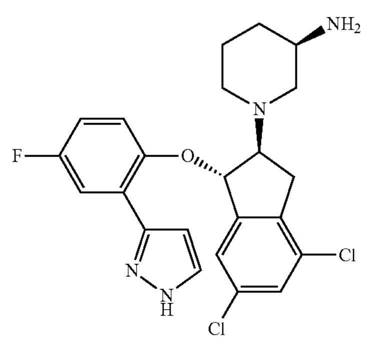 [SMILES: N[C@@H]1CCCN([C@H]2Cc3c(Cl)cc(Cl)cc3[C@@H]2Oc2ccc(F)cc2-c2cc[nH]n2)C1] | A | 1 | 2.65 | 461.16 |
| 114 | 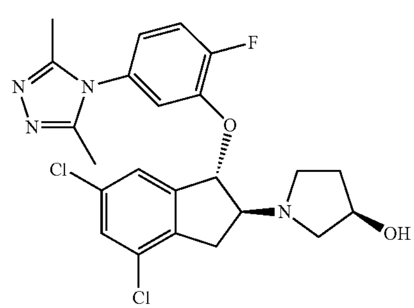 [SMILES: Cc1nnc(C)n1-c1ccc(F)c(O[C@H]2c3cc(Cl)cc(Cl)c3C[C@@H]2N2CC[C@@H](O)C2)c1] | A | 9 | 2.42 | 477.07 |

-continued

| Example | Structure | Synthetic method | LC method | Rt time [min] | MS [M + H+] ES+ |
|---------|-----------|------------------|-----------|---------------|------------------|
| 115 | 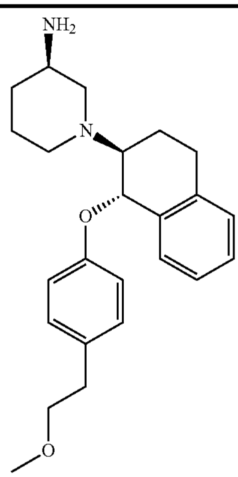 | A | 1 | 2.39 | 381.19 |
| 116 | 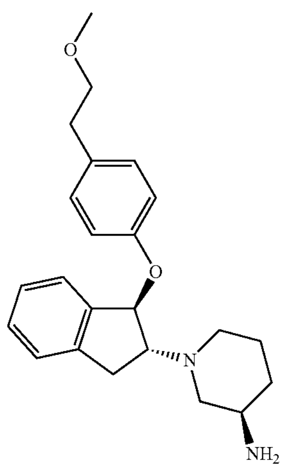 [SMILES: COCCc1ccc(O[C@@H]2c3ccccc3C[C@H]2N2CCC[C@@H](N)C2)cc1] | A | 12 | 1.15 | 367.23 |
| 117 | 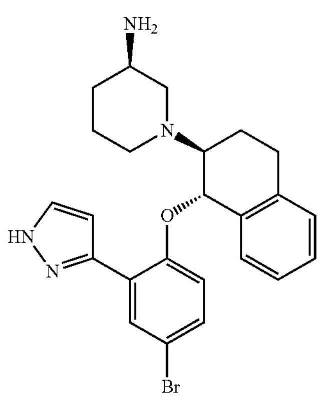 [SMILES: N[C@@H]1CCCN([C@H]2CCc3ccccc3[C@@H]2Oc2ccc(Br)cc2-c2cc[nH]n2)C1] | A | 1 | 2.54 | 469.11 M + H{Hal} |

-continued

| Example | Structure | Synthetic method | LC method | Rt time [min] | MS [M + H+] ES+ |
|---|---|---|---|---|---|
| 118 | 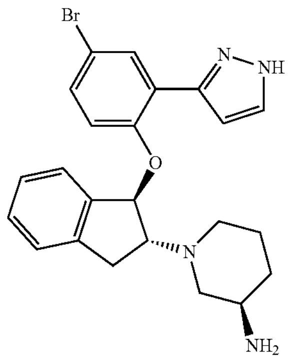 [SMILES: N[C@@H]1CCCN([C@@H]2Cc3ccccc3[C@H]2Oc2ccc(Br)cc2-c2cc[nH]n2)C1] | A | 12 | 1.32 | 453.10 |
| 119 | 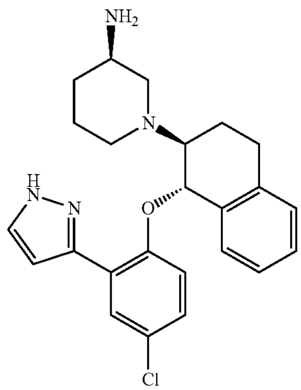 [SMILES: N[C@@H]1CCCN([C@H]2CCc3ccccc3[C@@H]2Oc2ccc(Cl)cc2-c2cc[nH]n2)C1] | A | 1 | 2.82 | 423.12 |
| 120 | 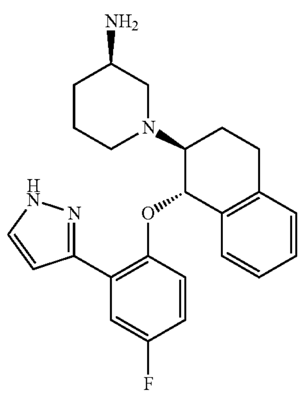 [SMILES: N[C@@H]1CCCN([C@H]2CCc3ccccc3[C@@H]2Oc2ccc(F)cc2-c2cc[nH]n2)C1] | A | 1 | 2.42 | 407.17 |
| 121 | 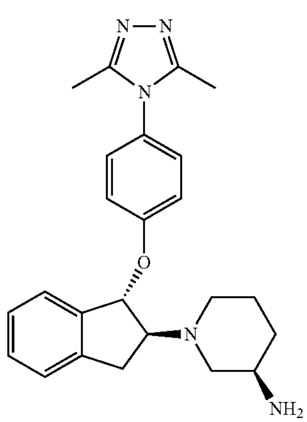 [SMILES: Cc1nnc(C)n1-c1ccc(O[C@H]2c3ccccc3C[C@@H]2N2CCC[C@@H](N)C2)cc1] | A | 14 | 1.42 | 404.26 |

-continued

| Example | Structure | Synthetic method | LC method | Rt time [min] | MS [M + H+] ES+ |
|---------|-----------|------------------|-----------|---------------|-----------------|
| 122 | 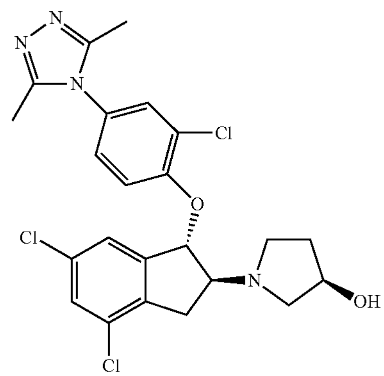 [SMILES: Cc1nnc(C)n1-c1ccc(O[C@H]2c3cc(Cl)cc(Cl)c3C[C@@H]2N2CC[C@@H](O)C2)c(Cl)c1] | A | 9 | 2.28 | 493.01 |
| 123 | 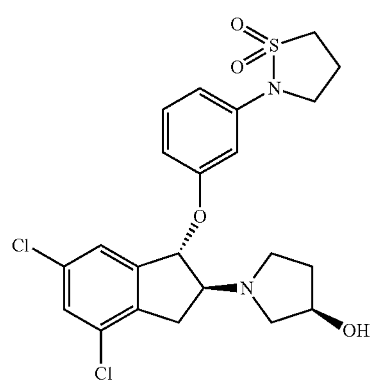 [SMILES: O=S1(=O)CCCN1c1cccc(O[C@H]2c3cc(Cl)cc(Cl)c3C[C@@H]2N2CC[C@@H](O)C2)c1] | A | 1 | 2.75 | 483.17 |
| 124 | 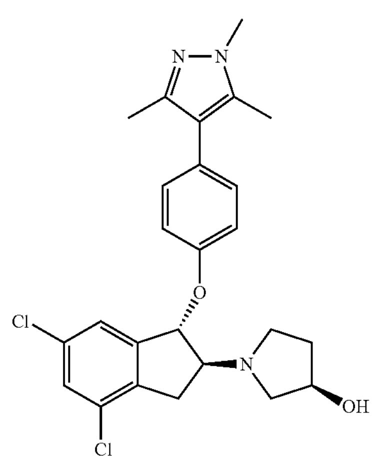 [SMILES: Cc1nn(C)c(C)c1-c1ccc(O[C@H]2c3cc(Cl)cc(Cl)c3C[C@@H]2N2CC[C@@H](O)C2)cc1] | A | 9 | 2.50 | 472.08 |

-continued

| Example | Structure | Synthetic method | LC method | Rt time [min] | MS [M + H+] ES+ |
|---|---|---|---|---|---|
| 125 | 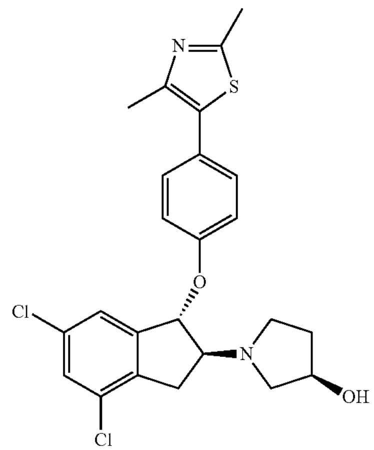 [SMILES: Cc1nc(C)c(-c2ccc(O[C@H]3c4cc(Cl)cc(Cl)c4C[C@@H]3N3CC[C@@H](O)C3)cc2)s1] | A | 9 | 2.62 | 475.02 |
| 126 | 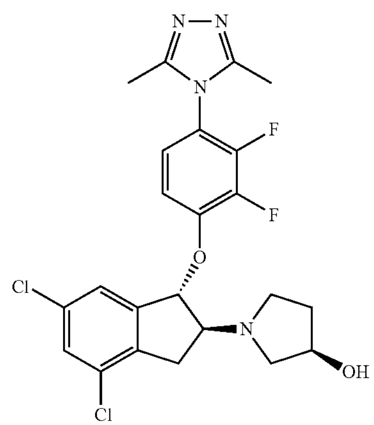 [SMILES: Cc1nnc(C)n1-c1ccc(O[C@H]2c3cc(Cl)cc(Cl)c3C[C@@H]2N2CC[C@@H](O)C2)c(F)c1F] | A | 9 | 2.42 | 495.04 |
| 127 | 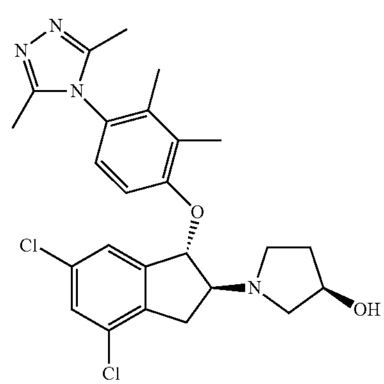 [SMILES: Cc1c(O[C@H]2c3cc(Cl)cc(Cl)c3C[C@@H]2N2CC[C@@H](O)C2)ccc(-n2c(C)nnc2C)c1C] | A | 1 | 2.48 | 487.19 |

-continued

| Example | Structure | Synthetic method | LC method | Rt time [min] | MS [M + H+] ES+ |
|---|---|---|---|---|---|
| 128 | 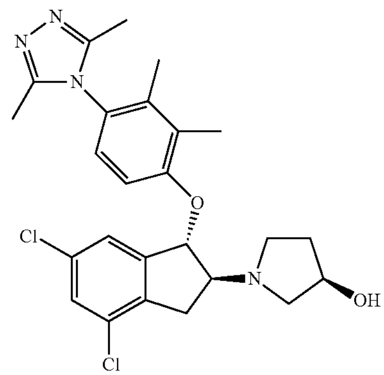 [SMILES: Cc1c(O[C@H]2c3cc(Cl)cc(Cl)c3C[C@@H]2N2CC[C@@H](O)C2)ccc(-n2c(C)nnc2C)c1C] | A | 9 | 2.41 | 487.14 |
| 130 | 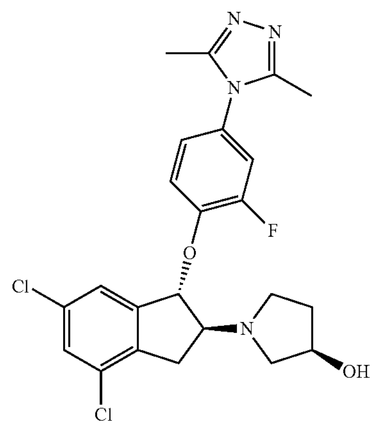 [SMILES: Cc1nnc(C)n1-c1ccc(O[C@H]2c3cc(Cl)cc(Cl)c3C[C@@H]2N2CC[C@@H](O)C2)c(F)c1] | A | 9 | 2.27 | 477.25 |
| 131 | 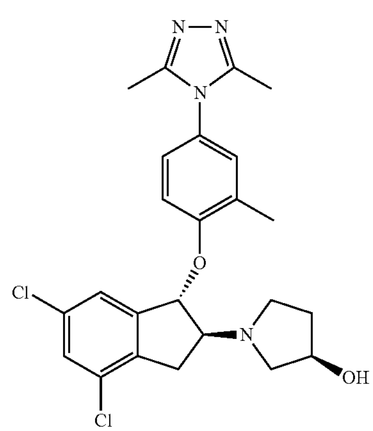 [SMILES: Cc1cc(-n2c(C)nnc2C)ccc1O[C@H]1c2cc(Cl)cc(Cl)c2C[C@@H]1N1CC[C@@H](O)C1] | A | 9 | 2.41 | 473.12 |

-continued

| Example | Structure | Synthetic method | LC method | Rt time [min] | MS [M + H+] ES+ |
|---|---|---|---|---|---|
| 132 | 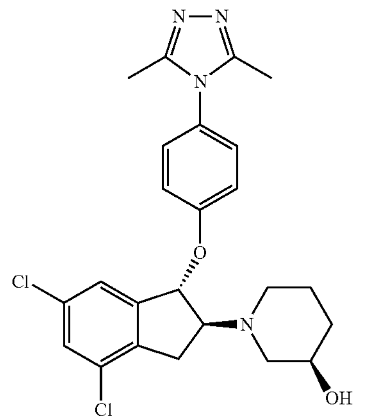 [SMILES: Cc1nnc(C)n1-c1ccc(O[C@H]2c3cc(Cl)cc(Cl)c3C[C@@H]2N2CCC[C@@H](O)C2)cc1] | A | 1 | 2.40 | 473.09 |
| 133 | 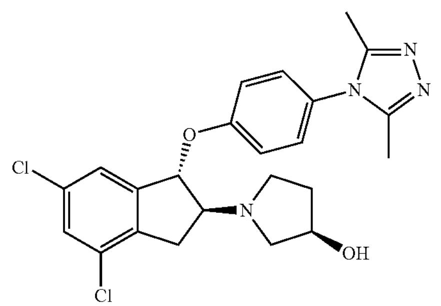 [SMILES: Cc1nnc(C)n1-c1ccc(O[C@H]2c3cc(Cl)cc(Cl)c3C[C@@H]2N2CC[C@@H](O)C2)cc1] | A | 9 | 2.22 | 459.25 |
| 134 | 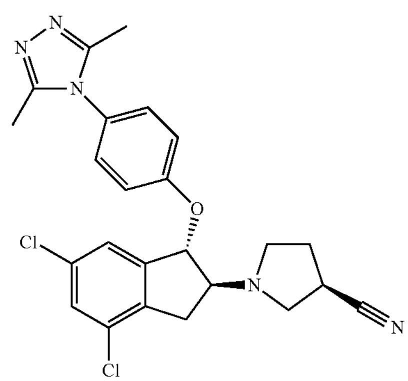 [SMILES: Cc1nnc(C)n1-c1ccc(O[C@H]2c3cc(Cl)cc(Cl)c3C[C@@H]2N2CC[C@@H](C#N)C2)cc1] | A | 1 | 2.59 | 468.18 |
| 135 | 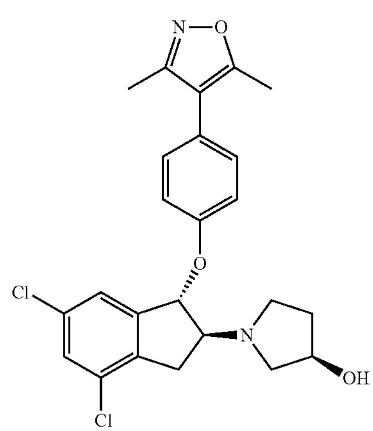 [SMILES: Cc1noc(C)c1-c1ccc(O[C@H]2c3cc(Cl)cc(Cl)c3C[C@@H]2N2CC[C@@H](O)C2)cc1] | A | 9 | 2.83 | 459.1 |

-continued

| Example | Structure | Synthetic method | LC method | Rt time [min] | MS [M + H+] ES+ |
|---------|-----------|------------------|-----------|---------------|-----------------|
| 136 | 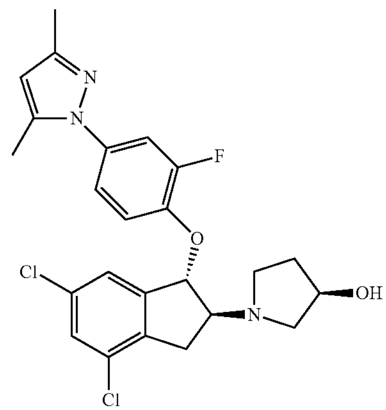 [SMILES: Cc1cc(C)n(-c2ccc(O[C@H]3c4cc(Cl)cc(Cl)c4C[C@@H]3N3CC[C@@H](O)C3)c(F)c2)n1] | A | 1 | 2.90 | 476.09 |
| 137 | 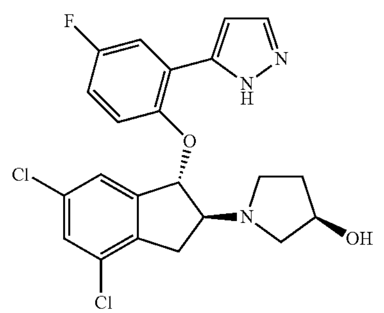 [SMILES: O[C@@H]1CCN([C@H]2Cc3c(Cl)cc(Cl)cc3[C@@H]2Oc2ccc(F)cc2-c2ccn[nH]2)C1] | A | 1 | 2.77 | 448.16 |
| 138 | 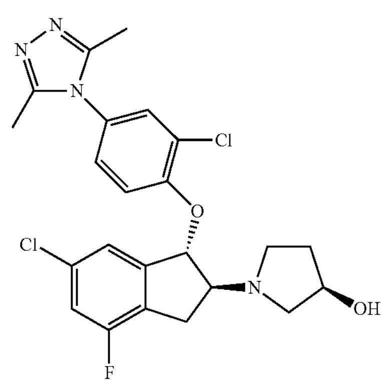 [SMILES: Cc1nnc(C)n1-c1ccc(O[C@H]2c3cc(Cl)cc(F)c3C[C@@H]2N2CC[C@@H](O)C2)c(Cl)c1] | A | 8 | 2.91 | 477.16 |
| 139 | 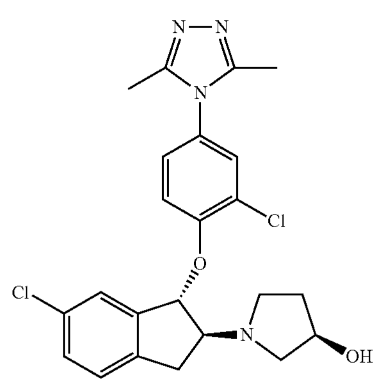 [SMILES: Cc1nnc(C)n1-c1ccc(O[C@H]2c3cc(Cl)ccc3C[C@@H]2N2CC[C@@H](O)C2)c(Cl)c1] | A | 1 | 2.39 | 459.08 |

-continued

| Example | Structure | Synthetic method | LC method | Rt time [min] | MS [M + H+] ES+ |
|---------|-----------|------------------|-----------|---------------|-----------------|
| 140 | 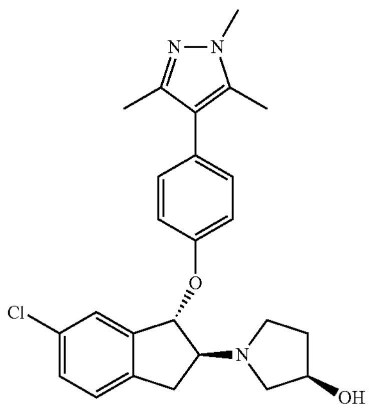 [SMILES: Cc1nn(C)c(C)c1-c1ccc(O[C@H]2c3cc(Cl)ccc3C[C@@H]2N2CC[C@@H](O)C2)cc1] | A | 1 | 2.55 | 438.21 |
| 141 | 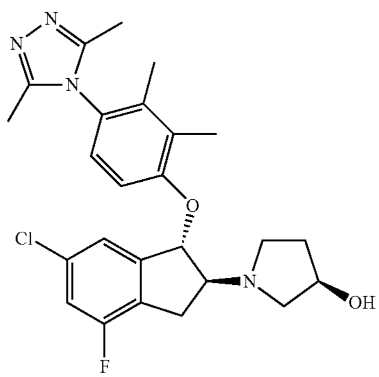 | A | 1 | 2.40 | 471.28 |
| 142 | 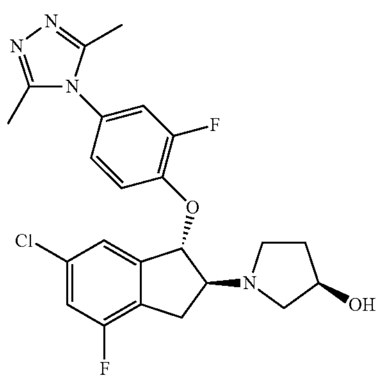 [SMILES: Cc1nnc(C)n1-c1ccc(O[C@H]2c3cc(Cl)cc(F)c3C[C@@H]2N2CC[C@@H](O)C2)c(F)c1] | A | 1 | 2.32 | 461.15 |
| 143 | 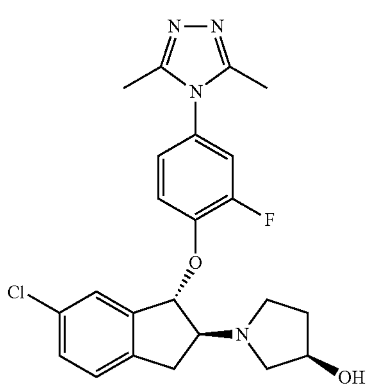 [SMILES: Cc1nnc(C)n1-c1ccc(O[C@H]2c3cc(Cl)ccc3C[C@@H]2N2CC[C@@H](O)C2)c(F)c1] | A | 9 | 2.11 | 443.13 |

-continued

| Example | Structure | Synthetic method | LC method | Rt time [min] | MS [M + H+] ES+ |
|---|---|---|---|---|---|
| 144 | 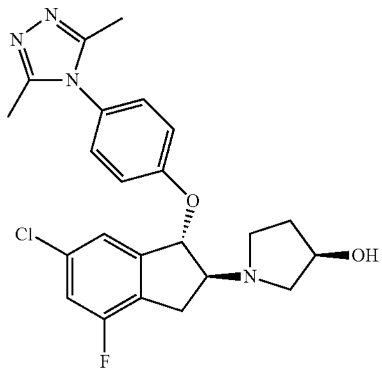 [SMILES: Cc1nnc(C)n1-c1ccc(O[C@H]2c3cc(Cl)cc(F)c3C[C@@H]2N2CC[C@@H](O)C2)cc1] | A | 1 | 2.34 | 443.13 |
| 145 | 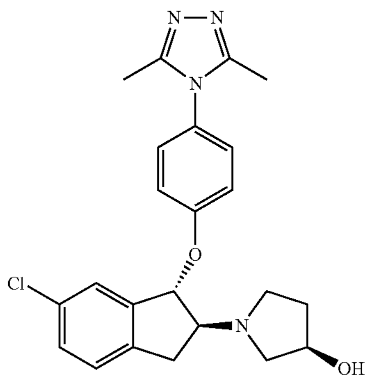 [SMILES: Cc1nnc(C)n1-c1ccc(O[C@H]2c3cc(Cl)ccc3C[C@@H]2N2CC[C@@H](O)C2)cc1] | A | 9 | 2.11 | 425.13 |
| 146 | 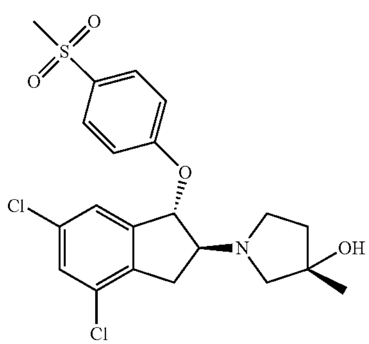 [SMILES: C[C@]1(O)CCN([C@H]2Cc3c(Cl)cc(Cl)cc3[C@@H]2Oc2ccc(S(C)(=O)=O)cc2)C1] | A | 9 | 2.87 | 456.03 |
| 147 | 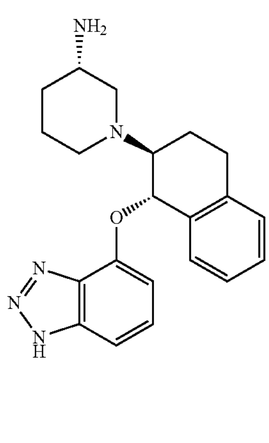 [SMILES: N[C@H]1CCCN([C@H]2CCc3ccccc3[C@@H]2Oc2cccc3[nH]nnc23)C1] | A | 1 | 2.39 | 364.16 |

-continued

| Example | Structure | Synthetic method | LC method | Rt time [min] | MS [M + H+] ES+ |
|---|---|---|---|---|---|
| 148 | 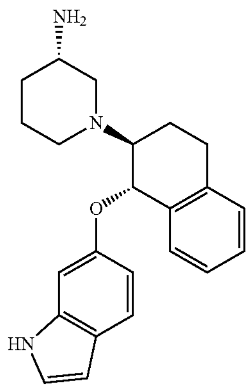 [SMILES: N[C@H]1CCCN([C@H]2CCc3ccccc3[C@@H]2Oc2ccc3cc[nH]c3c2)C1] | A | 1 | 2.34 | 362.18 |
| 149 | 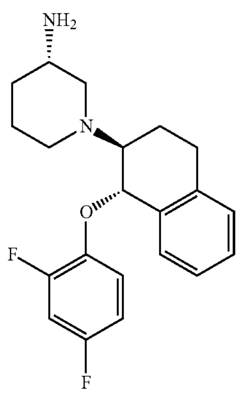 [SMILES: N[C@H]1CCCN([C@H]2CCc3ccccc3[C@@H]2Oc2ccc(F)cc2F)C1] | A | 1 | 2.43 | 359.13 |
| 150 | 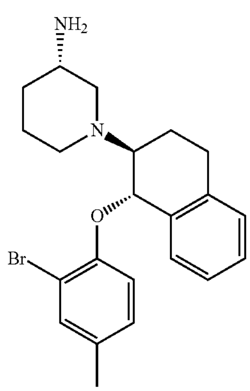 [SMILES: Cc1ccc(O[C@H]2c3ccccc3CC[C@@H]2N2CCC[C@H](N)C2)c(Br)c1] | A | 1 | 3.00 | 417.09 M + H{Hal} |
| 151 | 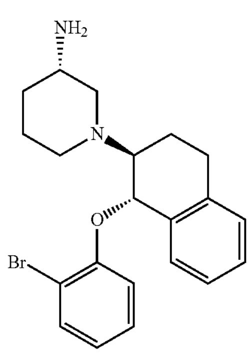 [SMILES: N[C@H]1CCCN([C@H]2CCc3ccccc3[C@@H]2Oc2ccccc2Br)C1] | A | 1 | 2.48 | 401.07 |

-continued
| Example | Structure | Synthetic method | LC method | Rt time [min] | MS [M + H+] ES+ |
|---|---|---|---|---|---|
| 152 | 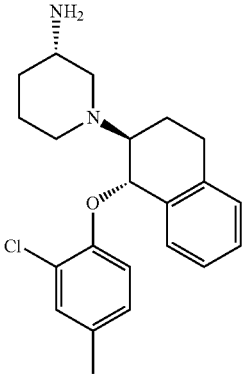 [SMILES: Cc1ccc(O[C@H]2c3ccccc3CC[C@@H]2N2CCC[C@H](N)C2)c(Cl)c1] | A | 1 | 2.57 | 371.14 |
| 153 | 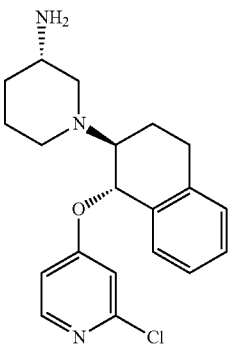 [SMILES: N[C@H]1CCCN([C@H]2CCc3ccccc3[C@@H]2Oc2ccnc(Cl)c2)C1] | A | 1 | 2.27 | 358.13 |
| 154 | 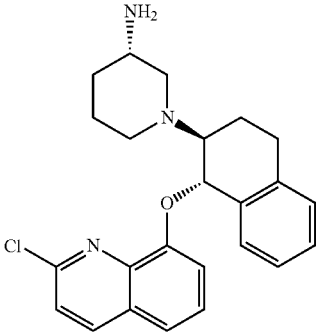 [SMILES: N[C@H]1CCCN([C@H]2CCc3ccccc3[C@@H]2Oc2cccc3ccc(Cl)nc23)C1] | A | 1 | 2.42 | 408.12 |
| 155 | 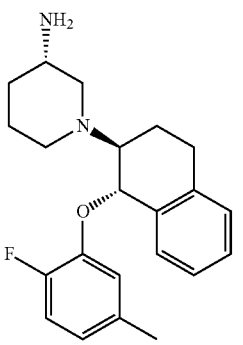 [SMILES: Cc1ccc(F)c(O[C@H]2c3ccccc3CC[C@@H]2N2CCC[C@H](N)C2)c1] | A | 1 | 2.50 | 355.17 |

-continued

| Example | Structure | Synthetic method | LC method | Rt time [min] | MS [M + H+] ES+ |
|---------|-----------|------------------|-----------|---------------|-----------------|
| 156 | 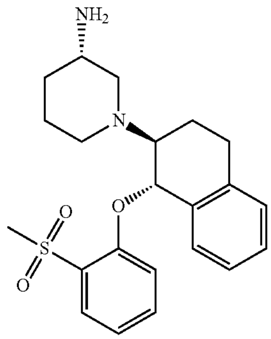 [SMILES: CS(=O)(=O)c1ccccc1O[C@H]1c2ccccc2CC[C@@H]1N1CCC[C@H](N)C1] | A | 9 | 2.12 | 401.13 |
| 157 | 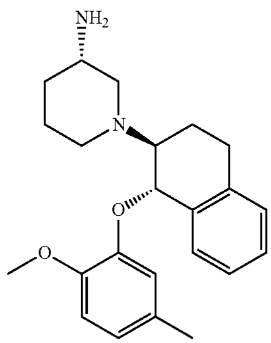 [SMILES: COc1ccc(C)cc1O[C@H]1c2ccccc2CC[C@@H]1N1CCC[C@H](N)C1] | A | 3 | 1.32 | 367.47 |
| 158 | 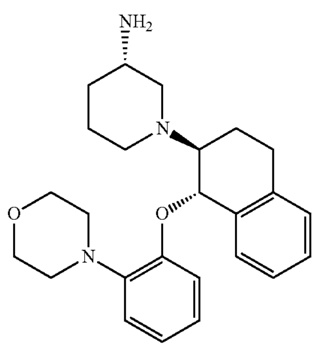 [SMILES: N[C@H]1CCCN([C@H]2CCc3ccccc3[C@@H]2Oc2ccccc2N2CCOCC2)C1] | A | 1 | 2.35 | 408.22 |
| 159 | 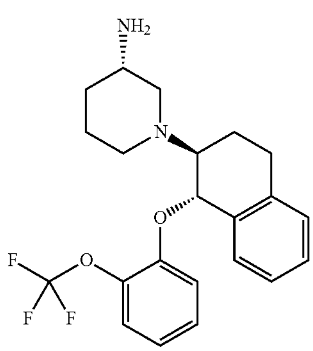 [SMILES: N[C@H]1CCCN([C@H]2CCc3ccccc3[C@@H]2Oc2ccccc2OC(F)(F)F)C1] | A | 1 | 2.60 | 407.11 |

-continued

| Example | Structure | Synthetic method | LC method | Rt time [min] | MS [M + H+] ES+ |
|---------|-----------|------------------|-----------|---------------|------------------|
| 160 | 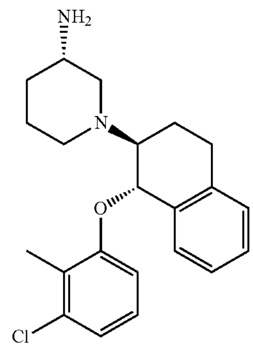 [SMILES: Cc1c(Cl)cccc1O[C@H]1c2ccccc2CC[C@@H]1N1CCC[C@H](N)C1] | A | 1 | 2.52 | 371.14 |
| 161 | 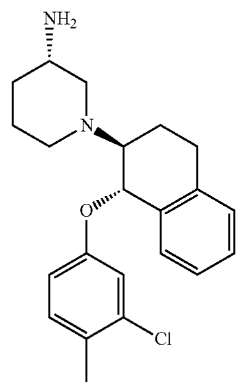 [SMILES: Cc1ccc(O[C@H]2c3ccccc3CC[C@@H]2N2CCC[C@H](N)C2)cc1Cl] | A | 1 | 2.62 | 371.14 |
| 162 | 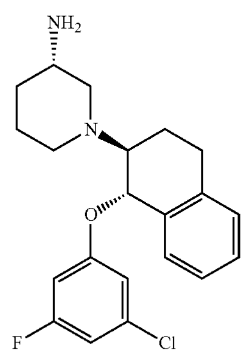 [SMILES: N[C@H]1CCCN([C@H]2CCc3ccccc3[C@@H]2Oc2cc(F)cc(Cl)c2)C1] | A | 1 | 2.57 | 375.1 |
| 163 | 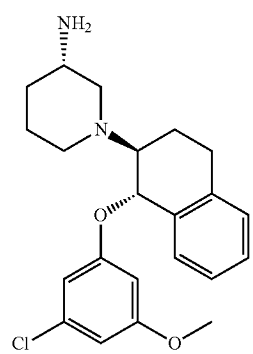 [SMILES: COc1cc(Cl)cc(O[C@H]2c3ccccc3CC[C@@H]2N2CCC[C@H](N)C2)c1] | A | 1 | 2.95 | 387.12 |

-continued

| Example | Structure | Synthetic method | LC method | Rt time [min] | MS [M + H+] ES+ |
|---------|-----------|------------------|-----------|---------------|------------------|
| 164 | 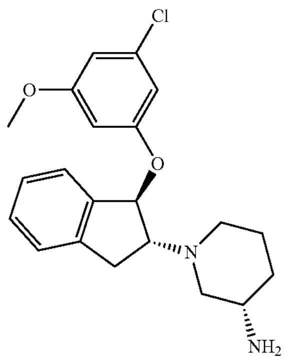 [SMILES: COc1cc(Cl)cc(O[C@@H]2c3ccccc3C[C@H]2N2CCC[C@H](N)C2)c1] | A | 12 | 1.30 | 373.18 |
| 165 | 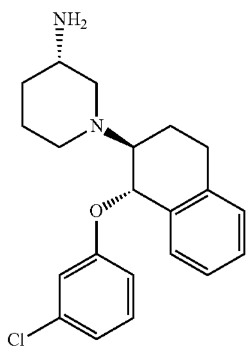 [SMILES: N[C@H]1CCCN([C@H]2CCc3ccccc3[C@@H]2Oc2cccc(Cl)c2)C1] | A | 1 | 2.47 | 357.12 |
| 166 | 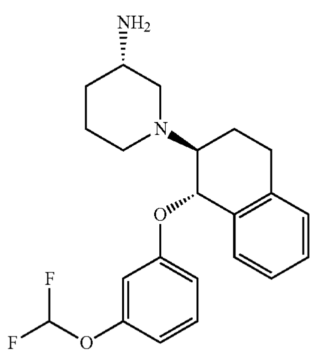 [SMILES: N[C@H]1CCCN([C@H]2CCc3ccccc3[C@@H]2Oc2cccc(OC(F)F)c2)C1] | A | 1 | 2.52 | 389.13 |
| 167 | 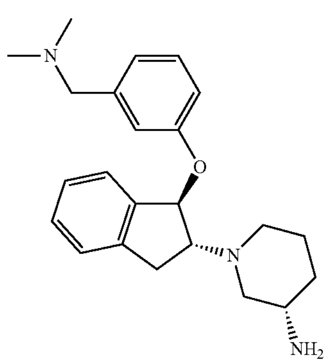 [SMILES: CN(C)Cc1cccc(O[C@@H]2c3ccccc3C[C@H]2N2CCC[C@H](N)C2)c1] | A | 12 | 0.80 | 366.27 |

-continued

| Example | Structure | Synthetic method | LC method | Rt time [min] | MS [M + H+] ES+ |
|---------|-----------|------------------|-----------|---------------|-----------------|
| 168 | 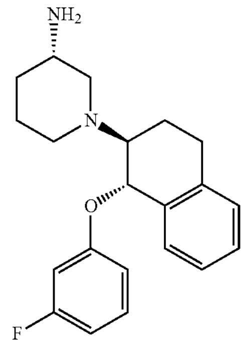 [SMILES: N[C@H]1CCCN([C@H]2CCc3ccccc3[C@@H]2Oc2cccc(F)c2)C1] | A | 1 | 2.39 | 341.15 |
| 169 | 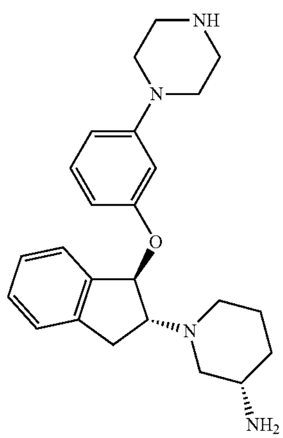 [SMILES: N[C@H]1CCCN([C@@H]2Cc3ccccc3[C@H]2Oc2cccc(N3CCNCC3)c2)C1] | A | 12 | 0.87 | 393.29 |
| 170 | 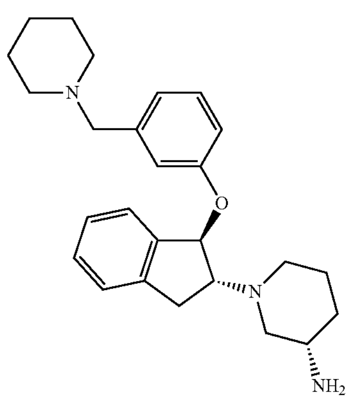 [SMILES: N[C@H]1CCCN([C@@H]2Cc3ccccc3[C@H]2Oc2cccc(CN3CCCCC3)c2)C1] | A | 12 | 0.90 | 406.30 |

| Example | Structure | Synthetic method | LC method | Rt time [min] | MS [M + H+] ES+ |
|---|---|---|---|---|---|
| 171 | 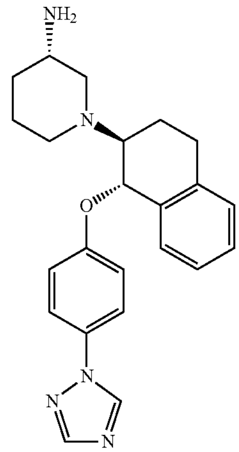 [SMILES: N[C@H]1CCCN([C@H]2CCc3ccccc3[C@@H]2Oc2ccc(-n3cncn3)cc2)C1] | A | 1 | 2.20 | 390.17 |
| 172 | 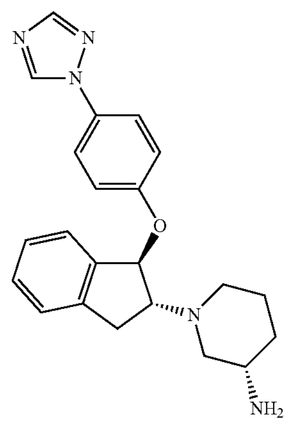 [SMILES: N[C@H]1CCCN([C@@H]2Cc3ccccc3[C@H]2Oc2ccc(-n3cncn3)cc2)C1] | A | 12 | 1.02 | 376.23 |
| 173 | 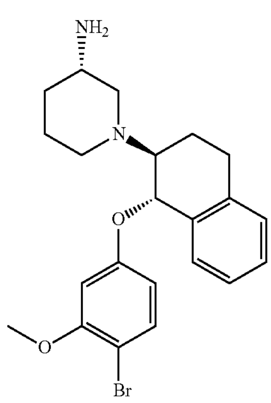 [SMILES: COc1cc(O[C@H]2c3ccccc3CC[C@@H]2N2CCC[C@H](N)C2)ccc1Br] | A | 1 | 2.57 | 431.08 |

-continued

| Example | Structure | Synthetic method | LC method | Rt time [min] | MS [M + H+] ES+ |
|---|---|---|---|---|---|
| 174 | 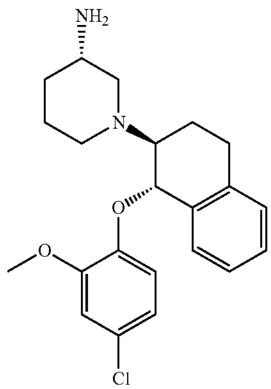 [SMILES: COc1cc(Cl)ccc1O[C@H]1c2ccccc2CC[C@@H]1N1CCC[C@H](N)C1] | A | 1 | 2.50 | 387.12 |
| 175 | 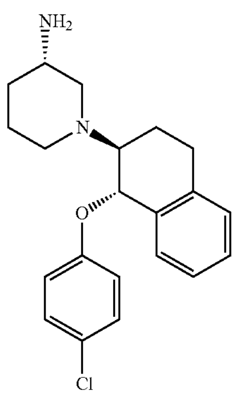 [SMILES: N[C@H]1CCCN([C@H]2CCc3ccccc3[C@@H]2Oc2ccc(Cl)cc2)C1] | A | 1 | 2.54 | 357.13 |
| 176 | 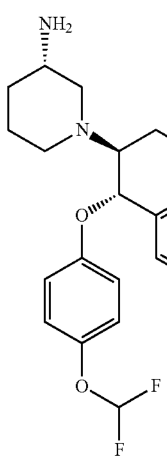 | A | 1 | 2.50 | 389.13 |

| Example | Structure | Synthetic method | LC method | Rt time [min] | MS [M + H+] ES+ |
|---------|-----------|------------------|-----------|---------------|-----------------|
| 177 | 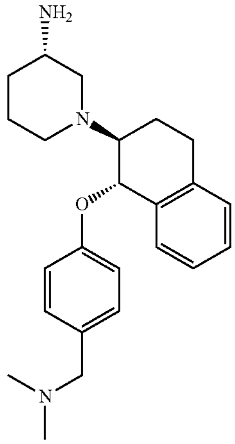 [SMILES: CN(C)Cc1ccc(O[C@H]2c3ccccc3CC[C@@H]2N2CCC[C@H](N)C2)cc1] | A | 1 | 2.05 | 380.24 |
| 178 | 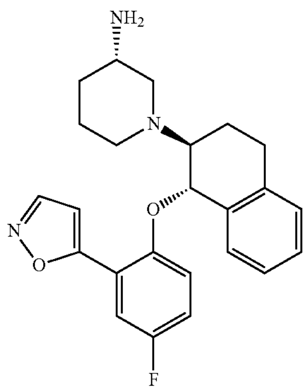 [SMILES: N[C@H]1CCCN([C@H]2CCc3ccccc3[C@@H]2Oc2ccc(F)cc2-c2ccno2)C1] | A | 1 | 2.57 | 408.13 |
| 179 | 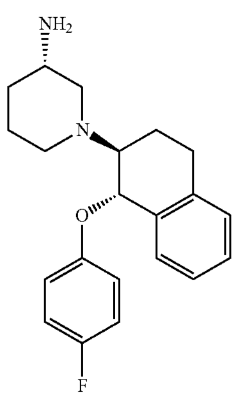 [SMILES: N[C@H]1CCCN([C@H]2CCc3ccccc3[C@@H]2Oc2ccc(F)cc2)C1] | A | 9 | 2.29 | 341.16 |

-continued

| Example | Structure | Synthetic method | LC method | Rt time [min] | MS [M + H+] ES+ |
|---|---|---|---|---|---|
| 180 | 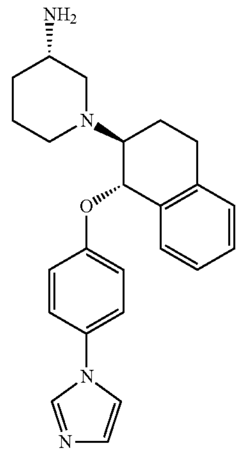 [SMILES: N[C@H]1CCCN([C@H]2CCc3ccccc3[C@@H]2Oc2ccc(-n3ccnc3)cc2)C1] | A | 1 | 1.97 | 389.19 |
| 181 | 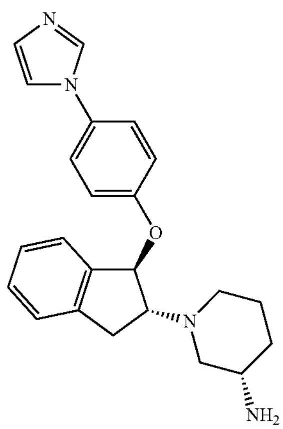 [SMILES: N[C@H]1CCCN([C@@H]2Cc3ccccc3[C@H]2Oc2ccc(-n3ccnc3)cc2)C1] | A | 12 | 0.80 | 375.23 |
| 182 | 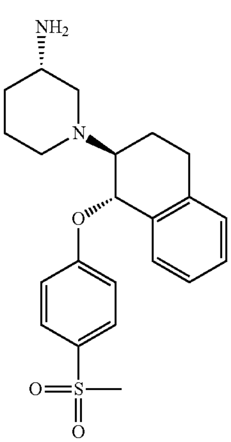 [SMILES: CS(=O)(=O)c1ccc(O[C@H]2c3ccccc3CC[C@@H]2N2CCC[C@H](N)C2)cc1] | A | 1 | 2.23 | 401.12 |

-continued

| Example | Structure | Synthetic method | LC method | Rt time [min] | MS [M + H+] ES+ |
|---|---|---|---|---|---|
| 183 | 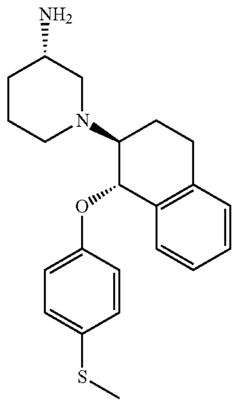 [SMILES: CSc1ccc(O[C@H]2c3ccccc3CC[C@@H]2N2CCC[C@H](N)C2)cc1] | A | 1 | 2.52 | 369.16 |
| 184 | 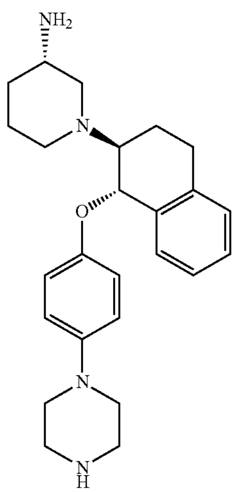 [SMILES: N[C@H]1CCCN([C@H]2CCc3ccccc3[C@@H]2Oc2ccc(N3CCNCC3)cc2)C1] | A | 1 | 1.92 | 407.23 |
| 185 | 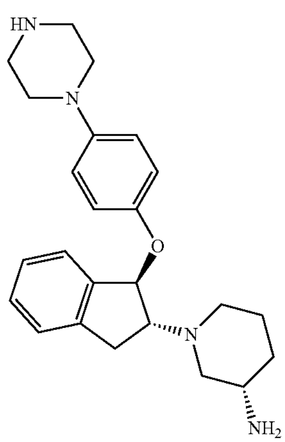 [SMILES: N[C@H]1CCCN([C@@H]2Cc3ccccc3[C@H]2Oc2ccc(N3CCNCC3)cc2)C1] | A | 12 | 0.82 | 393.29 |

-continued

| Example | Structure | Synthetic method | LC method | Rt time [min] | MS [M + H+] ES+ |
|---|---|---|---|---|---|
| 186 | 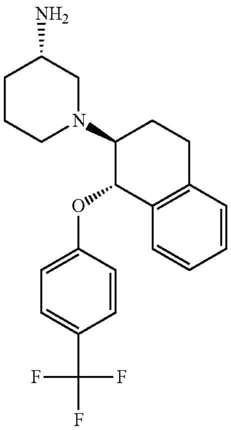 [SMILES: N[C@H]1CCCN([C@H]2CCc3ccccc3[C@@H]2Oc2ccc(C(F)(F)F)cc2)C1] | A | 1 | 2.64 | 391.13 |
| 187 | 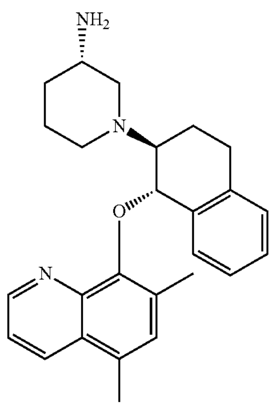 [SMILES: Cc1cc(C)c2cccnc2c1O[C@H]1c2ccccc2CC[C@@H]1N1CCC[C@H](N)C1] | A | 9 | 2.36 | 402.22 |
| 188 | 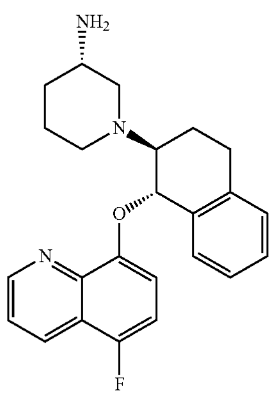 [SMILES: N[C@H]1CCCN([C@H]2CCc3ccccc3[C@@H]2Oc2ccc(F)c3cccnc23)C1] | A | 9 | 2.30 | 392.19 |
| 189 | 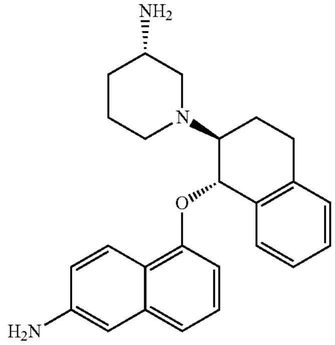 [SMILES: Nc1ccc2c(O[C@H]3c4ccccc4CC[C@@H]3N3CCC[C@H](N)C3)cccc2c1] | A | 1 | 2.37 | 388.2 |

-continued

| Example | Structure | Synthetic method | LC method | Rt time [min] | MS [M + H+] ES+ |
|---|---|---|---|---|---|
| 190 | 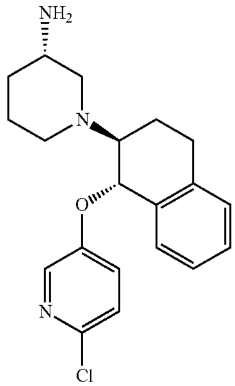 [SMILES: N[C@H]1CCCN([C@H]2CCc3ccccc3[C@@H]2Oc2ccc(Cl)nc2)C1] | A | 1 | 2.57 | 358.12 |
| 191 | 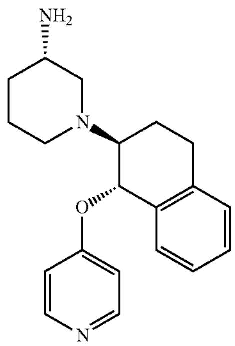 [SMILES: N[C@H]1CCCN([C@H]2CCc3ccccc3[C@@H]2Oc2ccncc2)C1] | A | 1 | 2.09 | 647.33 2M + H |
| 192 | 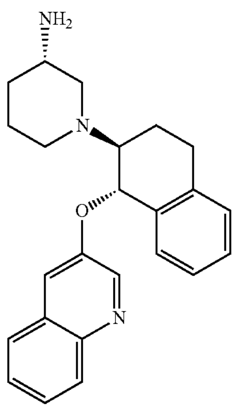 [SMILES: N[C@H]1CCCN([C@H]2CCc3ccccc3[C@@H]2Oc2cnc3ccccc3c2)C1] | A | 1 | 2.27 | 374.19 |
| 193 | 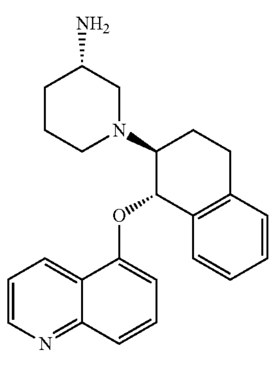 [SMILES: N[C@H]1CCCN([C@H]2CCc3ccccc3[C@@H]2Oc2cccc3ncccc23)C1] | A | 1 | 2.04 | 374.18 |

| Example | Structure | Synthetic method | LC method | Rt time [min] | MS [M + H+] ES+ |
|---------|-----------|------------------|-----------|---------------|-----------------|
| 194 | 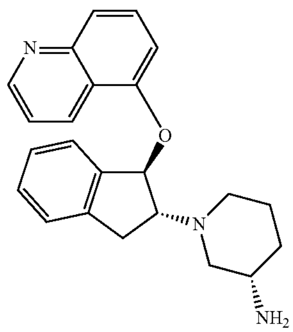 [SMILES: N[C@H]1CCCN([C@@H]2Cc3ccccc3[C@H]2Oc2cccc3ncccc23)C1] | A | 12 | 0.83 | 360.23 |
| 195 | 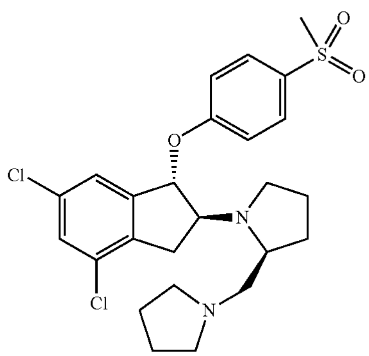 [SMILES: CS(=O)(=O)c1ccc(O[C@H]2c3cc(Cl)cc(Cl)c3C[C@@H]2N2CCC[C@H]2CN2CCCC2)cc1] | A | 4 | 1.28 | 509.18 |
| 196 | 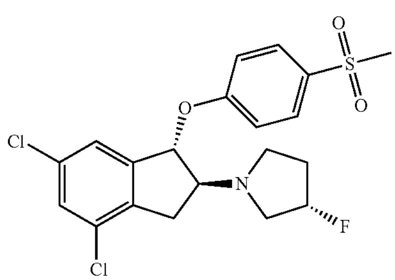 [SMILES: CS(=O)(=O)c1ccc(O[C@H]2c3cc(Cl)cc(Cl)c3C[C@@H]2N2CC[C@H](F)C2)cc1] | A | 1 | 2.68 | 444.13 |
| 197 | 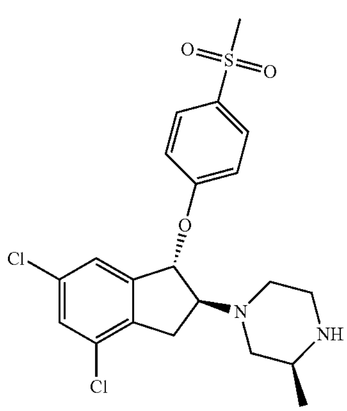 [SMILES: C[C@H]1CN([C@H]2Cc3c(Cl)cc(Cl)cc3[C@@H]2Oc2ccc(S(C)(=O)=O)cc2)CCN1] | A | 9 | 2.69 | 455.06 |

-continued

| Example | Structure | Synthetic method | LC method | Rt time [min] | MS [M + H+] ES+ |
|---|---|---|---|---|---|
| 198 | 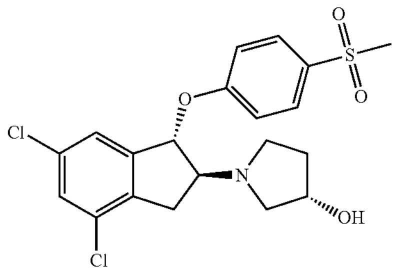 [SMILES: CS(=O)(=O)c1ccc(O[C@H]2c3cc(Cl)cc(Cl)c3C[C@@H]2N2CC[C@H](O)C2)cc1] | A | 1 | 2.65 | 442 |
| 199 | 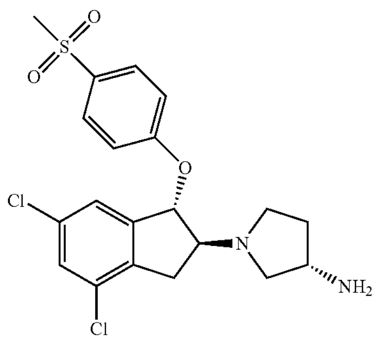 [SMILES: CS(=O)(=O)c1ccc(O[C@H]2c3cc(Cl)cc(Cl)c3C[C@@H]2N2CC[C@H](N)C2)cc1] | A | 1 | 2.54 | 440.98 |
| 200 | 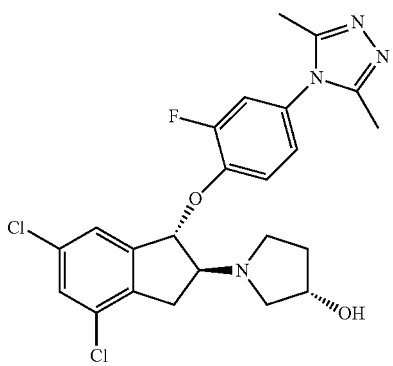 [SMILES: Cc1nnc(C)n1-c1ccc(O[C@H]2c3cc(Cl)cc(Cl)c3C[C@@H]2N2CC[C@H](O)C2)c(F)c1] | A | 17 | 2.40 | 477.21 |
| 201 | 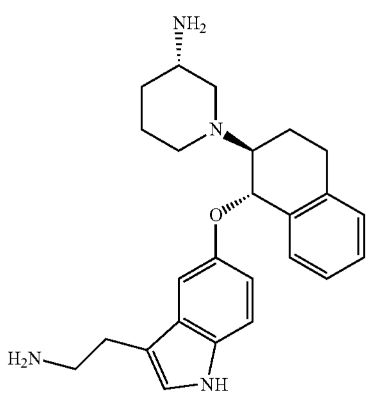 [SMILES: NCCc1c[nH]c2ccc(O[C@H]3c4ccccc4CC[C@@H]3N3CCC[C@H](N)C3)cc12] | A | 1 | 2.14 | 405.22 |

-continued

| Example | Structure | Synthetic method | LC method | Rt time [min] | MS [M + H+] ES+ |
|---|---|---|---|---|---|
| 202 | 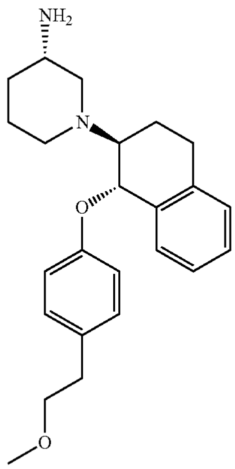 [SMILES: COCCc1ccc(O[C@H]2c3ccccc3CC[C@@H]2N2CCC[C@H](N)C2)cc1] | A | 1 | 2.40 | 381.2 |
| 203 | 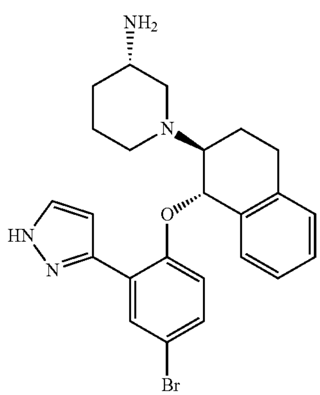 [SMILES: N[C@H]1CCCN([C@H]2CCc3ccccc3[C@@H]2Oc2ccc(Br)cc2-c2cc[nH]n2)C1] | A | 1 | 2.68 | 467.08 |
| 204 | 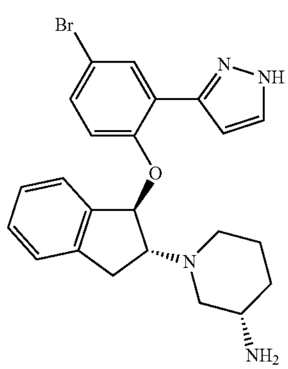 [SMILES: N[C@H]1CCCN([C@@H]2Cc3ccccc3[C@H]2Oc2ccc(Br)cc2-c2cc[nH]n2)C1] | A | 12 | 1.30 | 453.16 |

-continued

| Example | Structure | Synthetic method | LC method | Rt time [min] | MS [M + H+] ES+ |
|---------|-----------|------------------|-----------|---------------|-----------------|
| 205 | 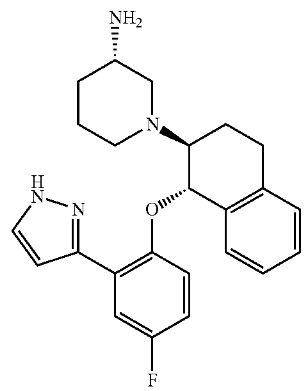 [SMILES: N[C@H]1CCCN([C@H]2CCc3ccccc3[C@@H]2Oc2ccc(F)cc2-c2cc[nH]n2)C1] | A | 9 | 2.63 | 407.17 |
| 206 | 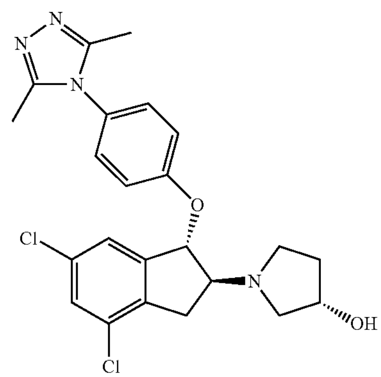 [SMILES: Cc1nnc(C)n1-c1ccc(O[C@H]2c3cc(Cl)cc(Cl)c3C[C@@H]2N2CC[C@H](O)C2)cc1] | A | 1 | 2.40 | 459.09 |
| 207 | 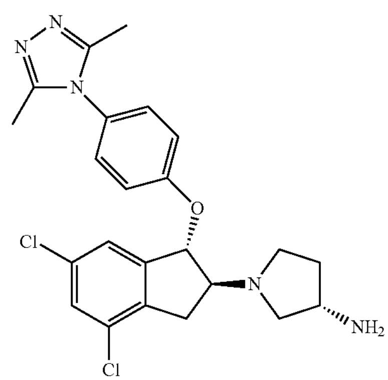 [SMILES: Cc1nnc(C)n1-c1ccc(O[C@H]2c3cc(Cl)cc(Cl)c3C[C@@H]2N2CC[C@H](N)C2)cc1] | A | 8 | 2.77 | 458.2 |
| 208 | 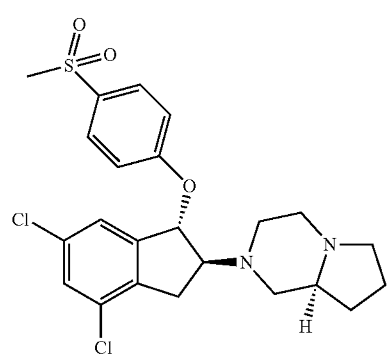 [SMILES: CS(=O)(=O)c1ccc(O[C@H]2c3cc(Cl)cc(Cl)c3C[C@@H]2N2CCN3CCC[C@H]3C2)cc1] | A | 14 | 2.06 | 481.14 |

-continued
| Example | Structure | Synthetic method | LC method | Rt time [min] | MS [M + H+] ES+ |
|---|---|---|---|---|---|
| 209 | 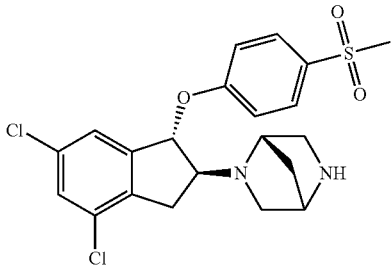 [SMILES: CS(=O)(=O)c1ccc(O[C@H]2c3cc(Cl)cc(Cl)c3C[C@@H]2N2CC3C[C@H]2CN3)cc1] | A | 14 | 1.88 | 453.14 |
| 210 | 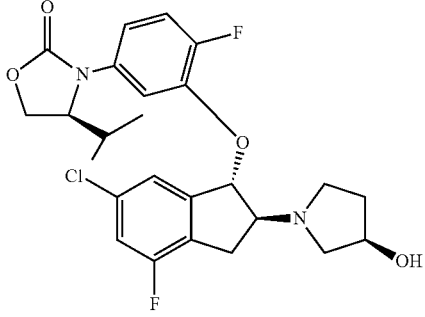 [SMILES: CC(C)[C@H]1COC(=O)N1c1ccc(F)c(O[C@H]2c3cc(Cl)cc(F)c3C[C@@H]2N2CC[C@@H](O)C2)c1] | A | 9 | 2.86 | 493.15 |
| 211 | 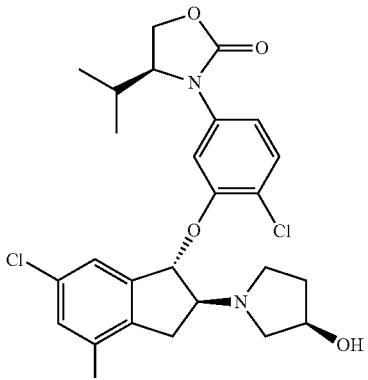 | A | 9 | 3.17 | 509.10 |
| 212 | 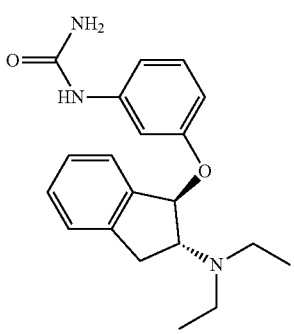 [SMILES: CCN(CC)[C@@H]1Cc2ccccc2[C@H]1Oc1cccc(NC(N)=O)c1] | A | 12 | 1.16 | 340.18 |

-continued

| Example | Structure | Synthetic method | LC method | Rt time [min] | MS [M + H+] ES+ |
|---|---|---|---|---|---|
| 213 | 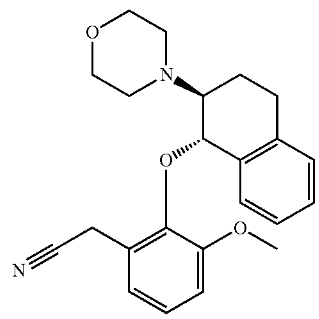 [SMILES: COc1cccc(CC#N)c1O[C@H]1c2ccccc2CC[C@@H]1N1CCOCC1] | A | 1 | 2.57 | 379.15 |
| 214 | 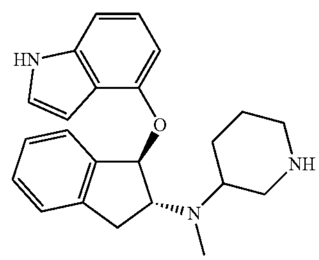 | A | 12 | 1.15 | 723.48 2M + H |
| 215 | 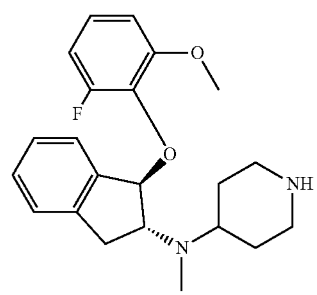 [SMILES: COc1cccc(F)c1O[C@@H]1c2ccccc2C[C@H]1N(C)C1CCNCC1] | A | 12 | 1.10 | 371.13 |
| 216 | 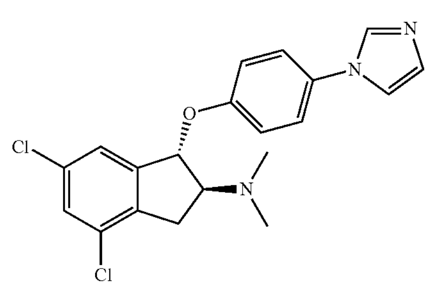 [SMILES: CN(C)[C@H]1Cc2c(Cl)cc(Cl)cc2[C@@H]1Oc1ccc(-n2ccnc2)cc1] | A | 13 | 1.06 | 388.05 |
| 218 | 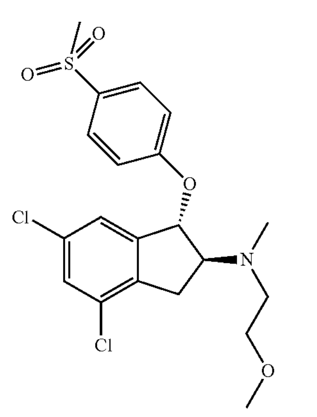 [SMILES: COCCN(C)[C@H]1Cc2c(Cl)cc(Cl)cc2[C@@H]1Oc1ccc(S(C)(=O)=O)cc1] | A | 1 | 2.77 | 443.99 |

-continued

| Example | Structure | Synthetic method | LC method | Rt time [min] | MS [M + H+] ES+ |
|---------|-----------|------------------|-----------|---------------|-----------------|
| 219 | 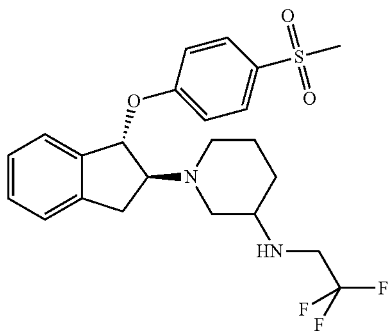 [SMILES: CS(=O)(=O)c1ccc(O[C@H]2c3ccccc3C[C@@H]2N2CCCC(NCC(F)(F)F)C2)cc1] | A | 14 | 1.86 | 469.16 |
| 220 | 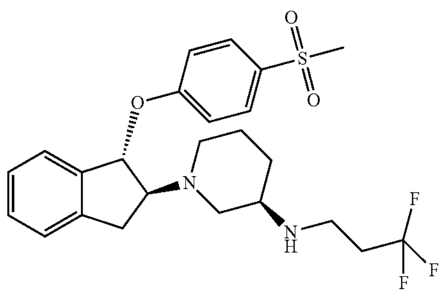 [SMILES: CS(=O)(=O)c1ccc(O[C@H]2c3ccccc3C[C@@H]2N2CCC[C@@H](NCCC(F)(F)F)C2)cc1] | A | 4 | 1.09 | 483.22 |
| 221 | 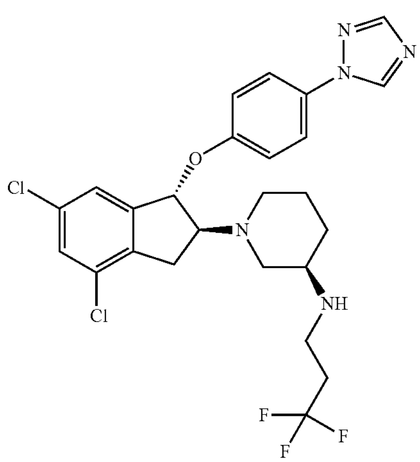 [SMILES: FC(F)(F)CCN[C@@H]1CCCN([C@H]2Cc3c(Cl)cc(Cl)cc3[C@@H]2Oc2ccc(-n3cncn3)cc2)C1] | A | 4 | 1.39 | 540.19 |
| 222 | 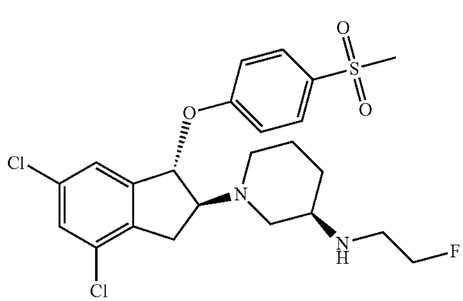 [SMILES: CS(=O)(=O)c1ccc(O[C@H]2c3cc(Cl)cc(Cl)c3C[C@@H]2N2CCC[C@@H](NCCF)C2)cc1] | A | 4 | 1.28 | 501.14 |

-continued
| Example | Structure | Synthetic method | LC method | Rt time [min] | MS [M + H+] ES+ |
|---|---|---|---|---|---|
| 223 | 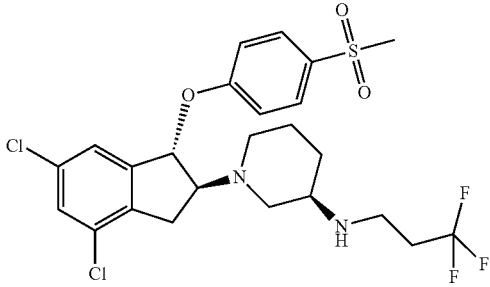 [SMILES: CS(=O)(=O)c1ccc(O[C@H]2c3cc(Cl)cc(Cl)c3C[C@@H]2N2CCC[C@@H](NCCC(F)(F)F)C2)cc1] | A | 4 | 1.40 | 551.14 |
| 224 | 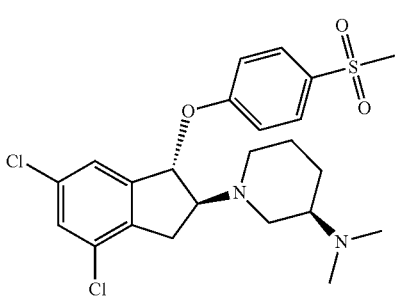 [SMILES: CN(C)[C@@H]1CCCN([C@H]2Cc3c(Cl)cc(Cl)cc3[C@@H]2Oc2ccc(S(C)(=O)=O)cc2)C1] | A | 4 | 1.28 | 483.15 |
| 225 | 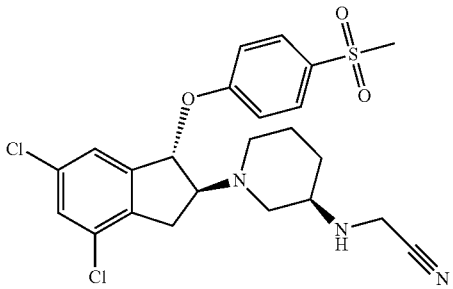 [SMILES: CS(=O)(=O)c1ccc(O[C@H]2c3cc(Cl)cc(Cl)c3C[C@@H]2N2CCC[C@@H](NCC#N)C2)cc1] | A | 4 | 1.30 | 494.13 |
| 226 | 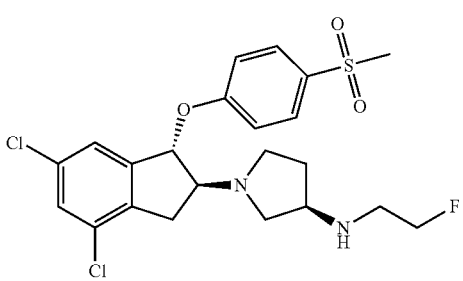 [SMILES: CS(=O)(=O)c1ccc(O[C@H]2c3cc(Cl)cc(Cl)c3C[C@@H]2N2CC[C@@H](NCCF)C2)cc1] | A | 9 | 2.22 | 487.09 |
| 227 | 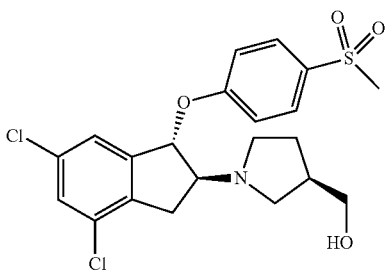 [SMILES: CS(=O)(=O)c1ccc(O[C@H]2c3cc(Cl)cc(Cl)c3C[C@@H]2N2CC[C@@H](CO)C2)cc1] | A | 1 | 2.64 | 456.06 |

-continued

| Example | Structure | Synthetic method | LC method | Rt time [min] | MS [M + H+] ES+ |
|---|---|---|---|---|---|
| 228 | 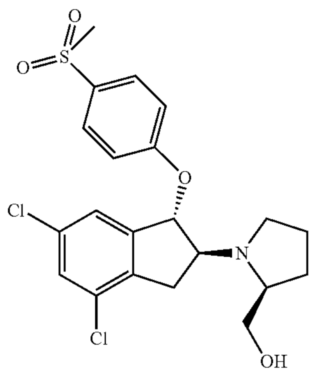 [SMILES: CS(=O)(=O)c1ccc(O[C@H]2c3cc(Cl)cc(Cl)c3C[C@@H]2N2CCC[C@H]2CO)cc1] | A | 1 | 2.67 | 456.03 |
| 229 | 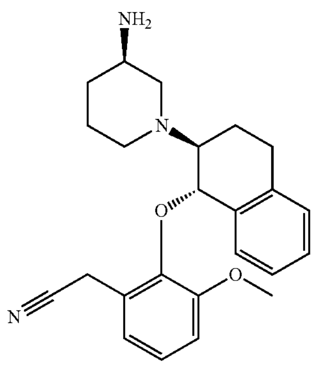 [SMILES: COc1cccc(CC#N)c1O[C@H]1c2ccccc2CC[C@@H]1N1CCC[C@@H](N)C1] | A | 9 | 2.22 | 392.19 |
| 230 | 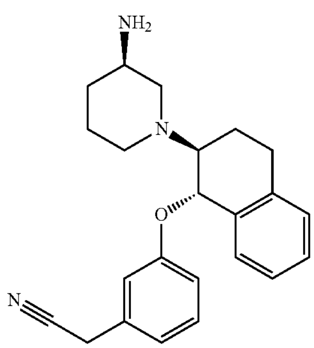 [SMILES: N#CCc1cccc(O[C@H]2c3ccccc3CC[C@@H]2N2CCC[C@@H](N)C2)c1] | A | 1 | 2.32 | 362.17 |
| 231 | 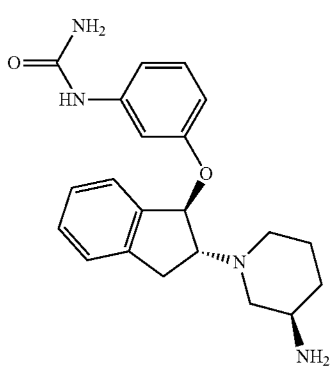 [SMILES: NC(=O)Nc1cccc(O[C@@H]2c3ccccc3C[C@H]2N2CCC[C@@H](N)C2)c1] | A | 12 | 0.97 | 367.21 |

| Example | Structure | Synthetic method | LC method | Rt time [min] | MS [M + H+] ES+ |
|---|---|---|---|---|---|
| 232 | 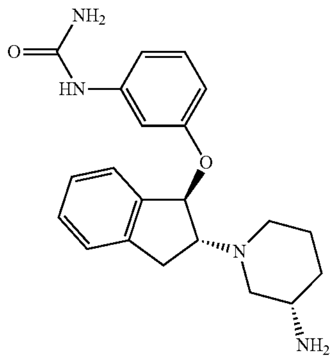 [SMILES: NC(=O)Nc1cccc(O[C@@H]2c3ccccc3C[C@H]2N2CCC[C@H](N)C2)c1] | A | 12 | 0.95 | 367.23 |
| 233 | 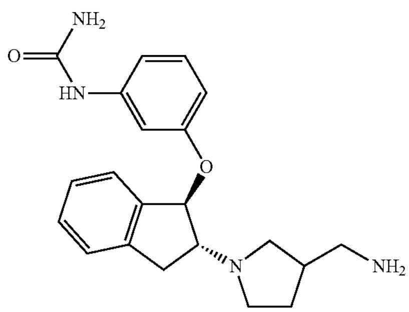 [SMILES: NCC1CCN([C@@H]2Cc3ccccc3[C@H]2Oc2cccc(NC(N)=O)c2)C1] | A | 12 | 0.97 | 367.24 |
| 234 | 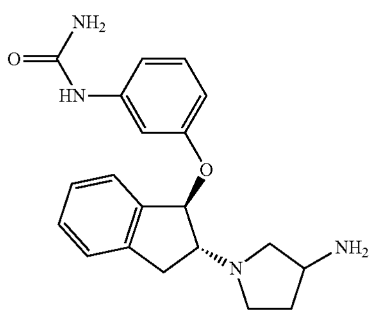 [SMILES: NC(=O)Nc1cccc(O[C@@H]2c3ccccc3C[C@H]2N2CCC(N)C2)c1] | A | 12 | 0.95 | 353.16 |
| 235 | 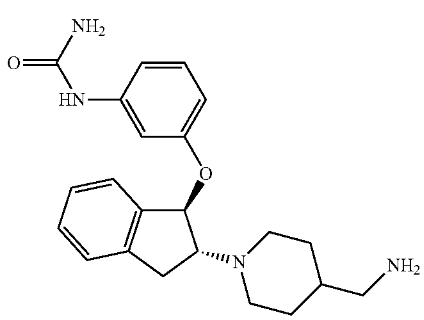 [SMILES: NCC1CCN([C@@H]2Cc3ccccc3[C@H]2Oc2cccc(NC(N)=O)c2)CC1] | A | 11 | 0.97 | 381.21 |

-continued
| Example | Structure | Synthetic method | LC method | Rt time [min] | MS [M + H+] ES+ |
|---|---|---|---|---|---|
| 236 | 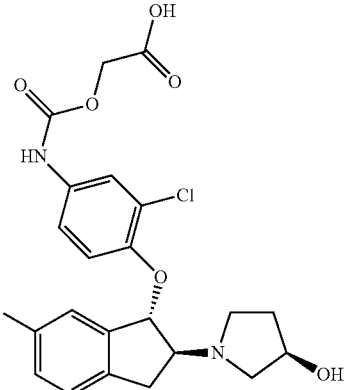 | A | 9 | 2.76 | 515.07 |
| 237 | 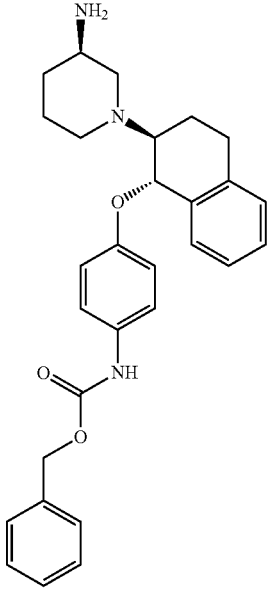 [SMILES: N[C@@H]1CCCN([C@H]2CCc3ccccc3[C@@H]2Oc2ccc(NC(=O)OCc3ccccc3)cc2)C1] | A | 1 | 2.67 | 472.21 |
| 238 | 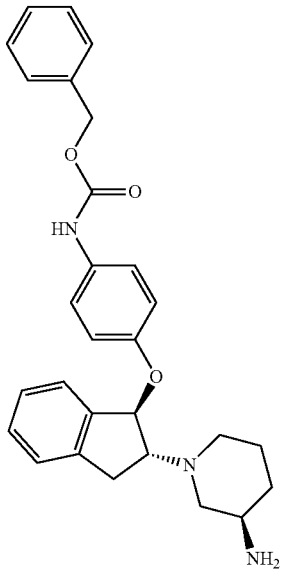 [SMILES: N[C@@H]1CCCN([C@@H]2Cc3ccccc3[C@H]2Oc2ccc(NC(=O)OCc3ccccc3)cc2)C1] | A | 12 | 1.40 | 458.21 |

| Example | Structure | Synthetic method | LC method | Rt time [min] | MS [M + H+] ES+ |
|---|---|---|---|---|---|
| 239 | 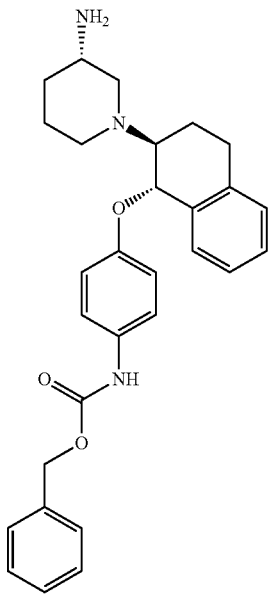 [SMILES: N[C@H]1CCCN([C@H]2CCc3ccccc3[C@@H]2Oc2ccc(NC(=O)OCc3ccccc3)cc2)C1] | A | 1 | 2.70 | 472.22 |
| 240 | 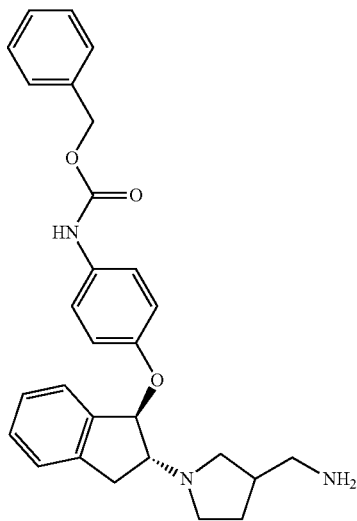 [SMILES: NCC1CCN([C@@H]2Cc3ccccc3[C@H]2Oc2ccc(NC(=O)OCc3ccccc3)cc2)C1] | A | 12 | 1.41 | 458.25 |

-continued
| Example | Structure | Synthetic method | LC method | Rt time [min] | MS [M + H+] ES+ |
|---|---|---|---|---|---|
| 241 | 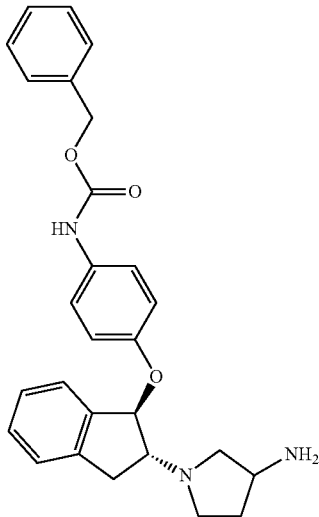 [SMILES: NC1CCN([C@@H]2Cc3ccccc3[C@H]2Oc2ccc(NC(=O)OCc3ccccc3)cc2)C1] | A | 12 | 1.41 | 444.16 |
| 242 | 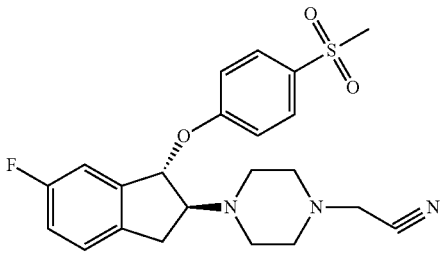 [SMILES: CS(=O)(=O)c1ccc(O[C@H]2c3cc(F)ccc3C[C@@H]2N2CCN(CC#N)CC2)cc1] | A | 4 | 1.12 | 430.18 |
| 243 | 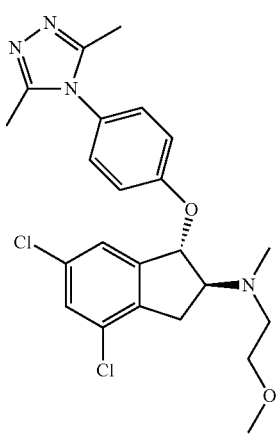 [SMILES: COCCN(C)[C@H]1Cc2c(Cl)cc(Cl)cc2[C@@H]1Oc1ccc(-n2c(C)nnc2C)cc1] | A | 1 | 2.45 | 461.11 |
| 245 | 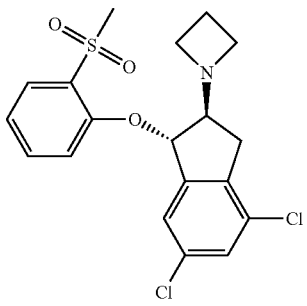 [SMILES: CS(=O)(=O)c1ccccc1O[C@H]1c2cc(Cl)cc(Cl)c2C[C@@H]1N1CCC1] | A | 1 | 2.65 | 412.09 |

-continued
| Example | Structure | Synthetic method | LC method | Rt time [min] | MS [M + H+] ES+ |
|---|---|---|---|---|---|
| 246 | 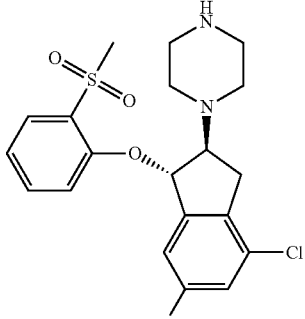 | A | 1 | 2.72 | 441.16 |
| 247 | 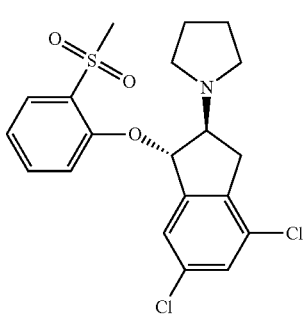 [SMILES: CS(=O)(=O)c1ccccc1O[C@H]1c2cc(Cl)cc(Cl)c2C[C@@H]1N1CCCC1] | A | 1 | 2.67 | 426.11 |
| 248 | 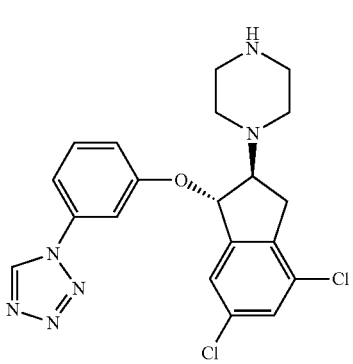 [SMILES: Clc1cc(Cl)c2c(c1)[C@H](Oc1cccc(-n3cnnn3)c1)[C@@H](N1CCNCC1)C2] | A | 1 | 2.80 | 431.18 |
| 249 | 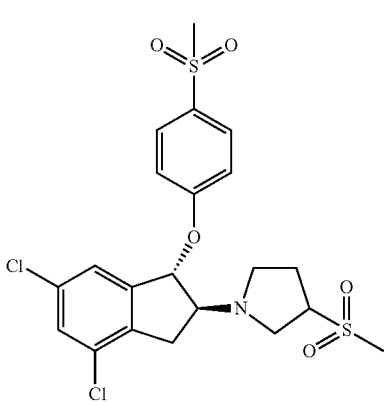 [SMILES: CS(=O)(=O)c1ccc(O[C@H]2c3cc(Cl)cc(Cl)c3C[C@@H]2N2CCC(S(C)(=O)=O)C2)cc1] | A | 17 | 2.82 | 504.13 |

| Example | Structure | Synthetic method | LC method | Rt time [min] | MS [M + H+] ES+ |
|---|---|---|---|---|---|
| 250 | 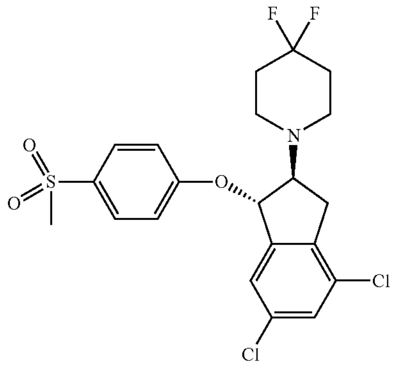 [SMILES: CS(=O)(=O)c1ccc(O[C@H]2c3cc(Cl)cc(Cl)c3C[C@@H]2N2CCC(F)(F)CC2)cc1] | A | 1 | 3.15 | 476.13 |
| 252 | 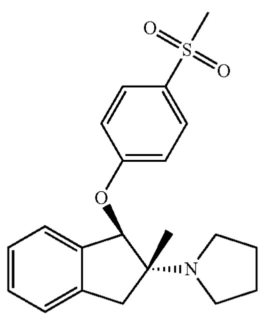 [SMILES: C[C@@]1(N2CCCC2)Cc2ccccc2[C@H]1Oc1ccc(S(C)(=O)=O)cc1] | A | 9 | 2.51 | 372.06 |
| 253 | 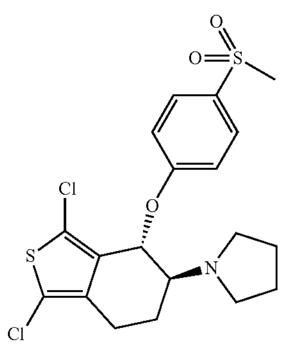 [SMILES: CS(=O)(=O)c1ccc(O[C@H]2c3c(Cl)sc(Cl)c3CC[C@@H]2N2CCCC2)cc1] | A | 9 | 2.73 | 446.06 |
| 254 | 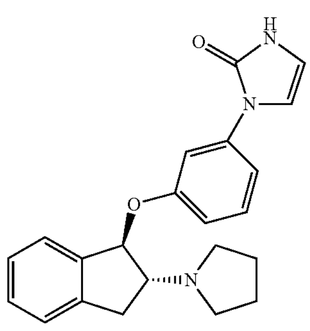 [SMILES: O=c1[nH]ccn1-c1cccc(O[C@@H]2c3ccccc3C[C@H]2N2CCCC2)c1] | A | 4 | 1.14 | 362.17 |

-continued

| Example | Structure | Synthetic method | LC method | Rt time [min] | MS [M + H+] ES+ |
|---------|-----------|------------------|-----------|---------------|------------------|
| 255 | 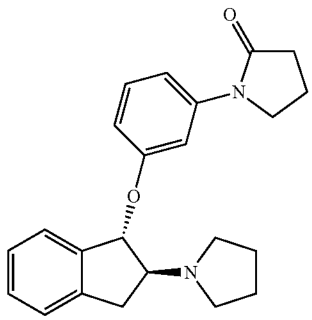 [SMILES: O=C1CCCN1c1cccc(O[C@H]2c3ccccc3C[C@@H]2N2CCCC2)c1] | A | 9 | 2.44 | 363.15 |
| 256 | 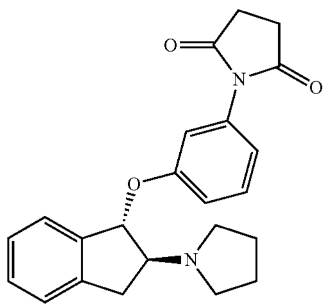 [SMILES: O=C1CCC(=O)N1c1cccc(O[C@H]2c3ccccc3C[C@@H]2N2CCCC2)c1] | A | 4 | 1.10 | 377.16 |
| 257 | 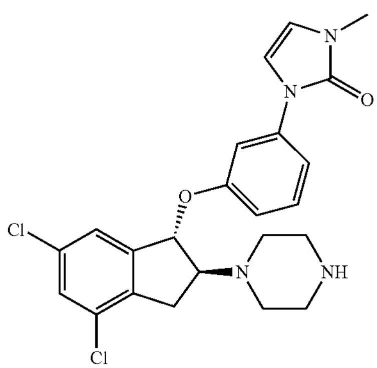 [SMILES: Cn1ccn(-c2cccc(O[C@H]3c4cc(Cl)cc(Cl)c4C[C@@H]3N3CCNCC3)c2)c1=O] | A | 1 | 2.79 | 459.21 |
| 258 | 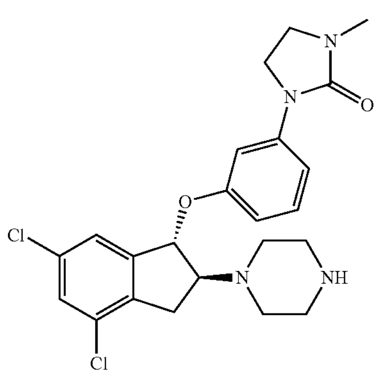 [SMILES: CN1CCN(c2cccc(O[C@H]3c4cc(Cl)cc(Cl)c4C[C@@H]3N3CCNCC3)c2)C1=O] | A | 14 | 2.03 | 461.17 |

-continued

| Example | Structure | Synthetic method | LC method | Rt time [min] | MS [M + H+] ES+ |
|---|---|---|---|---|---|
| 259 | 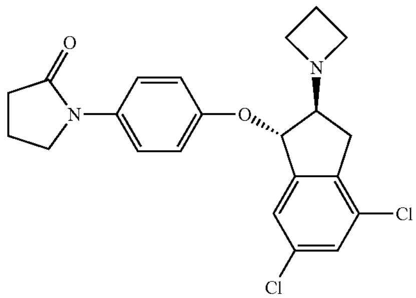 [SMILES: O=C1CCCN1c1ccc(O[C@H]2c3cc(Cl)cc(Cl)c3C[C@@H]2N2CCC2)cc1] | A | 1 | 2.72 | 417.15 |
| 260 | 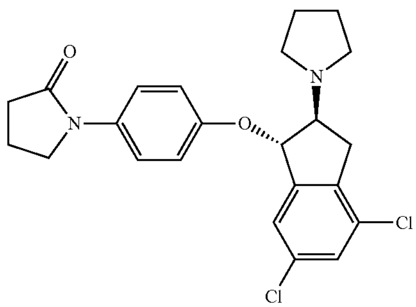 [SMILES: O=C1CCCN1c1ccc(O[C@H]2c3cc(Cl)cc(Cl)c3C[C@@H]2N2CCCC2)cc1] | A | 1 | 2.77 | 431.17 |
| 262 | 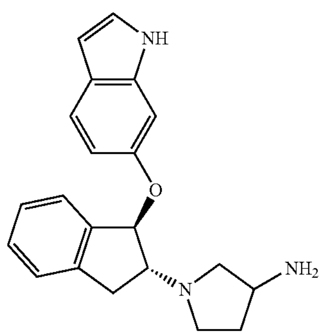 [SMILES: NC1CCN([C@@H]2Cc3ccccc3[C@H]2Oc2ccc3cc[nH]c3c2)C1] | A | 12 | 1.22 | 667.31 2M + H |
| 263 | 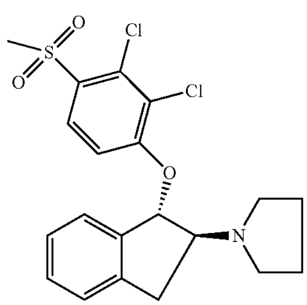 [SMILES: CS(=O)(=O)c1ccc(O[C@H]2c3ccccc3C[C@@H]2N2CCCC2)c(Cl)c1Cl] | A | 4 | 1.27 | 426.19 |
| 264 | 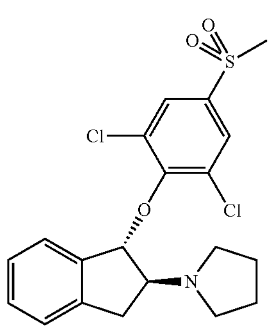 [SMILES: CS(=O)(=O)c1cc(Cl)c(O[C@H]2c3ccccc3C[C@@H]2N2CCCC2)c(Cl)c1] | A | 6 | 1.30 | 426.06 |

-continued

| Example | Structure | Synthetic method | LC method | Rt time [min] | MS [M + H+] ES+ |
|---|---|---|---|---|---|
| 265 | 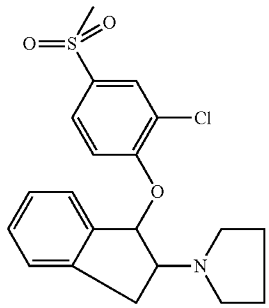 [SMILES: CS(=O)(=O)c1ccc(OC2c3ccccc3CC2N2CCCC2)c(Cl)c1] | A | 6 | 1.34 | 392.15 |
| 266 | 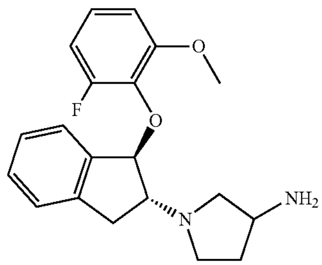 [SMILES: COc1cccc(F)c1O[C@@H]1c2ccccc2C[C@H]1N1CCC(N)C1] | A | 12 | 1.12 | 343.11 |
| 267 | 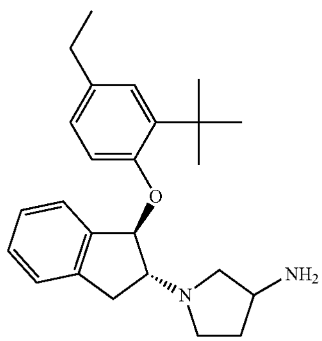 [SMILES: CCc1ccc(O[C@@H]2c3ccccc3C[C@H]2N2CCC(N)C2)c(C(C)(C)C)c1] | A | 12 | 1.22 | 379.09 |
| 268 | 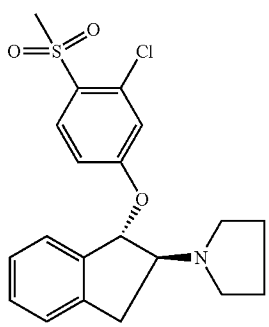 [SMILES: CS(=O)(=O)c1ccc(O[C@H]2c3ccccc3C[C@@H]2N2CCCC2)cc1Cl] | A | 14 | 1.77 | 392.13 |
| 269 | 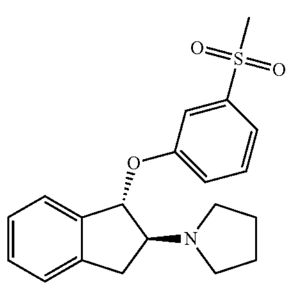 [SMILES: CS(=O)(=O)c1cccc(O[C@H]2c3ccccc3C[C@@H]2N2CCCC2)c1] | A | 4 | 1.09 | 358.14 |

-continued

| Example | Structure | Synthetic method | LC method | Rt time [min] | MS [M + H+] ES+ |
|---|---|---|---|---|---|
| 270 | 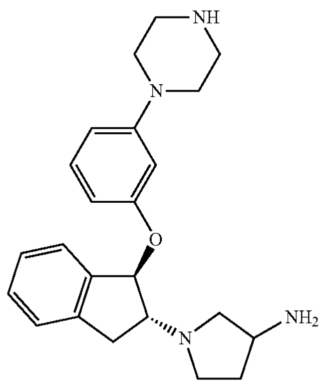 [SMILES: NC1CCN([C@@H]2Cc3ccccc3[C@H]2Oc2cccc(N3CCNCC3)c2)C1] | A | 11 | 0.87 | 379.22 |
| 271 | 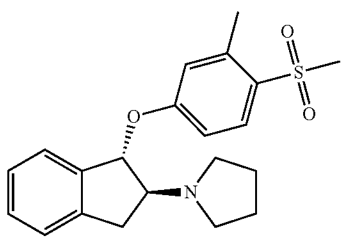 [SMILES: Cc1cc(O[C@H]2c3ccccc3C[C@@H]2N2CCCC2)ccc1S(C)(=O)=O] | A | 4 | 1.13 | 372.15 |
| 272 | 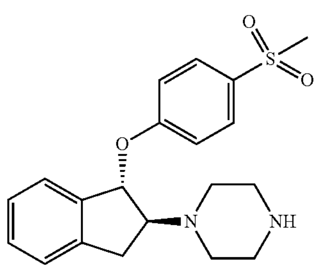 [SMILES: CS(=O)(=O)c1ccc(O[C@H]2c3ccccc3C[C@@H]2N2CCNCC2)cc1] | A | 4 | 1.05 | 373.26 |
| 273 | 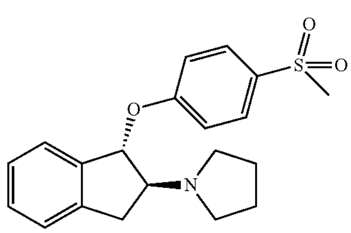 [SMILES: CS(=O)(=O)c1ccc(O[C@H]2c3ccccc3C[C@@H]2N2CCCC2)cc1] | A | 4 | 1.09 | 358.18 |
| 275 | 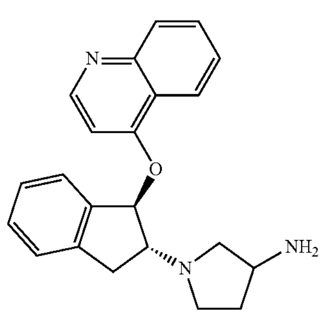 [SMILES: NC1CCN([C@@H]2Cc3ccccc3[C@H]2Oc2ccnc3ccccc23)C1] | A | 12 | 0.97 | 346.16 |

-continued

| Example | Structure | Synthetic method | LC method | Rt time [min] | MS [M + H+] ES+ |
|---|---|---|---|---|---|
| 276 | 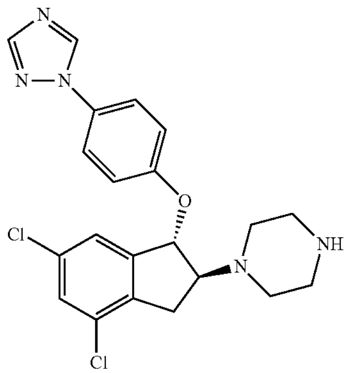 [SMILES: Clc1cc(Cl)c2c(c1)[C@H](Oc1ccc(-n3cncn3)cc1)[C@@H](N1CCNCC1)C2] | A | 4 | 1.32 | 430.17 |
| 277 | 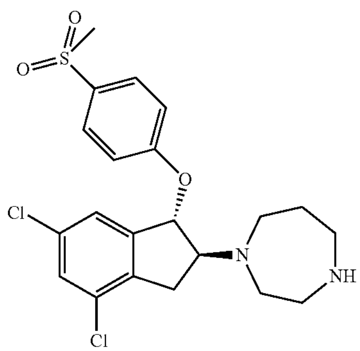 [SMILES: CS(=O)(=O)c1ccc(O[C@H]2c3cc(Cl)cc(Cl)c3C[C@@H]2N2CCCNCC2)cc1] | A | 4 | 1.30 | 455.26 |
| 279 | 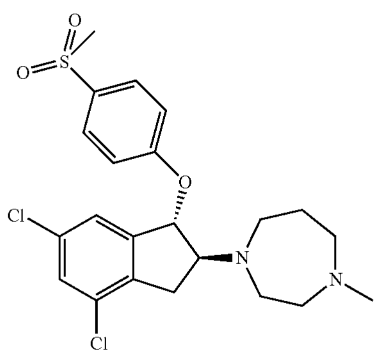 [SMILES: CN1CCCN([C@H]2Cc3c(Cl)cc(Cl)cc3[C@@H]2Oc2ccc(S(C)(=O)=O)cc2)CC1] | A | 4 | 1.35 | 469.17 |
| 281 | 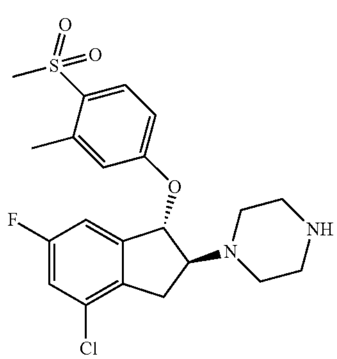 [SMILES: Cc1cc(O[C@H]2c3cc(F)cc(Cl)c3C[C@@H]2N2CCNCC2)ccc1S(C)(=O)=O] | A | 4 | 1.31 | 439.15 |

-continued
| Example | Structure | Synthetic method | LC method | Rt time [min] | MS [M + H+] ES+ |
|---|---|---|---|---|---|
| 282 | 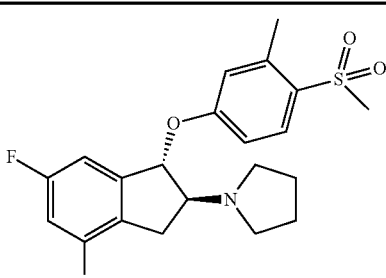 | A | 4 | 1.27 | 424.13 |
| 283 | 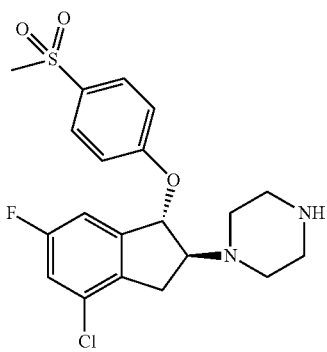 [SMILES: CS(=O)(=O)c1ccc(O[C@H]2c3cc(F)cc(Cl)c3C[C@@H]2N2CCNCC2)cc1] | A | 4 | 1.24 | 425.14 |
| 284 | 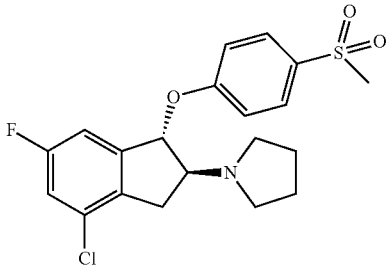 [SMILES: CS(=O)(=O)c1ccc(O[C@H]2c3cc(F)cc(Cl)c3C[C@@H]2N2CCCC2)cc1] | A | 4 | 1.21 | 410.11 |
| 285 | 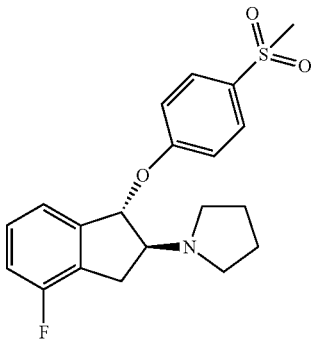 [SMILES: CS(=O)(=O)c1ccc(O[C@H]2c3cccc(F)c3C[C@@H]2N2CCCC2)cc1] | A | 4 | 1.18 | 376.22 |
| 286 | 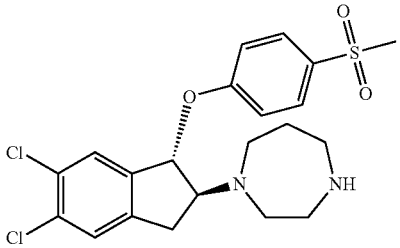 [SMILES: CS(=O)(=O)c1ccc(O[C@H]2c3cc(Cl)c(Cl)cc3C[C@@H]2N2CCCNCC2)cc1] | A | 14 | 1.84 | 455.16 |

-continued

| Example | Structure | Synthetic method | LC method | Rt time [min] | MS [M + H+] ES+ |
|---|---|---|---|---|---|
| 287 | 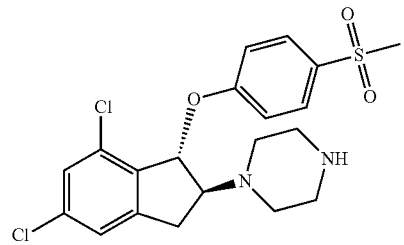 [SMILES: CS(=O)(=O)c1ccc(O[C@H]2c3c(Cl)cc(Cl)cc3C[C@@H]2N2CCNCC2)cc1] | A | 4 | 1.33 | 441.08 |
| 288 | 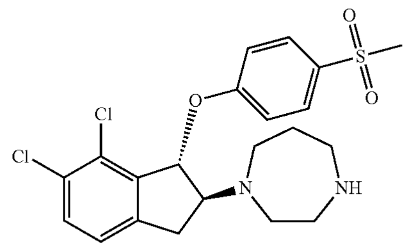 [SMILES: CS(=O)(=O)c1ccc(O[C@H]2c3c(ccc(Cl)c3Cl)C[C@@H]2N2CCCNCC2)cc1] | A | 14 | 1.90 | 455.15 |
| 289 | 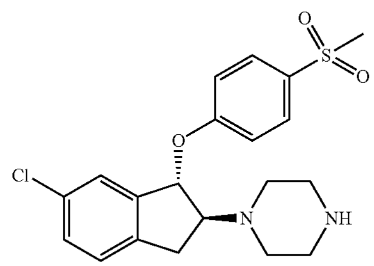 [SMILES: CS(=O)(=O)c1ccc(O[C@H]2c3cc(Cl)ccc3C[C@@H]2N2CCNCC2)cc1] | A | 4 | 1.19 | 407.24 |
| 290 | 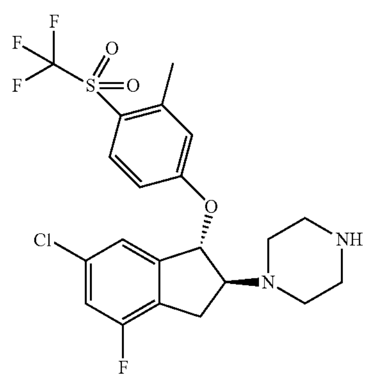 [SMILES: Cc1cc(O[C@H]2c3cc(Cl)cc(F)c3C[C@@H]2N2CCNCC2)ccc1S(=O)(=O)C(F)(F)F] | A | 14 | 2.32 | 493.09 |
| 291 | 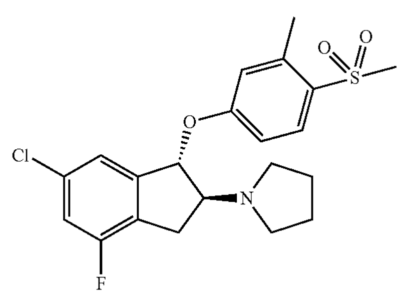 [SMILES: Cc1cc(O[C@H]2c3cc(Cl)cc(F)c3C[C@@H]2N2CCCC2)ccc1S(C)(=O)=O] | A | 14 | 1.94 | 424.1 |

| Example | Structure | Synthetic method | LC method | Rt time [min] | MS [M + H+] ES+ |
|---|---|---|---|---|---|
| 292 | 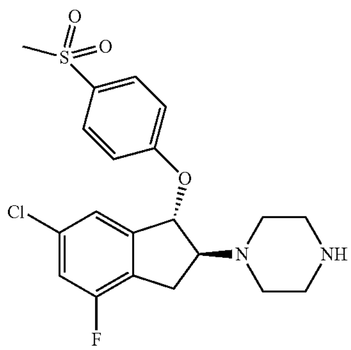 [SMILES: CS(=O)(=O)c1ccc(O[C@H]2c3cc(Cl)cc(F)c3C[C@@H]2N2CCNCC2)cc1] | A | 14 | 1.90 | 425.11 |
| 293 | 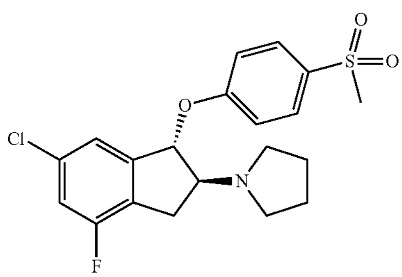 [SMILES: CS(=O)(=O)c1ccc(O[C@H]2c3cc(Cl)cc(F)c3C[C@@H]2N2CCCC2)cc1] | A | 14 | 1.85 | 410.09 |
| 294 | 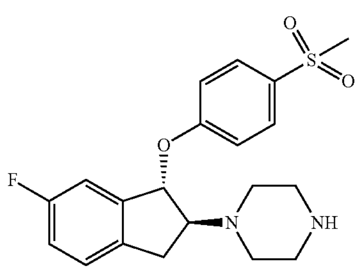 [SMILES: CS(=O)(=O)c1ccc(O[C@H]2c3cc(F)ccc3C[C@@H]2N2CCNCC2)cc1] | A | 1 | 1.10 | 391.25 |
| 295 | 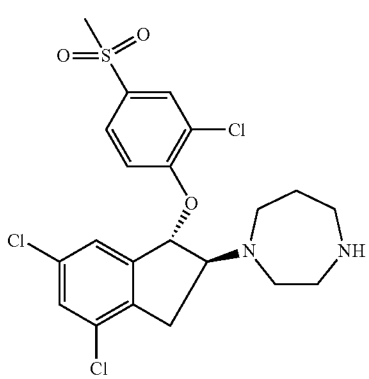 [SMILES: CS(=O)(=O)c1ccc(O[C@H]2c3cc(Cl)cc(Cl)c3C[C@@H]2N2CCCNCC2)c(Cl)c1] | A | 9 | 2.50 | 489.06 |

-continued

| Example | Structure | Synthetic method | LC method | Rt time [min] | MS [M + H+] ES+ |
|---|---|---|---|---|---|
| 296 | 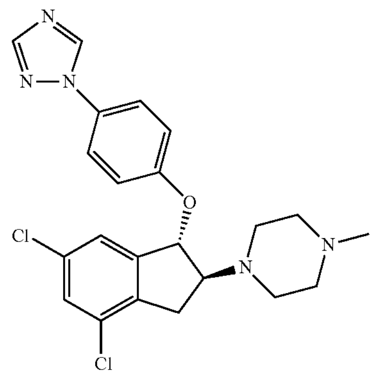 [SMILES: CN1CCN([C@H]2Cc3c(Cl)cc(Cl)cc3[C@@H]2Oc2ccc(-n3cncn3)cc2)CC1] | A | 4 | 1.35 | 444.19 |
| 297 | 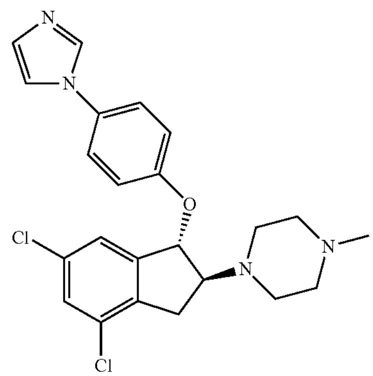 [SMILES: CN1CCN([C@H]2Cc3c(Cl)cc(Cl)cc3[C@@H]2Oc2ccc(-n3ccnc3)cc2)CC1] | A | 4 | 1.14 | 443.2 |
| 298 | 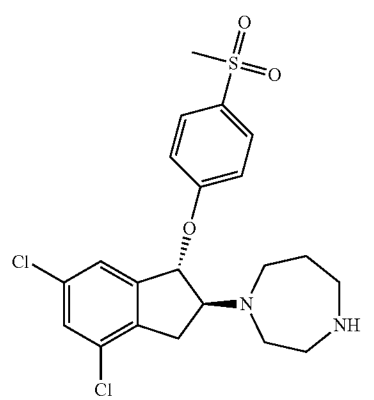 [SMILES: CS(=O)(=O)c1ccc(O[C@H]2c3cc(Cl)cc(Cl)c3C[C@@H]2N2CCCNCC2)cc1] | A | 14 | 1.92 | 455.1 |
| 299 | 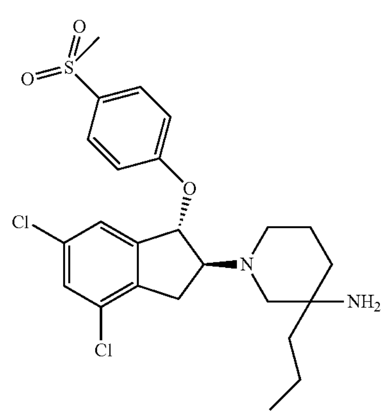 [SMILES: CCCC1(N)CCCN([C@H]2Cc3c(Cl)cc(Cl)cc3[C@@H]2Oc2ccc(S(C)(=O)=O)cc2)C1] | A | 4 | 1.51 | 497.31 |

-continued

| Example | Structure | Synthetic method | LC method | Rt time [min] | MS [M + H+] ES+ |
|---|---|---|---|---|---|
| 300 | 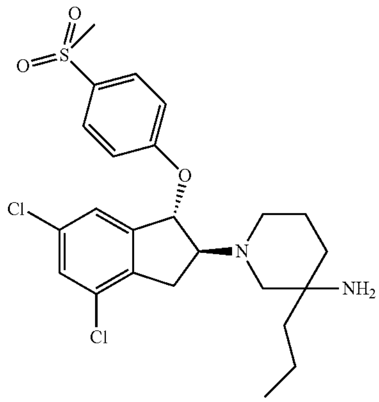 [SMILES: CCCC1(N)CCCN([C@H]2Cc3c(Cl)cc(Cl)cc3[C@@H]2Oc2ccc(S(C)(=O)=O)cc2)C1] | A | 4 | 1.54 | 497.32 |
| 301 | 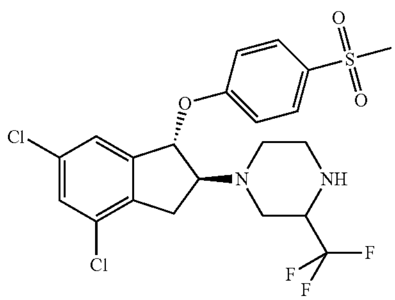 [SMILES: CS(=O)(=O)c1ccc(O[C@H]2c3cc(Cl)cc(Cl)c3C[C@@H]2N2CCNC(C(F)(F)F)C2)cc1] | A | 14 | 2.11 | 509.18 |
| 302 | 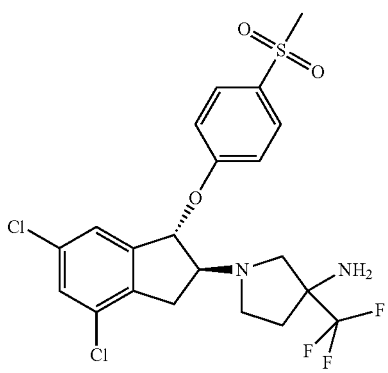 [SMILES: CS(=O)(=O)c1ccc(O[C@H]2c3cc(Cl)cc(Cl)c3C[C@@H]2N2CCC(N)(C(F)(F)F)C2)cc1] | A | 14 | 2.07 | 509.07 |
| 303 | 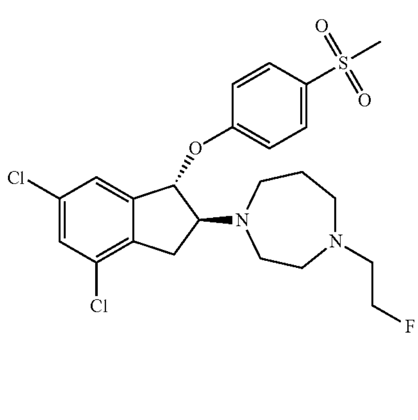 [SMILES: CS(=O)(=O)c1ccc(O[C@H]2c3cc(Cl)cc(Cl)c3C[C@@H]2N2CCCN(CCF)CC2)cc1] | A | 14 | 2.02 | 501.13 |

-continued

| Example | Structure | Synthetic method | LC method | Rt time [min] | MS [M + H+] ES+ |
|---------|-----------|------------------|-----------|---------------|-----------------|
| 304 | 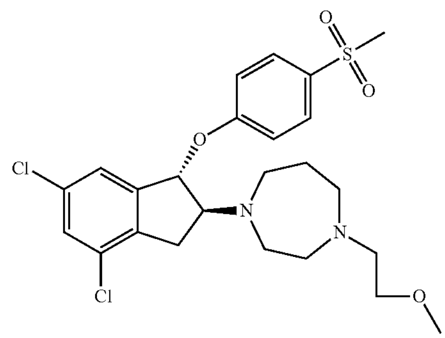 [SMILES: COCCN1CCCN([C@H]2Cc3c(Cl)cc(Cl)cc3[C@@H]2Oc2ccc(S(C)(=O)=O)cc2)CC1] | A | 1 | 2.84 | 513.05 |
| 305 | 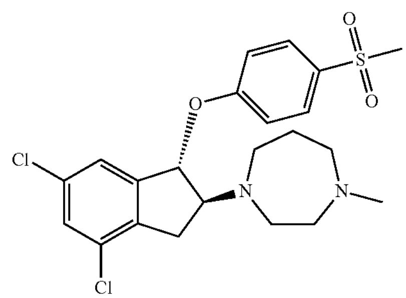 [SMILES: CN1CCCN([C@H]2Cc3c(Cl)cc(Cl)cc3[C@@H]2Oc2ccc(S(C)(=O)=O)cc2)CC1] | A | 14 | 1.98 | 469.11 |
| 306 | 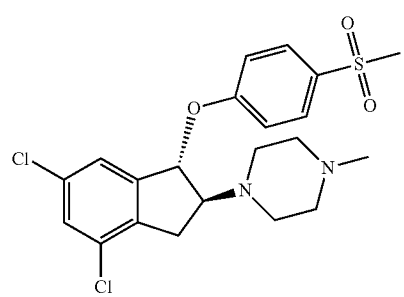 [SMILES: CN1CCN([C@H]2Cc3c(Cl)cc(Cl)cc3[C@@H]2Oc2ccc(S(C)(=O)=O)cc2)CC1] | A | 4 | 1.37 | 455.15 |
| 307 | 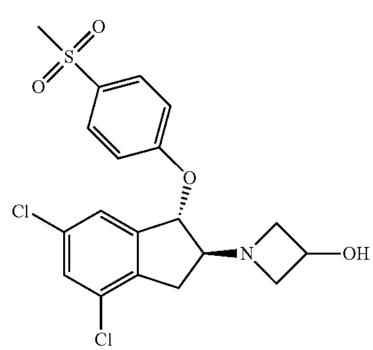 [SMILES: CS(=O)(=O)c1ccc(O[C@H]2c3cc(Cl)cc(Cl)c3C[C@@H]2N2CC(O)C2)cc1] | A | 1 | 2.60 | 428.04 |

-continued

| Example | Structure | Synthetic method | LC method | Rt time [min] | MS [M + H+] ES+ |
|---|---|---|---|---|---|
| 308 | 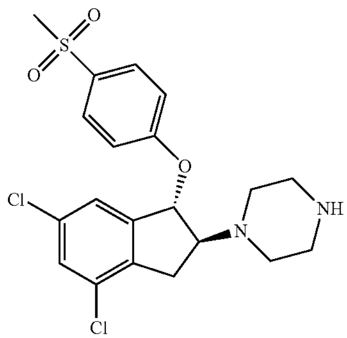 [SMILES: CS(=O)(=O)c1ccc(O[C@H]2c3cc(Cl)cc(Cl)c3C[C@@H]2N2CCNCC2)cc1] | A | 1 | 2.77 | 441.07 |
| 309 | 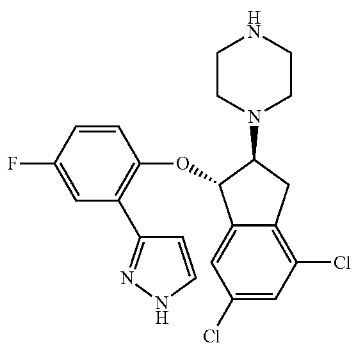 [SMILES: Fc1ccc(O[C@H]2c3cc(Cl)cc(Cl)c3C[C@@H]2N2CCNCC2)c(-c2cc[nH]n2)c1] | A | 1 | 2.87 | 447.19 |
| 310 | 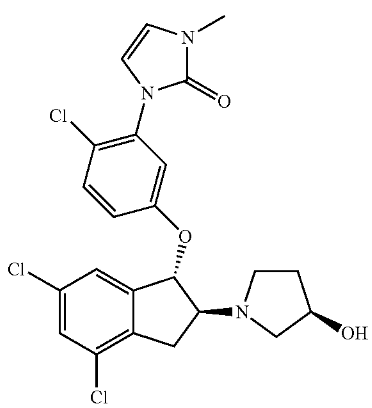 [SMILES: Cn1ccn(-c2cc(O[C@H]3c4cc(Cl)cc(Cl)c4C[C@@H]3N3CC[C@@H](O)C3)ccc2Cl)c1=O] | A | 9 | 2.75 | 494.04 |
| 311 | 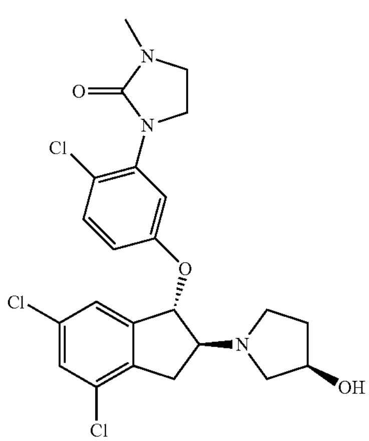 [SMILES: CN1CCN(c2cc(O[C@H]3c4cc(Cl)cc(Cl)c4C[C@@H]3N3CC[C@@H](O)C3)ccc2Cl)C1=O] | A | 9 | 2.97 | 496.07 |

-continued

| Example | Structure | Synthetic method | LC method | Rt time [min] | MS [M + H+] ES+ |
|---|---|---|---|---|---|
| 312 | 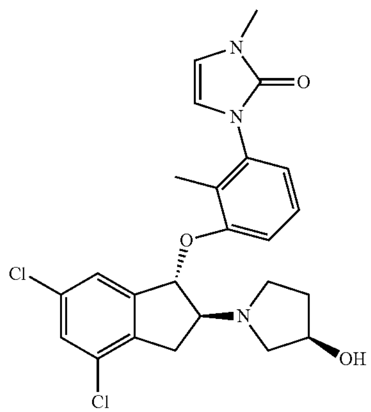 [SMILES: Cc1c(O[C@H]2c3cc(Cl)cc(Cl)c3C[C@@H]2N2CC[C@@H](O)C2)cccc1-n1ccn(C)c1=O] | A | 17 | 2.67 | 474.19 |
| 313 | 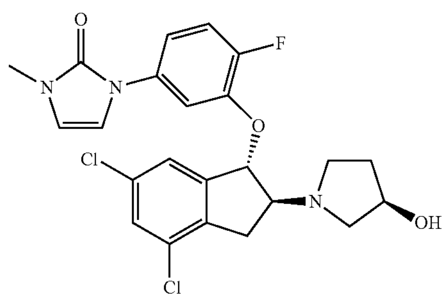 | A | 17 | 2.72 | 478.13 |
| 314 | 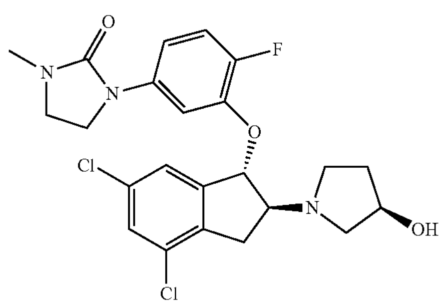 [SMILES: CN1CCN(c2ccc(F)c(O[C@H]3c4cc(Cl)cc(Cl)c4C[C@@H]3N3CC[C@@H](O)C3)c2)C1=O] | A | 17 | 2.80 | 480.15 |
| 315 | 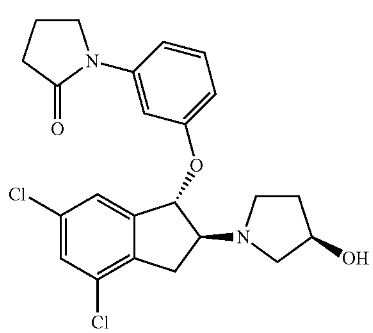 [SMILES: O=C1CCCN1c1cccc(O[C@H]2c3cc(Cl)cc(Cl)c3C[C@@H]2N2CC[C@@H](O)C2)c1] | A | 9 | 2.85 | 447.07 |

| Example | Structure | Synthetic method | LC method | Rt time [min] | MS [M + H+] ES+ |
|---|---|---|---|---|---|
| 316 | 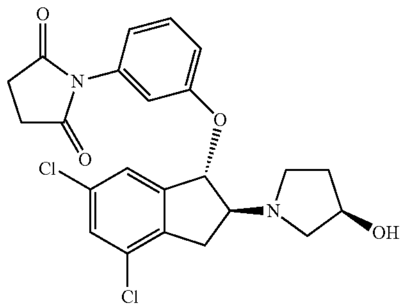 [SMILES: O=C1CCC(=O)N1c1cccc(O[C@H]2c3cc(Cl)cc(Cl)c3C[C@@H]2N2CC[C@@H](O)C2)c1] | A | 9 | 2.68 | 461.08 |
| 317 | 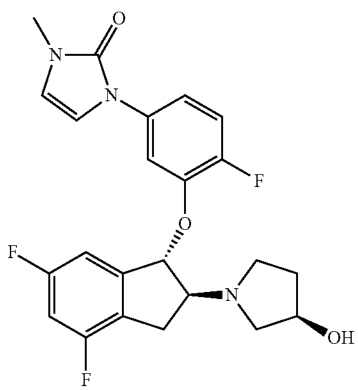 [SMILES: Cn1ccn(-c2ccc(F)c(O[C@H]3c4cc(F)cc(F)c4C[C@@H]3N3CC[C@@H](O)C3)c2)c1=O] | A | 9 | 2.70 | 446.30 |
| 318 | 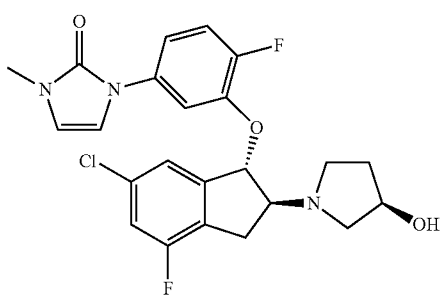 [SMILES: Cn1ccn(-c2ccc(F)c(O[C@H]3c4cc(Cl)cc(F)c4C[C@@H]3N3CC[C@@H](O)C3)c2)c1=O] | A | 17 | 2.60 | 462.17 |
| 319 | 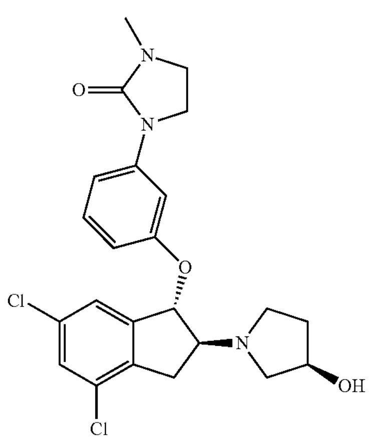 [SMILES: CN1CCN(c2cccc(O[C@H]3c4cc(Cl)cc(Cl)c4C[C@@H]3N3CC[C@@H](O)C3)c2)C1=O] | A | 1 | 2.77 | 462.05 |

| Example | Structure | Synthetic method | LC method | Rt time [min] | MS [M + H+] ES+ |
|---------|-----------|------------------|-----------|---------------|-----------------|
| 320 | 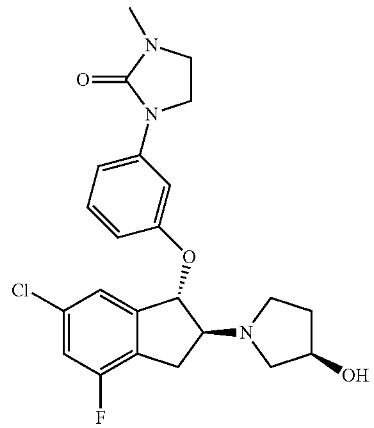 [SMILES: CN1CCN(c2cccc(O[C@H]3c4cc(Cl)cc(F)c4C[C@@H]3N3CC[C@@H](O)C3)c2)C1=O] | A | 9 | 2.74 | 446.08 |
| 321 | 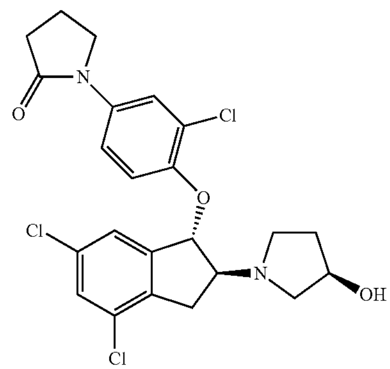 [SMILES: O=C1CCCN1c1ccc(O[C@H]2c3cc(Cl)cc(Cl)c3C[C@@H]2N2CC[C@@H](O)C2)c(Cl)c1] | A | 9 | 2.87 | 481.03 |
| 322 | 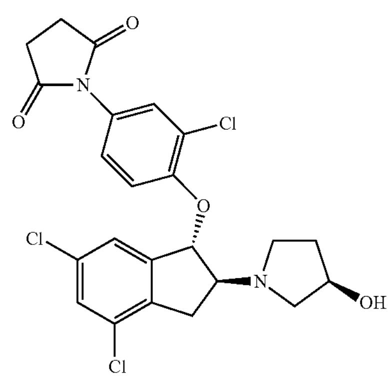 [SMILES: O=C1CCC(=O)N1c1ccc(O[C@H]2c3cc(Cl)cc(Cl)c3C[C@@H]2N2CC[C@@H](O)C2)c(Cl)c1] | A | 9 | 2.72 | 495.04 |
| 323 | 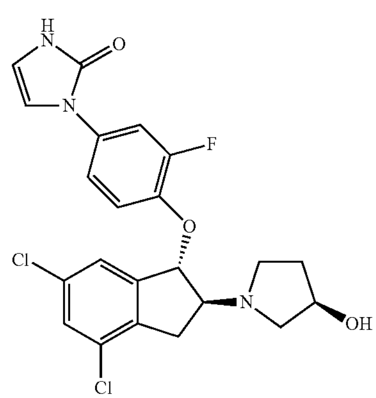 [SMILES: O=c1[nH]ccn1-c1ccc(O[C@H]2c3cc(Cl)cc(Cl)c3C[C@@H]2N2CC[C@@H](O)C2)c(F)c1] | A | 9 | 2.54 | 464.10 |

-continued

| Example | Structure | Synthetic method | LC method | Rt time [min] | MS [M + H+] ES+ |
|---------|-----------|------------------|-----------|---------------|-----------------|
| 324 | 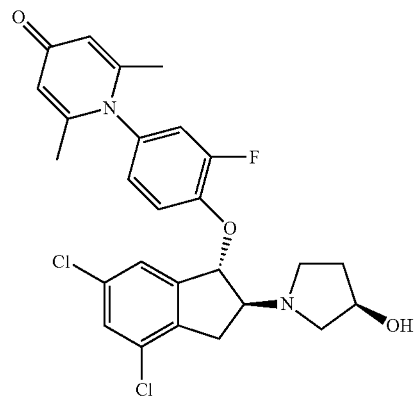 [SMILES: Cc1cc(=O)cc(C)n1-c1ccc(O[C@H]2c3cc(Cl)cc(Cl)c3C[C@@H]2N2CC[C@@H](O)C2)c(F)c1] | A | 17 | 2.43 | 503.16 |
| 325 | 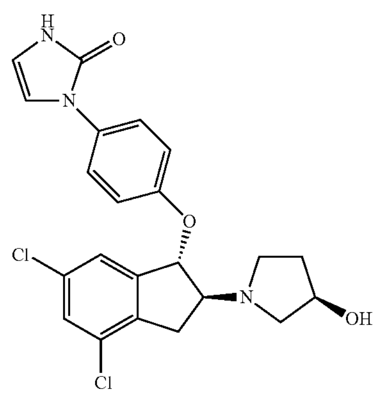 [SMILES: O=c1[nH]ccn1-c1ccc(O[C@H]2c3cc(Cl)cc(Cl)c3C[C@@H]2N2CC[C@@H](O)C2)cc1] | A | 9 | 2.59 | 446.04 |
| 326 | 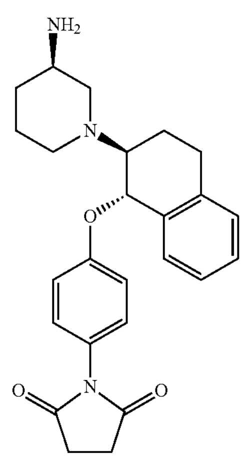 [SMILES: N[C@@H]1CCCN([C@H]2CCc3ccccc3[C@@H]2Oc2ccc(N3C(=O)CCC3=O)cc2)C1] | A | 1 | 2.17 | 420.17 |

-continued

| Example | Structure | Synthetic method | LC method | Rt time [min] | MS [M + H+] ES+ |
|---|---|---|---|---|---|
| 327 | 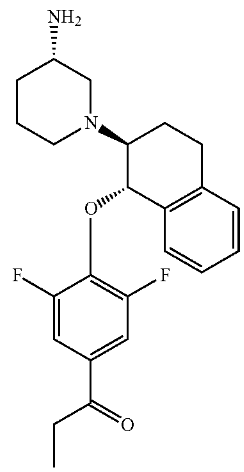 [SMILES: CCC(=O)c1cc(F)c(O[C@H]2c3ccccc3CC[C@@H]2N2CCC[C@H](N)C2)c(F)c1] | A | 1 | 2.70 | 415.18 |
| 328 | 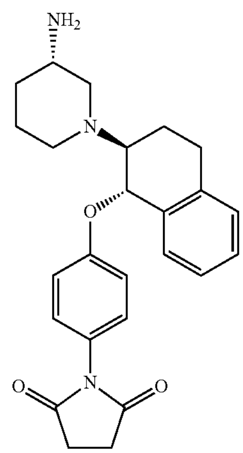 [SMILES: N[C@H]1CCCN([C@H]2CCc3ccccc3[C@@H]2Oc2ccc(N3C(=O)CCC3=O)cc2)C1] | A | 1 | 2.15 | 420.17 |
| 329 | 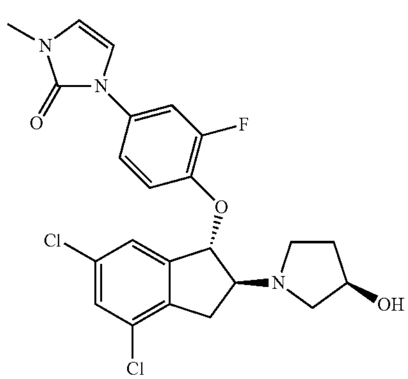 [SMILES: Cn1ccn(-c2ccc(O[C@H]3c4cc(Cl)cc(Cl)c4C[C@@H]3N3CC[C@@H](O)C3)c(F)c2)c1=O] | A | 1 | 2.67 | 478.09 |

| Example | Structure | Synthetic method | LC method | Rt time [min] | MS [M + H+] ES+ |
|---|---|---|---|---|---|
| 330 | 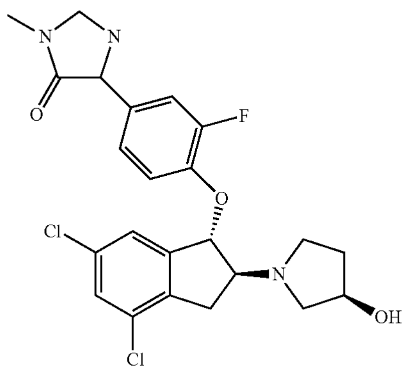 [SMILES: CN1CNC(c2ccc(O[C@H]3c4cc(Cl)cc(Cl)c4C[C@@H]3N3CC[C@@H](O)C3)c(F)c2)C1=O] | A | 9 | 2.79 | 480.05 |
| 331 | 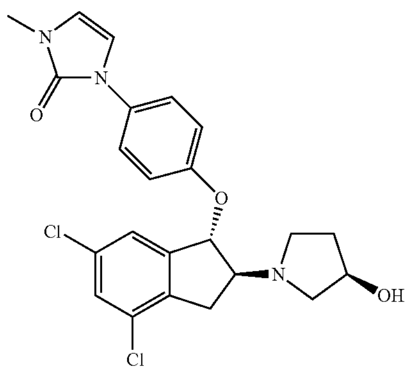 [SMILES: Cn1ccn(-c2ccc(O[C@H]3c4cc(Cl)cc(Cl)c4C[C@@H]3N3CC[C@@H](O)C3)cc2)c1=O] | A | 1 | 2.62 | 460.1 |
| 332 | 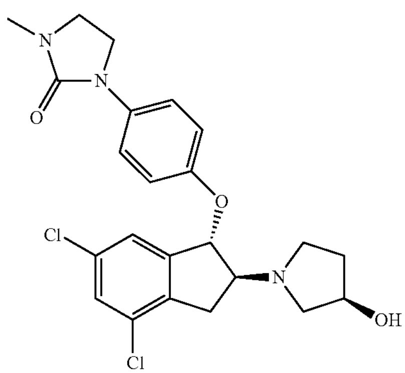 [SMILES: CN1CCN(c2ccc(O[C@H]3c4cc(Cl)cc(Cl)c4C[C@@H]3N3CC[C@@H](O)C3)cc2)C1=O] | A | 9 | 2.75 | 462.06 |
| 333 | 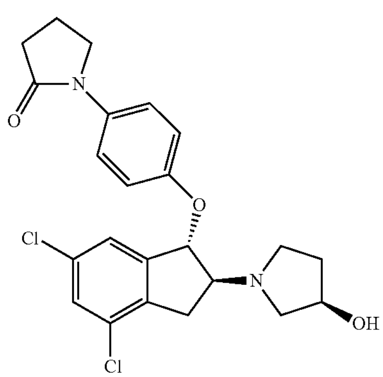 [SMILES: O=C1CCCN1c1ccc(O[C@H]2c3cc(Cl)cc(Cl)c3C[C@@H]2N2CC[C@@H](O)C2)cc1] | A | 9 | 2.71 | 447.05 |

-continued
| Example | Structure | Synthetic method | LC method | Rt time [min] | MS [M + H+] ES+ |
|---|---|---|---|---|---|
| 334 | 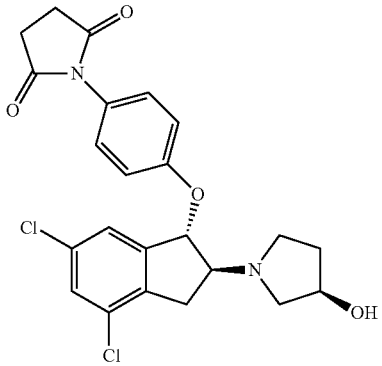 [SMILES: O=C1CCC(=O)N1c1ccc(O[C@H]2c3cc(Cl)cc(Cl)c3C[C@@H]2N2CC[C@@H](O)C2)cc1] | A | 9 | 2.59 | 461.04 |
| 335 | 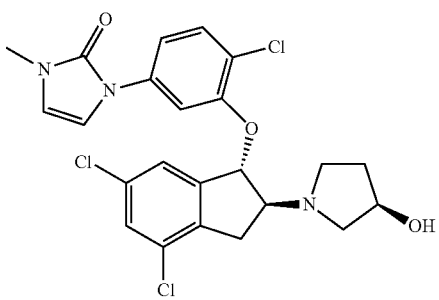 [SMILES: Cn1ccn(-c2ccc(Cl)c(O[C@H]3c4cc(Cl)cc(Cl)c4C[C@@H]3N3CC[C@@H](O)C3)c2)c1=O] | A | 9 | 2.86 | 494.03 |
| 336 | 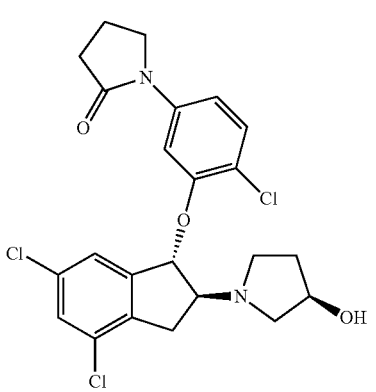 [SMILES: O=C1CCCN1c1ccc(Cl)c(O[C@H]2c3cc(Cl)cc(Cl)c3C[C@@H]2N2CC[C@@H](O)C2)c1] | A | 9 | 2.90 | 481.01 |
| 337 | 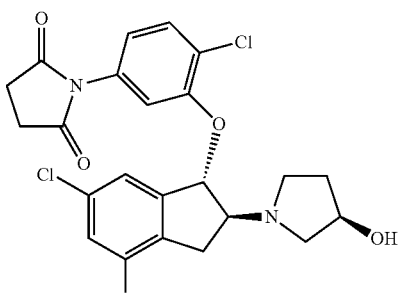 | A | 9 | 2.82 | 495.05 |

-continued

| Example | Structure | Synthetic method | LC method | Rt time [min] | MS [M + H+] ES+ |
|---|---|---|---|---|---|
| 338 | 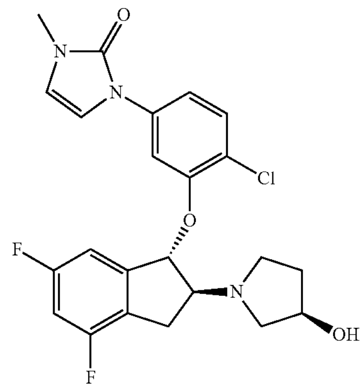 [SMILES: Cn1ccn(-c2ccc(Cl)c(O[C@H]3c4cc(F)cc(F)c4C[C@@H]3N3CC[C@@H](O)C3)c2)c1=O] | A | 9 | 2.58 | 462.29 |
| 339 | 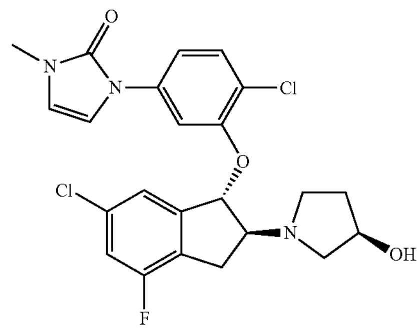 [SMILES: Cn1ccn(-c2ccc(Cl)c(O[C@H]3c4cc(Cl)cc(F)c4C[C@@H]3N3CC[C@@H](O)C3)c2)c1=O] | A | 9 | 2.78 | 478.04 |
| 340 | 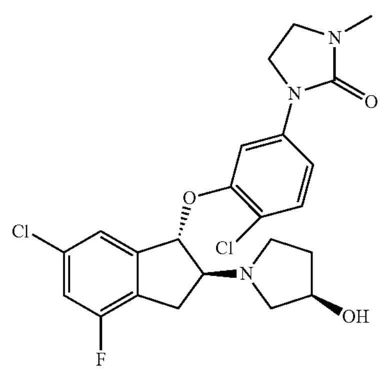 [SMILES: CN1CCN(c2ccc(Cl)c(O[C@H]3c4cc(Cl)cc(F)c4C[C@@H]3N3CC[C@@H](O)C3)c2)C1=O] | A | 9 | 2.97 | 480.10 |
| 341 | 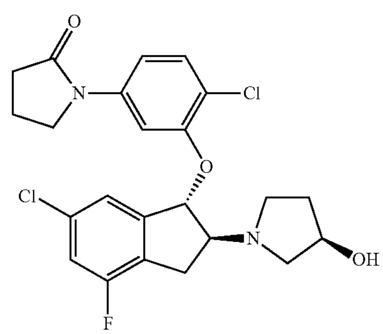 [SMILES: O=C1CCCN1c1ccc(Cl)c(O[C@H]2c3cc(Cl)cc(F)c3C[C@@H]2N2CC[C@@H](O)C2)c1] | A | 9 | 2.74 | 465.11 |

-continued

| Example | Structure | Synthetic method | LC method | Rt time [min] | MS [M + H+] ES+ |
|---|---|---|---|---|---|
| 342 | 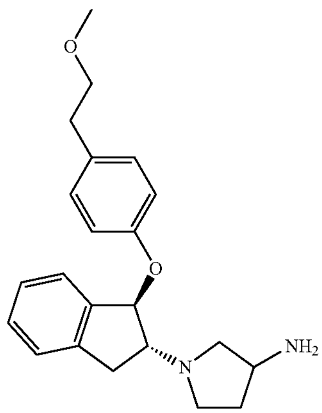 [SMILES: COCCc1ccc(O[C@@H]2c3ccccc3C[C@H]2N2CCC(N)C2)cc1] | A | 12 | 1.16 | 353.16 |
| 343 | 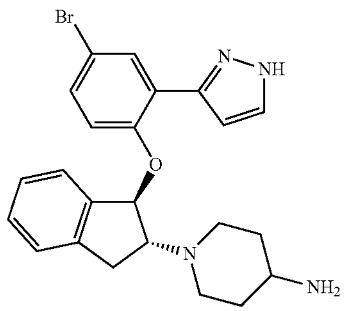 [SMILES: NC1CCN([C@@H]2Cc3ccccc3[C@H]2Oc2ccc(Br)cc2-c2cc[nH]n2)CC1] | A | 11 | 1.16 | 453.12 |
| 344 | 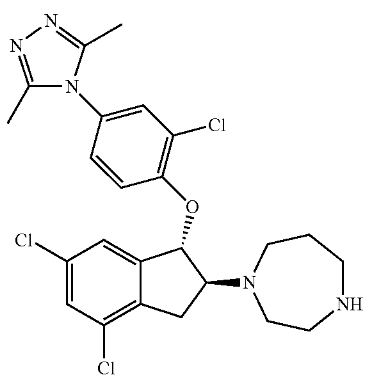 [SMILES: Cc1nnc(C)n1-c1ccc(O[C@H]2c3cc(Cl)cc(Cl)c3C[C@@H]2N2CCCNCC2)c(Cl)c1] | A | 9 | 2.17 | 506.12 |
| 345 | 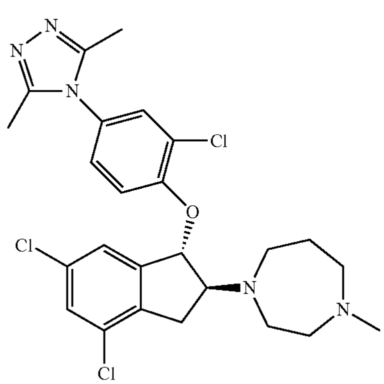 | A | 1 | 2.65 | 520.24 |

-continued

| Example | Structure | Synthetic method | LC method | Rt time [min] | MS [M + H+] ES+ |
|---|---|---|---|---|---|
| 346 | 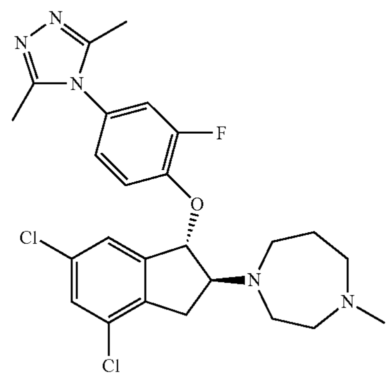 | A | 1 | 2.59 | 504.26 |
| 347 | 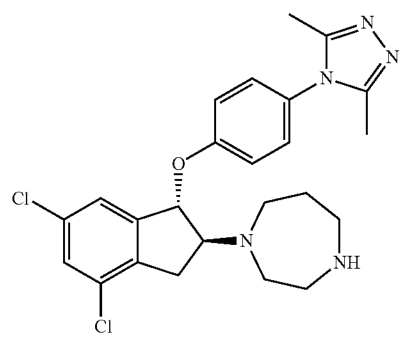 [SMILES: Cc1nnc(C)n1-c1ccc(O[C@H]2c3cc(Cl)cc(Cl)c3C[C@@H]2N2CCCNCC2)cc1] | A | 14 | 1.73 | 472.23 |
| 348 | 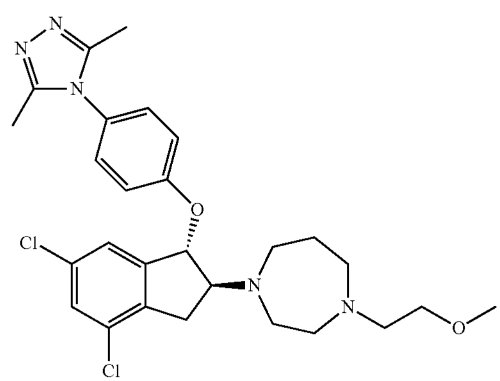 | A | 9 | 2.40 | 530.34 |
| 349 | 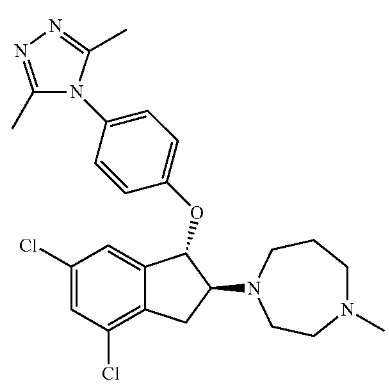 | A | 9 | 2.32 | 486.18 |

-continued
| Example | Structure | Synthetic method | LC method | Rt time [min] | MS [M + H+] ES+ |
|---|---|---|---|---|---|
| 350 | 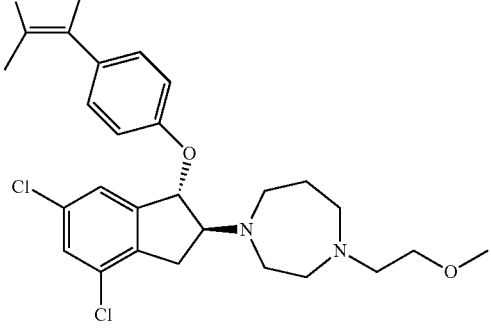 | A | 9 | 3.03 | 530.25 |
| 351 | 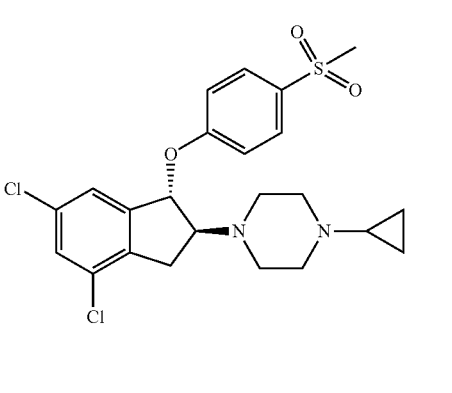 [SMILES: CS(=O)(=O)c1ccc(O[C@H]2c3cc(Cl)cc(Cl)c3C[C@@H]2N2CCN(C3CC3)CC2)cc1] | A | 4 | 1.39 | 481.14 |
| 352 | 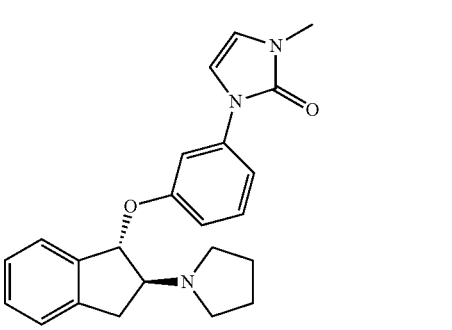 [SMILES: Cn1ccn(-c2cccc(O[C@H]3c4ccccc4C[C@@H]3N3CCCC3)c2)c1=O] | A | 4 | 1.30 | 376.13 |
| 353 | 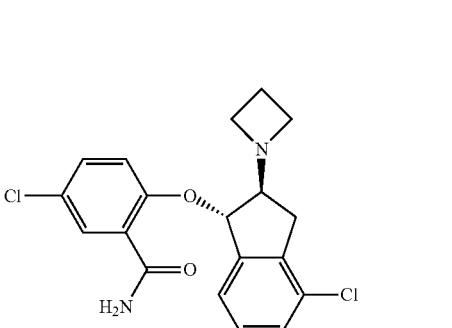 | A | 2 | 1.85 | 411.07 |

-continued

| Example | Structure | Synthetic method | LC method | Rt time [min] | MS [M + H+] ES+ |
|---------|-----------|------------------|-----------|---------------|-----------------|
| 354 | 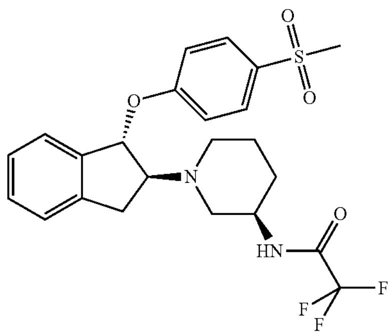 [SMILES: CS(=O)(=O)c1ccc(O[C@H]2c3ccccc3C[C@@H]2N2CCC[C@@H](NC(=O)C(F)(F)F)C2)cc1] | A | 14 | 1.83 | 483.08 |
| 355 | 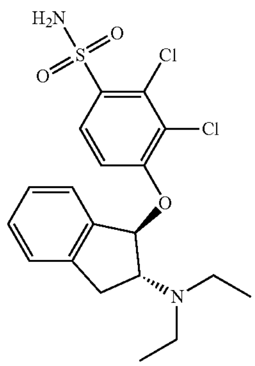 [SMILES: CCN(CC)[C@@H]1Cc2ccccc2[C@H]1Oc1ccc(S(N)(=O)=O)c(Cl)c1Cl] | A | 12 | 1.37 | 429.06 |
| 356 | 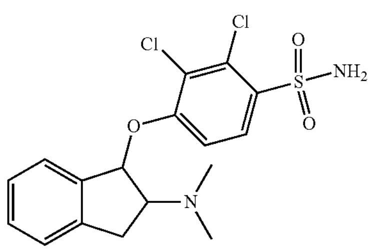 [SMILES: CN(C)C1Cc2ccccc2C1Oc1ccc(S(N)(=O)=O)c(Cl)c1Cl] | A | 12 | 1.24 | 401.15 |
| 357 | 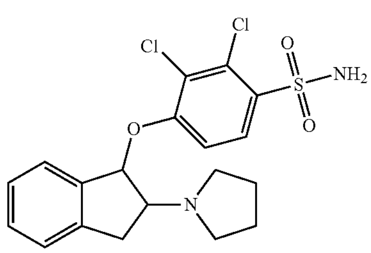 [SMILES: NS(=O)(=O)c1ccc(OC2c3ccccc3CC2N2CCCC2)c(Cl)c1Cl] | A | 4 | 1.19 | 427.15 |
| 358 | 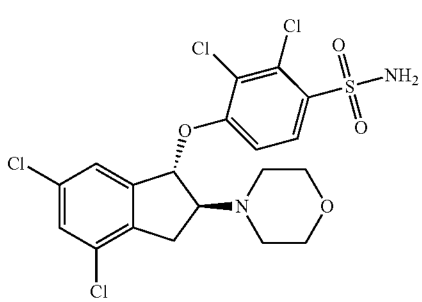 [SMILES: NS(=O)(=O)c1ccc(O[C@H]2c3cc(Cl)cc(Cl)c3C[C@@H]2N2CCOCC2)c(Cl)c1Cl] | A | 4 | 1.42 | 511.11 |

-continued
| Example | Structure | Synthetic method | LC method | Rt time [min] | MS [M + H+] ES+ |
|---|---|---|---|---|---|
| 359 | 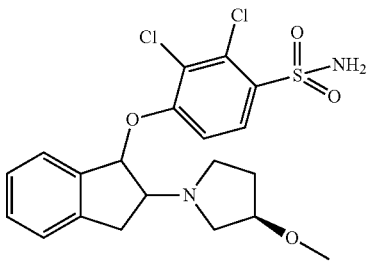 [SMILES: CO[C@@H]1CCN(C2Cc3ccccc3C2Oc2ccc(S(N)(=O)=O)c(Cl)c2Cl)C1] | A | 4 | 1.20 | 457.07 |
| 360 | 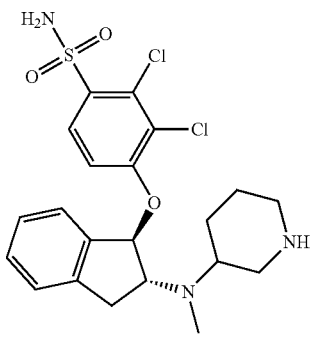 [SMILES: CN(C1CCCNC1)[C@@H]1Cc2ccccc2[C@H]1Oc1ccc(S(N)(=O)=O)c(Cl)c1Cl] | A | 12 | 1.18 | 470.13 |
| 361 | 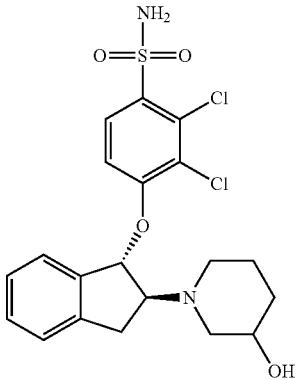 [SMILES: NS(=O)(=O)c1ccc(O[C@H]2c3ccccc3C[C@@H]2N2CCCC(O)C2)c(Cl)c1Cl] | A | 4 | 1.14 | 457.1 |
| 362 | 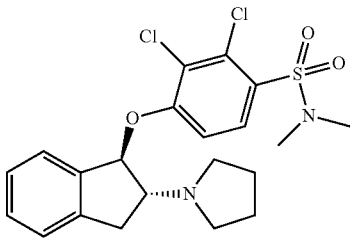 [SMILES: CN(C)S(=O)(=O)c1ccc(O[C@@H]2c3ccccc3C[C@H]2N2CCCC2)c(Cl)c1Cl] | A | 4 | 1.39 | 455.16 |
| 363 | 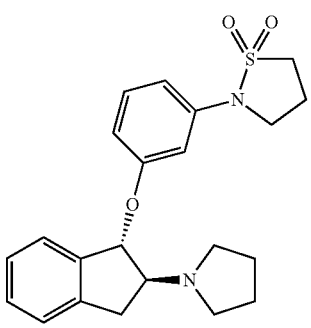 [SMILES: O=S1(=O)CCCN1c1cccc(O[C@H]2c3ccccc3C[C@@H]2N2CCCC2)c1] | A | 9 | 2.43 | 399.13 |

-continued

| Example | Structure | Synthetic method | LC method | Rt time [min] | MS [M + H+] ES+ |
|---------|-----------|------------------|-----------|---------------|-----------------|
| 364 | 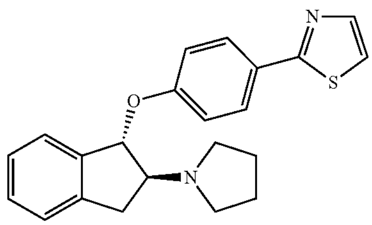 [SMILES: c1ccc2c(c1)C[C@H](N1CCCC1)[C@H]2Oc1ccc(-c2nccs2)cc1] | A | 3 | 1.41 | 363.32 |
| 365 | 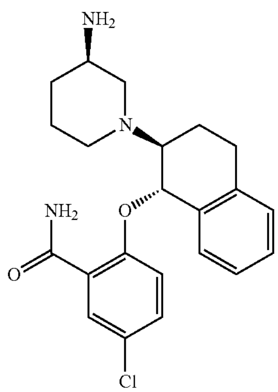 [SMILES: NC(=O)c1cc(Cl)ccc1O[C@H]1c2ccccc2CC[C@@H]1N1CCC[C@@H](N)C1] | A | 1 | 2.34 | 400.12 |
| 366 | 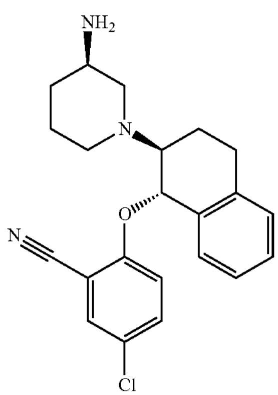 [SMILES: N#Cc1cc(Cl)ccc1O[C@H]1c2ccccc2CC[C@@H]1N1CCC[C@@H](N)C1] | A | 1 | 2.55 | 382.09 |
| 367 | 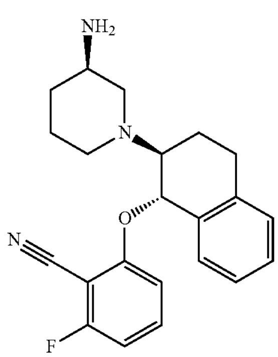 [SMILES: N#Cc1c(F)cccc1O[C@H]1c2ccccc2CC[C@@H]1N1CCC[C@@H](N)C1] | A | 9 | 2.40 | 366.16 |

| Example | Structure | Synthetic method | LC method | Rt time [min] | MS [M + H+] ES+ |
|---|---|---|---|---|---|
| 368 | 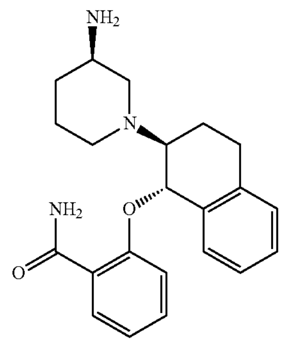 [SMILES: NC(=O)c1ccccc1O[C@H]1c2ccccc2CC[C@@H]1N1CCC[C@@H](N)C1] | A | 1 | 2.12 | 366.18 |
| 369 | 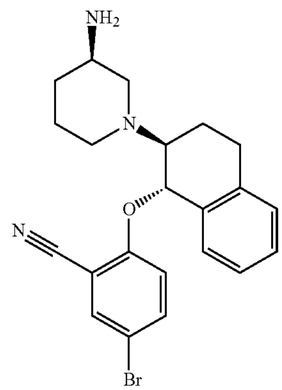 [SMILES: N#Cc1cc(Br)ccc1O[C@H]1c2ccccc2CC[C@@H]1N1CCC[C@@H](N)C1] | A | 1 | 2.59 | 426.04 |
| 370 | 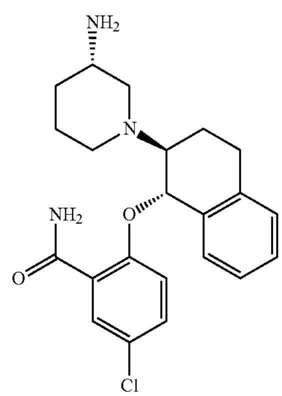 [SMILES: NC(=O)c1cc(Cl)ccc1O[C@H]1c2ccccc2CC[C@@H]1N1CCC[C@H](N)C1] | A | 1 | 2.29 | 400.11 |
| 371 | 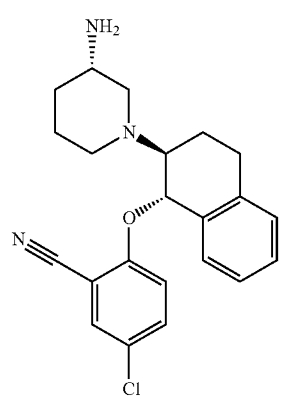 [SMILES: N#Cc1cc(Cl)ccc1O[C@H]1c2ccccc2CC[C@@H]1N1CCC[C@H](N)C1] | A | 1 | 2.57 | 382.12 |

| Example | Structure | Synthetic method | LC method | Rt time [min] | MS [M + H+] ES+ |
|---|---|---|---|---|---|
| 372 | 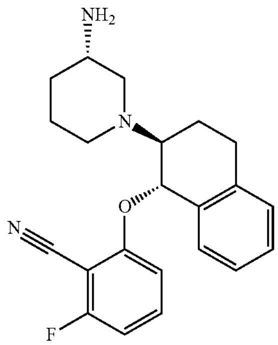 [SMILES: N#Cc1c(F)cccc1O[C@H]1c2ccccc2CC[C@@H]1N1CCC[C@H](N)C1] | A | 1 | 2.48 | 366.13 |
| 373 | 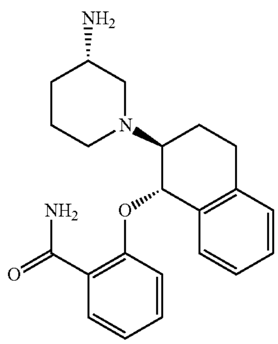 [SMILES: NC(=O)c1ccccc1O[C@H]1c2ccccc2CC[C@@H]1N1CCC[C@H](N)C1] | A | 1 | 2.12 | 366.18 |
| 374 | 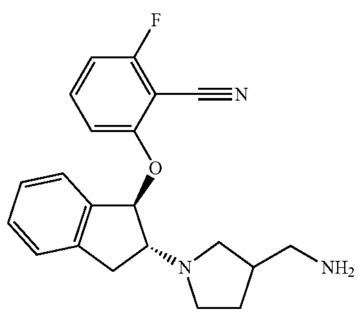 [SMILES: N#Cc1c(F)cccc1O[C@@H]1c2ccccc2C[C@H]1N1CCC(CN)C1] | A | 12 | 1.18 | 352.20 |
| 375 | 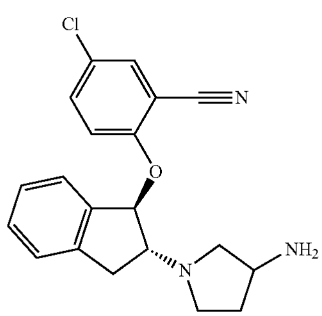 [SMILES: N#Cc1cc(Cl)ccc1O[C@@H]1c2ccccc2C[C@H]1N1CCC(N)C1] | A | 12 | 1.27 | 354.11 |

-continued

| Example | Structure | Synthetic method | LC method | Rt time [min] | MS [M + H+] ES+ |
|---|---|---|---|---|---|
| 376 | 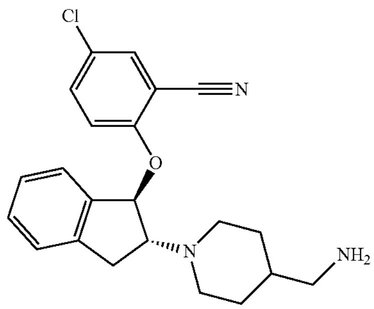 [SMILES: N#Cc1cc(Cl)ccc1O[C@@H]1c2ccccc2C[C@H]1N1CCC(CN)CC1] | A | 12 | 1.22 | 382.16 |
| 377 | 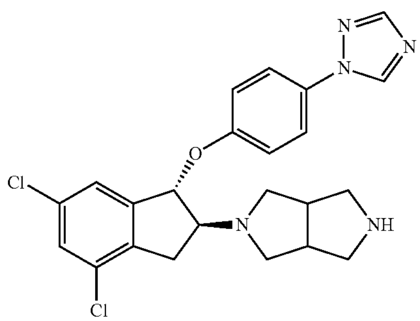 [SMILES: Clc1cc(Cl)c2c(c1)[C@H](Oc1ccc(-n3cncn3)cc1)[C@@H](N1CC3CNCC3C1)C2] | A | 4 | 1.17 | 456.2 |
| 378 | 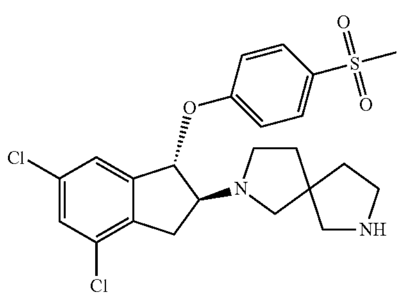 [SMILES: CS(=O)(=O)c1ccc(O[C@H]2c3cc(Cl)cc(Cl)c3C[C@@H]2N2CCC3(CCNC3)C2)cc1] | A | 14 | 1.74 | 481.17 |
| 379 | 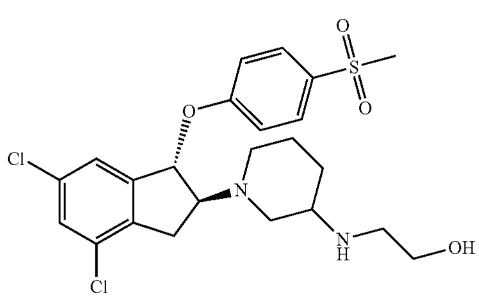 [SMILES: CS(=O)(=O)c1ccc(O[C@H]2c3cc(Cl)cc(Cl)c3C[C@@H]2N2CCCC(NCCO)C2)cc1] | A | 4 | 1.36 | 499.02 |

-continued

| Example | Structure | Synthetic method | LC method | Rt time [min] | MS [M + H+] ES+ |
|---|---|---|---|---|---|
| 380 | 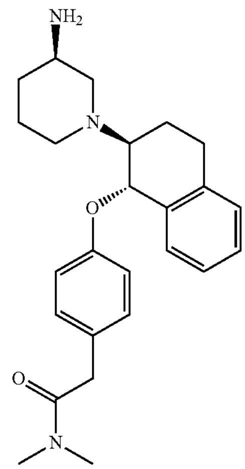 [SMILES: CN(C)C(=O)Cc1ccc(O[C@H]2c3ccccc3CC[C@@H]2N2CCC[C@@H](N)C2)cc1] | A | 1 | 2.27 | 408.19 |
| 381 | 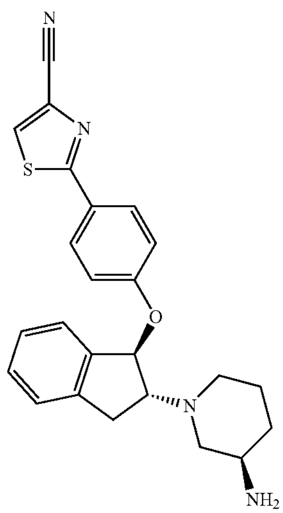 [SMILES: N#Cc1csc(-c2ccc(O[C@@H]3c4ccccc4C[C@H]3N3CCC[C@@H](N)C3)cc2)n1] | A | 12 | 1.28 | 417.17 |
| 382 | 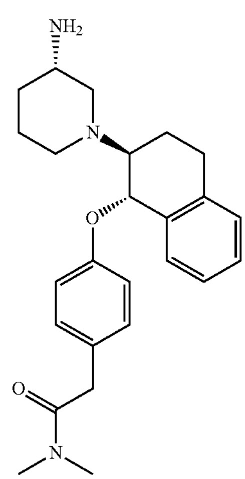 [SMILES: CN(C)C(=O)Cc1ccc(O[C@H]2c3ccccc3CC[C@@H]2N2CCC[C@H](N)C2)cc1] | A | 1 | 2.25 | 408.19 |

-continued

| Example | Structure | Synthetic method | LC method | Rt time [min] | MS [M + H+] ES+ |
|---------|-----------|------------------|-----------|---------------|-----------------|
| 383 | 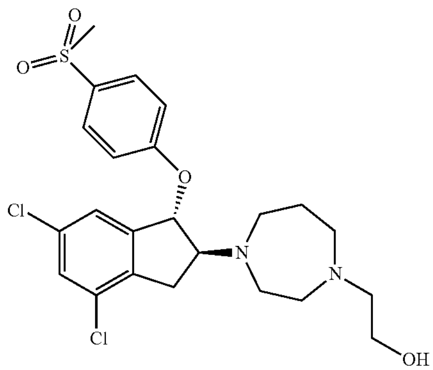 [SMILES: CS(=O)(=O)c1ccc(O[C@H]2c3cc(Cl)cc(Cl)c3C[C@@H]2N2CCCN(CCO)CC2)cc1] | A | 4 | 1.28 | 499.18 |
| 384 | 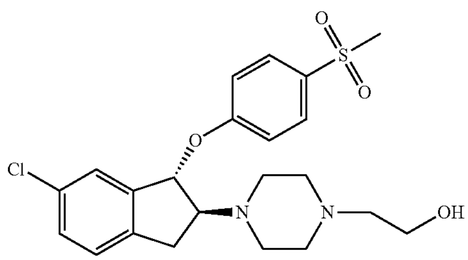 [SMILES: CS(=O)(=O)c1ccc(O[C@H]2c3cc(Cl)ccc3C[C@@H]2N2CCN(CCO)CC2)cc1] | A | 4 | 1.20 | 451.3 |
| 385 | 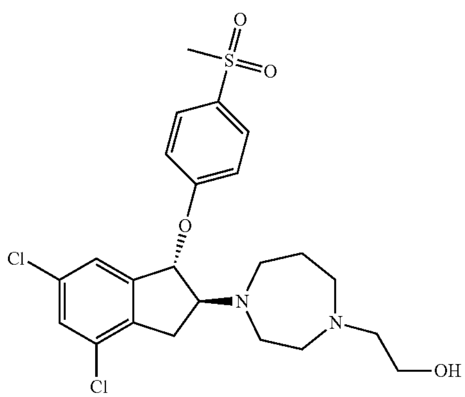 [SMILES: CS(=O)(=O)c1ccc(O[C@H]2c3cc(Cl)cc(Cl)c3C[C@@H]2N2CCCN(CCO)CC2)cc1] | A | 14 | 1.91 | 499.22 |
| 386 | 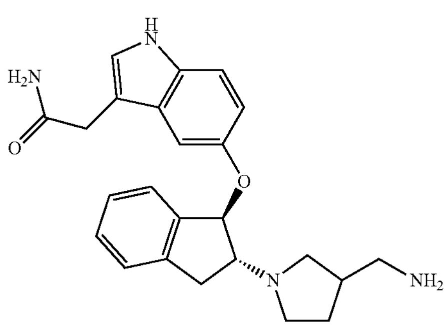 [SMILES: NCC1CCN([C@@H]2Cc3ccccc3[C@H]2Oc2ccc3[nH]cc(CC(N)=O)c3c2)C1] | A | 12 | 0.97 | 405.27 |

-continued
| Example | Structure | Synthetic method | LC method | Rt time [min] | MS [M + H+] ES+ |
|---|---|---|---|---|---|
| 387 | 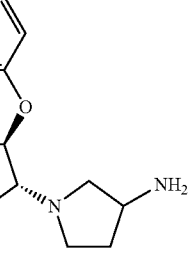 | A | 11 | 0.94 | 391.19 |
| 388 | 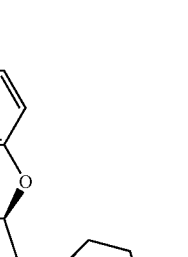 | A | 12 | 0.97 | 419.27 |
| 392 | 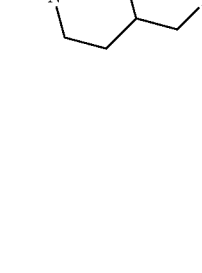 | A | 4 | 1.31 | 339.14 |
| 393 | 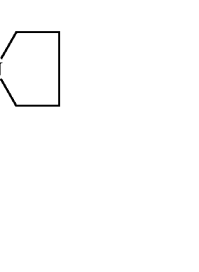 | A | 12 | 1.25 | 380.20 |

-continued

| Example | Structure | Synthetic method | LC method | Rt time [min] | MS [M + H+] ES+ |
|---------|-----------|------------------|-----------|---------------|-----------------|
| 394 | 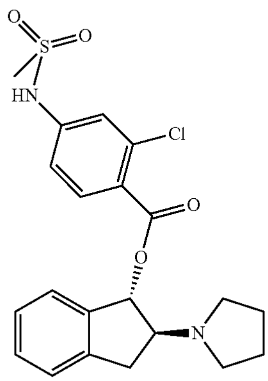 [SMILES: CS(=O)(=O)Nc1ccc(C(=O)O[C@H]2c3ccccc3C[C@@H]2N2CCCC2)c(Cl)c1] | A | 15 | 1.85 | 435.07 |
| 395 | 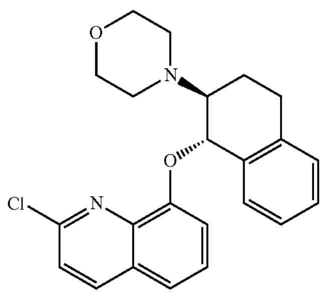 [SMILES: Clc1ccc2cccc(O[C@H]3c4ccccc4CC[C@@H]3N3CCOCC3)c2n1] | A | 1 | 2.72 | 395.11 |
| 396 | 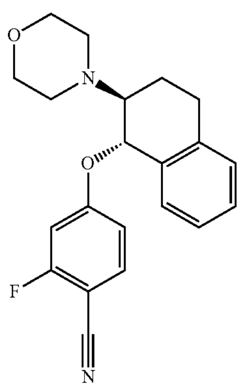 [SMILES: N#Cc1ccc(O[C@H]2c3ccccc3CC[C@@H]2N2CCOCC2)cc1F] | A | 1 | 2.64 | 353.13 |
| 397 | 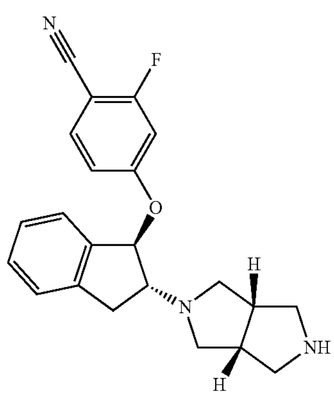 [SMILES: N#Cc1ccc(O[C@@H]2c3ccccc3C[C@H]2N2C[C@H]3CNC[C@H]3C2)cc1F] | A | 12 | 1.20 | 364.23 |

-continued

| Example | Structure | Synthetic method | LC method | Rt time [min] | MS [M + H+] ES+ |
|---|---|---|---|---|---|
| 398 | 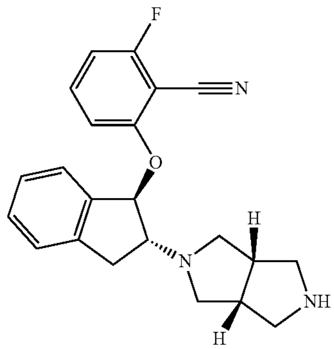 [SMILES: N#Cc1c(F)cccc1O[C@@H]1c2ccccc2C[C@H]1N1C[C@H]2CNC[C@H]2C1] | A | 12 | 1.16 | 364.22 |
| 399 | 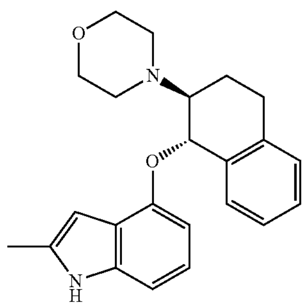 [SMILES: Cc1cc2c(O[C@H]3c4ccccc4CC[C@@H]3N3CCOCC3)cccc2[nH]1] | A | 1 | 2.65 | 363.17 |
| 400 | 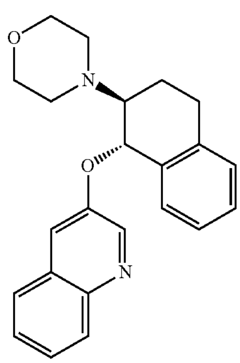 [SMILES: c1ccc2c(c1)CC[C@H](N1CCOCC1)[C@H]2Oc1cnc2ccccc2c1] | A | 1 | 2.37 | 361.14 |
| 401 | 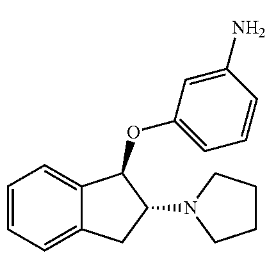 [SMILES: Nc1cccc(O[C@@H]2c3ccccc3C[C@H]2N2CCCC2)c1] | A | 12 | 0.84 | 295.31 |

-continued

| Example | Structure | Synthetic method | LC method | Rt time [min] | MS [M + H+] ES+ |
|---------|-----------|------------------|-----------|---------------|-----------------|
| 402 | 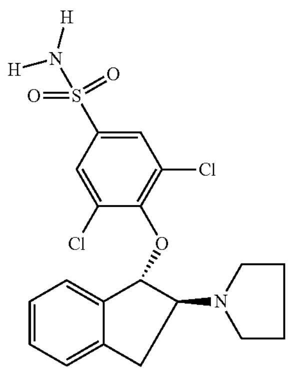 [SMILES: NS(=O)(=O)c1cc(Cl)c(O[C@H]2c3ccccc3C[C@@H]2N2CCCC2)c(Cl)c1] | A | 14 | 1.69 | 427.13 |
| 403 | 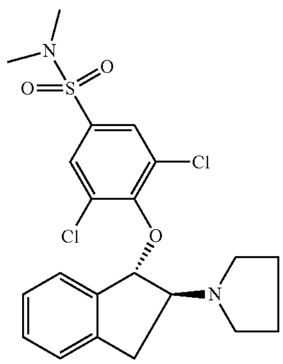 [SMILES: CN(C)S(=O)(=O)c1cc(Cl)c(O[C@H]2c3ccccc3C[C@@H]2N2CCCC2)c(Cl)c1] | A | 14 | 2.01 | 455.1 |
| 404 | 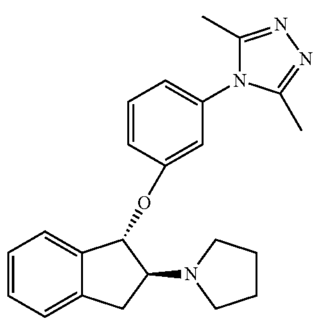 [SMILES: Cc1nnc(C)n1-c1cccc(O[C@H]2c3ccccc3C[C@@H]2N2CCCC2)c1] | A | 14 | 1.44 | 375.24 |
| 405 | 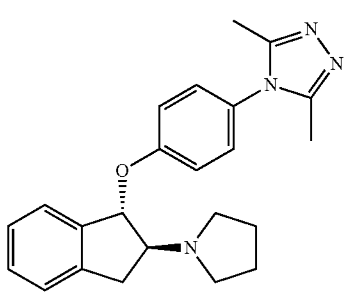 [SMILES: Cc1nnc(C)n1-c1ccc(O[C@H]2c3ccccc3C[C@@H]2N2CCCC2)cc1] | A | 14 | 1.50 | 375.24 |

-continued

| Example | Structure | Synthetic method | LC method | Rt time [min] | MS [M + H+] ES+ |
|---|---|---|---|---|---|
| 406 | 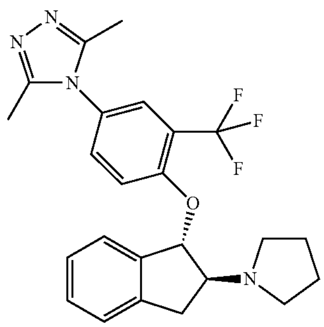 [SMILES: Cc1nnc(C)n1-c1ccc(O[C@H]2c3ccccc3C[C@@H]2N2CCCC2)c(C(F)(F)F)c1] | A | 9 | 2.22 | 443.13 |
| 407 | 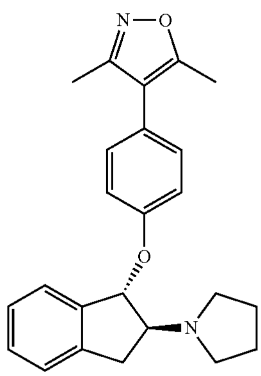 [SMILES: Cc1noc(C)c1-c1ccc(O[C@H]2c3ccccc3C[C@@H]2N2CCCC2)cc1] | A | 1 | 2.85 | 375.12 |
| 408 | 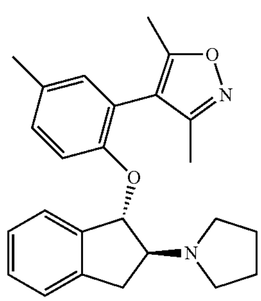 [SMILES: Cc1ccc(O[C@H]2c3ccccc3C[C@@H]2N2CCCC2)c(-c2c(C)noc2C)c1] | A | 9 | 2.82 | 389.21 |
| 409 | 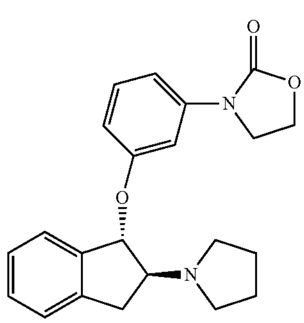 [SMILES: O=C1OCCN1c1cccc(O[C@H]2c3ccccc3C[C@@H]2N2CCCC2)c1] | A | 9 | 2.40 | 365.15 |

-continued

| Example | Structure | Synthetic method | LC method | Rt time [min] | MS [M + H+] ES+ |
|---|---|---|---|---|---|
| 410 | 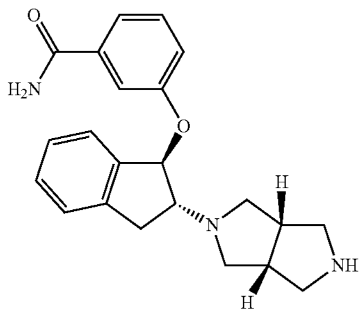 [SMILES: NC(=O)c1cccc(O[C@@H]2c3ccccc3C[C@H]2N2C[C@H]3CNC[C@H]3C2)c1] | A | 11 | 0.88 | 364.19 |
| 411 | 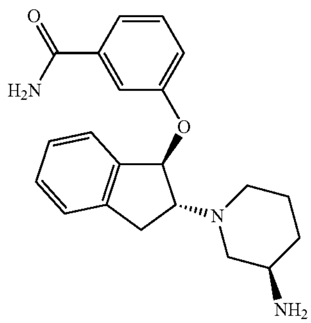 [SMILES: NC(=O)c1cccc(O[C@@H]2c3ccccc3C[C@H]2N2CCC[C@@H](N)C2)c1] | A | 12 | 0.92 | 352.22 |
| 412 | 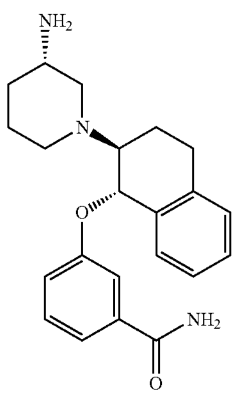 [SMILES: NC(=O)c1cccc(O[C@H]2c3ccccc3CC[C@@H]2N2CCC[C@H](N)C2)c1] | A | 1 | 2.10 | 366.18 |
| 413 | 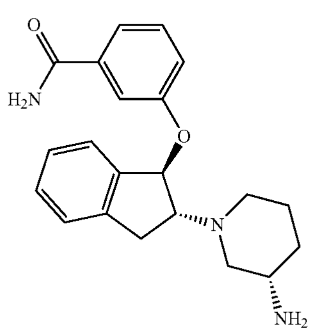 [SMILES: NC(=O)c1cccc(O[C@@H]2c3ccccc3C[C@H]2N2CCC[C@H](N)C2)c1] | A | 12 | 0.90 | 352.22 |

-continued

| Example | Structure | Synthetic method | LC method | Rt time [min] | MS [M + H+] ES+ |
|---|---|---|---|---|---|
| 414 | 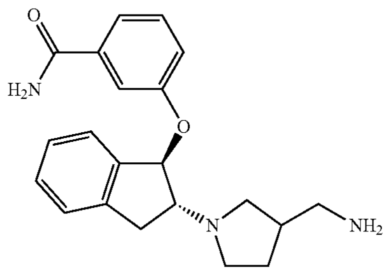 [SMILES: NCC1CCN([C@@H]2Cc3ccccc3[C@H]2Oc2cccc(C(N)=O)c2)C1] | A | 12 | 0.93 | 352.24 |
| 415 | 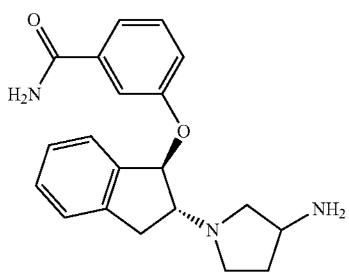 [SMILES: NC(=O)c1cccc(O[C@@H]2c3ccccc3C[C@H]2N2CCC(N)C2)c1] | A | 12 | 0.92 | 338.15 |
| 416 | 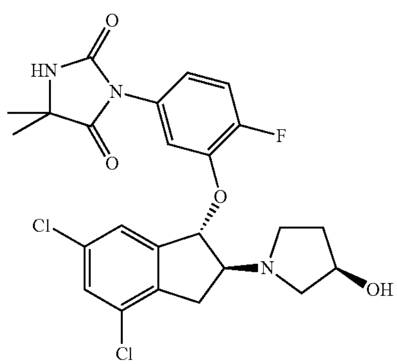 [SMILES: CC1(C)NC(=O)N(c2ccc(F)c(O[C@H]3c4cc(Cl)cc(Cl)c4C[C@@H]3N3CC[C@@H](O)C3)c2)C1=O] | A | 9 | 2.76 | 508.03 |
| 417 | 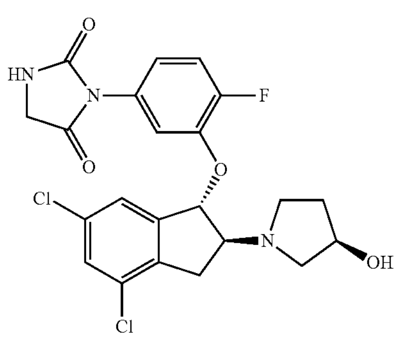 [SMILES: O=C1CNC(=O)N1c1ccc(F)c(O[C@H]2c3cc(Cl)cc(Cl)c3C[C@@H]2N2CC[C@@H](O)C2)c1] | A | 9 | 2.58 | 480.05 |

-continued

| Example | Structure | Synthetic method | LC method | Rt time [min] | MS [M + H+] ES+ |
|---|---|---|---|---|---|
| 418 | 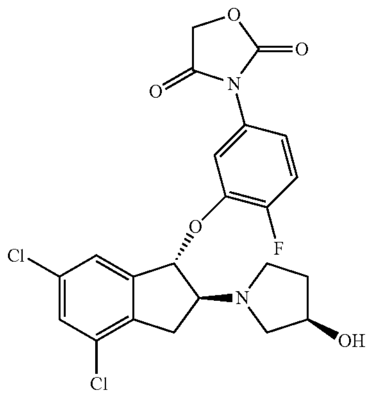 [SMILES: O=C1COC(=O)N1c1ccc(F)c(O[C@H]2c3cc(Cl)cc(Cl)c3C[C@@H]2N2CC[C@@H](O)C2)c1] | A | 17 | 2.74 | 481.12 |
| 419 | 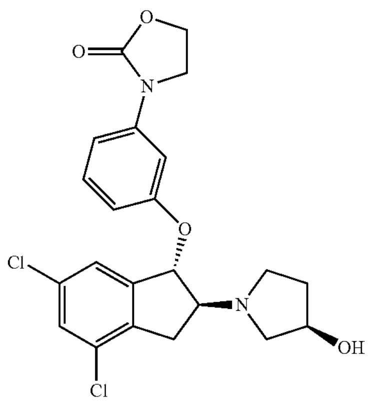 [SMILES: O=C1OCCN1c1cccc(O[C@H]2c3cc(Cl)cc(Cl)c3C[C@@H]2N2CC[C@@H](O)C2)c1] | A | 9 | 2.69 | 449.08 |
| 420 | 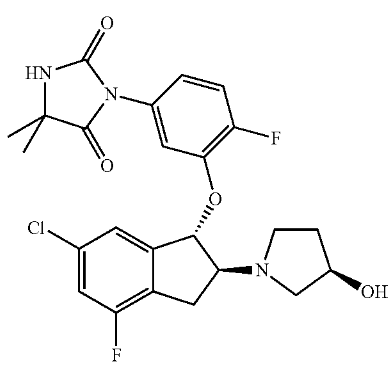 [SMILES: CC1(C)NC(=O)N(c2ccc(F)c(O[C@H]3c4cc(Cl)cc(F)c4C[C@@H]3N3CC[C@@H](O)C3)c2)C1=O] | A | 9 | 2.64 | 492.08 |
| 421 | 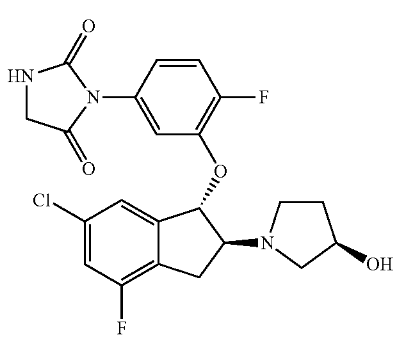 | A | 9 | 2.48 | 464.05 |

-continued

| Example | Structure | Synthetic method | LC method | Rt time [min] | MS [M + H+] ES+ |
|---|---|---|---|---|---|
| 422 | 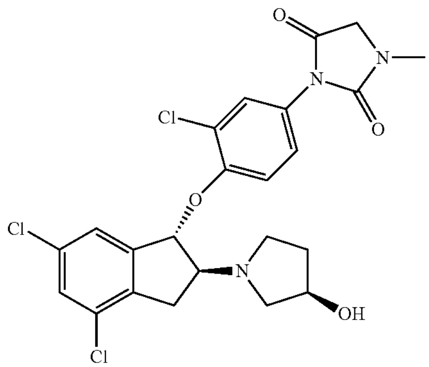 [SMILES: CN1CC(=O)N(c2ccc(O[C@H]3c4cc(Cl)cc(Cl)c4C[C@@H]3N3CC[C@@H](O)C3)c(Cl)c2)C1=O] | A | 17 | 2.65 | 510.13 |
| 423 | 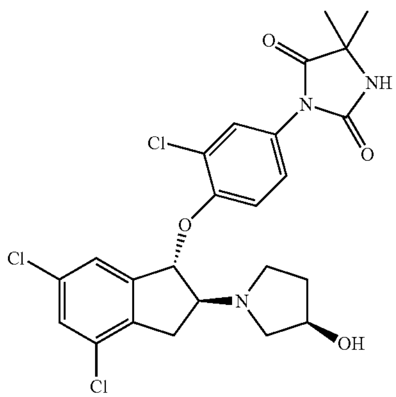 [SMILES: CC1(C)NC(=O)N(c2ccc(O[C@H]3c4cc(Cl)cc(Cl)c4C[C@@H]3N3CC[C@@H](O)C3)c(Cl)c2)C1=O] | A | 17 | 2.79 | 524.15 |
| 424 | 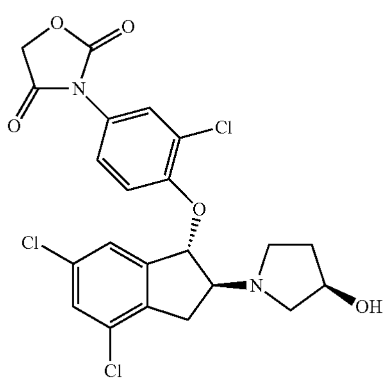 [SMILES: O=C1COC(=O)N1c1ccc(O[C@H]2c3cc(Cl)cc(Cl)c3C[C@@H]2N2CC[C@@H](O)C2)c(Cl)c1] | A | 17 | 2.75 | 497.13 |
| 425 | 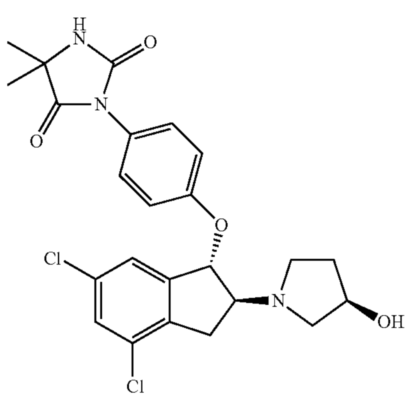 [SMILES: CC1(C)NC(=O)N(c2ccc(O[C@H]3c4cc(Cl)cc(Cl)c4C[C@@H]3N3CC[C@@H](O)C3)cc2)C1=O] | A | 17 | 2.59 | 490.16 |

-continued

| Example | Structure | Synthetic method | LC method | Rt time [min] | MS [M + H+] ES+ |
|---|---|---|---|---|---|
| 426 | 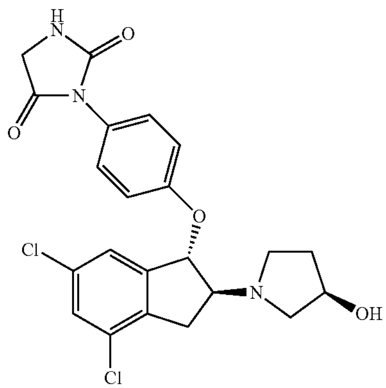 [SMILES: O=C1CNC(=O)N1c1ccc(O[C@H]2c3cc(Cl)cc(Cl)c3C[C@@H]2N2CC[C@@H](O)C2)cc1] | A | 17 | 2.43 | 462.14 |
| 427 | 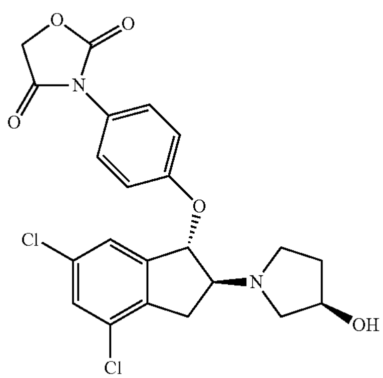 [SMILES: O=C1COC(=O)N1c1ccc(O[C@H]2c3cc(Cl)cc(Cl)c3C[C@@H]2N2CC[C@@H](O)C2)cc1] | A | 9 | 2.65 | 463.08 |
| 428 | 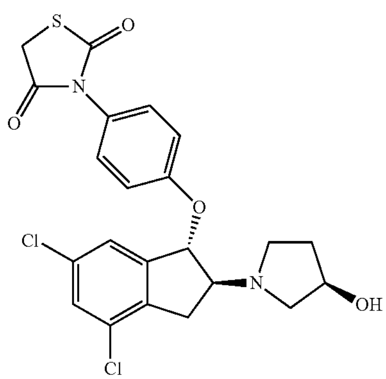 [SMILES: O=C1CSC(=O)N1c1ccc(O[C@H]2c3cc(Cl)cc(Cl)c3C[C@@H]2N2CC[C@@H](O)C2)cc1] | A | 17 | 2.68 | 479.11 |
| 429 | 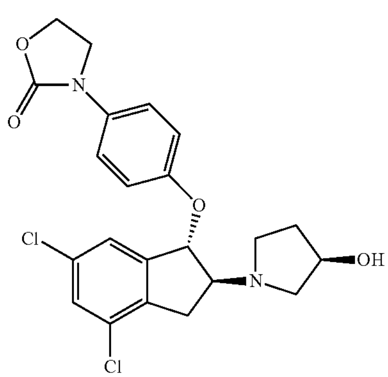 [SMILES: O=C1OCCN1c1ccc(O[C@H]2c3cc(Cl)cc(Cl)c3C[C@@H]2N2CC[C@@H](O)C2)cc1] | A | 1 | 2.65 | 449.09 |

-continued

| Example | Structure | Synthetic method | LC method | Rt time [min] | MS [M + H+] ES+ |
|---|---|---|---|---|---|
| 430 | 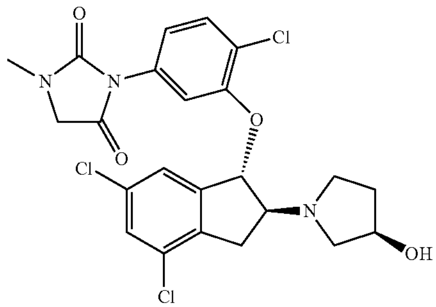 [SMILES: CN1CC(=O)N(c2ccc(Cl)c(O[C@H]3c4cc(Cl)cc(Cl)c4C[C@@H]3N3CC[C@@H](O)C3)c2)C1=O] | A | 17 | 2.75 | 510.16 |
| 431 | 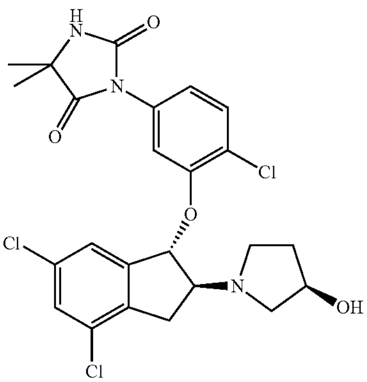 [SMILES: CC1(C)NC(=O)N(c2ccc(Cl)c(O[C@H]3c4cc(Cl)cc(Cl)c4C[C@@H]3N3CC[C@@H](O)C3)c2)C1=O] | A | 9 | 2.88 | 524.03 |
| 432 | 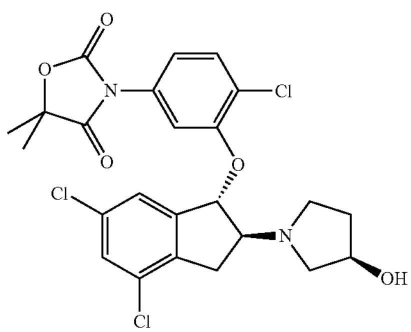 [SMILES: CC1(C)OC(=O)N(c2ccc(Cl)c(O[C@H]3c4cc(Cl)cc(Cl)c4C[C@@H]3N3CC[C@@H](O)C3)c2)C1=O] | A | 9 | 3.16 | 524.99 |
| 433 | 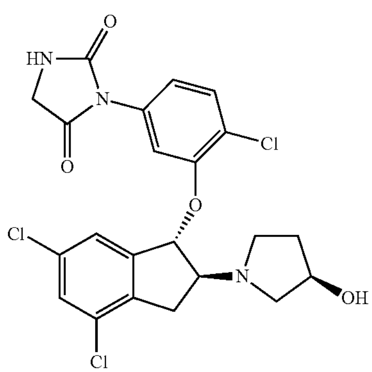 [SMILES: O=C1CNC(=O)N1c1ccc(Cl)c(O[C@H]2c3cc(Cl)cc(Cl)c3C[C@@H]2N2CC[C@@H](O)C2)c1] | A | 17 | 2.67 | 496.11 |

| Example | Structure | Synthetic method | LC method | Rt time [min] | MS [M + H+] ES+ |
|---------|-----------|------------------|-----------|---------------|-----------------|
| 434 | 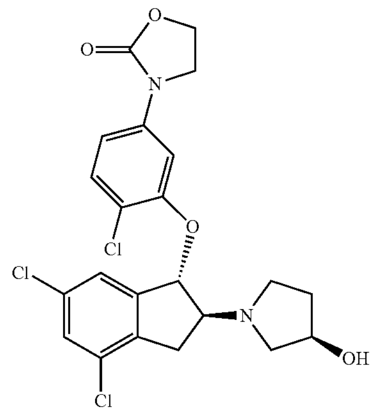 [SMILES: O=C1OCCN1c1ccc(Cl)c(O[C@H]2c3cc(Cl)cc(Cl)c3C[C@@H]2N2CC[C@@H](O)C2)c1] | A | 9 | 2.82 | 483.04 |
| 435 | 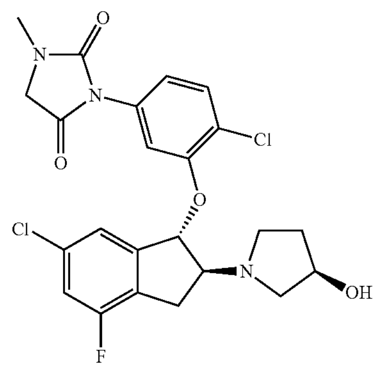 [SMILES: CN1CC(=O)N(c2ccc(Cl)c(O[C@H]3c4cc(Cl)cc(F)c4C[C@@H]3N3CC[C@@H](O)C3)c2)C1=O] | A | 9 | 2.60 | 494.10 |
| 436 | 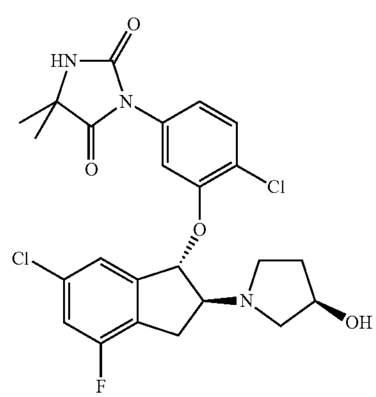 [SMILES: CC1(C)NC(=O)N(c2ccc(Cl)c(O[C@H]3c4cc(Cl)cc(F)c4C[C@@H]3N3CC[C@@H](O)C3)c2)C1=O] | A | 9 | 2.77 | 508.06 |
| 437 | 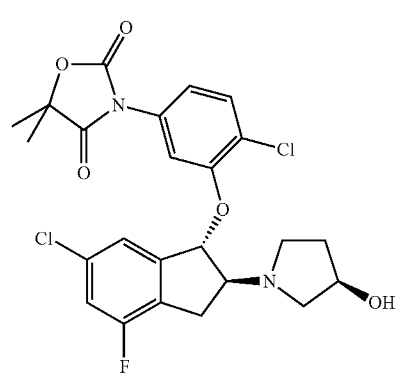 [SMILES: CC1(C)OC(=O)N(c2ccc(Cl)c(O[C@H]3c4cc(Cl)cc(F)c4C[C@@H]3N3CC[C@@H](O)C3)c2)C1=O] | A | 9 | 2.88 | 508.99 |

-continued

| Example | Structure | Synthetic method | LC method | Rt time [min] | MS [M + H+] ES+ |
|---|---|---|---|---|---|
| 438 | 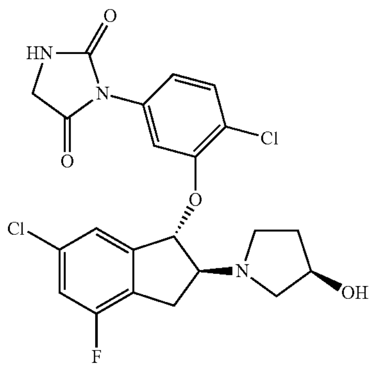 [SMILES: O=C1CNC(=O)N1c1ccc(Cl)c(O[C@H]2c3cc(Cl)cc(F)c3C[C@@H]2N2CC[C@@H](O)C2)c1] | A | 17 | 2.55 | 480.14 |
| 439 | 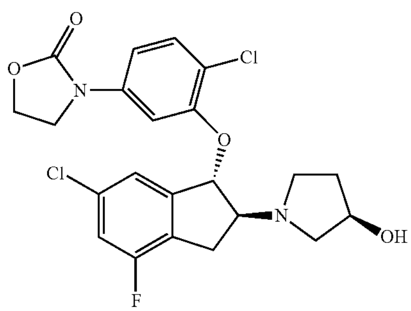 [SMILES: O=C1OCCN1c1ccc(Cl)c(O[C@H]2c3cc(Cl)cc(F)c3C[C@@H]2N2CC[C@@H](O)C2)c1] | A | 9 | 2.87 | 467.09 |
| 444 | 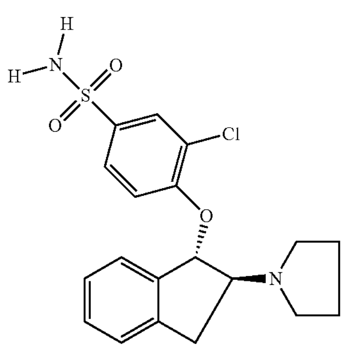 [SMILES: NS(=O)(=O)c1ccc(O[C@H]2c3ccccc3C[C@@H]2N2CCCC2)c(Cl)c1] | A | 13 | 1.26 | 434.23 M + H + CH3CN |
| 445 | 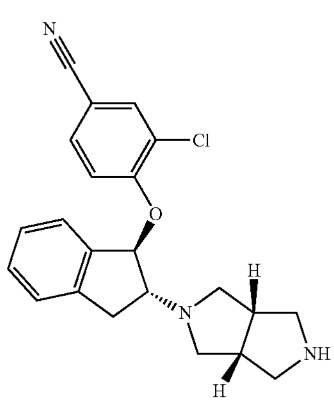 [SMILES: N#Cc1ccc(O[C@@H]2c3ccccc3C[C@H]2N2C[C@H]3CNC[C@H]3C2)c(Cl)c1] | A | 12 | 1.25 | 380.21 |

-continued

| Example | Structure | Synthetic method | LC method | Rt time [min] | MS [M + H+] ES+ |
|---|---|---|---|---|---|
| 446 | 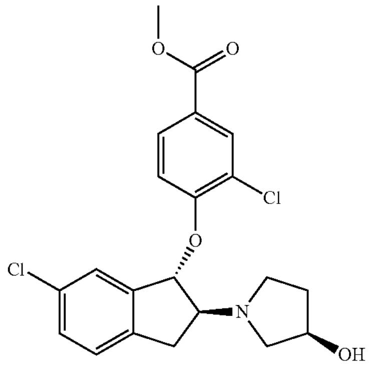 [SMILES: COC(=O)c1ccc(O[C@H]2c3cc(Cl)ccc3C[C@@H]2N2CC[C@@H](O)C2)c(Cl)c1] | A | 9 | 2.74 | 422.14 |
| 447 | 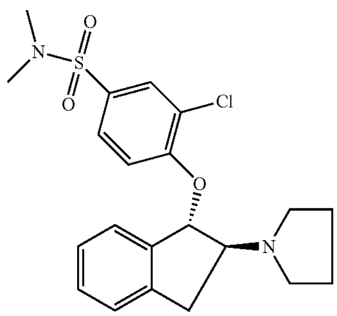 [SMILES: CN(C)S(=O)(=O)c1ccc(O[C@H]2c3ccccc3C[C@@H]2N2CCCC2)c(Cl)c1] | A | 4 | 1.33 | 421.16 |
| 448 | 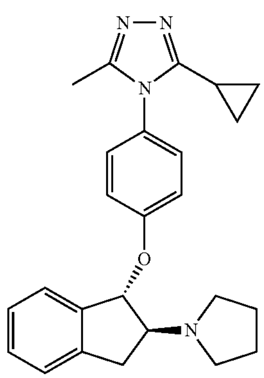 [SMILES: Cc1nnc(C2CC2)n1-c1ccc(O[C@H]2c3ccccc3C[C@@H]2N2CCCC2)cc1] | A | 9 | 2.08 | 401.21 |
| 453 | 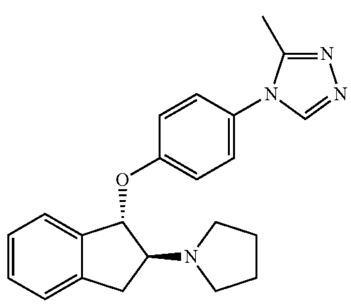 [SMILES: Cc1nncn1-c1ccc(O[C@H]2c3ccccc3C[C@@H]2N2CCCC2)cc1] | A | 14 | 1.56 | 361.21 |

-continued

| Example | Structure | Synthetic method | LC method | Rt time [min] | MS [M + H+] ES+ |
|---|---|---|---|---|---|
| 454 | 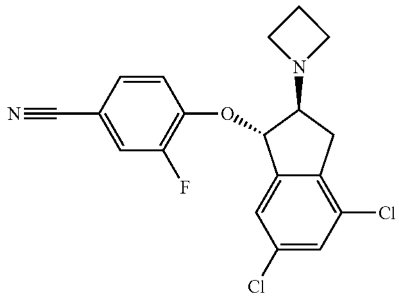 [SMILES: N#Cc1ccc(O[C@H]2c3cc(Cl)cc(Cl)c3C[C@@H]2N2CCC2)c(F)c1] | A | 2 | 2.01 | 377.08 |
| 455 | 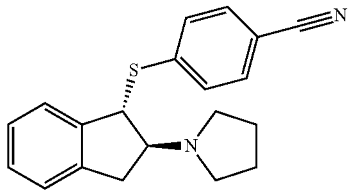 [SMILES: N#Cc1ccc(S[C@H]2c3ccccc3C[C@@H]2N2CCCC2)cc1] | A | 15 | 1.94 | 320.13 |
| 456 | 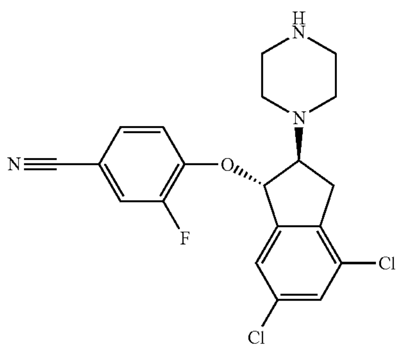 [SMILES: N#Cc1ccc(O[C@H]2c3cc(Cl)cc(Cl)c3C[C@@H]2N2CCNCC2)c(F)c1] | A | 2 | 2.12 | 406.12 |
| 457 | 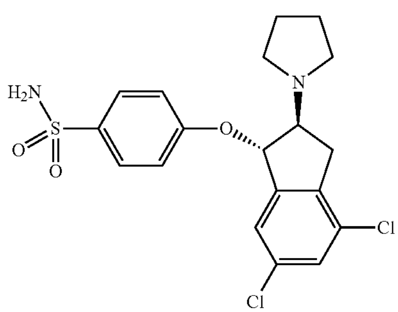 [SMILES: NS(=O)(=O)c1ccc(O[C@H]2c3cc(Cl)cc(Cl)c3C[C@@H]2N2CCCC2)cc1] | A | 1 | 2.59 | 427.11 |
| 458 | 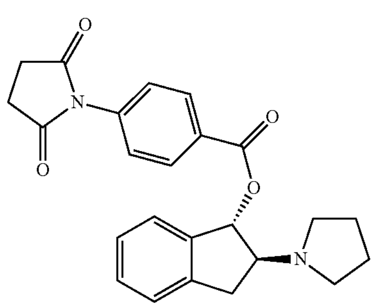 [SMILES: O=C(O[C@H]1c2ccccc2C[C@@H]1N1CCCC1)c1ccc(N2C(=O)CCC2=O)cc1] | A | 15 | 1.77 | 405.15 |

-continued

| Example | Structure | Synthetic method | LC method | Rt time [min] | MS [M + H+] ES+ |
|---|---|---|---|---|---|
| 461 | 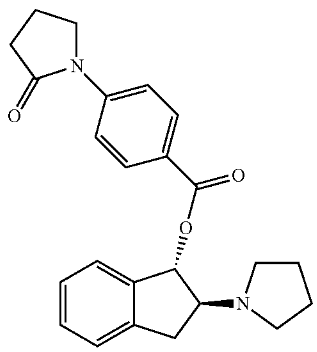 [SMILES: O=C(O[C@H]1c2ccccc2C[C@@H]1N1CCCC1)c1ccc(N2CCCC2=O)cc1] | A | 15 | 1.85 | 391.17 |
| 463 | 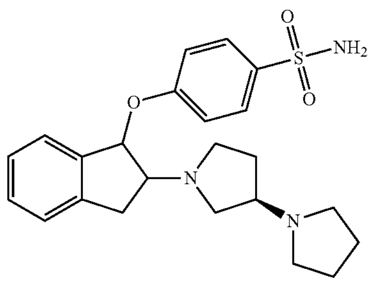 [SMILES: NS(=O)(=O)c1ccc(OC2c3ccccc3CC2N2CC[C@@H](N3CCCC3)C2)cc1] | A | 13 | 1.04 | 428.2 |
| 464 | 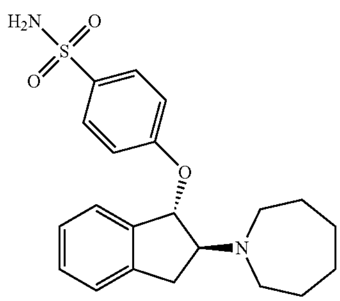 [SMILES: NS(=O)(=O)c1ccc(O[C@H]2c3ccccc3C[C@@H]2N2CCCCCC2)cc1] | A | 4 | 1.12 | 387.23 |
| 465 | 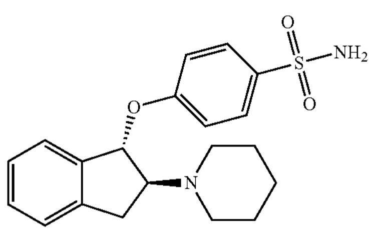 [SMILES: NS(=O)(=O)c1ccc(O[C@H]2c3ccccc3C[C@@H]2N2CCCCC2)cc1] | A | 4 | 1.04 | 373.19 |
| 466 | 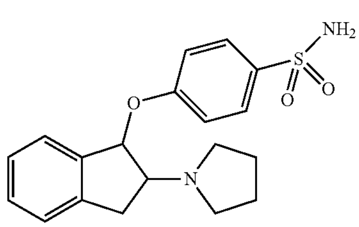 [SMILES: NS(=O)(=O)c1ccc(OC2c3ccccc3CC2N2CCCC2)cc1] | A | 12 | 1.05 | 359.25 |

-continued

| Example | Structure | Synthetic method | LC method | Rt time [min] | MS [M + H+] ES+ |
|---------|-----------|------------------|-----------|---------------|-----------------|
| 467 | 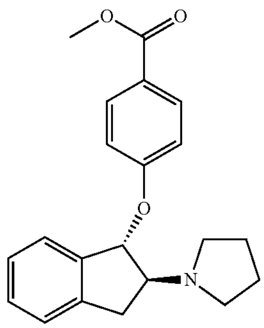 [SMILES: COC(=O)c1ccc(O[C@H]2c3ccccc3C[C@@H]2N2CCCC2)cc1] | A | 14 | 1.88 | 338.25 |
| 468 | 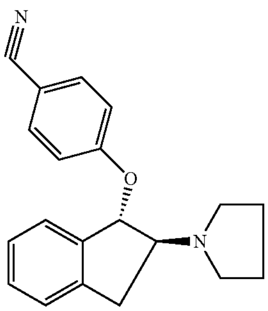 [SMILES: N#Cc1ccc(O[C@H]2c3ccccc3C[C@@H]2N2CCCC2)cc1] | A | 4 | 1.30 | 305.13 |
| 469 | 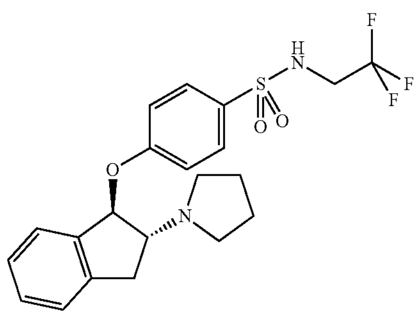 [SMILES: O=S(=O)(NCC(F)(F)F)c1ccc(O[C@@H]2c3ccccc3C[C@H]2N2CCCC2)cc1] | A | 4 | 1.30 | 441.22 |
| 470 | 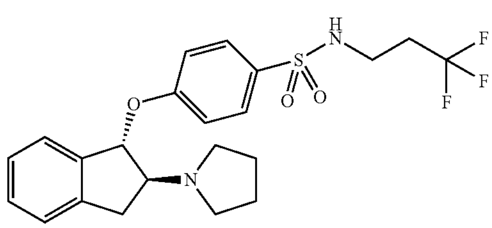 [SMILES: O=S(=O)(NCCC(F)(F)F)c1ccc(O[C@H]2c3ccccc3C[C@@H]2N2CCCC2)cc1] | A | 4 | 1.35 | 455.16 |
| 471 | 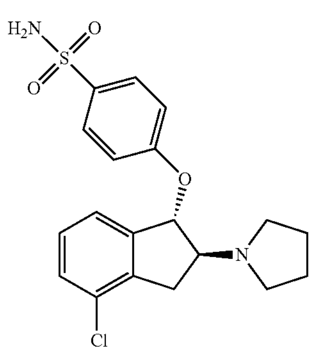 [SMILES: NS(=O)(=O)c1ccc(O[C@H]2c3cccc(Cl)c3C[C@@H]2N2CCCC2)cc1] | A | 4 | 1.13 | 393.14 |

-continued

| Example | Structure | Synthetic method | LC method | Rt time [min] | MS [M + H+] ES+ |
|---------|-----------|------------------|-----------|---------------|-----------------|
| 472 | 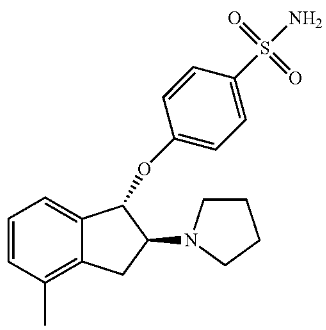 [SMILES: Cc1cccc2c1C[C@H](N1CCCC1)[C@H]2Oc1ccc(S(N)(=O)=O)cc1] | A | 4 | 1.10 | 373.14 |
| 473 | 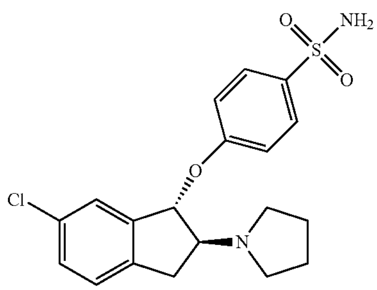 [SMILES: NS(=O)(=O)c1ccc(O[C@H]2c3cc(Cl)ccc3C[C@@H]2N2CCCC2)cc1] | A | 4 | 1.15 | 393.11 |
| 474 | 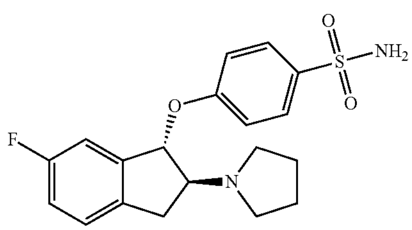 [SMILES: NS(=O)(=O)c1ccc(O[C@H]2c3cc(F)ccc3C[C@@H]2N2CCCC2)cc1] | A | 4 | 1.12 | 377.16 |
| 475 | 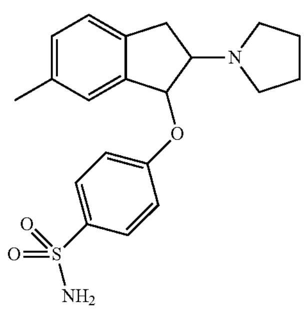 [SMILES: Cc1ccc2c(c1)C(Oc1ccc(S(N)(=O)=O)cc1)C(N1CCCC1)C2] | A | 4 | 1.08 | 373.13 |
| 476 | 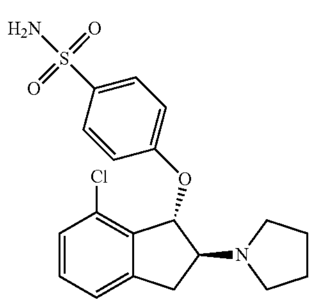 [SMILES: NS(=O)(=O)c1ccc(O[C@H]2c3c(Cl)cccc3C[C@@H]2N2CCCC2)cc1] | A | 6 | 1.14 | 393.1 |

-continued

| Example | Structure | Synthetic method | LC method | Rt time [min] | MS [M + H+] ES+ |
|---|---|---|---|---|---|
| 477 | 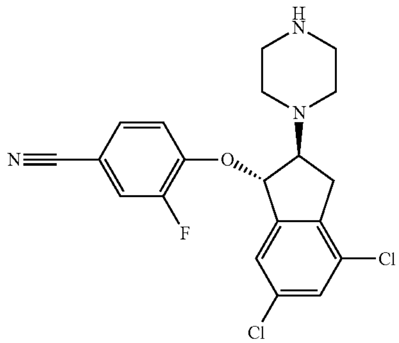 [SMILES: N#Cc1ccc(O[C@H]2c3cc(Cl)cc(Cl)c3C[C@@H]2N2CCNCC2)c(F)c1] | A | 14 | 2.12 | 406.12 |
| 479 | 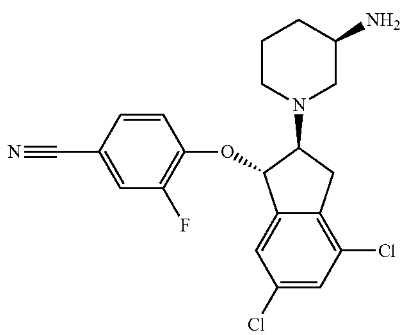 [SMILES: N#Cc1ccc(O[C@H]2c3cc(Cl)cc(Cl)c3C[C@@H]2N2CCC[C@@H](N)C2)c(F)c1] | A | 2 | 2.02 | 420.14 |
| 480 | 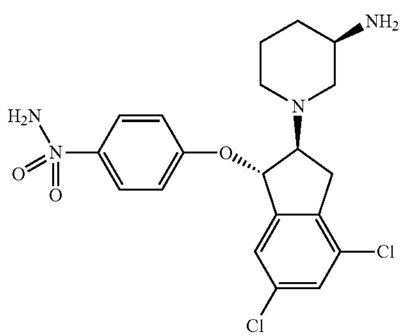 | A | 1 | 2.47 | 456.15 |
| 483 | 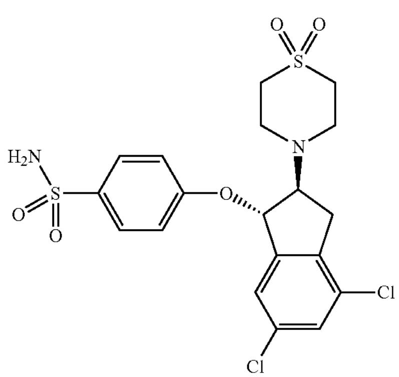 [SMILES: NS(=O)(=O)c1ccc(O[C@H]2c3cc(Cl)cc(Cl)c3C[C@@H]2N2CCS(=O)(=O)CC2)cc1] | A | 1 | 3.39 | 491.11 |

-continued

| Example | Structure | Synthetic method | LC method | Rt time [min] | MS [M + H+] ES+ |
|---|---|---|---|---|---|
| 484 | 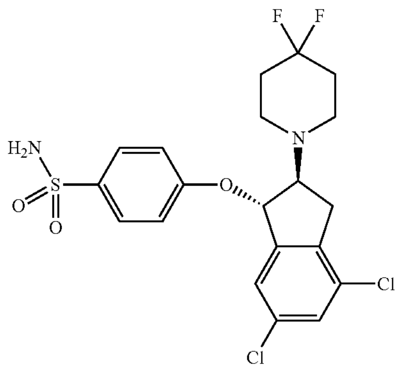 [SMILES: NS(=O)(=O)c1ccc(O[C@H]2c3cc(Cl)cc(Cl)c3C[C@@H]2N2CCC(F)(F)CC2)cc1] | A | 1 | 2.99 | 477.12 |
| 485 | 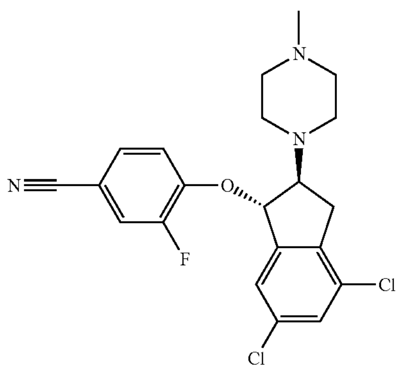 [SMILES: CN1CCN([C@H]2Cc3c(Cl)cc(Cl)cc3[C@@H]2Oc2ccc(C#N)cc2F)CC1] | A | 2 | 2.14 | 420.14 |
| 488 | 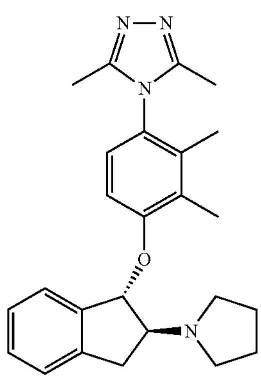 [SMILES: Cc1c(O[C@H]2c3ccccc3C[C@@H]2N2CCCC2)ccc(-n2c(C)nnc2C)c1C] | A | 9 | 2.14 | 403.23 |
| 489 | 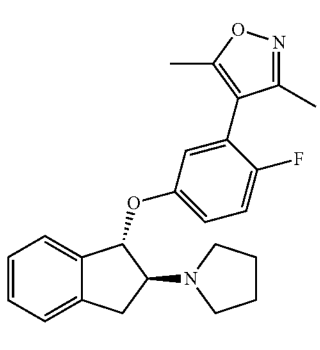 [SMILES: Cc1noc(C)c1-c1cc(O[C@H]2c3ccccc3C[C@@H]2N2CCCC2)ccc1F] | A | 1 | 2.80 | 393.23 |

| Example | Structure | Synthetic method | LC method | Rt time [min] | MS [M + H+] ES+ |
|---|---|---|---|---|---|
| 490 | 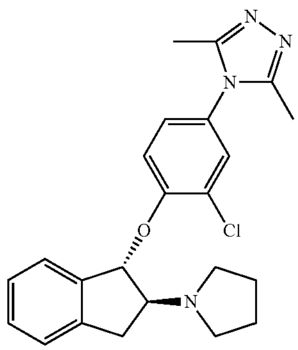 [SMILES: Cc1nnc(C)n1-c1ccc(O[C@H]2c3ccccc3C[C@@H]2N2CCCC2)c(Cl)c1] | A | 14 | 1.57 | 409.2 |
| 491 | 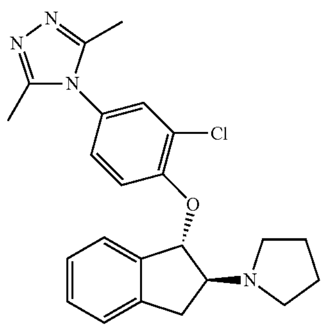 [SMILES: Cc1nnc(C)n1-c1ccc(O[C@H]2c3ccccc3C[C@@H]2N2CCCC2)c(Cl)c1] | A | 9 | 2.13 | 409.13 |
| 492 | 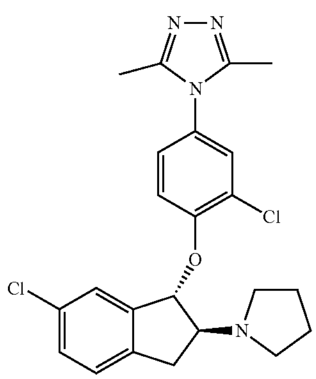 [SMILES: Cc1nnc(C)n1-c1ccc(O[C@H]2c3cc(Cl)ccc3C[C@@H]2N2CCCC2)c(Cl)c1] | A | 9 | 2.31 | 443.16 |
| 493 | 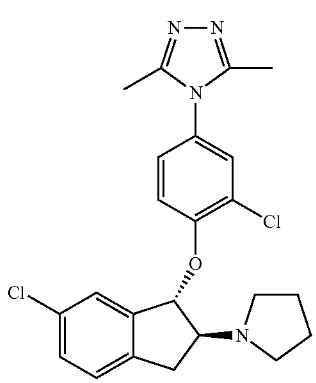 [SMILES: Cc1nnc(C)n1-c1ccc(O[C@H]2c3cc(Cl)ccc3C[C@@H]2N2CCCC2)c(Cl)c1] | A | 1 | 2.42 | 443.07 |

-continued
| Example | Structure | Synthetic method | LC method | Rt time [min] | MS [M + H+] ES+ |
|---|---|---|---|---|---|
| 494 | 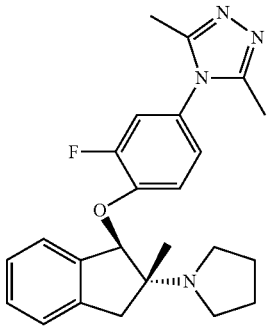 [SMILES: Cc1nnc(C)n1-c1ccc(O[C@@H]2c3ccccc3C[C@@]2(C)N2CCCC2)c(F)c1] | A | 9 | 2.37 | 407.21 |
| 495 | 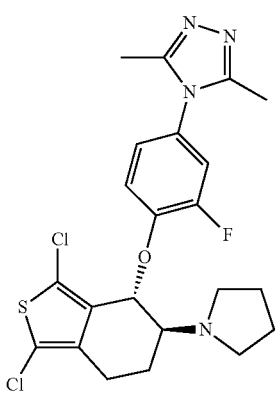 [SMILES: Cc1nnc(C)n1-c1ccc(O[C@H]2c3c(Cl)sc(Cl)c3CC[C@@H]2N2CCCC2)c(F)c1] | A | 9 | 2.46 | 481.02 |
| 496 | 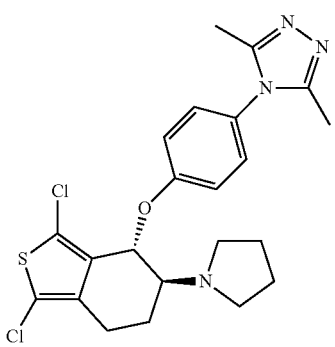 [SMILES: Cc1nnc(C)n1-c1ccc(O[C@H]2c3c(Cl)sc(Cl)c3CC[C@@H]2N2CCCC2)cc1] | A | 8 | 2.83 | 463.14 |
| 497 | 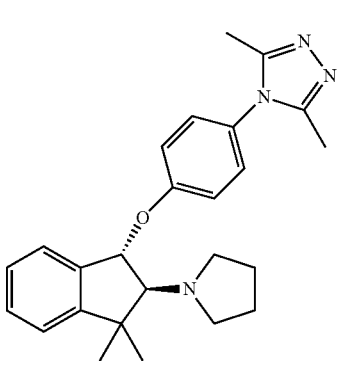 [SMILES: Cc1nnc(C)n1-c1ccc(O[C@H]2c3ccccc3C(C)(C)[C@@H]2N2CCCC2)cc1] | A | 9 | 2.16 | 403.18 |

-continued

| Example | Structure | Synthetic method | LC method | Rt time [min] | MS [M + H+] ES+ |
|---|---|---|---|---|---|
| 498 | 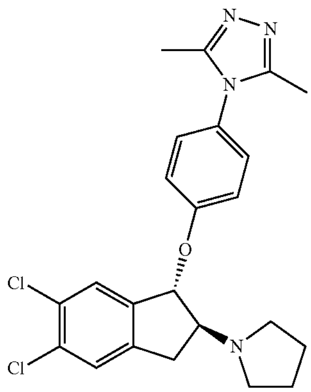 [SMILES: Cc1nnc(C)n1-c1ccc(O[C@H]2c3cc(Cl)c(Cl)cc3C[C@@H]2N2CCCC2)cc1] | A | 9 | 2.28 | 443.13 |
| 499 | 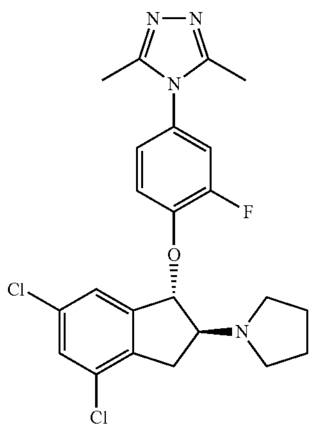 [SMILES: Cc1nnc(C)n1-c1ccc(O[C@H]2c3cc(Cl)cc(Cl)c3C[C@@H]2N2CCCC2)c(F)c1] | A | 9 | 2.46 | 461.19 |
| 500 | 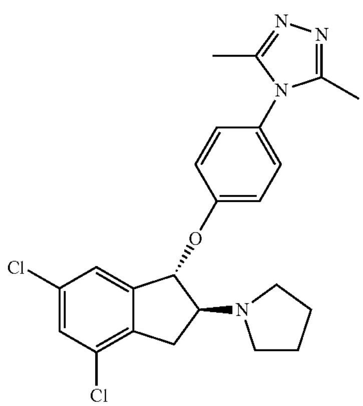 [SMILES: Cc1nnc(C)n1-c1ccc(O[C@H]2c3cc(Cl)cc(Cl)c3C[C@@H]2N2CCCC2)cc1] | A | 14 | 1.70 | 443.17 |
| 501 | 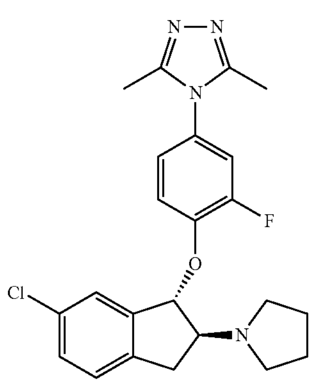 [SMILES: Cc1nnc(C)n1-c1ccc(O[C@H]2c3cc(Cl)ccc3C[C@@H]2N2CCCC2)c(F)c1] | A | 1 | 2.43 | 427.09 |

-continued

| Example | Structure | Synthetic method | LC method | Rt time [min] | MS [M + H+] ES+ |
|---|---|---|---|---|---|
| 502 | 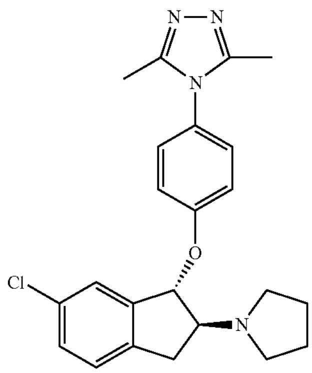 [SMILES: Cc1nnc(C)n1-c1ccc(O[C@H]2c3cc(Cl)ccc3C[C@@H]2N2CCCC2)cc1] | A | 1 | 2.30 | 409.12 |
| 503 | 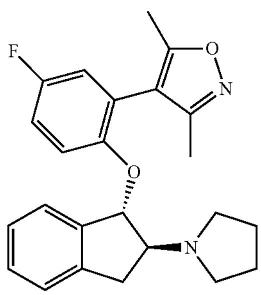 [SMILES: Cc1noc(C)c1-c1cc(F)ccc1O[C@H]1c2ccccc2C[C@@H]1N1CCCC1] | A | 9 | 2.74 | 393.2 |
| 504 | 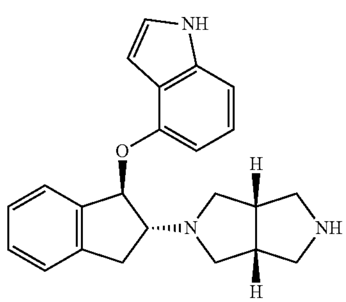 [SMILES: c1ccc2c(c1)C[C@@H](N1C[C@H]3CNC[C@H]3C1)[C@@H]2Oc1cccc2[nH]ccc12] | A | 12 | 1.10 | 360.26 |
| 505 | 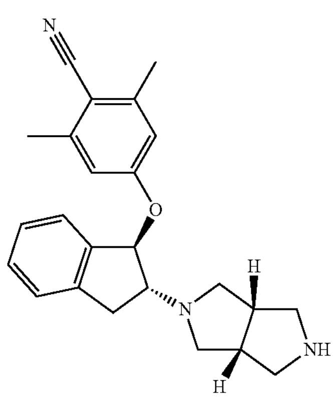 [SMILES: Cc1cc(O[C@@H]2c3ccccc3C[C@H]2N2C[C@H]3CNC[C@H]3C2)cc(C)c1C#N] | A | 12 | 1.28 | 374.26 |

| Example | Structure | Synthetic method | LC method | Rt time [min] | MS [M + H+] ES+ |
|---|---|---|---|---|---|
| 506 | 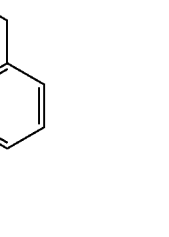 | A | 1 | 2.39 | 388.08 |
| 507 | 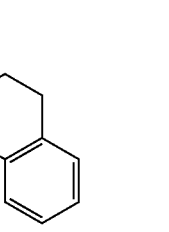 | A | 1 | 2.77 | 395.12 |
| 508 | 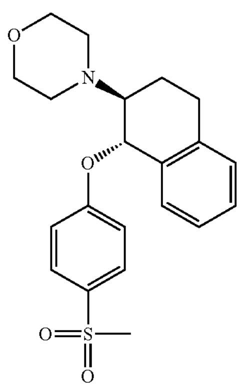 [SMILES: CS(=O)(=O)c1ccc(O[C@H]2c3ccccc3CC[C@@H]2N2CCOCC2)cc1] | A | 1 | 2.35 | 388.11 |
| 509 | 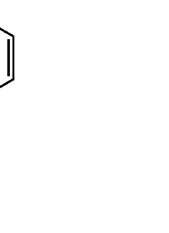 | A | 1 | 2.59 | 384.12 |

| Example | Structure | Synthetic method | LC method | Rt time [min] | MS [M + H+] ES+ |
|---------|-----------|------------------|-----------|---------------|-----------------|
| 510 | 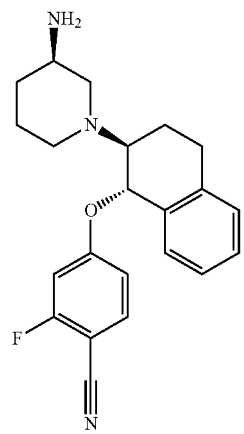 [SMILES: N#Cc1ccc(O[C@H]2c3ccccc3CC[C@@H]2N2CCC[C@@H](N)C2)cc1F] | A | 1 | 2.42 | 366.14 |
| 511 | 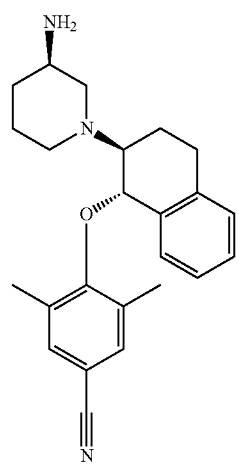 [SMILES: Cc1cc(C#N)cc(C)c1O[C@H]1c2ccccc2CC[C@@H]1N1CCC[C@@H](N)C1] | A | 1 | 2.55 | 376.2 |
| 512 | 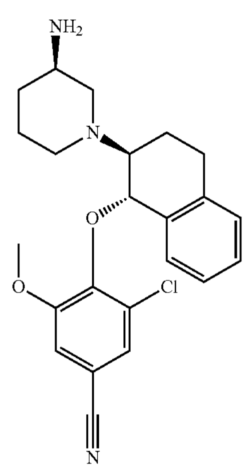 [SMILES: COc1cc(C#N)cc(Cl)c1O[C@H]1c2ccccc2CC[C@@H]1N1CCC[C@@H](N)C1] | A | 1 | 2.55 | 412.12 |

| Example | Structure | Synthetic method | LC method | Rt time [min] | MS [M + H+] ES+ |
|---|---|---|---|---|---|
| 513 | 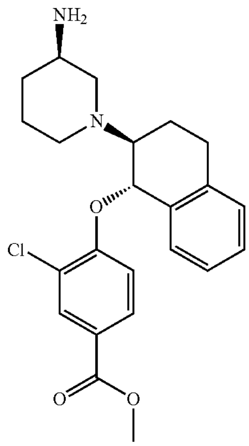 [SMILES: COC(=O)c1ccc(O[C@H]2c3ccccc3CC[C@@H]2N2CCC[C@@H](N)C2)c(Cl)c1] | A | 1 | 2.60 | 415.12 |
| 514 | 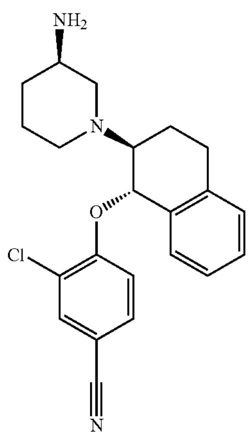 [SMILES: N#Cc1ccc(O[C@H]2c3ccccc3CC[C@@H]2N2CCC[C@@H](N)C2)c(Cl)c1] | A | 1 | 2.57 | 382.14 |
| 515 | 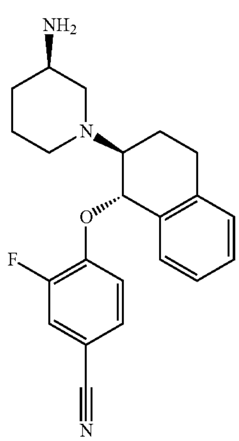 [SMILES: N#Cc1ccc(O[C@H]2c3ccccc3CC[C@@H]2N2CCC[C@@H](N)C2)c(F)c1] | A | 1 | 2.42 | 366.15 |

-continued

| Example | Structure | Synthetic method | LC method | Rt time [min] | MS [M + H+] ES+ |
|---|---|---|---|---|---|
| 516 | 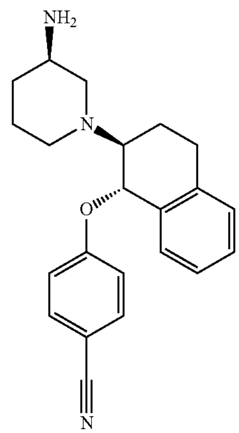 [SMILES: N#Cc1ccc(O[C@H]2c3ccccc3CC[C@@H]2N2CCC[C@@H](N)C2)cc1] | A | 1 | 2.32 | 348.15 |
| 517 | 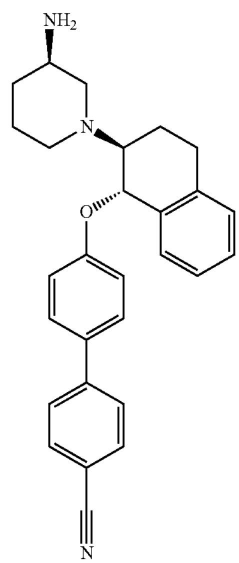 [SMILES: N#Cc1ccc(-c2ccc(O[C@H]3c4ccccc4CC[C@@H]3N3CCC[C@@H](N)C3)cc2)cc1] | A | 1 | 2.68 | 424.18 |
| 518 | 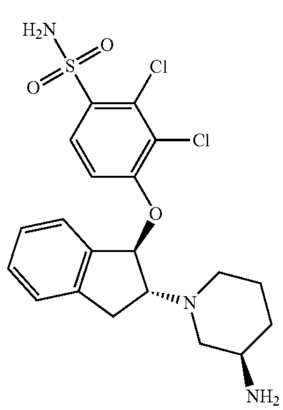 [SMILES: N[C@@H]1CCCN([C@@H]2Cc3ccccc3[C@H]2Oc2ccc(S(N)(=O)=O)c(Cl)c2Cl)C1] | A | 12 | 1.12 | 456.13 |

-continued

| Example | Structure | Synthetic method | LC method | Rt time [min] | MS [M + H+] ES+ |
|---|---|---|---|---|---|
| 519 | 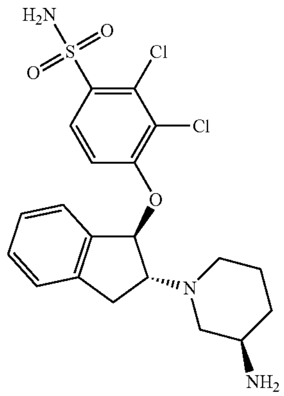 [SMILES: N[C@@H]1CCCN([C@@H]2Cc3ccccc3[C@H]2Oc2ccc(S(N)(=O)=O)c(Cl)c2Cl)C1] | A | 12 | 1.12 | 456.07 |
| 520 | 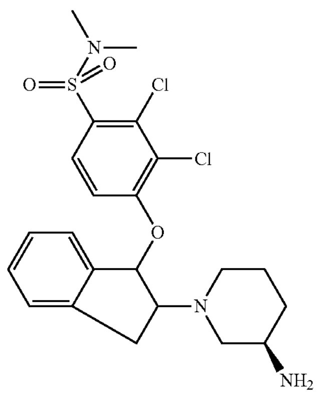 [SMILES: CN(C)S(=O)(=O)c1ccc(OC2c3ccccc3CC2N2CCC[C@@H](N)C2)c(Cl)c1Cl] | A | 6 | 1.35 | 484.17 |
| 521 | 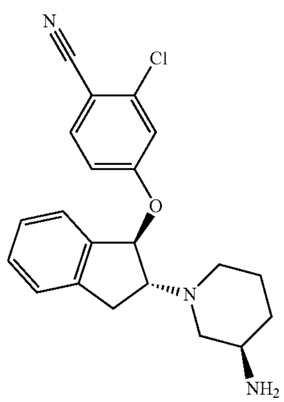 [SMILES: N#Cc1ccc(O[C@@H]2c3ccccc3C[C@H]2N2CCC[C@@H](N)C2)cc1Cl] | A | 12 | 1.27 | 368.16 |
| 522 | 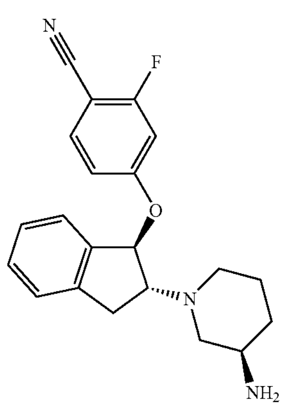 [SMILES: N#Cc1ccc(O[C@@H]2c3ccccc3C[C@H]2N2CCC[C@@H](N)C2)cc1F] | A | 12 | 1.22 | 352.18 |

-continued

| Example | Structure | Synthetic method | LC method | Rt time [min] | MS [M + H+] ES+ |
|---|---|---|---|---|---|
| 523 | 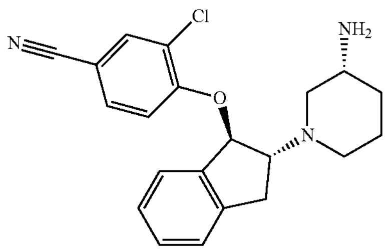 [SMILES: N#Cc1ccc(O[C@@H]2c3ccccc3C[C@H]2N2CCC[C@@H](N)C2)c(Cl)c1] | A | 12 | 1.20 | 368.13 |
| 524 | 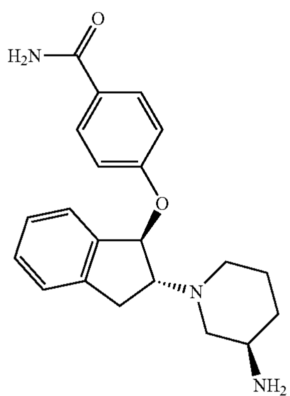 [SMILES: NC(=O)c1ccc(O[C@@H]2c3ccccc3C[C@H]2N2CCC[C@@H](N)C2)cc1] | A | 12 | 0.88 | 352.23 |
| 525 | 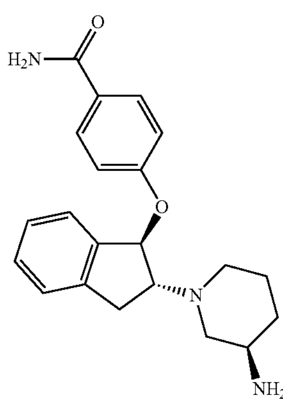 [SMILES: NC(=O)c1ccc(O[C@@H]2c3ccccc3C[C@H]2N2CCC[C@@H](N)C2)cc1] | A | 12 | 0.88 | 352.23 |
| 526 | 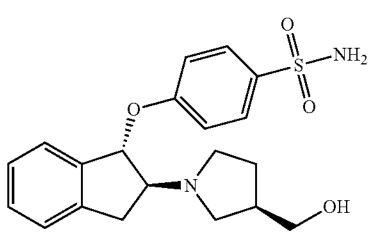 [SMILES: NS(=O)(=O)c1ccc(O[C@H]2c3ccccc3C[C@@H]2N2CC[C@@H](CO)C2)cc1] | A | 4 | 1.05 | 389.23 |
| 527 | 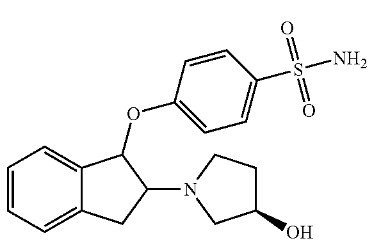 [SMILES: NS(=O)(=O)c1ccc(OC2c3ccccc3CC2N2CC[C@@H](O)C2)cc1] | A | 13 | 1.00 | 375.21 |

-continued

| Example | Structure | Synthetic method | LC method | Rt time [min] | MS [M + H+] ES+ |
|---|---|---|---|---|---|
| 528 | 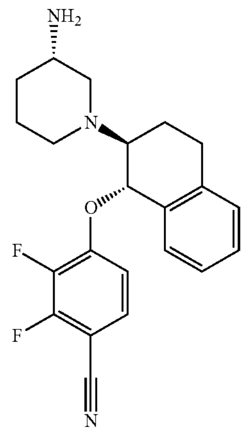 [SMILES: N#Cc1ccc(O[C@H]2c3ccccc3CC[C@@H]2N2CCC[C@H](N)C2)c(F)c1F] | A | 1 | 2.59 | 384.13 |
| 529 | 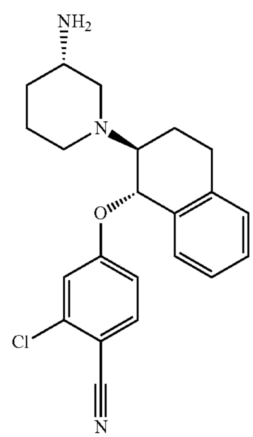 [SMILES: N#Cc1ccc(O[C@H]2c3ccccc3CC[C@@H]2N2CCC[C@H](N)C2)cc1Cl] | A | 1 | 2.54 | 382.12 |
| 530 | 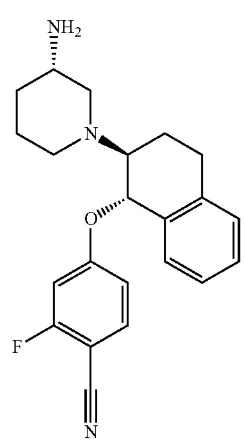 [SMILES: N#Cc1ccc(O[C@H]2c3ccccc3CC[C@@H]2N2CCC[C@H](N)C2)cc1F] | A | 1 | 2.43 | 366.15 |

-continued

| Example | Structure | Synthetic method | LC method | Rt time [min] | MS [M + H+] ES+ |
|---|---|---|---|---|---|
| 531 | 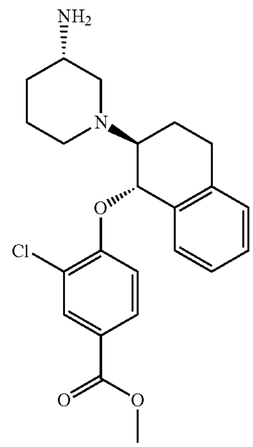 [SMILES: COC(=O)c1ccc(O[C@H]2c3ccccc3CC[C@@H]2N2CCC[C@H](N)C2)c(Cl)c1] | A | 1 | 2.60 | 415.12 |
| 532 | 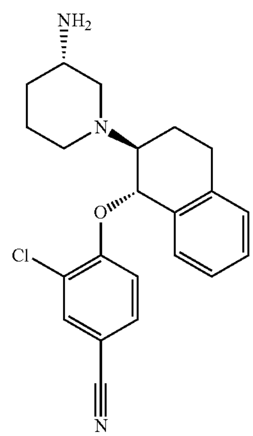 [SMILES: N#Cc1ccc(O[C@H]2c3ccccc3CC[C@@H]2N2CCC[C@H](N)C2)c(Cl)c1] | A | 1 | 2.59 | 382.12 |
| 533 | 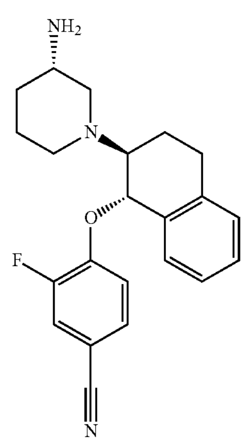 [SMILES: N#Cc1ccc(O[C@H]2c3ccccc3CC[C@@H]2N2CCC[C@H](N)C2)c(F)c1] | A | 9 | 2.35 | 366.15 |

-continued

| Example | Structure | Synthetic method | LC method | Rt time [min] | MS [M + H+] ES+ |
|---------|-----------|------------------|-----------|---------------|-----------------|
| 534 | 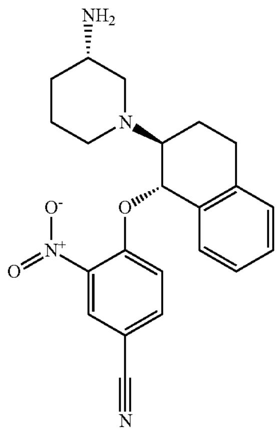 [SMILES: N#Cc1ccc(O[C@H]2c3ccccc3CC[C@@H]2N2CCC[C@H](N)C2)c([N+](=O)[O-])c1] | A | 1 | 2.60 | 393.16 |
| 535 | 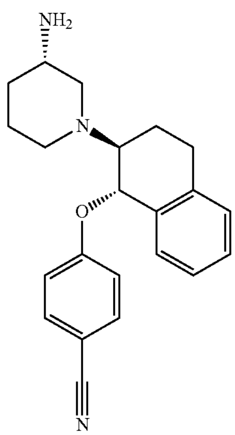 [SMILES: N#Cc1ccc(O[C@H]2c3ccccc3CC[C@@H]2N2CCC[C@H](N)C2)cc1] | A | 1 | 2.32 | 348.15 |
| 536 | 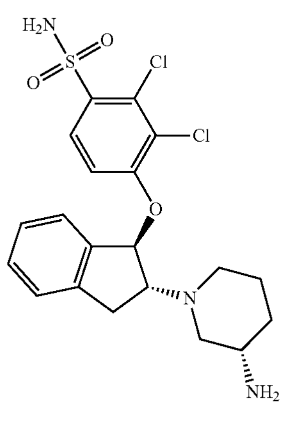 [SMILES: N[C@H]1CCCN([C@@H]2Cc3ccccc3[C@H]2Oc2ccc(S(N)(=O)=O)c(Cl)c2Cl)C1] | A | 12 | 1.12 | 456.12 |

-continued

| Example | Structure | Synthetic method | LC method | Rt time [min] | MS [M + H+] ES+ |
|---|---|---|---|---|---|
| 537 | 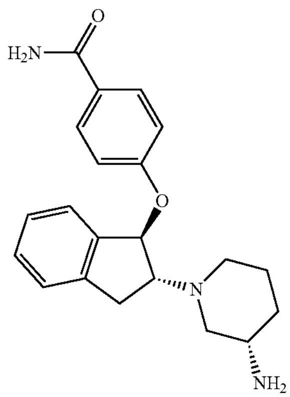 [SMILES: NC(=O)c1ccc(O[C@@H]2c3ccccc3C[C@H]2N2CCC[C@H](N)C2)cc1] | A | 12 | 0.88 | 352.22 |
| 538 | 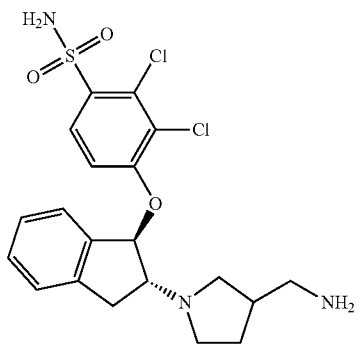 [SMILES: NCC1CCN([C@@H]2Cc3ccccc3[C@H]2Oc2ccc(S(N)(=O)=O)c(Cl)c2Cl)C1] | A | 12 | 1.10 | 456.12 |
| 539 | 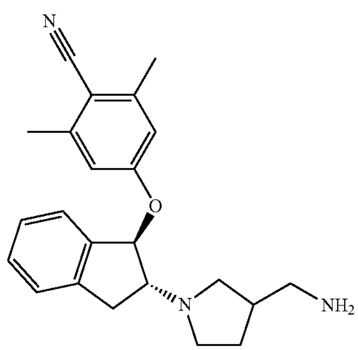 [SMILES: Cc1cc(O[C@@H]2c3ccccc3C[C@H]2N2CCC(CN)C2)cc(C)c1C#N] | A | 12 | 1.32 | 362.25 |
| 540 | 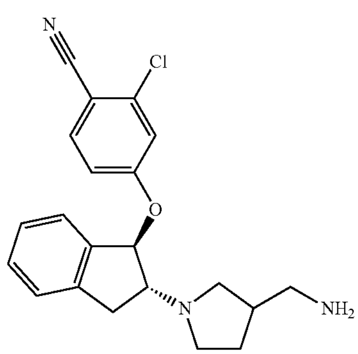 [SMILES: N#Cc1ccc(O[C@@H]2c3ccccc3C[C@H]2N2CCC(CN)C2)cc1Cl] | A | 12 | 1.25 | 368.18 |

-continued

| Example | Structure | Synthetic method | LC method | Rt time [min] | MS [M + H+] ES+ |
|---|---|---|---|---|---|
| 541 | 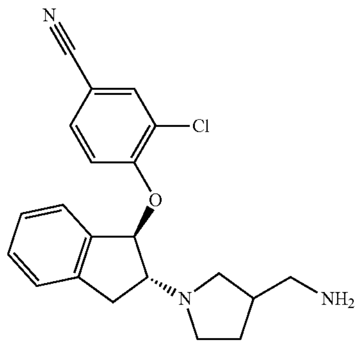 [SMILES: N#Cc1ccc(O[C@@H]2c3ccccc3C[C@H]2N2CCC(CN)C2)c(Cl)c1] | A | 12 | 1.22 | 368.17 |
| 542 | 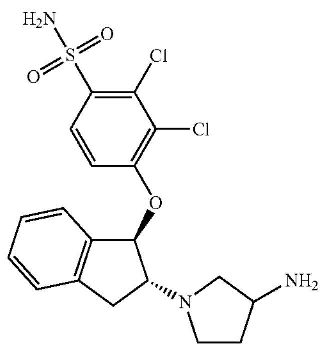 [SMILES: NC1CCN([C@@H]2Cc3ccccc3[C@H]2Oc2ccc(S(N)(=O)=O)c(Cl)c2Cl)C1] | A | 12 | 1.08 | 442.01 |
| 543 | 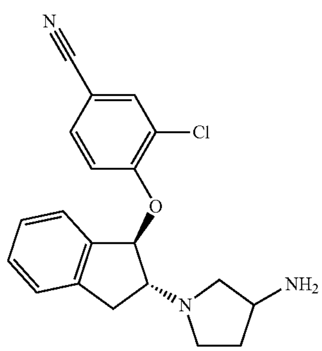 [SMILES: N#Cc1ccc(O[C@@H]2c3ccccc3C[C@H]2N2CCC(N)C2)c(Cl)c1] | A | 12 | 1.20 | 354.08 |
| 544 | 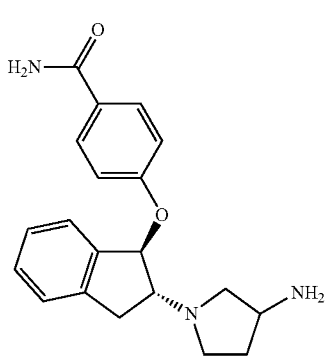 [SMILES: NC(=O)c1ccc(O[C@@H]2c3ccccc3C[C@H]2N2CCC(N)C2)cc1] | A | 11 | 0.91 | 338.16 |

-continued

| Example | Structure | Synthetic method | LC method | Rt time [min] | MS [M + H+] ES+ |
|---|---|---|---|---|---|
| 545 | 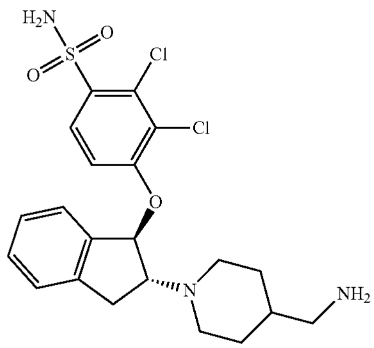 [SMILES: NCC1CCN([C@@H]2Cc3ccccc3[C@H]2Oc2ccc(S(N)(=O)=O)c(Cl)c2Cl)CC1] | A | 11 | 1.09 | 470.10 |
| 546 | 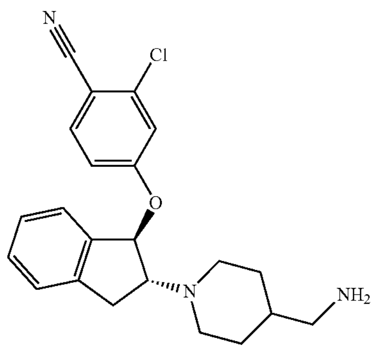 [SMILES: N#Cc1ccc(O[C@@H]2c3ccccc3C[C@H]2N2CCC(CN)CC2)cc1Cl] | A | 12 | 1.22 | 382.14 |
| 547 | 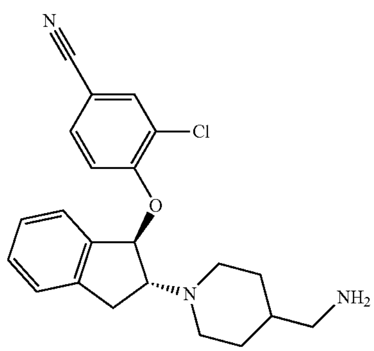 [SMILES: N#Cc1ccc(O[C@@H]2c3ccccc3C[C@H]2N2CCC(CN)CC2)c(Cl)c1] | A | 11 | 1.15 | 382.15 |
| 548 | 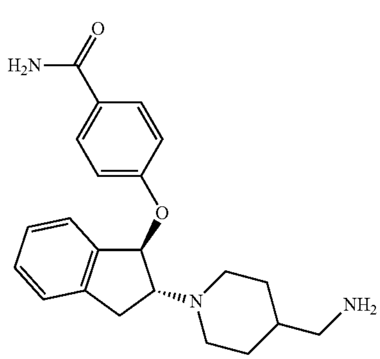 [SMILES: NCC1CCN([C@@H]2Cc3ccccc3[C@H]2Oc2ccc(C(N)=O)cc2)CC1] | A | 12 | 0.85 | 366.23 |

-continued

| Example | Structure | Synthetic method | LC method | Rt time [min] | MS [M + H+] ES+ |
|---|---|---|---|---|---|
| 549 | 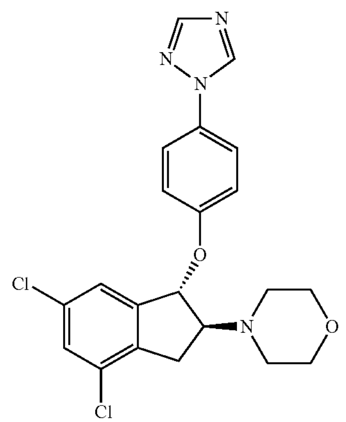 [SMILES: Clc1cc(Cl)c2c(c1)[C@H](Oc1ccc(-n3cncn3)cc1)[C@@H](N1CCOCC1)C2] | A | 4 | 1.28 | 431.1 |
| 550 | 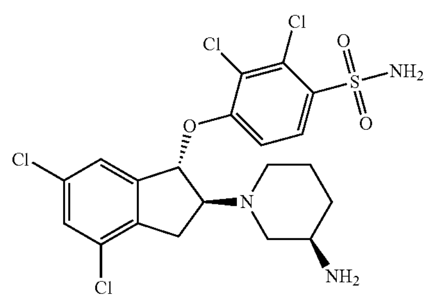 [SMILES: N[C@@H]1CCCN([C@H]2Cc3c(Cl)cc(Cl)cc3[C@@H]2Oc2ccc(S(N)(=O)=O)c(Cl)c2Cl)C1] | A | 4 | 1.37 | 525.98 M + H{Hal} |
| 551 | 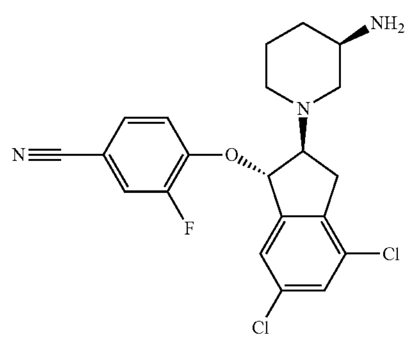 [SMILES: N#Cc1ccc(O[C@H]2c3cc(Cl)cc(Cl)c3C[C@@H]2N2CCC[C@@H](N)C2)c(F)c1] | A | 14 | 2.02 | 420.14 |
| 552 | 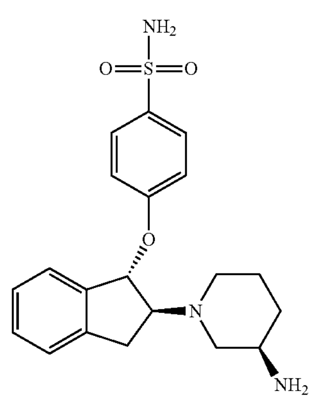 [SMILES: N[C@@H]1CCCN([C@H]2Cc3ccccc3[C@@H]2Oc2ccc(S(N)(=O)=O)cc2)C1] | A | 12 | 0.87 | 388.27 |

-continued

| Example | Structure | Synthetic method | LC method | Rt time [min] | MS [M + H+] ES+ |
|---|---|---|---|---|---|
| 553 | 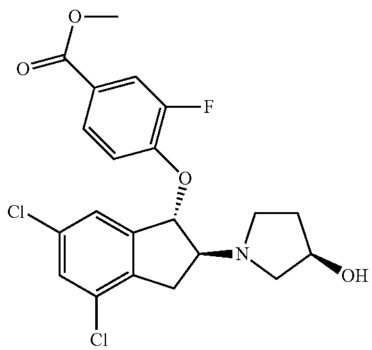 [SMILES: COC(=O)c1ccc(O[C@H]2c3cc(Cl)cc(Cl)c3C[C@@H]2N2CC[C@@H](O)C2)c(F)c1] | A | 9 | 2.79 | 440.13 |
| 554 | 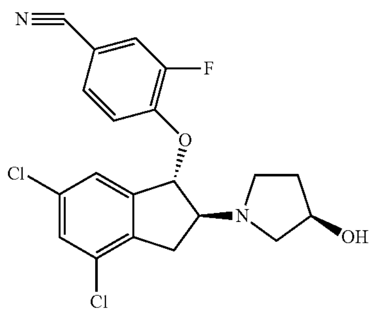 [SMILES: N#Cc1ccc(O[C@H]2c3cc(Cl)cc(Cl)c3C[C@@H]2N2CC[C@@H](O)C2)c(F)c1] | A | 9 | 2.71 | 407.03 |
| 555 | 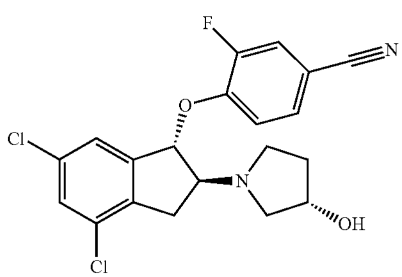 [SMILES: N#Cc1ccc(O[C@H]2c3cc(Cl)cc(Cl)c3C[C@@H]2N2CC[C@H](O)C2)c(F)c1] | A | 1 | 2.85 | 407.04 |
| 556 | 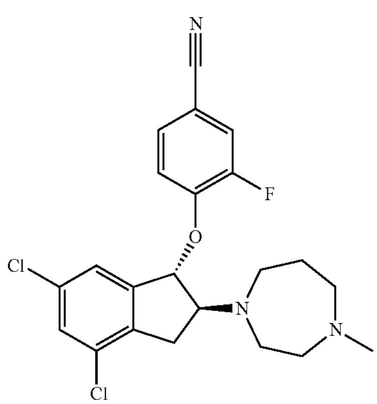 [SMILES: CN1CCCN([C@H]2Cc3c(Cl)cc(Cl)cc3[C@@H]2Oc2ccc(C#N)cc2F)CC1] | A | 1 | 3.02 | 434.03 |

-continued

| Example | Structure | Synthetic method | LC method | Rt time [min] | MS [M + H+] ES+ |
|---------|-----------|------------------|-----------|---------------|------------------|
| 557 | 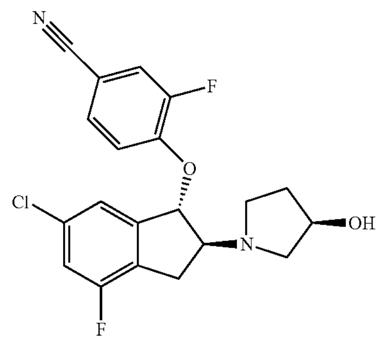 [SMILES: N#Cc1ccc(O[C@H]2c3cc(Cl)cc(F)c3C[C@@H]2N2CC[C@@H](O)C2)c(F)c1] | A | 1 | 2.75 | 391.06 |
| 558 | 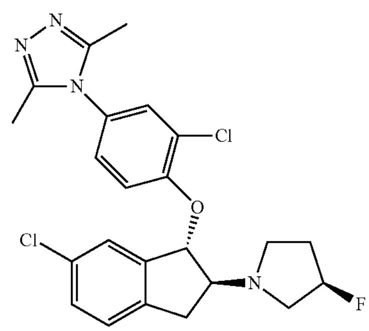 [SMILES: Cc1nnc(C)n1-c1ccc(O[C@H]2c3cc(Cl)ccc3C[C@@H]2N2CC[C@@H](F)C2)c(Cl)c1] | A | 9 | 2.41 | 461.1 |
| 559 | 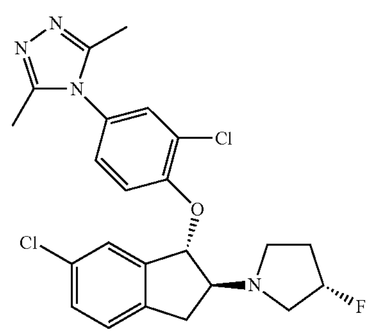 [SMILES: Cc1nnc(C)n1-c1ccc(O[C@H]2c3cc(Cl)ccc3C[C@@H]2N2CC[C@H](F)C2)c(Cl)c1] | A | 1 | 2.37 | 461.25 |
| 560 | 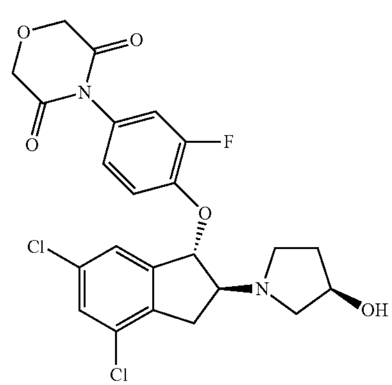 [SMILES: O=C1COCC(=O)N1c1ccc(O[C@H]2c3cc(Cl)cc(Cl)c3C[C@@H]2N2CC[C@@H](O)C2)c(F)c1] | A | 9 | 2.71 | 495.09 |

-continued

| Example | Structure | Synthetic method | LC method | Rt time [min] | MS [M + H+] ES+ |
|---------|-----------|------------------|-----------|---------------|-----------------|
| 561 | 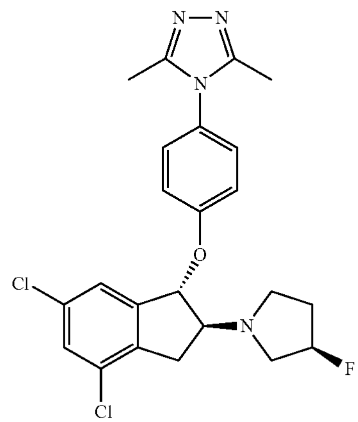 [SMILES: Cc1nnc(C)n1-c1ccc(O[C@H]2c3cc(Cl)cc(Cl)c3C[C@@H]2N2CC[C@@H](F)C2)cc1] | A | 9 | 2.35 | 461.13 |
| 562 | 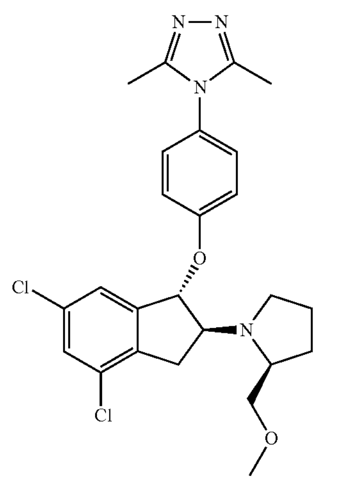 [SMILES: COC[C@@H]1CCCN1[C@H]1Cc2c(Cl)cc(Cl)cc2[C@@H]1Oc1ccc(-n2c(C)nnc2C)cc1] | A | 9 | 2.36 | 487.09 |
| 563 | 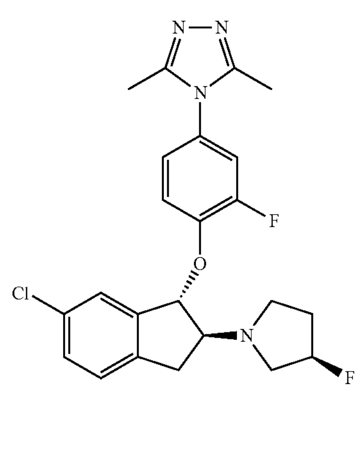 [SMILES: Cc1nnc(C)n1-c1ccc(O[C@H]2c3cc(Cl)ccc3C[C@@H]2N2CC[C@@H](F)C2)c(F)c1] | A | 9 | 2.22 | 445.17 |

-continued

| Example | Structure | Synthetic method | LC method | Rt time [min] | MS [M + H+] ES+ |
|---|---|---|---|---|---|
| 564 | 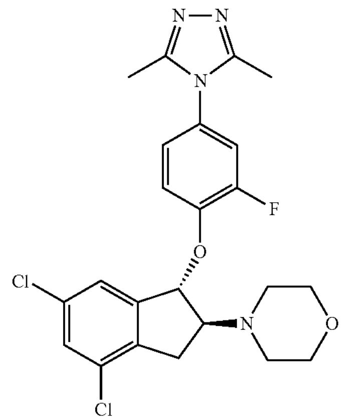 [SMILES: Cc1nnc(C)n1-c1ccc(O[C@H]2c3cc(Cl)cc(Cl)c3C[C@@H]2N2CCOCC2)c(F)c1] | A | 1 | 2.47 | 477.25 |
| 565 | 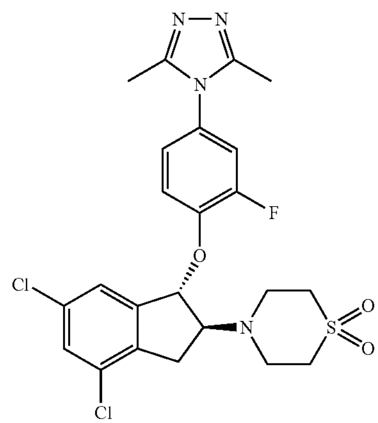 [SMILES: Cc1nnc(C)n1-c1ccc(O[C@H]2c3cc(Cl)cc(Cl)c3C[C@@H]2N2CCS(=O)(=O)CC2)c(F)c1] | A | 1 | 3.04 | 525.2 |
| 566 | 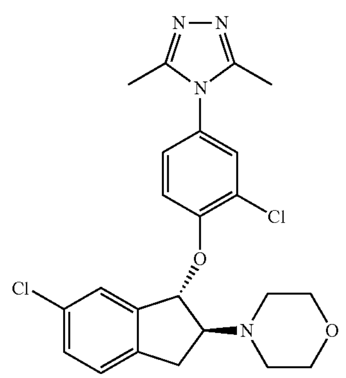 [SMILES: Cc1nnc(C)n1-c1ccc(O[C@H]2c3cc(Cl)ccc3C[C@@H]2N2CCOCC2)c(Cl)c1] | A | 9 | 2.90 | 459.14 |
| 567 | 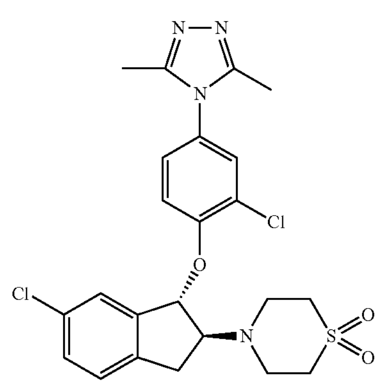 [SMILES: Cc1nnc(C)n1-c1ccc(O[C@H]2c3cc(Cl)ccc3C[C@@H]2N2CCS(=O)(=O)CC2)c(Cl)c1] | A | 9 | 2.76 | 507.09 |

-continued
| Example | Structure | Synthetic method | LC method | Rt time [min] | MS [M + H+] ES+ |
|---|---|---|---|---|---|
| 568 | 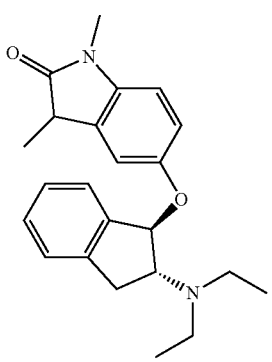 [SMILES: CCN(CC)[C@@H]1Cc2ccccc2[C@H]1Oc1ccc2c(c1)C(C)C(=O)N2C] | A | 12 | 1.33 | 365.23 |
| 569 | 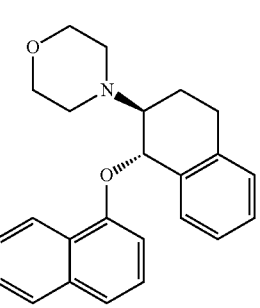 | A | 1 | 2.57 | 375.17 |
| 570 | 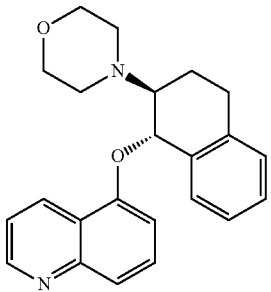 [SMILES: c1ccc2c(c1)CC[C@H](N1CCOCC1)[C@H]2Oc1cccc2ncccc12] | A | 1 | 2.07 | 361.16 |
| 571 | 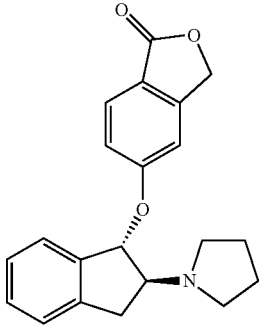 [SMILES: O=C1OCc2cc(O[C@H]3c4ccccc4C[C@@H]3N3CCCC3)ccc21] | A | 14 | 1.71 | 336.13 |

-continued

| Example | Structure | Synthetic method | LC method | Rt time [min] | MS [M + H+] ES+ |
|---------|-----------|------------------|-----------|---------------|-----------------|
| 572 | 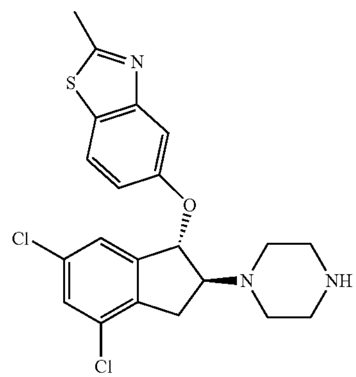 [SMILES: Cc1nc2cc(O[C@H]3c4cc(Cl)cc(Cl)c4C[C@@H]3N3CCNCC3)ccc2s1] | A | 1 | 2.92 | 434.02 |
| 573 | 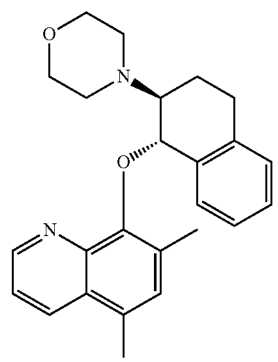 [SMILES: Cc1cc(C)c2cccnc2c1O[C@H]1c2ccccc2CC[C@@H]1N1CCOCC1] | A | 1 | 2.70 | 389.17 |
| 574 | 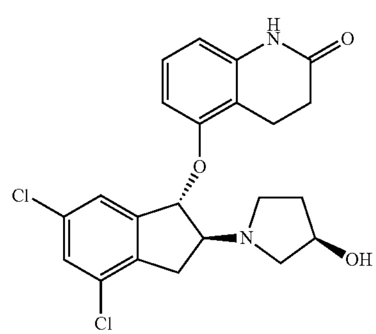 [SMILES: O=C1CCc2c(cccc2O[C@H]2c3cc(Cl)cc(Cl)c3C[C@@H]2N2CC[C@@H](O)C2)N1] | A | 9 | 2.51 | 433.09 |
| 575 | 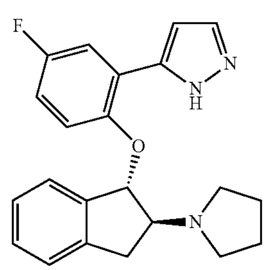 [SMILES: Fc1ccc(O[C@H]2c3ccccc3C[C@@H]2N2CCCC2)c(-c2ccn[nH]2)c1] | A | 9 | 2.52 | 364.23 |

-continued

| Example | Structure | Synthetic method | LC method | Rt time [min] | MS [M + H+] ES+ |
|---|---|---|---|---|---|
| 576 | 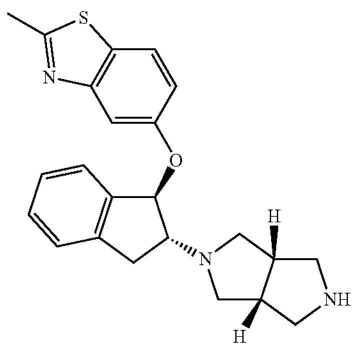 [SMILES: Cc1nc2cc(O[C@@H]3c4ccccc4C[C@H]3N3C[C@H]4CNC[C@H]4C3)ccc2s1] | A | 12 | 1.20 | 392.23 |
| 577 | 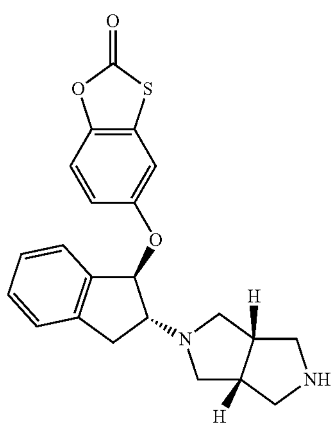 [SMILES: O=c1oc2ccc(O[C@@H]3c4ccccc4C[C@H]3N3C[C@H]4CNC[C@H]4C3)cc2s1] | A | 12 | 1.23 | 395.20 |
| 578 | 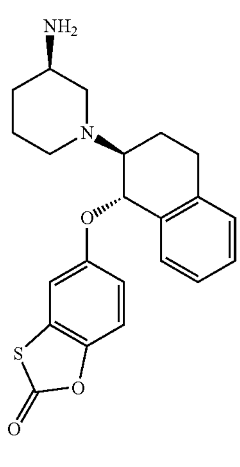 [SMILES: N[C@@H]1CCCN([C@H]2CCc3ccccc3[C@@H]2Oc2ccc3oc(=O)sc3c2)C1] | A | 1 | 2.43 | 397.09 |

-continued

| Example | Structure | Synthetic method | LC method | Rt time [min] | MS [M + H+] ES+ |
|---|---|---|---|---|---|
| 579 | 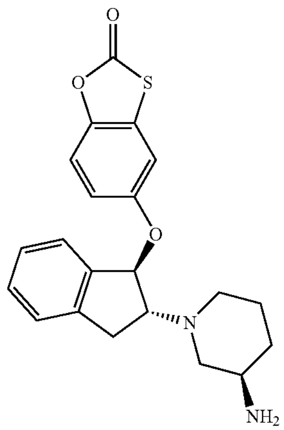 [SMILES: N[C@@H]1CCCN([C@@H]2Cc3ccccc3[C@H]2Oc2ccc3oc(=O)sc3c2)C1] | A | 12 | 1.22 | 383.13 |
| 580 | 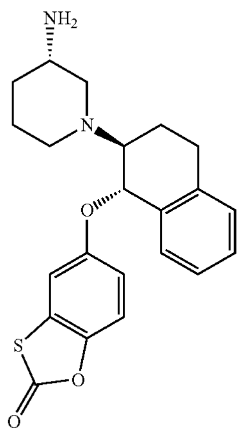 [SMILES: N[C@H]1CCCN([C@H]2CCc3ccccc3[C@@H]2Oc2ccc3oc(=O)sc3c2)C1] | A | 1 | 2.43 | 397.09 |
| 581 | 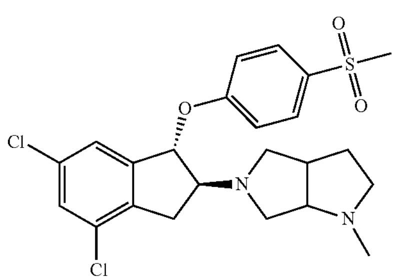 [SMILES: CN1CCC2CN([C@H]3Cc4c(Cl)cc(Cl)cc4[C@@H]3Oc3ccc(S(C)(=O)=O)cc3)CC21] | A | 14 | 1.95 | 481.15 |
| 582 | 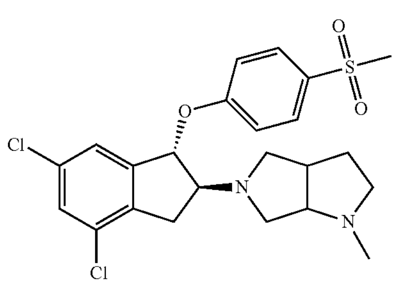 [SMILES: CN1CCC2CN([C@H]3Cc4c(Cl)cc(Cl)cc4[C@@H]3Oc3ccc(S(C)(=O)=O)cc3)CC21] | A | 14 | 2.02 | 481.14 |

-continued

| Example | Structure | Synthetic method | LC method | Rt time [min] | MS [M + H+] ES+ |
|---------|-----------|------------------|-----------|---------------|-----------------|
| 583 | 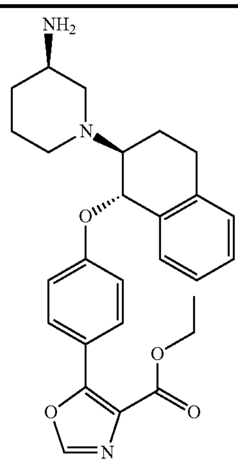 | A | 9 | 2.32 | 462.18 |
| 584 | 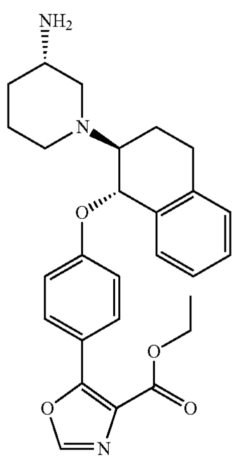 [SMILES: CCOC(=O)c1ncoc1-c1ccc(O[C@H]2c3ccccc3CC[C@@H]2N2CCC[C@H](N)C2)cc1] | A | 1 | 2.47 | 462.18 |
| 585 | 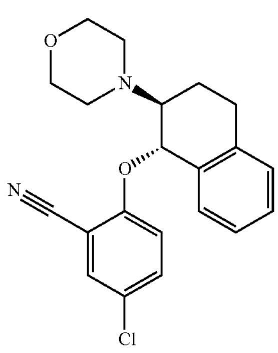 [SMILES: N#Cc1cc(Cl)ccc1O[C@H]1c2ccccc2CC[C@@H]1N1CCOCC1] | A | 1 | 2.77 | 369.09 |
| 586 | 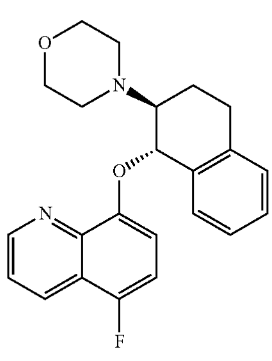 [SMILES: Fc1ccc(O[C@H]2c3ccccc3CC[C@@H]2N2CCOCC2)c2ncccc12] | A | 1 | 2.62 | 379.13 |

| Example | Structure | Synthetic method | LC method | Rt time [min] | MS [M + H+] ES+ |
|---|---|---|---|---|---|
| 587 | 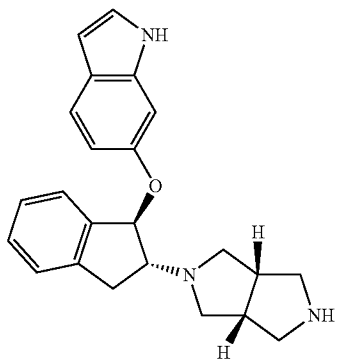 [SMILES: c1ccc2c(c1)C[C@@H](N1C[C@H]3CNC[C@H]3C1)[C@@H]2Oc1ccc2cc[nH]c2c1] | A | 12 | 0.98 | 360.28 |
| 588 | 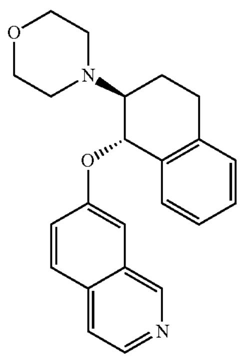 [SMILES: c1ccc2c(c1)CC[C@H](N1CCOCC1)[C@H]2Oc1ccc2ccncc2c1] | A | 1 | 2.04 | 361.16 |
| 589 | 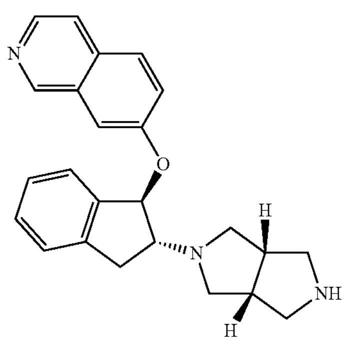 [SMILES: c1ccc2c(c1)C[C@@H](N1C[C@H]3CNC[C@H]3C1)[C@@H]2Oc1ccc2ccncc2c1] | A | 12 | 0.83 | 372.26 |
| 590 | 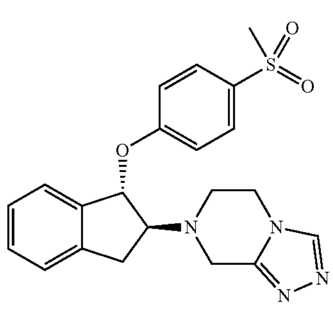 [SMILES: CS(=O)(=O)c1ccc(O[C@H]2c3ccccc3C[C@@H]2N2CCn3cnnc3C2)cc1] | A | 4 | 1.27 | 411.16 |

-continued

| Example | Structure | Synthetic method | LC method | Rt time [min] | MS [M + H+] ES+ |
|---|---|---|---|---|---|
| 591 | 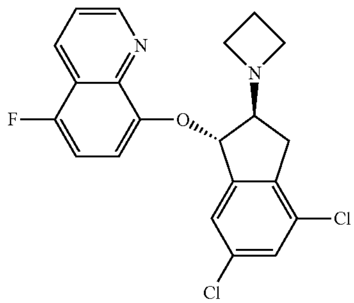 [SMILES: Fc1ccc(O[C@H]2c3cc(Cl)cc(Cl)c3C[C@@H]2N2CCC2)c2ncccc12] | A | 1 | 2.74 | 403.11 |
| 592 | 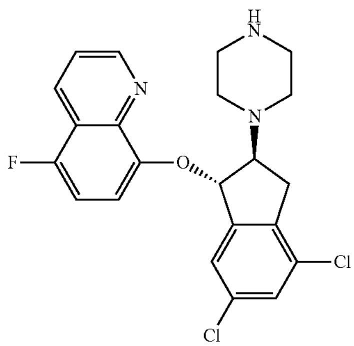 [SMILES: Fc1ccc(O[C@H]2c3cc(Cl)cc(Cl)c3C[C@@H]2N2CCNCC2)c2ncccc12] | A | 1 | 2.68 | 432.16 |
| 593 | 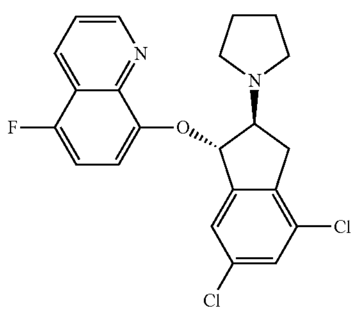 [SMILES: Fc1ccc(O[C@H]2c3cc(Cl)cc(Cl)c3C[C@@H]2N2CCCC2)c2ncccc12] | A | 1 | 2.77 | 417.12 |
| 594 | 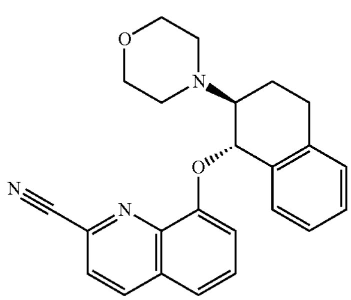 [SMILES: N#Cc1ccc2cccc(O[C@H]3c4ccccc4CC[C@@H]3N3CCOCC3)c2n1] | A | 1 | 2.65 | 386.14 |
| 595 | 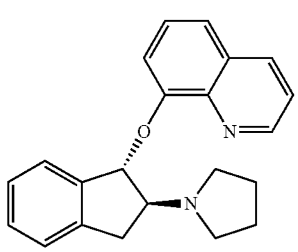 [SMILES: c1ccc2c(c1)C[C@H](N1CCCC1)[C@H]2Oc1cccc2cccnc12] | A | 14 | 1.38 | 331.24 |

-continued

| Example | Structure | Synthetic method | LC method | Rt time [min] | MS [M + H+] ES+ |
|---------|-----------|------------------|-----------|---------------|-----------------|
| 596 | 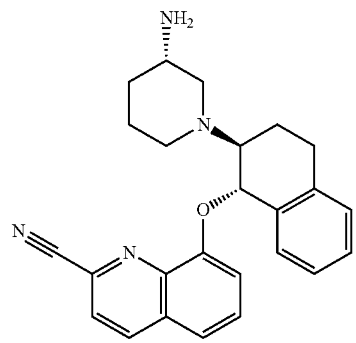 [SMILES: N#Cc1ccc2cccc(O[C@H]3c4ccccc4CC[C@@H]3N3CCC[C@H](N)C3)c2n1] | A | 1 | 2.37 | 399.15 |
| 598 | 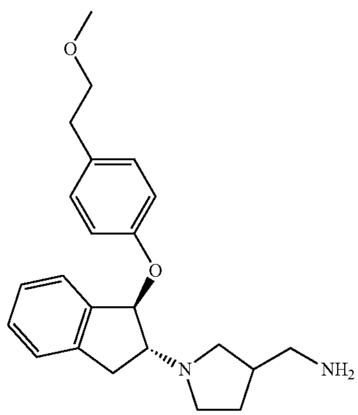 [SMILES: COCCc1ccc(O[C@@H]2c3ccccc3C[C@H]2N2CCC(CN)C2)cc1] | A | 12 | 1.18 | 367.26 |
| 599 | 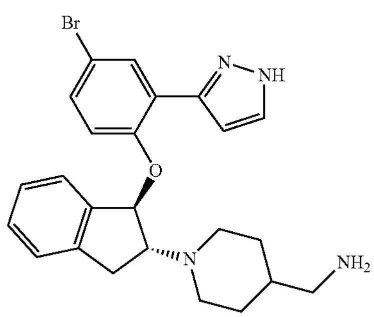 [SMILES: NCC1CCN([C@@H]2Cc3ccccc3[C@H]2Oc2ccc(Br)cc2-c2cc[nH]n2)CC1] | A | 11 | 1.20 | 467.14 |
| 600 | 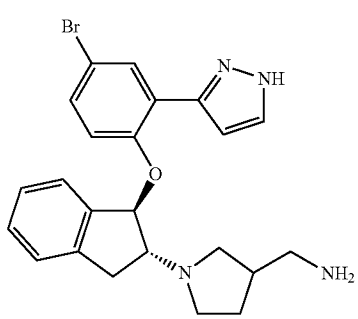 [SMILES: NCC1CCN([C@@H]2Cc3ccccc3[C@H]2Oc2ccc(Br)cc2-c2cc[nH]n2)C1] | A | 12 | 1.30 | 453.16 |

-continued

| Example | Structure | Synthetic method | LC method | Rt time [min] | MS [M + H+] ES+ |
|---|---|---|---|---|---|
| 601 | 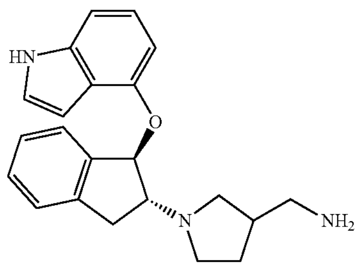 [SMILES: NCC1CCN([C@@H]2Cc3ccccc3[C@H]2Oc2cccc3[nH]ccc23)C1] | A | 12 | 1.13 | 348.24 |
| 602 | 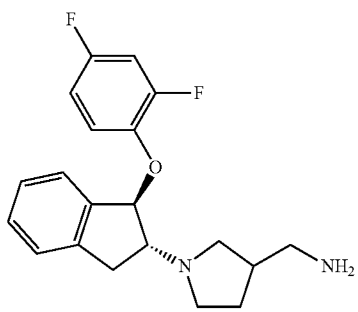 [SMILES: NCC1CCN([C@@H]2Cc3ccccc3[C@H]2Oc2ccc(F)cc2F)C1] | A | 12 | 1.16 | 345.19 |
| 603 | 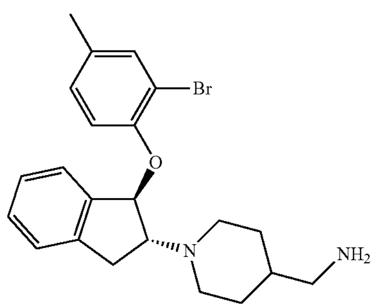 [SMILES: Cc1ccc(O[C@@H]2c3ccccc3C[C@H]2N2CCC(CN)CC2)c(Br)c1] | A | 11 | 1.22 | 415.12 |
| 604 | 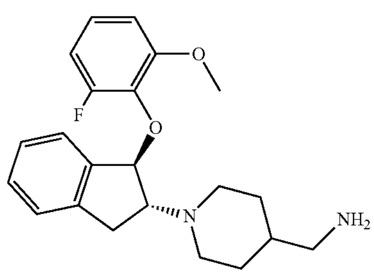 [SMILES: COc1cccc(F)c1O[C@@H]1c2ccccc2C[C@H]1N1CCC(CN)CC1] | A | 11 | 1.08 | 371.18 |
| 605 | 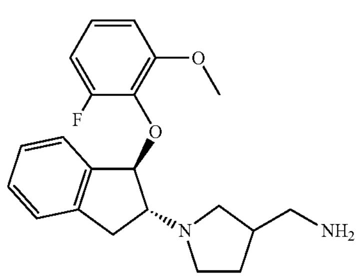 [SMILES: COc1cccc(F)c1O[C@@H]1c2ccccc2C[C@H]1N1CCC(CN)C1] | A | 12 | 1.13 | 357.21 |

-continued

| Example | Structure | Synthetic method | LC method | Rt time [min] | MS [M + H+] ES+ |
|---|---|---|---|---|---|
| 606 | 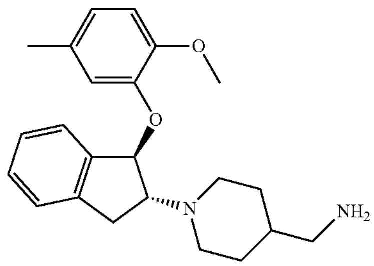 [SMILES: COc1ccc(C)cc1O[C@@H]1c2ccccc2C[C@H]1N1CCC(CN)CC1] | A | 11 | 1.15 | 367.22 |
| 607 | 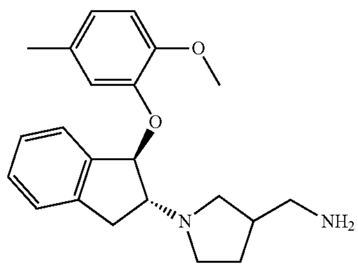 [SMILES: COc1ccc(C)cc1O[C@@H]1c2ccccc2C[C@H]1N1CCC(CN)C1] | A | 12 | 1.20 | 353.24 |
| 608 | 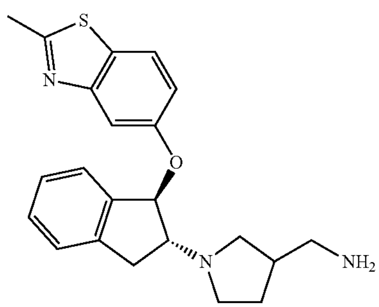 [SMILES: Cc1nc2cc(O[C@@H]3c4ccccc4C[C@H]3N3CCC(CN)C3)ccc2s1] | A | 12 | 1.20 | 380.20 |
| 609 | 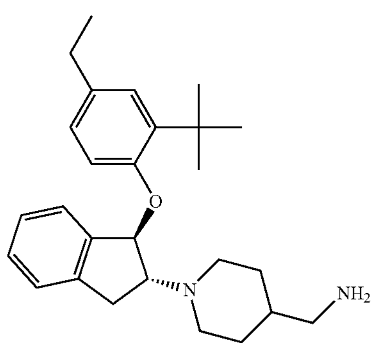 [SMILES: CCc1ccc(O[C@@H]2c3ccccc3C[C@H]2N2CCC(CN)CC2)c(C(C)(C)C)c1] | A | 11 | 1.11 | 407.16 |
| 610 | 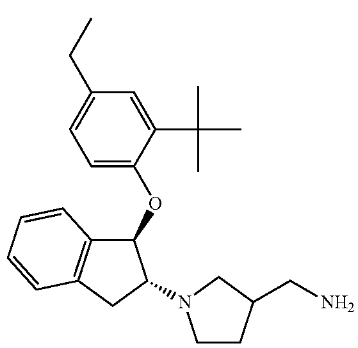 [SMILES: CCc1ccc(O[C@@H]2c3ccccc3C[C@H]2N2CCC(CN)C2)c(C(C)(C)C)c1] | A | 12 | 1.23 | 393.20 |

-continued

| Example | Structure | Synthetic method | LC method | Rt time [min] | MS [M + H+] ES+ |
|---|---|---|---|---|---|
| 611 | 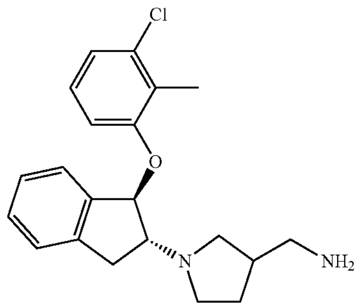 [SMILES: Cc1c(Cl)cccc1O[C@@H]1c2ccccc2C[C@H]1N1CCC(CN)C1] | A | 12 | 1.38 | 357.20 |
| 612 | 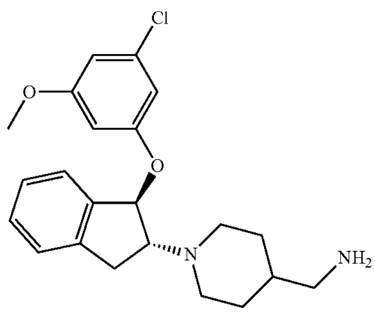 [SMILES: COc1cc(Cl)cc(O[C@@H]2c3ccccc3C[C@H]2N2CCC(CN)CC2)c1] | A | 12 | 1.32 | 387.19 |
| 613 | 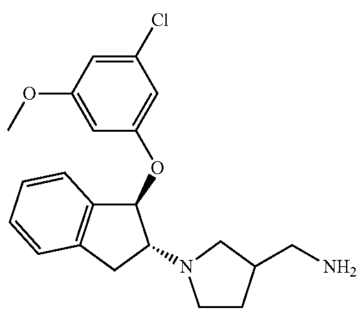 [SMILES: COc1cc(Cl)cc(O[C@@H]2c3ccccc3C[C@H]2N2CCC(CN)C2)c1] | A | 12 | 1.33 | 373.20 |
| 614 | 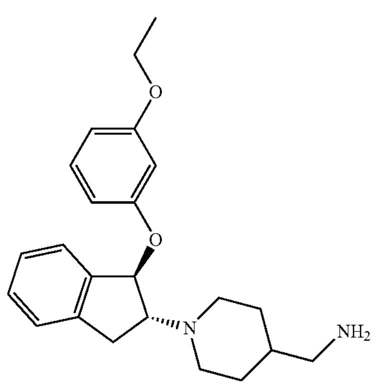 [SMILES: CCOc1cccc(O[C@@H]2c3ccccc3C[C@H]2N2CCC(CN)CC2)c1] | A | 12 | 1.25 | 367.22 |

-continued

| Example | Structure | Synthetic method | LC method | Rt time [min] | MS [M + H+] ES+ |
|---------|-----------|------------------|-----------|---------------|-----------------|
| 615 | 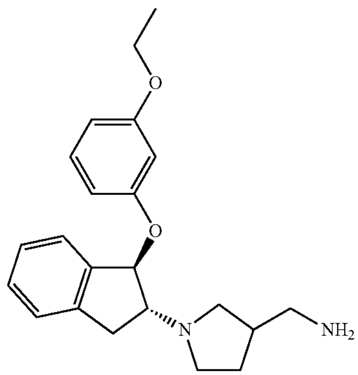 [SMILES: CCOc1cccc(O[C@@H]2c3ccccc3C[C@H]2N2CCC(CN)C2)c1] | A | 12 | 1.30 | 353.26 |
| 616 | 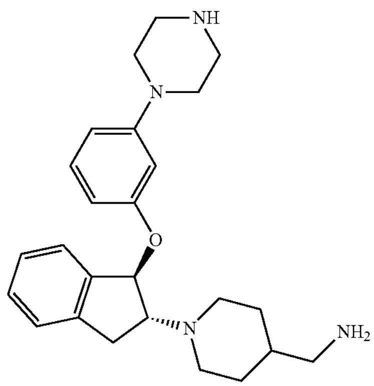 [SMILES: NCC1CCN([C@@H]2Cc3ccccc3[C@H]2Oc2cccc(N3CCNCC3)c2)CC1] | A | 12 | 0.87 | 407.30 |
| 617 | 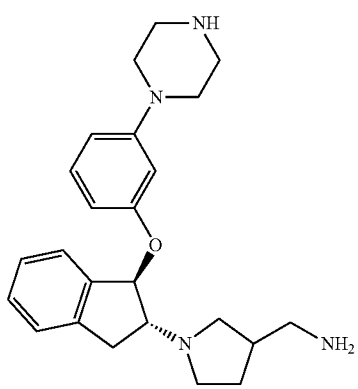 [SMILES: NCC1CCN([C@@H]2Cc3ccccc3[C@H]2Oc2cccc(N3CCNCC3)c2)C1] | A | 12 | 0.87 | 393.31 |
| 618 | 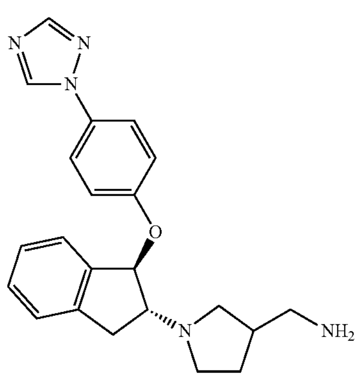 [SMILES: NCC1CCN([C@@H]2Cc3ccccc3[C@H]2Oc2ccc(-n3cncn3)cc2)C1] | A | 12 | 1.03 | 376.24 |

| Example | Structure | Synthetic method | LC method | Rt time [min] | MS [M + H+] ES+ |
|---|---|---|---|---|---|
| 619 | 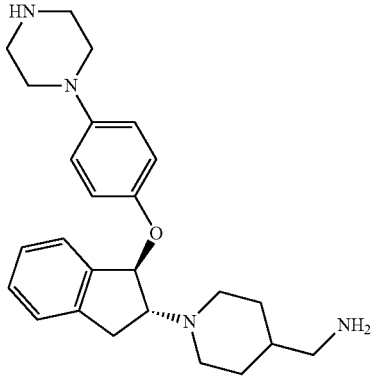 [SMILES: NCC1CCN([C@@H]2Cc3ccccc3[C@H]2Oc2ccc(N3CCNCC3)cc2)CC1] | A | 11 | 0.78 | 407.27 |
| 620 | 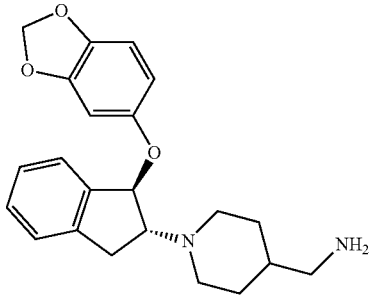 [SMILES: NCC1CCN([C@@H]2Cc3ccccc3[C@H]2Oc2ccc3c(c2)OCO3)CC1] | A | 12 | 1.13 | 367.21 |
| 621 | 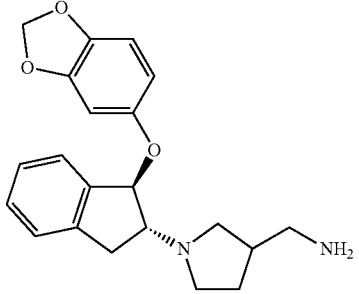 [SMILES: NCC1CCN([C@@H]2Cc3ccccc3[C@H]2Oc2ccc3c(c2)OCO3)C1] | A | 12 | 1.15 | 353.21 |
| 622 | 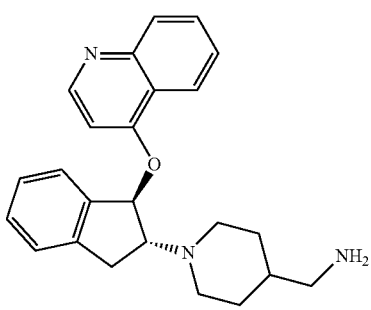 [SMILES: NCC1CCN([C@@H]2Cc3ccccc3[C@H]2Oc2ccnc3ccccc23)CC1] | A | 12 | 0.78 | 374.22 |

| Example | Structure | Synthetic method | LC method | Rt time [min] | MS [M + H+] ES+ |
|---|---|---|---|---|---|
| 625 | 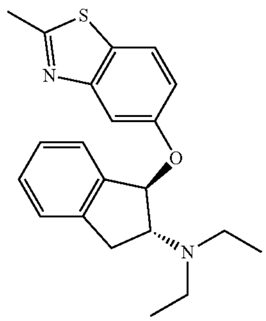 [SMILES: CCN(CC)[C@@H]1Cc2ccccc2[C@H]1Oc1ccc2sc(C)nc2c1] | A | 12 | 1.43 | 353.15 |
| 626 | 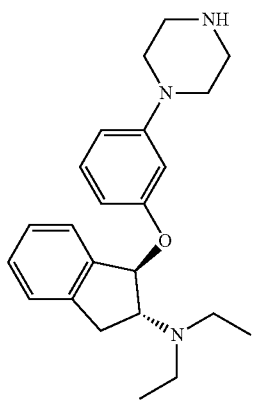 [SMILES: CCN(CC)[C@@H]1Cc2ccccc2[C@H]1Oc1cccc(N2CCNCC2)c1] | A | 12 | 1.02 | 366.28 |
| 627 | 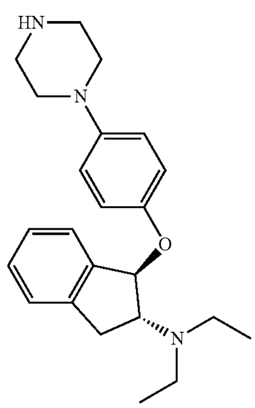 [SMILES: CCN(CC)[C@@H]1Cc2ccccc2[C@H]1Oc1ccc(N2CCNCC2)cc1] | A | 12 | 0.97 | 366.25 |
| 628 | 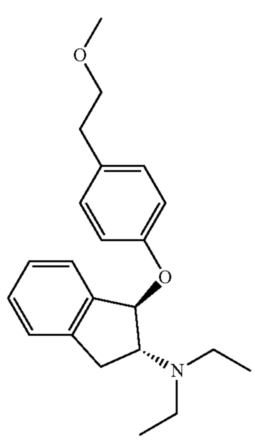 [SMILES: CCN(CC)[C@@H]1Cc2ccccc2[C@H]1Oc1ccc(CCOC)cc1] | A | 12 | 1.48 | 340.21 |

| Example | Structure | Synthetic method | LC method | Rt time [min] | MS [M + H+] ES+ |
|---|---|---|---|---|---|
| 629 | 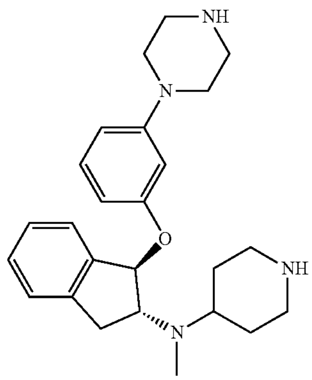 [SMILES: CN(C1CCNCC1)[C@@H]1Cc2ccccc2[C@H]1Oc1cccc(N2CCNCC2)c1] | A | 12 | 0.83 | 407.34 |
| 630 | 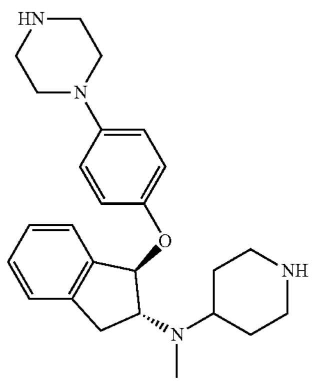 [SMILES: CN(C1CCNCC1)[C@@H]1Cc2ccccc2[C@H]1Oc1ccc(N2CCNCC2)cc1] | A | 11 | 0.95 | 407.27 |
| 631 | 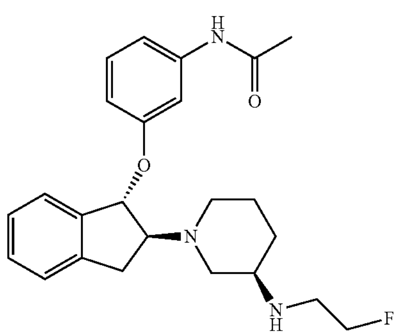 [SMILES: CC(=O)Nc1cccc(O[C@H]2c3ccccc3C[C@@H]2N2CCC[C@@H](NCCF)C2)c1] | A | 4 | 1.05 | 412.22 |
| 632 | 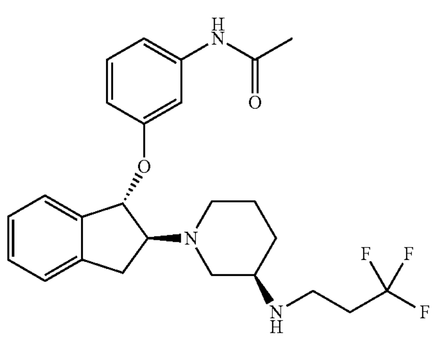 [SMILES: CC(=O)Nc1cccc(O[C@H]2c3ccccc3C[C@@H]2N2CCC[C@@H](NCCC(F)(F)F)C2)c1] | A | 12 | 1.15 | 462.19 |

| Example | Structure | Synthetic method | LC method | Rt time [min] | MS [M + H+] ES+ |
|---|---|---|---|---|---|
| 633 | 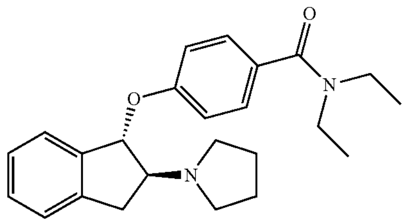 [SMILES: CCN(CC)C(=O)c1ccc(O[C@H]2c3ccccc3C[C@@H]2N2CCCC2)cc1] | A | 9 | 2.51 | 379.21 |
| 634 | 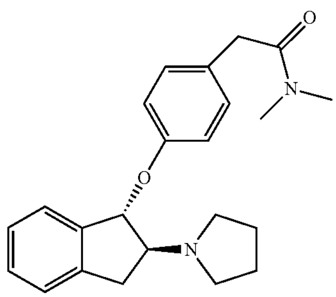 [SMILES: CN(C)C(=O)Cc1ccc(O[C@H]2c3ccccc3C[C@@H]2N2CCCC2)cc1] | A | 3 | 1.31 | 365.42 |
| 635 | 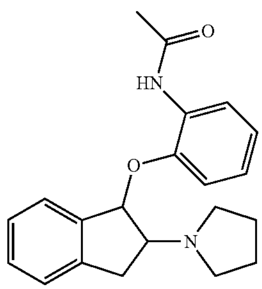 [SMILES: CC(=O)Nc1ccccc1OC1c2ccccc2CC1N1CCCC1] | A | 13 | 1.16 | 337.2 |
| 636 | 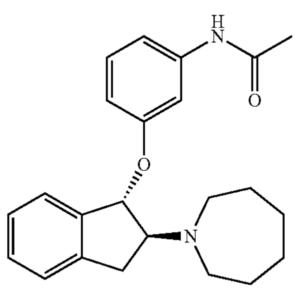 [SMILES: CC(=O)Nc1cccc(O[C@H]2c3ccccc3C[C@@H]2N2CCCCCC2)c1] | A | 4 | 1.19 | 365.29 |
| 637 | 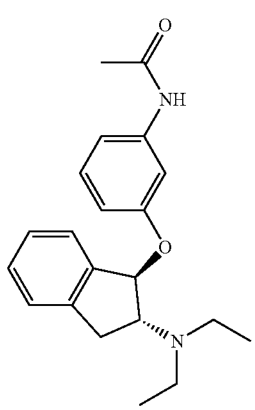 [SMILES: CCN(CC)[C@@H]1Cc2ccccc2[C@H]1Oc1cccc(NC(C)=O)c1] | A | 12 | 1.22 | 339.18 |

-continued

| Example | Structure | Synthetic method | LC method | Rt time [min] | MS [M + H+] ES+ |
|---------|-----------|------------------|-----------|---------------|-----------------|
| 638 | 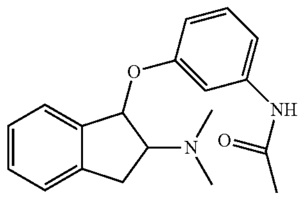 [SMILES: CC(=O)Nc1cccc(OC2c3ccccc3CC2N(C)C)c1] | A | 12 | 1.08 | 311.24 |
| 639 | 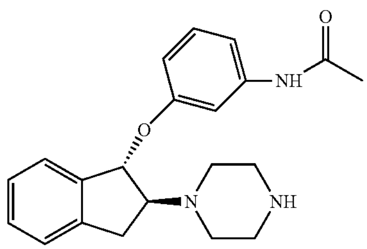 [SMILES: CC(=O)Nc1cccc(O[C@H]2c3ccccc3C[C@@H]2N2CCNCC2)c1] | A | 1 | 2.25 | 352.18 |
| 640 | 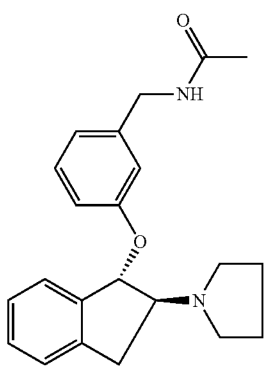 [SMILES: CC(=O)NCc1cccc(O[C@H]2c3ccccc3C[C@@H]2N2CCCC2)c1] | A | 9 | 2.27 | 351.14 |
| 641 | 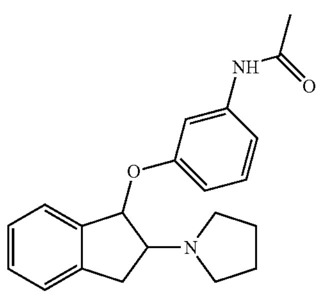 [SMILES: CC(=O)Nc1cccc(OC2c3ccccc3CC2N2CCCC2)c1] | A | 4 | 1.10 | 337.25 |
| 642 | 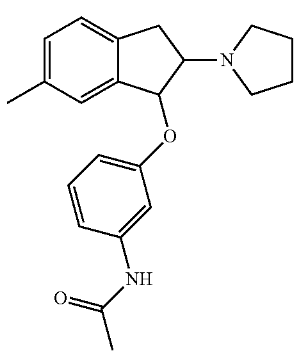 [SMILES: CC(=O)Nc1cccc(OC2c3cc(C)ccc3CC2N2CCCC2)c1] | A | 4 | 1.11 | 369.16 |

-continued

| Example | Structure | Synthetic method | LC method | Rt time [min] | MS [M + H+] ES+ |
|---|---|---|---|---|---|
| 643 | 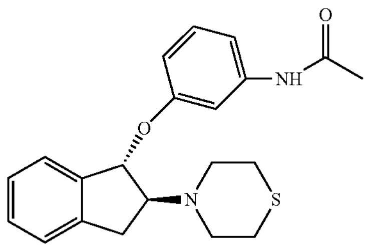 [SMILES: CC(=O)Nc1cccc(O[C@H]2c3ccccc3C[C@@H]2N2CCSCC2)c1] | A | 18 | 1.11 | 368.16 |
| 644 | 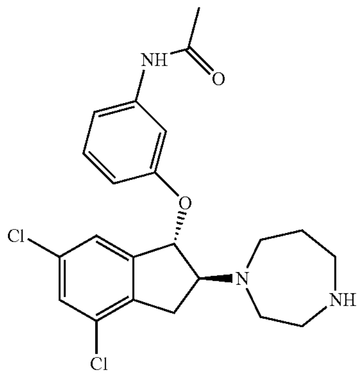 [SMILES: CC(=O)Nc1cccc(O[C@H]2c3cc(Cl)cc(Cl)c3C[C@@H]2N2CCCNCC2)c1] | A | 3 | 1.44 | 434.3 |
| 645 | 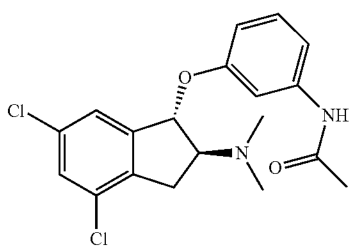 [SMILES: CC(=O)Nc1cccc(O[C@H]2c3cc(Cl)cc(Cl)c3C[C@@H]2N(C)C)c1] | A | 4 | 1.27 | 379.09 |
| 646 | 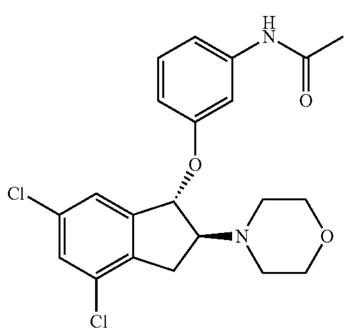 [SMILES: CC(=O)Nc1cccc(O[C@H]2c3cc(Cl)cc(Cl)c3C[C@@H]2N2CCOCC2)c1] | A | 4 | 1.29 | 421.09 |
| 647 | 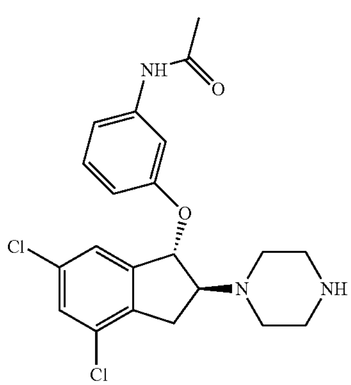 [SMILES: CC(=O)Nc1cccc(O[C@H]2c3cc(Cl)cc(Cl)c3C[C@@H]2N2CCNCC2)c1] | A | 4 | 1.28 | 420.21 |

-continued

| Example | Structure | Synthetic method | LC method | Rt time [min] | MS [M + H+] ES+ |
|---|---|---|---|---|---|
| 648 | 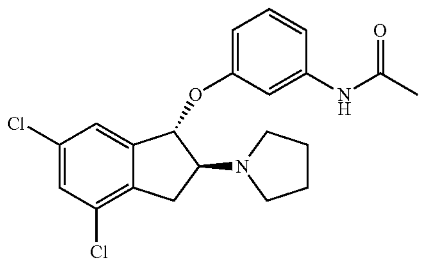 [SMILES: CC(=O)Nc1cccc(O[C@H]2c3cc(Cl)cc(Cl)c3C[C@@H]2N2CCCC2)c1] | A | 4 | 1.30 | 405.08 |
| 649 | 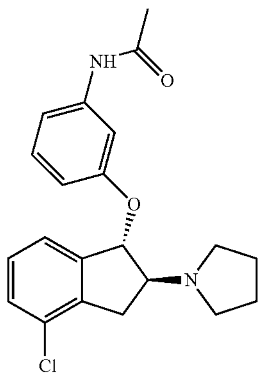 [SMILES: CC(=O)Nc1cccc(O[C@H]2c3cccc(Cl)c3C[C@@H]2N2CCCC2)c1] | A | 4 | 1.20 | 371.18 |
| 650 | 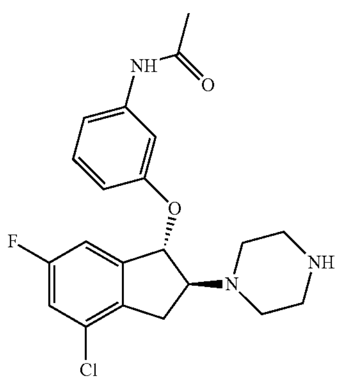 [SMILES: CC(=O)Nc1cccc(O[C@H]2c3cc(F)cc(Cl)c3C[C@@H]2N2CCNCC2)c1] | A | 14 | 1.83 | 404.13 |
| 651 | 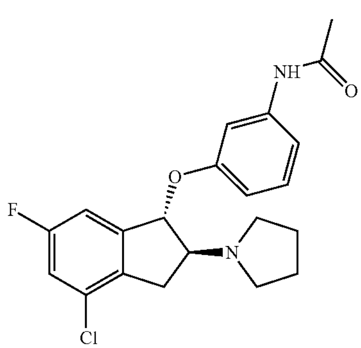 [SMILES: CC(=O)Nc1cccc(O[C@H]2c3cc(F)cc(Cl)c3C[C@@H]2N2CCCC2)c1] | A | 4 | 1.21 | 389.14 |

-continued

| Example | Structure | Synthetic method | LC method | Rt time [min] | MS [M + H+] ES+ |
|---|---|---|---|---|---|
| 652 | 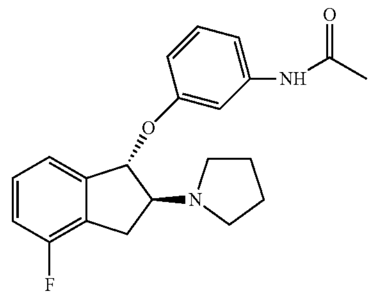 [SMILES: CC(=O)Nc1cccc(O[C@H]2c3cccc(F)c3C[C@@H]2N2CCCC2)c1] | A | 13 | 1.29 | 355.31 |
| 653 | 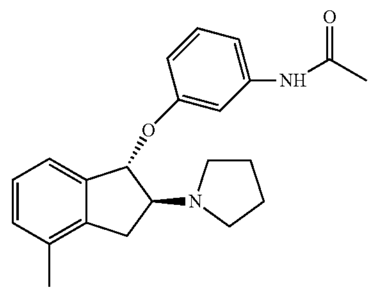 [SMILES: CC(=O)Nc1cccc(O[C@H]2c3cccc(C)c3C[C@@H]2N2CCCC2)c1] | A | 12 | 1.27 | 351.19 |
| 654 | 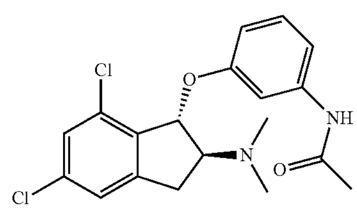 [SMILES: CC(=O)Nc1cccc(O[C@H]2c3c(Cl)cc(Cl)cc3C[C@@H]2N(C)C)c1] | A | 4 | 1.28 | 379.1 |
| 655 | 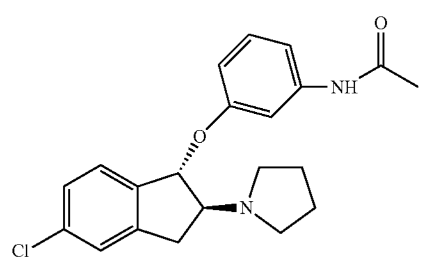 [SMILES: CC(=O)Nc1cccc(O[C@H]2c3ccc(Cl)cc3C[C@@H]2N2CCCC2)c1] | A | 4 | 1.21 | 371.14 |
| 656 | 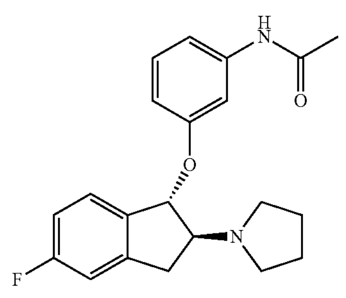 [SMILES: CC(=O)Nc1cccc(O[C@H]2c3ccc(F)cc3C[C@@H]2N2CCCC2)c1] | A | 4 | 1.11 | 355.17 |

-continued

| Example | Structure | Synthetic method | LC method | Rt time [min] | MS [M + H+] ES+ |
|---|---|---|---|---|---|
| 657 | 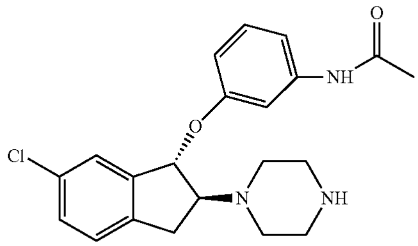 [SMILES: CC(=O)Nc1cccc(O[C@H]2c3cc(Cl)ccc3C[C@@H]2N2CCNCC2)c1] | A | 4 | 1.16 | 386.2 |
| 658 | 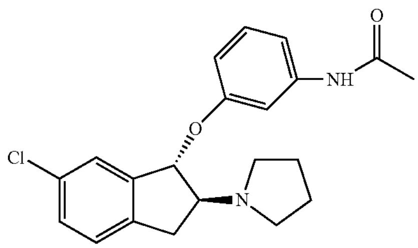 [SMILES: CC(=O)Nc1cccc(O[C@H]2c3cc(Cl)ccc3C[C@@H]2N2CCCC2)c1] | A | 4 | 1.23 | 371.14 |
| 659 | 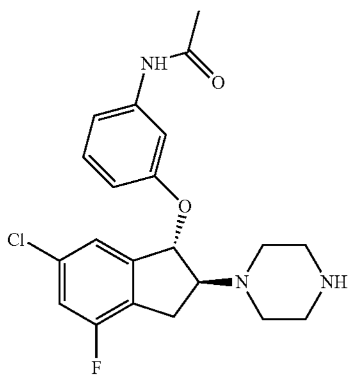 [SMILES: CC(=O)Nc1cccc(O[C@H]2c3cc(Cl)cc(F)c3C[C@@H]2N2CCNCC2)c1] | A | 14 | 1.83 | 404.15 |
| 660 | 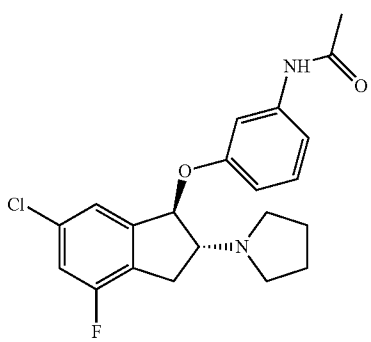 [SMILES: CC(=O)Nc1cccc(O[C@@H]2c3cc(Cl)cc(F)c3C[C@H]2N2CCCC2)c1] | A | 14 | 1.87 | 389.12 |
| 661 | 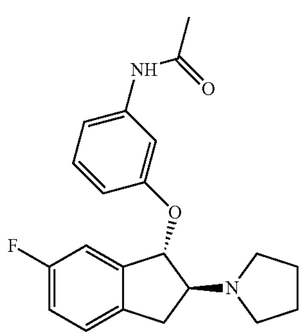 [SMILES: CC(=O)Nc1cccc(O[C@H]2c3cc(F)ccc3C[C@@H]2N2CCCC2)c1] | A | 12 | 1.24 | 355.16 |

-continued

| Example | Structure | Synthetic method | LC method | Rt time [min] | MS [M + H+] ES+ |
|---------|-----------|------------------|-----------|---------------|-----------------|
| 662 | 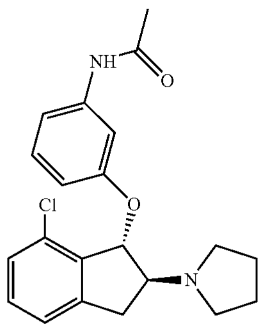 [SMILES: CC(=O)Nc1cccc(O[C@H]2c3c(Cl)cccc3C[C@@H]2N2CCCC2)c1] | A | 4 | 1.14 | 371.11 |
| 663 | 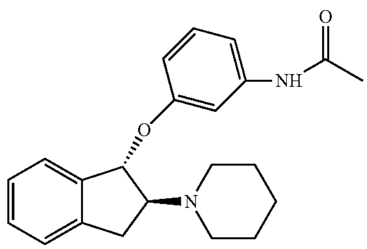 | A | 13 | 1.26 | 351.23 |
| 664 | 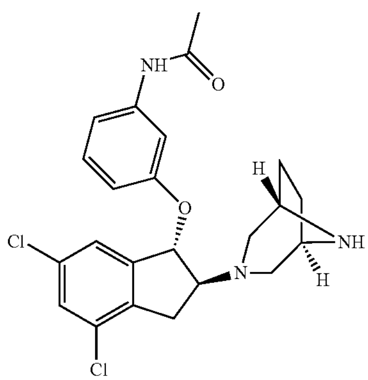 [SMILES: CC(=O)Nc1cccc(O[C@H]2c3cc(Cl)cc(Cl)c3C[C@@H]2N2C[C@H]3CC[C@@H](C2)N3)c1] | A | 4 | 1.42 | 446.19 |
| 665 | 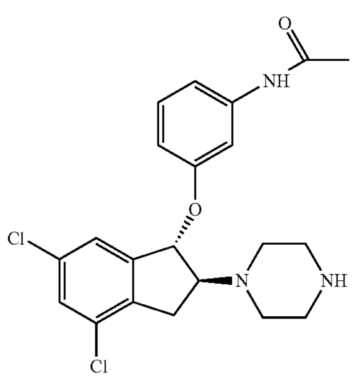 [SMILES: CC(=O)Nc1cccc(O[C@H]2c3cc(Cl)cc(Cl)c3C[C@@H]2N2CCNCC2)c1] | A | 13 | 1.45 | 420.21 |
| 666 | 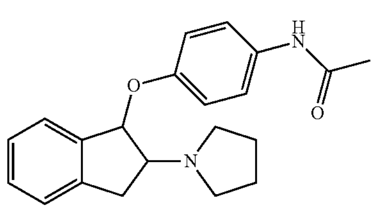 [SMILES: CC(=O)Nc1ccc(OC2c3ccccc3CC2N2CCCC2)cc1] | A | 13 | 1.15 | 337.2 |

-continued
| Example | Structure | Synthetic method | LC method | Rt time [min] | MS [M + H+] ES+ |
|---|---|---|---|---|---|
| 667 | 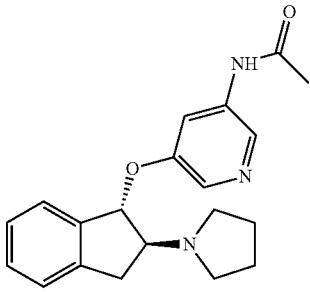 [SMILES: CC(=O)Nc1cncc(O[C@H]2c3ccccc3C[C@@H]2N2CCCC2)c1] | A | 4 | 0.77 | 338.19 |
| 668 | 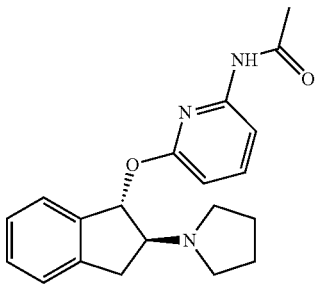 [SMILES: CC(=O)Nc1cccc(O[C@H]2c3ccccc3C[C@@H]2N2CCCC2)n1] | A | 4 | 1.14 | 338.15 |
| 669 | 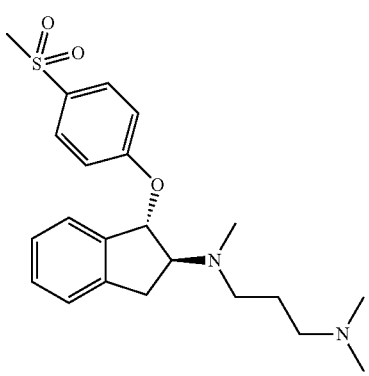 | A | 1 | 2.14 | 403.16 |
| 670 | 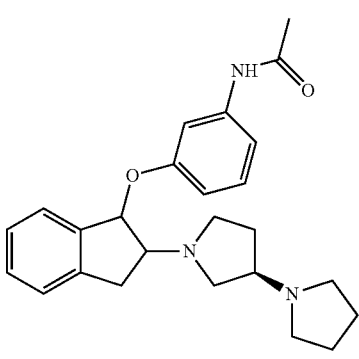 [SMILES: CC(=O)Nc1cccc(OC2c3ccccc3CC2N2CC[C@@H](N3CCCC3)C2)c1] | A | 13 | 1.14 | 406.21 |

-continued

| Example | Structure | Synthetic method | LC method | Rt time [min] | MS [M + H+] ES+ |
|---------|-----------|------------------|-----------|---------------|-----------------|
| 671 | 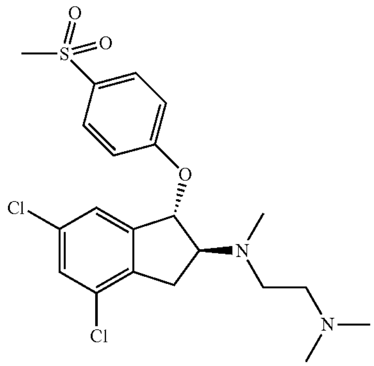 | A | 1 | 2.75 | 457.05 |
| 672 | 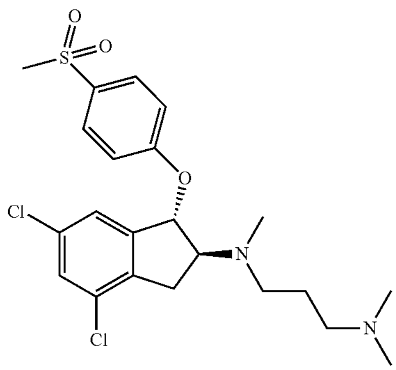 [SMILES: CN(C)CCCN(C)[C@H]1Cc2c(Cl)cc(Cl)cc2[C@@H]1Oc1ccc(S(C)(=O)=O)cc1] | A | 1 | 2.39 | 471.05 |
| 673 | 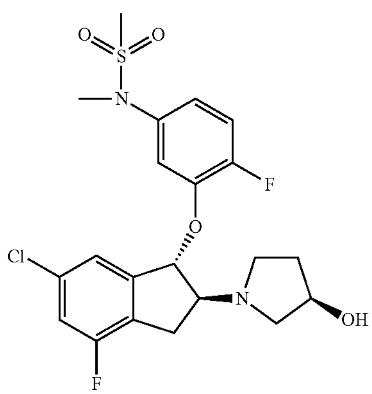 [SMILES: CN(c1ccc(F)c(O[C@H]2c3cc(Cl)cc(F)c3C[C@@H]2N2CC[C@@H](O)C2)c1)S(C)(=O)=O] | A | 17 | 2.68 | 473.12 |
| 674 | 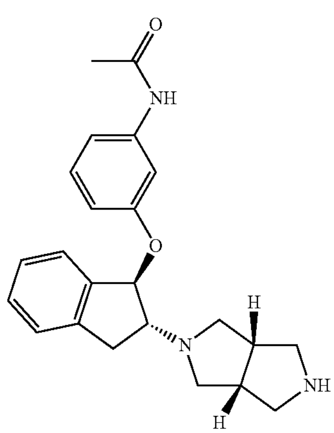 [SMILES: CC(=O)Nc1cccc(O[C@@H]2c3ccccc3C[C@H]2N2C[C@H]3CNC[C@H]3C2)c1] | A | 12 | 1.05 | 378.28 |

-continued

| Example | Structure | Synthetic method | LC method | Rt time [min] | MS [M + H+] ES+ |
|---|---|---|---|---|---|
| 675 | 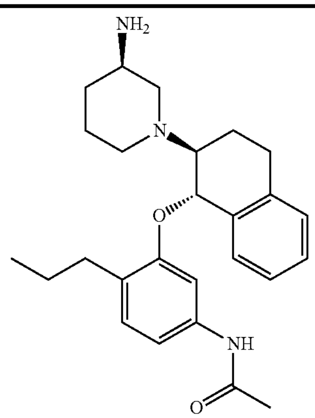 | A | 1 | 2.54 | 422.2 |
| 676 | 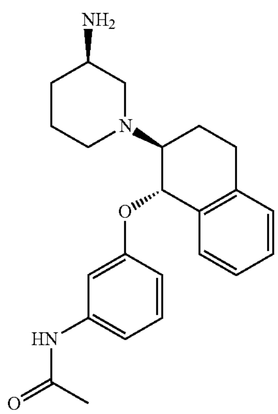 [SMILES: CC(=O)Nc1cccc(O[C@H]2c3ccccc3CC[C@@H]2N2CCC[C@@H](N)C2)c1] | A | 1 | 2.20 | 380.2 |
| 677 | 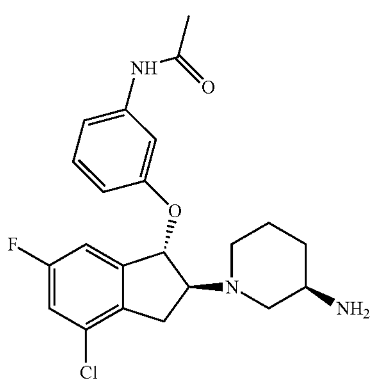 [SMILES: CC(=O)Nc1cccc(O[C@H]2c3cc(F)cc(Cl)c3C[C@@H]2N2CCC[C@@H](N)C2)c1] | A | 1 | 2.37 | 418.18 |
| 678 | 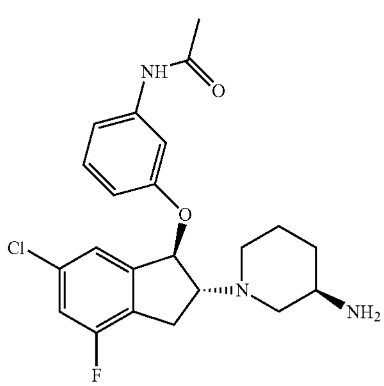 [SMILES: CC(=O)Nc1cccc(O[C@@H]2c3cc(Cl)cc(F)c3C[C@H]2N2CCC[C@@H](N)C2)c1] | A | 1 | 2.40 | 418.18 |

| Example | Structure | Synthetic method | LC method | Rt time [min] | MS [M + H+] ES+ |
|---------|-----------|------------------|-----------|---------------|-----------------|
| 679 | 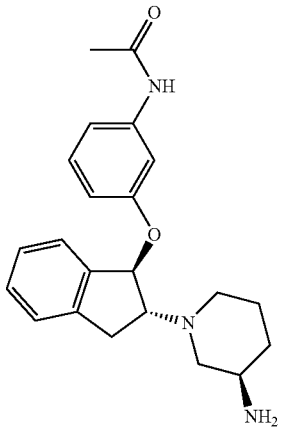 [SMILES: CC(=O)Nc1cccc(O[C@@H]2c3ccccc3C[C@H]2N2CCC[C@@H](N)C2)c1] | A | 12 | 0.98 | 366.20 |
| 680 | 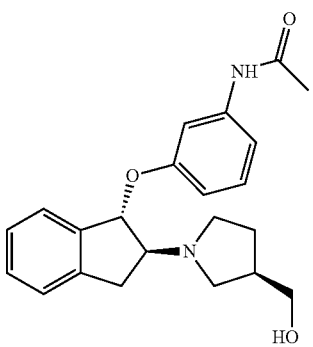 [SMILES: CC(=O)Nc1cccc(O[C@H]2c3ccccc3C[C@@H]2N2CC[C@@H](CO)C2)c1] | A | 4 | 1.07 | 367.17 |
| 681 | 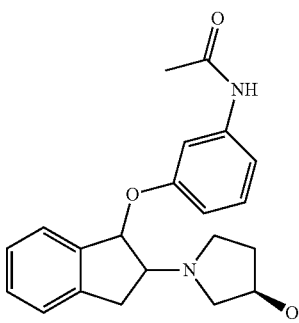 | A | 13 | 1.21 | 353.23 |
| 682 | 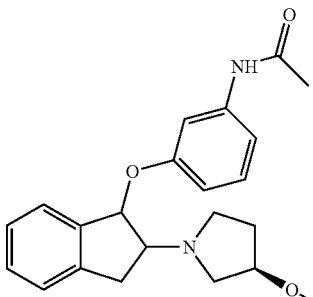 | A | 4 | 1.11 | 367.16 |

-continued

| Example | Structure | Synthetic method | LC method | Rt time [min] | MS [M + H+] ES+ |
|---|---|---|---|---|---|
| 683 | 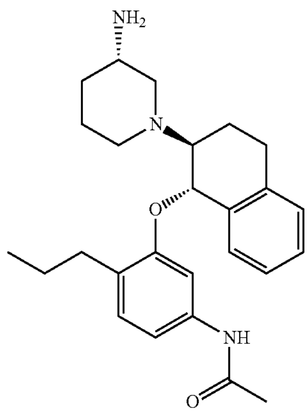 [SMILES: CCCc1ccc(NC(C)=O)cc1O[C@H]1c2ccccc2CC[C@@H]1N1CCC[C@H](N)C1] | A | 1 | 2.52 | 422.21 |
| 684 | 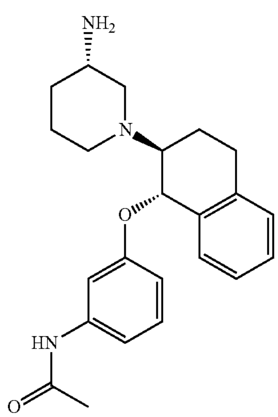 [SMILES: CC(=O)Nc1cccc(O[C@H]2c3ccccc3CC[C@@H]2N2CCC[C@H](N)C2)c1] | A | 1 | 2.20 | 380.19 |
| 685 | 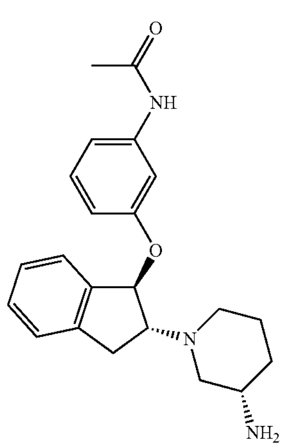 [SMILES: CC(=O)Nc1cccc(O[C@@H]2c3ccccc3C[C@H]2N2CCC[C@H](N)C2)c1] | A | 12 | 1.02 | 366.24 |

-continued

| Example | Structure | Synthetic method | LC method | Rt time [min] | MS [M + H+] ES+ |
|---|---|---|---|---|---|
| 686 | 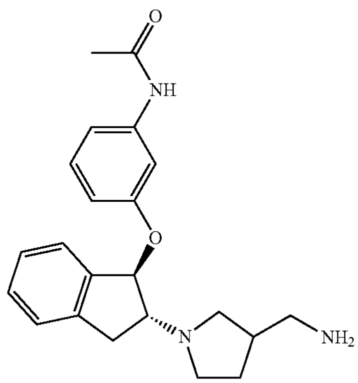 [SMILES: CC(=O)Nc1cccc(O[C@@H]2c3ccccc3C[C@H]2N2CCC(CN)C2)c1] | A | 12 | 1.02 | 366.24 |
| 687 | 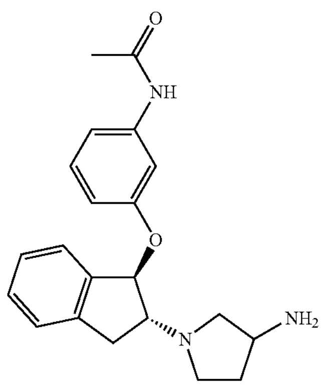 [SMILES: CC(=O)Nc1cccc(O[C@@H]2c3ccccc3C[C@H]2N2CCC(N)C2)c1] | A | 12 | 1.00 | 352.15 |
| 688 | 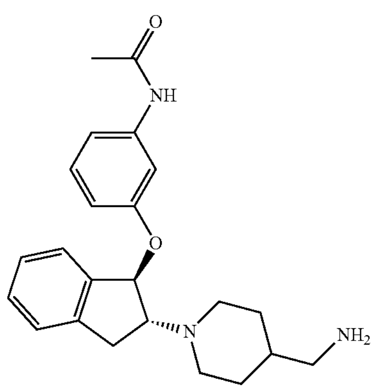 [SMILES: CC(=O)Nc1cccc(O[C@@H]2c3ccccc3C[C@H]2N2CCC(CN)CC2)c1] | A | 11 | 0.96 | 380.19 |
| 689 | 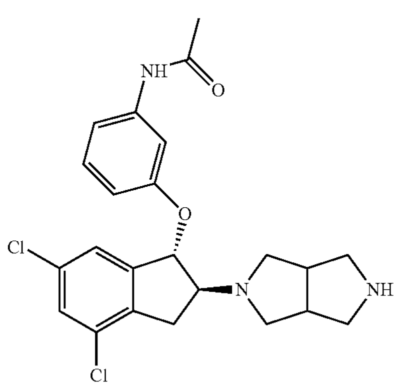 [SMILES: CC(=O)Nc1cccc(O[C@H]2c3cc(Cl)cc(Cl)c3C[C@@H]2N2CC3CNCC3C2)c1] | A | 4 | 1.16 | 446.2 |

-continued

| Example | Structure | Synthetic method | LC method | Rt time [min] | MS [M + H+] ES+ |
|---|---|---|---|---|---|
| 690 | 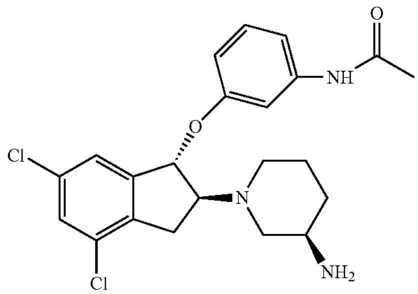 [SMILES: CC(=O)Nc1cccc(O[C@H]2c3cc(Cl)cc(Cl)c3C[C@@H]2N2CCC[C@@H](N)C2)c1] | A | 4 | 1.22 | 434.16 |
| 691 | 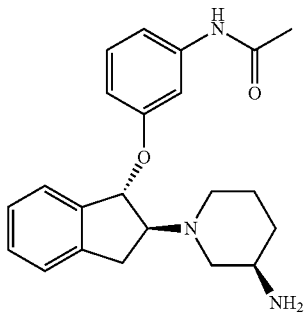 [SMILES: CC(=O)Nc1cccc(O[C@H]2c3ccccc3C[C@@H]2N2CCC[C@@H](N)C2)c1] | A | 12 | 0.99 | 366.39 |
| 692 | 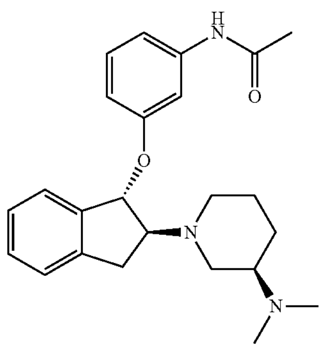 [SMILES: CC(=O)Nc1cccc(O[C@H]2c3ccccc3C[C@@H]2N2CCC[C@@H](N(C)C)C2)c1] | A | 4 | 1.06 | 394.25 |
| 693 | 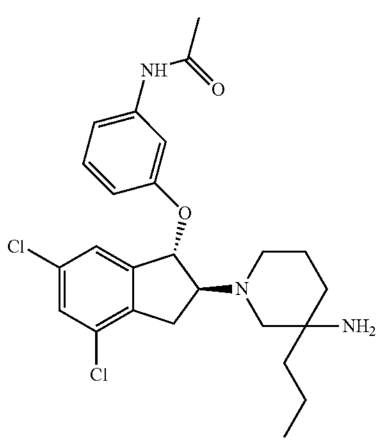 [SMILES: CCCC1(N)CCCN([C@H]2Cc3c(Cl)cc(Cl)cc3[C@@H]2Oc2cccc(NC(C)=O)c2)C1] | A | 4 | 1.54 | 476.2 |

| Example | Structure | Synthetic method | LC method | Rt time [min] | MS [M + H+] ES+ |
|---|---|---|---|---|---|
| 694 | 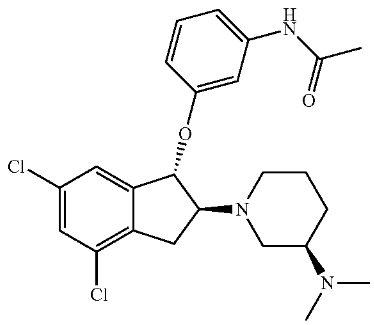 [SMILES: CC(=O)Nc1cccc(O[C@H]2c3cc(Cl)cc(Cl)c3C[C@@H]2N2CCC[C@@H](N(C)C)C2)c1] | A | 4 | 1.24 | 462.32 |
| 695 | 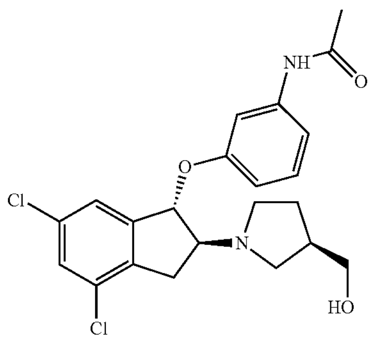 [SMILES: CC(=O)Nc1cccc(O[C@H]2c3cc(Cl)cc(Cl)c3C[C@@H]2N2CC[C@@H](CO)C2)c1] | A | 1 | 2.60 | 435.11 |
| 696 | 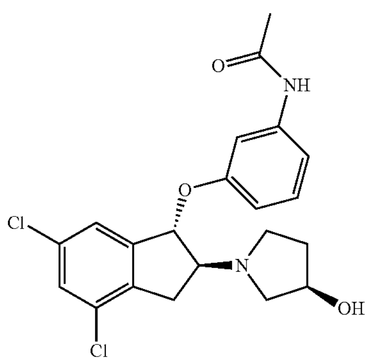 [SMILES: CC(=O)Nc1cccc(O[C@H]2c3cc(Cl)cc(Cl)c3C[C@@H]2N2CC[C@@H](O)C2)c1] | A | 4 | 1.24 | 421.24 |
| 697 | 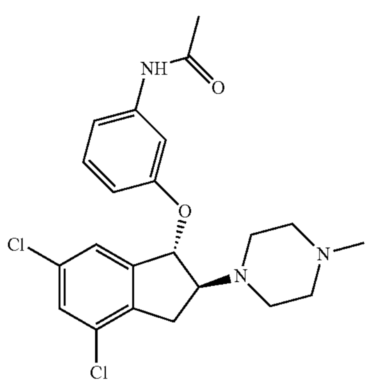 [SMILES: CC(=O)Nc1cccc(O[C@H]2c3cc(Cl)cc(Cl)c3C[C@@H]2N2CCN(C)CC2)c1] | A | 4 | 1.34 | 434.19 |

-continued

| Example | Structure | Synthetic method | LC method | Rt time [min] | MS [M + H+] ES+ |
|---------|-----------|------------------|-----------|---------------|------------------|
| 698 | 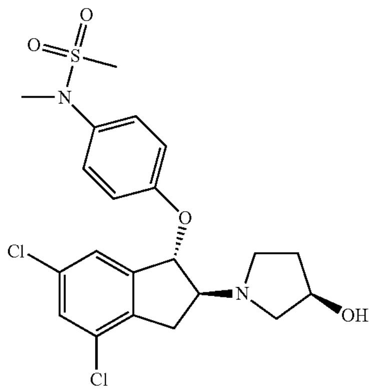 [SMILES: CN(c1ccc(O[C@H]2c3cc(Cl)cc(Cl)c3C[C@@H]2N2CC[C@@H](O)C2)cc1)S(C)(=O)=O] | A | 8 | 3.33 | 471.11 |
| 699 | 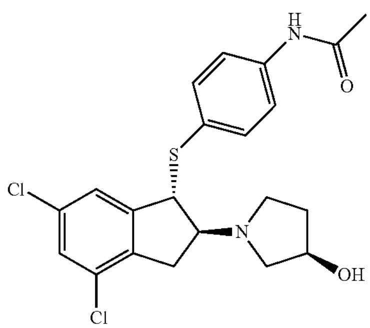 [SMILES: CC(=O)Nc1ccc(S[C@H]2c3cc(Cl)cc(Cl)c3C[C@@H]2N2CC[C@@H](O)C2)cc1] | A | 9 | 2.71 | 437.02 |
| 700 | 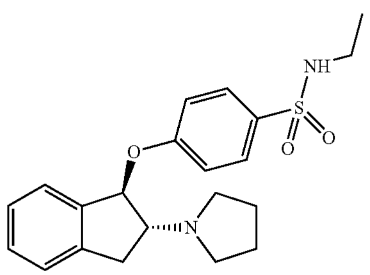 | A | 4 | 1.18 | 773.47 2M + H |
| 702 | 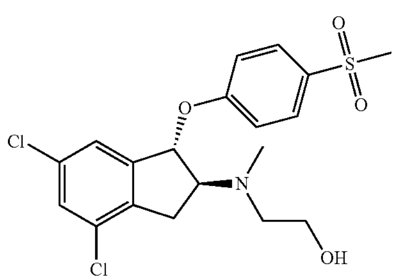 [SMILES: CN(CCO)[C@H]1Cc2c(Cl)cc(Cl)cc2[C@@H]1Oc1ccc(S(C)(=O)=O)cc1] | A | 15 | 1.90 | 430.00 |
| 704 | 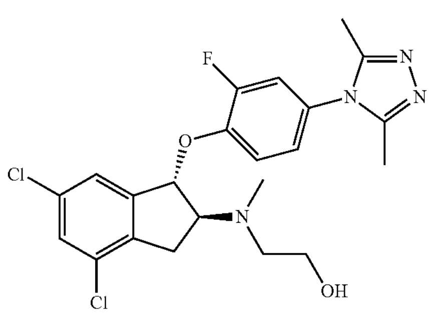 [SMILES: Cc1nnc(C)n1-c1ccc(O[C@H]2c3cc(Cl)cc(Cl)c3C[C@@H]2N(C)CCO)c(F)c1] | A | 15 | 1.74 | 465.07 |

| Example | Structure | Synthetic method | LC method | Rt time [min] | MS [M + H+] ES+ |
|---|---|---|---|---|---|
| 710 | 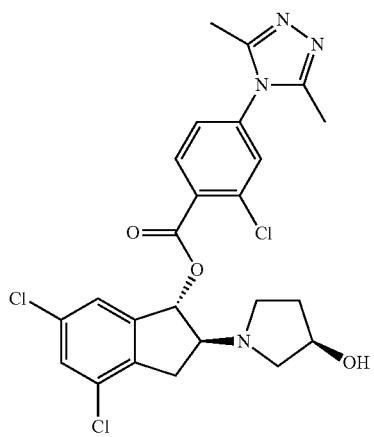 [SMILES: Cc1nnc(C)n1-c1ccc(C(=O)O[C@H]2c3cc(Cl)cc(Cl)c3C[C@@H]2N2CC[C@@H](O)C2)c(Cl)c1] | A | 15 | 1.88 | 521.06 |
| 712 | 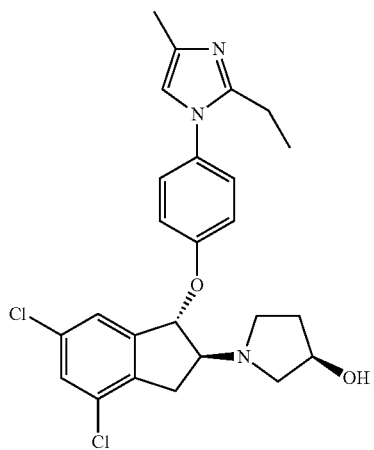 [SMILES: CCc1nc(C)cn1-c1ccc(O[C@H]2c3cc(Cl)cc(Cl)c3C[C@@H]2N2CC[C@@H](O)C2)cc1] | A | 24 | 1.70 | 472.14 |
| 714 | 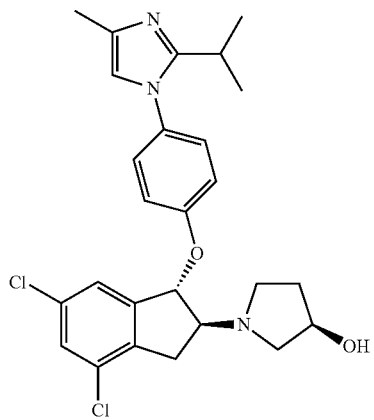 [SMILES: Cc1cn(-c2ccc(O[C@H]3c4cc(Cl)cc(Cl)c4C[C@@H]3N3CC[C@@H](O)C3)cc2)c(C(C)C)n1] | A | 24 | 1.75 | 486.13 |

| Example | Structure | Synthetic method | LC method | Rt time [min] | MS [M + H+] ES+ |
|---|---|---|---|---|---|
| 715 | 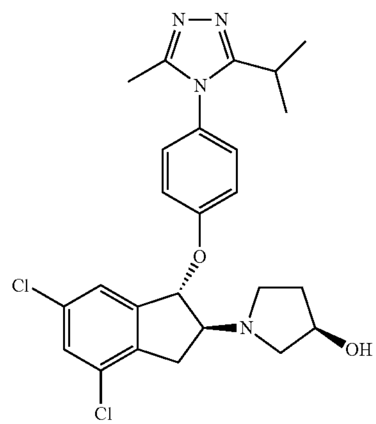 [SMILES: Cc1nnc(C(C)C)n1-c1ccc(O[C@H]2c3cc(Cl)cc(Cl)c3C[C@@H]2N2CC[C@@H](O)C2)cc1] | A | 24 | 1.76 | 487.14 |
| 716 | 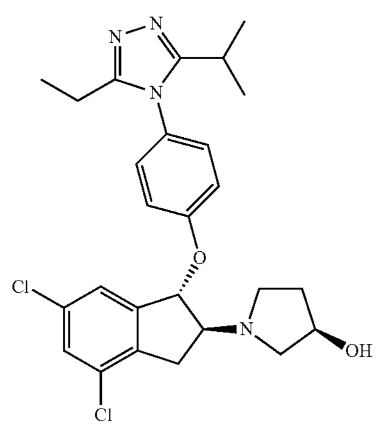 [SMILES: CCc1nnc(C(C)C)n1-c1ccc(O[C@H]2c3cc(Cl)cc(Cl)c3C[C@@H]2N2CC[C@@H](O)C2)cc1] | A | 24 | 1.79 | 501.12 |
| 719 | 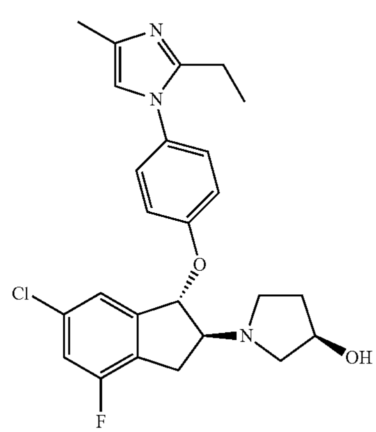 [SMILES: CCc1nc(C)cn1-c1ccc(O[C@H]2c3cc(Cl)cc(F)c3C[C@@H]2N2CC[C@@H](O)C2)cc1] | A | 24 | 1.68 | 456.27 |

-continued

| Example | Structure | Synthetic method | LC method | Rt time [min] | MS [M + H+] ES+ |
|---|---|---|---|---|---|
| 720 | 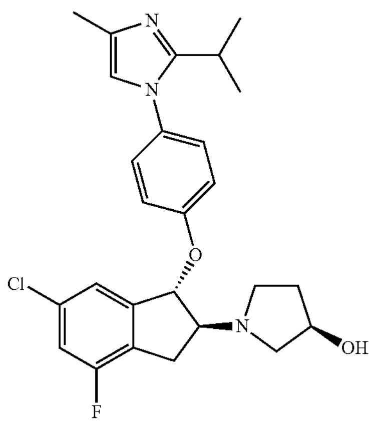 [SMILES: Cc1cn(-c2ccc(O[C@H]3c4cc(Cl)cc(F)c4C[C@@H]3N3CC[C@@H](O)C3)cc2)c(C(C)C)n1] | A | 24 | 1.72 | 470.26 |
| 721 | 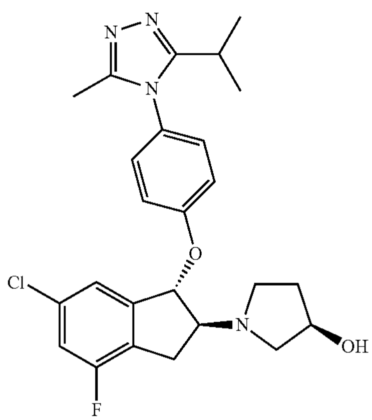 [SMILES: Cc1nnc(C(C)C)n1-c1ccc(O[C@H]2c3cc(Cl)cc(F)c3C[C@@H]2N2CC[C@@H](O)C2)cc1] | A | 24 | 1.70 | 471.29 |
| 722 | 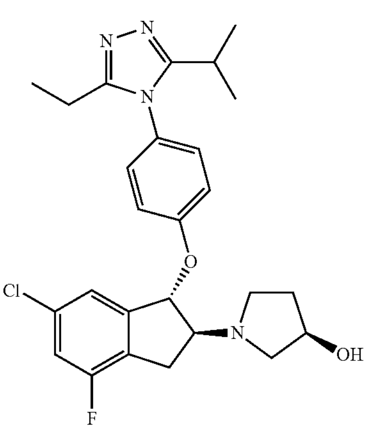 | A | 24 | 1.75 | 485.30 |

-continued

| Example | Structure | Synthetic method | LC method | Rt time [min] | MS [M + H+] ES+ |
|---------|-----------|------------------|-----------|---------------|------------------|
| 724 | 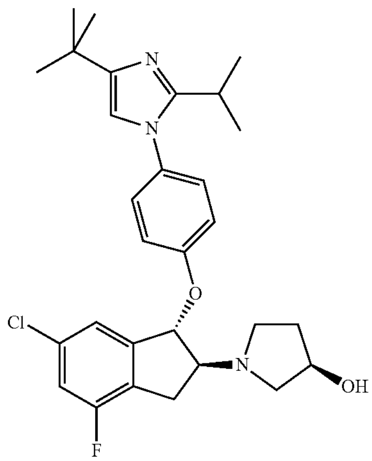 [SMILES: CC(C)c1nc(C(C)(C)C)cn1-c1ccc(O[C@H]2c3cc(Cl)cc(F)c3C[C@@H]2N2CC[C@@H](O)C2)cc1] | A | 24 | 1.87 | 512.30 |
| 725 | 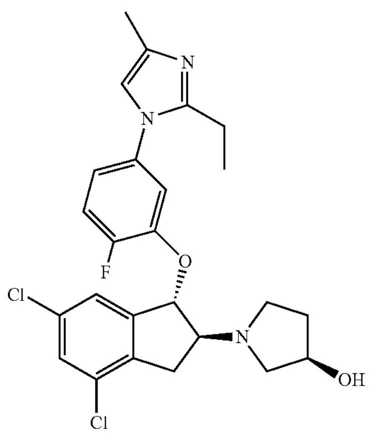 [SMILES: CCc1nc(C)cn1-c1ccc(F)c(O[C@H]2c3cc(Cl)cc(Cl)c3C[C@@H]2N2CC[C@@H](O)C2)c1] | A | 24 | 1.76 | 490.20 |
| 726 | 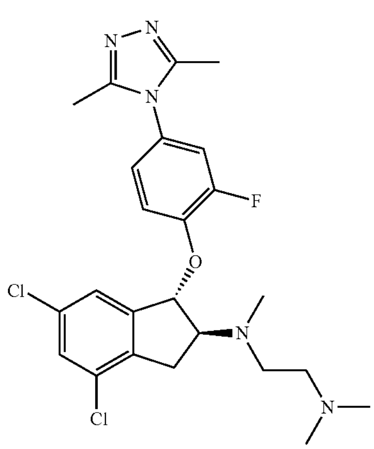 [SMILES: Cc1nnc(C)n1-c1ccc(O[C@H]2c3cc(Cl)cc(Cl)c3C[C@@H]2N(C)CCN(C)C)c(F)c1] | A | 23 | 3.19 | 491.96 |

| Example | Structure | Synthetic method | LC method | Rt time [min] | MS [M + H+] ES+ |
|---|---|---|---|---|---|
| 727 | 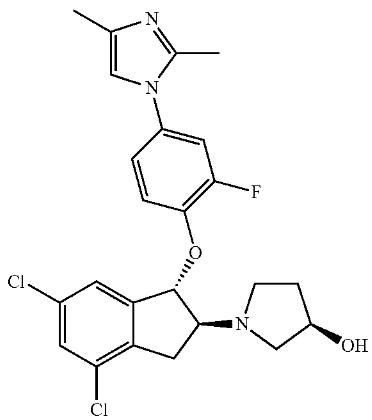 [SMILES: Cc1cn(-c2ccc(O[C@H]3c4cc(Cl)cc(Cl)c4C[C@@H]3N3CC[C@@H](O)C3)c(F)c2)c(C)n1] | A | 24 | 1.73 | 476.14 |
| 728 | 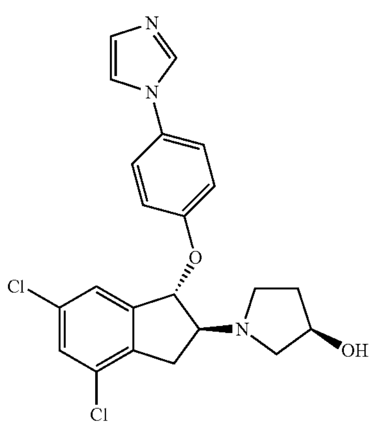 [SMILES: O[C@@H]1CCN([C@H]2Cc3c(Cl)cc(Cl)cc3[C@@H]2Oc2ccc(-n3ccnc3)cc2)C1] | A | 24 | 1.64 | 430.14 |
| 729 | 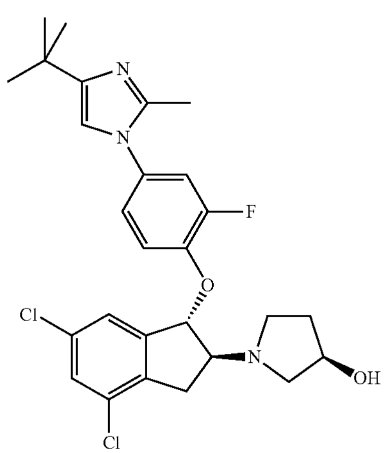 [SMILES: Cc1nc(C(C)(C)C)cn1-c1ccc(O[C@H]2c3cc(Cl)cc(Cl)c3C[C@@H]2N2CC[C@@H](O)C2)c(F)c1] | A | 24 | 1.85 | 518.24 |

| Example | Structure | Synthetic method | LC method | Rt time [min] | MS [M + H+] ES+ |
|---|---|---|---|---|---|
| 731 | 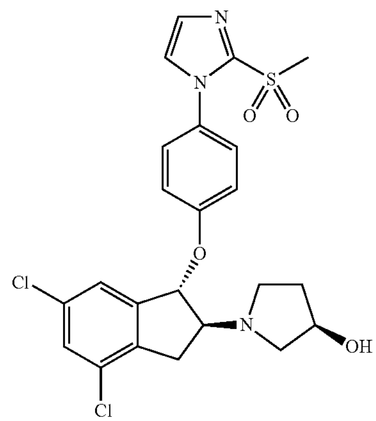 [SMILES: CS(=O)(=O)c1nccn1-c1ccc(O[C@H]2c3cc(Cl)cc(Cl)c3C[C@@H]2N2CC[C@@H](O)C2)cc1] | A | 21 | 1.30 | 508.14 |
| 732 | 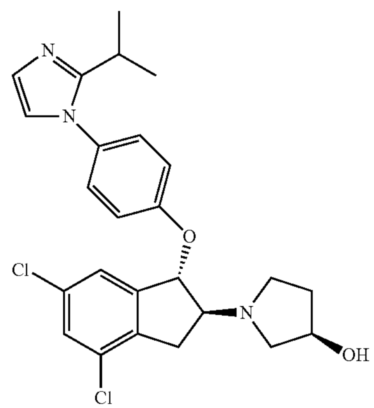 [SMILES: CC(C)c1nccn1-c1ccc(O[C@H]2c3cc(Cl)cc(Cl)c3C[C@@H]2N2CC[C@@H](O)C2)cc1] | A | 21 | 1.18 | 472.18 |
| 733 | 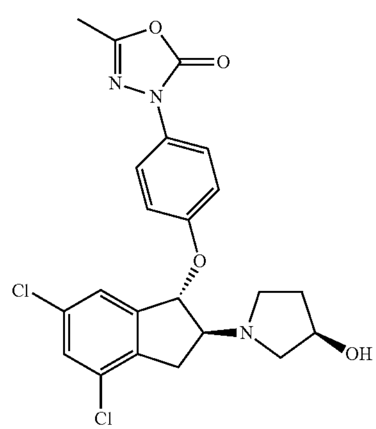 [SMILES: Cc1nn(-c2ccc(O[C@H]3c4cc(Cl)cc(Cl)c4C[C@@H]3N3CC[C@@H](O)C3)cc2)c(=O)o1] | A | 21 | 1.38 | 462.09 |

-continued

| Example | Structure | Synthetic method | LC method | Rt time [min] | MS [M + H+] ES+ |
|---------|-----------|------------------|-----------|---------------|------------------|
| 735 | 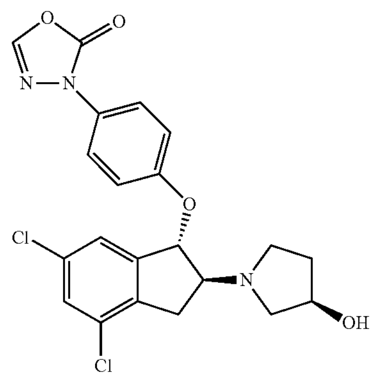 [SMILES: O=c1ocnn1-c1ccc(O[C@H]2c3cc(Cl)cc(Cl)c3C[C@@H]2N2CC[C@@H](O)C2)cc1] | A | 25 | 2.74 | 448.02 |
| 736 | 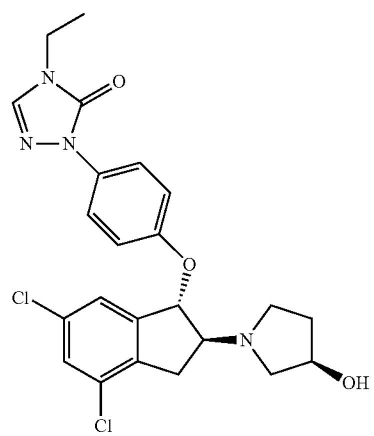 [SMILES: CCn1cnn(-c2ccc(O[C@H]3c4cc(Cl)cc(Cl)c4C[C@@H]3N3CC[C@@H](O)C3)cc2)c1=O] | A | 25 | 2.67 | 475.05 |
| 737 | 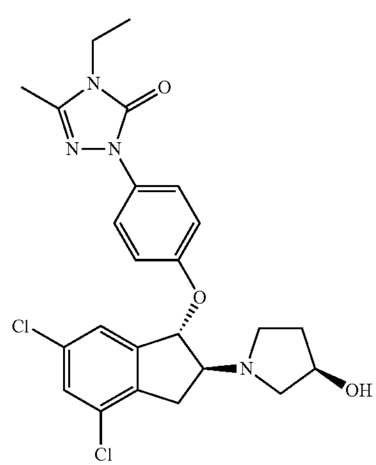 [SMILES: CCn1c(C)nn(-c2ccc(O[C@H]3c4cc(Cl)cc(Cl)c4C[C@@H]3N3CC[C@@H](O)C3)cc2)c1=O] | A | 21 | 1.33 | 489.19 |

| Example | Structure | Synthetic method | LC method | Rt time [min] | MS [M + H+] ES+ |
|---|---|---|---|---|---|
| 738 | 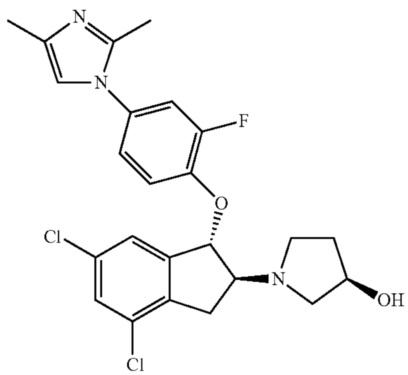 [SMILES: Cc1cn(-c2ccc(O[C@H]3c4cc(Cl)cc(Cl)c4C[C@@H]3N3CC[C@@H](O)C3)c(F)c2)c(C)n1] | A | 25 | 2.27 | 460.15 |
| 739 | 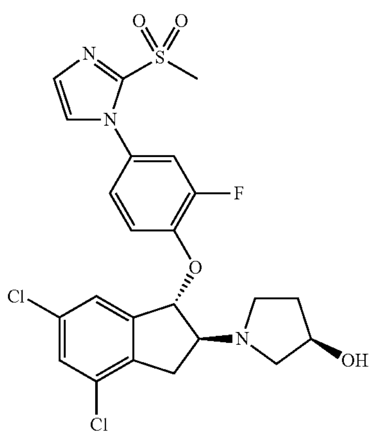 [SMILES: CS(=O)(=O)c1nccn1-c1ccc(O[C@H]2c3cc(Cl)cc(Cl)c3C[C@@H]2N2CC[C@@H](O)C2)c(F)c1] | A | 20 | 1.42 | 526.03 |
| 740 | 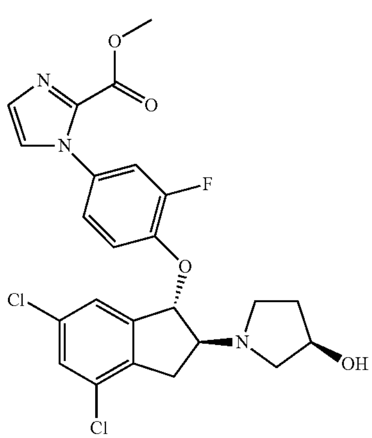 [SMILES: COC(=O)c1nccn1-c1ccc(O[C@H]2c3cc(Cl)cc(Cl)c3C[C@@H]2N2CC[C@@H](O)C2)c(F)c1] | A | 20 | 1.39 | 506.05 |

-continued

| Example | Structure | Synthetic method | LC method | Rt time [min] | MS [M + H+] ES+ |
|---------|-----------|------------------|-----------|---------------|-----------------|
| 741 | 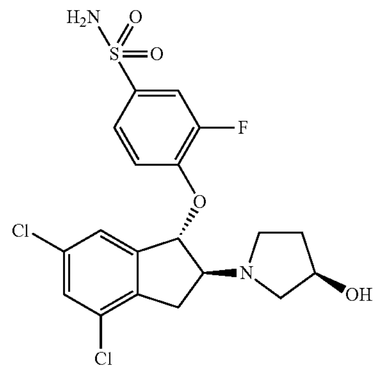 [SMILES: NS(=O)(=O)c1ccc(O[C@H]2c3cc(Cl)cc(Cl)c3C[C@@H]2N2CC[C@@H](O)C2)c(F)c1] | A | 20 | 1.36 | 461.03 |
| 742 | 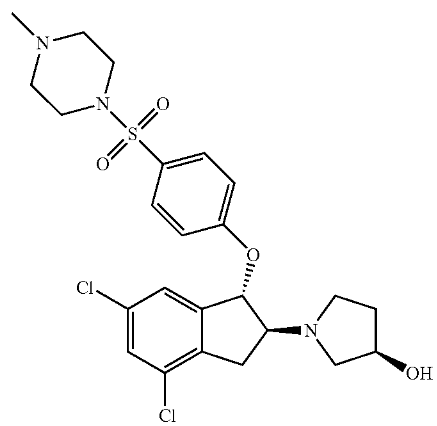 [SMILES: CN1CCN(S(=O)(=O)c2ccc(O[C@H]3c4cc(Cl)cc(Cl)c4C[C@@H]3N3CC[C@@H](O)C3)cc2)CC1] | A | 20 | 1.30 | 526.17 |
| 743 | 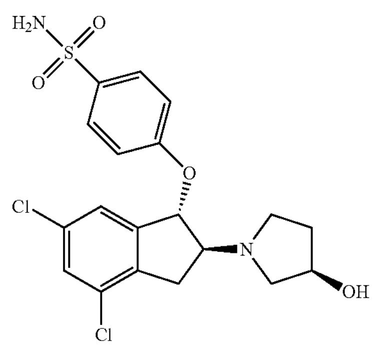 [SMILES: NS(=O)(=O)c1ccc(O[C@H]2c3cc(Cl)cc(Cl)c3C[C@@H]2N2CC[C@@H](O)C2)cc1] | A | 20 | 1.31 | 443.09 |
| 744 | 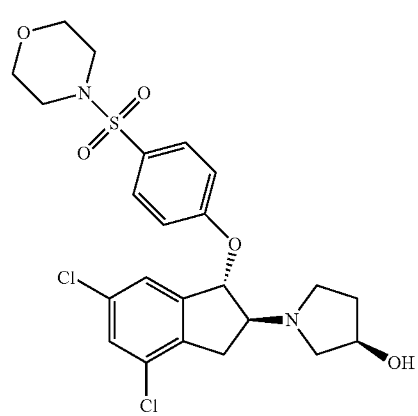 [SMILES: O=S(=O)(c1ccc(O[C@H]2c3cc(Cl)cc(Cl)c3C[C@@H]2N2CC[C@@H](O)C2)cc1)N1CCOCC1] | A | 20 | 1.43 | 513.13 |

| Example | Structure | Synthetic method | LC method | Rt time [min] | MS [M + H+] ES+ |
|---|---|---|---|---|---|
| 745 | 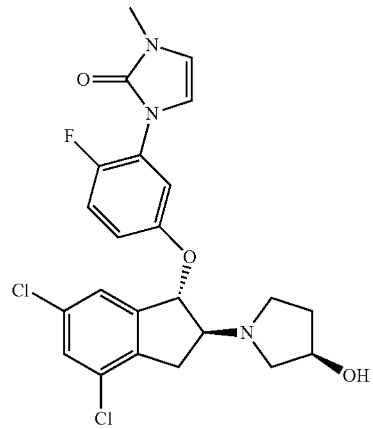 [SMILES: Cn1ccn(-c2cc(O[C@H]3c4cc(Cl)cc(Cl)c4C[C@@H]3N3CC[C@@H](O)C3)ccc2F)c1=O] | A | 20 | 1.43 | 478.14 |

Synthesis of a Specific Example (Example 623) by Method B:

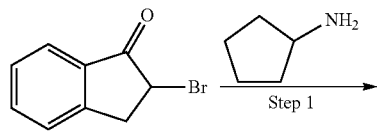

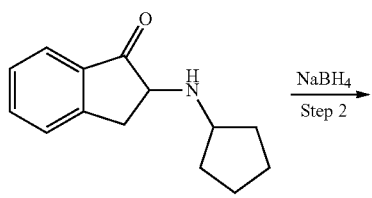

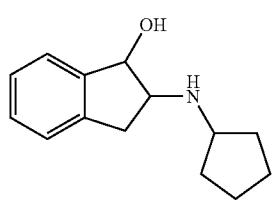

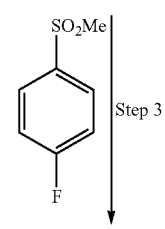

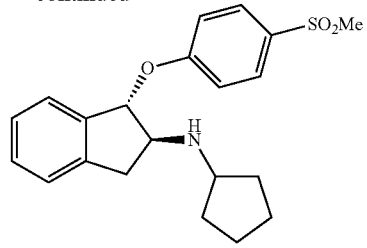

Example 623

Step 1: 1.055 g of 2-bromoindanone (5 mmol) are dissolved in 7.5 ml of dimethylformamide and, while stirring with ice-bath cooling, 0.98 ml of cyclopentylamine is added over the course of 60 seconds. After a further 25 minutes at ice-bath temperature, 7.5 ml of 2N hydrochloric acid and 15 ml of water are added, and the mixture is thoroughly stirred. It is extracted 3 times with 15 ml of ethyl acetate each time. The product, 2-cyclopentylaminoindanone, is obtained as a solution in the aqueous hydrochloric acid phase.

Step 2: 0.5 g of sodium borohydride, divided into 4 portions, is added over a period of about 1 hour while stirring to the 2-cyclopentylaminoindanone obtained in step 1 in aqueous solution of pH 3 (about 20 ml). After further stirring at room temperature for about 3-4 hours, a white precipitate separates out. After filtration with suction and drying in air, it is stirred with n-heptane. 320 mg of trans-2-cyclopentylamino-1-hydroxyindane are obtained.

Step 3: 300 mg (1.38 mmol) of trans-2-cyclopentylamino-1-hydroxyindane are dissolved in 3.5 ml of DMSO, and 481 mg (2.76 mmol) of 4-fluorophenyl methyl sulfone and 300 mg of powdered sodium hydroxide are added. The mixture is stirred until the components have completely dissolved and is left at room temperature overnight. Addition of 5 ml of water is followed by extraction several times with acetic acid ethyl acetate, and the combined ethyl acetate phases are briefly washed with a little water until neutral and dried with magnesium sulfate, and the solvent is stripped off in vacuo. The remaining residue is subjected to flash chromatography on a 20 g prepacked silica gel column. The product is eluted with pure ethyl acetate.

The following examples were synthesized in analogy to Example 623:

| Example | Structure | Synthesis method | LC method | Rt time [min] | MS [M + H+] ES+ |
|---|---|---|---|---|---|
| 251 | 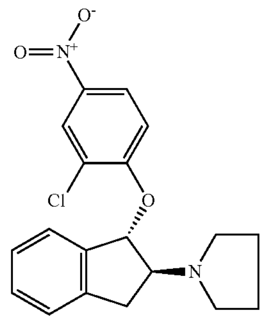 [SMILES: O=[N+]([O-])c1ccc(O[C@H]2c3ccccc3C[C@@H]2N2CCCC2)c(Cl)c1] | B | 9 | 3.06 | 359.08 |
| 261 | 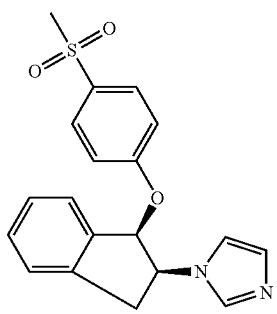 [SMILES: CS(=O)(=O)c1ccc(O[C@@H]2c3ccccc3C[C@@H]2n2ccnc2)cc1] | B | 1 | 2.40 | 355.08 |
| 278 | 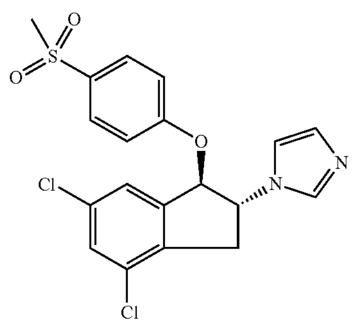 [SMILES: CS(=O)(=O)c1ccc(O[C@@H]2c3cc(Cl)cc(Cl)c3C[C@H]2n2ccnc2)cc1] | B | 9 | 2.62 | 423.08 |
| 441 | 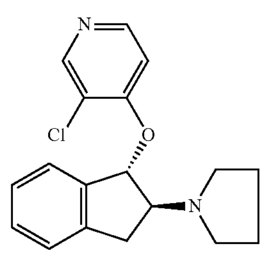 [SMILES: Clc1cnccc1O[C@H]1c2ccccc2C[C@@H]1N1CCCC1] | B | 8 | 2.56 | 315.15 |
| 451 | 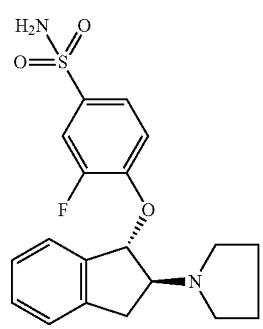 [SMILES: NS(=O)(=O)c1ccc(O[C@H]2c3ccccc3C[C@@H]2N2CCCC2)c(F)c1] | B | 9 | 2.34 | 377.22 |

-continued

| Example | Structure | Synthesis method | LC method | Rt time [min] | MS [M + H+] ES+ |
|---|---|---|---|---|---|
| 459 | 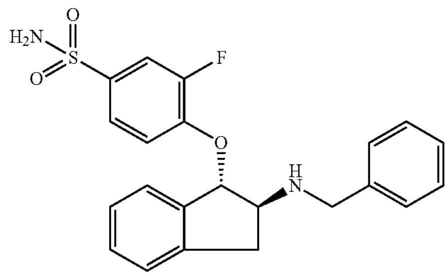 [SMILES: NS(=O)(=O)c1ccc(O[C@H]2c3ccccc3C[C@@H]2NCc2ccccc2)c(F)c1] | B | 9 | 2.63 | 413.06 |
| 460 | 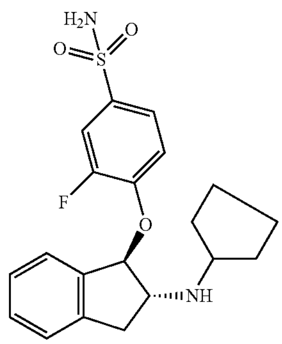 [SMILES: NS(=O)(=O)c1ccc(O[C@@H]2c3ccccc3C[C@H]2NC2CCCC2)c(F)c1] | B | 9 | 2.52 | 391.06 |
| 478 | 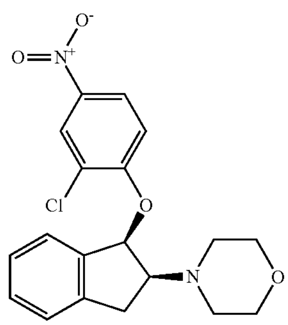 [SMILES: O=[N+]([O-])c1ccc(O[C@@H]2c3ccccc3C[C@@H]2N2CCOCC2)c(Cl)c1] | B | 9 | 2.92 | 375.06 |
| 597 | 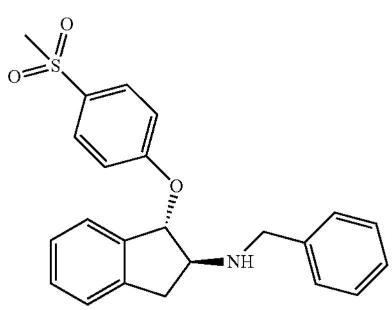 [SMILES: CS(=O)(=O)c1ccc(O[C@H]2c3ccccc3C[C@@H]2NCc2ccccc2)cc1] | B | 9 | 2.62 | 394.01 |
| 623 | 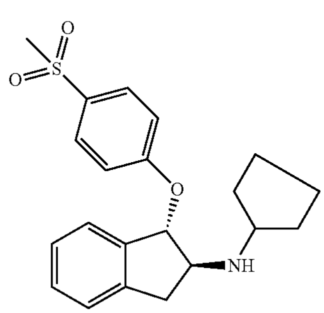 [SMILES: CS(=O)(=O)c1ccc(O[C@H]2c3ccccc3C[C@@H]2NC2CCCC2)cc1] | B | 8 | 2.94 | 372.36 |

| Example | Structure | Synthesis method | LC method | Rt time [min] | MS [M + H+] ES+ |
|---|---|---|---|---|---|
| 624 | 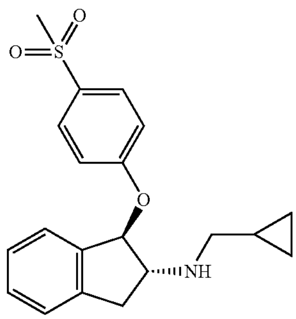 [SMILES: CS(=O)(=O)c1ccc(O[C@@H]2c3ccccc3C[C@H]2NCC2CC2)cc1] | B | 15 | 1.76 | 358.10 |
| 701 | 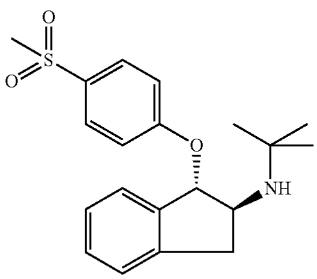 [SMILES: CC(C)(C)N[C@H]1Cc2ccccc2[C@@H]1Oc1ccc(S(C)(=O)=O)cc1] | B | 9 | 2.47 | 360.10 |
| 703 | 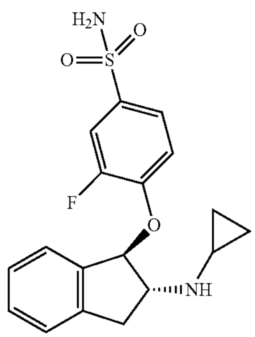 [SMILES: NS(=O)(=O)c1ccc(O[C@@H]2c3ccccc3C[C@H]2NC2CC2)c(F)c1] | B | 25 | 2.32 | 363.08 |
| 705 | 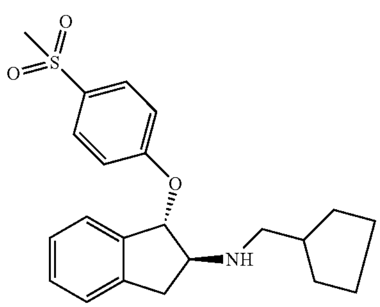 [SMILES: CS(=O)(=O)c1ccc(O[C@H]2c3ccccc3C[C@@H]2NCC2CCCC2)cc1] | B | 15 | 1.96 | 386.13 |
| 706 | 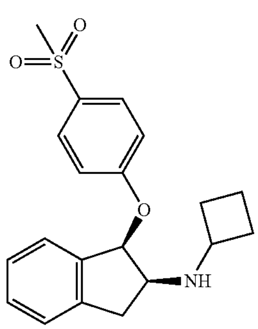 [SMILES: CS(=O)(=O)c1ccc(O[C@@H]2c3ccccc3C[C@@H]2NC2CCC2)cc1] | B | 15 | 1.76 | 358.16 |

| Example | Structure | Synthesis method | LC method | Rt time [min] | MS [M + H+] ES+ |
|---------|-----------|------------------|-----------|---------------|-----------------|
| 708 | 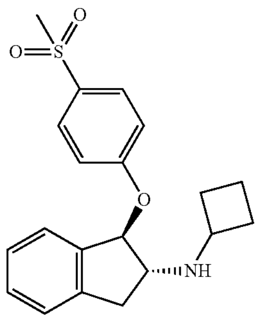 [SMILES: CS(=O)(=O)c1ccc(O[C@@H]2c3ccccc3C[C@H]2NC2CCC2)cc1] | B | 15 | 1.82 | 358.17 |
| 709 | 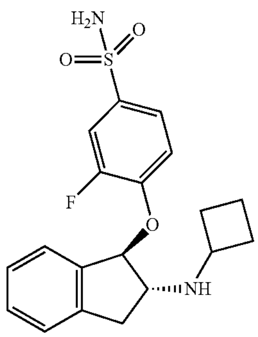 [SMILES: NS(=O)(=O)c1ccc(O[C@@H]2c3ccccc3C[C@H]2NC2CCC2)c(F)c1] | B | 15 | 1.83 | 377.15 |
| 711 | 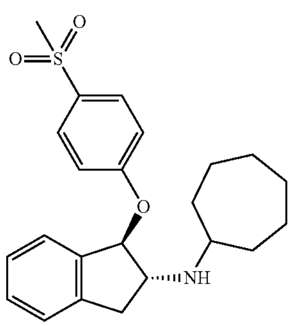 [SMILES: CS(=O)(=O)c1ccc(O[C@@H]2c3ccccc3C[C@H]2NC2CCCCCC2)cc1] | B | 15 | 2.24 | 400.15 |
| 713 | 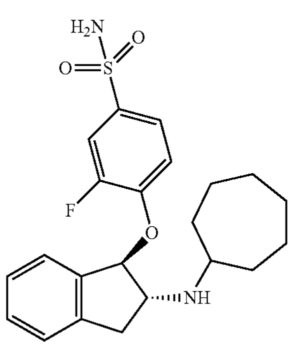 [SMILES: NS(=O)(=O)c1ccc(O[C@@H]2c3ccccc3C[C@H]2NC2CCCCCC2)c(F)c1] | B | 24 | 1.90 | 419.07 |

-continued

| Example | Structure | Synthesis method | LC method | Rt time [min] | MS [M + H+] ES+ |
|---|---|---|---|---|---|
| 717 | 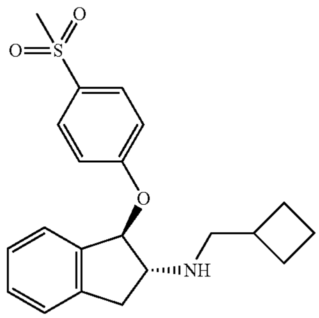 [SMILES: CS(=O)(=O)c1ccc(O[C@@H]2c3ccccc3C[C@H]2NCC2CCC2)cc1] | B | 24 | 1.85 | 372.10 |
| 718 | 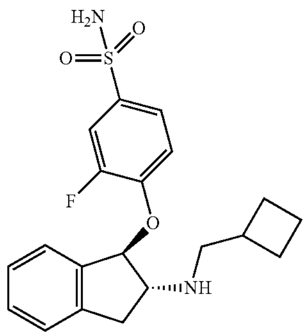 [SMILES: NS(=O)(=O)c1ccc(O[C@@H]2c3ccccc3C[C@H]2NCC2CCC2)c(F)c1] | B | 23 | 2.83 | 391.08 |
| 723 | 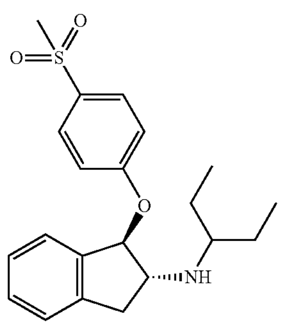 [SMILES: CCC(CC)N[C@@H]1Cc2ccccc2[C@H]1Oc1ccc(S(C)(=O)=O)cc1] | B | 24 | 1.87 | 374.18 |
| 730 | 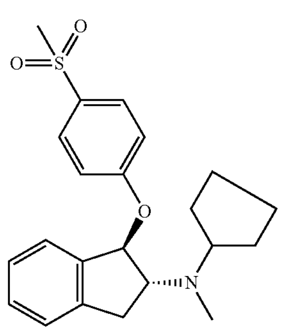 [SMILES: CN(C1CCCC1)[C@@H]1Cc2ccccc2[C@H]1Oc1ccc(S(C)(=O)=O)cc1] | B | 24 | 1.85 | 386.20 |

| Example | Structure | Synthesis method | LC method | Rt time [min] | MS [M + H+] ES+ |
|---|---|---|---|---|---|
| 734 | 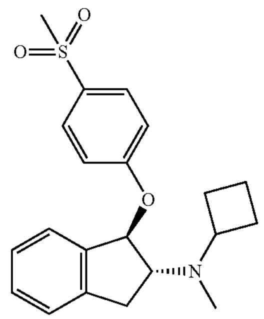 [SMILES: CN(C1CCC1)[C@@H]1Cc2ccccc2[C@H]1Oc1ccc(S(C)(=O)=O)cc1] | B | 23 | 2.73 | 372.17 |

Synthesis of a Specific Example (Example 280) by Method C:

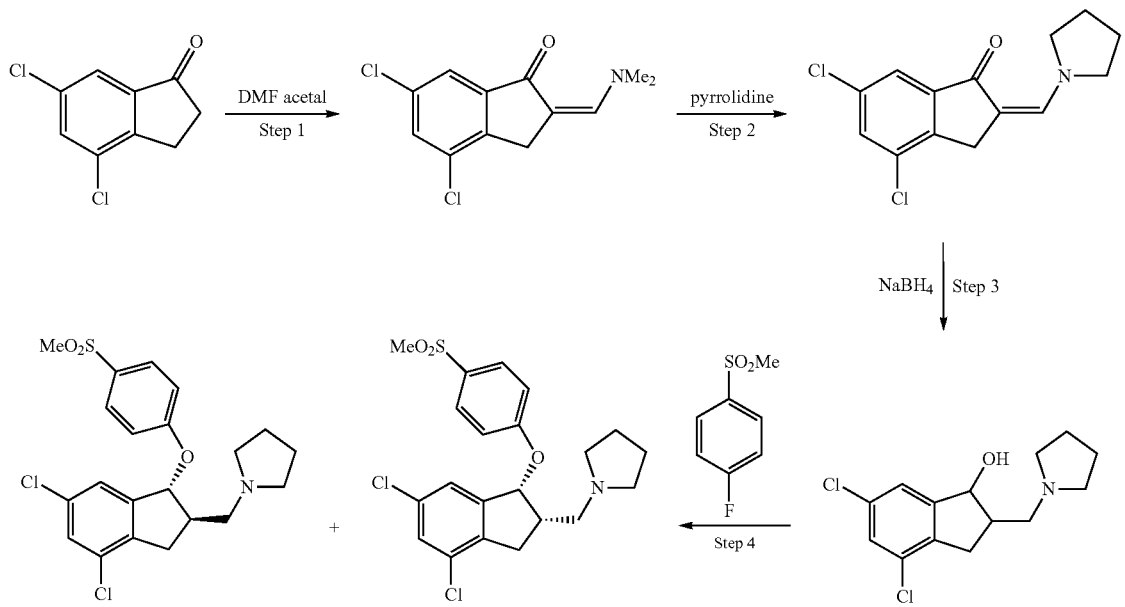

Example 280

Step 1: 202 mg (1 mmol) of 4,6-dichloroindan-1-one are dissolved in 2 ml of tetrahydrofuran, and 263 mg of dimethylformamide dimethyl acetal (2.2 mmol) are added. The solution is stirred at 83° C. for 3 hours and concentrated in vacuo. The residue is triturated with diethyl ether and filtered off with suction. 216 mg of yellow crystals of 4,6-dichloro-2-[1-dimethylaminomethylidene]indan-1-one are obtained.

Step 2: 255 mg (1 mmol) of 4,6-dichloro-2-[1-dimethylaminomethylidene]indan-1-one are dissolved in 2.5 ml of dimethylformamide and, after addition of 140 mg of pyrrolidine, stirred at 70° C. for 4.5 hours. The reaction mixture is stirred into hot water and left to crystallize at room temperature for 1 day. Filtration with suction results in 270 mg of yellow crystals.

Step 3: The product obtained in stage 2,4,6-dichloro-2-pyrrolidin-1-ylmethylindan-1-one, is dissolved in 5 ml of methanol and, over a period of 7 hours, a total of 700 mg of NaBH4 (18.5 equivalents) are added in portions. The mixture is concentrated in vacuo, and the residue is taken up in 50 ml of water. 4 extractions with 10 ml of ethyl acetate each time are followed by drying with magnesium sulfate and removal of the solvent. The residue is chromatographed on silica gel with methanol and ethyl acetate in the ratio 3:10 as eluent. The product is obtained as a mixture of cis/trans isomers.

Step 4: The cis/trans mixture of 4,6-dichloro-2-pyrrolidinylmethylindanol (84 mg) obtained in step 3 is dissolved in 1 ml of DMSO, and 100 mg of 4-fluorophenyl methyl sulfone and 100 mg of powdered sodium hydroxide are added. The mixture is stirred at room temperature for up to 40 minutes. Addition of 5 ml of water is followed by extraction with acetic acid ethyl acetate several times, and the combined ethyl acetate phases are briefly washed with a little water until neutral and dried with magnesium sulfate, and the solvent is stripped off in vacuo. The remaining residue is subjected to flash chromatography on a 20 g prepacked silica gel column. Elution with pure ethyl acetate firstly gives 64 mg of trans-4,6-dichloro-1-(4-methylsulfonyl-phenyloxy)-2-pyrrolidinyl-methylindane and with ethyl acetate/methanol 9:1 subsequently gives 9 mg of the corresponding cis isomer.

The following examples were synthesized in analogy to Example 280:

| Example | Structure | Synthesis method | LC method | Rt time [min] | MS [M + H+] ES+ |
|---|---|---|---|---|---|
| 217 | 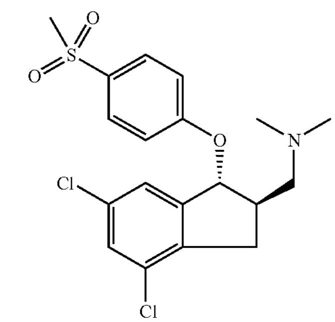 [SMILES: CN(C)C[C@H]1Cc2c(Cl)cc(Cl)cc2[C@@H]1Oc1ccc(S(C)(=O)=O)cc1] | C | 1 | 2.70 | 414.15 |
| 244 | 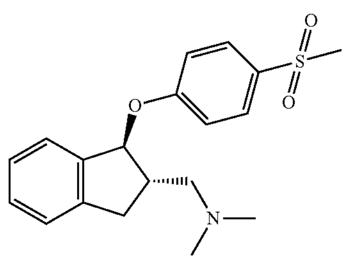 [SMILES: CN(C)C[C@@H]1Cc2ccccc2[C@H]1Oc1ccc(S(C)(=O)=O)cc1] | C | 9 | 2.42 | 346.12 |
| 274 | 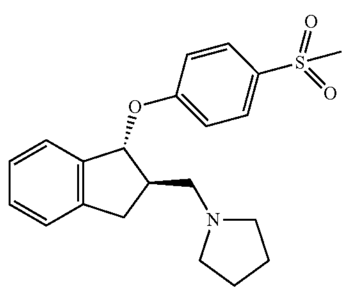 [SMILES: CS(=O)(=O)c1ccc(O[C@H]2c3ccccc3C[C@@H]2CN2CCCC2)cc1] | C | 1 | 2.42 | 372.2 |
| 280 | 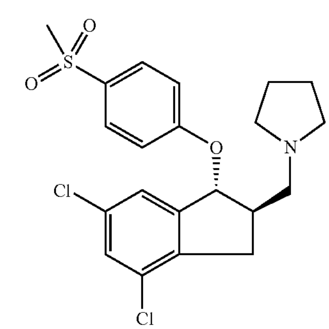 [SMILES: CS(=O)(=O)c1ccc(O[C@H]2c3cc(Cl)cc(Cl)c3C[C@@H]2CN2CCCC2)cc1] | C | 9 | 2.74 | 440 |
| 389 | 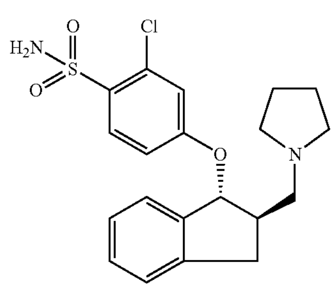 [SMILES: NS(=O)(=O)c1ccc(O[C@H]2c3ccccc3C[C@@H]2CN2CCCC2)cc1Cl] | C | 9 | 2.52 | 407.08 |

-continued
| Example | Structure | Synthesis method | LC method | Rt time [min] | MS [M + H+] ES+ |
|---|---|---|---|---|---|
| 390 | 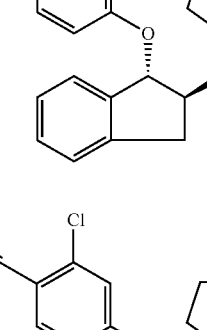 | C | 9 | 2.51 | 372.12 |
| 391 | 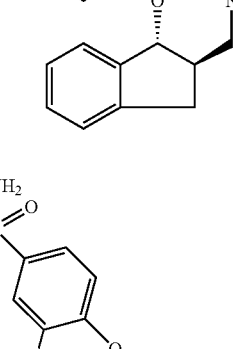 | C | 9 | 2.91 | 353.13 |
| 440 | 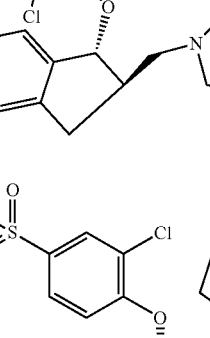 | C | 8 | 3.09 | 421.20 |
| 442 | 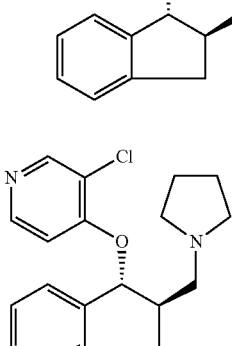 | C | 9 | 2.55 | 407.08 |
| 443 | 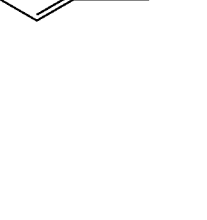 | C | 9 | 2.04 | 329.17 |

-continued

| Example | Structure | Synthesis method | LC method | Rt time [min] | MS [M + H+] ES+ |
|---|---|---|---|---|---|
| 449 | 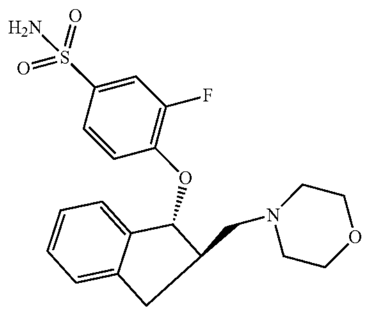 [SMILES: NS(=O)(=O)c1ccc(O[C@H]2c3ccccc3C[C@@H]2CN2CCOCC2)c(F)c1] | C | 9 | 2.62 | 407.13 |
| 450 | 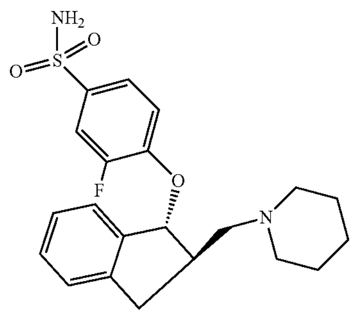 [SMILES: NS(=O)(=O)c1ccc(O[C@H]2c3ccccc3C[C@@H]2CN2CCCCC2)c(F)c1] | C | 17 | 2.43 | 405.18 |
| 452 | 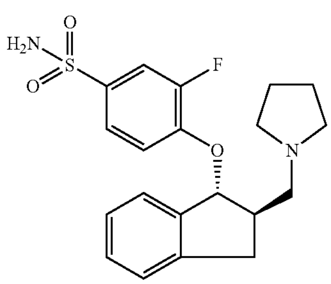 [SMILES: NS(=O)(=O)c1ccc(O[C@H]2c3ccccc3C[C@@H]2CN2CCCC2)c(F)c1] | C | 8 | 2.96 | 391.18 |
| 462 | 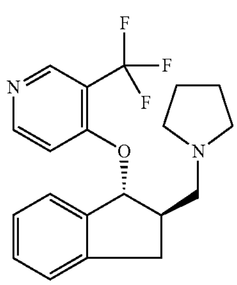 [SMILES: FC(F)(F)c1cnccc1O[C@H]1c2ccccc2C[C@@H]1CN1CCCC1] | C | 9 | 2.33 | 363.20 |
| 486 | 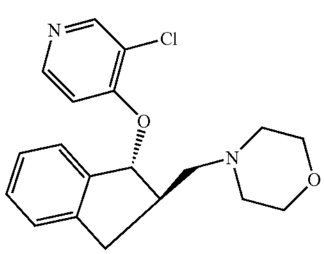 [SMILES: Clc1cnccc1O[C@H]1c2ccccc2C[C@@H]1CN1CCOCC1] | C | 9 | 2.02 | 345.17 |

| Example | Structure | Synthesis method | LC method | Rt time [min] | MS [M + H+] ES+ |
|---|---|---|---|---|---|
| 487 | 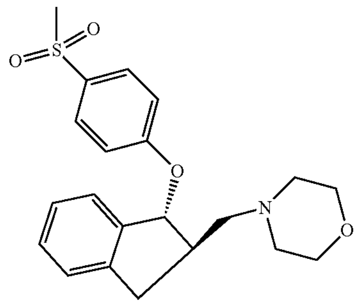 [SMILES: CS(=O)(=O)c1ccc(O[C@H]2c3ccccc3C[C@@H]2CN2CCOCC2)cc1] | C | 9 | 2.37 | 388.17 |

Synthesis of a Specific Example (Example 26) by Method D:

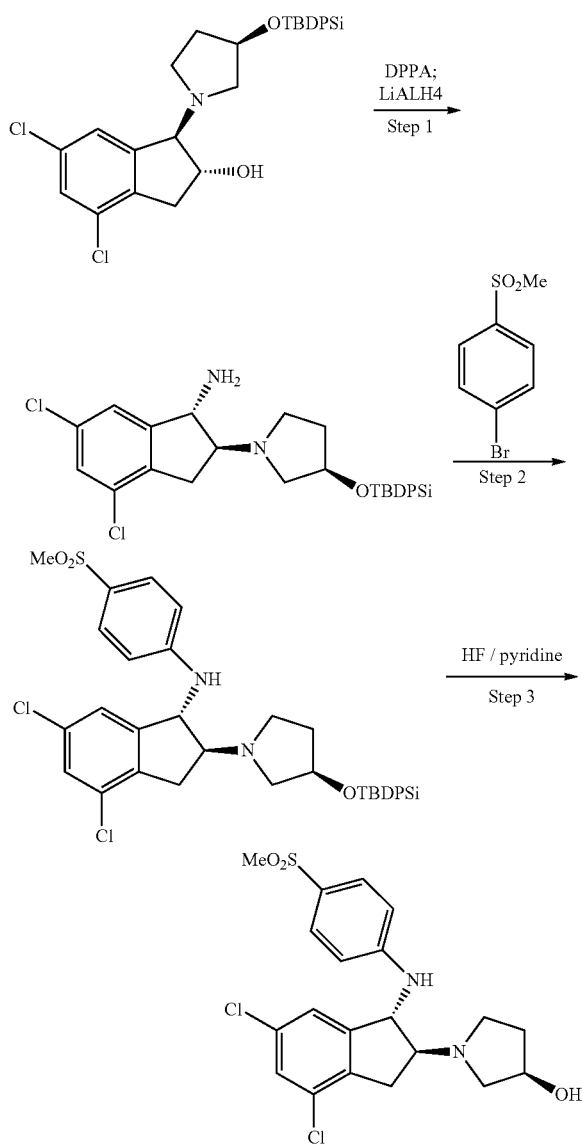

Step 1: A 1M solution of DIAD (0.84 ml, 1.10 eq.) in THF was added dropwise to a solution of the silyl-protected amino alcohol (400 mg, 1 eq.), PPh$_3$ (220 mg, 1.10 eq.) and DPPA (0.23 ml, 1.10 eq.) in anhydrous THF (5 ml) at 0° C. under an Ar atmosphere. The suspension was stirred at 0° C. for 60 min (LC/MS monitoring) and cooled to −10° C. At this temperature, LiAlH4 (57 mg, 2 mol eq.) was cautiously added in one portion, and the mixture was stirred while cooling in ice for a further 60 min. The suspension was poured onto ice-water, and the aqueous phase was extracted with ethyl acetate. The combined organic phases were dried with Na$_2$SO$_4$ and filtered, and the solvent was removed in vacuo. The crude products were purified by column chromatography (ethyl acetate/methanol). The product was obtained as a colorless oil (90 mg).

Step 2: 4-Bromophenyl methyl sulfone (38.2 mg, 0.95 eq.) was added to a solution of the diamine (90 mg, 1. eq.), Pd$_2$(dba)$_3$ (6.3 mg, 0.04 eq.), rac-BINAP (8.5 mg, 0.08 eq.), NaOtBu (23.0 mg, 1.40 eq.) in toluene (2 ml) and the mixture was heated at 70° C. for 10 h (TLC monitoring). The reaction was diluted with ethyl acetate and washed with water. The aqueous phase was extracted with ethyl acetate, and the combined organic phases were dried with Na$_2$SO$_4$ and filtered, and the solvent was removed in vacuo. The crude product was purified by column chromatography (ethyl acetate/MeOH). The product was obtained as a colorless oil (75 mg).

Step 3: HF/pyridine (100 μl, 65-70% pure) was added to a solution of the silyl-protected diamine (75 mg, 1 equivalent) in THF (2 ml) at rt, and the mixture was stirred at rt for 6 h. It was poured into saturated aqueous NaHCO$_3$ solution, and the aqueous phase was extracted with ethyl acetate. The combined organic phases were dried with Na$_2$SO$_4$ and filtered, and the solvent was removed in vacuo. The crude product was purified by column chromatography (ethyl acetate/MeOH). The desired product was obtained as a pale yellow oil (20 mg).

The following examples were synthesized in analogy to Example 26:
| Example | Structure | Synthesis method | LC method | Rt time [min] | MS [M + H+] ES+ |
|---|---|---|---|---|---|
| 26 | 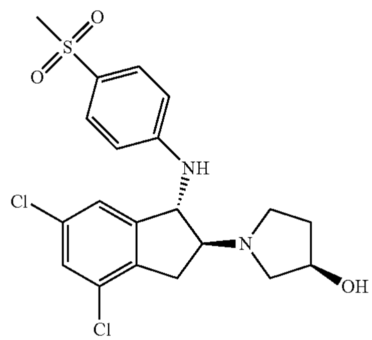 [SMILES: CS(=O)(=O)c1ccc(N[C@H]2c3cc(Cl)cc(Cl)c3C[C@@H]2N2CC[C@@H](O)C2)cc1] | D | 16 | 2.03 | 441.10 |
| 481 | 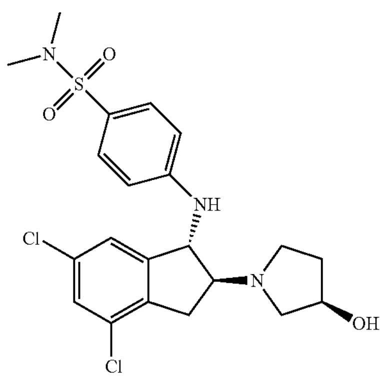 [SMILES: CN(C)S(=O)(=O)c1ccc(N[C@H]2c3cc(Cl)cc(Cl)c3C[C@@H]2N2CC[C@@H](O)C2)cc1] | D | 19 | 1.94 | 469.10 |
| 707 | 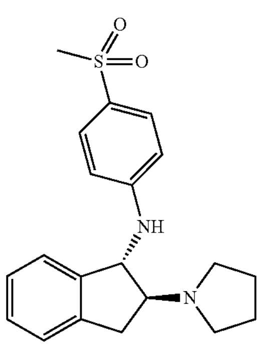 [SMILES: CS(=O)(=O)c1ccc(N[C@H]2c3ccccc3C[C@@H]2N2CCCC2)cc1] | D | 15 | 1.73 | 357.16 |
Synthesis of a Specific Example (Example 482) by Method E:
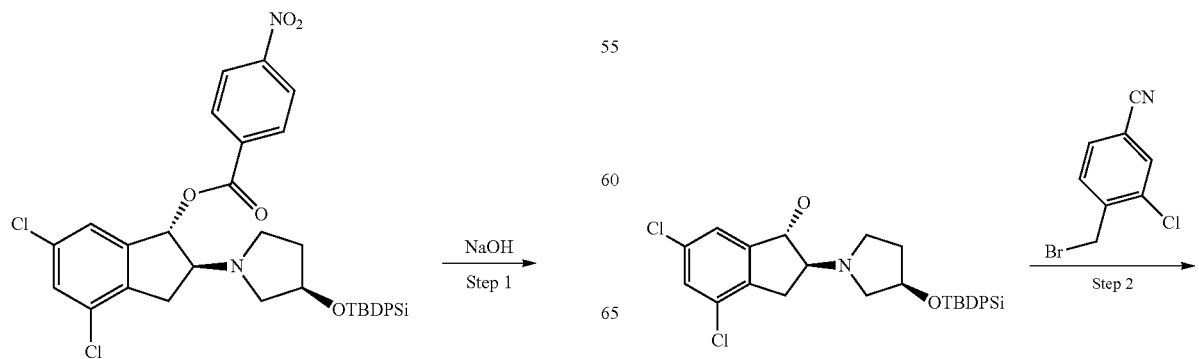
-continued

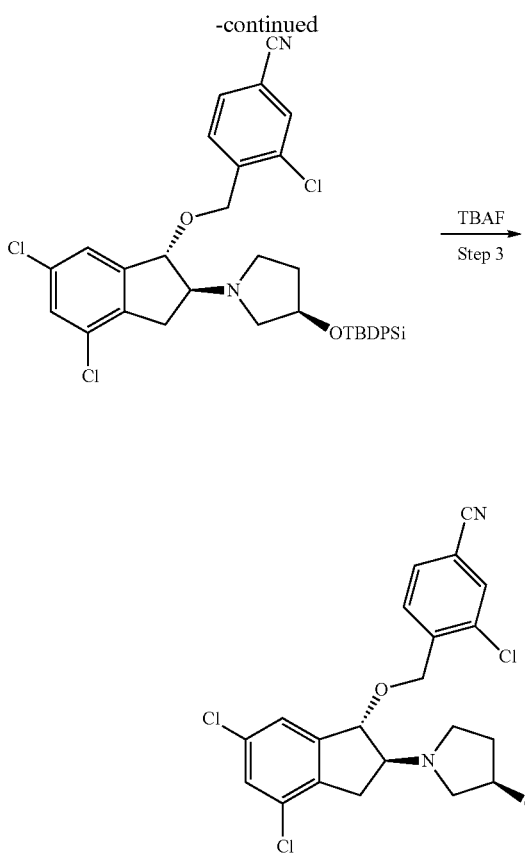

Example 482

Step 1: A 2N aqueous NaOH solution (3.59 ml, 1.10 eq.) was added to a solution of the benzoic ester (4.41 g, 1 eq.) in acetone (125 ml) at rt, and the mixture was stirred at rt for 5 h hours until the precursor was completely reacted (TLC monitoring). The acetone was removed in vacuo, and the residue was mixed with water. The aqueous phase was extracted with ethyl acetate, and the combined organic phases were dried with $Na_2SO_4$ and filtered, and the solvent was removed in vacuo. The crude products were purified by column chromatography (ethyl acetate/n-heptane). The product was obtained as a pale yellow oil (3.20 g).

Step 2: NaH (24 mg, 1.30 eq. 80% in mineral oil) was added to a solution of the amino alcohol (300 mg, 1 eq.) in THF (4 ml) at 0° C., and the ice bath was removed and the mixture was allowed to warm to it over the course of 1 hour. 4-Cyano-2-fluorobenzyl bromide (134 mg, 1.10 eq.) was added, and the reaction was stirred at it for 3 h (TLC check). The mixture was poured into saturated aqueous $NaHCO_3$ solution, and the aqueous phase was extracted with ethyl acetate. The combined organic phases were dried with $Na_2SO_4$ and filtered, and the solvent was removed in vacuo. The crude products were purified by column chromatography ($CH_2Cl_2$/MeOH). The product was obtained as a colorless oil (227 mg).

Step 3: A 1 M TBAF solution in THF (0.52 ml, 1.5 eq.) was added to a solution of the silyl-protected aminobenzyloxy alcohol (227 mg, 1 equivalent) in THF (2 ml) at it, and the mixture was stirred at it for 2 h. It was poured into saturated aqueous $NaHCO_3$ solution, and the aqueous phase was extracted with ethyl acetate. The combined organic phases were dried with $Na_2SO_4$ and filtered, and the solvent was removed in vacuo. The crude product was purified by column chromatography ($CH_2Cl_2$/MeOH). The desired product was obtained as a pale yellow oil (68 mg).

The following examples were synthesized in analogy to Example 482:

| Example | Structure | Synthesis method | LC method | Rt time [min] | MS [M + H+] ES+ |
|---------|-----------|------------------|-----------|---------------|-----------------|
| 24 | 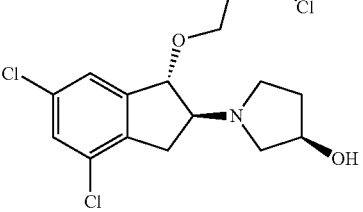 | E | 15 | 2.00 | 489.03 |

| Example | Structure | Synthesis method | LC method | Rt time [min] | MS [M + H+] ES+ |
|---|---|---|---|---|---|
| 482 | 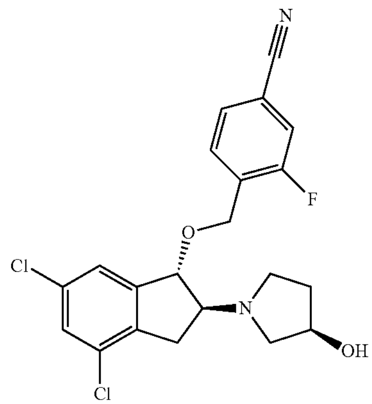 [SMILES: N#Cc1ccc(CO[C@H]2c3cc(Cl)cc(Cl)c3C[C@@H]2N2CC[C@@H](O)C2)c(F)c1] | E | 15 | 2.06 | 420.08 |

Synthesis of a Specific Example (Example 755) by Method G:

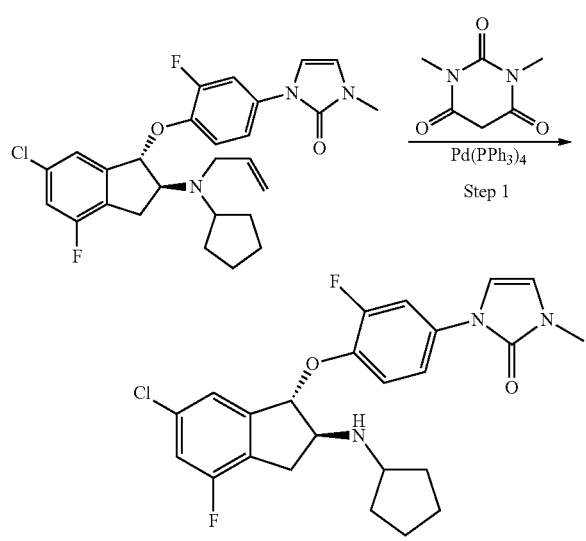

Step 1: To a suspension of 1,3-dimethyl barbituric acid (364 mg, 2 equivalents) and Pd(PPh$_3$)$_4$ (67 mg, 0.05 equivalents) in CH$_2$Cl$_2$ (2.0 ml) under an argon atmosphere a solution of the allyl amine (583 mg, 1 equivalent) in CH$_2$Cl$_2$ (2.0 ml/mmol allyl amine) was added at room temperature. The solution was heated to reflux for 1 h. The reaction mixture was cooled to room temperature and diluted with ethyl acetate. The organic layer was washed with saturated aqueous Na$_2$CO$_3$ solution, dried over Na$_2$SO$_4$ and the solvent removed in vacuo. The crude product was purified by flash chromatography on silica gel using ethyl acetate/heptane/MeOH (5:10:1) for elution. The product was obtained as a colourless oil (211 mg).

The following examples were synthesized in analogy to Example 755:

| example | structure | Synthesis method | LC method | Rt time [min] | MS [M + H+] ES+ |
|---|---|---|---|---|---|
| 746 | 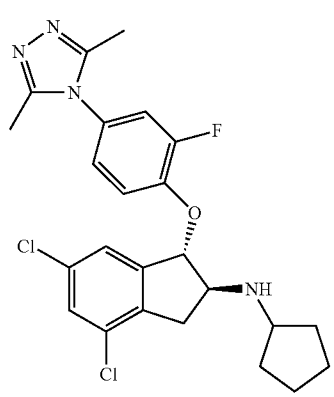 [SMILES: Cc1nnc(C)n1-c1ccc(O[C@H]2c3cc(Cl)cc(Cl)c3C[C@@H]2NC2CCCC2)c(F)c1] | G | 23 | 3.28 | 475.16 |

-continued

| example | structure | Synthesis method | LC method | Rt time [min] | MS [M + H+] ES+ |
|---|---|---|---|---|---|
| 747 | 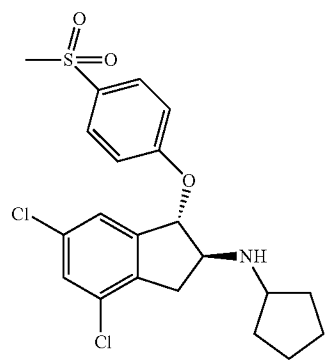 [SMILES: CS(=O)(=O)c1ccc(O[C@H]2c3cc(Cl)cc(Cl)c3C[C@@H]2NC2CCCC2)cc1] | G | 22 | 1.02 | 440.15 |
| 748 | 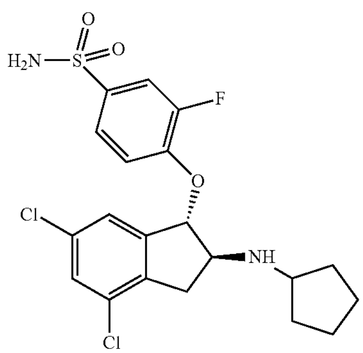 [SMILES: NS(=O)(=O)c1ccc(O[C@H]2c3cc(Cl)cc(Cl)c3C[C@@H]2NC2CCCC2)c(F)c1] | G | 25 | 2.79 | 459.22 |
| 749 | 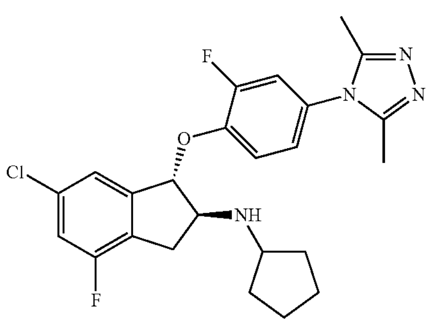 [SMILES: Cc1nnc(C)n1-c1ccc(O[C@H]2c3cc(Cl)cc(F)c3C[C@@H]2NC2CCCC2)c(F)c1] | G | 20 | 1.31 | 459.16 |
| 750 | 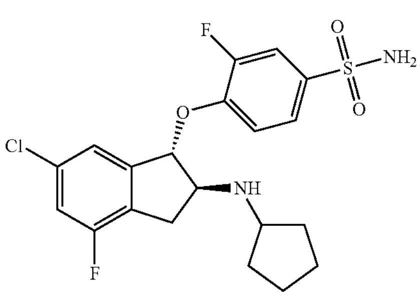 [SMILES: NS(=O)(=O)c1ccc(O[C@H]2c3cc(Cl)cc(F)c3C[C@@H]2NC2CCCC2)c(F)c1] | G | 20 | 1.38 | 443.10 |

-continued

| example | structure | Synthesis method | LC method | Rt time [min] | MS [M + H+] ES+ |
|---------|-----------|------------------|-----------|---------------|-----------------|
| 751 | 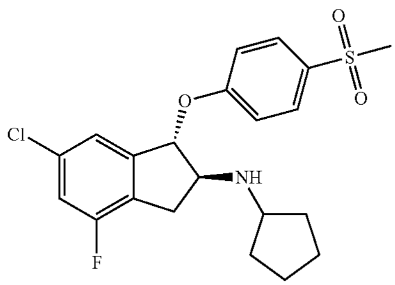 [SMILES: CS(=O)(=O)c1ccc(O[C@H]2c3cc(Cl)cc(F)c3C[C@@H]2NC2CCCC2)cc1] | G | 20 | 1.41 | 424.10 |
| 752 | 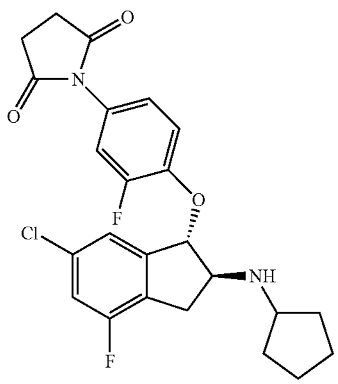 [SMILES: O=C1CCC(=O)N1c1ccc(O[C@H]2c3cc(Cl)cc(F)c3C[C@@H]2NC2CCCC2)c(F)c1] | G | 20 | 1.41 | 461.19 |
| 753 | 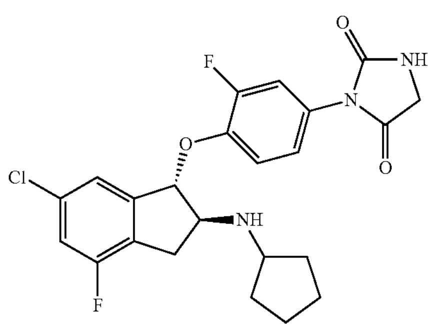 [SMILES: O=C1CNC(=O)N1c1ccc(O[C@H]2c3cc(Cl)cc(F)c3C[C@@H]2NC2CCCC2)c(F)c1] | G | 20 | 1.37 | 462.19 |
| 754 | 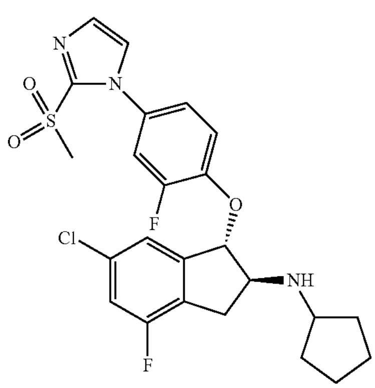 [SMILES: CS(=O)(=O)c1nccn1-c1ccc(O[C@H]2c3cc(Cl)cc(F)c3C[C@@H]2NC2CCCC2)c(F)c1] | G | 20 | 1.42 | 508.16 |

| example | structure | Synthesis method | LC method | Rt time [min] | MS [M + H+] ES+ |
|---|---|---|---|---|---|
| 755 | 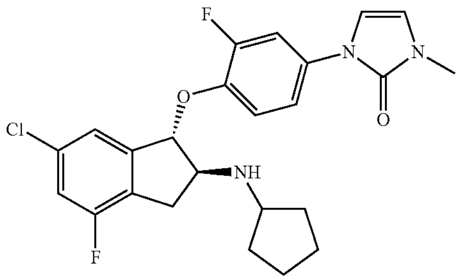 [SMILES: Cn1ccn(-c2ccc(O[C@H]3c4cc(Cl)cc(F)c4C[C@@H]3NC3CCCC3)c(F)c2)c1=O] | G | 20 | 1.43 | 460.20 |
| 756 | 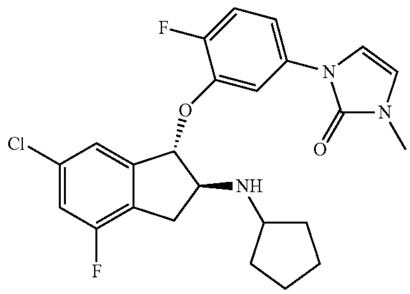 [SMILES: Cn1ccn(-c2ccc(F)c(O[C@H]3c4cc(Cl)cc(F)c4C[C@@H]3NC3CCCC3)c2)c1=O] | G | 20 | 1.46 | 460.19 |

Assay Method for Determining the Pharmacological Activity:

In this assay, the recovery of the intracellular pH ($pH_i$) of LAP1 cells which stably express the sodium-proton exchanger of subtype 3 (NHE3) after acidification was determined. The recovery occurs even under bicarbonate-free conditions with functional NHE3. To this end, the $pH_i$ was determined using the pH-sensitive fluorescent dye BCECF (Molecular Probes, Eugene, Oreg., USA, employing the precursors BCECF-AM). The cells were initially incubated with BCECF (5 µM BCECF-AM) in NH$_4$Cl buffer (NH$_4$Cl buffer: 115 mM cholineCl, 20 mM NH$_4$Cl, 5 mM KCl, 1 mM CaCl$_2$, 1 mM MgCl$_2$, 20 mM Hepes, 5 mM glucose, a pH of 7.4 was adjusted with 1 M KOH). The intracellular acidification was induced by washing the cells incubated in NH$_4$Cl buffer with NH$_4$Cl-free buffer (133.8 mM choline chloride, 4.7 mM KCl, 1.25 mM CaCl$_2$, 1.25 mM MgCl$_2$, 0.97 mM K$_2$HPO$_4$, 0.23 mM KH$_2$PO$_4$, 5 mM Hepes, 5 mM glucose, a pH of 7.4 was adjusted with 1 M KOH). After the washing step, 90 µl of the NH$_4$Cl-free buffer were left on the cells. The pH recovery was started by adding 90 µl of Na$^+$-containing buffer (133.8 mM NaCl, 4.7 mM KCl, 1.25 mM CaCl$_2$, 1.25 mM MgCl$_2$, 0.97 mM Na$_2$HPO$_4$, 0.23 mM NaH$_2$PO$_4$, 10 mM Hepes, 5 mM glucose, a pH of 7.4 was adjusted with 1 M NaOH) in a measuring instrument (FLIPR, "Fluorometric Imaging Plate Reader", Molecular Devices, Sunnyvale, Calif., USA). The BCECF fluorescence was determined with an excitation wavelength of 498 nm and the FLIPR emission filter 1 (bandpass from 510 to 570 nm). The subsequent changes in fluorescence as a measure of pH recovery were recorded for two minutes. To calculate the NHE3-inhibitory power of the tested substances, the cells were initially investigated in buffers with which complete or absolutely no pH recovery took place. For complete pH recovery (100%), the cells were incubated in Na$^+$-containing buffer (see above), and to determine the 0% value were incubated in Na$^+$-free buffer (see above). The substances to be tested were made up in Na$^+$-containing buffer. The recovery of the intracellular pH at each tested concentration of a substance was expressed as percent of the maximum recovery.

The $IC_{50}$ of the respective substance for NHE3 was calculated from the percentages of pH recovery using the program XLFit (idbs, Surrey, UK).

The inhibitory effect on NHE3 is detailed in the following table, divided into three activity ranges:
where the meanings are
activity range 1: 20-50% inhibition at 10 µM
activity range 2: $IC_{50}$ 1-10 µM
activity range 3: $IC_{50}$<1 µM

| Example | Activity range |
|---|---|
| 1 | 2 |
| 2 | 2 |
| 3 | 3 |
| 4 | 2 |
| 5 | 2 |
| 6 | 2 |
| 7 | 2 |
| 8 | 3 |
| 9 | 2 |
| 10 | 2 |
| 11 | 2 |
| 12 | 3 |
| 13 | 2 |
| 14 | 2 |
| 15 | 2 |
| 16 | 2 |
| 17 | 2 |
| 18 | 2 |
| 19 | 2 |
| 20 | 2 |
| 21 | 3 |
| 22 | 2 |
| 23 | 2 |
| 24 | 1 |
| 25 | 3 |
| 26 | 2 |

-continued

| Example | Activity range |
|---------|----------------|
| 27 | 3 |
| 28 | 2 |
| 29 | 2 |
| 30 | 2 |
| 31 | 3 |
| 32 | 1 |
| 33 | 2 |
| 34 | 1 |
| 35 | 1 |
| 36 | 1 |
| 37 | 3 |
| 38 | 1 |
| 39 | 1 |
| 40 | 1 |
| 41 | 2 |
| 42 | 1 |
| 43 | 1 |
| 44 | 1 |
| 45 | 1 |
| 46 | 1 |
| 47 | 3 |
| 48 | 1 |
| 49 | 2 |
| 50 | 1 |
| 51 | 1 |
| 52 | 1 |
| 53 | 1 |
| 54 | 1 |
| 55 | 1 |
| 56 | 1 |
| 57 | 1 |
| 58 | 2 |
| 59 | 2 |
| 60 | 2 |
| 61 | 2 |
| 62 | 3 |
| 63 | 1 |
| 64 | 1 |
| 65 | 1 |
| 66 | 1 |
| 67 | 1 |
| 68 | 1 |
| 69 | 1 |
| 70 | 1 |
| 71 | 2 |
| 72 | 3 |
| 73 | 3 |
| 74 | 1 |
| 75 | 1 |
| 76 | 2 |
| 77 | 1 |
| 78 | 1 |
| 79 | 3 |
| 80 | 2 |
| 81 | 1 |
| 82 | 2 |
| 83 | 2 |
| 84 | 3 |
| 85 | 2 |
| 86 | 2 |
| 87 | 1 |
| 88 | 2 |
| 89 | 2 |
| 90 | 2 |
| 91 | 3 |
| 92 | 1 |
| 93 | 3 |
| 94 | 1 |
| 95 | 3 |
| 96 | 1 |
| 97 | 3 |
| 98 | 3 |
| 99 | 3 |
| 100 | 3 |
| 101 | 3 |
| 102 | 3 |

-continued

| Example | Activity range |
|---------|----------------|
| 103 | 3 |
| 104 | 3 |
| 105 | 2 |
| 106 | 3 |
| 107 | 2 |
| 108 | 2 |
| 109 | 3 |
| 110 | 3 |
| 111 | 3 |
| 112 | 2 |
| 113 | 3 |
| 114 | 2 |
| 115 | 1 |
| 116 | 2 |
| 117 | 2 |
| 118 | 2 |
| 119 | 3 |
| 120 | 3 |
| 121 | 2 |
| 122 | 3 |
| 123 | 2 |
| 124 | 2 |
| 125 | 1 |
| 126 | 3 |
| 127 | 3 |
| 128 | 3 |
| 130 | 3 |
| 131 | 3 |
| 132 | 3 |
| 133 | 3 |
| 134 | 3 |
| 135 | 1 |
| 136 | 1 |
| 137 | 1 |
| 138 | 3 |
| 139 | 3 |
| 140 | 2 |
| 141 | 3 |
| 142 | 3 |
| 143 | 3 |
| 144 | 3 |
| 145 | 3 |
| 146 | 2 |
| 147 | 3 |
| 148 | 1 |
| 149 | 1 |
| 150 | 1 |
| 151 | 1 |
| 152 | 1 |
| 153 | 1 |
| 154 | 2 |
| 155 | 1 |
| 156 | 1 |
| 157 | 1 |
| 158 | 1 |
| 159 | 1 |
| 160 | 1 |
| 161 | 1 |
| 162 | 1 |
| 163 | 2 |
| 164 | 2 |
| 165 | 1 |
| 166 | 1 |
| 167 | 2 |
| 168 | 1 |
| 169 | 3 |
| 170 | 2 |
| 171 | 2 |
| 172 | 2 |
| 173 | 1 |
| 174 | 1 |
| 175 | 1 |
| 176 | 1 |
| 177 | 1 |
| 178 | 1 |
| 179 | 1 |

| Example | Activity range |
|---|---|
| 180 | 1 |
| 181 | 2 |
| 182 | 2 |
| 183 | 1 |
| 184 | 1 |
| 185 | 2 |
| 186 | 1 |
| 187 | 1 |
| 188 | 2 |
| 189 | 2 |
| 190 | 1 |
| 191 | 1 |
| 192 | 1 |
| 193 | 2 |
| 194 | 2 |
| 195 | 3 |
| 196 | 3 |
| 197 | 3 |
| 198 | 3 |
| 199 | 3 |
| 200 | 3 |
| 201 | 2 |
| 202 | 1 |
| 203 | 1 |
| 204 | 2 |
| 205 | 1 |
| 206 | 3 |
| 207 | 3 |
| 208 | 1 |
| 209 | 3 |
| 210 | 2 |
| 211 | 1 |
| 212 | 2 |
| 213 | 1 |
| 214 | 2 |
| 215 | 2 |
| 216 | 1 |
| 217 | 1 |
| 218 | 1 |
| 219 | 1 |
| 220 | 3 |
| 221 | 3 |
| 222 | 3 |
| 223 | 3 |
| 224 | 3 |
| 225 | 3 |
| 226 | 3 |
| 227 | 2 |
| 228 | 2 |
| 229 | 1 |
| 230 | 1 |
| 231 | 3 |
| 232 | 2 |
| 233 | 2 |
| 234 | 2 |
| 235 | 2 |
| 236 | 3 |
| 237 | 1 |
| 238 | 2 |
| 239 | 1 |
| 240 | 2 |
| 241 | 2 |
| 242 | 1 |
| 243 | 3 |
| 244 | 1 |
| 245 | 1 |
| 246 | 2 |
| 247 | 1 |
| 248 | 3 |
| 249 | 1 |
| 250 | 1 |
| 251 | 1 |
| 252 | 1 |
| 253 | 1 |
| 254 | 3 |
| 255 | 2 |
| 256 | 2 |
| 257 | 3 |
| 258 | 3 |
| 259 | 1 |
| 260 | 2 |
| 261 | 1 |
| 262 | 2 |
| 263 | 3 |
| 264 | 2 |
| 265 | 3 |
| 266 | 2 |
| 267 | 2 |
| 268 | 1 |
| 269 | 1 |
| 270 | 2 |
| 271 | 2 |
| 272 | 2 |
| 273 | 3 |
| 274 | 2 |
| 275 | 2 |
| 276 | 3 |
| 277 | 3 |
| 278 | 2 |
| 279 | 3 |
| 280 | 2 |
| 281 | 3 |
| 282 | 1 |
| 283 | 3 |
| 284 | 2 |
| 285 | 2 |
| 286 | 2 |
| 287 | 3 |
| 288 | 3 |
| 289 | 3 |
| 290 | 1 |
| 291 | 2 |
| 292 | 3 |
| 293 | 2 |
| 294 | 2 |
| 295 | 3 |
| 296 | 1 |
| 297 | 1 |
| 298 | 3 |
| 299 | 3 |
| 300 | 2 |
| 301 | 1 |
| 302 | 1 |
| 303 | 3 |
| 304 | 3 |
| 305 | 3 |
| 306 | 2 |
| 307 | 2 |
| 308 | 3 |
| 309 | 3 |
| 310 | 1 |
| 311 | 1 |
| 312 | 1 |
| 313 | 3 |
| 314 | 3 |
| 315 | 2 |
| 316 | 2 |
| 317 | 2 |
| 318 | 3 |
| 319 | 2 |
| 320 | 2 |
| 321 | 3 |
| 322 | 3 |
| 323 | 3 |
| 324 | 3 |
| 325 | 3 |
| 326 | 2 |
| 327 | 1 |
| 328 | 1 |
| 329 | 3 |
| 330 | 3 |
| 331 | 3 |

| Example | Activity range |
|---|---|
| 332 | 2 |
| 333 | 3 |
| 334 | 3 |
| 335 | 3 |
| 336 | 3 |
| 337 | 2 |
| 338 | 2 |
| 339 | 3 |
| 340 | 3 |
| 341 | 3 |
| 342 | 2 |
| 343 | 2 |
| 344 | 3 |
| 345 | 3 |
| 346 | 3 |
| 347 | 3 |
| 348 | 3 |
| 349 | 3 |
| 350 | 2 |
| 351 | 1 |
| 352 | 3 |
| 353 | 1 |
| 354 | 1 |
| 355 | 2 |
| 356 | 3 |
| 357 | 3 |
| 358 | 2 |
| 359 | 2 |
| 360 | 2 |
| 361 | 2 |
| 362 | 3 |
| 363 | 2 |
| 364 | 2 |
| 365 | 2 |
| 366 | 1 |
| 367 | 1 |
| 368 | 2 |
| 369 | 1 |
| 370 | 3 |
| 371 | 1 |
| 372 | 1 |
| 373 | 3 |
| 374 | 2 |
| 375 | 2 |
| 376 | 2 |
| 377 | 3 |
| 378 | 3 |
| 379 | 3 |
| 380 | 1 |
| 381 | 2 |
| 382 | 1 |
| 383 | 3 |
| 384 | 1 |
| 385 | 3 |
| 386 | 2 |
| 387 | 2 |
| 388 | 2 |
| 389 | 2 |
| 390 | 1 |
| 391 | 1 |
| 392 | 2 |
| 393 | 2 |
| 394 | 2 |
| 395 | 1 |
| 396 | 1 |
| 397 | 2 |
| 398 | 2 |
| 399 | 1 |
| 400 | 1 |
| 401 | 2 |
| 402 | 2 |
| 403 | 2 |
| 404 | 1 |
| 405 | 3 |
| 406 | 3 |
| 407 | 3 |

| Example | Activity range |
|---|---|
| 408 | 1 |
| 409 | 3 |
| 410 | 2 |
| 411 | 3 |
| 412 | 1 |
| 413 | 2 |
| 414 | 2 |
| 415 | 2 |
| 416 | 2 |
| 417 | 2 |
| 418 | 2 |
| 419 | 2 |
| 420 | 2 |
| 421 | 2 |
| 422 | 3 |
| 423 | 2 |
| 424 | 3 |
| 425 | 3 |
| 426 | 3 |
| 427 | 2 |
| 428 | 3 |
| 429 | 2 |
| 430 | 3 |
| 431 | 2 |
| 432 | 2 |
| 433 | 2 |
| 434 | 3 |
| 435 | 2 |
| 436 | 2 |
| 437 | 2 |
| 438 | 2 |
| 439 | 3 |
| 440 | 1 |
| 441 | 2 |
| 442 | 2 |
| 443 | 1 |
| 444 | 3 |
| 445 | 3 |
| 446 | 1 |
| 447 | 3 |
| 448 | 3 |
| 449 | 1 |
| 450 | 1 |
| 451 | 3 |
| 452 | 2 |
| 453 | 3 |
| 454 | 1 |
| 455 | 1 |
| 456 | 3 |
| 457 | 3 |
| 458 | 1 |
| 459 | 1 |
| 460 | 3 |
| 461 | 1 |
| 462 | 1 |
| 463 | 2 |
| 464 | 3 |
| 465 | 3 |
| 466 | 3 |
| 467 | 2 |
| 468 | 2 |
| 469 | 2 |
| 470 | 2 |
| 471 | 1 |
| 472 | 2 |
| 473 | 3 |
| 474 | 2 |
| 475 | 2 |
| 476 | 2 |
| 477 | 3 |
| 478 | 1 |
| 479 | 3 |
| 480 | 3 |
| 481 | 2 |
| 482 | 1 |
| 483 | 3 |

| Example | Activity range |
|---|---|
| 484 | 1 |
| 485 | 1 |
| 486 | 1 |
| 487 | 1 |
| 488 | 3 |
| 489 | 1 |
| 490 | 3 |
| 491 | 3 |
| 492 | 3 |
| 493 | 3 |
| 494 | 2 |
| 495 | 2 |
| 496 | 2 |
| 497 | 1 |
| 498 | 1 |
| 499 | 3 |
| 500 | 3 |
| 501 | 3 |
| 502 | 3 |
| 503 | 1 |
| 504 | 2 |
| 505 | 2 |
| 506 | 1 |
| 507 | 1 |
| 508 | 1 |
| 509 | 2 |
| 510 | 3 |
| 511 | 1 |
| 512 | 1 |
| 513 | 1 |
| 514 | 2 |
| 515 | 2 |
| 516 | 3 |
| 517 | 1 |
| 518 | 3 |
| 519 | 3 |
| 520 | 3 |
| 521 | 2 |
| 522 | 2 |
| 523 | 2 |
| 524 | 3 |
| 525 | 2 |
| 526 | 2 |
| 527 | 2 |
| 528 | 2 |
| 529 | 1 |
| 530 | 1 |
| 531 | 1 |
| 532 | 2 |
| 533 | 3 |
| 534 | 1 |
| 535 | 2 |
| 536 | 2 |
| 537 | 2 |
| 538 | 2 |
| 539 | 2 |
| 540 | 2 |
| 541 | 2 |
| 542 | 3 |
| 543 | 2 |
| 544 | 2 |
| 545 | 2 |
| 546 | 2 |
| 547 | 2 |
| 548 | 2 |
| 549 | 1 |
| 550 | 3 |
| 551 | 3 |
| 552 | 3 |
| 553 | 2 |
| 554 | 2 |
| 555 | 2 |
| 556 | 3 |
| 557 | 2 |
| 558 | 3 |
| 559 | 3 |
| 560 | 3 |
| 561 | 3 |
| 562 | 2 |
| 563 | 3 |
| 564 | 3 |
| 565 | 3 |
| 566 | 3 |
| 567 | 2 |
| 568 | 2 |
| 569 | 1 |
| 570 | 1 |
| 571 | 2 |
| 572 | 2 |
| 573 | 1 |
| 574 | 2 |
| 575 | 1 |
| 576 | 2 |
| 577 | 2 |
| 578 | 1 |
| 579 | 2 |
| 580 | 1 |
| 581 | 3 |
| 582 | 2 |
| 583 | 2 |
| 584 | 2 |
| 585 | 1 |
| 586 | 1 |
| 587 | 2 |
| 588 | 1 |
| 589 | 2 |
| 590 | 1 |
| 591 | 1 |
| 592 | 1 |
| 593 | 1 |
| 594 | 1 |
| 595 | 2 |
| 596 | 2 |
| 597 | 1 |
| 598 | 2 |
| 599 | 2 |
| 600 | 2 |
| 601 | 2 |
| 602 | 2 |
| 603 | 2 |
| 604 | 3 |
| 605 | 2 |
| 606 | 2 |
| 607 | 2 |
| 608 | 2 |
| 609 | 2 |
| 610 | 2 |
| 611 | 2 |
| 612 | 2 |
| 613 | 2 |
| 614 | 2 |
| 615 | 2 |
| 616 | 2 |
| 617 | 2 |
| 618 | 2 |
| 619 | 2 |
| 620 | 2 |
| 621 | 2 |
| 622 | 2 |
| 623 | 2 |
| 624 | 2 |
| 625 | 2 |
| 626 | 2 |
| 627 | 2 |
| 628 | 2 |
| 629 | 2 |
| 630 | 2 |
| 631 | 3 |
| 632 | 3 |
| 633 | 2 |
| 634 | 2 |
| 635 | 1 |

| Example | Activity range |
|---|---|
| 636 | 3 |
| 637 | 2 |
| 638 | 2 |
| 639 | 1 |
| 640 | 3 |
| 641 | 3 |
| 642 | 2 |
| 643 | 1 |
| 644 | 3 |
| 645 | 2 |
| 646 | 1 |
| 647 | 2 |
| 648 | 2 |
| 649 | 1 |
| 650 | 3 |
| 651 | 2 |
| 652 | 2 |
| 653 | 2 |
| 654 | 1 |
| 655 | 2 |
| 656 | 2 |
| 657 | 2 |
| 658 | 3 |
| 659 | 3 |
| 660 | 2 |
| 661 | 3 |
| 662 | 2 |
| 663 | 3 |
| 664 | 3 |
| 665 | 3 |
| 666 | 2 |
| 667 | 2 |
| 668 | 3 |
| 669 | 2 |
| 670 | 1 |
| 671 | 3 |
| 672 | 3 |
| 673 | 2 |
| 674 | 2 |
| 675 | 2 |
| 676 | 2 |
| 677 | 3 |
| 678 | 3 |
| 679 | 3 |
| 680 | 2 |
| 681 | 2 |
| 682 | 2 |
| 683 | 2 |
| 684 | 1 |
| 685 | 2 |
| 686 | 2 |
| 687 | 2 |
| 688 | 2 |
| 689 | 3 |
| 690 | 3 |
| 691 | 3 |
| 692 | 3 |
| 693 | 3 |
| 694 | 3 |
| 695 | 2 |
| 696 | 3 |
| 697 | 2 |
| 698 | 3 |
| 699 | 2 |
| 700 | 3 |
| 701 | 2 |
| 702 | 3 |
| 703 | 2 |
| 704 | 3 |
| 705 | 2 |
| 706 | 1 |
| 707 | 2 |
| 708 | 2 |
| 709 | 3 |
| 710 | 2 |
| 711 | 1 |
| 712 | 2 |
| 713 | 2 |
| 714 | 2 |
| 715 | 3 |
| 716 | 3 |
| 717 | 2 |
| 718 | 3 |
| 719 | 2 |
| 720 | 2 |
| 721 | 2 |
| 722 | 2 |
| 723 | 1 |
| 724 | 1 |
| 725 | 2 |
| 726 | 3 |
| 727 | 3 |
| 728 | 2 |
| 729 | 2 |
| 730 | 2 |
| 731 | 3 |
| 732 | 2 |
| 733 | 2 |
| 734 | 2 |
| 735 | 2 |
| 736 | 2 |
| 737 | 2 |
| 738 | 3 |
| 739 | 3 |
| 740 | 3 |
| 741 | 3 |
| 742 | 2 |
| 743 | 3 |
| 744 | 2 |
| 745 | 1 |
| 746 | 3 |
| 747 | 2 |
| 748 | 2 |
| 749 | 2 |
| 750 | 2 |
| 751 | 2 |
| 752 | 2 |
| 753 | 2 |
| 754 | 3 |
| 755 | 2 |
| 756 | 2 |

The invention claimed is:
1. A compound of the formula I

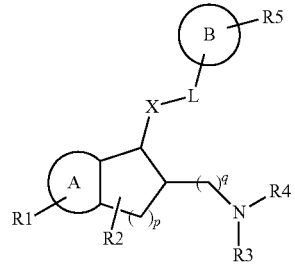

in which
A is a phenyl radical where one or more hydrogen atoms in said phenyl radical may be replaced by substituents R1 which are selected independently of one another from the group of F, Cl, Br, I, $(C_1-C_{10})$-alkyl-, $(C_2-C_{10})$-alkenyl-, $(C_2-C_{10})$-alkynyl-, $(C_3-C_{14})$-cycloalkyl-, $(C_4-C_{20})$-cycloalkylalkyl-, $(C_4-C_{20})$-cycloalkylalkyloxy-, $(C_1-C_{10})$-alkoxy-, $(C_1-C_{14})$-alkylthio-, $(C_6-C_{14})$-aryl-, $(C_2-C_{13})$-heteroaryl, —CN, —NR13R14, —C(O)R12, —SF$_5$, —S(O)$_n$R12, —C(O)OR12, —C(O)NR13R14 and —S(O)$_n$NR13R14;

where said alkyl, alkenyl, alkynyl, cycloalkyl, cycloalkylalkyl, cycloalkylalkyloxy, cycloheteroalkyl, alkoxy, and alkylthio radicals may be substituted independently of one another one or more times by F, OH or (C$_1$-C$_{10}$)-alkoxy;

B is a mono-or fused bicyclic radical selected from the group of 6to 10 membered aryl radicals, of 5 to 10 membered heteroaryl radicals, of 3 to 10 membered cycloalkyl radicals, of 9 to 14 membered cycloalkylaryl radicals, of 8 to 14 membered cycloalkylheteroaryl radicals, of 3 to 10 membered cycloheteroalkyl radicals, of 9 to 14 membered cycloheteroalkylaryl radicals and of 8 to 14 membered cycloheteroalkylheteroaryl radicals, where the cycloalkyl or cycloheteroalkyl units may be saturated or partly unsaturated, and where the heterocyclic groups may comprise one or more heteroatoms selected from the group of nitrogen, oxygen and sulfur;

where one or more hydrogen atoms in the radicals B may be replaced by substituents R5 which are selected independently of one another from the group of (C$_1$-C$_{10}$)-alkyl radicals, of (C$_2$-C$_{10}$)-alkenyl radicals, of (C$_2$-C$_{10}$)-alkynyl radicals, of (C$_1$-C$_{10}$)-alkoxy radicals, of (C$_1$-C$_{10}$)-alkylthio radicals, of (C$_3$-C$_{14}$)-cycloalkyl radicals, of (C$_4$-C$_{20}$)-cycloalkylalkyl radicals, of (C$_4$-C$_{20}$)-cycloalkylalkyloxy, of (C$_2$-C$_{19}$)-cycloheteroalkyl radicals, of (C$_3$-C$_{19}$)-cycloheteroalkylalkyl radicals, of (C$_3$-C$_{11}$)-cycloalkyloxy radicals, of (C$_2$-C$_{11}$)-cycloheteroalkyloxy radicals, of (C$_6$-C$_{10}$)-aryl radicals, of (C$_1$-C$_9$)-heteroaryl radicals, of (C$_9$-C$_{14}$)-cycloalkylaryl radicals, of (C$_5$-C$_{13}$)-cycloalkylheteroaryl radicals, (C$_7$-C$_{13}$)-cycloheteroalkylaryl radicals and (C$_4$-C$_{12}$)-cycloheteroalkylheteroaryl radicals, where the cycloalkyl and cycloheteroalkyl units may be saturated or partly unsaturated, and where one or more hydrogen atoms in said radicals R5 may be replaced by further radicals which are selected independently of one another from the group of R11 radicals, it is further possible for R5 to be one or more radicals which are selected independently of one another from the group of OH, (=O), NH$_2$, F, Cl, Br, I, CN, NO$_2$, —NR17R18, —NR16COR17, —NR16COOR17, —NR16CONR17R18, —NR16—S(O)$_2$—R17, —NR16—S(O)$_2$—NR17R18, —COOR16, —COR6; —CO(NR17R18), S(O)$_n$R16 and —S(O)$_2$NR17R18, where R16, R17 and R18 independently of one another for a radical selected from the group of H, (C$_2$-C$_{19}$)-cycloheteroalkyl, (C$_3$-C$_{14}$)-cycloalkyl, (C$_6$-C$_{10}$)-aryl and (C$_1$-C$_{10}$)-alkyl radicals, all of which may be substituted independently of one another by OH, (=O), F, Cl, Br, I, CN, NO$_2$, —NR13R14, —NR13COR12, —NR13COOR12, —NR12CONR13R14, —NR13—S(O)$_2$—R12, —NR12—S(O)$_2$—R13R14, —COOR12, —COR12; —CO(NR13R14), —S(O)$_n$R12, —S(O)$_2$NR13R14, (C$_3$-C$_{14}$)-cycloalkyl, (C$_4$-C$_{20}$)-cycloalkylalkyl, (C$_2$-C$_{19}$)-cycloheteroalkyl, (C$_3$-C$_{19}$)-cycloheteroalkylalkyl, (C$_6$-C$_{10}$)-aryl or (C$_1$-C$_9$)-heteroaryl, and where R17 and R18 can form together with the nitrogen to which they are bonded a 4-7 membered, saturated, unsaturated or partly unsaturated heterocycle having 1 to 13 carbon atoms which may additionally comprise one or more heteroatoms from the list —O—, —S(O)$_n$—, =N— and —NR15-, where the heterocycle formed may be substituted independently of one another one or more times by F, OH, (=O), NH$_2$, NH(C$_1$-C$_4$)alkyl, N((C$_1$-C$_4$)alkyl)$_2$, CN or (C$_1$-C$_{10}$)-alkoxy, (C$_1$-C$_{10}$)-alkyl, (C$_2$-C$_{10}$)-alkenyl, (C$_2$-C$_{10}$)-alkynyl, (C$_3$-C$_{14}$)-cycloalkyl, (C$_4$-C$_{20}$)-cycloalkylalkyl, (C$_2$-C$_{20}$)-cycloheteroalkyl, (C$_3$-C$_{19}$)-cycloheteroalkylalkyl, each of which may in turn carry independently of one another one or more radicals F, OH, (=O), NH$_2$, NH(C$_1$-C$_4$)alkyl, N((C$_1$-C$_4$)alkyl)$_2$, CN or (C$_1$-C$_{10}$)-alkoxy;

L is a covalent bond;

X is a group —O—;

R2 is absent or is one or more substituents which may be selected independently of one another from the group of F, (C$_1$-C$_{10}$)-alkyl and (C$_1$-C$_{10}$)-alkoxy radical, where the alkyl and alkoxy radicals may be substituted independently of one another one or more times by F;

R3 and R4 are independently of one another a radical which is selected from the group of (C$_1$-C$_{10}$)-alkyl radicals, of (C$_2$-C$_{10}$)-alkenyl radicals, of (C$_2$-C$_{10}$)-alkynyl radicals, of (C$_3$-C$_{14}$)-cycloalkyl radicals, of (C$_4$-C$_{20}$)-cycloalkylalkyl radicals, of (C$_2$-C$_{19}$)-cycloheteroalkyl radicals, of (C$_3$-C$_{19}$)-cycloheteroalkylalkyl radicals, of (C$_6$-C$_{10}$)-aryl radicals, of (C$_7$-C$_{20}$)-arylalkyl radicals, of (C$_1$-C$_9$)-heteroaryl radicals and of (C$_2$-C$_{19}$)-heteroarylalkyl radicals, where the radicals R3 and R4 may be substituted independently of one another one or more times by a radical from the group of OH, NH$_2$, (=O), F, Cl, Br, I, CN, NO$_2$, —NR13R14, —NR13COR12, —NR13COOR12, —NR12CONR13R14, —NR13—S(O)$_2$—R12, —NR13—S(O)$_2$NR13R14, —COOR12, —COR12; —CO(NR13R14) and S(O)$_n$R12, —S(O)$_2$R13R14, or R3 and R4 form together with the nitrogen to which they are bonded a 4-10 membered, saturated, unsaturated or partly unsaturated heterocycle which may additionally comprise one or more heteroatoms from the list —O—, —S(O)$_n$—, =N— and —NR8-, where the heterocyclic radicals may be substituted independently of one another one or more times by radicals selected from the group of R7 and R9, and where the heterocyclic radicals formed by R3 and R4 may be bridged by a bond, by a saturated or unsaturated (C$_1$-C$_{10}$)-alkyl or (C$_1$-C$_9$)-heteroalkyl chain or by —NR15-, —O— or —S—, and where the alkyl and heteroalkyl chains may also form a spirocyclic ring system with the ring system formed by R3 and R4, where the alkyl and heteroalkyl bridges may be substituted independently of one another one or more times by radicals selected from the group of R7 and R9, and where R8 in the group —NR8- may form with the ring which R3 and R4 may form a further saturated, unsaturated or partly unsaturated heterocycle which may be substituted independently of one another one or more times by radicals selected from the group of R7 and R9, and may additionally comprise one or more heteroatoms from the list —O—, —S(O)$_n$—, —N= and —NR19-;

R7 are a (C$_1$-C$_{10}$)-alkyl radical or (C$_1$-C$_{14}$)-cycloalkyl radical, where the alkyl radical may be substituted independently of one another one or more times by R9;

R8 is H, a (C$_1$-C$_{10}$)-alkyl radical or (C$_1$-C$_{14}$)-cycloalkyl radical, COR12, —CO(NR13R14), S(O)$_n$R12 or —S(O)$_2$NR13R14, where the alkyl radical may be substituted independently of one another one or more times by R10;

R9 is a radical selected from the group of OH, (=O), F, Cl, Br, I, CN, NO$_2$, —NR13R14, —NR13COR12, —NR13COOR12, —NR12CONR13R14, —NR13—S(O)$_2$—R12, —NR13—S(O)$_2$—NR13R14, —COOR12, —COR12, —CO(NR13R14), S(O)$_n$R12, —S(O)$_2$NR13R14, (C$_3$-C$_{14}$)-cycloalkyl, (C$_4$-C$_{20}$)-cycloalkylalkyl, (C$_1$-C$_{10}$)-alkoxy, (C$_2$-C$_{19}$)-cycloheteroalkyl, (C$_3$-C$_{19}$) -cycloheteroalkylalkyl, (C$_6$-C$_{10}$)-aryl radicals and (C$_1$-C$_9$)-heteroaryl radicals;

R10 is a radical selected from the group of F, OH, CN, (C$_1$-C$_{10}$)-alkoxy, (C$_1$-C$_{10}$)-alkylthio, NO$_2$, —NR13R14, —NR13COR12, —NR13COOR12, —NR13CONR13R14, —NR13—S(O)$_2$—R12, —NR12—S(O)$_2$—NR13R14, —COOR12, —COR12, —CO(NR13R14), S(O)$_n$R12 and —S(O)$_2$NR13R14;

R11 is a radical selected from the group of (C$_1$-C$_{10}$)-alkyl, (C$_2$-C$_{10}$)-alkenyl, (C$_2$-C$_{10}$)-alkynyl, (C$_1$-C$_{10}$)-alkoxy, (C$_1$-C$_{20}$)-alkylthio, (C$_3$-C$_{14}$) -cycloalkyl, (C$_4$-C$_{10}$)-cycloalkylalkyl, (C$_2$-C$_{13}$)-cycloheteroalkyl, (C$_4$-C$_{19}$)-cycloheteroalkylalkyl, (C$_3$-C$_{14}$) -cycloalkyloxya and (C$_2$-C$_{13}$)-cycloheteroalkyloxy; all of which may be substituted independently of one another one or more times by R10; R11 can also be a radical selected from the group of (=O), Cl, Br, I and R10;

R12, R13 and R14 may independently of one another be H, (C$_1$-C$_{10}$)-alkyl, (C$_2$-C$_{10}$)-alkenyl, (C$_2$-C$_{10}$)-alkynyl, (C$_3$-C$_{14}$)-cycloalkyl, (C$_4$-C$_{10}$)-cycloalkylalkyl, (C$_2$-C$_{13}$)-cycloheteroalkyl, (C$_3$-C$_{19}$) -cycloheteroalkylalkyl, (C$_6$-C$_{10}$)-aryl, each of which may be substituted independently of one another one or more times by F, OH, (=O), NH$_2$, NH(C$_1$-C$_4$)alkyl, N((C$_1$-C$_4$)alkyl)$_2$, CN or (C$_1$-C$_{10}$)-alkoxy; or R13 and R14 may form together with the nitrogen to which they are bonded a 4-7 membered, saturated, unsaturated or partly unsaturated heterocycle having 1 to 13 carbon atoms, which may additionally comprise one or more heteroatoms from the list —O—, =N— and —NR15-, where
the formed heterocycle may be substituted independently of one another one or more times by F, OH, (=O), NH$_2$, NH(C$_1$-C$_4$)alkyl, N((C$_1$-C$_4$)alkyl)$_2$, CN or (C$_1$-C$_{10}$)-alkoxy, (C$_1$-C$_{10}$)-alkyl, (C$_2$-C$_{10}$)-alkenyl, (C$_2$-C$_{10}$)-alkynyl, (C$_3$-C$_{14}$)-cycloalkyl, (C$_4$-C$_{20}$)-cycloalkylalkyl, (C$_2$-C$_{20}$)-cycloheteroalkyl or (C$_3$-C$_{19}$)-cycloheteroalkylalkyl, each of which may in turn carry independently of one another one or more radicals F, OH, (=O), NH$_2$, NH(C$_1$-C$_4$)alkyl, N((C$_1$-C$_4$)alkyl)$_2$, CN or (C$_1$-C$_{10}$)-alkoxy;

R15 is a radical selected from the group of H, (C$_1$-C$_{10}$)-alkyl, (C$_2$-C$_{10}$)-alkenyl, (C$_2$-C$_{10}$)-alkynyl, (C$_3$-C$_{14}$)-cycloalkyl, (C$_4$-C$_{20}$)-cycloalkylalkyl, (C$_2$-C$_{13}$)-cycloheteroalkyl and (C$_3$-C$_{19}$)-cycloheteroalkylalkyl, each of which may be substituted independently of one another one or more times by F, OH, CN or (C$_1$-C$_{10}$)-alkoxy;

R19 is an H, a (C$_1$-C$_{10}$)-alkyl radical or (C$_1$-C$_{14}$)-cycloalkyl radical, COR12, —CO(NR13R14), S(O)$_n$, R12 or —S(O)$_2$NR13R14, where the alkyl radical may be substituted independently of one another one or more times by R10;

and in which
n is 0, 1or 2;
p is 1and
q is 0,
and the pharmaceutically acceptable salts thereof,
and in which
i) in the case where A is phenyl, B is phenyl or benzodioxolanyl and R3 and R4 are (C$_1$-C$_{10}$)-alkyl, (C$_3$-C$_{14}$)-cycloalkyl or (C$_7$-C$_{20}$)-arylalkyl or R3 and R4 together are an unsubstituted pyrrolidinyl, morpholinyl, piperidinyl, piperazinyl radical or 4-methylpiperazinyl radical, at least one R5 radical which is not a (C$_1$-C$_{10}$)-alkyl, (C$_1$-C$_{10}$)-alkoxy, OH, CF$_3$, F, Cl, Br or I radical must be present, ii) in the case where A is phenyl and R3 and R4 are a (C$_1$-C$_{10}$)-alkyl, (C$_3$-C$_{14}$)-cycloalkyl or a (C$_4$-C$_{20}$)-cycloalkylalkyl radical, at least one R5 radical which is not an F, Cl, Br, I, (C$_1$-C$_4$)-alkyl, (C$_1$-C$_4$)-alkoxy, CF$_3$, OCF$_3$, CN, NO$_2$, NH$_2$, —NH((C$_1$-C$_{10}$)-alkyl), -N((C$_1$-C$_{10}$)-alkyl)$_2$, unsubstituted or substituted benzoyl or an unsubstituted or substituted phenyl must be present.

2. A compound as claimed in claim 1 with formula Ic

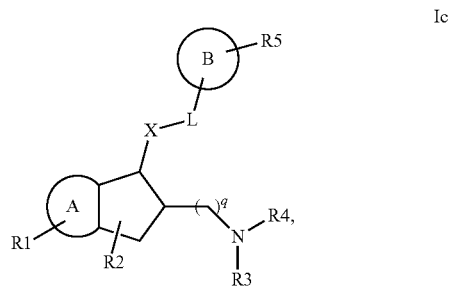

where
B is a 6 to 10 membered monocyclic or fused bicyclic aryl group, a 5 to 10 membered monocyclic or fused bicyclic heteroaryl group, a 9 to 14 membered fused bicyclic cycloalkylaryl group, an 8 to 14 membered fused bicyclic cycloalkylheteroaryl group, a fused 9 to 14 membered bicyclic cycloheteroalkylaryl group or an 8 to 14 membered fused bicyclic cycloheteroalkylheteroaryl group, each of which may be substituted independently of one another one or more times by R5,
where the cycloalkyl and cycloheteroalkyl units may be saturated or partly unsaturated, and
where the cycloheteroalkylaryl groups may comprise as heteroatoms 1 or 2 nitrogen atoms, 1 or 2 oxygen atoms, 1 or 2sulfur atoms, 1 nitrogen atom and 1 oxygen or 1 sulfur atom, or 1 oxygen and 1 sulfur atom,
and the heteroaryl and cycloalkylheteroaryl groups may comprise 1, 2, 3 or 4 nitrogen atoms, 1 oxygen atom, 1 sulfur atom, 1 or 2 nitrogen atoms and 1 oxygen or 1 sulfur atom, or 1 oxygen and 1sulfur atom,
and the cycloheteroalkylheteroaryl group may comprise as heteroatoms 1, 2, 3 or 4 nitrogen atoms, 1 or 2 oxygen atoms, 1 or 2 sulfur atoms, 1, 2 or 3 nitrogen atom and 1 oxygen or 1 sulfur atom, or 1 oxygen and 1 sulfur atom,
R2 is absent or is one or more substituents which may be selected independently of one another from the group of F and of (C$_1$-C$_6$)-alkyl radicals, where the alkyl radicals may be substituted independently of one another one or more times by F,
where the radicals A, X, L, q, R1, R3, R4 and R5 have the meaning stated in claim 1, and the pharmaceutically acceptable salts thereof.

3. A compound as claimed in claim 1 or 2, where
A is a phenyl where one or more hydrogen atoms in the phenyl may be replaced independently of one another by a radical R1;
B is a 6 to 10 membered monocyclic or fused bicyclic aryl group, a 5 to 10 membered monocyclic or fused bicyclic heteroaryl group, a 9 to 14 membered fused bicyclic cycloalkylaryl group, an 8 to 14 membered fused bicyclic cycloalkylheteroaryl group, a fused 9 to 14 membered bicyclic cycloheteroalkylaryl group or an 8 to 14 membered fused bicyclic cycloheteroalkylheteroaryl group, each of which may be substituted independently of one another one or more times by R5, where the cycloalkyl and cycloheteroalkyl units may be saturated or partly unsaturated, and where the cycloheteroalkylaryl groups may comprise as heteroatoms 1nitrogen atom, 1or 2 oxygen atoms, 1 or 2 sulfur atoms, 1nitrogen atom and 1oxygen or 1sulfur atom, or 1 oxygen and 1 sulfur atom, and the heteroaryl and cycloalkylheteroaryl groups may comprise 1, 2 or 3 nitrogen atoms, 1 oxygen atom, 1 sulfur atom, 1 nitrogen and 1 oxygen or sulfur atom, or 1 oxygen and one sulfur atom, and the cycloheteroalkylheteroaryl group may comprise as heteroatoms 1, 2, 3or 4nitrogen atoms, 1 or 2 oxygen atoms, 1 or 2 sulfur atoms, 1 or 2 nitrogen atoms and 1 oxygen or 1 sulfur atom, or 1 oxygen and 1 sulfur atom;

R2 is absent or is one or more substituents which may be selected independently of one another from the group of F and of $(C_1-C_6)$-alkyl radicals, where the alkyl radicals may be substituted independently of one another one or more times by F;

where said radical X, L, q, R1, R3, R4 and R5 have the meaning stated in claim 1, and the pharmaceutically acceptable salts thereof.

4. A compound as claimed in claim 1 or 2 with formula Id

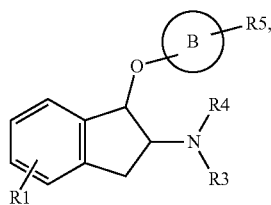

Id where
B is a phenyl group, a naphthyl group, a pyridinyl group, a quinolinyl group, an isoquinolinyl group, an indolyl group, a benzothiophenyl group, a benzodihydrothiophenyl group, a benzofuranyl group, a benzodihydrofuranyl group, a benzopyrrolidinyl group, an isobenzodihydrofuranyl, a benzoimidazolyl group, a benzopyrazolyl group, a benzotriazolyl group, a benzothiazolyl group, a benzoxathiolyl group, an indolinyl group, benzodioxolyl group, a tetrahydroisoquinolinyl group or a tetrahydroquinolinyl group, where one, two, three or four hydrogen atoms in the group B may be replaced by radicals from the group R5, where each R5 radical is selected independently of one another from the group of $(C_1-C_4)$-alkyl which may be wholly or partly fluorinated, or one hydrogen may be replaced by a CN, $NH_2$, OH, $NH(C_1-C_4)$alkyl, $N((C_1-C_4)$alkyl$)_2$, $(C_1-C_4)$ alkoxy, $(C_1-C_4)$-alkoxy which may be wholly or partly fluorinated, $(C_1-C_4)$-alkylthio which may be wholly or partly fluorinated, $(C_2-C_5)$-cycloheteroalkyl, $(C_2-C_5)$-cycloheteroalkyl-$(C_1-C_4)$-alkyl, where the cycloheteroalkyl ring may be saturated or partly unsaturated and may comprise 1 or 2 nitrogen atoms, 1 oxygen atom, 1 nitrogen and 1 sulfur atom or 1 nitrogen and 1 oxygen atom, and where the cycloheteroalkyl ring may carry further substituents from the group of —F, —Cl, —Br, =O, —$NH_2$, —CN, $(C_1-C_4)$-alkyl, $(C_3-C_{10})$-cycloalkyl, OH, $NH(C_1-C_4)$-alkyl, $N((C_1-C_4)$-alkyl$)_2$ and $(C_1-C_{10})$-alkoxy, phenyl, naphthyl, $(C_1-C_6)$-heteroaryl, where the heteroaryl ring may be a monocyclic or fused bicyclic ring which may comprise 1, 2, 3or 4 nitrogen atoms, 1 oxygen atom, 1 sulfur atom, 1 or 2 nitrogen atoms and 1 oxygen or sulfur atom, and where the heteroaryl ring may carry further substituents from the group of —F, —Cl, —Br, =O, —$NH_2$, —CN, $(C_1-C_4)$-alkyl, $(C_3-C_{10})$-cycloalkyl, OH, $NH(C_1-C_4)$-alkyl, $N((C_1-C_4)$-alkyl$)_2$, $(C_1-C_{10})$-alkoxy and —C(O)O—$(C_1-C_4)$-alkyl, H, OH, (=O), F, Cl, Br, CN, $NO_2$, —NR17R18, —NR16COR17,

—NR16COOR17, —NR16CONR17R18, —NR16—S$(O)_2$—R17,

—NR16—S$(O)_2$—NR17R18, —COOR16, —COR16; —CO(NR17R18), S$(O)_n$R16, with n=1 or 2 and —S$(O)_2$NR17R18, where R16, R17 and R18 may be independently of one another a hydrogen radical or a radical selected from the group of unsubstituted or substituted $(C_1-C_4)$-alkyl radicals, where the substituents of the alkyl radicals are selected from F, OH, (=O), $NH_2$, $NH(C_1-C_4)$alkyl, $N((C_1-C_4)$alkyl$)_2$, CN and $(C_1-C_{10})$-alkoxy, R17 and R18 may form together with the nitrogen to which they are bonded a 5-6 membered, saturated, unsaturated or partly unsaturated heterocycle having 1 to 5 carbon atoms, which may additionally comprise one or more heteroatoms from the list —O—, —S$(O)_n$— with n=0, 1 or 2, =N—, —NH— and $N((C_1-C_4)$alkyl)-, where the formed heterocycle independently of one another may be substituted one or more times by $(C_1-C_{10})$-alkyl, $(C_3-C_{14})$-cycloalkyl, $(C_4-C_{20})$-cycloalkylalkyl, $(C_2-C_{20})$-cycloheteroalkyl or $(C_3-C_{19})$-cycloheteroalkylalkyl, each of which may in turn carry independently of one another one or more radicals F, OH, (=O), $NH_2$, $NH(C_1-C_4)$alkyl, $N((C_1-C_4)$alkyl$)_2$, CN or $(C_1-C_{10})$-alkoxy;

R1 is absent or is one, two or three radicals which are selected independently of one another from the group of F, Cl, Br, I, $(C_1-C_6)$-alkyl and $(C_1-C_6)$-alkoxy, where the alkyl and alkoxy radical may be substituted one or more times by F;

R3 and R4 are independently of one another a radical selected from the group of, $(C_1-C_4)$-alkyl, $(C_3-C_7)$-cycloalkyl-, $(C_3-C_7)$-cycloalkyl-$(C_1-C_4)$-alkyl-, $(C_3-C_6)$-cycloheteroalkyl-, phenyl-, phenyl-$(C_1-C_4)$-alkyl-and $(C_1-C_5)$-heteroaryl, where the radicals R3 and R4 may be substituted independently of one another one, two or three times by a radical from the group of OH, (=O), F, Cl, Br, CN, $NO_2$, —NR13R14, —NR13COR12, —NR13COOR12, —NR12CONR13R14, —NR13—S$(O)_2$—R12, —NR13—S$(O)_2$—NR13R14, —COOR12, —COR12; —CO(NR13R14), —S$(O)_n$R12 and —S$(O)_2$NR13R14, where R12, R13 and R14 are independently of one another H or $(C_1-C_4)$-alkyl, or R3 and R4 form together with the nitrogen to which they are bonded a 4-8 membered, saturated, unsaturated or partly unsaturated heterocycle which may additionally comprise one or more heteroatoms from the list —O—, —S$(O)_n$—, with n=0, 1or 2, =N— and —NR8, where the heterocyclic radicals may be substituted independently of one another one or more times by a radical selected from the group of radicals R7 and R9, where the heterocyclic radicals may be bridged by a bond, ($C_1$-$C_7$)-alkyl, ($C_1$-$C_6$)-saturated or unsaturated heteroalkyl chains or by —NH— or —N($C_1$-$C_4$)-alkyl-, and where the alkyl and heteroalkyl chains may also form a spirocyclic ring system with the ring system formed by R3 and R4, and where R8 in the group NR8 may form with the ring which the radicals R3 and R4 may form a further saturated, unsaturated or partly unsaturated heterocycle which may additionally comprise one or two heteroatoms from the list —O—, —S(O)$_n$—, with n=0, 1 or 2, =N— and —NR19-, with R19 equal to H or ($C_1$-$C_4$)-alkyl;

where the radicals R7, R8 and R9 have the meaning stated in claim 1, and the pharmaceutically acceptable salts thereof.

5. A compound as claimed in claim 1 or 2 where

B is a phenyl group, a naphthyl group, a pyridinyl group, a quinolinyl group, an isoquinolinyl group, an indolyl group, a benzothiophenyl group, a benzodihydrothiophenyl group, a benzofuranyl group, a benzodihydrofuranyl group, an isobenzodihydrofuranyl group, a benzopyrrolidinyl group, a benzoimidazolyl group, a benzopyrazolyl group, a benzotriazolyl group, a benzothiazolyl group, a benzoxathiolyl group, an indolinyl group, benzodioxolyl group, a tetrahydroisoquinolinyl group, and a tetrahydroquinolinyl group, where one, two, three or four hydrogen atoms in group B may be replaced by radicals from the group R5, where one of the R5 radicals is selected from the group of ($C_2$-$C_5$)-cycloheteroalkyl, where the cycloheteroalkyl ring may be saturated or partly unsaturated and may comprise 1 or 2 nitrogen atoms, 1 oxygen atoms, 1 nitrogen and 1 sulfur atom or 1 nitrogen and 1 oxygen atom, and where the cycloheteroalkyl ring may carry further substituents from the group of —F, —Cl, —Br, =O, —NH$_2$—, —CN, ($C_1$-$C_4$)-alkyl and ($C_3$-$C_{10}$)-cycloalkyl, ($C_1$-$C_6$)-heteroaryl, where the heteroaryl ring may be a monocyclic or fused bicyclic ring which may comprise 1, 2, 3 or 4 nitrogen atoms, 1 oxygen atom, 1 sulfur atom, 1 or 2 nitrogen atoms and 1 oxygen or sulfur atom, and where the heteroaryl ring may carry further substituents from the group of —F, —Cl, —Br, =O, —NH$_2$, —CN, ($C_1$-$C_4$)-alkyl, ($C_3$-$C_{10}$)-cycloalky and —C(O)O-($C_1$-$C_4$)-alkyl,

OH, (=O), NH$_2$, NO$_2$, —NR17R18, —NR16COR17, —NR16COOR17,

—NR16CONR17R18, —NR16—S(O)$_2$—R17, —NR16—S(O)$_2$—NR17R18,

—COOR16, —COR16; —CO(NR17R18), S(O)$_2$R16 and —S(O)$_2$NR17R18, where

R16, R17 and R18 may be independently of one another a hydrogen radical or a radical selected from the group of unsubstituted or substituted ($C_1$-$C_4$)-alkyl radicals, where the substituents of the alkyl radicals are selected from F, OH, (=O), NH$_2$, NH($C_1$-$C_4$)alkyl, N(($C_1$-$C_4$) alkyl)$_2$, CN and ($C_1$-$C_{10}$)-alkoxy R17 and R18 may form together with the nitrogen to which they are bonded a 5-6 membered, saturated, unsaturated or partly unsaturated heterocycle having 1 to 5 carbon atoms which may additionally comprise one or more heteroatoms from the list —O—, —S(O)$_n$—, with n=0, 1 or 2, =N—, —NH— and —N(($C_1$-$C_4$)-alkyl)-, where the formed heterocycle independently of one another may be substituted one or more times by ($C_1$-$C_{10}$)-alkyl, ($C_3$-$C_{14}$) -cycloalkyl, ($C_4$-$C_{20}$) -cycloalkylalkyl, ($C_2$-$C_{20}$)-cycloheteroalkyl or ($C_3$-$C_{19}$) -cycloheteroalkylalkyl, each of which in turn may carry independently of one another one or more radicals F, OH, (=O), NH$_2$, NH($C_1$-$C_4$)alkyl, N(($C_1$-$C_4$)alkyl)$_2$, CN or ($C_1$-$C_{10}$)-alkoxy, and further radicals R5 are selected independently of one another from the group of ($C_1$-$C_4$)-alkyl which may be wholly or partly fluorinated, or a hydrogen may be replaced by a CN, NH$_2$, OH, NH($C_1$-$C_4$)alkyl, N(($C_1$-$C_4$)alkyl)$_2$or ($C_1$-$C_4$)-alkoxy, ($C_1$-$C_4$)-alkoxy which may be wholly or partly fluorinated, ($C_1$-$C_4$)-alkylthio which may be wholly or partly fluorinated, phenyl, OH, (=O), F, Cl, Br, CN, —NR17R18, NR16COR17, —COOR16, —COR16 and CO(NR17R18), where R16, R17 and R18 may be independently of one another a hydrogen radical or a radical selected from the group of unsubstituted or substituted ($C_1$-$C_4$)-alkyl radicals, where the substituents of the alkyl radicals are selected from F, OH, (=O), NH$_2$, NH($C_1$-$C_4$)alkyl, N(($C_1$-$C_4$) alkyl)$_2$, CN and ($C_1$-$C_{10}$)-alkoxy-, or R17 and R18 may form together with the nitrogen to which they are bonded a 4-7 membered, saturated, unsaturated or partly unsaturated heterocycle having 1 to 5 carbon atoms, which may additionally comprise one or more heteroatoms from the list —O—, —S(O)$_n$—, with n=0, 1 or 2, =N—, —NH— and N(($C_1$-$C_4$)alkyl)-, where the formed heterocycle independently of one another may be substituted one or more times by ($C_1$-$C_{10}$)-alkyl, ($C_3$-$C_{14}$)-cycloalkyl, ($C_4$-$C_{20}$)-cycloalkylalkyl, ($C_2$-$C_{20}$)-cycloheteroalkyl or ($C_3$-$C_{19}$)-cycloheteroalkylalkyl, each of which in turn may carry independently of one another one or more radicals F, OH, (=O), NH$_2$, NH($C_1$-$C_4$)alkyl, N(($C_1$-$C_4$)alkyl)$_2$, CN or ($C_1$-$C_{10}$)-alkoxy;

R1 is absent or is one, two or three radicals which are selected independently of one another from the group of F, Cl, Br, I, ($C_1$-$C_6$)-alkyl and ($C_1$-$C_6$)-alkoxy, where the alkyl and alkoxy radical may be substituted one or more times by F;

R3 and R4 are independently of one another a radical selected from the group of ($C_1$-$C_5$)-alkyl-, phenyl-($C_1$-$C_4$)-alkyl-, NH$_2$-($C_1$-$C_4$)-alkyl-, N(($C_1$-$C_4$)-alkyl)$_2$-($C_1$-$C_4$)-alkyl-, ($C_1$-$C_4$)-alkoxy-($C_1$-$C_4$)-alkyl-, ($C_3$-$C_7$)-cycloalkyl-($C_1$-$C_4$)-alkyl- and ($C_4$-$C_6$)-cycloheteroalkyl-that comprises an —NH-, —O— or —S— group, or R3 and R4 form together with the nitrogen to which they are bonded a 4-8 membered, saturated, unsaturated or partly unsaturated heterocycle which may additionally comprise one or more heteroatoms from the list —O—, —S(O)$_n$—, with n=0, 1 or 2, =N— and —NR8-, where the heterocyclic radicals may be substituted independently of one another one or more times by radicals selected from the group of radicals R7 and R9, where the heterocyclic radicals may be bridged by a bond, ($C_1$-$C_7$)-alkyl, ($C_1$-$C_6$)-saturated or unsaturated heteroalkyl chains or by —NH-, N(($C_1$-$C_4$)alkyl)-, and where the alkyl and heteroalkyl chains may also form a spirocyclic ring system with the ring system formed by R3 and R4, and where R8 may form with the ring which the radicals R3 and R4 form a further saturated, unsaturated or partly unsaturated heterocycle which may additionally comprise one or two heteroatoms from the list —O—, —S(O)$_n$—, with n=0, 1 or 2, —NH— and —N(($C_1$-$C_4$)alkyl)-;

R7 is H, a ($C_1$-$C_5$)-alkyl radical or ($C_3$-$C_6$)-cycloalkyl radical, where the alkyl radical may be substituted independently of one another one or more times by R9;

R8 is H, a ($C_1$-$C_5$)-alkyl radical or ($C_1$-$C_6$)-cycloalkyl radical, where the alkyl radical may be substituted independently of one another one or more times by F, OH, NH$_2$, CN, NO$_2$, ($C_1$-$C_{10}$)-alkoxy, ($C_1$-$C_{10}$)-alkylthio, —NR13R14, —NR13COR12, —NR13COOR12, —NR13CONR13R14, —NR13—S(O)$_2$—R12, —NR12—S(O)$_2$—NR13R14, —COOR12, —COR12; —CO(NR13R14), S(O)$_n$R12, —S(O)$_2$NR13R14, COR12, —CO(NR13R14), S(O)$_n$R12or —S(O)$_2$NR13R14;

R9 is a radical selected from the group of OH, NH$_2$, (=O), F, Cl, Br, I, CN, —NR13R14, —NR13COR12, —NR13COOR12, —NR12CONR13R14, —NR13—S(O)$_2$—R12, —NR13—S(O)$_2$NR13R14, —COOR12, —COR12; —CO(NR13R14), S(O)$_n$R12, —S(O)$_2$NR13R14, ($C_3$-$C_6$)-cycloalkyl, ($C_4$-$C_7$)-cycloalkylalkyl, ($C_1$-$C_5$)-alkoxy, ($C_2$-$C_6$)-cycloheteroalkyl, ($C_3$-$C_{10}$)-cycloheteroalkylalkyl, phenyl or ($C_1$-$C_5$)-heteroaryl radicals, where R12, R13 and R14 are independently of one another a hydrogen radical or a radical selected from the group of unsubstituted or substituted (C1-C4)-alkyl radicals, where the substituents of the alkyl radicals are selected from F, OH, (=O), NH$_2$, NH($C_1$-$C_4$)alkyl, N(($C_1$-$C_4$)alkyl)$_2$, CN and ($C_1$-$C_{10}$)-alkoxy;

and the pharmaceutically acceptable salts thereof.

6. A compound as claimed in claim 1 or 2 where R3 and R4 form together with the nitrogen to which they are bonded a 4-10membered, saturated, unsaturated or partly unsaturated heterocycle which may additionally comprise one or more heteroatoms from the list —O—, —S(O)$_n$—, =N— and —NR8-, where the heterocyclic radicals may be substituted independently of one another one or more times by radicals selected from the group of R7 and R9, and where the heterocyclic radicals formed by R3 and R4 may be bridged by a bond, by a saturated or unsaturated ($C_1$-$C_{10}$)-alkyl or ($C_1$-$C_9$)-heteroalkyl chain or by —NR15-, —O— or —S—, and where the alkyl and heteroalkyl chains may also form a spirocyclic ring system with the ring system formed by R3 and R4, where the alkyl and heteroalkyl bridges may be substituted independently of one another one or more times by radicals selected from the group of R7 and R9, and where R8 in the group —NR8- may form with the ring which R3 and R4 may form a further saturated, unsaturated or partly unsaturated heterocycle which may be substituted independently of one another one or more times by radicals selected from the group of R7 and R9, and may additionally comprise one or more heteroatoms from the list —O—, —S(O)$_n$—, —N=and —NR19-;

where n, R7, R8, R9 and R19 have the meaning indicated in claim 1, and the pharmaceutically acceptable salts thereof.

7. A compound as claimed in claim 1 or 2 where R3 and R4 form together with the nitrogen to which they are bonded a 4-8 membered, saturated, unsaturated or partly unsaturated heterocycle which may additionally comprise one or more heteroatoms from the list —O—, —S(O)$_n$—, with n=0, 1 or 2, =N-and —NR8—, where the heterocyclic radicals may be substituted independently of one another one or more times by radicals selected from the group of radicals R7 and R9, and where R8 may form with the ring which the radicals R3 and R4 form may form together with an adjacent C atom a fused triazole or pyrrolidine ring;

where R7, R8 and R9 have the meaning indicated in claim 1, and the pharmaceutically acceptable salts thereof.

8. A compound as claimed in claim 1, where

R3 and R4 are independently of one another a radical which is selected from the group of ($C_1$-$C_{10}$)-alkyl radicals, of ($C_2$-$C_{10}$)-alkenyl radicals, of ($C_2$-$C_{10}$)-alkynyl radicals, of ($C_3$-$C_{14}$)-cycloalkyl radicals, of ($C_4$-$C_{20}$)-cycloalkylalkyl radicals, of ($C_2$-$C_{19}$)-cycloheteroalkyl radicals, of ($C_3$-$C_{19}$)-cycloheteroalkylalkyl radicals, of ($C_6$-$C_{10}$)-aryl radicals, of ($C_7$-$C_{20}$)-arylalkyl radicals, of ($C_1$-$C_9$)-heteroaryl radicals and of ($C_2$-$C_{19}$)-heteroarylalkyl radicals, where the radicals R3 and R4 may be substituted independently of one another one or more times by a radical from the group of OH, NH$_2$, (=O), F, Cl, Br, I, CN, NO$_2$, —NR13R14, —NR13COR12, —NR13COOR12, —NR12CONR13R14, —NR13—S(O)$_2$—R12, —NR13—S(O)$_2$NR13R14, —COOR12, —COR12; —CO(NR13R14), S(O)$_n$R12and —S(O)$_2$R13R14;

where R12, R13 and R14 have the meaning indicated in claim 1, and the pharmaceutically acceptable salts thereof.

9. A compound according to claim 1 selected from the group consisting of:

(S)-1-[rac-trans-(1,2)-1-(3-dimethylaminomethylphenoxy)indan-2-yl]piperidin-3-ylamine;

{3-chloro-4-[(1S,2S)-4,6-dichloro-2-((R)-3-hydroxypyrrolidin-1-yl)indan-1-yloxy]phenylcarbamoyloxy}acetic acid;

{4-[rac-trans-(1,2)-2-((R)-3-aminopiperidin-1-yl)indan-1-yloxy]phenyl}carbamic acid benzyl ester;

1-[1-(4-methanesulfonylphenoxy)-2-methylindan-2-yl]pyrrolidine;

2-{5-[rac-trans-(1,2)-2-(3-aminomethylpyrrolidin-1-yl)indan-1-yloxy]-1H-indo-3-yl}acetamide;

2-{5-[rac-trans-(1,2)-2-(3-aminopyrrolidin-1-yl)indan-1-yloxy]-1H-indo1-3-yl}acetamide;

2-{5-[rac-trans-(1,2)-2-(4-aminomethylpiperidin-1-yl)indan-1-yloxy]-1H-indol-3-yl}acetamide;

4-[4-(rac-trans-(1,2)-3, 3-dimethyl-2-pyrrolidin-1-ylindan-1-yloxy)phenyl]-3,5-dimethyl-4H -[1,2,4]triazole;

((R)-1-{trans-(1S,2S)-1-[4-(3,5-dimethyl-[1,2,4]triazol-4-yl)phenoxy]indan-2-yl}piperidin-3-yl)-(3,3,3-trifluoropropyl)amine;

2-[rac-trans-(1,2)-1-(2,4-dichloro-3-methylphenoxy)indan-2-yl]octahydropyrrolo[3,4-c]pyrrole;

2-[rac-trans-(1,2)-1-(2-fluoro-6-methoxyphenoxy)indan-2-yl]octahydropyrrolo[3,4-c]pyrrole;

2-[rac-trans-(1,2)-1-(3-chloro-2-methylphenoxy)indan-2-yl]octahydropyrrolo[3,4-c]pyrrole;

2-[rac-trans-(1,2)-1-(4-imidazol-1-ylphenoxy)indan-2-yl]octahydropyrrolo[3,4-c]pyrrole;

2-[rac-trans-(1,2)-1-(2,4-difluorophenoxy)indan-2-yl]octahydropyrrolo[3,4-c]pyrrole;

2-[rac-trans-(1,2)-1-(2-bromo-4-methylphenoxy)indan-2-yl]octahydropyrrolo[3,4-c]pyrrole;

2-[rac-trans-(1,2)-1-(2-bromophenoxy)indan-2-yl]octahydropyrrolo[3,4-c]pyrrole;

2-[rac-trans-(1,2)-1-(2-tert-butyl-4-ethylphenoxy)indan-2-yl]octahydropyrrolo[3,4-c]pyrrole;
2-[rac-trans-(1,2)-1-(3-piperazin-1-ylphenoxy)indan-2-yl]octahydropyrrolo[3,4-c]pyrrole;
2-[rac-trans-(1,2)-1-(3-piperidin-1-ylmethylphenoxy)indan-2-yl]octahydropyrrolo[3,4-c]pyrrole;
2-[rac-trans-(1,2)-1-(3-piperidin-1-ylphenoxy)indan-2-yl]octahydropyrrolo[3,4-c]pyrrole;
2-[rac-trans-(1,2)-1-(4-fluoro-2-methylphenoxy)indan-2-yl]octahydropyrrolo[3,4-c]pyrrole;
2-[rac-trans-(1,2)-1-(4-piperazin-1-ylphenoxy)indan-2-yl]octahydropyrrolo[3,4-c]pyrrole;
2-[rac-trans-(1,2)-1-(6-chloropyridin-3-yloxy)indan-2-yl]octahydropyrrolo[3,4-c]pyrrole;
2-{rac-trans-(1,2)-1-[4-(2-methoxyethyl)phenoxy]indan-2-yl}octahydropyrrolo[3,4-c]pyrrole;
2-{rac-trans-(1,2)-1-[4-bromo-2-(1H-pyrazol-3-yl)phenoxy]indan-2-yl}-octahydropyrrolo[3,4-c]pyrrole;
(4-methylpiperazin-1-yl)-[4-(rac-trans-(1,2)-2-pyrrolidin-1-ylindan-1-yloxy)phenyl]methanone;
(R)-1-(trans-(1R, 2R)-4,6-dichloro-1-phenoxyindan-2-yl)piperidin-3-ylamine;
(R)-1-[(1S,2S)-4,6-dichloro-1-(2-methanesulfonylphenoxy)indan-2-yl]piperidin-3-ylamine;
(R)-1-[(1S,2S)-4,6-dichloro-1-(5-fluoroquinolin-8-yloxy)indan-2-yl]piperidin-3-ylamine;
(R)-1-[rac-trans-(1,2)-1-(1H-indo4-yloxy)indan-2-yl]piperidin-3-ylamine;
(R)-1-[rac-trans-(1,2)-1-(2, 3-dichloro-4-methanesulfonylphenoxy)indan-2-yl]piperidin-3-ylamine;
(R)-1-[rac-trans-(1,2)-1-(2,4-difluorophenoxy)indan-2-yl]piperidin-3-ylamine;
(R)-1-[rac-trans-(1,2)-1-(2-chloro-4-methanesulfonylphenoxy)indan-2-yl]piperidin-3-ylamine;
(R)-1-[rac-trans-(1,2)-1-(2-methylbenzothiazol-5-yloxy)indan-2-yl]piperidin-3-ylamine;
(R)-1-[rac-trans-(1,2)-1-(2-tert-butyl-4-ethylphenoxy)indan-2-yl]piperidin-3-ylamine;
(R)-1-[rac-trans-(1,2)-1-(3-piperidin-1-ylmethylphenoxy)indan-2-yl]piperidin-3-ylamine;
(R)-1-[rac-trans-(1,2)-1-(3-piperidin-1-ylphenoxy)indan-2-yl]piperidin-3-ylamine;
(R)-1-[rac-trans-(1,2)-1-(4-[1,2,4]triazol-1-ylphenoxy)indan-2-yl]piperidin-3-ylamine;
(R)-1-[rac-trans-(1,2)-1-(4-imidazol-1-ylphenoxy)indan-2-yl]piperidin-3-ylamine;
(R)-1-[rac-trans-(1,2)-1-(4-piperazin-1-ylphenoxy)indan-2-yl]piperidin-3-ylamine;
(R)-1-[rac-trans-(1,2)-1-(6-chloropyridin-3-yloxy)indan-2-yl]piperidin-3-ylamine;
(R)-1-[rac-trans-(1,2)-1-(benzo[1,3]dioxo1-5-yloxy)indan-2-yl]piperidin-3-ylamine;
(R)-1-[rac-trans-(1,2)-1-(isoquinolin-7-yloxy)indan-2-yl]piperidin-3-ylamine;
(R)-1-[rac-trans-(1,2)-1-(pyridin-4-yloxy)indan-2-yl]piperidin-3-ylamine;
(R)-1-[rac-trans-(1,2)-1-(quinolin-4-yloxy)indan-2-yl]piperidin-3-ylamine;
(R)-1-[trans-(1R, 2R)-4,6-dichloro-1-(2-fluoro-6-methoxyphenoxy)indan-2-yl]piperidin-3-ylamine;
(R)-1-[trans-(1S,2S)-1-(4-methanesulfonylphenoxy)indan-2-yl]piperidin-3-ylamine;
(R)-1-{rac-trans-(1,2)-1-[4-(2-methoxyethyl)phenoxy]indan-2-yl}piperidin-3-ylamine;
(R)-1-{rac-trans-(1,2)-1-[4-bromo-2-(1H-pyrazol-3-yl)phenoxy]indan-2-yl}piperidin-3-ylamine;
(R)-1-{trans-(1S,2S)-1-[4-(3,5-dimethyl-[1,2,4]triazol-4-yl)phenoxy]indan-2-yl}piperidin-3-ylamine;
(S)-1-[rac-trans-(1,2)-1-(3-chloro-5-methoxyphenoxy)indan-2-yl]piperidin-3-ylamine;
(S)-1-[rac-trans-(1,2)-1-(3-piperazin-1-ylphenoxy)indan-2-yl]piperidin-3-ylamine;
(S)-1-[rac-trans-(1,2)-1-(3-piperidin-1-ylmethylphenoxy)indan-2-yl]piperidin-3-ylamine;
(S)-1-[rac-trans-(1,2)-1-(4-[1,2,4]triazol-1-ylphenoxy)indan-2-yl]piperidin-3-ylamine;
(S)-1-[rac-trans-(1,2)-1-(4-imidazol-1-ylphenoxy)indan-2-yl]piperidin-3-ylamine;
(S)-1-[rac-trans-(1,2)-1-(4-piperazin-1-ylphenoxy)indan-2-yl]piperidin-3-ylamine;
(S)-1-[rac-trans-(1,2)-1-(quinolin-5-yloxy)indan-2-yl]piperidin-3-ylamine;
(S)-1-{rac-trans-(1,2)-1-[4-bromo-2-(1H-pyrazol-3-yl)phenoxy]indan-2-yl}piperidin-3-ylamine;
[3-(rac-trans-(1,2)-2-diethylaminoindan-1-yloxy)phenyl]urea;
[rac-trans-(1,2)-1-(1H-indol-4-yloxy)indan-2-yl]methylpiperidin-3-ylamine;
[rac-trans-(1,2)-1-(2-fluoro-6-methoxyphenoxy)indan-2-yl]methylpiperidin-4-ylamine;
[rac-trans-(1,2)-4,6-dichloro-1-(4-imidazol-1-ylphenoxy)indan-2-yl]-dimethylamine;
[trans-(1S,2S)-4,6-dichloro-1-(4-methanesulfonylphenoxy)indan-2-yl]-(2-methoxyethyl)methylamine;
{(R)-1-[trans-(1S,2S)-1-(4-methanesulfonylphenoxy)indan-2-yl]piperidin-3-yl}-(2,2,2-trifluoroethyl)amine;
{(R)-1-[trans-(1S,2S)-1-(4-methanesulfonylphenoxy)indan-2-yl]piperidin-3-yl}-(3,3,3-trifluoropropyl)amine;
{3-[rac-trans-(1,2)-2-((R)-3-aminopiperidin-1-yl)indan-1-yloxy]phenyl}urea;
{3-[rac-trans-(1,2)-2-((S)-3-aminopiperidin-1-yl)indan-1-yloxy]phenyl}urea;
{3-[rac-trans-(1,2)-2-(3-aminomethylpyrrolidin-1-yl)indan-1-yloxy]phenyl}urea;
{3-[rac-trans-(1,2)-2-(3-aminopyrrolidin-1-yl)indan-1-yloxy]phenyl}urea;
{3-[rac-trans-(1,2)-2-(4-aminomethylpiperidin-1-yl)indan-1-yloxy]phenyl}urea;
{4-[rac-trans-(1,2)-2-(3-aminomethylpyrrolidin-1-yl)indan-1-yloxy]phenyl}carbamic acid benzyl ester;
{4-[rac-trans-(1,2)-2-(3-aminopyrrolidin-1-yl)indan-1-yloxy]phenyl}carbamic acid benzyl ester;
{trans-(1S,2S)-4,6-dichloro-1-[4-(3,5-dimethyl-[1,2,4]triazol-4-yl)phenoxy]indan-2-yl}-(2-methoxyethyl)methylamine;
1-[1-(2-chloro-4-nitrophenoxy)indan-2-yl]pyrrolidine;
1-[3-(rac-trans-(1,2)-2-pyrrolidin-1-ylindan-1-yloxy)phenyl]-1,3-dihydroimidazol-2-one;
1-[3-(rac-trans-(1,2)-2-pyrrolidin-1-ylindan-1-yloxy)phenyl]pyrrolidin-2-one;
1-[3-(rac-trans-(1,2)-2-pyrrolidin-1-ylindan-1-yloxy)phenyl]pyrrolidine-2,5-dione;
1-[rac-cis-(1,2)-1-(4-methanesulfonylphenoxy)indan-2-yl]-1H-imidazole;
1-[rac-trans-(1,2)-1-(1H-indol1-6-yloxy)indan-2-yl]pyrrolidin-3-ylamine;
1-[rac-trans-(1,2)-1-(2, 3-dichloro-4-methanesulfonylphenoxy)indan-2-yl]pyrrolidine,
1-[rac-trans-(1,2)-1-(2, 6-dichloro-4-methanesulfonylphenoxy)indan-2-yl]pyrrolidine;
1-[rac-trans-(1,2)-1-(2-chloro-4-methanesulfonylphenoxy)indan-2-yl]pyrrolidine;

1-[rac-trans-(1,2)-1-(2-fluoro-6-methoxyphenoxy)indan-2-yl]pyrrolidin-3-ylamine;
1-[rac-trans-(1,2)-1-(2-tert-butyl-4-ethylphenoxy)indan-2-yl]pyrrolidin-3-ylamine;
1-[rac-trans-(1,2)-1-(3-chloro-4-methanesulfonylphenoxy)indan-2-yl]pyrrolidine;
1-[rac-trans-(1,2)-1-(3-methanesulfonylphenoxy)indan-2-yl]pyrrolidine;
1-[rac-trans-(1,2)-1-(3-piperazin-1-ylphenoxy)indan-2-yl]pyrrolidin-3-ylamine;
1-[rac-trans-(1,2)-1-(4-methanesulfonyl-3-methylphenoxy)indan-2-yl]pynolidine;
1-[rac-trans-(1,2)-1-(4-methanesulfonylphenoxy)indan-2-yl]piperazine;
1-[rac-trans-(1,2)-1-(4-methanesulfonylphenoxy)indan-2-yl]pyrrolidine;
1-[rac-trans-(1,2)-1-(quinolin-4-yloxy)indan-2-yl]pyrrolidin-3-ylamine;
1-{rac-trans-(1,2)-1-[4(2-methoxyethy)phenoxy]indan-2-yl}pyrrolidin-3-ylamine;
1-{rac-trans-(1,2)-1-[4-bromo-2-(1H-pyrazol-3-yl)phenoxy]indan-2-yl}piperidin-4-ylamine;
1-methyl-3-[3-(rac-trans-(1,2)-2-pyrrolidin-1-ylindan-1-yloxy)phenyl]-1,3-dihydroimidazol-2-one;
2,2,2-trifluoro-N-{(R)-1-[trans-(1S,2S)-1-(4-methanesulfonylphenoxy)indan-2-yl]piperidin-3-yl}acetamide;
2,3-dichloro-4-(rac-trans-(1,2)-2-diethylaminoindan-1-yloxy)benzenesulfonamide;
2,3-dichloro-4-(rac-trans-(1,2)-2-dimethylaminoindan-1-yloxy)benzenesulfonamide;
2,3-dichloro-4-(rac-trans-(1,2)-2-pyrrolidin-1-ylindan-1-yloxy)benzenesulfonamide;
2,3-dichloro-4-[rac-trans-(1,2)-2-((R)-3-methoxypyrrolidin-1-yl)indan-1-yloxy]benzenesulfonamide;
2,3-dichloro-4-[rac-trans-(1,2)-2-(methylpiperidin-3-ylamino)indan-1-yloxy]benzenesulfonamide;
2,3-dichloro-4-[trans-(1S,2S)-2-(3-hydroxypiperidin-1-yl)indan-1-yloxy]benzenesulfonamide;
2,3-dichloro-N,N-dimethyl-4-(rac-trans-(1,2)-2-pyrrolidin-1-ylindan-1-yloxy)benzenesulfonamide;
2-[3-(rac-trans-(1,2)-2-pyrrolidin-1-ylindan-1-yloxy)phenyl]isothiazolidine 1,1-dioxide;
2-[4-(rac-trans-(1,2)-2-pyrrolidin-1-ylindan-1-yloxy)phenyl]thiazole;
2-[rac-trans-(1,2)-2-(3-aminomethylpyrrolidin-1-yl)indan-1-yloxy]-6-fluorobenzonitrile;
2-[rac-trans-(1,2)-2-(3-aminopyrrolidin-1-yl)indan-1-yloxy]-5-chlorobenzonitrile;
2-[rac-trans-(1,2)-2-(4-aminomethylpiperidin-1-yl)indan-1-yloxy]-5-chlorobenzonitrile;
2-{4-[rac-trans-(1,2)-2-((R)-3-aminopiperidin-1-yl)indan-1-yloxy]phenyl}-thiazole-4-carbonitrile;
2-chloro-4-(rac-trans-(1,2)-2-pyrrolidin-1-ylindan-1-yloxy)benzonitrile;
2-chloro-4-[rac-trans-(1,2)-2-(hexahydropyrrolo[3,4-c]pyrrol-2-yl)indan-1-yloxy]benzonitrile;
2-fluoro-4-[rac-trans-(1,2)-2-(hexahydropyrrolo[3,4-c]pyrrol-2-yl)indan-1-yloxy]benzonitrile;
2-fluoro-6-[rac-trans-(1,2)-2-(hexahydropyrrolo[3,4-c]pyrrol-2-yl)indan-1-yloxy]benzonitrile;
3-(rac-trans-(1,2)-2-pyrrolidin-1-ylindan-1-yloxy)phenylamine;
3,5-dichloro-4-(rac-trans-(1,2)-2-pyrrolidin-1-ylindan-1-yloxy)benzenesulfonamide;
3,5-dichloro-N,N-dimethyl-4-(rac-trans-(1,2)-2-pyrrolidin-1-ylindan-1-yloxy)benzenesulfonamide;
3,5-dimethyl-4-[3-(rac-trans-(1,2)-2-pyrrolidin-1-ylindan-1-yloxy)phenyl]-4H-[1,2,4]triazole;
3,5-dimethyl-4-[4-(rac-trans-(1,2)-2-pyrrolidin-1-ylindan-1-yloxy)phenyl]-4H-[1,2,4]triazole;
3,5-dimethyl-4-[4-(trans-(1S,2S)-2-pyrrolidin-1-ylindan-1-yloxy)-3-trifluoromethylphenyl]-4H-[1,2,4]triazole;
3,5-dimethyl-4-[4-(trans-(1S,2S)-2-pyrrolidin-1-ylindan-1-yloxy)phenyl]-isoxazole;
3,5-dimethyl-4-[5-methyl-2-(trans-(1S,2S)-2-pyrrolidin-1-ylindan-1-yloxy)phenyl]isoxazole;
3-[3-(rac-trans-(1,2)-2-pyrrolidin-1-ylindan-1-yloxy)phenyl]oxazolidin-2-one;
3-[rac-trans-(1,2)-2-(hexahydropyrrolo[3,4-c]pyrrol-2-ylindan-1-yloxy]benzamide;
3-[rac-trans-(1,2)-2-((R)-3-aminopiperidin-1-yl)indan-1-yloxy]benzamide;
3-[rac-trans-(1,2)-2-((S)-3-aminopiperidin-1-yl)indan-1-yloxy]benzamide;
3-[rac-trans-(1,2)-2-(3-aminomethylpyrrolidin-1-yl)indan-1-yloxy]benzamide;
3-[rac-trans-(1,2)-2-(3-aminopyrrolidin-1-yl)indan-1-yloxy]benzamide;
3-chloro-4-(2-pyrrolidin-1-ylindan-1-yloxy)pyridine;
3-chloro-4-(rac-trans-(1,2)-2-pyrrolidin-1-ylindan-1-yloxy)benzenesulfonamide;
3-chloro-4-[rac-trans-(1,2)-2-(hexahydropyrrolo[3,4-c]pyrrol-2-yl)indan-1-yloxy]benzonitrile;
3-chloro-N,N-dimethyl-4-(rac-trans-(1,2)-2-pyrrolidin-1-ylindan-1-yloxy)benzenesulfonamide;
3-cyclopropyl-5-methyl-4-[4-(rac-trans-(1,2)-2-pyrrolidin-1-ylindan-1-yloxy)phenyl]-4H-[1,2,4]triazole;
3-fluoro-4-(2-pyrrolidin-1-ylindan-1-yloxy)benzenesulfonamide;
3-methyl-4-[4-(rac-trans-(1,2)-2-pyrrolidin-1-ylindan-1-yloxy)phenyl]-4H-[1,2,4]triazole;
4-((1S,2S)-2-azetidin-1-yl-4,6-dichloroindan-1-yloxy)-3-fluorobenzonitrile;
4-((1S,2S)-4,6-dichloro-2-piperazin-1-ylindan-1-yloxy)-3-fluorobenzonitrile;
4-(2-benzylaminoindan-1-yloxy)-3-fluorobenzenesulfonamide;
4-(2-cyclopentylaminoindan-1-yloxy)-3-fluorobenzenesulfonamide;
4-(rac-trans-(1,2)-(R)-2-[1,3']bipyrrolidinyl-1'-ylindan-1-yloxy)benzenesulfonamide;
4-(rac-trans-(1,2)-2-azepan-1-ylindan-1-yloxy)benzenesulfonamide;
4-(rac-trans-(1,2)-2-piperidin-1-ylindan-1-yloxy)benzenesulfonamide;
4-(rac-trans-(1,2)-2-pyrrolidin-1-ylindan-1-yloxy)benzenesulfonamide;
4-(rac-trans-(1,2)-2-pyrrolidin-1-ylindan-1-yloxy)benzoic acid methyl ester;
4-(rac-trans-(1,2)-2-pyrrolidin-1-ylindan-1-yloxy)benzonitrile;
4-(rac-trans-(1,2)-2-pyrrolidin-1-ylindan-1-yloxy)-N-(2,2,2-trifluoroethy)benzenesulfonamide;
4-(rac-trans-(1,2)-2-pyrrolidin-1-ylindan-1-yloxy)-N-(3,3,3-trifluoropropyl)benzenesulfonamide;
4-(trans-(1S,2S)-4,6-dichloro-2-piperazin-1-ylindan-1-yloxy)-3-fluorobenzonitrile;
4-[(1R, 2S)-1-(2-chloro-4-nitrophenoxy)indan-2-yl]morpholine;
4-[(1S,2S)-2-((R)-3-aminopiperidin-1-yl)-4,6-dichloroindan-1-yloxy]-3-fluorobenzonitrile;
4-[(1S,2S)-4,6-dichloro-2-(4-methylpiperazin-1-yl)indan-1-yloxy]-3-fluorobenzonitrile;

4-[2, 3-dimethyl-4-(rac-trans-(1,2)-2-pyrrolidin-1-ylindan-1-yloxy)phenyl]-3,5-dimethyl-4H-[1,2,4]triazole;
4-[2-fluoro-5-(trans-(1S,2S)-2-pyrrolidin-1-ylindan-1-yloxy)phenyl]-3,5-dimethylisoxazole;
4-[3-chloro-4-(rac-trans-(1,2)-2-pyrrolidin-1-ylindan-1-yloxy)phenyl]-3,5-dimethyl-4H-[1,2,4]triazole;
4-[3-chloro-4-(trans-(1S,2S)-2-pyrrolidin-1-ylindan-1-yloxy)phenyl]-3,5-dimethyl-4H-[1,2,4]triazole;
4-[3-fluoro-4-(-2-methyl-2-pyrrolidin-1-ylindan-1-yloxy)phenyl]-3,5-dimethyl-4H-[1,2,4]triazole;
4-[5-fluoro-2-(trans-(1S,2S)-2-pyrrolidin-1-ylindan-1-yloxy)phenyl]-3,5-dimethylisoxazole;
4-[rac-trans-(1,2)-2-(hexahydropyrrolo[3,4-c]pyrrol-2-yl)indan-1-yloxy]-1H-indole;
4-[rac-trans-(1,2)-2-(hexahydropyrrolo[3,4-c]pyrrol-2-yl)indan-1-yloxy]-2,6-dimethylbenzonitrile;
4-[rac-trans-(1,2)-2-((R)-3-aminopiperidin-1-yl)indan-1-yloxy]-2,3-dichlorobenzenesulfonamide;
4-[rac-trans-(1,2)-2-((R)-3-aminopiperidin-1-yl)indan-1-yloxy]-2,3-dichloro-N,N-dimethylbenzenesulfonamide;
4-[rac-trans-(1,2)-2-((R)-3-aminopiperidin-1-yl)indan-1-yloxy]-2-chlorobenzonitrile;
4-[rac-trans-(1,2)-2-((R)-3-aminopiperidin-1-yl)indan-1-yloxy]-2-fluorobenzonitrile;
4-[rac-trans-(1,2)-2-((R)-3-aminopiperidin-1-yl)indan-1-yloxy]-3-chlorobenzonitrile;
4-[rac-trans-(1,2)-2-((R)-3-aminopiperidin-1-yl)indan-1-yloxy]benzamide;
4-[rac-trans-(1,2)-2-((R)-3-hydroxymethylpyrrolidin-1-yl)indan-1-yloxy]benzenesulfonamide;
4-[rac-trans-(1,2)-2-((R)-3-hydroxypyrrolidin-1-yl)indan-1-yloxy]benzenesulfonamide;
4-[rac-trans-(1,2)-2-((S)-3-aminopiperidin-1-yl)indan-1-yloxy]-2,3-dichlorobenzenesulfonamide;
4-[rac-trans-(1,2)-2-((S)-3-aminopiperidin-1-yl)indan-1-yloxy]benzamide;
4-[rac-trans-(1,2)-2-(3-aminomethylpyrrolidin-1-yl)indan-1-yloxy]-2,3-dichlorobenzenesulfonamide;
4-[rac-trans-(1,2)-2-(3-aminomethylpyrrolidin-1-yl)indan-1-yloxy]-2,6-dimethylbenzonitrile;
4-[rac-trans-(1,2)-2-(3-aminomethylpyrrolidin-1-yl)indan-1-yloxy]-2-chlorobenzonitrile;
4-[rac-trans-(1,2)-2-(3-aminomethylpyrrolidin-1-yl)indan-1-yloxy]-3-chlorobenzonitrile;
4-[rac-trans-(1,2)-2-(3-aminopyrrolidin-1-yl)indan-1-yloxy]-2,3-dichlorobenzenesulfonamide;
4-[rac-trans-(1,2)-2-(3-aminopyrrolidin-1-yl)indan-1-yloxy]-3-chlorobenzonitrile;
4-[rac-trans-(1,2)-2-(3-aminopyrrolidin-1-yl)indan-1-yloxy]benzamide;
4-[rac-trans-(1,2)-2-(4-aminomethylpiperidin-1-yl)indan-1-yloxy]-2,3-dichlorobenzenesulfonamide;
4-[rac-trans-(1,2)-2-(4-aminomethylpiperidin-1-yl)indan-1-yloxy]-2-chlorobenzonitrile;
4-[rac-trans-(1,2)-2-(4-aminomethylpiperidin-1-yl)indan-1-yloxy]-3-chlorobenzonitrile;
4-[rac-trans-(1,2)-2-(4-aminomethylpiperidin-1-yl)indan-1-yloxy]benzamide;
4-[trans-(1S,2S)-2-((R)-3-aminopiperidin-1-yl)-4,6-dichloroindan-1-yloxy]-3-fluorobenzonitrile;
4-[trans-(1S,2S)-2-((R)-3-aminopiperidin-1-yl)indan-1-yloxy]benzenesulfonamide;
4-[trans-(1S,2S)-4,6-dichloro-2-((R)-3-hydroxypyrrolidin-1-yl)indan-1-yloxy]-3-fluorobenzonitrile;
4-[trans-(1S,2S)-4,6-dichloro-2-((S)-3-hydroxypyrrolidin-1-yl)indan-1-yloxy]-3-fluorobenzonitrile;
4-[trans-(1S,2S)-4,6-dichloro-2-(4-methyl-[1,4]diazepan-1-yl)indan-1-yloxy]-3-fluorobenzonitrile;
4-[trans-(1S,2S)-6-chloro-4-fluoro-2-((R)-3-hydroxypyrrolidin-1-yl)indan-1-yloxy]-3-fluorobenzonitrile;
5-(rac-trans-(1,2)-2-diethylaminoindan-1-yloxy)-1,3-dimethyl-1,3-dihydro-indol-2-one;
5-(rac-trans-(1,2)-2-pyrrolidin-1-ylindan-1-yloxy)-3H-isobenzofuran-1-one;
5-[5-fluoro-2-(trans-(1S,2S)-2-pyrrolidin-1-ylindan-1-yloxy)phenyl]-1H-pyrazole;
5-[rac-trans-(1,2)-2-(hexahydropynolo[3,4-c]pyrrol-2-yl)indan-1-yloxy]-2-methylbenzothiazole;
5-[rac-trans-(1,2)-2-(hexahydropyrrolo[3,4-c]pyrrol-2-yl)indan-1-yloxy]benzo[1,3]oxathiol-2-one;
5-[rac-trans-(1,2)-2-((R)-3-aminopiperidin-1-yl)indan-1-yloxy]benzo[1,3]oxathiol-2-one;
6[rac-trans-(1,2)-2-(hexahydropyrrolo[3,4-c]pyrrol-2-ylindan-1-yloxy)-1H-indole;
7-[rac-trans-(1,2)-2-(hexahydropyrrolo[3,4-c]pyrrol-2-yl)indan-1-yloxy]-isoquinoline;
7-[rac-trans-(1,2)-1-(4-methanesulfonylphenoxy)indan-2-yl]-5,6,7,8-tetrahydro-[1,2,4]triazolo[4,3-a]pyrazine;
8-((1S,2S)-2-azetidin-1-yl-4,6-dichloroindan-1-yloxy)-5-fluoroquinoline;
8-((1S,2S)-4,6-dichloro-2-piperazin-1-ylindan-1-yloxy)-5-fluoroquinoline;
8-((1S,2S)-4,6-dichloro-2-pyrrolidin-1-ylindan-1-yloxy)-5-fluoroquinoline;
8-(rac-trans-(1,2)-2-pyrrolidin-1-ylindan-1-yloxy)quinoline;
benzyl[1-(4-methanesulfonylphenoxy)indan-2-yl]amine;
C-(1-{rac-trans-(1,2)-1-[4-(2-methoxyethyl)phenoxy]indan-2-yl}pyrrolidin-3-yl)-methylamine;
C-(1-{rac-trans-(1,2)-1-[4-bromo-2-(1H-pyrazol-3-yl)phenoxy]indan-2-yl}piperidin-4-yl)methylamine;
C-(1-{rac-trans-(1,2)-1-[4-bromo-2-(1H-pyrazol-3-yl)phenoxy]indan-2-yl}pyrrolidin-3-ylmethylamine;
C-{1-[rac-trans-(1,2)-1-(1H-indol-4-yloxy)indan-2-yl]pyrrolidin-3-yl}methylamine;
C-{1-[rac-trans-(1,2)-1-(2,4-difluorophenoxy)indan-2-yl]pyrrolidin-3-yl}methylamine;
C-{1-[rac-trans-(1,2)-1-(2-bromo-4-methylphenoxy)indan-2-yl]piperidin-4-yl}methylamine;
C-{1-[rac-trans-(1,2)-1-(2-fluoro-6-methoxyphenoxy)indan-2-yl]piperidin-4-yl}methylamine;
C-{1-[rac-trans-(1,2)-1-(2-fluoro-6-methoxyphenoxy)indan-2-yl]pyrrolidin-3-yl}methylamine;
C-{1-[rac-trans-(1,2)-1-(2-methoxy-5-methylphenoxy)indan-2-yl]piperidin-4-yl}methylamine;
C-{1-[rac-trans-(1,2)-1-(2-methoxy-5-methylphenoxy)indan-2-yl]pyrrolidin-3-yl}methylamine;
C-{1-[rac-trans-(1,2)-1-(2-methylbenzothiazol-5-yloxy)indan-2-yl]pyrrolidin-3-yl}methylamine;
C-{1-[rac-trans-(1,2)-1-(2-tert-butyl-4-ethylphenoxy)indan-2-yl]piperidin-4-yl}methylamine;
C-{1-[rac-trans-(1,2)-1-(2-tert-butyl-4-ethylphenoxy)indan-2-yl]pyrrolidin-3-yl}methylamine;
C-{1-[rac-trans-(1,2)-1-(3-chloro-2-methylphenoxy)indan-2-yl]pyrrolidin-3-yl}methylamine;
C-{1-[rac-trans-(1,2)-1-(3-chloro-5-methoxyphenoxy)indan-2-yl]piperidin-4-yl}methylamine;
C-{1-[rac-trans-(1,2)-1-(3-chloro-5-methoxyphenoxy)indan-2-yl]pyrrolidin-3-yl}methylamine;
C-{1-[rac-trans-(1,2)-1-(3-ethoxyphenoxy)indan-2-yl]piperidin-4-yl}methylamine;
C-{1-[rac-trans-(1,2)-1-(3-ethoxyphenoxy)indan-2-yl]pyrrolidin-3-yl}methylamine;

C-{1-[rac-trans-(1,2)-1-(3-piperazin-1-ylphenoxy)indan-2-yl]piperidin-4-yl}methylamine;
C-{1-[rac-trans-(1,2)-1-(3-piperazin-1-ylphenoxy)indan-2-yl]pyrrolidin-3-yl}methylamine;
C-{1-[rac-trans-(1,2)-1-(4-[1,2,4]triazol-1-ylphenoxy)indan-2-yl]pyrrolidin-3-yl}methylamine;
C-{1-[rac-trans-(1,2)-1-(4-piperazin-1-ylphenoxy)indan-2-yl]piperidin-4-yl}methylamine;
C-{1-[rac-trans-(1,2)-1-(benzo[1,3]dioxol-5-yloxy)indan-2-yl]piperidin-4-yl}methylamine;
C-{1-[rac-trans-(1,2)-1-(benzo[1,3]dioxol-5-yloxy)indan-2-yl]pyrolidin-3-yl}methylamine;
C-{1-[rac-trans-(1,2)-1-(quinolin-4-yloxy)indan-2-yl]piperidin-4-yl}methylamine cyclopentyl-[1-(4-methanesulfonylphenoxy)indan-2-yl]amine;
cyclopropylmethyl-[1-(4-methanesulfonylphenoxy)indan-2-yl]amine;
diethyl-[rac-trans-(1,2)-1-(2-methylbenzothiazol-5-yloxy)indan-2-yl]amine;
diethyl-[rac-trans-(1,2)-1-(3-piperazin-1-ylphenoxy)indan-2-yl]amine;
diethyl-[rac-trans-(1,2)-1-(4-piperazin-1-ylphenoxy)indan-2-yl]amine;
diethyl-{rac-trans-(1,2)-1-[4-(2-methoxyethyl)phenoxy]indan-2-yl}amine;
methyl-[rac-trans-(1,2)-1-(3-piperazin-1-ylphenoxy)indan-2-yl]piperidin-4-ylamine;
methyl-[rac-trans-(1,2)-1-(4-piperazin-1-ylphenoxy)indan-2-yl]piperidin-4-ylamine;
N-(3-{trans-(1S,2S)-2-[(R)-3-(2-fluoroethylamino)piperidin-1-yl]indan-1-yloxy}phenyl)acetamide;
N-(3-{trans-(1S,2S)-2-[(R)-3-(3,3,3-trifluoropropylamino)piperidin-1-yl]indan-1-yloxy}phenyl)acetamide;
N, N-diethyl-4-(rac-trans-(1,2)-2-pyrrolidin-1-ylindan-1-yloxy)benzamide;
N-[2-(rac-trans-(1,2)-2-pyrrolidin-1-ylindan-1-yloxy)phenyl]acetamide;
N-[3-(rac-trans-(1,2)-2-azepan-1-ylindan-1-yloxy)phenyl]acetamide;
N-[3-(rac-trans-(1,2)-2-diethylaminoindan-1-yloxy)phenyl]acetamide;
N-[3-(rac-trans-(1,2)-2-dimethylaminoindan-1-yloxy)phenyl]acetamide;
N-[3-(rac-trans-(1,2)-2-piperazin-1-ylindan-1-yloxy)phenyl]acetamide;
N-[3-(rac-trans-(1,2)-2-pyrrolidin-1-ylindan-1-yloxy)phenyl]acetamide;
N-[3-(rac-trans-(1,2)-2-thiomorpholin-4-ylindan-1-yloxy)phenyl]acetamide;
N-[3-(rac-trans-(1,2)-4,6-dichloro-2-dimethylaminoindan-1-yloxy)phenyl]acetamide;
N-[3-(trans-(1S,2S)-2-piperidin-1-ylindan-1-yloxy)phenyl]acetamide;
N-[4-(rac-trans-(1,2)-2-pyrrolidin-1-ylindan-1-yloxy)phenyl]acetamide;
N-[4-(rac-trans-(1,2)-2-pyrrolidin-1-ylindan-1-yloxy)pyridin-2-yl]acetamide;
N-[6-(rac-trans-(1,2)-2-pyrrolidin-1-ylindan-1-yloxy)pyridin-2-yl]acetamide;
N-[rac-trans-(1,2)-1-(4-methanesulfonylphenoxy)indan-2-yl]-N,N',N'-trimethylpropane-1,3-diamine;
N-[rac-trans-(1,2)-3-((R)-2-[1,3]pyrrolidinyl-1'-ylindan-1-yloxy)phenyl]acetamide;
N-[trans-(1S,2S)-4,6-dichloro-1-(4-methanesulfonylphenoxy)indan-2-yl]-N,N',N'-trimethylethane-1,2-diamine;
N-[trans-(1S,2S)-4,6-dichloro-1-(4-methanesulfonylphenoxy)indan-2-yl]-N,N',N'-trimethylpropane-1,3-diamine;
N-{3-[rac-trans-(1,2)-2-(hexahydropyrrolo[3,4-c]pyrrol-2-yl)indan-1-yloxy]phenyl}acetamide;
N-{3-[rac-trans-(1,2)-2-((R)-3-aminopiperidin-1-yl)indan-1-yloxy]phenyl}acetamide;
N-{3-[rac-trans-(1,2)-2-((R)-3-hydroxymethylpyrrolidin-1-yl)indan-1-yloxy]phenyl}acetamide;
N-{3-[rac-trans-(1,2)-2-((R)-3-hydroxypyrrolidin-1-yl)indan-1-yloxy]phenyl}acetamide;
N-{3-[rac-trans-(1,2)-2-((R)-3-methoxypyrrolidin-1-yl)indan-1-yloxy]phenyl}acetamide;
N-{3-[rac-trans-(1,2)-2-((S)-3-aminopiperidin-1-yl)indan-1-yloxy]phenyl}acetamide;
N-{3-[rac-trans-(1,2)-2-(3-aminomethylpyrrolidin-1-yl)indan-1-yloxy]phenyl}acetamide;
N-{3-[rac-trans-(1,2)-2-(3-aminopyrrolidin-1-yl)indan-1-yloxy]phenyl}acetamide;
N-{3-[rac-trans-(1,2)-2-(4-aminomethylpiperidin-1-yl)indan-1-yloxy]phenyl}acetamide;
N-{3-[trans-(1S,2S)-2-((R)-3-aminopiperidin-1-yl)indan-1-yloxy]phenyl}acetamide;
N-{3-[trans-(1S,2S)-2-((R)-3-dimethylaminopiperidin-1-yl)indan-1-yloxy]phenyl}acetamide;
N-ethyl-4-(rac-trans-(1,2)-2-pyrrolidin-1-ylindan-1-yloxy)benzenesulfonamide;
tert-butyl-[1-(4-methanesulfonylphenoxy)indan-2-yl]amine;
3-[trans-(1S,2S)-4,6-dichloro-1-(4-[1,2,4]triazol-1-ylphenoxy)indan-2-yl]-3,8-diazabicyclo[3.2.1]octane;
2-[trans-(1S,2S)-4,6-dichloro-1-(4-methanesulfonylphenoxy)indan-2-yl]octahydropyrrolo[3,4-c]pyrrole;
2-[trans-(1S,2S)-4,6-dichloro-1-(4-methanesulfonylphenoxy)indan-2-yl]-5-methyloctahydropyrrolo[3,4-c]pyrrole;
(3R, 5S)-1-[trans-(1S,2S)-4,6-dichloro-1-(4-methanesulfonylphenoxy)indan-2-yl]-3,5-dimethylpiperazine;
(R)-1-[(1S,2S)-4,6-difluoro-1-(4-methanesulfonylphenoxy)indan-2-yl]pyrrolidin-3-ol;
(R)-1-[rac-trans-(1,2)-4-chloro-6-fluoro-1-(3-methyl-4-trifluoromethanesulfonylphenoxy)indan-2-yl]piperidin-3-ylamine;
(R)-1-[rac-trans-(1,2)-4-chloro-6-fluoro-1-(4-methanesulfonylphenoxy)indan-2-yl]piperidin-3-ylamine;
(R)-1-[rac-trans-(1,2)-6-chloro-4-fluoro-1-(3-methyl-4-trifluoromethanesulfonylphenoxy)indan-2-yl]piperidin-3-ylamine;
(R)-1-[rac-trans-(1,2)-6-chloro-4-fluoro-1-(4-methanesulfonylphenoxy)indan-2-yl]piperidin-3-ylamine;
(R)-1-[trans-(1S,2S)-4,6-dichloro-1-(2-methylbenzothiazol-5-yloxy)indan-2-yl]pyrrolidin-3-ol;
(R)-1-[trans-(1S,2S)-4,6-dichloro-1-(4-[1,2,4]triazol-1-ylphenoxy)indan-2-yl]piperidin-3-ylamine;
(R)-1-[trans-(1S,2S)-4,6-dichloro-1-(4-imidazol-1-ylphenoxy)indan-2-yl]piperidin-3-ylamine;
(R)-1'-[trans-(1S,2S)-4,6-dichloro-1-(4-methanesulfonylphenoxy)indan-2-yl]-[1,3']bipyrrolidinyl;
(R)-1-[trans-(1S,2S)-4,6-dichloro-1-(4-methanesulfonylphenoxy)indan-2-yl]-3-fluoropyrrolidine;
(R)-1-[trans-(1S,2S)-4,6-dichloro-1-(4-methanesulfonylphenoxy)indan-2-yl]-3-methylpiperazine;
(R)-1-[trans-(1S,2S)-4,6-dichloro-1-(4-methanesulfonylphenoxy)indan-2-yl]piperidin-3-ylamine;
(R)-1-[trans-(1S,2S)-4,6-dichloro-1-(4-methanesulfonylphenoxy)indan-2-yl]pyrrolidin-3-ol;

(R)-1-[trans-(1S,2S)-4,6-dichloro-1-(4-methanesulfonylphenoxy)indan-2-yl]pyrrolidin-3-ylamine;
(R)-1-[trans-(1S,2S)-4,6-dichloro-1-(4-methanesulfonylphenoxy)indan-2-yl]pyrrolidine-3-carbonitrile;
(R)-1-[trans-(1S,2S)-6-chloro-1-(2-chloro-4-methanesulfonylphenoxy)-4-fluoroindan-2-yl]pyrrolidin-3-ol
(R)-1-[trans-(1S,2S)-6-chloro-1-(2-chloro-4-methanesulfonylphenoxy)indan-2-yl]pyrrolidin-3-ol;
(R)-1-[trans-(1S,2S)-6-chloro-4-fluoro-1-(4-methanesulfonylphenoxy)indan-2-yl]pyrrolidin-3-ol;
(R)-1-{(1S,2S)-1-[2-chloro-4-(3,5-dimethyl-[1,2,4]triazol-4-yl)phenoxy]-4,6-difluoroindan-2-y1yl}pyrrolidan-3-ol;
(R)-1-{(1S,2S)-1-[4-(3,5-dimethyl-[1,2,4]triazol-4-yl)-2-fluorophenoxy]-4,6-difluoroindan-2-yl}pyrrolidin-3-ol;
(R)-1-{(1S,2S)-4,6-dichloro-1-[4-(3,5-dimethyl-[1,2,4]triazol-4-yl)phenoxy]indan-2-yl}-3-methylpyrrolidin-3-ol;
(R)-1-{(1S,2S)-4,6-dichloro-1-[4-(5-methyltetrazol-1-yl)phenoxy]indan-2-yl}pyrrolidin-3-ol;
(R)-1-{(1S,2S)-4,6-dichloro-1-[4-fluoro-2-(1H-pyrazol-3-yl)phenoxy]indan-2-yl}piperidin-3-ylamine;
(R)-1-{(1S,2S)-4,6-dichloro-1-[5-(3,5-dimethyl-[1,2,4]triazol-4-yl)-2-fluorophenoxy]indan-2-yl}pyrrolidin-3-ol;
(R)-1-{trans-(1S,2S)-4,6-dichloro-1-[2-chloro-4-(3,5-dimethyl-[1,2,4]triazol-4-yl)phenoxy]indan-2-yl}pyrrolidin-3-ol;
(R)-1-{trans-(1S,2S)-4,6-dichloro-1-[3-(1,1-dioxo-1lambda6-isothiazolidin-2-yl)phenoxy]indan-2-yl}pyrrolidin-3-ol;
(R)-1-{trans-(1S,2S)-4,6-dichloro-1-[4-(1,3,5-trimethyl-1H-pyrazol-4-yl)phenoxy]indan-2-yl}pyrrolidin-3-ol;
(R)-1-{trans-(1S,2S)-4,6-dichloro-1-[4-(2,4-dimethylthiazol-5-yl)phenoxy]indan-2-yl}pyrrolidin-3-ol;
(R)-1-{trans-(1S,2S)-4,6-dichloro-1-[4-(3,5-dimethyl-[1,2,4]triazol-4-yl)-2,3-difluorophenoxy]indan-2-yl}pyrrolidin-3-ol;
(R)-1-{trans-(1S,2S)-4,6-dichloro-1-[4-(3,5-dimethyl-[1,2,4]triazol-4-yl)-2,3-dimethylphenoxy]indan-2-yl}pyrrolidin-3-ol;
(R)-1-{trans-(1S,2S)-4,6-dichloro-1-[4-(3,5-dimethyl-[1,2,4]triazol-4-yl)-2-fluorophenoxy]indan-2-yl}pyrrolidin-3-ol;
(R)-1-{trans-(1S,2S)-4,6-dichloro-1-[4-(3,5-dimethyl-[1,2,4]triazol-4-yl)-2-methylphenoxy]indan-2-yl}pyrrolidin-3-ol;
(R)-1-{trans-(1S,2S)-4,6-dichloro-1-[4-(3,5-dimethyl-[1,2,4]triazol-4-yl)phenoxy]indan-2-yl}piperidin-3-ol;
(R)-1-{trans-(1S,2S)-4,6-dichloro-1-[4-(3,5-dimethyl-[1,2,4]triazol-4-yl)phenoxy]indan-2-yl}pyrrolidin-3-ol;
(R)-1-{trans-(1S,2S)-4,6-dichloro-1-[4-(3,5-dimethyl-[1,2,4]triazol-4-yl)phenoxy]indan-2-yl}pyrrolidine-3-carbonitrile;
(R)-1-{trans-(1S,2S)-4,6-dichloro-1-[4-(3,5-dimethylisoxazol-4-yl)phenoxy]indan-2-yl}pyrrolidin-3-ol;
(R)-1-{trans-(1S,2S)-4,6-dichloro-1-[4-(3,5-dimethylpyrazol-1-yl)-2-fluorophenoxy]indan-2-yl}pyrrolidin-3-ol;
(R)-1-{trans-(1S,2S)-4,6-dichloro-1-[4-fluoro-2-(2H-pyrazol-3-yl)phenoxy]indan-2-yl}pyrrolidin-3-ol;
(R)-1-{trans-(1S,2S)-6-chloro-1-[2-chloro-4-(3,5-dimethyl-[1,2,4]triazol-4-yl)phenoxy]-4-fluoroindan-2-yl}pyrrolidin-3-ol;
(R)-1-{trans-(1S,2S)-6-chloro-1-[2-chloro-4-(3,5-dimethyl-[1,2,4]triazol-4-yl)phenoxy]indan-2-yl}pyrrolidin-3-ol;
(R)-1-{trans-(1S,2S)-6-chloro-1-[4-(1,3,5-trimethyl-1H-pyrazol-4-yl)phenoxy]indan-2-yl}pyrrolidin-3-ol;
(R)-1-{trans-(1S,2S)-6-chloro-1-[4-(3,5-dimethyl-[1,2,4]triazol-4-yl)-2,3-dimethylphenoxy]-4-fluoroindan-2-yl}pyrrolidin-3-ol;
(R)-1-{trans-(1S,2S)-6-chloro-1-[4-(3,5-dimethyl-[1,2,4]triazol-4-yl)-2-fluorophenoxy]-4-fluoroindan-2-yl}pyrrolidin-3-ol
(R)-1-{trans-(1S,2S)-6-chloro-1-[4-(3,5-dimethyl-[1,2,4]triazol-4-yl)-2-fluorophenoxy]indan-2-yl}pyrrolidin-3-ol;
(R)-1-{trans-(1S,2S)-6-chloro-1-[4-(3,5-dimethyl-[1,2,4]triazol-4-yl)phenoxy]-4-fluoroindan-2-yl}pyrrolidin-3-ol;
(R)-1-{trans-(1S,2S)-6-chloro-1-[4-(3,5-dimethyl-[1,2,4]triazol-4-yl)phenoxy]indan-2-yl}pyrrolidin-3-ol;
(S)-1-[(1S,2S)-4,6-dichloro-1-(4-methanesulfonylphenoxy)indan-2-yl]-3-methylpyrrolidin-3-ol;
(S)-1-[trans-(1S,2S)-4,6-dichloro-1-(4-methanesulfonylphenoxy)indan-2-yl]-2-pyrrolidin-1-ylmethylpyrrolidine;
(S)-1-[trans-(1S,2S)-4,6-dichloro-1-(4-methanesulfonylphenoxy)indan-2-yl]-3-fluoropyrrolidine;
(S)-1-[trans-(1S,2S)-4,6-dichloro-1-(4-methanesulfonylphenoxy)indan-2-yl]-3-methylpiperazine;
(S)-1-[trans-(1S,2S)-4,6-dichloro-1-(4-methanesulfonylphenoxy)indan-2-yl]pyrrolidin-3-ol
(S)-1-[trans-(1S,2S)-4,6-dichloro-1-(4-methanesulfonylphenoxy)indan-2-yl]pyrrolidin-3-ylamine;
(S)-1-{(1S,2S)-4,6-dichloro-1-[4-(3,5-dimethyl-[1,2,4]triazol-4-yl)-2-fluorophenoxy]indan-2-yl}pyrrolidin-3-ol;
(S)-1-{trans-(1S,2S)-4,6-dichloro-1-[4-(3,5-dimethyl-[1,2,4]triazol-4-yl)phenoxy]indan-2-yl}pyrrolidin-3-ol;
(S)-1-{trans-(1S,2S)-4,6-dichloro-1-[4-(3,5-dimethyl-[1,2,4]triazol-4-yl)phenoxy]indan-2-yl}pyrrolidin-3-ylamine;
(S)-2-[(S)-4-(S)-chloro-6-chloro-1-(4-methanesulfonylphenoxy)indan-2-yl]octahydropyrrolo[1,2-a]pyrazine;
(S)-2-[trans-(1S,2S)-4,6-dichloro-1-(4-methanesulfonylphenoxy)indan-2-yl]-2,5-diazabicyclo[2.2.1]heptane;
(S)-3-{3-[(1S,2S)-6-chloro-4-fluoro-2-((R)-3-hydroxypyrrolidin-1-yl)indan-1-yloxy]-4-fluorophenyl}-4-isopropyloxazolidin-2-one;
(S)-3-{4-chloro-3-[(1S,2S)-6-chloro-4-fluoro-2-((R)-3-hydroxypyrrolidin-1-yl)indan-1-yloxy]phenyl}-4-isopropyloxazolidin-2-one;
{(R)-1-[trans-(1S,2S)-4,6-dichloro-1-(4-[1,2,4]triazol-1-ylphenoxy)indan-2-yl]piperidin-3-yl}-(3,3,3-trifluoropropyl)amine;
{(R)-1-[trans-(1S,2S)-4,6-dichloro-1-(4-methanesulfonylphenoxy)indan-2-yl]piperidin-3-yl}-(2-fluoroethyl)amine;
{(R)-1-[trans-(1S,2S)-4,6-dichloro-1-(4-methanesulfonylphenoxy)indan-2-yl]piperidin-3-yl}-(3,3,3-trifluoropropyl)amine;
{(R)-1-[trans-(1S,2S)-4,6-dichloro-1-(4-methanesulfonylphenoxy)indan-2-yl]piperidin-3-yl}dimethylamine;
{(R)-1-[trans-(1S,2S)-4,6-dichloro-1-(4-methanesulfonylphenoxy)indan-2-yl]piperidin-3-ylamino}acetonitrile;

{(R)-1-[trans-(1S,2S)-4,6-dichloro-1-(4-methanesulfonylphenoxy)indan-2-yl]pyrrolidin-3-yl}-(2-fluoroethyl)amine;
{(R)-1-[trans-(1S,2S)-4,6-dichloro-1-(4-methanesulfonylphenoxy)indan-2-yl]pyrrolidin-3-yl}methanol;
{(S)-1-[trans-(1S,2S)-4,6-dichloro-1-(4-methanesulfonylphenoxy)indan-2-yl]pyrrolidin-2-yl}methanol;
{4-[rac-trans-(1,2)-6-fluoro-1-(4-methanesulfonylphenoxy)indan-2-yl]piperazin-1-yl}acetonitrile;
1-[(1S,2S)-4,6-dichloro-1-(2-methanesulfonylphenoxy)indan-2-yl]azetidine;
1-[(1S,2S)-4,6-dichloro-1-(2-methanesulfonylphenoxy)indan-2-yl]piperazine;
1-[(1S,2S)-4,6-dichloro-1-(2-methanesulfonylphenoxy)indan-2-yl]pyrrolidine;
1-[(1S,2S)-4,6-dichloro-1-(3-tetrazol-1-ylphenoxy)indan-2-yl]piperazine;
1-[(1S,2S)-4,6-dichloro-1-(4-methanesulfonylphenoxy)indan-2-yl]-3-methanesulfonylpyrrolidine;
1-[(1S,2S)-4,6-dichloro-1-(4-methanesulfonylphenoxy)indan-2-yl]-4,4-difluoropiperidine;
1-[3-(rac-trans-(1,2)-4,6-dichloro-2-piperazin-1-ylindan-1-yloxy)phenyl]-3-methyl-1,3-dihydroimidazol-2-one;
1-[3-(rac-trans-(1,2)-4,6-dichloro-2-piperazin-1-ylindan-1-yloxy)phenyl]-3-methylimidazolidin-2-one;
1-[4-((1S,2S)-2-azetidin-1-yl-4,6-dichloroindan-1-yloxy)phenyl]pyrrolidin-2-one;
1-[4-((1S,2S)-4,6-dichloro-2-pyrrolidin-1-ylindan-1-yloxy)phenyl]pyrrolidin-2-one;
1-[rac-trans-(1,2)-4,6-dichloro-1-(4-[1,2,4]triazol-1-ylphenoxy)indan-2-yl]piperazine;
1-[rac-trans-(1,2)-4,6-dichloro-1-(4-methanesulfonylphenoxy)indan-2-yl]-[1,4]diazepane;
1-[rac-trans-(1,2)-4,6-dichloro-1-(4-methanesulfonylphenoxy)indan-2-yl]-1H-imidazole;
1-[rac-trans-(1,2)-4,6-dichloro-1-(4-methanesulfonylphenoxy)indan-2-yl]-4-methyl-[1,4]diazepane;
1-[rac-trans-(1,2)-4-chloro-6-fluoro-1-(4-methanesulfonyl-3-methylphenoxy)indan-2-yl]piperazine;
1-[rac-trans-(1,2)-4-chloro-6-fluoro-1-(4-methanesulfonyl-3-methylphenoxy)indan-2-yl]pyrrolidine;
1-[rac-trans-(1,2)-4-chloro-6-fluoro-1-(4-methanesulfonylphenoxy)indan-2-yl]piperazine;
1-[rac-trans-(1,2)-4-chloro-6-fluoro-1-(4-methanesulfonylphenoxy)indan-2-yl]pyrrolidine;
1-[rac-trans-(1,2)-4-fluoro-1-(4-methanesulfonylphenoxy)indan-2-yl]pyrrolidine;
1-[rac-trans-(1,2)-5,6-dichloro-1-(4-methanesulfonylphenoxy)indan-2-yl]-[1,4]diazepane;
1-[rac-trans-(1,2)-5,7-dichloro-1-(4-methanesulfonylphenoxy)indan-2-yl]piperazine;
1-[rac-trans-(1,2)-6,7-dichloro-1-(4-methanesulfonylphenoxy)indan-2-yl]-[1,4]diazepane;
1-[rac-trans-(1,2)-6-chloro-1-(4-methanesulfonylphenoxy)indan-2-yl]piperazine;
1-[rac-trans-(1,2)-6-chloro-4-fluoro-1-(3-methyl-4-trifluoromethanesulfonylphenoxy)indan-2-yl]piperazine;
1-[rac-trans-(1,2)-6-chloro-4-fluoro-1-(4-methanesulfonyl-3-methylphenoxy)indan-2-yl]pyrrolidine;
1-[rac-trans-(1,2)-6-chloro-4-fluoro-1-(4-methanesulfonylphenoxy)indan-2-yl]piperazine;
1-[rac-trans-(1,2)-6-chloro-4-fluoro-1-(4-methanesulfonylphenoxy)indan-2-yl]pyrrolidine;
1[rac-trans-(1,2)-6-fluoro-1-(4-methanesulfonylphenoxy)indan-2-yl]piperazine;
1-[trans-(1S,2S)-4,6-dichloro-1-(2-chloro-4-methanesulfonylphenoxy)indan-2-yl]-[1,4]diazepane;
1-[trans-(1S,2S)-4,6-dichloro-1-(4-[1,2,4]triazol-1-ylphenoxy)indan-2-yl]-4-methylpiperazine;
1-[trans-(1S,2S)-4,6-dichloro-1-(4-imidazol-1-ylphenoxy)indan-2-yl]-4-methylpiperazine;
1-[trans-(1S,2S)-4,6-dichloro-1-(4-methanesulfonylphenoxy)indan-2-yl]-[1,4]diazepane;
1-[trans-(1S,2S)-4,6-dichloro-1-(4-methanesulfonylphenoxy)indan-2-yl]-3-propylpiperidin-3-ylamine;
1-[trans-(1S,2S)-4,6-dichloro-1-(4-methanesulfonylphenoxy)indan-2-yl]-3-trifluoromethylpiperazine;
1-[trans-(1S,2S)-4,6-dichloro-1-(4-methanesulfonylphenoxy)indan-2-yl]-3-trifluoromethylpyrrolidin-3-yl amine;
1-[trans-(1S,2S)-4,6-dichloro-1-(4-methanesulfonylphenoxy)indan-2-yl]-4-(2-fluoroethyl)-[1,4]diazepane;
1-[trans-(1S,2S)-4,6-dichloro-1-(4-methanesulfonylphenoxy)indan-2-yl]-4-(2-methoxyethyl)-[1,4]diazepane;
1-[trans-(1S,2S)-4,6-dichloro-1-(4-methanesulfonylphenoxy)indan-2-yl]-4-methyl-[1,4]diazepane;
1-[trans-(1S,2S)-4,6-dichloro-1-(4-methanesulfonylphenoxy)indan-2-yl]-4-methylpiperazine;
1-[trans-(1S,2S)-4,6-dichloro-1-(4-methanesulfonylphenoxy)indan-2-yl]-azetidin-3-ol;
1-[trans-(1S,2S)-4,6-dichloro-1-(4-methanesulfonylphenoxy)indan-2-yl]piperazine;
1-{(1S,2S)-4,6-dichloro-1-[4-fluoro-2-(1H-pyrazol-3-yl)phenoxy]indan-2-yl}piperazine;
1-{2-chloro-5-[(1S,2S)-4,6-dichloro-2-((R)-3-hydroxypyrrolidin-1-yl)indan-1-yloxy]phenyl}-3-methyl-1,3-dihydroimidazol-2-one;
1-{2-chloro-5-[(1S,2S)-4,6-dichloro-2-((R)-3-hydroxypyrrolidin-1-yl)indan-1-yloxy]phenyl}-3-methylimidazolidin-2-one;
1-{3-[(1S, 2S)-4,6-dichloro-2-((R)-3-hydroxypyrrolidin-1-yl)indan-1-yloxy]-2-methylphenyl}-3-methyl-1,3-dihydroimidazol-2-one;
1-{3-[(1S,2S)-4,6-dichloro-2-((R)-3-hydroxypyrrolidin-1-yl)indan-1-yloxy]-4-fluorophenyl}-3-methyl-1,3-dihydroimidazol-2-one;
1-{3-[(1S, 2S)-4,6-dichloro-2-((R)-3-hydroxypyrrolidin-1-yl)indan-1-yloxy]-4-fluorophenyl}-3-methylimidazolidin-2-one;
1-{3-[(1S,2S)-4,6-dichloro-2-((R)-3-hydroxypyrrolidin-1-yl)indan-1-yloxy]phenyl}pyrrolidin-2-one;
1-{3-[(1S, 2S)-4,6-dichloro-2-((R)-3-hydroxypyrrolidin-1-yl)indan-1-yloxy]phenyl}pyrrolidine-2,5-dione;
1-{3-[(1S,2S)-4,6-difluoro-2-((R)-3-hydroxypyrrolidin-1-yl)indan-1-yloxy]-4-fluorophenyl}-3-methyl-1,3-dihydroimidazol-2-one;
1-{3-[(1S,2S)-6-chloro-4-fluoro-2-((R)-3-hydroxypyrrolidin-1-yl)indan-1-yloxy]-4-fluorophenyl}-3-methyl-1,3-dihydroimidazol-2-one;
1-{3-[trans-(1S,2S)-4,6-dichloro-2-((R)-3-hydroxypyrrolidin-1-yl)indan-1-yloxy]phenyl}-3-methylimidazolidin-2-one;
1-{3-[trans-(1S,2S)-6-chloro-4-fluoro-2-((R)-3-hydroxypyrrolidin-1-yl)indan-1-yloxy]phenyl}-3-methylimidazolidin-2-one;
1-{3-chloro-4-[(1S,2S)-4,6-dichloro-2-((R)-3-hydroxypyrrolidin-1-yl)indan-1-yloxy]phenyl}pyrrolidin-2-one;
1-{3-chloro-4-[(1S,2S)-4,6-dichloro-2-((R)-3-hydroxypyrrolidin-1-yl)indan-1-yloxy]phenyl}pyrrolidine-2,5-dione;
1-{4-[(1S,2S)-4,6-dichloro-2-((R)-3-hydroxypyrrolidin-1-yl)indan-1-yloxy]-3-fluorophenyl}-1,3-dihydroimidazol-2-one;

1-{4-[(1S, 2S)-4,6-dichloro-2-((R)-3-hydroxypyrrolidin-1-yl)indan-1-yloxy]-3-fluorophenyl}-2,6-dimethyl-1H-pyridin-4-one;
1-{4-[(1S,2S)-4,6-dichloro-2-((R)-3-hydroxypyrrolidin-1-yl)indan-1-yloxy]phenyl}-1,3-dihydroimidazol-2-one;
1-{4-[trans-(1S,2S)-4,6-dichloro-2-((R)-3-hydroxypyrrolidin-1-yl)indan-1-yloxy]-3-fluorophenyl}-3-methyl-1,3-dihydroimidazol-2-one;
1-{4-[trans-(1S,2S)-4,6-dichloro-2-((R)-3-hydroxypyrrolidin-1-yl)indan-1-yloxy]-3-fluorophenyl}-3-methylimidazolidin-2-one;
1-{4-[trans-(1S,2S)-4,6-dichloro-2-((R)-3-hydroxypyrrolidin-1-yl)indan-1-yloxy]phenyl}-3-methyl-1,3-dihydroimidazol-2-one;
1-{4-[trans-(1S,2S)-4,6-dichloro-2-((R)-3-hydroxypyrrolidin-1-yl)indan-1-yloxy]phenyl}-3-methylimidazolidin-2-one;
1-{4-[trans-(1S,2S)-4,6-dichloro-2-((R)-3-hydroxypyrrolidin-1-yl)indan-1-yloxy]phenyl}pyrrolidin-2-one;
1-{4-[trans-(1S,2S)-4,6-dichloro-2-((R)-3-hydroxypyrrolidin-1-yl)indan-1-yloxy]phenyl}pyrrolidine-2,5-dione;
1-{4-chloro-3-[(1S,2S)-4,6-dichloro-2-((R)-3-hydroxypyrrolidin-1-yl)indan-1-yloxy]phenyl}-3-methyl-1,3-dihydroimidazol-2-one;
1-{4-chloro-3-[(1S,2S)-4,6-dichloro-2-((R)-3-hydroxypyrrolidin-1-yl)indan-1-yloxy]phenyl}pyrrolidin-2-one;
1-{4-chloro-3-[(1S,2S)-4,6-dichloro-2-((R)-3-hydroxypyrrolidin-1-yl)indan-1-yloxy]phenyl}pyrrolidine-2,5-dione;
1-{4-chloro-3-[(1S,2S)-4,6-difluoro-2-((R)-3-hydroxypyrrolidin-1-yl)indan-1-yloxy]phenyl}-3-methyl-1,3-dihydroimidazol-2-one;
1-{4-chloro-3-[(1S,2S)-6-chloro-4-fluoro-2-((R)-3-hydroxypyrrolidin-1-yl)indan-1-yloxy]phenyl}-3-methyl-1,3-dihydroimidazol-2-one;
1-{4-chloro-3-[(1S,2S)-6-chloro-4-fluoro-2-((R)-3-hydroxypyrrolidin-1-yl)indan-1-yloxy]phenyl}-3-methylimidazolidin-2-one;
1-{4-chloro-3-[(1S,2S)-6-chloro-4-fluoro-2-((R)-3-hydroxypyrrolidin-1-yl)indan-1-yloxy]phenyl}pyrrolidin-2-one;
1-{trans-(1S,2S)-4,6-dichloro-1-[2-chloro-4-(3,5-dimethyl-[1,2,4]triazol-4-yl)phenoxy]indan-2-yl}-[1,4]diazepane;
1-{trans-(1S,2S)-4,6-dichloro-1-[2-chloro-4-(3,5-dimethyl[1,2,4]triazol-4-yl)phenoxy]indan-2-yl}-4-methyl-[1,4]diazepane;
1-{trans-(1S,2S)-4,6-dichloro-1-[4-(3,5-dimethyl-[1,2,4]triazol-4-yl)-2-fluorophenoxy]indan-2-yl}-4-methyl-[1,4]diazepane;
1-{trans-(1S,2S)-4,6-dichloro-1-[4-(3,5-dimethyl-[1,2,4]triazol-4-yl)phenoxy]indan-2-yl}-[1,4]diazepane;
1-{trans-(1S,2S)-4,6-dichloro-1-[4-(3,5-dimethyl-[1,2,4]triazol-4-yl)phenoxy]indan-2-yl}-4-(2-methoxyethyl)-[1,4]diazepane;
1-{trans-(1S,2S)-4,6-dichloro-1-[4-(3,5-dimethyl-[1,2,4]triazol-4-yl)phenoxy]indan-2-yl}-4-methyl-[1,4]diazepane;
1-{trans-(1S,2S)-4,6-dichloro-1-[4-(3,5-dimethylisoxazol-4-yl)phenoxy]indan-2-yl}-4-(2-methoxyethyl)-[1,4]diazepane;
1-cyclopropyl-4-[trans-(1S,2S)-4,6-dichloro-1-(4-methanesulfonylphenoxy)indan-2-yl]piperazine;
2-((1S,2S)-2-azetidin-1-yl-4,6-dichloroindan-1-yloxy)-5-chlorobenzamide;
2,3-dichloro-4-(rac-trans-(1,2)-4,6-dichloro-2-morpholin-4-ylindan-1-yloxy)benzenesulfonamide;
2-[rac-trans-(1,2)-4,6-dichloro-1-(4-[1,2,4]triazol-1-ylphenoxy)indan-2-yl]octahydropyrrolo[3,4-c]pyrrole;
2-[trans-(1S,2S)-4,6-dichloro-1-(4-methanesulfonylphenoxy)indan-2-yl]-2,7-diaza-spiro[4.4]nonane;
2-{(R)-1-[trans-(1S,2S)-4,6-dichloro-1-(4-methanesulfonylphenoxy)indan-2-yl]piperidin-3-ylamino}ethanol;
2-{4-[rac-trans-(1,2)-4,6-dichloro-1-(4-methanesulfonylphenoxy)indan-2-yl]-[1,4]diazepan-1-yl}ethanol;
2-{4-[rac-trans-(1,2)-6-chloro-1-(4-methanesulfonylphenoxy)indan-2-yl]piperazin-1-yl}ethanol;
2-{4-[trans-(1S,2S)-4,6-dichloro-1-(4-methanesulfonylphenoxy)indan-2-yl]-[1,4]diazepan-1-yl}ethanol;
3-{3-[(1S,2S)-4,6-dichloro-2-((R)-3-hydroxypyrrolidin-1-yl)indan-1-yloxy]-4-fluorophenyl}-5,5-dimethylimidazolidine-2,4-dione;
3-{3-[(1S,2S)-4,6-dichloro-2-((R)-3-hydroxypyrrolidin-1-yl)indan-1-yloxy]-4-fluorophenyl}imidazolidine-2,4-dione;
3-{3-[(1S,2S)-4,6-dichloro-2-((R)-3-hydroxypyrrolidin-1-yl)indan-1-yloxy]-4-fluorophenyl}oxazolidine-2,4-dione;
3-{3-[(1S, 2S)-4,6-dichloro-2-((R)-3-hydroxypyrrolidin-1-yl)indan-1-yloxy]phenyl}oxazolidin-2-one;
3-{3-[(1S,2S)-6-chloro-4-fluoro-2-((R)-3-hydroxypyrrolidin-1-yl)indan-1-yloxy]-4-fluorophenyl}-5,5-dimethylimidazolidine-2,4-dione;
3-{3-[(1S,2S)-6-chloro-4-fluoro-2-((R)-3-hydroxypyrrolidin-1-yl)indan-1-yloxy]-4-fluorophenyl}imidazolidine-2,4-dione;
3-{3-chloro-4-[(1S,2S)-4,6-dichloro-2-((R)-3-hydroxypyrrolidin-1-yl)indan-1-yloxy]phenyl}-1-methylimidazolidine-2,4-dione;
3-{3-chloro-4-[(1S,2S)-4,6-dichloro-2-((R)-3-hydroxypyrrolidin-1-yl)indan-1-yloxy]phenyl}-5,5-dimethylimidazolidine-2,4-dione;
3-{3-chloro-4-[(1S,2S)-4,6-dichloro-2-((R)-3-hydroxypyrrolidin-1-yl)indan-1-yloxy]phenyl}oxazolidine-2,4-dione;
3-{4-[(1S,2S)-4,6-dichloro-2-((R)-3-hydroxypyrrolidin-1-yl)indan-1-yloxy]phenyl}-5,5-dimethylimidazolidine-2,4-dione;
3-{4-[(1S,2S)-4,6-dichloro-2-((R)-3-hydroxypyrrolidin-1-yl)indan-1-yloxy]phenyl}imidazolidine-2,4-dione;
3-{4-[(R1S, 2S)-4,6-dichloro-2-((R)-3-hydroxypyrrolidin-1-yl)indan-1-yloxy]phenyl}oxazolidine -2,4-dione;
3-{4-[(1S,2S)-4,6-dichloro-2-((R)-3-hydroxypyrrolidin-1-yl)indan-1-yloxy]phenyl}thiazolidine -2,4-dione;
3-{4-[trans-(1S,2S)-4,6-dichloro-2-((R)-3-hydroxypyrrolidin-1-yl)indan-1-yloxy]phenyl}oxazolidin-2-one;
3-{4-chloro-3-[(1S,2S)-4,6-dichloro-2-((R)-3-hydroxypyrrolidin-1-yl)indan-1-yloxy]phenyl}-1-methylimidazolidine-2,4-dione;
3-{4-chloro-3-[(1S,2S)-4,6-dichloro-2-((R)-3-hydroxypyrrolidin-1-yl)indan-1-yloxy]phenyl}-5,5-dimethylimidazolidine-2,4-dione;
3-{4-chloro-3-[(1S,2S)-4,6-dichloro-2-((R)-3-hydroxypyrrolidin-1-yl)indan-1-yloxy]phenyl}-5,5-dimethyloxazolidine-2,4-dione;
3-{4-chloro-3-[(1S,2S)-4,6-dichloro-2-((R)-3-hydroxypyrrolidin-1-yl)indan-1-yloxy]phenyl}imidazolidine-2,4-dione;

3-{4-chloro-3-[(1S,2S)-4,6-dichloro-2-((R)-3-hydroxy-pyrrolidin-1-yl)indan-1-yloxy]phenyl}oxazolidin-2-one;

3-{4-chloro-3-[(1S,2S)-6-chloro-4-fluoro-2-((R)-3-hydroxypyrradin-1-yl)indan-1-yloxy]phenyl}-1-methylimidazolidine-2,4-dione, 3-{4-chloro-3-[(1S,2S)-6-chloro-4-fluoro-2-((R)-3-hydroxypyrrolidin-1-yl)indan-1-yloxy]phenyl}-5,5-dimethylimidazolidine-2,4-dione;

3-{4-chloro-3-[(1S,2S)-6-chloro-4-fluoro-2-((R)-3-hydroxypyrrolidin-1-yl)indan-1-yloxy]phenyl}-5,5-dimethyloxazolidine-2,4-dione;

3-{4-chloro-3-[(1S,2S)-6-chloro-4-fluoro-2-((R)-3-hydroxypynolidin-1-yl)indan-1-yloxy]phenyl}imidazolidine-2,4-dione;

3-{4-chloro-3-[(1S,2S)-6-chloro-4-fluoro-2-((R)-3-hydroxypyrrolidin-1-yl)indan-1-yloxy]phenyl}oxazolidin-2-one;

3-chloro-4-[trans-(1S,2S)-6-chloro-2-((R)-3-hydroxypyrrolidin-1-yl)indan-1-yloxy]benzoic acid methyl ester;

4-((1S,2S)-4,6-dichloro-2-pyrrolidin-1-ylindan-1-yloxy) benzene sulfonamide ;

4-(rac-trans-(1,2)-4-chloro-2-pyrrolidin-1-ylindan-1-yloxy)benzenesulfonamide;

4-(rac-trans-(1,2)-4-methyl-2-pyrrolidin-1-ylindan-1-yloxy)benzenesulfonamide ;

4-(rac-trans-(1,2)-6-chloro-2-pyrrolidin-1-ylindan-1-yloxy)benzenesulfonamide ;

4-(rac-trans-(1,2)-6-fluoro-2-pyrrolidin-1-ylindan-1-yloxy)benzenesulfonamide ;

4-(rac-trans-(1,2)-6-methyl-2-pyrrolidin-1-ylindan-1-yloxy)benzenesulfonamide;

4-(rac-trans-(1,2)-7-chloro-2-pyrrolidin-1-ylindan-1-yloxy)benzenesulfonamide;

4-[(1S,2S)-2-((R)-3-aminopiperidin-1-yl)-4,6-dichloroindan-1-yloxy]benzenesulfonamide ;

4-[(1S,2S)-4,6-dichloro-2-(1,1-dioxo-1lambda6-thiomorpholin-4-yl)indan-1-yloxy]benzenesulfonamide;

4-[(1S,2S)-4,6-dichloro-2-(4,4-difluoropiperidin-1-yl)indan-1-yloxy]benzenesulfonamide ;

4-[3-chloro-4-(trans-(1S,2S)-6-chloro-2-pyrrolidin-1-ylindan-1-yloxy)phenyl]-3,5-dimethyl-4H -[1,2,4]triazole;

4-[3-chloro-4-(trans-(1S,2S)-6-chloro-2-pyrrolidin-1-ylindan-1-yloxy)phenyl]-3,5-dimethyl-4H -[1,2,4]triazole;

4-[4-(rac-trans-(1,2)-5,6-dichloro-2-pyrrolidin-1-ylindan-1-yloxy)phenyl]-3,5-dimethyl-4H-[1,2,4]triazole;

4-[4-(trans-(1S,2S)-4,6-dichloro-2-pyrrolidin-1-ylindan-1-yloxy)-3-fluorophenyl]-3,5-dimethyl -4H[1,2,4]triazole;

4-[4-(trans-(1S, 2 5)-4,6-dichloro-2-pyrrolidin-1-ylindan-1-yloxy)phenyl]-3,5-dimethyl-4H -[1,2,4]triazole;

4-[4-(trans-(1S,2S)-6-chloro-2-pyrrolidin-1-ylindan-1-yloxy)-3-fluorophenyl]-3,5-dimethyl-4H -[1,2,4]triazole;

4-[4-(trans-(1S,2S)-6-chloro-2-pyrrolidin-1-ylindan-1-yloxy)phenyl]-3,5-dimethyl-4H -[1,2,4]triazole;

4-[rac-trans-(1,2)-4,6-dichloro-1-(4-[1,2,4]triazol-1-ylphenoxy)indan-2-yl]morpholine ;

4-[trans-(1S,2S)-2-((R)-3-aminopiperidin-1-yl)-4,6-dichloroindan-1-yloxy]-2,3-dichlorobenzenesulfonamide;

4-[trans-(1S,2S)-4,6-dichloro-2-((R)-3-hydroxypyrrolidin-1-yl)indan-1-yloxy]-3-fluorobenzoic acid methyl ester;

4-{3-chloro-4-[trans-(1S,2S)-6-chloro-2-((R)-3-fluoropyrrolidin-1-yl)indan-1-yloxy]phenyl}-3,5-dimethyl-4H-[1,2,4]triazole;

4-{3-chloro-4-[trans-(1S,2S)-6-chloro-2-((S)-3-fluoropyrrolidin-1-yl)indan-1-yloxy]phenyl}-3,5-dimethyl-4H-[1,2,4]triazole;

4-{4-[(1S,2S)-4,6-dichloro-2-((R)-3-hydroxypyrrolidin-1-yl)indan-1-yloxy]-3-fluorophenyl}morpholine-3,5-dione;

4-{4-[trans-(1S,2S)-4,6-dichloro-2-((R)-3-fluoropyrrolidin-1-yl)indan-1-yloxy]phenyl}-3,5-dimethyl-4H-[1,2,4]triazole;

4-{4-[trans-(1S,2S)-4,6-dichloro-2-((S)-2-methoxymethylpyrrolidin-1-yl)indan-1-yloxy]phenyl}-3,5-dimethyl-4H-[1,2,4]triazole;

4-{4-[trans-(1S,2S)-6-chloro-2-((R)-3-fluoropyrrolidin-1-yl)indan-1-yloxy]-3-fluorophenyl}-3,5-dimethyl-4H-[1,2,4]triazole;

4-{trans-(1S,2S)-4,6-dichloro-1-[4-(3,5-dimethyl-[1,2,4]triazol-4-yl)-2-fluorophenoxy]indan-2-yl}morpholine;

4-{trans-(1S,2S)-4,6-dichloro-1-[4-(3,5-dimethyl-[1,2,4]triazol-4-yl)-2-fluorophenoxy]indan-2-yl}thiomorpholine-1,1-dioxide;

4-{trans-(1S,2S)-6-chloro-1-[2-chloro-4-(3,5-dimethyl-[1,2,4]triazol-4-yl)phenoxy]indan-2-yl}morpholine;

4-{trans-(1S,2S)-6-chloro-1-[2-chloro-4-(3,5-dimethyl-[1,2,4]triazol-4-yl)phenoxy]indan-2-yl}thiomorpholine-1,1-dioxide;

5-(rac-trans-(1,2)-4,6-dichloro-2-piperazin-1-ylindan-1-yloxy)-2-methylbenzothiazole;

5-[(1S,2S)-4,6-dichloro-2-((R)-3-hydroxypyrrolidin-1-yl)indan-1-yloxy]-3, 4-dihydro-1H -quinolin-2-one;

5-[trans-(1S,2S)-4,6-dichloro-1-(4-methanesulfonylphenoxy)indan-2-yl]-1-methyloctahydropyrrolo[3,4-b]pyrrole;

5-[trans-(1S,2S)-4,6-dichloro-1-(4-methanesulfonylphenoxy)indan-2-yl]-1-methyloctahydropyrrolo[3,4-b]pyrrole;

N-[3-(rac-trans-(1,2)-2-thiomorpholin-4-ylindan-1-yloxy)phenyl]acetamide;

N-[3-(rac-trans-(1,2)-4,6-dichloro-2-[1,4]diazepan-1-ylindan-1-yloxy)phenyl]acetamide;

N-[3-(rac-trans-(1,2)-4,6-dichloro-2-morpholin-4-ylindan-1-yloxy)phenyl]acetamide;

N-[3-(rac-trans-(1,2)-4,6-dichloro-2-piperazin-1-ylindan-1-yloxy)phenyl]acetamide;

N-[3-(rac-trans-(1,2)-4,6-dichloro-2-pyrrolidin-1-ylindan-1-yloxy)phenyl]acetamide;

N-[3-(rac-trans-(1,2)-4-chloro-2-pyrrolidin-1-ylindan-1-yloxy)phenyl]acetamide;

N-[3-(rac-trans-(1,2)-4-chloro-6-fluoro-2-piperazin-1-ylindan-1-yloxy)phenyl]acetamide;

N-[3-(rac-trans-(1,2)-4-chloro-6-fluoro-2-pyrrolidin-1-ylindan-1-yloxy)phenyl]acetamide;

N-[3-(rac-trans-(1,2)-4-fluoro-2-pyrrolidin-1-ylindan-1-yloxy)phenyl]acetamide;

N-[3-(rac-trans-(1,2)-4-methyl-2-pyrrolidin-1-ylindan-1-yloxy)phenyl]acetamide;

N-[3-(rac-trans-(1,2)-5,7-dichloro-2-dimethylaminoindan-1-yloxy)phenyl]acetamide;

N-[3-(rac-trans-(1,2)-5-chloro-2-pyrrolidin-1-ylindan-1-yloxy)phenyl]acetamide;

N-[3-(rac-trans-(1,2)-5-fluoro-2-pyrrolidin-1-ylindan-1-yloxy)phenyl]acetamide;

N-[3-(rac-trans-(1,2)-6-chloro-2-piperazin-1-ylindan-1-yloxy)phenyl]acetamide;

N-[3-(rac-trans-(1,2)-6-chloro-2-pyrrolidin-1-ylindan-1-yloxy)phenyl]acetamide;
N-[3-(rac-trans-(1,2)-6-chloro-4-fluoro-2-piperazin-1-ylindan-1-yloxy)phenyl]acetamide;
N-[3-(rac-trans-(1,2)-6-chloro-4-fluoro-2-pyrrolidin-1-ylindan-1-yloxy)phenyl]acetamide;
N-[3-(rac-trans-(1,2)-6-fluoro-2-pyrrolidin-1-ylindan-1-yloxy)phenyl]acetamide;
N-[3-(rac-trans-(1,2)-7-chloro-2-pyrrolidin-1-ylindan-1-yloxy)phenyl]acetamide;
N-[3-(trans-(1S,2S)-4,6-dichloro-2-3,8-diazabicyclo[3.2.1]oct-3-ylindan-1-yloxy)phenyl]acetamide;
N-[3-(trans-(1S,2S)-4,6-dichloro-2-piperazin-1-ylindan-1-yloxy)phenyl]acetamide;
N-{3-[(1S,2S)-6-chloro-4-fluoro-2-((R)-3-hydroxypyrrolidin-1-yl)indan-1-yloxy]-4-fluorophenyl}-N-methyl-methanesulfonamide;
N-{3-[rac-trans-(1,2)-2-((R)-3-aminopiperidin-1-yl)-4-chloro-6-fluoroindan-1-yloxy]phenyl}acetamide;
N-{3-[rac-trans-(1,2)-2-((R)-3-aminopiperidin-1-yl)-6-chloro-4-fluoroindan-1-yloxy]phenyl}acetamide;
N-{3-[rac-trans-(1,2)-4,6-dichloro-2-(hexahydropyrrolo[3,4-c]pyrrol-2-yl)indan-1-yloxy]phenyl}acetamide;
N-{3-[trans-(1S,2S)-2-((R)-3-aminopiperidin-1-yl)-4,6-dichloroindan-1-yloxy]phenyl}acetamide;
N-{3-[trans-(1S,2S)-2-(3-amino-3-propylpiperidin-1-yl)-4,6-dichloroindan-1-yloxy]phenyl}acetamide;
N-{3-[trans-(1S,2S)-4,6-dichloro-2-((R)-3-dimethylaminopiperidin-1-yl)indan-1-yloxy]phenyl}acetamide;
N-{3-[trans-(1S,2S)-4,6-dichloro-2-((R)-3-hydroxymethylpyrrolidin-1-yl)indan-1-yloxy]phenyl}acetamide;
N-{3-[trans-(1S,2S)-4,6-dichloro-2-((R)-3-hydroxypyrrolidin-1-yl)indan-1-yloxy]phenyl}acetamide;
N-{3-[trans-(1S,2S)-4,6-dichloro-2-(4-methylpiperazin-1-yl)indan-1-yloxy]phenyl}acetamide;
N-{4-[(R1S,2S)-4,6-dichloro-2-((R)-3-hydroxypyrrolidin-1-yl)indan-1-yloxy]phenyl}-N-methylmethanesulfonamide;
2-{[trans-(1S,2S)-4,6-Dichloro-1-(4-methanesulfonyl-phenoxy)-indan-2-yl]-methyl-amino}-ethanol;
2-({trans-(1S,2S)-4,6-Dichloro-1-[4-(3,5-dimethyl-[1,2,4]triazol-4-yl)-2-fluoro-phenoxy]-indan-2-yl}-methyl-amino)-ethanol;
(R)-1-{trans-(1S,2S)-4,6-Dichloro-1-[4-(2-ethyl-4-methyl-imidazol-1-yl)-phenoxy]-indan-2-yl}-pyrrolidin-3-ol;
(R)-1-{trans-(1S,2S)-4,6-Dichloro-1-[4-(2-isopropyl-4-methyl-imidazol-1-yl)-phenoxy]-indan-2-yl}-pyrrolidin-3-ol;
(R)-1-{trans-(1S,2S)-4,6-Dichloro-1-[4-(3-isopropyl-5-methyl-[1,2,4]triazol-4-yl)-phenoxy]-indan-2-yl}-pyrrolidin-3-ol;
(R)-1-{trans-(1S,2S)-4,6-Dichloro-1-[4-(3-ethyl-5-isopropyl-[1,2,4]triazol-4-yl)-phenoxy]-indan-2-yl}-pyrrolidin-3-ol;
(R)-1-{trans-(1S,2S)-6-Chloro-1-[4-(2-ethyl-4-methyl-imidazol-1-yl)-phenoxy]-4-fluoro-indan-2-yl}-pyrrolidin-3-ol;
(R)-1-{trans-(1S,2S)-6-Chloro-4-fluoro-1-[4-(2-isopropyl-4-methyl-imidazol-1-yl)-phenoxy]-indan-2-yl}-pyrrolidin-3-ol;
(R)-1-{trans-(1S,2S)-6-Chloro-4-fluoro-1-[4-(3-isopropyl-5-methyl-[1,2,4]triazol-4-yl)-phenoxy]-indan-2-yl}-pyrrolidin-3-ol;
(R)-1-{trans-(1S,2S)-6-Chloro-1-[4-(3-ethyl-5-isopropyl-[1,2,4]triazol-4-yl)-phenoxy]-4-fluoro-indan-2-yl}-pyrrolidin-3-ol;
(R)-1-{trans-(1S,2S)-1-[4-(4-tert-Butyl-2-isopropyl-imidazol-1-yl)-phenoxy]-6-chloro-4-fluoro-indan-2-yl}-pyrrolidin-3-ol;
(R)-1-{trans-(1S,2S)-4,6-Dichloro-1-[5-(2-ethyl-4-methyl-imidazol-1-yl)-2-fluoro-phenoxy]-indan-2-yl}-pyrrolidin-3-ol;
N-{trans-(1S,2S)-4,6-Dichloro-1-[4-(3,5-dimethyl-[1,2,4]triazol-4-yl)-2-fluoro-phenoxy]-indan-2-yl}N, N', N'-trimethyl ethane-1,2-diamine;
(R)-1-{trans-(1S,2S)-4,6-Dichloro-1-[4-(2,4-dimethyl-imidazol-1-yl)-2-fluoro-phenoxy]-indan-2-yl}pyrrolidin-3-ol;
(R)-1-[trans-(1S,2S)-4,6-Dichloro-1-(4-imidazol-1-yl-phenoxy)-indan-2-yl]-pyrrolidin-3-ol;
(R)-1-{trans-(1S,2S)-1-[4-(4-tert-Butyl-2-methyl-imidazol-1-yl)-2-fluoro-phenoxy]-4,6-dichloro-indan-2-yl}-pyrrolidin-3-ol;
Cyclopentyl-[rac-trans-(1,2)-1-(4-methanesulfonyl-phenoxy)-indan-2-yl]-methyl-amine;
(R)-1-{trans-(1S,2S)-4,6-Dichloro-1-[4-(2-methanesulfonyl-imidazol-1-yl)-phenoxy]-indan-2-yl}-pyrrolidin-3-ol;
(R)-1-{trans-(1S,2S)-4,6-Dichloro-1-[4-(2-isopropyl-imidazol-1-yl)-phenoxy]-indan-2-yl}-pyrrolidin-3-ol;
3-{4-[trans-(1S,2S)-4,6-Dichloro-2-((R)-3-hydroxy-pyrrolidin-1-yl)-indan-1-yloxy]-phenyl}-5-methyl-3H-[1,3,4]oxadiazol-2-one;
Cyclobutyl-[rac-trans-(1,2)-1-(4-methanesulfonyl-phenoxy)-indan-2-yl]-methyl-amine;
3-{4-[trans-(1S,2S)-4,6-Dichloro-2-((R)-3-hydroxy-pyrrolidin-1-yl)-indan-1-yloxy]-phenyl}-3H-[1,3,4]oxadiazol-2-one;
2-{4-[trans-(1S,2S)-4,6-Dichloro-2-((R)-3-hydroxy-pyrrolidin-1-yl)-indan-1-yloxy]-phenyl}-4-ethyl-2,4-dihydro-[1,2,4]triazol-3-one;
2-{4-[trans-(1S,2S)-4,6-Dichloro-2-((R)-3-hydroxy-pyrrolidin-1-yl)-indan-1-yloxy]-phenyl}-4-ethyl-5-methyl-2,4-dihydro-[1,2,4]triazol-3-one;
(R)-1-{trans-(1S,2S)-6-Chloro-1-[4-(2,4-dimethyl-imidazol-1-yl)-2-fluoro-phenoxy]-4-fluoro-indan-2-yl}-pyrrolidin-3-ol;
(R)-1-{trans-(1S,2S)-4,6-Dichloro-1-[2-fluoro-4-(2-methanesulfonyl-imidazol-1-yl)-phenoxy]-indan-2-yl}-pyrrolidin-3-ol;
1-{4-[trans-(1S,2S)-4,6-Dichloro-2-((R)-3-hydroxy-pyrrolidin-1-yl)-indan-1-yloxy]-3-fluoro-phenyl}-1H-imidazole-2-carboxylic acid methyl ester;
4-[trans-(1S,2S)-4,6-Dichloro-2-((R)-3-hydroxy-pyrrolidin-1-yl)-indan-1-yloxy]-3-fluoro-benzenesulfonamide;
(R)-1-{trans-(1S,2S)-4,6-Dichloro-1-[4-(4-methyl-piperazine-1-sulfonyl)-phenoxy]-indan-2-yl}-pyrrolidin-3-ol;
4-[trans-(1S,2S)-4,6-Dichloro-2-((R)-3-hydroxy-pyrrolidin-1-yl)-indan-1-yloxy]-benzenesulfonamide;
(R)-1-{trans-(1S,2S)-4,6-Dichloro-1-[4-(morpholine-4-sulfonyl)-phenoxy]-indan-2-yl}-pyrrolidin-3-ol and
1-{5-[trans-(1S,2S)-4,6-Dichloro-2-((R)-3-hydroxy-pyrrolidin-1-yl)-indan-1-yloxy]-2-fluoro-phenyl}-3-methyl-1,3-dihydro-imidazol-2-one;
and the pharmaceutically acceptable salts thereof.

10. A compound according to claim 1 selected from the group consisting of:
((R)-1-{trans-(1S,2S)-1-[4-(3,5-dimethyl-[1,2,4]triazol-4-yl)phenoxy]indan-2-yl}piperidin-3-yl)-(3,3,3-trifluoropropyl)amine;

2-[rac-trans-(1,2)-1-(2,4-dichloro-3-methylphenoxy)indan-2-yl]octahydropyrrolo[3,4-c]pyrrole;
2-[rac-trans-(1,2)-1-(2-fluoro-6-methoxyphenoxy)indan-2-yl]octahydropyrrolo[3,4-c]pyrrole;
2-[rac-trans-(1,2)-1-(3-chloro-2-methylphenoxy)indan-2-yl]octahydropyrrolo[3,4-c]pyrrole;
2-[rac-trans-(1,2)-1-(4-imidazol-1-ylphenoxy)indan-2-yl]octahydropyrrolo[3,4-c]pyrrole;
2-[rac-trans-(1,2)-1-(2,4-difluorophenoxy)indan-2-yl]octahydropyrrolo[3,4-c]pyrrole;
2-[rac-trans-(1,2)-1-(2-bromo-4-methylphenoxy)indan-2-yl]octahydropyrrolo[3,4-c]pyrrole;
2-[rac-trans-(1,2)-1-(2-bromophenoxy)indan-2-yl]octahydropyrrolo[3,4-c]pyrrole;
2-[rac-trans-(1,2)-1-(2-tert-butyl-4-ethylphenoxy)indan-2-yl]octahydropyrrolo[3,4-c]pyrrole;
2-[rac-trans-(1,2)-1-(3-piperazin-1-ylphenoxy)indan-2-yl]octahydropyrrolo[3,4-c]pyrrole;
2-[rac-trans-(1,2)-1-(3-piperidin-1-ylmethylphenoxy)indan-2-yl]octahydropyrrolo[3,4-c]pyrrole ;
2-[rac-trans-(1,2)-1-(3-piperidin-1-ylphenoxy)indan-2-yl]octahydropyrrolo[3,4-c]pyrrole;
2-[rac-trans-(1,2)-1-(4-fluoro-2-methylphenoxy)indan-2-yl]octahydropyrrolo[3,4-c]pyrrole;
2-[rac-trans-(1,2)-1-(4-piperazin-1-ylphenoxy)indan-2-yl]octahydropyrrolo[3,4-c]pyrrole;
2-[rac-trans-(1,2)-1-(6-chloropyridin-3-yloxy)indan-2-yl]octahydropyrrolo[3,4-c]pyrrole;
2-{rac-trans-(1,2)-1-[4-(2-methoxyethyl)phenoxy]indan-2-yl}-octahydropyrrolo[3,4-c]pyrrole;
2-{rac-trans-(1,2)-1-[4-bromo-2-(1H-pyrazol-3-yl)phenoxy]indan-2-yl}-octahydropyrrolo[3,4-c]pyrrole;
(4-methylpiperazin-1-yl)-[4-(rac-trans-(1,2)-2-pyrrolidin-1-ylindan-1-yloxy)phenyl]methanone;
(R)-1-(trans-(1R, 2R)-4,6-dichloro-1-phenoxyindan-2-yl)piperidin-3-ylamine;
(R)-1-[(1S,2S)-4,6-dichloro-1-(5-fluoroquinolin-8-yloxy)indan-2-yl]piperidin-3-ylamine;
(R)-1-[rac-trans-(1,2)-1-(1H-indol-4-yloxy)indan-2-yl]piperidin-3-ylamine;
(R)-1-[rac-trans-(1,2)-1-(2, 3-dichloro-4-methanesulfonylphenoxy)indan-2-yl]piperidin-3-ylamine;
(R)-1-[rac-trans-(1,2)-1-(2,4-difluorophenoxy)indan-2-yl]piperidin-3-ylamine;
(R)-1-[rac-trans-(1,2)-1-(2-chloro-4-methanesulfonylphenoxy)indan-2-yl]piperidin-3-ylamine;
(R)-1-[rac-trans-(1,2)-1-(2-methylbenzothiazol-5-yloxy)indan-2-yl]piperidin-3-ylamine;
(R)-1-[rac-trans-(1,2)-1-(2-tert-butyl-4-ethylphenoxy)indan-2-yl]piperidin-3-ylamine;
(R)-1-[rac-trans-(1,2)-1-(3-piperidin-1-ylmethylphenoxy)indan-2-yl]piperidin-3-ylamine;
(R)-1-[rac-trans-(1,2)-1-(3-piperidin-1-ylphenoxy)indan-2-yl]piperidin-3-ylamine;
(R)-1-[rac-trans-(1,2)-1-(4-[1,2,4]triazol-1-ylphenoxy)indan-2-yl]piperidin-3-ylamine;
(R)-1-[rac-trans-(1,2)-1-(4-imidazol-1-ylphenoxy)indan-2-yl]piperidin-3-ylamine;
(R)-1-[rac-trans-(1,2)-1-(4-piperazin-1-ylphenoxy)indan-2-yl]piperidin-3-ylamine;
(R)-1-[rac-trans-(1,2)-1-(6-chloropyridin-3-yloxy)indan-2-yl]piperidin-3-ylamine;
(R)-1-[rac-trans-(1,2)-1-(benzo[1,3]dioxol-5-yloxy)indan-2-yl]piperidin-3-ylamine;
(R)-1-[rac-trans-(1,2)-1-(isoquinolin-7-yloxy)indan-2-yl]piperidin-3-ylamine;
(R)-1-[rac-trans-(1,2)-1-(pyridin-4-yloxy)indan-2-yl]piperidin-3-ylamine;
(R)-1-[rac-trans-(1,2)-1-(quinolin-4-yloxy)indan-2-yl]piperidin-3-ylamine;
(R)-1-[trans-(1R, 2R)-4,6-dichloro-1-(2-fluoro-6-methoxyphenoxy)indan-2-yl]piperidin-3-ylamine;
(R)-1-[trans-(1S,2S)-1-(4-methanesulfonylphenoxy)indan-2-yl]piperidin-3-ylamine;
(R)-1-{rac-trans-(1,2)-1-[4-(2-methoxyethyl)phenoxy]indan-2-yl}piperidin-3-ylamine;
(R)-1-{rac-trans-(1,2)-1-[4-bromo-2-(1H-pyrazol-3-yl)phenoxy]indan-2-yl}piperidin-3-ylamine;
(R)-1-{trans-(1S,2S)-1-[4-(3,5-dimethyl-[1,2,4]triazol-4-yl)phenoxy]indan-2-yl}piperidin-3-ylamine;
(S)-1-[rac-trans-(1,2)-1-(3-chloro-5-methoxyphenoxy)indan-2-yl]piperidin-3-ylamine;
(S)-1-[rac-trans-(1,2)-1-(3-piperazin-1-ylphenoxy)indan-2-yl]piperidin-3-ylamine;
(S)-1-[rac-trans-(1,2)-1-(3-piperidin-1-ylmethylphenoxy)indan-2-yl]piperidin-3-ylamine;
(S)-1-[rac-trans-(1,2)-1-(4-[1,2,4]triazol-1-ylphenoxy)indan-2-yl]piperidin-3-ylamine;
(S)-1-[rac-trans-(1,2)-1-(4-imidazol-1-ylphenoxy)indan-2-yl]piperidin-3-ylamine;
(S)-1-[rac-trans-(1,2)-1-(4-piperazin-1-ylphenoxy)indan-2-yl]piperidin-3-ylamine;
(S)-1-[rac-trans-(1,2)-1-(quinolin-5-yloxy)indan-2-yl]piperidin-3-ylamine;
(S)-1-{rac-trans-(1,2)-1-[4-bromo-2-(1H-pyrazol-3-yl)phenoxy]indan-2-yl}piperidin-3-ylamine;
[3-(rac-trans-(1,2)-2-diethylaminoindan-1-yloxy)phenyl]urea ;
[rac-trans-(1,2)-1-(1H-indol-4-yloxy)indan-2yl]methylpiperidin-3-ylamine;
[rac-trans-(1,2)-1-(2-fluoro-6-methoxyphenoxy)indan-2-yl]-methylpiperidin-4-ylamine;
[rac-trans-(1,2)-4,6-dichloro-1-(4-imidazol-1-ylphenoxy)indan-2-yl]-dimethylamine;
[trans-(1S,2S)-4,6-dichloro-1-(4-methanesulfonylphenoxy)indan-2-yl]-(2-methoxyethyemethylamine;
{(R)-1-[trans-(1S,2S)-1-(4-methanesulfonylphenoxy)indan-2-yl]piperidin-3-yl}-(2,2,2-trifluoroethyl)amine;
{(R)-1-[trans-(1S,2S)-1-(4-methanesulfonylphenoxy)indan-2-yl]piperidin-3-yl}-(3,3,3-trifluoropropyl)amine;
{3-[rac-trans-(1,2)-2-((R)-3-aminopiperidin-1-yl)indan-1-yloxy]phenyl}urea;
{3-[rac-trans-(1,2)-2-((S)-3-aminopiperidin-1-yl)indan-1-yloxy]phenyl}urea;
{3-[rac-trans-(1,2)-2-(3-aminomethylpyrrolidin-1-yl)indan-1-yloxy]phenyl}urea;
{3-[rac-trans-(1,2)-2-(3-aminopyrrolidin-1-yl)indan-1-yloxy]phenyl}urea;
{3-[rac-trans-(1,2)-2-(4-aminomethylpiperidin-1-yl)indan-1-yloxy]phenyl}urea;
{4-[rac-trans-(1,2)-2-(3-aminomethylpyrrolidin-1-yl)indan-1-yloxy]phenyl}carbamic acid benzyl ester;
{4-[rac-trans-(1,2)-2-(3-aminopyrrolidin-1-yl)indan-1-yloxy]phenyl}carbamic acid benzyl ester;
{trans-(1S,2S)-4,6-dichloro-1-[4-(3,5-dimethyl-[1,2,4]triazol-4-yl)phenoxy]indan-2-yl}-(2-methoxyethyl)methylamine;
1-[1-(2-chloro-4-nitrophenoxy)indan-2-yl]pyrrolidine;
1-[3-(rac-trans-(1,2)-2-pyrrolidin-1-ylindan-1-yloxy)phenyl]-1,3-dihydroimidazol-2-one;
1-[3-(rac-trans-(1,2)-2-pyrrolidin-1-ylindan-1-yloxy)phenyl]pyrrolidin-2-one;

1-[3-(rac-trans-(1,2)-2-pyrrolidin-1-ylindan-1-yloxy)phenyl]pyrrolidine-2,5-dione;
1-[rac-cis-(1,2)-1-(4-methanesulfonylphenoxy)indan-2-yl]-1H-imidazole;
1-[rac-trans-(1,2)-1-(1H-indol-6-yloxy)indan-2-yl]pyrrolidin-3-ylamine;
1-[rac-trans-(1,2)-1-(2,3-dichloro-4-methanesulfonylphenoxy)indan-2-yl]pyrrolidine;
1-[rac-trans-(1,2)-1-(2,6-dichloro-4-methanesulfonylphenoxy)indan-2-yl]pyrrolidine;
1-[rac-trans-(1,2)-1-(2-chloro-4-methanesulfonylphenoxy)indan-2-yl]pyrrolidine;
1-[rac-trans-(1,2)-1-(2-fluoro-6-methoxyphenoxy)indan-2-yl]pyrrolidin-3-ylamine;
1-[rac-trans-(1,2)-1-(2-tert-butyl-4-ethylphenoxy)indan-2-yl]pyrrolidin-3-ylamine;
1-[rac-trans-(1,2)-1-(3-chloro-4-methanesulfonylphenoxy)indan-2-yl]pyrrolidine;
1-[rac-trans-(1,2)-1-(3-methanesulfonylphenoxy)indan-2-yl]pyrrolidine;
1-[rac-trans-(1,2)-1-(3-piperazin-1-ylphenoxy)indan-2-yl]pyrrolidin-3-ylamine;
1-[rac-trans-(1,2)-1-(4-methanesulfonyl-3-methylphenoxy)indan-2-yl]pyrrolidine;
1-[rac-trans-(1,2)-1-(4-methanesulfonylphenoxy)indan-2-yl]piperazine;
1-[rac-trans-(1,2)-1-(4-methanesulfonylphenoxy)indan-2-yl]pyrrolidine;
1-[rac-trans-(1,2)-1-(quinolin-4-yloxy)indan-2-yl]pyrrolidin-3-ylamine;
1-{rac-trans-(1,2)-1-[4-(2-methoxyethyl)phenoxy]indan-2-yl}pyrrolidin-3-ylamine;
1-{rac-trans-(1,2)-1-[4-bromo-2-(1H-pyrazol-3-yl)phenoxy]indan-2-yl}piperidin-4-ylamine;
1-methyl-3-[3-(rac-trans-(1,2)-2-pyrrolidin-1-ylindan-1-yloxy)phenyl]-1,3-dihydroimidazol-2-one;
2,2,2-trifluoro-N-{(R)-1-[trans-(1S,2S)-1-(4-methanesulfonylphenoxy)indan-2-yl]piperidin-3-yl}acetamide;
2,3-dichloro-4-(rac-trans-(1,2)-2-diethylaminoindan-1-yloxy)benzenesulfonamide;
2,3-dichloro-4-(rac-trans-(1,2)-2-dimethylaminoindan-1-yloxy)benzenesulfonamide;
2,3-dichloro-4-(rac-trans-(1,2)-2-pyrrolidin-1-ylindan-1-yloxy)benzenesulfonamide;
2,3-dichloro-4-[rac-trans-(1,2)-2-((R)-3-methoxypyrrolidin-1-yl)indan-1-yloxy]benzenesulfonamide;
2,3-dichloro-4-[rac-trans-(1,2)-2-(methylpiperidin-3-ylamino)indan-1-yloxy]benzenesulfonamide;
2,3-dichloro-4-[trans-(1S,2S)-2-(3-hydroxypiperidin-1-yl)indan-1-yloxy]benzenesulfonamide;
2,3-dichloro-N,N-dimethyl-4-(rac-trans-(1,2)-2-pyrrolidin-1-ylindan-1-yloxy)benzenesulfonamide;
2-[3-(rac-trans-(1,2)-2-pyrrolidin-1-ylindan-1-yloxy)phenyl]isothiazolidine-1,1-dioxide;
2-[4-(rac-trans-(1,2)-2-pyrrolidin-1-ylindan-1-yloxy)phenyl]thiazole;
2-[rac-trans-(1,2)-2-(3-aminomethylpyrrolidin-1-yl)indan-1-yloxy]-6-fluorobenzonitrile ;
2-[rac-trans-(1,2)-2-(3-aminopyrrolidin-1-yl)indan-1-yloxy]-5-chlorobenzonitrile;
2-[rac-trans-(1,2)-2-(4-aminomethylpiperidin-1-yl)indan-1-yloxy]-5-chlorobenzonitrile ;
2-{4-[rac-trans-(1,2)-2-((R)-3-aminopiperidin-1-yl)indan-1-yloxy]phenyl}-thiazole-4-carbonitrile;
2-chloro-4-(rac-trans-(1,2)-2-pyrrolidin-1-ylindan-1-yloxy)benzonitrile;
2-chloro-4-[rac-trans-(1,2)-2-(hexahydropyrrolo[3,4-c]pyrrol-2-yl)indan-1-yloxy]benzonitrile;
2-fluoro-4-[rac-trans-(1,2)-2-(hexahydropyrrolo[3,4-c]pyrrol-2-yl)indan-1-yloxy]benzonitrile;
2-fluoro-6-[rac-trans-(1,2)-2-(hexahydropyrrolo[3,4-c]pyrrol-2-yl)indan-1-yloxy]benzonitrile;
3-(rac-trans-(1,2)-2-pyrrolidin-1-ylindan-1-yloxy)phenylamine;
3,5-dichloro-4-(rac-trans-(1,2)-2-pyrrolidin-1-ylindan-1-yloxy)benzenesulfonamide;
3,5-dichloro-N,N-dimethyl-4-(rac-trans-(1,2)-2-pyrrolidin-1-ylindan-1-yloxy)benzenesulfonamide;
3,5-dimethyl-4-[3-(rac-trans-(1,2)-2-pyrrolidin-1-ylindan-1-yloxy)phenyl]-4H-[1,2,4]triazole;
3,5-dimethyl-4-[4-(rac-trans-(1,2)-2-pyrrolidin-1-ylindan-1-yloxy)phenyl]-4H-[1,2,4]triazole;
3,5-dimethyl-4-[4-(trans-(1S,2S)-2-pyrrolidin-1-ylindan-1-yloxy)-3-trifluoromethylphenyl]-4H-[1,2,4]triazole;
3,5-dimethyl-4-[4-(trans-(1S,2S)-2-pyrrolidin-1-ylindan-1-yloxy)phenyl]-isoxazole;
3,5-dimethyl-4-[5-methyl-2-(trans-(1S,2S)-2-pyrrolidin-1-ylindan-1-yloxy)phenyl]isoxazole;
3-[3-(rac-trans-(1,2)-2-pyrrolidin-1-ylindan-1-yloxy)phenyl]oxazolidin-2-one;
3-[rac-trans-(1,2)-2-(hexahydropyrrolo[3,4-c]pyrrol-2-yl)indan-1-yloxy]benzamide;
3-[rac-trans-(1,2)-2-((R)-3-aminopiperidin-1-yl)indan-1-yloxy]benzamide;
3-[rac-trans-(1,2)-2-((S)-3-aminopiperidin-1-yl)indan-1-yloxy]benzamide;
3-[rac-trans-(1,2)-2-(3-aminomethylpyrrolidin-1-yl)indan-1-yloxy]benzamide;
3-[rac-trans-(1,2)-2-(3-aminopyrrolidin-1-yl)indan-1-yloxy]benzamide;
3-chloro-4-(2-pyrrolidin-1-ylindan-1-yloxy)pyridine;
3-chloro-4-(rac-trans-(1,2)-2-pyrrolidin-1-ylindan-1-yloxy)benzenesulfonamide;
3-chloro-4-[rac-trans-(1,2)-2-(hexahydropyrrolo[3,4-c]pyrrol-2-yl)indan-1-yloxy]benzonitrile;
3-chloro-N,N-dimethyl-4-(rac-trans-(1,2)-2-pyrrolidin-1-ylindan-1-yloxy)benzenesulfonamide;
3-cyclopropyl-5-methyl-4-[4-(rac-trans-(1,2)-2-pyrrolidin-1-ylindan-1-yloxy)phenyl]-4H-[1,2,4]triazole;
3-fluoro-4-(2-pyrrolidin-1-ylindan-1-yloxy)benzenesulfonamide;
3-methyl-4-[4-(rac-trans-(1,2)-2-pyrrolidin-1-ylindan-1-yloxy)phenyl]-4H-[1,2,4]triazole
4-((1S,2S)-2-azetidin-1-yl-4,6-dichloroindan-1-yloxy)-3-fluorobenzonitrile;
4-((1S,2S)-4,6-dichloro-2-piperazin-1-ylindan-1-yloxy)-3-fluorobenzonitrile;
4-(2-benzylaminoindan-1-yloxy)-3-fluorobenzenesulfonamide;
4-(2-cyclopentylaminoindan-1-yloxy)-3-fluorobenzenesulfonamide;
4-(rac-trans-(1,2)-(R)-2-,[3,']bipyrrolidinyl-1'-ylindan-1-yloxy)benzenesulfonamide;
4-(rac-trans-(1,2)-2-azepan-1-ylindan-1-yloxy)benzenesulfonamide;
4-(rac-trans-(1,2)-2-piperidin-1-ylindan-1-yloxy)benzenesulfonamide;
4-(rac-trans-(1,2)-2-pyrrolidin-1-ylindan-1-yloxy)benzenesulfonamide;
4-(rac-trans-(1,2)-2-pyrrolidin-1-ylindan-1-yloxy)benzoic acid methyl ester;
4-(rac-trans-(1,2)-2-pyrrolidin-1-ylindan-1-yloxy)benzonitrile;

4-(rac-trans-(1,2)-2-pyrrolidin-1-ylindan-1-yloxy)-N-(2,2,2-trifluoroethyl)benzenesulfonamide;
4-(rac-trans-(1,2)-2-pyrrolidin-1-ylindan-1-yloxy)-N-(3,3,3-trifluoropropyl)benzenesulfonamide;
4-(trans-(1S,2S)-4,6-dichloro-2-piperazin-1-ylindan-1-yloxy)-3-fluorobenzonitrile;
4-[(1R, 2S)-1-(2-chloro-4-nitrophenoxy)indan-2-yl]morpholine;
4-[(1S,2S)-2-((R)-3-aminopiperidin-1-yl)-4,6-dichloroindan-1-yloxy]-3-fluorobenzonitrile;
4-[(1S,2S)-4,6-dichloro-2-(4-methylpiperazin-1-yl)indan-1-yloxy]-3-fluorobenzonitrile;
4-[2, 3-dimethyl-4-(rac-trans-(1,2)-2-pyrrolidin-1-ylindan-1-yloxy)phenyl]-3,5-dimethyl-4H -[1,2,4]triazole;
4-[2-fluoro-5-(trans-(1S,2S)-2-pyrrolidin-1-ylindan-1-yloxy)phenyl]-3,5-dimethylisoxazole;
4-[3-chloro-4-(rac-trans-(1,2)-2-pyrrolidin-1-ylindan-1-yloxy)phenyl]-3,5-dimethyl-4H -[1,2,4]triazole;
4-[3-chloro-4-(trans-(1S,2S)-2-pyrrolidin-1-ylindan-1-yloxy)phenyl]-3,5-dimethyl-4H -[1,2,4]triazole;
4-[3-fluoro-4-(-2-methyl-2-pyrrolidin-1-ylindan-1-yloxy)phenyl]-3,5-dimethyl-4H -[1,2,4]triazole;
4-[5-fluoro-2-(trans-(1S,2S)-2-pyrrolidin-1-ylindan-1-yloxy)phenyl]-3,5-dimethylisoxazole;
4-[rac-trans-(1,2)-2-(hexahydropyrrolo[3,4-c]pyrrol-2-yl)indan-1-yloxy]-1H-indole;
4-[rac-trans-(1,2)-2-(hexahydropyrrolo[3,4-c]pyrrol-2-yl)indan-1-yloxy]-2,6-dimethylbenzonitrile;
4-[rac-trans-(1,2)-2-((R)-3-aminopiperidin-1-yl)indan-1-yloxy]-2,3-dichlorobenzenesulfonamide;
4-[rac-trans-(1,2)-2-((R)-3-aminopiperidin-1-yl)indan-1-yloxy]-2,3-dichloro-N,N -dimethylbenzenesulfonamide;
4-[rac-trans-(1,2)-2-((R)-3-aminopiperidin-1-yl)indan-1-yloxy]-2-chlorobenzonitrile;
4-[rac-trans-(1,2)-2-((R)-3-aminopiperidin-1-yl)indan-1-yloxy]-2-fluorobenzonitrile;
4-[rac-trans-(1,2)-2-((R)-3-aminopiperidin-1-yl)indan-1-yloxy]-3-chlorobenzonitrile;
4-[rac-trans-(1,2)-2-((R)-3-aminopiperidin-1-yl)indan-1-yloxy]benzamide;
4-[rac-trans-(1,2)-2-((R)-3-hydroxymethylpyrrolidin-1-yl)indan-1-yloxy]benzenesulfonamide;
4-[rac-trans-(1,2)-2-((R)-3-hydroxypyrrolidin-1-yl)indan-1-yloxy]benzenesulfonamide;
4-[rac-trans-(1,2)-2-((S)-3-aminopiperidin-1-yl)indan-1-yloxy]-2,3-dichlorobenzenesulfonamide;
4-[rac-trans-(1,2)-2-((S)-3-aminopiperidin-1-yl)indan-1-yloxy]benzamide;
4-[rac-trans-(1,2)-2-(3-aminomethylpyrrolidin-1-yl)indan-1-yloxy]-2,3-dichlorobenzenesulfonamide;
4-[rac-trans-(1,2)-2-(3-aminomethylpyrrolidin-1-yl)indan-1-yloxy]-2,6-dimethylbenzonitrile;
4-[rac-trans-(1,2)-2-(3-aminomethylpyrrolidin-1-yl)indan-1-yloxy]-2-chlorobenzonitrile;
4-[rac-trans-(1,2)-2-(3-aminomethylpyrrolidin-1-yl)indan-1-yloxy]-3-chlorobenzonitrile;
4-[rac-trans-(1,2)-2-(3-aminopynolidin-1-yl)indan-1-yloxy]-2,3-dichlorobenzenesulfonamide;
4-[rac-trans-(1,2)-2-(3-aminopyrrolidin-1-yl)indan-1-yloxy]-3-chlorobenzonitrile;
4-[rac-trans-(1,2)-2-(3-aminopyrrolidin-1-yl)indan-1-yloxy]benzamide;
4-[rac-trans-(1,2)-2-(4-aminomethylpiperidin-1-yl)indan-1-yloxy]-2,3-dichlorobenzenesulfonamide;
4-[rac-trans-(1,2)-2-(4-aminomethylpiperidin-1-yl)indan-1-yloxy]-2-chlorobenzonitrile;
4-[rac-trans-(1,2)-2-(4-aminomethylpiperidin-1-yl)indan-1-yloxy]-3-chlorobenzonitrile;
4-[rac-trans-(1,2)-2-(4-aminomethylpiperidin-1-yl)indan-1-yloxy]benzamide;
4-[trans-(1S,2S)-2-((R)-3-aminopiperidin-1-yl)-4,6-dichloroindan-1-yloxy]-3-fluorobenzonitrile;
4-[trans-(1S,2S)-2-((R)-3-aminopiperidin-1-yl)indan-1-yloxy]benzenesulfonamide;
4-[trans-(1S,2S)-4,6-dichloro-2-((R)-3-hydroxypyrrolidin-1-yl)indan-1-yloxy]-3-fluorobenzonitrile;
4-[trans-(1S,2S)-4,6-dichloro-2-((S)-3-hydroxypyrrolidin-1-yl)indan-1-yloxy]-3-fluorobenzonitrile;
4-[trans-(1S,2S)-4,6-dichloro-2-(4-methyl-[1,4]diazepan-1-yl)indan-1-yloxy]-3-fluorobenzonitrile;
4-[trans-(1S,2S)-6-chloro-4-fluoro-2-((R)-3-hydroxypyrrolidin-1-yl)indan-1-yloxy]-3-fluorobenzonitrile;
5-(rac-trans-(1,2)-2-diethylaminoindan-1-yloxy)-1,3-dimethyl-1,3-dihydro-indol-2-one;
5-(rac-trans-(1,2)-2-pyrrolidin-1-ylindan-1-yloxy)-3H-isobenzofuran-1-one;
5-[5-fluoro-2-(trans-(1S,2S)-2-pyrrolidin-1-ylindan-1-yloxy)phenyl]-1H-pyrazole;
5-[rac-trans-(1,2)-2-(hexahydropyrrolo[3,4-c]pyrrol-2-yl)indan-1-yloxy]-2-methylbenzothiazole;
5-[rac-trans-(1,2)-2-(hexahydropyrrolo[3,4-c]pyrrol-2-yl)indan-1-yloxy]benzo[1,3]oxathiol-2-one;
5-[rac-trans-(1,2)-2-((R)-3-aminopiperidin-1-yl)indan-1-yloxy]benzo[1,3]oxathiol-2-one;
6-[rac-trans-(1,2)-2-(hexahydropyrrolo[3,4-c]pyrrol-2-yl)indan-1-yloxy]-1H-indole;
7-[rac-trans-(1,2)-2-(hexahydropynolo[3,4-c]pyrrol-2-yl)indan-1-yloxy]-isoquinoline;
7-[rac-trans-(1,2)-1-(4-methanesulfonylphenoxy)indan-2-yl]-5,6,7,8-tetrahydro-[1,2,4]triazolo[4,3-a]pyrazine;
8-((1S,2S)-2-azetidin-1-yl-4,6-dichloroindan-1-yloxy)-5-fluoroquinoline;
8-((1S,2S)-4,6-dichloro-2-piperazin-1-ylindan-1-yloxy)-5-fluoroquinoline;
8-((1S,2S)-4,6-dichloro-2-pyrrolidin-1-ylindan-1-yloxy)-5-fluoroquinoline;
8-(rac-trans-(1,2)-2-pyrrolidin-1-ylindan-1-yloxy)quinoline;
benzyl[1-(4-methanesulfonylphenoxy)indan-2-yl]amine;
C-(1-{rac-trans-(1,2)-1-[4-(2-methoxyethyl)phenoxy]indan-2-yl}pyrrolidin-3-yl)methylamine;
C-(1-{rac-trans-(1,2)-1-[4-bromo-2-(1H-pyrazol-3-yl)phenoxy]indan-2-yl}piperidin-4-yl)methylamine;
C-(1-{rac-trans-(1,2)-1-[4-bromo-2-(1H-pyrazol-3-yl)phenoxy]indan-2-yl}pyrrolidin-3-yl)methylamine;
C-{1-[rac-trans-(1,2)-1-(1H-indol-4-yloxy)indan-2-yl]pyrrolidin-3-yl}methylamine;
C-{1-[rac-trans-(1,2)-1-(2,4-difluorophenoxy)indan-2-yl]pyrrolidin-3-yl}methylamine;
C-{1-[rac-trans-(1,2)-1-(2-bromo-4-methylphenoxy)indan-2-yl]piperidin-4-yl}methylamine;
C-{1-[rac-trans-(1,2)-1-(2-fluoro-6-methoxyphenoxy)indan-2-yl]piperidin-4-yl}methylamine;
C-{1-[rac-trans-(1,2)-1-(2-fluoro-6-methoxyphenoxy)indan-2-yl]pyrrolidin-3-yl}methylamine;
C-{1-[rac-trans-(1,2)-1-(2-methoxy-5-methylphenoxy)indan-2-yl]piperidin-4-yl}methylamine;
C-{1-[rac-trans-(1,2)-1-(2-methoxy-5-methylphenoxy)indan-2-yl]pyrrolidin-3-yl}methylamine;
C-{1-[rac-trans-(1,2)-1-(2-methylbenzothiazol-5-yloxy)indan-2-yl]pyrrolidin-3-yl}methylamine;
C-{1-[rac-trans-(1,2)-1-(2-tert-butyl-4-ethylphenoxy)indan-2-yl]piperidin-4-yl}methylamine;

C-{1-[rac-trans-(1,2)-1-(2-tert-butyl-4-ethylphenoxy)indan-2-yl]pyrrolidin-3-yl}methylamine;
C-{1-[rac-trans-(1,2)-1-(3-chloro-2-methylphenoxy)indan-2-yl]pyrrolidin-3-yl}methylamine;
C-{1-[rac-trans-(1,2)-1-(3-chloro-5-methoxyphenoxy)indan-2-yl]piperidin-4-yl}methylamine;
C-{1-[rac-trans-(1,2)-1-(3-chloro-5-methoxyphenoxy)indan-2-yl]pyrrolidin-3-yl}methylamine ;
C-{1-[rac-trans-(1,2)-1-(3-ethoxyphenoxy)indan-2-yl]piperidin-4-yl}methylamine;
C-{1-[rac-trans-(1,2)-1-(3-ethoxyphenoxy)indan-2-yl]pyrrolidin-3-yl}methylamine;
C-{1-[rac-trans-(1,2)-1-(3-piperazin-1-ylphenoxy)indan-2-yl]piperidin-4-yl}methylamine;
C-{1-[rac-trans-(1,2)-1-(3-piperazin-1-ylphenoxy)indan-2-yl]pyrrolidin-3-yl}methylamine;
C-{1-[rac-trans-(1,2)-1-(4-[1,2,4]triazol-1-ylphenoxy)indan-2-yl]pyrrolidin-3-yl}methylamine;
C-{1-[rac-trans-(1,2)-1-(4-piperazin-1-ylphenoxy)indan-2-yl]piperidin-4-yl}methylamine;
C-{1-[rac-trans-(1,2)-1-(benzo[1,3]dioxol-5-yloxy)indan-2-yl]piperidin-4-yl}methylamine;
C-{1-[rac-trans-(1,2)-1-(benzo[1,3]dioxol-5-yloxy)indan-2-yl]pyrrolidin-3-yl}methylamine;
C-{1-[rac-trans-(1,2)-1-(quinolin-4-yloxy)indan-2-yl]piperidin-4-yl}methylamine;
diethyl[rac-trans-(1,2)-1-(2-methylbenzothiazol-5-yloxy)indan-2-yl]amine;
diethyl[rac-trans-(1,2)-1-(3-piperazin-1-ylphenoxy)indan-2-yl]amine;
diethyl[rac-trans-(1,2)-1-(4-piperazin-1-ylphenoxy)indan-2-yl]amine;
methyl[rac-trans-(1,2)-1-(3-piperazin-1-ylphenoxy)indan-2-yl]piperidin-4-ylamine;
methyl[rac-trans-(1,2)-1-(4-piperazin-1-ylphenoxy)indan-2-yl]piperidin-4-ylamine;
N-(3-{trans-(1S,2S)-2-[(R)-3-(2-fluoroethylamino)piperidin-1-yl]indan-1-yloxy}phenyl)acetamide;
N-(3-{trans-(1S,2S)-2-[(R)-3-(3,3,3-trifluoropropylamino)piperidin-1-yl]indan-1-yloxy}phenyl)acetamide;
N, N-diethyl-4-(rac-trans-(1,2)-2-pyrrolidin-1-ylindan-1-yloxy)benzamide;
N-[2-(rac-trans-(1,2)-2-pyrrolidin-1-ylindan-1-yloxy)phenyl]acetamide;
N-[3-(rac-trans-(1,2)-2-azepan-1-ylindan-1-yloxy)phenyl]acetamide;
N-[3-(rac-trans-(1,2)-2-diethylaminoindan-1-yloxy)phenyl]acetamide;
N-[3-(rac-trans-(1,2)-2-dimethylaminoindan-1-yloxy)phenyl]acetamide;
N-[3-(rac-trans-(1,2)-2-piperazin-1-ylindan-1-yloxy)phenyl]acetamide;
N-[3-(rac-trans-(1,2)-2-pyrrolidin-1-ylindan-1-yloxy)phenyl]acetamide;
N-[3-(rac-trans-(1,2)-2-thiomorpholin-4-ylindan-1-yloxy)phenyl]acetamide;
N-[3-(rac-trans-(1,2)-4,6-dichloro-2-dimethylaminoindan-1-yloxy)phenyl]acetamide;
N-[3-(trans-(1S,2S)-2-piperidin-1-ylindan-1-yloxy)phenyl]acetamide;
N-[4-(rac-trans-(1,2)-2-pyrrolidin-1-ylindan-1-yloxy)phenyl]acetamide;
N-[4-(rac-trans-(1,2)-2-pyrrolidin-1-ylindan-1-yloxy)pyridin-2-yl]acetamide;
N-[6-(rac-trans-(1,2)-2-pyrrolidin-1-ylindan-1-yloxy)pyridin-2-yl]acetamide;
N-[rac-trans-(1,2)-1-(4-methanesulfonylphenoxy)indan-2-yl]-N, N', N'-trimethylpropane-1,3-diamine;
N-[rac-trans-(1,2)-3-((R)-2-[1,3]bipyrrolidinyl-1'-ylindan-1-yloxy)phenyl]acetamide;
N-[trans-(1S,2S)-4,6-dichloro-1-(4-methanesulfonylphenoxy)indan-2-yl]-N,N',N'-trimethylethane-1,2-diamine;
N-[trans-(1S,2S)-4,6-dichloro-1-(4-methanesulfonylphenoxy)indan-2-yl]-N,N',N'-trimethylpropane-1,3-diamine;
N-{3-[rac-trans-(1,2)-2-(hexahydropyrrolo[3,4-c]pyrrol-2-yl)indan-1-yloxy]phenyl}acetamide;
N-{3-[rac-trans-(1,2)-2-((R)-3-aminopiperidin-1-yl)indan-1-yloxy]phenyl}acetamide;
N-{3-[rac-trans-(1,2)-2-((R)-3-hydroxymethylpyrrolidin-1-yl)indan-1-yloxy]phenyl}acetamide;
N-{3-[rac-trans-(1,2)-2-((R)-3-hydroxypyrrolidin-1-yl)indan-1-yloxy]phenyl}acetamide;
N-{3-[rac-trans-(1,2)-2-((R)-3-methoxypyrrolidin-1-yl)indan-1-yloxy]phenyl}acetamide;
N-{3-[rac-trans-(1,2)-2-((S)-3-aminopiperidin-1-yl)indan-1-yloxy]phenyl}acetamide;
N-{3-[rac-trans-(1,2)-2-(3-aminomethylpyrrolidin-1-yl)indan-1-yloxy]phenyl}acetamide;
N-{3-[rac-trans-(1,2)-2-(3-aminopyrrolidin-1-yl)indan-1-yloxy]phenyl}acetamide;
N-{3-[rac-trans-(1,2)-2-(4-aminomethylpiperidin-1-yl)indan-1-yloxy]phenyl}acetamide;
N-{3-[trans-(1S,2S)-2-((R)-3-aminopiperidin-1-yl)indan-1-yloxy]phenyl}acetamide;
N-{3-[trans-(1S,2S)-2-((R)-3-dimethylaminopiperidin-1-yl)indan-1-yloxy]phenyl}acetamide;
N-ethyl-4-(rac-trans-(1,2)-2-pyrrolidin-1-ylindan-1-yloxy)benzenesulfonamide;
3-[trans-(1S,2S)-4,6-dichloro-1-(4-[1,2,4]triazol-1-ylphenoxy)indan-2-yl]-3,8-diazabicyclo[3.2.1]octane;
2-[trans-(1S,2S)-4,6-dichloro-1-(4-methanesulfonylphenoxy)indan-2-yl]octahydropyrrolo[3,4-c]pyrrole;
2-[trans-(1S,2S)-4,6-dichloro-1-(4-methanesulfonylphenoxy)indan-2-yl]-5-methyloctahydropyrrolo[3,4-c]pyrrole;
(3R, 5S)-1-[trans-(1S,2S)-4,6-dichloro-1-(4-methanesulfonylphenoxy)indan-2-yl]-3,5-dimethylpiperazine;
(R)-1-[(1S,2S)-4,6-difluoro-1-(4-methanesulfonylphenoxy)indan-2-yl]pyrrolidin-3-ol;
(R)-1-[rac-trans-(1,2)-4-chloro-6-fluoro-1-(3-methyl-4-trifluoromethanesulfonylphenoxy)indan -2-yl]piperidin-3-ylamine;
(R)-1-[rac-trans-(1,2)-4-chloro-6-fluoro-1-(4-methanesulfonylphenoxy)indan-2-yl]piperidin-3-ylamine;
(R)-1-[rac-trans-(1,2)-6-chloro-4-fluoro-1-(3-methyl-4-trifluoromethanesulfonylphenoxy)indan -2-yl]piperidin-3-ylamine;
(R)-1-[rac-trans-(1,2)-6-chloro-4-fluoro-1-(4-methanesulfonylphenoxy)indan-2-yl]piperidin-3-ylamine;
(R)-1-[trans-(1S,2S)-4,6-dichloro-1-(2-methylbenzothiazol-5-yloxy)indan-2-yl]pyrrolidin-3-ol;
(R)-1-[trans-(1S,2S)-4,6-dichloro-1-(4-[1,2,4]triazol-1-ylphenoxy)indan-2-yl]piperidin-3-ylamine;
(R)-1-[trans-(1S,2S)-4,6-dichloro-1-(4-imidazol-1-ylphenoxy)indan-2-yl]piperidin-3-ylamine;
(R)-1'-[trans-(1S,2S)-4,6-dichloro-1-(4-methanesulfonylphenoxy)indan-2-yl]-[1, 3']bipyrrolidinyl;
(R)-1-[trans-(1S,2S)-4,6-dichloro-1-(4-methanesulfonylphenoxy)indan-2-yl]-3-fluoropyrrolidine;
(R)-1-[trans-(1S,2S)-4,6-dichloro-1-(4-methanesulfonylphenoxy)indan-2-yl]-3-methylpiperazine;

(R)-1-[trans-(1S,2S)-4,6-dichloro-1-(4-methanesulfonylphenoxy)indan-2-yl]piperidin-3-ylamine;
(R)-1-[trans-(1S,2S)-4,6-dichloro-1-(4-methanesulfonylphenoxy)indan-2-yl]pynolidin-3-ol;
(R)-1-[trans-(1S,2S)-4,6-dichloro-1-(4-methanesulfonylphenoxy)indan-2-yl]pyrrolidin-3-ylamine;
(R)-1-[trans-(1S,2S)-4,6-dichloro-1-(4-methanesulfonylphenoxy)indan-2-yl]pyrrolidine-3-carbonitrile;
(R)-1-[trans-(1S,2S)-6-chloro-1-(2-chloro-4-methanesulfonylphenoxy)-4-fluoroindan-2-yl]pyrrolidin-3-ol;
(R)-1-[trans-(1S,2S)-6-chloro-1-(2-chloro-4-methanesulfonylphenoxy)indan-2-yl]pyrrolidin-3-ol
(R)-1-[trans-(1S,2S)-6-chloro-4-fluoro-1-(4-methanesulfonylphenoxy)indan-2-yl]pyrrolidin-3-ol;
(R)-1-{(1S,2S)-1-[2-chloro-4-(3,5-dimethyl-[1,2,4]triazol-4-yl)phenoxy]-4,6-difluoroindan-2-yl}pynolidin-3-ol;
(R)-1-{(1S,2S)-1-[4-(3,5-dimethyl-[1,2,4]triazol-4-yl)-2-fluorophenoxy]-4,6-difluoroindan-2-yl}pyrrolidin-3-ol;
(R)-1-{(1S,2S)-4,6-dichloro-1-[4-(3,5-dimethyl-[1,2,4]triazol-4-yl)phenoxy]indan-2-yl}-3-methylpyrrolidin-3-ol;
(R)-1-{(1S,2S)-4,6-dichloro-1-[4-(5-methyltetrazol-1-yl)phenoxy]indan-2-yl}pyrrolidin-3-ol;
(R)-1-{(1S,2S)-4,6-dichloro-1-[4-fluoro-2-(1H-pyrazol-3-yl)phenoxy]indan-2-yl}piperidin-3-ylamine;
(R)-1-{(1S,2S)-4,6-dichloro-1-[5-(3,5-dimethyl-[1,2,4]triazol-4-yl)-2-fluorophenoxy]indan-2-yl}pyrrolidin-3-ol;
(R)-1-{trans-(1S,2S)-4,6-dichloro-1-[2-chloro-4-(3,5-dimethyl-[1,2,4]triazol-4-yl)phenoxy]indan-2-yl}pyrrolidin-3-ol;
(R)-1-{trans-(1S,2S)-4,6-dichloro-1-[3-(1,1-dioxo-1lambda6-isothiazolidin-2-yl)phenoxy]indan-2-yl}pyrrolidin-3-ol;
(R)-1-{trans-(1S,2S)-4,6-dichloro-1-[4-(1,3,5-trimethyl-1H-pyrazol-4-yl)phenoxy]indan-2-yl}pyrrolidin-3-ol;
(R)-1-{trans-(1S,2S)-4,6-dichloro-1-[4-(2,4-dimethylthiazol-5-yl)phenoxy]indan-2-yl}pyrrolidin-3-ol;
(R)-1-{trans-(1S,2S)-4,6-dichloro-1-[4-(3,5-dimethyl-[1,2,4]triazol-4-yl)-2,3-difluorophenoxy]indan-2-yl}pyrrolidin-3-ol;
(R)-1-{trans-(1S,2S)-4,6-dichloro-1-[4-(3,5-dimethyl-[1,2,4]triazol-4-yl)-2,3-dimethylphenoxy]indan-2-yl}pyrrolidin-3-ol;
(R)-1-{trans-(1S,2S)-4,6-dichloro-1-[4-(3,5-dimethyl-[1,2,4]triazol-4-yl)-2-fluorophenoxy]indan-2-yl}pyrrolidin-3-ol;
(R)-1-{trans-(1S,2S)-4,6-dichloro-1-[4-(3,5-dimethyl-[1,2,4]triazol-4-yl)-2-methylphenoxy]indan-2-yl}pyrrolidin-3-ol;
(R)-1-{trans-(1S,2S)-4,6-dichloro-1-[4-(3,5-dimethyl-[1,2,4]triazol-4-yl)phenoxy]indan-2-yl}piperidin-3-ol;
(R)-1-{trans-(1S,2S)-4,6-dichloro-1-[4-(3,5-dimethyl-[1,2,4]triazol-4-yl)phenoxy]indan-2-yl}pyrrolidin-3-ol;
(R)-1-{trans-(1S,2S)-4,6-dichloro-1-[4-(3,5-dimethyl-[1,2,4]triazol-4-yl)phenoxy]indan-2-yl}pyrrolidine-3-carbonitrile;
(R)-1-{trans-(1S,2S)-4,6-dichloro-1-[4-(3,5-dimethylisoxazol-4-yl)phenoxy]indan-2-yl}pyrrolidin-3-ol;
(R)-1-{trans-(1S,2S)-4,6-dichloro-1-[4-(3,5-dimethylpyrazol-1-yl)-2-fluorophenoxy]indan-2-yl}pyrrolidin-3-ol;
(R)-1-{trans-(1S,2S)-4,6-dichloro-1-[4-fluoro-2-(2H-pyrazol-3-yl)phenoxy]indan-2-yl}pyrrolidin-3-ol;
(R)-1-{trans-(1S,2S)-6-chloro-1-[2-chloro-4-(3,5-dimethyl-[1,2,4]triazol-4-yl)phenoxy]-4-fluoroindan-2-yl}pyrrolidin-3-ol;
(R)-1-{trans-(1S,2S)-6-chloro-1-[2-chloro-4-(3,5-dimethyl-[1,2,4]triazol-4-yl)phenoxy]indan-2-yl}pyrrolidin-3-ol;
(R)-1-{trans-(1S,2S)-6-chloro-1-[4-(1,3,5-trimethyl-1H-pyrazol-4-yl)phenoxy]indan-2-yl}pyrrolidin-3-ol;
(R)-1-{trans-(1S,2S)-6-chloro-1-[4-(3,5-dimethyl-[1,2,4]triazol-4-yl)-2,3-dimethylphenoxy]-4-fluoroindan-2-yl}pyrrolidin-3-ol;
(R)-1-{trans-(1S,2S)-6-chloro-1-[4-(3,5-dimethyl-[1,2,4]triazol-4-yl)-2-fluorophenoxy]-4-fluoroindan-2-yl}pyrrolidin-3-ol;
(R)-1-{trans-(1S,2S)-6-chloro-1-[4-(3,5-dimethyl-[1,2,4]triazol-4-yl)-2-fluorophenoxy]indan-2-yl}pyrrolidin-3-ol;
(R)-1-{trans-(1S,2S)-6-chloro-1-[4-(3,5-dimethyl-[1,2,4]triazol-4-yl)phenoxy]-4-fluoroindan-2-yl}pyrrolidin-3-ol;
(R)-1-{trans-(1S,2S)-6-chloro-1-[4-(3,5-dimethyl-[1,2,4]triazol-4-yl)phenoxy]indan-2-yl}pyrrolidin-3-ol;
(S)-1-[(1S,2S)-4,6-dichloro-1-(4-methanesulfonylphenoxy)indan-2-yl]-3-methylpyrrolidin-3-ol;
(S)-1-[trans-(1S,2S)-4,6-dichloro-1-(4-methanesulfonylphenoxy)indan-2-yl]-2-pyrrolidin-1-ylmethylpyrrolidine;
(S)-1-[trans-(1S,2S)-4,6-dichloro-1-(4-methanesulfonylphenoxy)indan-2-yl]-3-fluoropyrrolidine;
(S)-1-[trans-(1S,2S)-4,6-dichloro-1-(4-methanesulfonylphenoxy)indan-2-yl]-3-methylpiperazine;
(S)-1-[trans-(1S,2S)-4,6-dichloro-1-(4-methanesulfonylphenoxy)indan-2-yl]pyrrolidin-3-ol;
(S)-1-[trans-(1S,2S)-4,6-dichloro-1-(4-methanesulfonylphenoxy)indan-2-yl]pyrrolidin-3-ylamine;
(S)-1-{(1S,2S)-4,6-dichloro-1-[4-(3,5-dimethyl-[1,2,4]triazol-4-yl)-2-fluorophenoxy]indan-2-yl}pyrrolidin-3-ol;
(S)-1-{trans-(1S,2S)-4,6-dichloro-1-[4-(3,5-dimethyl-[1,2,4]triazol-4-yl)phenoxy]indan-2-yl}pyrrolidin-3-ol;
(S)-1-{trans-(1S,2S)-4,6-dichloro-1-[4-(3,5-dimethyl-[1,2,4]triazol-4-yl)phenoxy]indan-2-yl}pyrrolidin-3-ylamine;
(S)-2-[(S)-4-(S)-chloro-6-chloro-1-(4-methanesulfonylphenoxy)indan-2-yl]octahydropyrrolo[1,2-a]pyrazine;
(S)-2-[trans-(1S,2S)-4,6-dichloro-1-(4-methanesulfonylphenoxy)indan-2-yl]-2,5-diazabicyclo[2.2.1]heptane;
(S)-3-{3-[(1S,2S)-6-chloro-4-fluoro-2-((R)-3-hydroxypyrrolidin-1-yl)indan-1-yloxy]-4-fluorophenyl}-4-isopropyloxazolidin-2-one;
(S)-3-{4-chloro-3-[(1S,2S)-6-chloro-4-fluoro-2-((R)-3-hydroxypyrrolidin-1-yl)indan-1-yloxy]phenyl}-4-isopropyloxazolidin-2-one;
{(R)-1-[trans-(1S,2S)-4,6-dichloro-1-(4-[1,2,4]triazol-1-ylphenoxy)indan-2-yl]piperidin-3-yl}-(3,3,3-trifluoropropyl)amine;
{(R)-1-[trans-(1S,2S)-4,6-dichloro-1-(4-methanesulfonylphenoxy)indan-2-yl]piperidin-3-yl}-(2-fluoroethyl)amine;
{(R)-1-[trans-(1S,2S)-4,6-dichloro-1-(4-methanesulfonylphenoxy)indan-2-yl]piperidin-3-yl}-(3,3,3-trifluoropropyl)amine;
{(R)-1-[trans-(1S,2S)-4,6-dichloro-1-(4-methanesulfonylphenoxy)indan-2-yl]piperidin-3-yl}dimethylamine;

{(R)-1-[trans-(1S,2S)-4,6-dichloro-1-(4-methanesulfonylphenoxy)indan-2-yl]piperidin-3-ylamino}acetonitrile;

{(R)-1-[trans-(1S,2S)-4,6-dichloro-1-(4-methanesulfonylphenoxy)indan-2-yl]pyrrolidin-3-yl}-(2-fluoroethyl)amine;

{(R)-1-[trans-(1S,2S)-4,6-dichloro-1-(4-methanesulfonylphenoxy)indan-2-yl]pyrrolidin-3-yl}methanol;

{(S)-1-[trans-(1S,2S)-4,6-dichloro-1-(4-methanesulfonylphenoxy)indan-2-yl]pyrrolidin-2-yl}methanol;

{4-[rac-trans-(1,2)-6-fluoro-1-(4-methanesulfonylphenoxy)indan-2-yl]piperazin-1-yl}acetonitrile;

1-[(1S,2S)-4,6-dichloro-1-(2-methanesulfonylphenoxy)indan-2-yl]-azetidine;

1-[(1S,2S)-4,6-dichloro-1-(2-methanesulfonylphenoxy)indan-2-yl]piperazine;

1-[(1S,2S)-4,6-dichloro-1-(2-methanesulfonylphenoxy)indan-2-yl]pyrrolidine;

1-[(1S,2S)-4,6-dichloro-1-(3-tetrazol-1-ylphenoxy)indan-2-yl]piperazine;

1-[(1S,2S)-4,6-dichloro-1-(4-methanesulfonylphenoxy)indan-2-yl]-3-methanesulfonylpyrrolidine;

1-[(1S,2S)-4,6-dichloro-1-(4-methanesulfonylphenoxy)indan-2-yl]-4,4-difluoropiperidine;

1-[3-(rac-trans-(1,2)-4,6-dichloro-2-piperazin-1-ylindan-1-yloxy)phenyl]-3-methyl-1,3-dihydroimidazol-2-one;

1-[3-(rac-trans-(1,2)-4,6-dichloro-2-piperazin-1-ylindan-1-yloxy)phenyl]-3-methylimidazolidin-2-one;

1-[4-((1S,2S)-2-azetidin-1-yl-4,6-dichloroindan-1-yloxy)phenyl]pyrrolidin-2-one;

1-[4-((1S,2S)-4,6-dichloro-2-pyrrolidin-1-ylindan-1-yloxy)phenyl]pyrrolidin-2-one;

1-[rac-trans-(1,2)-4,6-dichloro-1-(4-[1,2,4]triazol-1-ylphenoxy)indan-2-yl]piperazine;

1-[rac-trans-(1,2)-4,6-dichloro-1-(4-methanesulfonylphenoxy)indan-2-yl]-[1,4]diazepane;

1-[rac-trans-(1,2)-4,6-dichloro-1-(4-methanesulfonylphenoxy)indan-2-yl]-1H-imidazole;

1-[rac-trans-(1,2)-4,6-dichloro-1-(4-methanesulfonylphenoxy)indan-2-yl]-4-methyl-[1,4]diazepane;

1-[rac-trans-(1,2)-4-chloro-6-fluoro-1-(4-methanesulfonyl-3-methylphenoxy)indan-2-yl]piperazine;

1-[rac-trans-(1,2)-4-chloro-6-fluoro-1-(4-methanesulfonyl-3-methylphenoxy)indan-2-yl]pyrrolidine;

1-[rac-trans-(1,2)-4-chloro-6-fluoro-1-(4-methanesulfonylphenoxy)indan-2-yl]piperazine;

1-[rac-trans-(1,2)-4-chloro-6-fluoro-1-(4-methanesulfonylphenoxy)indan-2-yl]pyrrolidine;

1-[rac-trans-(1,2)-4-fluoro-1-(4-methanesulfonylphenoxy)indan-2-yl]pyrrolidine;

1-[rac-trans-(1,2)-5,6-dichloro-1-(4-methanesulfonylphenoxy)indan-2-yl]-[1,4]diazepane;

1-[rac-trans-(1,2)-5,7-dichloro-1-(4-methanesulfonylphenoxy)indan-2-yl]piperazine;

1-[rac-trans-(1,2)-6, 7-dichloro-1-(4-methanesulfonylphenoxy)indan-2-yl]-[1,4]diazepane;

1-[rac-trans-(1,2)-6-chloro-1-(4-methanesulfonylphenoxy)indan-2-yl]piperazine;

1-[rac-trans-(1,2)-6-chloro-4-fluoro-1-(3-methyl-4-trifluoromethanesulfonylphenoxy)indan-2-yl]piperazine;

1-[rac-trans-(1,2)-6-chloro-4-fluoro-1-(4-methanesulfonyl-3-methylphenoxy)indan-2-yl]pyrrolidine;

1-[rac-trans-(1,2)-6-chloro-4-fluoro-1-(4-methanesulfonylphenoxy)indan-2-yl]piperazine;

1-[rac-trans-(1,2)-6-chloro-4-fluoro-1-(4-methanesulfonylphenoxy)indan-2-yl]pyrrolidine;

1-[rac-trans-(1,2)-6-fluoro-1-(4-methanesulfonylphenoxy)indan-2-yl]piperazine;

1-[trans-(1S,2S)-4,6-dichloro-1-(2-chloro-4-methanesulfonylphenoxy)indan-2-yl]-[1,4]diazepane;

1-[trans-(1S,2S)-4,6-dichloro-1-(4-[1,2,4]triazol-1-ylphenoxy)indan-2-yl]-4-methylpiperazine;

1-[trans-(1S,2S)-4,6-dichloro-1-(4-imidazol-1-ylphenoxy)indan-2-yl]-4-methylpiperazine;

1-[trans-(1S,2S)-4,6-dichloro-1-(4-methanesulfonylphenoxy)indan-2-yl]-[1,4]diazepane;

1-[trans-(1S,2S)-4,6-dichloro-1-(4-methanesulfonylphenoxy)indan-2-yl]-3-propylpiperidin-3-ylamine;

1-[trans-(1S,2S)-4,6-dichloro-1-(4-methanesulfonylphenoxy)indan-2-yl]-3-trifluoromethylpiperazine;

1-[trans-(1S,2S)-4,6-dichloro-1-(4-methanesulfonylphenoxy)indan-2-yl]-3-trifluoromethylpyrrolidin-3-ylamine;

1-[trans-(1S,2S)-4,6-dichloro-1-(4-methanesulfonylphenoxy)indan-2-yl]-4-(2-fluoroethyl)-[1,4]diazepane;

1-[trans-(1S,2S)-4,6-dichloro-1-(4-methanesulfonylphenoxy)indan-2-yl]-4-(2-methoxyethyl)-[1,4]diazepane;

1-[trans-(1S,2S)-4,6-dichloro-1-(4-methanesulfonylphenoxy)indan-2-yl]-4-methyl-[1,4]diazepane;

1-[trans-(1S,2S)-4,6-dichloro-1-(4-methanesulfonylphenoxy)indan-2-yl]-4-methylpiperazine;

1-[trans-(1S,2S)-4,6-dichloro-1-(4-methanesulfonylphenoxy)indan-2-yl]-azetidin-3-ol;

1-[trans-(1S,2S)-4,6-dichloro-1-(4-methanesulfonylphenoxy)indan-2-yl]piperazine;

1-{(1S,2S)-4,6-dichloro-1-[4-fluoro-2-(1H-pyrazol-3-yl)phenoxy]indan-2-yl}piperazine;

1-2-chloro-5-[(1S,2S)-4,6-dichloro-2-((R)-3-hydroxypyrrolidin-1-yl)indan-1-yloxy]phenyl1-3-methyl-1,3-dihydroimidazol-2-one;

1-{2-chloro-5-[(1S,2S)-4,6-dichloro-2-((R)-3-hydroxypyrrolidin-1-yl)indan-1-yloxy]phenyl}-3-methylimidazolidin-2-one;

1-{3-[(1S,2S)-4,6-dichloro-2-((R)-3-hydroxypyrrolidin-1-yl)indan-1-yloxy]-2-methylphenyl}-3-methyl-1,3-dihydroimidazol-2-one;

1-{3-[(1S,2S)-4,6-dichloro-2-((R)-3-hydroxypyrrolidin-1-yl)indan-1-yloxy]-4-fluorophenyl }-3-methyl-1,3-dihydroimidazol-2-one;

1-{3-[(1S,2S)-4,6-dichloro-2-((R)-3-hydroxypyrrolidin-1-yl)indan-1-yloxy]-4-fluorophenyl}-3-methylimidazolidin-2-one;

1-{3-[(1S,2S)-4,6-dichloro-2-((R)-3-hydroxypyrrolidin-1-yl)indan-1-yloxy]phenyl}pyrrolidin-2-one;

1-{3-[(1, 2S)-4,6-dichloro-2-((R)-3-hydroxypyrrolidin-1-yl)indan-1-yloxy]phenyl}pyrrolidine-2,5-dione;

1-{3-[(1S,2S)-4,6-difluoro-2-((R)-3-hydroxypyrrolidin-1-yl)indan-1-yloxy]-4-fluorophenyl}-3-methyl-1,3-dihydroimidazol-2-one;

1-{3-[(1S,2S)-6-chloro-4-fluoro-2-((R)-3-hydroxypyrrolidin-1-yl)indan-1-yloxy]-4-fluorophenyl}-3-methyl-1,3-dihydroimidazol-2-one;

1-{3-[trans-(1S,2S)-4,6-dichloro-2-((R)-3-hydroxypyrrolidin-1-yl)indan-1-yloxy]phenyl}-3-methylimidazolidin-2-one;

1-{3-[trans-(1S,2S)-6-chloro-4-fluoro-2-((R)-3-hydroxypyrrolidin-1-yl)indan-1-yloxy]phenyl}-3-methylimidazolidin-2-one;

1-{3-chloro-4-[(1S,2S)-4,6-dichloro-2-((R)-3-hydroxypyrrolidin-1-yl)indan-1-yloxy]phenyl}pyrrolidin-2-one;

1-{3-chloro-4-[(1S,2S)-4,6-dichloro-2-((R)-3-hydroxy-pyrrolidin-1-yl)indan-1-yloxy]phenyl}pyrrolidine-2,5-dione;
1-{4-[(1S,2S)-4,6-dichloro-2-((R)-3-hydroxypyrrolidin-1-yl)indan-1-yloxy]-3-fluorophenyl}-1,3-dihydroimidazol-2-one;
1-{4-[(1S,2S)-4,6-dichloro-2-((R)-3-hydroxypyrrolidin-1-yl)indan-1-yloxy]-3-fluorophenyl}-2,6-dimethyl-1H-pyridin-4-one;
1-{4-[(1S,2S)-4,6-dichloro-2-((R)-3-hydroxypyrrolidin-1-yl)indan-1-yloxy]phenyl}-1,3-dihydroimidazol-2-one;
1-{4-[trans-(1S,2S)-4,6-dichloro-2-((R)-3-hydroxypyrrolidin-1-yl)indan-1-yloxy]-3-fluorophenyl}-3-methyl-1,3-dihydroimidazol-2-one;
1-{4-[trans-(1S,2S)-4,6-dichloro-2-((R)-3-hydroxypyrrolidin-1-yl)indan-1-yloxy]-3-fluorophenyl}-3-methylimidazolidin-2-one;
1-{4-[trans-(1S,2S)-4,6-dichloro-2-((R)-3-hydroxypyrrolidin-1-yl)indan-1-yloxy]phenyl}-3-methyl-1,3-dihydroimidazol-2-one;
1-{4-[trans-(1S,2S)-4,6-dichloro-2-((R)-3-hydroxypyrrolidin-1-yl)indan-1-yloxy]phenyl}-3-methylimidazolidin-2-one;
1-{4-[trans-(1S,2S)-4,6-dichloro-2-((R)-3-hydroxypyrrolidin-1-yl)indan-1-yloxy]phenyl}pyrrolidin-2-one;
1-{4-[trans-(1S,2S)-4,6-dichloro-2-((R)-3-hydroxypyrrolidin-1-yl)indan-1-yloxy]phenyl}pyrrolidine-2,5-dione;
1-{4-chloro-3-[(1S,2S)-4,6-dichloro-2-((R)-3-hydroxy-pyrrolidin-1-yl)indan-1-yloxy]phenyl}-3-methyl-1,3-dihydroimidazol-2-one;
1-{4-chloro-3-[(1S,2S)-4,6-dichloro-2-((R)-3-hydroxy-pyrrolidin-1-yl)indan-1-yloxy]phenyl}pyrrolidin-2-one;
1-{4-chloro-3-[(1S,2S)-4,6-dichloro-2-((R)-3-hydroxy-pyrrolidin-1-yl)indan-1-yloxy]phenyl}pyrrolidine-2,5-dione;
1-{4-chloro-3-[(1S,2S)-4,6-difluoro-2-((R)-3-hydroxy-pyrrolidin-1-yl)indan-1-yloxy]phenyl}-3-methyl-1,3-dihydroimidazol-2-one;
1-{4-chloro-3-[(1S,2S)-6-chloro-4-fluoro-2-((R)-3-hydroxypyrrolidin-1-yl)indan-1-yloxy]phenyl}-3-methyl-1,3-dihydroimidazol-2-one;
1-{4-chloro-3-[(1S,2S)-6-chloro-4-fluoro-2-((R)-3-hydroxypyrrolidin-1-yl)indan-1-yloxy]phenyl}-3-methylimidazolidin-2-one;
1-{4-chloro-3-[(1S,2S)-6-chloro-4-fluoro-2-((R)-3-hydroxypyrrolidin-1-yl)indan-1-yloxy]phenyl}pyrrolidin-2-one;
1-{trans-(1S,2S)-4,6-dichloro-1-[2-chloro-4-(3,5-dimethyl-[1,2,4]triazol-4-yl)phenoxy]indan-2-yl}-[1,4]diazepane;
1-{trans-(1S,2S)-4,6-dichloro-1-[2-chloro-4-(3,5-dimethyl-[1,2,4]triazol-4-yl)phenoxy]indan-2-yl}-4-methyl-[1,4]diazepane;
1-{trans-(1S,2S)-4,6-dichloro-1-[4-(3,5-dimethyl-[1,2,4]triazol-4-yl)-2-fluorophenoxy]indan-2-yl}-4-methyl-[1,4]diazepane;
1-{trans-(1S,2S)-4,6-dichloro-1-[4-(3,5-dimethyl-[1,2,4]triazol-4-yl)phenoxy]indan-2-yl}-[1,4]diazepane;
1-{trans-(1S,2S)-4,6-dichloro-1-[4-(3,5-dimethyl-[1,2,4]triazol-4-yl)phenoxy]indan-2-yl}-4-(2-methoxyethyl)-[1,4]diazepane;
1-{trans-(1S,2S)-4,6-dichloro-1-[4-(3,5-dimethyl-[1,2,4]triazol-4-yl)phenoxy]indan-2-yl}-4-methyl-[1,4]diazepane;
1-{trans-(1S,2S)-4,6-dichloro-1-[4-(3,5-dimethylisoxazol-4-yl)phenoxy]indan-2-yl}-4-(2-methoxyethyl)-[1,4]diazepane;
1-cyclopropyl-4-[trans-(1S,2S)-4,6-dichloro-1-(4-methanesulfonylphenoxy)indan-2-yl]piperazine;
2-((1S,2S)-2-azetidin-1-yl-4,6-dichloroindan-1-yloxy)-5-chlorobenzamide;
2,3-dichloro-4-(rac-trans-(1,2)-4,6-dichloro-2-morpholin-4-ylindan-1-yloxy)benzenesulfonamide;
2-[rac-trans-(1,2)-4,6-dichloro-1-(4-[1,2,4]triazol-1-ylphenoxy)indan-2-yl]octahydropyrrolo[3,4-c]pyrrole;
2-[trans-(1S,2S)-4,6-dichloro-1-(4-methanesulfonylphenoxy)indan-2-yl]-2,7-diaza-spiro[4.4]nonane;
2-{(R)-1-[trans-(1S,2S)-4,6-dichloro-1-(4-methanesulfonylphenoxy)indan-2-yl]piperidin-3-ylamino}ethanol;
2-{4-[rac-trans-(1,2)-4,6-dichloro-1-(4-methanesulfonylphenoxy)indan-2-yl]-[1,4]diazepan-1-yl}ethanol;
2-{4-[rac-trans-(1,2)-6-chloro-1-(4-methanesulfonylphenoxy)indan-2-yl]piperazin-1-yl}ethanol;
2-{4-[trans-(1S,2S)-4,6-dichloro-1-(4-methanesulfonylphenoxy)indan-2-yl]-[1,4]diazepan-1-yl}ethanol;
3-{3-[(1S,2S)-4,6-dichloro-2-((R)-3-hydroxypyrrolidin-1-yl)indan-1-yloxy]-4-fluorophenyl}-5,5-dimethylimidazolidine-2,4-dione;
3-{3-[(1S,2S)-4,6-dichloro-2-((R)-3-hydroxypyrrolidin-1-yl)indan-1-yloxy]-4-fluorophenyl}imidazolidine-2,4-dione;
3-{3-[(1S,2S)-4,6-dichloro-2-((R)-3-hydroxypyrrolidin-1-yl)indan-1-yloxy]-4-fluorophenyl}oxazolidine-2,4-dione;
3-{3-[(1S,2S)-4,6-dichloro-2-((R)-3-hydroxypyrrolidin-1-yl)indan-1-yloxy]phenyl}oxazolidin-2-one;
3-{3-[(1S,2S)-6-chloro-4-fluoro-2-((R)-3-hydroxypyrrolidin-1-yl)indan-1-yloxy]-4-fluorophenyl}-5,5-dimethylimidazolidine-2,4-dione;
3-{3-[(1S,2S)-6-chloro-4-fluoro-2-((R)-3-hydroxypyrrolidin-1-yl)indan-1-yloxy]-4-fluorophenyl}imidazolidine-2,4-dione;
3-{3-chloro-4-[(1S,2S)-4,6-dichloro-2(R)-3-hydroxypyrrolidin-1-yl)indan-1-yloxy]phenyl}-1-methylimidazolidine-2,4-dione;
3-{3-chloro-4-[(1S,2S)-4,6-dichloro-2-((R)-3-hydroxypyrrolidin-1-yl)indan-1-yloxy]phenyl}-5,5-dimethylimidazolidine-2,4-dione;
3-{3-chloro-4-[(1S,2S)-4,6-dichloro-2-((R)-3-hydroxypyrrolidin-1-yl)indan-1-yloxy]phenyl}oxazolidine-2,4-dione;
3-{4-[(1S,2S)-4,6-dichloro-2-((R)-3-hydroxypyrrolidin-1-yl)indan-1-yloxy]phenyl}-5,5-dimethylimidazolidine-2,4-dione;
3-{4-[(1S,2S)-4,6-dichloro-2-((R)-3-hydroxypyrrolidin-1-yl)indan-1-yloxy]phenyl}imidazolidine-2,4-dione;
3-{4-[(1S,2S)-4,6-dichloro-2-((R)-3-hydroxypyrrolidin-1-yl)indan-1-yloxy]phenyl}oxazolidine-2,4-dione;
3-{4-[(1S,2S)-4,6-dichloro-2-((R)-3-hydroxypyrrolidin-1-yl)indan-1-yloxy]phenyl}thiazolidine-2,4-dione;
3-{4-[trans-(1S,2S)-4,6-dichloro-2-((R)-3-hydroxypyrrolidin-1-yl)indan-1-yloxy]phenyl}oxazolidin-2-one;
3-{4-chloro-3-[(1S,2S)-4,6-dichloro-2-((R)-3-hydroxy-pyrrolidin-1-yl)indan-1-yloxy]phenyl}-1-methylimidazolidine-2,4-dione;
3-{4-chloro-3-[(1S,2S)-4,6-dichloro-2(R)-3-hydroxypyrrolidin-1-yl)indan-1-yloxy]phenyl}-5,5-dimethylimidazolidine-2,4-dione;
3-{4-chloro-3-[(1S,2S)-4,6-dichloro-2-((R)-3-hydroxypyrrolidin-1-yl)indan-1-yloxy]phenyl}-5,5-dimethyloxazolidine-2,4-dione;

3-{4-chloro-3-[(1S,2S)-4,6-dichloro-2-((R)-3-hydroxypyrrolidin-1-yl)indan-1-yloxy]phenyl}imidazolidine-2,4-dione;
3-{4-chloro-3-[(1S,2S)-4,6-dichloro-2-((R)-3-hydroxypyrrolidin-1-yl)indan-1-yloxy]phenyl}oxazolidin-2-one;
3-{4-chloro-3-[(1S,2S)-6-chloro-4-fluoro-2-((R)-3-hydroxypyrrolidin-1-yl)indan-1-yloxy]phenyl}-1-methylimidazolidine-2,4-dione;
3-{4-chloro-3-[(1S,2S)-6-chloro-4-fluoro-2-((R)-3-hydroxypyrrolidin-1-yl)indan-1-yloxy]phenyl}-5,5-dimethylimidazolidine-2,4-dione;
3-{4-chloro-3-[(1S,2S)-6-chloro-4-fluoro-2-((R)-3-hydroxypyrrolidin-1-yl)indan-1-yloxy]phenyl}-5,5-dimethyloxazolidine-2,4-dione;
3-{4-chloro-3-[(1S,2S)-6-chloro-4-fluoro-2-((R)-3-hydroxypyrrolidin-1-yl)indan-1-yloxy]phenyl}imidazolidine-2,4-dione;
3-{4-chloro-3-[(1S,2S)-6-chloro-4-fluoro-2-((R)-3-hydroxypyrrolidin-1-yl)indan-1-yloxy]phenyl}oxazolidin-2-one;
3-chloro-4-[trans-(1S,2S)-6-chloro-2-((R)-3-hydroxypyrrolidin-1-yl)indan-1-yloxy]benzoic acid methyl ester;
4-((1S,2S)-4,6-dichloro-2-pyrrolidin-1-ylindan-1-yloxy)benzenesulfonamide;
4-(rac-trans-(1,2)-4-chloro-2-pyrrolidin-1-ylindan-1-yloxy)benzenesulfonamide;
4-(rac-trans-(1,2)-4-methyl-2-pyrrolidin-1-ylindan-1-yloxy)benzenesulfonamide;
4-(rac-trans-(1,2)-6-chloro-2-pyrrolidin-1-ylindan-1-yloxy)benzenesulfonamide;
4-(rac-trans-(1,2)-6-fluoro-2-pyrrolidin-1-ylindan-1-yloxy)benzenesulfonamide;
4-(rac-trans-(1,2)-6-methyl-2-pyrrolidin-1-ylindan-1-yloxy)benzenesulfonamide;
4-(rac-trans-(1,2)-7-chloro-2-pyrrolidin-1-ylindan-1-yloxy)benzenesulfonamide;
4-[(1S,2S)-2-((R)-3-aminopiperidin-1-yl)-4,6-dichloroindan-1-yloxy]benzenesulfonamide;
4-[(1S,2S)-4,6-dichloro-2-(1,1-dioxo-1lambda6-thiomorpholin-4-yl)indan-1-yloxy]benzenesulfonamide;
4-[(1S,2S)-4,6-dichloro-2-(4,4-difluoropiperidin-1-yl)indan-1-yloxy]benzenesulfonamide;
4-[3-chloro-4-(trans-(1S,2S)-6-chloro-2-pyrrolidin-1-ylindan-1-yloxy)phenyl]-3,5-dimethyl-4H-[1,2,4]triazole;
4-[3-chloro-4-(trans-(1S,2S)-6-chloro-2-pyrrolidin-1-ylindan-1-yloxy)phenyl]-3,5-dimethyl-4H-[1,2,4]triazole;
4-[4-(rac-trans-(1,2)-5,6-dichloro-2-pyrrolidin-1-ylindan-1-yloxy)phenyl]-3,5-dimethyl-4H-[1,2,4]triazole;
4-[4-(trans-(1S,2S)-4,6-dichloro-2-pyrrolidin-1-ylindan-1-yloxy)-3-fluorophenyl]-3,5-dimethyl-4H-[1,2,4]triazole;
4-[4-(trans-(1S,2S)-4,6-dichloro-2-pyrrolidin-1-ylindan-1-yloxy)phenyl]-3,5-dimethyl-4H-[1,2,4]triazole;
4-[4-(trans-(1S,2S)-6-chloro-2-pyrrolidin-1-ylindan-1-yloxy)-3-fluorophenyl]-3,5-dimethyl-4H-[1,2,4]triazole;
4-[4-(trans-(1S,2S)-6-chloro-2-pyrrolidin-1-ylindan-1-yloxy)phenyl]-3,5-dimethyl-4H-[1,2,4]triazole;
4-[rac-trans-(1,2)-4,6-dichloro-1-(4-[1,2,4]triazol-1-ylphenoxy)indan-2-yl]morpholine;
4-[trans-(1S,2S)-2-((R)-3-aminopiperidin-1-yl)-4,6-dichloroindan-1-yloxy]-2,3-dichlorobenzenesulfonamide;
4-[trans-(1S,2S)-4,6-dichloro-2-((R)-3-hydroxypyrrolidin-1-yl)indan-1-yloxy]-3-fluorobenzoic acid methyl ester;
4-{3-chloro-4-[trans-(1S,2S)-6-chloro-2-((R)-3-fluoropyrrolidin-1-yl)indan-1-yloxy]phenyl}-3,5-dimethyl-4H-[1,2,4]triazole;
4-{3-chloro-4-[trans-(1S,2S)-6-chloro-2-((S)-3-fluoropyrrolidin-1-yl)indan-1-yloxy]phenyl}-3,5-dimethyl-4H-[1,2,4]triazole;
4-{4-[(1S,2S)-4,6-dichloro-2-((R)-3-hydroxypyrrolidin-1-yl)indan-1-yloxy]-3-fluorophenyl}morpholine-3,5-dione;
4-{4-[trans-(1S,2S)-4,6-dichloro-2-((R)-3-fluoropyrrolidin-1-yl)indan-1-yloxy]phenyl}-3,5-dimethyl-4H-[1,2,4]triazole;
4-{4-[trans-(1S,2S)-4,6-dichloro-2-((S)-2-methoxymethylpyrrolidin-1-yl)indan-1-yloxy]phenyl}-3,5-dimethyl-4H-[1,2,4]triazole;
4-{4-[trans-(1S,2S)-6-chloro-2-((R)-3-fluoropyrrolidin-1-yl)indan-1-yloxy]-3-fluorophenyl}-3,5-dimethyl-4H[1,2,4]triazole;
4-{trans-(1S,2S)-4,6-dichloro-1-[4-(3,5-dimethyl-[1,2,4]triazol-4-yl)-2-fluorophenoxy]indan-2-yl}morpholine;
4-{trans-(1S,2S)-4,6-dichloro-1-[4-(3,5-dimethyl-[1,2,4]triazol-4-yl)-2-fluorophenoxy]indan-2-yl}thiomorpholine-1,1-dioxide;
4-{trans-(1S,2S)-6-chloro-1-[2-chloro-4-(3,5-dimethyl-[1,2,4]triazol-4-yl)phenoxy]indan-2-yl}morpholine;
4-{trans-(1S,2S)-6-chloro-1-[2-chloro-4-(3,5-dimethyl-[1,2,4]triazol-4-yl)phenoxy]indan-2-y}thiomorpholine-1,1-dioxide;
5-(rac-trans-(1,2)-4,6-dichloro-2-piperazin-1-ylindan-1-yloxy)-2-methylbenzothiazole;
5-[(1S,2S)-4,6-dichloro-2-((R)-3-hydroxypyrrolidin-1-yl)indan-1-yloxy]-3, 4-dihydro-1H-quinolin-2-one;
5-[trans-(1S,2S)-4,6-dichloro-1-(4-methanesulfonylphenoxy)indan-2-yl]-1-methyloctahydropynnlo[3,4-b]pyrrole;
5-[trans-(1S,2S)-4,6-dichloro-1-(4-methanesulfonylphenoxy)indan-2-yl]-1-methyloctahydropyrrolo[3,4-b]pyrrole;
N-[3-(rac-trans-(1,2)-2-thiomorpholin-4-ylindan-1-yloxy)phenyl]acetamide;
N-[3-(rac-trans-(1,2)-4,6-dichloro-2-[1,4]diazepan-1-ylindan-1-yloxy)phenyl]acetamide;
N-[3-(rac-trans-(1,2)-4,6-dichloro-2-morpholin-4-ylindan-1-yloxy)phenyl]acetamide;
N-[3-(rac-trans-(1,2)-4,6-dichloro-2-piperazin-1-ylindan-1-yloxy)phenyl]acetamide;
N-[3-(rac-trans-(1,2)-4,6-dichloro-2-pyrrolidin-1-ylindan-1-yloxy)phenyl]acetamide;
N-[3-(rac-trans-(1,2)-4-chloro-2-pyrrolidin-1-ylindan-1-yloxy)phenyl]acetamide;
N-[3-(rac-trans-(1,2)-4-chloro-6-fluoro-2-piperazin-1-ylindan-1-yloxy)phenyl]acetamide;
N-[3-(rac-trans-(1,2)-4-chloro-6-fluoro-2-pyrrolidin-1-ylindan-1-yloxy)phenyl]acetamide;
N-[3-(rac-trans-(1,2)-4-fluoro-2-pyrrolidin-1-ylindan-1-yloxy)phenyl]acetamide;
N-[3-(rac-trans-(1,2)-4-methyl-2-pyrrolidin-1-ylindan-1-yloxy)phenyl]acetamide;
N-[3-(rac-trans-(1,2)-5,7-dichloro-2-dimethylaminoindan-1-yloxy)phenyl]acetamide;
N-[3-(rac-trans-(1,2)-5-chloro-2-pyrrolidin-1-ylindan-1-yloxy)phenyl]acetamide;
N-[3-(rac-trans-(1,2)-5-fluoro-2-pyrrolidin-1-ylindan-1-yloxy)phenyl]acetamide;

N-[3-(rac-trans-(1,2)-6-chloro-2-piperazin-1-ylindan-1-yloxy)phenyl]acetamide;
N-[3-(rac-trans-(1,2)-6-chloro-2-pyrrolidin-1-ylindan-1-yloxy)phenyl]acetamide;
N-[3-(rac-trans-(1,2)-6-chloro-4-fluoro-2-piperazin-1-ylindan-1-yloxy)phenyl]acetamide;
N-[3-(rac-trans-(1,2)-6-chloro-4-fluoro-2-pyrrolidin-1-ylindan-1-yloxy)phenyl]acetamide;
N-[3-(rac-trans-(1,2)-6-fluoro-2-pyrrolidin-1-ylindan-1-yloxy)phenyl]acetamide;
N-[3-(rac-trans-(1,2)-7-chloro-2-pyrrolidin-1-ylindan-1-yloxy)phenyl]acetamide;
N-[3-(trans-(1S,2S)-4,6-dichloro-2-3,8-diazabicyclo[3.2.1]oct-3-ylindan-1-yloxy)phenyl]acetamide;
N-[3-(trans-(1S,2S)-4,6-dichloro-2-piperazin-1-ylindan-1-yloxy)phenyl]acetamide;
N-{3-[(1S,2S)-6-chloro-4-fluoro-2-((R)-3-hydroxypyrrolidin-1-yl)indan-1-yloxy]-4-fluorophenyl}-N-methyl-methanesulfonamide;
N-{3-[rac-trans-(1,2)-2-((R)-3-aminopiperidin-1-yl)-4-chloro-6-fluoroindan-1-yloxy]phenyl}acetamide;
N-{3-[rac-trans-(1,2)-2-((R)-3-aminopiperidin-1-yl)-6-chloro-4-fluoroindan-1-yloxy]phenyl}acetamide;
N-{3-[rac-trans-(1,2)-4,6-dichloro-2-(hexahydropyrrolo[3,4-c]pyrrol-2-yl)indan-1-yloxy]phenyl}acetamide;
N-{3-[trans-(1S,2S)-2-((R)-3-aminopiperidin-1-yl)-4,6-dichloroindan-1-yloxy]phenyl}acetamide;
N-{3-[trans-(1S,2S)-2-(3-amino-3-propylpiperidin-1-yl)-4,6-dichloroindan-1-yloxy]phenyl}acetamide;
N-{3-[trans-(1S,2S)-4,6-dichloro-2-((R)-3-dimethylaminopiperidin-1-yl)indan-1-yloxy]phenyl}acetamide;
N-{3-[trans-(1S,2S)-4,6-dichloro-2-((R)-3-hydroxymethylpyrrolidin-1-yl)indan-1-yloxy]phenyl}acetamide;
N-{3-[trans-(1S,2S)-4,6-dichloro-2-((R)-3-hydroxypyrrolidin-1-yl)indan-1-yloxy]phenyl}acetamide;
N-{3-[trans-(1S,2S)-4,6-dichloro-2-(4-methylpiperazin-1-yl)indan-1-yloxy]phenyl}acetamide;
N-{4-[(1S,2S)-4,6-dichloro-2-((R)-3-hydroxypyrrolidin-1-yl)indan-1-yloxy]phenyl}-N -methylmethanesulfonamide;
(R)-1-[(1S,2S)-4,6-dichloro-1-(2-methanesulfonylphenoxy)indan-2-yl]piperidin-3-ylamine;
2-{[trans-(1S,2S)-4,6-Dichloro-1-(4-methanesulfonylphenoxy)-indan-2-yl]-methyl-amino}-ethanol;
2-({trans-(1S,2S)-4,6-Dichloro-1-[4-(3,5-dimethyl-[1,2,4]triazol-4-yl)-2-fluoro-phenoxy]-indan -2-yl}-methyl-amino)-ethanol;
N-{trans-(1S,2S)-4,6-Dichloro-1-[4-(3,5-dimethyl-[1,2,4]triazol-4-yl)-2-fluoro-phenoxy]-indan -2-yl}-N,N', N'-trimethyl ethane-1,2-diamine;
Cyclopentyl-[rac-trans-(1,2)-1-(4-methanesulfonyl-phenoxy)-indan-2-yl]-methyl-amine;
Cyclobutyl-[rac-trans-(1,2)-1-(4-methanesulfonyl-phenoxy)-indan-2-yl]-methyl-amine;
(R)-1-{trans-(1S,2S)-4,6-Dichloro-1-[4-(2-ethyl-4-methyl-imidazol-1-yl)-phenoxy]-indan-2-yl}-pyrrolidin-3-ol;
(R)-1-{trans-(1S,2S)-4,6-Dichloro-1-[4-(2-isopropyl-4-methyl-imidazol-1-yl)-phenoxy]-indan-2-yl}-pyrrolidin-3-ol;
(R)-1-{trans-(1S,2S)-4,6-Dichloro-1-[4-(3-isopropyl-5-methyl-[1,2,4]triazol-4-yl)-phenoxy]-indan-2-yl}-pyrrolidin-3-ol;
(R)-1-{trans-(1S,2S)-4,6-Dichloro-1-[4-(3-ethyl-5-isopropyl-[1,2,4]triazol-4-yl)-phenoxy]-indan-2-yl}-pyrrolidin-3-ol;
(R)-1-{trans-(1S,2S)-6-Chloro-1-[4-(2-ethyl-4-methyl-imidazol-1-yl)-phenoxy]-4-fluoro-indan -2-yl}-pyrrolidin-3-ol;
(R)-1-{trans-(1S,2S)-6-Chloro-4-fluoro-1-[4-(2-isopropyl-4-methyl-imidazol-1-yl)-phenoxy]-indan-2-yl}-pyrrolidin-3-ol;
(R)-1-{trans-(1S,2S)-6-Chloro-4-fluoro-1-[4-(3-isopropyl-5-methyl-[1,2,4]triazol-4-yl)-phenoxy]-indan-2-yl}-pyrrolidin-3-ol;
(R)-1-{trans(1S, 2S)6-Chloro-1-[4-(3-ethyl-5-isopropyl-[1,2,4]triazol-4-yl)-phenoxy]-4-fluoro-indan-2-yl}-pyrrolidin-3-ol;
(R)-1-{trans-(1S,2S)-1-[4-(4-tert-Butyl-2-isopropyl-imidazol-1-yl)-phenoxy]-6-chloro-4-fluoro -indan-2-yl}-pyrrolidin-3-ol;
(R)-1-{trans-(1S,2S)-4,6-Dichloro-1-[5-(2-ethyl-4-methyl-imidazol-1-yl)-2-fluoro-phenoxy]-indan-2-yl}-pyrrolidin-3-ol;
(R)-1-{trans-(1S,2S)-4,6-Dichloro-1-[4-(2,4-dimethyl-imidazol-1-yl)-2-fluoro-phenoxy]-indan-2-yl}-pyrrolidin-3-ol;
(R)-1-[trans-(1S,2S)-4,6-Dichloro-1-(4-imidazol-1-yl-phenoxy)-indan-2-yl]-pyrrolidin-3-ol;
(R)-1-{trans-(1S,2S)-1-[4-(4-tert-Butyl-2-methyl-imidazol-1-yl)-2-fluoro-phenoxy]-4,6-dichloro-indan-2-yl}-pyrrolidin-3-ol;
(R)-1-{trans-(1S,2S)-4,6-Dichloro-1-[4-(2-isopropyl-imidazol-1-yl)-phenoxy]-indan-2-yl}-pyrrolidin-3-ol;
3-{4-[trans-(1S,2S)-4,6-Dichloro-2-((R)-3-hydroxy-pyrrolidin-1-yl)-indan-1-yloxy]-phenyl}-5-methyl-3H-[1,3,4]oxadiazol-2-one;
3-{4-[trans-(1S,2S)-4,6-Dichloro-2-((R)-3-hydroxy-pyrrolidin-1-yl)-indan-1-yloxy]-phenyl}-3H-[1,3,4]oxadiazol-2-one;
2-{4-[trans-(1S,2S)-4,6-Dichloro-2-((R)-3-hydroxy-pyrrolidin-1-yl)-indan-1-yloxy]-phenyl}-4-ethyl-2,4-dihydro-[1,2,4]triazol-3-one;
2-{4-[trans-(1S,2S)-4,6-Dichloro-2-((R)-3-hydroxy-pyrrolidin-1-yl)-indan-1-yloxy]-phenyl}-4-ethyl-5-methyl-2,4-dihydro-[1,2,4]triazol-3-one;
(R)-1-{trans-(1S,2S)-6-Chloro-1-[4-(2,4-dimethyl-imidazol-1-yl)-2-fluoro-phenoxy]-4-fluoro -indan-2-yl}-pyrrolidin-3-ol;
1-{4-[trans-(1S,2S)-4,6-Dichloro-2-((R)-3-hydroxy-pyrrolidin-1-yl)-indan-1-yloxy]-3-fluoro -phenyl}-1H-imidazole-2-carboxylic acid methyl ester;
4-[trans-(1S,2S)-4,6-Dichloro-2-((R)-3-hydroxy-pyrrolidin-1-yl)-indan-1-yloxy]-3-fluoro -benzenesulfonamide;
(R)-1-{trans-(1S,2S)-4,6-Dichloro-1-[4-(4-methyl-piperazine-1-sulfonyl)-phenoxy]-indan-2-yl}-pyrrolidin-3-ol;
4-[trans-(1S,2S)-4,6-Dichloro-2-((R)-3-hydroxy-pyrrolidin-1-yl)-indan-1-yloxy]-benzenesulfonamide;
(R)-1-{trans-(1S,2S)-4,6-Dichloro-1-[4-(morpholine-4-sulfonyl)-phenoxy]-indan-2-yl}-pyrrolidin-3-ol and
1-{5-[trans-(1S,2S)-4,6-Dichloro-2-((R)-3-hydroxy-pyrrolidin-1-yl)-indan-1-yloxy]-2-fluoro-phenyl}-3-methyl-1,3-dihydro-imidazol-2-one;
and the pharmaceutically acceptable salts thereof.

11. A compound according to claim 1 selected from the group consisting of:
3-[trans-(1S,2S)-4,6-dichloro-1-(4-[1,2,4]triazol-1-ylphenoxy)indan-2-yl]-3,8-diazabicyclo[3.2.1]octane;
2-[trans-(1S,2S)-4,6-dichloro-1-(4-methanesulfonylphenoxy)indan-2-yl]octahydropyrrolo[3,4-c]pyrrole;
2-[trans-(1S,2S)-4,6-dichloro-1-(4-methanesulfonylphenoxy)indan-2-yl]-5-methyloctahydropyrrolo[3,4-c]pyrrole;
(3R, 5S)-1-[trans-(1S,2S)-4,6-dichloro-1-(4-methanesulfonylphenoxy)indan-2-yl]-3,5-dimethylpiperazine;
(R)-1-[(1S,2S)-4,6-difluoro-1-(4-methanesulfonylphenoxy)indan-2-yl]pyrrolidin-3-ol;
(R)-1-[rac-trans-(1,2)-4-chloro-6-fluoro-1-(3-methyl-4-trifluoromethanesuffonylphenoxy)indan -2-yl]piperidin-3-ylamine;
(R)-1-[rac-trans-(1,2)-4-chloro-6-fluoro-1-(4-methanesulfonylphenoxy)indan-2-yl]piperidin-3-ylamine;

(R)-1-[rac-trans-(1,2)-6-chloro-4-fluoro-1-(3-methyl-4-trifluoromethanesulfonylphenoxy)indan-2-yl]piperidin-3-ylamine;
(R)-1-[rac-trans-(1,2)-6-chloro-4-fluoro-1-(4-methanesulfonylphenoxy)indan-2-yl]piperidin-3-ylamine;
(R)-1-[trans-(1S,2S)-4,6-dichloro-1-(2-methylbenzothiazol-5-yloxy)indan-2-yl]pyrrolidin-3-ol;
(R)-1-[trans-(1S,2S)-4,6-dichloro-1-(4-[1,2,4]triazol-1-ylphenoxy)indan-2-yl]piperidin-3-ylamine;
(R)-1-[trans-(1S,2S)-4,6-dichloro-1-(4-imidazol-1-ylphenoxy)indan-2-yl]piperidin-3-ylamine;
(R)-1'-[trans-(1S,2S)-4,6-dichloro-1-(4-methanesulfonylphenoxy)indan-2-yl]-[1,3']bipyrrolidinyl;
(R)-1-[trans-(1S,2S)-4,6-dichloro-1-(4-methanesulfonylphenoxy)indan-2-yl]-3-fluoropyrrolidine;
(R)-1-[trans-(1S,2S)-4,6-dichloro-1-(4-methanesulfonylphenoxy)indan-2-yl]-3-methylpiperazine;
(R)-1-[trans-(1S,2S)-4,6-dichloro-1-(4-methanesulfonylphenoxy)indan-2-yl]piperidin-3-ylamine;
(R)-1-[trans-(1S,2S)-4,6-dichloro-1-(4-methanesulfonylphenoxy)indan-2-yl]pyrrolidin-3-ol,
(R)-1-[trans-(1S,2S)-4,6-dichloro-1-(4-methanesulfonylphenoxy)indan-2-yl]pyrrolidin-3-ylamine;
(R)-1-[trans-(1S,2S)-4,6-dichloro-1-(4-methanesulfonylphenoxy)indan-2-yl]pyaolidine-3-carbonitrile;
(R)-1-[trans-(1S,2S)-6-chloro-1-(2-chloro-4-methanesulfonylphenoxy)-4-fluoroindan-2-yl]pyrrolidin-3-ol;
(R)-1-[trans-(1S,2S)-6-chloro-1-(2-chloro-4-methanesulfonylphenoxy)indan-2-yl]pyrrolidin-3-ol;
(R)-1-[trans-(1S,2S)-6-chloro-4-fluoro-1-(4-methanesulfonylphenoxy)indan-2-yl]pyrrolidin-3-ol;
(R)-1-{(1S,2S)-1-[2-chloro-4-(3,5-dimethyl-[1,2,4]triazol-4-yl)phenoxy]-4,6-difluoroindan-2-yl}pyrrolidin-3-ol;
(R)-1-{(1S,2S)-1-[4-(3,5-dimethyl-[1,2,4]triazol-4-yl)-2-fluorophenoxy]-4,6-difluoroindan-2-yl}pyrrolidin-3-ol;
(R)-1-{(1S,2S)-4,6-dichloro-1-[4-(3,5-dimethyl-[1,2,4]triazol-4-yl)phenoxy]indan-2-yl}-3-methylpyrrolidin-3-ol;
(R)-1-{(1S,2S)-4,6-dichloro-1-[4-(5-methyltetrazol-1-yl)phenoxy]indan-2-yl}pyrrolidin-3-ol;
(R)-1-(1S,2S)-4,6-dichloro-1-[4-fluoro-2-(1H-pyrazol-3-yl)phenoxy]indan-2-yl]piperidin-3-ylamine;
(R)-1-{(1S,2S)-4,6-dichloro-1-[5-(3,5-dimethyl-[1,2,4]triazol-4-yl)-2-fluorophenoxy]indan-2-yl}pyrrolidin-3-ol;
(R)-1-{trans-(1S,2S)-4,6-dichloro-1-[2-chloro-4-(3,5-dimethyl-[1,2,4]triazol-4-yl)phenoxy]indan-2-yl}pyrrolidin-3-ol;
(R)-1-{trans-(1S,2S)-4,6-dichloro-1-[3-(1,1-dioxo-1lambda6-isothiazolidin-2-yl)phenoxy]indan-2-yl}pyrrolidin-3-ol;
(R)-1-{trans-(1, 2S)-4,6-dichloro-1-[4-(1,3,5-trimethyl-1H-pyrazol-4-yl)phenoxy]indan-2-yl}pyrrolidin-3-ol;
(R)-1-{trans-(1S,2S)-4,6-dichloro-1-[4-(2,4-dimethylthiazol-5-yl)phenoxy]indan-2-yl}pyrrolidin-3-ol;
(R)-1-{trans-(1S,2S)-4,6-dichloro-1-[4-(3,5-dimethyl-[1,2,4]triazol-4-yl)-2,3-difluorophenoxy]indan-2-yl}pyrrolidin-3-ol;
(R)-1-{trans-(1S,2S)-4,6-dichloro-1-[4-(3,5-dimethyl-[1,2,4]triazol-4-yl)-2,3-dimethylphenoxy]indan-2-yl}pyrrolidin-3-ol;
(R)-1-{trans-(1S,2S)-4,6-dichloro-1-[4-(3,5-dimethyl-[1,2,4]triazol-4-yl)-2-fluorophenoxy]indan-2-yl}pyrrolidin-3-ol;
(R)-1-{trans-(1S,2S)-4,6-dichloro-1-[4-(3,5-dimethyl-[1,2,4]triazol-4-yl)-2-methylphenoxy]indan-2-yl}pyrrolidin-3-ol;
(R)-1-{trans-(1S,2S)-4,6-dichloro-1-[4-(3,5-dimethyl1,2,4triazol-4-yl)phenoxy]indan-2-yl}piperidin-3-ol;
(R)-1-{trans-(1S,2S)-4,6-dichloro-1-[4-(3,5-dimethyl-[1,2,4]triazol-4-yl)phenoxy]indan-2-yl}pynolidin-3-ol;
(R)-1-{trans-(1S,2S)-4,6-dichloro-1-[4-(3,5-dimethyl-[1,2,4]triazol-4-yl)phenoxy]indan-2-yl}pyrrolidine-3-carbonitrile;
(R)-1-{trans-(1S,2S)-4,6-dichloro-1-[4-(3,5-dimethylisoxazol-4-yl)phenoxy]indan-2-yl}pyrrolidin-3-ol;
(R)-1-{trans-(1S,2S)-4,6-dichloro-1-[4-(3,5-dimethylpyrazol-1-yl)-2-fluorophenoxy]indan-2-yl}pyrrolidin-3-ol;
(R)-1-{trans-(1S,2S)-4,6-dichloro-1-[4-fluoro-2-(2H-pyrazol-3-yl)phenoxy]indan-2-yl}pyrrolidin-3-ol;
(R)-1-{trans-(1S,2S)-6-chloro-1-[2-chloro-4-(3,5-dimethyl-[1,2,4]triazol-4-yl)phenoxy]-4-fluoroindan-2-yl}pyrrolidin-3-ol;
(R)-1-{trans-(1S,2S)-6-chloro-1-[2-chloro-4-(3,5-dimethyl-[1,2,4]triazol-4-yl)phenoxy]indan-2-yl}pyrrolidin-3-ol;
(R)-1-{trans-(1S,2S)-6-chloro-1-[4-(1,3,5-trimethyl-1H-pyrazol-4yl)phenoxy]indan-2-yl}pyrrolidin-3-ol;
(R)-1-{trans-(1S,2S)-6-chloro-1-[4-(3,5-dimethyl-[1,2,4]triazol-4-yl)-2,3-dimethylphenoxy]-4-fluoroindan-2-yl}pyrrolidin-3-ol;
(R)-1-{trans-(1S,2S)-6-chloro-1-[4-(3,5-dimethyl-[1,2,4]triazol-4-yl)-2-fluorophenoxy]-4-fluoroindan-2-yl}pyrrolidin-3-ol;
(R)-1-{trans-(1S,2S)-6-chloro-1-[4-(3,5-dimethyl-[1,2,4]triazol-4-yl)-2-fluorophenoxy]indan-2-yl}pyrrolidin-3-ol;
(R)-1-{trans-(1S,2S)-6-chloro-1-[4-(3,5-dimethyl-[1,2,4]triazol-4-yl)phenoxy]-4-fluoroindan-2-yl}pyrrolidin-3-ol;
(R)-1-{trans-(1S,2S)-6-chloro-1-[4-(3,5-dimethyl-[1,2,4]triazol-4-yl)phenoxy]indan-2-yl}pyrrolidin-3-ol;
(S)-1-[(1S,2S)-4,6-dichloro-1-(4-methanesuffonylphenoxy)indan-2-yl]-3-methylpyrrolidin-3-ol;
(S)-1-[trans-(1S,2S)-4,6-dichloro-1-(4-methanesulfonylphenoxy)indan-2-yl]-2-pyrrolidin-1-ylmethylpyrrolidine;
(S)-1-[trans-(1S,2S)-4,6-dichloro-1-(4-methanesulfonylphenoxy)indan-2-yl]-3-fluoropyrrolidine;
(S)-1-[trans-(1S,2S)-4,6-dichloro-1-(4-methanesulfonylphenoxy)indan-2-yl]-3-methylpiperazine;
(S)-1-[trans-(1S,2S)-4,6-dichloro-1-(4-methanesulfonylphenoxy)indan-2-yl]pyrrolidin-3-ol;
(S)-1-[trans-(1S,2S)-4,6-dichloro-1-(4-methanesulfonylphenoxy)indan-2-yl]pyrrolidin-3-ylamine;
(S)-1-{(1S,2S)-4,6-dichloro-1-[4-(3,5-dimethyl-[1,2,4]triazol-4-yl)-2-fluorophenoxy]indan-2-yl}pyrrolidin-3-ol
(S)-1-{trans-(1S,2S)-4,6-dichloro-1-[4-(3,5-dimethyl-[1,2,4]triazol-4-yl)phenoxy]indan-2-yl}pyrrolidin-3-ol;
(S)-1-{trans-(1S,2S)-4,6-dichloro-1-[4-(3,5-dimethyl-[1,2,4]triazol-4-yl)phenoxy]indan-2-yl}pyrrolidin-3-ylamine;
(S)-2-[(S)-4-(S)-chloro-6-chloro-1-(4-methanesulfonylphenoxy)indan-2-yl]octahydropyrrolo[1,2-a]pyrazine;
(S)-2-[trans-(1S,2S)-4,6-dichloro-1-(4-methanesulfonylphenoxy)indan-2-yl]-2,5-diazabicyclo[2.2.1]heptane;
(S)-3-{3-[(1S,2S)-6-chloro-4-fluoro-2(R)-3-hydroxypyrrolidin-1-yl)indan-1-yloxy]-4-fluorophenyl}-4-isopropyloxazolidin-2-one;
(S)-3-{4-chloro-3-[(1S,2S)-6-chloro-4-fluoro-2-((R)-3-hydroxypyrrolidin-1-yl)indan-1-yloxy]phenyl}-4-isopropyloxazolidin-2-one;
{(R)-1-[trans-(1S,2S)-4,6-dichloro-1-(4-[1,2,4]triazol-1-ylphenoxy)indan-2-yl]piperidin-3-yl}-(3,3,3-trifluoropropyl)amine;

{(R)-1-[trans-(1S,2S)-4,6-dichloro-1-(4-methanesulfonylphenoxy)indan-2-yl]piperidin-3-yl}-(2-fluoroethyl)amine;
{(R)-1-[trans-(1S,2S)-4,6-dichloro-1-(4-methanesulfonylphenoxy)indan-2-yl]piperidin-3-yl}-(3,3,3-trifluoropropyl)amine;
{(R)-1-[trans-(1S,2S)-4,6-dichloro-1-(4-methanesulfonylphenoxy)indan-2-yl]piperidin-3-yl}dimethylamine;
{(R)-1-[trans-(1S,2S)-4,6-dichloro-1-(4-methanesulfonylphenoxy)indan-2-yl]piperidin-3-ylamino}acetonitrile;
{(R)-1-[trans-(1S,2S)-4,6-dichloro-1-(4-methanesulfonylphenoxy)indan-2-yl]pyrrolidin-3-yl}-(2-fluoroethyl)amine;
{(R)-1-[trans-(1S,2S)-4,6-dichloro-1-(4-methanesulfonylphenoxy)indan-2-yl]pyrrolidin-3-yl}methanol;
{(S)-1-[trans-(1S,2S)-4,6-dichloro-1-(4-methanesulfonylphenoxy)indan-2-yl]pyrrolidin-2-yl}methanol;
{4-[rac-trans-(1,2)-6-fluoro-1-(4-methanesulfonylphenoxy)indan-2-yl]piperazin-1-yl}acetonitrile;
1-[(1S,2S)-4,6-dichloro-1-(2-methanesulfonylphenoxy)indan-2-yl]-azetidine;
1-[(1S,2S)-4,6-dichloro-1-(2-methanesulfonylphenoxy)indan-2-yl]piperazine;
1-[(1S,2S)-4,6-dichloro-1-(2-methanesulfonylphenoxy)indan-2-yl]pyrrolidine;
1-[(1S,2S)-4,6-dichloro-1-(3-tetrazol-1-ylphenoxy)indan-2-yl]piperazine;
1-[(1S,2S)-4,6-dichloro-1-(4-methanesulfonylphenoxy)indan-2-yl]-3-methanesulfonylpyrrolidine;
1-[(1S,2S)-4,6-dichloro-1-(4-methanesulfonylphenoxy)indan-2-yl]-4,4-difluoropiperidine;
1-[3-(rac-trans-(1,2)-4,6-dichloro-2-piperazin-1-ylindan-1-yloxy)phenyl]-3-methyl-1,3-dihydroimidazol-2-one;
1-[3-(rac-trans-(1,2)-4,6-dichloro-2-piperazin-1-ylindan-1-yloxy)phenyl]-3-methylimidazolidin-2-one;
1-[4-((1S,2S)-2-azetidin-1-yl-4,6-dichloroindan-1-yloxy)phenyl]pyrrolidin-2-one;
1-[4-((1S, 2S)-4,6-dichloro-2-pyrrolidin-1-ylindan-1-yloxy)phenyl]pyrrolidin-2-one;
1-[rac-trans-(1,2)-4,6-dichloro-1-(4-[1,2,4]triazol-1-ylphenoxy)indan-2-yl]piperazine;
1-[rac-trans-(1,2)-4,6-dichloro-1-(4-methanesulfonylphenoxy)indan-2-yl]-[1,4]diazepane;
1-[rac-trans-(1,2)-4,6-dichloro-1-(4-methanesulfonylphenoxy)indan-2-yl]-1H-imidazole;
1-[rac-trans-(1,2)-4,6-dichloro-1-(4-methanesulfonylphenoxy)indan-2-yl]-4-methyl-[1,4]diazepane;
1-[rac-trans-(1,2)-4-chloro-6-fluoro-1-(4-methanesulfonyl-3-methylphenoxy)indan-2-yl]piperazine;
1-[rac-trans-(1,2)-4-chloro-6-fluoro-1-(4-methanesulfonyl-3-methylphenoxy)indan-2-yl]pyrrolidine;
1-[rac-trans-(1,2)-4-chloro-6-fluoro-1-(4-methanesulfonylphenoxy)indan-2-yl]piperazine;
1-[rac-trans-(1,2)-4-chloro-6-fluoro-1-(4-methanesulfonylphenoxy)indan-2-yl]pyrrolidine;
1-[rac-trans-(1,2)-4-fluoro-1-(4-methanesulfonylphenoxy)indan-2-yl]pyrrolidine;
1-[rac-trans-(1,2)-5,6-dichloro-1-(4-methanesulfonylphenoxy)indan-2-yl]-[1,4]diazepane;
1-[rac-trans-(1,2)-5,7-dichloro-1-(4-methanesulfonylphenoxy)indan-2-yl]piperazine;
1-[rac-trans-(1,2)-6, 7-dichloro-1-(4-methanesulfonylphenoxy)indan-2-yl]-[1,4]diazepane;
1-[rac-trans-(1,2)-6-chloro-1-(4-methanesulfonylphenoxy)indan-2-yl]piperazine;
1-[rac-trans-(1,2)-6-chloro-4-fluoro-1-(3-methyl-4-trifluoromethanesulfonylphenoxy)indan-2-yl]piperazine;
1-[rac-trans-(1,2)-6-chloro-4-fluoro-1-(4-methanesulfonyl-3-methylphenoxy)indan-2-yl]pyrrolidine;
1-[rac-trans-(1,2)-6-chloro-4-fluoro-1-(4-methanesulfonylphenoxy)indan-2-yl]piperazine;
1-[rac-trans-(1,2)-6-chloro-4-fluoro-1-(4-methanesulfonylphenoxy)indan-2-yl]pyrrolidine;
1-[rac-trans-(1,2)-6-chloro-4-fluoro-1-(4-methanesulfonylphenoxy)indan-2-yl]piperazine;
1-[trans-(1S,2S)-4,6-dichloro-1-(2-chloro-4-methanesulfonylphenoxy)indan-2-yl]-[1,4]diazepane;
1-[trans-(1S,2S)-4,6-dichloro-1-(4-[1,2,4]triazol-1-ylphenoxy)indan-2-yl]-4-methylpiperazine;
1-[trans-(1S,2S)-4,6-dichloro-1-(4-imidazol-1-ylphenoxy)indan-2-yl]-4-methylpiperazine;
1-[trans-(1S,2S)-4,6-dichloro-1-(4-methanesulfonylphenoxy)indan-2-yl]-[1,4]diazepane;
1-[trans-(1S,2S)-4,6-dichloro-1-(4-methanesulfonylphenoxy)indan-2-yl]-3-propylpiperidin-3-ylamine;
1-[trans-(1S,2S)-4,6-dichloro-1-(4-methanesulfonylphenoxy)indan-2-yl]-3-trifluoromethylpiperazine;
1-[trans-(1S,2S)-4,6-dichloro-1-(4-methanesulfonylphenoxy)indan-2-yl]-3-trifluoromethylpyrrolidin-3-ylamine;
1-[trans-(1S,2S)-4,6-dichloro-1-(4-methanesulfonylphenoxy)indan-2-yl]-4-(2-fluoroethyl)-[1,4]diazepane;
1-[trans-(1S,2S)-4,6-dichloro-1-(4-methanesulfonylphenoxy)indan-2-yl]-4-(2-methoxyethyl)-[1,4]diazepane;
1-[trans-(1S,2S)-4,6-dichloro-1-(4-methanesulfonylphenoxy)indan-2-yl]-4-methyl-[1,4]diazepane;
1-[trans-(1S,2S)-4,6-dichloro-1-(4-methanesulfonylphenoxy)indan-2-yl]-4-methylpiperazine;
1-[trans-(1S,2S)-4,6-dichloro-1-(4-methanesulfonylphenoxy)indan-2-yl]-azetidin-3-ol
1-[trans-(1S,2S)-4,6-dichloro-1-(4-methanesulfonylphenoxy)indan-2-yl]piperazine, 1-{(1S,2S)-4,6-dichloro-1-[4-fluoro-2-(1H-pyrazol-3-yl)phenoxy]indan-2-yl}piperazine;
1-{2-chloro-5-[(1S,2S)-4,6-dichloro-2-((R)-3-hydroxypyrrolidin-1-yl)indan-1-yloxy]phenyl}-3-methyl-1,3-dihydroimidazol-2-one;
1-{2-chloro-5-[(1S,2S)-4,6-dichloro-2-((R)-3-hydroxypyrrolidin-1-yl)indan-1-yloxy]phenyl}-3-methylimidazolidin-2-one;
1-{3-[(1S,2S)-4,6-dichloro-2-((R)-3-hydroxypyrrolidin-1-yl)indan-1-yloxy]-2-methylphenyl}-3-methyl-1,3-dihydroimidazol-2-one;
1-{3-[(1S,2S)-4,6-dichloro-2-((R)-3-hydroxypyrrolidin-1-yl)indan-1-yloxy]-4-fluorophenyl}-3-methyl-1,3-dihydroimidazol-2-one;
1-{3-[(1S,2S)-4,6-dichloro-2-((R)-3-hydroxypyrrolidin-1-yl)indan-1-yloxy]-4-fluorophenyl}-3-methylimidazolidin-2-one;
1-{3-[(1S,2S)-4,6-dichloro-2-((R)-3-hydroxypyrrolidin-1-yl)indan-1-yloxy]phenyl}pyrrolidin-2-one;
1-{3-[(R1S, 2S)-4,6-dichloro-2-((R)-3-hydroxypyrrolidin-1-yl)indan-1-yloxy]phenyl}pyrrolidine -2,5-dione;
1-{3-[(1S,2S)-4,6-difluoro-2-((R)-3-hydroxypyrrolidin-1-yl)indan-1-yloxy]-4-fluorophenyl}-3-methyl-1,3-dihydroimidazol-2-one;
1-{3-[(1S,2S)-6-chloro-4-fluoro-2-((R)-3-hydroxypyrrolidin-1-yl)indan-1-yloxy]-4-fluorophenyl}-3-methyl-1, 3-dihydroimidazol-2-one;
1-{3-[trans-(1S,2S)-4,6-dichloro-2-((R)-3-hydroxypyrrolidin-1-yl)indan-1-yloxy]phenyl}-3-methylimidazolidin-2-one;
1-{3-[trans-(1S,2S)-6-chloro-4-fluoro-2-((R)-3-hydroxypyrrolidin-1-yl)indan-1-yloxy]phenyl1}-3-methylimidazolidin-2-one;
1-{3-chloro-4-[(1S,2S)-4,6-dichloro-2-((R)-3-hydroxypyrrolidin-1-yl)indan-1-yloxy]phenyl}pyrrolidin-2-one;
1-{3-chloro-4-[(1S,2S)-4,6-dichloro-2-((R)-3-hydroxypyrrolidin-1-yl)indan-1-yloxy]phenyl}pyrrolidine-2,5-dione;

1-{4-[(1S,2S)-4,6-dichloro-2-((R)-3-hydroxypyrrolidin-1-yl)indan-1-yloxy]-3-fluorophenyl}-1,3-dihydroimidazol-2-one;
1-{4-[(1S,2S)-4,6-dichloro-2-((R)-3-hydroxypyrrolidin-1-yl)indan-1-yloxy]-3-fluorophenyl}-2,6-dimethyl-1H-pyridin-4-one;
1-{4-[(1S,2S)-4,6-dichloro-2-((R)-3-hydroxypyrrolidin-1-yl)indan-1-yloxy]phenyl}-1,3-dihydroimidazol-2-one;
1-{4-[trans-(1S,2S)-4,6-dichloro-2-((R)-3-hydroxypyrrolidin-1-yl)indan-1-yloxy]-3-fluorophenyl}-3-methyl-1,3-dihydroimidazol-2-one;
1-{4-[trans-(1S,2S)-4,6-dichloro-2-((R)-3-hydroxypyrrolidin-1-yl)indan-1-yloxy]-3-fluorophenyl}-3-methylimidazolidin-2-one;
1-{4-[trans-(1S,2S)-4,6-dichloro-2-((R)-3-hydroxypyrrolidin-1-yl)indan-1-yloxy]phenyl}-3-methyl-1,3-dihydroimidazol-2-one;
1-{4-[trans-(1S,2S)-4,6-dichloro-2-((R)-3-hydroxypyrrolidin-1-yl)indan-1-yloxy]phenyl}-3-methylimidazolidin-2-one;
1-{4-[trans-(1S,2S)-4,6-dichloro-2-((R)-3-hydroxypyrrolidin-1-yl)indan-1-yloxy]phenyl}pyrrolidin-2-one;
1-{4-[trans-(1S,2S)-4,6-dichloro-2-((R)-3-hydroxypyrrolidin-1-yl)indan-1-yloxy]phenyl}pyrrolidine-2,5-dione;
1-{4-chloro-3-[(1S,2S)-4,6-dichloro-2-((R)-3-hydroxypyrrolidin-1-yl)indan-1-yloxy]phenyl}-3-methyl-1,3-dihydroimidazol-2-one;
1-{4-chloro-3-[(1S,2S)-4,6-dichloro-2-((R)-3-hydroxypyrrolidin-1-yl)indan-1-yloxy]phenyl}pyrrolidin-2-one;
1-{4-chloro-3-[(1S,2S)-4,6-dichloro-2-((R)-3-hydroxypyrrolidin-1-yl)indan-1-yloxy]phenyl}pyrrolidine-2,5-dione;
1-{4-chloro-3-[(1S,2S)-4,6-difluoro-2-((R)-3-hydroxypyrrolidin-1-yl)indan-1-yloxy]phenyl}-3-methyl-1,3-dihydroimidazol-2-one;
1-{4-chloro-3-[(1S,2S)-6-chloro-4-fluoro-2-((R)-3-hydroxypyrrolidin-1-yl)indan-1-yloxy]phenyl}-3-methyl-1,3-dihydroimidazol-2-one;
1-{4-chloro-3-[(1S,2S)-6-chloro-4-fluoro-2-((R)-3-hydroxypyrrolidin-1-yl)indan-1-yloxy]phenyl}-3-methylimidazolidin-2-one;
1-{4-chloro-3-[(1S,2S)-6-chloro-4-fluoro-2-((R)-3-hydroxypyrrolidin-1-yl)indan-1-yloxy]phenyl}pyrrolidin-2-one;
1-{trans-(1S,2S)-4,6-dichloro-1-[2-chloro-4-(3,5-dimethyl-[1,2,4]triazol-4-yl)phenoxy]indan-2-yl}-[1,4]diazepane;
1-{trans-(1S,2S)-4,6-dichloro-1-[2-chloro-4-(3,5-dimethyl-[1,2,4]triazol-4-yl)phenoxy]indan-2-yl}-4-methyl-[1,4]diazepane;
1-{trans-(1S,2S)-4,6-dichloro-1-[4-(3,5-dimethyl-[1,2,4]triazol-4-yl)-2-fluorophenoxy]indan-2-yl}-4-methyl-[1,4]diazepane;
1-{trans-(1S,2S)-4,6-dichloro-1-[4-(3,5-dimethyl-[1,2,4]triazol-4-yl)phenoxy]indan-2-yl}-[1,4]diazepane;
1-{trans-(1S,2S)-4,6-dichloro-1-[4-(3,5-dimethyl-[1,2,4]triazol-4-yl)phenoxy]indan-2-yl}-4-(2-methoxyethyl)-[1,4]diazepane;
1-{trans-(1S,2S)-4,6-dichloro-1-[4-(3,5-dimethyl-[1,2,4]triazol-4-yl)phenoxy]indan-2-yl}-4-methyl-[1,4]diazepane;
1-{trans-(1S,2S)-4,6-dichloro-1-[4-(3,5-dimethylisoxazol-4-yl)phenoxy]indan-2-yl}-4-(2-methoxyethyl)-[1,4]diazepane;
1-cyclopropyl-4-[trans-(1S,2S)-4,6-dichloro-1-(4-methanesulfonylphenoxy)indan-2-yl]piperazine;
2-((1S,2S)-2-azetidin-1-yl-4,6-dichloroindan-1-yloxy)-5-chlorobenzamide;
2,3-dichloro-4-(rac-trans-(1,2)-4,6-dichloro-2-morpholin-4-ylindan-1-yloxy)benzenesulfonamide;
2-[rac-trans-(1,2)-4,6-dichloro-1-(4-[1,2,4]triazol-1-ylphenoxy)indan-2-yl]octahydropyrrolo[3,4-c]pyrrole;
2-[trans-(1S,2S)-4,6-dichloro-1-(4-methanesulfonylphenoxy)indan-2-yl]-2,7-diaza-spiro[4.4]nonane;
2-{(R)-1-[trans-(1S,2S)-4,6-dichloro-1-(4-methanesulfonylphenoxy)indan-2-yl]piperidin-3-ylamino}ethanol;
2-{4-[rac-trans-(1,2)-4,6-dichloro-1-(4-methanesulfonylphenoxy)indan-2-yl]-[1,4]diazepan-1-yl}ethanol;
2-{4-[rac-trans-(1,2)-6-chloro-1-(4-methanesulfonylphenoxy)indan-2-yl]piperazin-1-yl}ethanol;
2-{4-[trans-(1S,2S)-4,6-dichloro-1-(4-methanesulfonylphenoxy)indan-2-yl]-[1,4]diazepan-1-yl}ethanol;
3-{3-[(1S,2S)-4,6-dichloro-2-((R)-3-hydroxypyrrolidin-1-yl)indan-1-yloxy]-4-fluorophenyl}-5,5-dimethylimidazolidine-2,4-dione;
3-{3-[(1S,2S)-4,6-dichloro-2-((R)-3-hydroxypyrrolidin-1-yl)indan-1-yloxy]-4-fluorophenyl}imidazolidine-2,4-dione;
3-{3-[(1S,2S)-4,6-dichloro-2-((R)-3-hydroxypyrrolidin-1-yl)indan-1-yloxy]-4-fluorophenyl}oxazolidine-2,4-dione;
3-{3-[(1S,2S)-4,6-dichloro-2-((R)-3-hydroxypyrrolidin-1-yl)indan-1-yloxy]phenyl}oxazolidin-2-one;
3-{3-[(1S,2S)-6-chloro-4-fluoro-2-((R)-3-hydroxypyrrolidin-1-yl)indan-1-yloxy]-4-fluorophenyl}-5,5-dimethylimidazolidine-2,4-dione;
3-{3-[(1S,2S)-6-chloro-4-fluoro-2-((R)-3-hydroxypyrrolidin-1-yl)indan-1-yloxy]-4-fluorophenyl}imidazolidine-2,4-dione;
3-{3-chloro-4-[(1S, 2S)-4,6-dichloro-2-((R) -3-hydroxypyrrolidin-1-yl)indan-1-yloxy]phenyl}-1-methylimidazolidine-2,4-dione;
3-{3-chloro-4-[(1S,2S)-4,6-dichloro-2-((R) -3-hydroxypyrrolidin-1-yl)indan-1-yloxy]phenyl}-5,5-dimethylimidazolidine-2,4-dione;
3-{3-chloro-4-[(1S, 2S)-4,6-dichloro-2-((R) -3-hydroxypyrrolidin-1-yl)indan-1-yloxy]phenyl}oxazolidine-2,4-dione;
3-{4-[(1S,2S)-4,6-dichloro-2-((R)-3-hydroxypyrrolidin-1-yl)indan-1-yloxy]phenyl}-5,5-dimethylimidazolidine-2,4-dione;
3-{4-[(1S,2S)-4,6-dichloro-2-((R)-3-hydroxypyrrolidin-1-yl)indan-1-yloxy]phenyl}imidazolidine-2,4-dione;
3-{4-[(1S,2S)-4,6-dichloro-2-((R)-3-hydroxypyrrolidin-1-yl)indan-1-yloxy]phenyl}oxazolidine-2,4-dione;
3-{4-[(1S, 2S)-4,6-dichloro-2-((R)-3-hydroxypyrrolidin-1-yl)indan-1-yloxy]phenyl}thiazolidine -2,4-dione;
3-{4-[trans-(1S,2S)-4,6-dichloro-2-((R)-3-hydroxypyrrolidin-1-yl)indan-1-yloxy]phenyl}oxazolidin-2-one;
3-{4-chloro-3-[(1S,2S)-4,6-dichloro-2-((R) -3-hydroxypyrrolidin-1-yl)indan-1-yloxy]phenyl}-1-methylimidazolidine-2,4-dione;
3-{4-chloro-3-[(1S,2S)-4,6-dichloro-2-((R) -3-hydroxypyrrolidin-1-yl)indan-1-yloxy]phenyl}-5,5-dimethylimidazolidine-2,4-dione;
3-{4-chloro-3-[(1S,2S)-4,6-dichloro-2-((R)-3-hydroxypyrrolidin-1-yl)indan-1-yloxy]phenyl}-5,5-dimethyloxazolidine-2,4-dione;
3-{4-chloro-3-[(1S,2S)-4,6-dichloro-2-((R)-3-hydroxypyrrolidin-1-yl)indan-1-yloxy]phenyl}imidazolidine-2,4-dione;
3-{4-chloro-3-[(1S,2S)-4,6-dichloro-2-((R)-3-hydroxypyrrolidin-1-yl)indan-1-yloxy]phenyl}oxazolidin-2-one;
3-{4-chloro-3-[(1S,2S)-6-chloro-4-fluoro-2-((R)-3-hydroxypyrrolidin-1-yl)indan-1-yloxy]phenyl}-1-methylimidazolidine-2,4-dione;
3-{4-chloro-3-[(1S,2S)-6-chloro-4-fluoro-2-((R)-3-hydroxypyrrolidin-1-yl)indan-1-yloxy]phenyl}-5,5-dimethylimidazolidine-2,4-dione;

3-{4-chloro-3-[(1S,2S)-6-chloro-4-fluoro-2-((R)-3-hydroxypyrrolidin-1-yl)indan-1-yloxy]phenyl }-5,5-dimethyloxazolidine-2,4-dione;
3-{4-chloro-3-[(1S,2S)-6-chloro-4-fluoro-2-((R)-3-hydroxypyrrolidin-1-yl)indan-1-yloxy]phenyl}imidazolidine-2,4-dione;
3-{4-chloro-3-[(1S,2S)-6-chloro-4-fluoro-2-((R)-3-hydroxypyrrolidin-1-yl)indan-1-yloxy]phenyl}oxazolidin-2-one;
3-chloro-4-[trans-(1S,2S)-6-chloro-2-((R)-3-hydroxypyrrolidin-1-yl)indan-1-yloxy]benzoic acid methyl ester;
4-((1S,2S)-4,6-dichloro-2-pyrrolidin-1-ylindan-1-yloxy)benzenesulfonamide;
4-(rac-trans-(1,2)-4-chloro-2-pyrrolidin-1-ylindan-1-yloxy)benzenesulfonamide;
4-(rac-trans-(1,2)-4-methyl-2-pyrrolidin-1-ylindan-1-yloxy)benzenesulfonamide;
4-(rac-trans-(1,2)-6-chloro-2-pyrrolidin-1-ylindan-1-yloxy)benzenesulfonamide;
4-(rac-trans-(1,2)-6-fluoro-2-pyrrolidin-1-ylindan-1-yloxy)benzenesulfonamide;
4-(rac-trans-(1,2)-6-methyl-2-pyrrolidin-1-ylindan-1-yloxy)benzenesulfonamide;
4-(rac-trans-(1,2)-7-chloro-2-pyrrolidin-1-ylindan-1-yloxy)benzenesulfonamide;
4-[(1S,2S)-2-((R)-3-aminopiperidin-1-yl)-4,6-dichloroindan-1-yloxy]benzenesulfonamide;
4-[(1S,2S)-4,6-dichloro-2-(1,1-dioxo-1lambda6-thiomorpholin-4-yl)indan-1-yloxy ]benzenesulfonamide;
4-[(1S,2S)-4,6-dichloro-2-(4,4-difluoropiperidin-1-yl)indan-1-yloxy]benzenesulfonamide;
4-[3-chloro-4-(trans-(1S,2S)-6-chloro-2-pyrrolidin-1-ylindan-1-yloxy)phenyl]-3,5-dimethyl-4H-[1,2,4]triazole;
4-[3-chloro-4-(trans-(1S,2S)-6-chloro-2-pyrrolidin-1-ylindan-1-yloxy)phenyl]-3,5-dimethyl-4H-[1,2,4]triazole;
4-[4-(rac-trans-(1,2)-5,6-dichloro-2-pyrrolidin-1-ylindan-1-yloxy)phenyl]-3,5-dimethyl-4H-[1,2,4]triazole;
4-[4-(trans-(1S,2S)-4,6-dichloro-2-pyrrolidin-1-ylindan-1-yloxy)-3-fluorophenyl]-3,5-dimethyl-4H -[1,2,4]triazole;
4-[4-(trans-(1S,2S)-4,6-dichloro-2-pyrrolidin-1-ylindan-1-yloxy)phenyl]-3,5-dimethyl-4H-[1,2,4]triazole;
4-[4-(trans-(1S,2S)-6-chloro-2-pyrrolidin-1-ylindan-1-yloxy)-3-fluorophenyl]-3,5-dimethyl-4H-[1,2,4]triazole;
4-[4-(trans-(1S,2S)-6-chloro-2-pyrrolidin-1-ylindan-1-yloxy)phenyl]-3,5-dimethyl-4H-[1,2,4]triazole;
4-[rac-trans-(1,2)-4,6-dichloro-1-(4-[1,2,4]triazol-1-ylphenoxy)indan-2-yl]morpholine;
4-[trans-(1S,2S)-2-((R)-3-aminopiperidin-1-yl)-4,6-dichloroindan-1-yloxy]-2,3-dichlorobenzenesulfonamide;
4-[trans-(1S,2S)-4,6-dichloro-2((R)-3-hydroxypyrrolidin-1-yl)indan-1-yloxy]-3-fluorobenzoic acid methyl ester;
4-{3-chloro-4-[trans-(1S,2S)-6-chloro-2-((R)-3-fluoropyrrolidin-1-yl)indan-1-yloxy]phenyl}-3,5-dimethyl-4H-[1,2,4]triazole;
4-{3-chloro-4-[trans-(1S,2S)-6-chloro-2-((S)-3-fluoropyrrolidin-1-yl)indan-1-yloxy]phenyl}-3,5-dimethyl-4H-[1,2,4]triazole;
4-{4-[(1S,2S)-4,6-dichloro-2-((R)-3-hydroxypyrrolidin-1-yl)indan-1-yloxy]-3-fluorophenyl}morpholine-3,5-dione;
4-{4-[trans-(1S,2S)-4,6-dichloro-2-((R)-3-fluoropyrrolidin-1-yl)indan-1-yloxy]phenyl}-3,5-dimethyl-4H-[1,2,4]triazole;
4-{4-[trans-(1S,2S)-4,6-dichloro-2-((S)-2-methoxymethylpyrrolidin-1-yl)indan-1-yloxy]phenyl}-3,5-dimethyl-4H-[1,2,4]triazole;
4-{4-[trans-(1S,2S)-6-chloro-2-((R)-3-fluoropynolidin-1-yl)indan-1-yloxy]-3-fluorophenyl}-3,5-dimethyl-4H-[1,2,4]triazole;
4-{trans-(1S,2S)-4,6-dichloro-1-[4-(3,5-dimethyl-[1,2,4]triazol-4-yl)-2-fluorophenoxy]indan-2-yl }morpholine;
4-{trans-(1S,2S)-4,6-dichloro-1-[4-(3,5-dimethyl-[1,2,4]triazol-4-yl)-2-fluorophenoxy]indan-2-yl}thiomorpholine-1,1-dioxide;
4-{trans-(1S,2S)-6-chloro-1-[2-chloro-4-(3,5-dimethyl-[1,2,4]triazol-4-yl)phenoxy]indan-2-yl}morpholine;
4-{trans-(1S,2S)-6-chloro-1-[2-chloro-4-(3,5-dimethyl-[1,2,4]triazol-4-yl)phenoxy]indan-2-yl}thiomorpholine 1,1-dioxide;
5-(rac-trans-(1,2)-4,6-dichloro-2-piperazin-1-ylindan-1-yloxy)-2-methylbenzothiazole;
5-[(1S,2S)-4,6-dichloro-2-((R)-3-hydroxypyrrolidin-1-yl)indan-1-yloxy]-3, 4-dihydro-1H-quinolin-2-one;
5-[trans-(1S,2S)-4,6-dichloro-1-(4-methanesulfonylphenoxy)indan-2-yl]-1-methyloctahydropyrrolo[3,4-b]pyrrole;
5-[trans-(1S,2S)-4,6-dichloro-1-(4-methanesulfonylphenoxy)indan-2-yl]-1-methyloctahydropyrrolo[3,4-b]pyrrole;
N-[3-(rac-trans-(1,2)-2-thiomorphol-4-ylindan-1-yloxy)phenyl]acetamide;
N-[3-(rac-trans-(1,2)-4,6-dichloro-2-[1,4]diazepan-1-ylindan-1-yloxy)phenyl]acetamide;
N-[3-(rac-trans-(1,2)-4,6-dichloro-2-morpholin-4-ylindan-1-yloxy)phenyl]acetamide;
N-[3-(rac-trans-(1,2)-4,6-dichloro-2-piperazin-1-ylindan-1-yloxy)phenyl]acetamide;
N-[3-(rac-trans-(1,2)-4,6-dichloro-2-pyrrolidin-1-ylindan-1-yloxy)phenyl]acetamide;
N-[3-(rac-trans-(1,2)-4-chloro-2-pyrrolidin-1-ylindan-1-yloxy)phenyl]acetamide;
N-[3-(rac-trans-(1,2)-4-chloro-6-fluoro-2-piperazin-1-ylindan-1-yloxy)phenyl]acetamide;
N-[3-(rac-trans-(1,2)-4-chloro-6-fluoro-2-pyrrolidin-1-ylindan-1-yloxy)phenyl]acetamide;
N-[3-(rac-trans-(1,2)-4-fluoro-2-pyrrolidin-1-ylindan-1-yloxy)phenyl]acetamide;
N-[3-(rac-trans-(1,2)-4-methyl-2-pyrrolidin-1-ylindan-1-yloxy)phenyl]acetamide;
N-[3-(rac-trans-(1,2)-5-chloro-2-pyrrolidin-1-ylindan-1-yloxy)phenyl]acetamide;
N-[3-(rac-trans-(1,2)-5-fluoro-2-pyrrolidin-1-ylindan-1-yloxy)phenyl]acetamide;
N-[3-(rac-trans-(1,2)-6-chloro-2-piperazin-1-ylindan-1-yloxy)phenyl]acetamide;
N-[3-(rac-trans-(1,2)-6-chloro-2-pyrrolidin-1-ylindan-1-yloxy)phenyl]acetamide;
N-[3-(rac-trans-(1,2)-6-chloro-4-fluoro-2-piperazin-1-ylindan-1-yloxy)phenyl]acetamide;
N-[3-(rac-trans-(1,2)-6-chloro-4-fluoro-2-pyrrolidin-1-ylindan-1-yloxy)phenyl]acetamide;
N-[3-(rac-trans-(1,2)-6-fluoro-2-pyrrolidin-1-ylindan-1-yloxy)phenyl]acetamide;
N-[3-(rac-trans-(1,2)-7-chloro-2-pyrrolidin-1-ylindan-1-yloxy)phenyl]acetamide;
N-[3-(trans-(1S,2S)-4,6-dichloro-2-3,8-diazabicyclo[3.2.1]oct-3-ylindan-1-yloxy)phenyl]acetamide;
N-[3-(trans-(1S,2S)-4,6-dichloro-2-piperazin-1-ylindan-1-yloxy)phenyl]acetamide;
N-{3-[(1S,2S)-6-chloro-4-fluoro-2-((R)-3-hydroxypyrrolidin-1-yl)indan-1-yloxy]-4-fluorophenyl }-N-methylmethanesulfonamide;
N-{3-[rac-trans-(1,2)-2(R)-3-aminopiperidin-1-yl)-4-chloro-6-fluoroindan-1-yloxy]phenyl}acetamide;
N-{3-[rac-trans-(1,2)-2-((R)-3-aminopiperidin-1-yl)-6-chloro-4-fluoroindan-1-yloxy]phenyl}acetamide;
N-{3-[rac-trans-(1,2)-4,6-dichloro-2-(hexahydropyrrolo[3,4-c]pyrrol-2-yl)indan-1-yloxy]phenyl}acetamide;

N-{3-[trans-(1S,2S)-2-((R)-3-aminopiperidin-1-yl)-4,6-dichloroindan-1-yloxy]phenyl}acetamide;
N-{3-[trans-(1S,2S)-2-(3-amino-3-propylpiperidin-1-yl)-4,6-dichloroindan-1-yloxy]phenyl}acetamide;
N-{3-[trans-(1S,2S)-4,6-dichloro-2-((R)-3-dimethylaminopiperidin-1-yl)indan-1-yloxy]phenyl}acetamide;
N-{3-[trans-(1S,2S)-4,6-dichloro-2-((R)-3-hydroxymethylpyrrolidin-1-yl)indan-1-yloxy]phenyl}acetamide;
N-{3-[trans-(1S,2S)-4,6-dichloro-2-((R)-3-hydroxypyrrolidin-1-yl)indan-1-yloxy]phenyl}acetamide;
N-{3-[trans-(1S,2S)-4,6-dichloro-2-(4-methylpiperazin-1-yl)indan-1-yloxy]phenyl}acetamide;
N-{4-[(1S,2S)-4,6-dichloro-2-((R)-3-hydroxypyrrolidin-1-yl)indan-1-yloxy]phenyl}-N-methylmethanesulfonamide;
(R)-1-[(1S,2S)-4,6-dichloro-1-(2-methanesulfonylphenoxy)indan-2-yl]piperidin-3-ylamine;
(R)-1-{trans-(1S,2S)-4,6-Dichloro-1-[4-(2-ethyl-4-methyl-imidazol-1-yl)-phenoxy]-indan-2-yl}-pyrrolidin-3-ol;
(R)-1-{trans-(1S,2S)-4,6-Dichloro-1-[4-(2-isopropyl-4-methyl-imidazol-1-yl)-phenoxy]-indan-2-yl}-pyrrolidin-3-ol;
(R)-1-{trans-(1S,2S)-4,6-Dichloro-1-[4-(3-isopropyl-5-methyl-[1,2,4]triazol-4-yl)-phenoxy]-indan-2-yl}-pyrrolidin-3-ol;
(R)-1-{trans-(1S,2S)-4,6-Dichloro-1-[4-(3-ethyl-5-isopropyl-[1,2,4]triazol-4-yl)-phenoxy]-indan-2-yl}-pyrrolidin-3-ol;
(R)-1-{trans-(1S,2S)-6-Chloro-1-[4-(2-ethyl-4-methyl-imidazol-1-yl)-phenoxy]-4-fluoro-indan-2-yl}-pyrrolidin-3-ol;
(R)-1-{trans-(1S,2S)-6-Chloro-4-fluoro-1-[4-(2-isopropyl-4-methyl-imidazol-1-yl)-phenoxy]-indan-2-yl}-pyrrolidin-3-ol
(R)-1-{trans-(1S,2S)-6-Chloro-4-fluoro-1-[4-(3-isopropyl-5-methyl [1,2,4]triazol-4-yl)-phenoxy]-indan-2-yl}-pyrrolidin-3-ol;
(R)-1-{trans-(1S,2S)-6-Chloro-1-[4-(3-ethyl-5-isopropyl [1,2,4]triazol-4-yl)-phenoxy]-4-fluoro-indan-2-yl}-pyrrolidin-3-ol;
(R)-1-{trans-(1S,2S)-1-[4-(4-tert-Butyl-2-isopropyl-imidazol-1-yl)-phenoxy]-6-chloro-4-fluoro-indan-2-yl}-pyrrolidin-3-ol;
(R)-1-{trans-(1S,2S)-4,6-Dichloro-1-[5-(2-ethyl-4-methyl-imidazol-1-yl)-2-fluoro-phenoxy]-indan-2-yl}-pyrrolidin-3-ol;
(R)-1-{trans-(1S,2S)-4,6-Dichloro-1-[4-(2,4-dimethyl-imidazol-1-yl)-2-fluoro-phenoxy]-indan-2-yl}-pyrrolidin-3-ol;
(R)-1-[trans-(1S,2S)-4,6-Dichloro-1-(4-imidazol-1-yl-phenoxy)-indan-2-yl]-pyrrolidin-3-ol;
(R)-1-{trans-(1S,2S)-1-[4-(4-tert-Butyl-2-methyl-imidazol-1-yl)-2-fluoro-phenoxy]-4,6-dichloro-indan-2-yl}-pyrrolidin-3-ol;
(R)-1-{trans-(1S,2S)-4,6-Dichloro-1-[4-(2-isopropyl-imidazol-1-yl)-phenoxy]-indan-2-yl}-pyrrolidin-3-ol;
3-{4-[trans-(1S,2S)-4,6-Dichloro-2-((R)-3-hydroxy-pyrrolidin-1-yl)-indan-1-yloxy]-phenyl}-5-methyl-3H-[1,3,4]oxadiazol-2-one;
3-{4-[trans-(1S,2S)-4,6-Dichloro-2-((R)-3-hydroxy-pyrrolidin-1-yl)-indan-1-yloxy]-phenyl}-3H-[1,3,4]oxadiazol-2-one;
2-{4-[trans-(1S,2S)-4,6-Dichloro-2-((R)-3-hydroxy-pyrrolidin-1-yl)-indan-1-yloxy]-phenyl}-4-ethyl-2,4-dihydro-[1,2,4]triazol-3-one;
2-{4-[trans-(1S,2S)-4,6-Dichloro-2-((R)-3-hydroxy-pyrrolidin-1-yl)-indan-1-yloxy]-phenyl}-4-ethyl-5-methyl-2,4-dihydro-[1,2,4]triazol-3-one;
(R)-1-{trans-(1S,2S)-6-Chloro-1-[4-(2,4-dimethyl-imidazol-1-yl)-2-fluoro-phenoxy]-4-fluoro-indan-2-yl}-pyrrolidin-3-ol;
1-{4-[trans-(1S,2S)-4,6-Dichloro-2-((R)-3-hydroxy-pyrrolidin-1-yl)-indan-1-yloxy]-3-fluoro-phenyl}-1H-imidazole-2-carboxylic acid methyl ester;
4-[trans-(1S,2S)-4,6-Dichloro-2-((R)-3-hydroxy-pyrrolidin-1-yl)-indan-1-yloxy]-3-fluoro-benzenesulfonamide;
(R)-1-{trans-(1S,2S)-4,6-Dichloro-1-[4-(4-methyl-piperazine-1-sulfonyl)-phenoxy]-indan-2-yl}pyrrolidin-3-ol;
4-[trans-(1S,2S)-4,6-Dichloro-2-((R)-3-hydroxy-pyrrolidin-1-yl)-indan-1-yloxy]-benzenesulfonamide;
(R)-1-{trans-(1S,2S)-4,6-Dichloro-1-[4-(morpholine-4-sulfonyl)-phenoxy]-indan-2-yl}-pyrrolidin-3-ol and
1-{5-[trans-(1S,2S)-4,6-Dichloro-2-((R)-3-hydroxy-pyrrolidin-1-yl)-indan-1-yloxy]-2-fluoro-phenyl}-3-methyl-1,3-dihydro-imidazol-2-one;
and the pharmaceutically acceptable salts thereof.

12. A compound of the formula I according to claim 1 and the pharmaceutically acceptable salts thereof, wherein the radical XLBR5 bonded at position 1 is directed downwards and the radical —(CH$_2$)$_q$NR3R4 bonded at position 2 is directed upwards, with the direction being determined starting from a plane which is spanned by the three carbon atoms in positions 1,2 and 3, and the compounds are oriented as in formula Ie

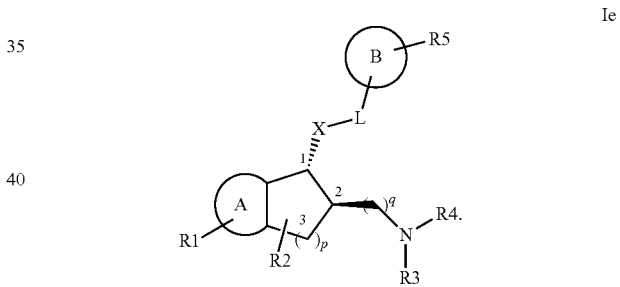

13. A compound of the formula I and/or the pharmaceutically acceptable salts thereof as claimed in claim 1, 2, 9, 10, or 11 for use as a medicament.

14. A pharmaceutical preparation for human, veterinary or phytoprotective use comprising an effective amount of a compound of the formula I and/or of a pharmaceutically acceptable salt thereof as claimed in claim 1, 2, 9, 10 or 11.

15. A pharmaceutical preparation for human, veterinary or phytoprotective use comprising an effective amount of a compound of the formula I and/or of a pharmaceutically acceptable salt thereof as claimed in claim 1, 2, 9, 10 or 11, in combination with other pharmacological active ingredients or pharmaceuticals.

* * * * *